United States Patent
Eis et al.

(10) Patent No.: US 9,884,063 B2
(45) Date of Patent: Feb. 6, 2018

(54) AMIDO-SUBSTITUTED AZOLE COMPOUNDS

(71) Applicant: Bayer Pharma Aktiengesellschaft, Berlin (DE)

(72) Inventors: Knut Eis, Berlin (DE); Jens Ackerstaff, Düsseldorf (DE); Sarah Wagner, Berlin (DE); Daniel Basting, Köln (DE); Stefan Golz, Mülheim an der Ruhr (DE); Eckhard Bender, Langenfeld (DE); Volkhart Min-Jian Li, Velbert (DE); Philip Lienau, Berlin (DE); Ningshu Liu, Berlin (DE); Franziska Siegel, Berlin (DE); Marcus Bauser, Berlin (DE); Detlev Sülzle, Berlin (DE); Simon Holton, Berlin (DE); Michaela Bairlein, Wuppertal (DE); Philipp Buchgraber, Berlin (DE); József Bálint, Berlin (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 15/301,443

(22) PCT Filed: Apr. 1, 2015

(86) PCT No.: PCT/EP2015/057167
§ 371 (c)(1),
(2) Date: Oct. 3, 2016

(87) PCT Pub. No.: WO2015/150449
PCT Pub. Date: Oct. 8, 2015

(65) Prior Publication Data
US 2017/0020886 A1    Jan. 26, 2017

Related U.S. Application Data
(60) Provisional application No. 61/973,925, filed on Apr. 2, 2014.

(30) Foreign Application Priority Data
Apr. 2, 2014 (EP) .................... 14163261

(51) Int. Cl.
C07D 233/90    (2006.01)
C07D 263/34    (2006.01)
(Continued)

(52) U.S. Cl.
CPC ........ *A61K 31/541* (2013.01); *A61K 31/4164* (2013.01); *A61K 31/4178* (2013.01); *A61K 31/421* (2013.01); *A61K 31/4439* (2013.01); *A61K 31/454* (2013.01); *A61K 31/4545* (2013.01); *A61K 31/496* (2013.01); *A61K 31/497* (2013.01); *A61K 31/5355* (2013.01);
(Continued)

(58) Field of Classification Search
CPC .. C07D 233/90; C07D 263/34; C07D 401/12; C07D 413/12
See application file for complete search history.

(56) References Cited

U.S. PATENT DOCUMENTS 6,747,041 B1    6/2004 Katsuhira et al.
2016/0272733 A1    9/2016 Wang et al.

FOREIGN PATENT DOCUMENTS

EP    0023045    1/1981
WO    WO-2001000575    1/2001
(Continued)

OTHER PUBLICATIONS

PubChem CID 69228021—National Center for Biotechnology Information. PubChem Compound Database; CID=69228021, https://pubchem.ncbi.nlm.nih.gov/compound/69228021 (accessed Jun. 22, 2017), create date Nov. 30, 2012.*
(Continued)

*Primary Examiner* — Laura L. Stockton
(74) *Attorney, Agent, or Firm* — Morrison & Foerster LLP

(57) ABSTRACT

The present invention relates to amido-substituted azole compounds of general formula (I), in which $X_1$, $X_2$, $R^1$, $R^2$, $R^4$, $R^5$, $R^7$ and $R^8$ are as defined in the claims which are inhibitors of TNKS1 and/or TNKS2, to methods of preparing said compounds, to intermediate compounds useful for preparing said compounds, to pharmaceutical compositions and combinations comprising said compounds and to the use of said compounds for manufacturing a pharmaceutical composition for the treatment or prophylaxis of a disease, in particular of neoplasms, as a sole agent or in combination with other active ingredients.

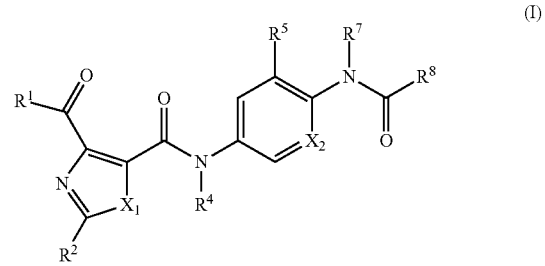

(I)

17 Claims, No Drawings

(51) Int. Cl.
| | |
|---|---|
| C07D 401/12 | (2006.01) |
| C07D 413/12 | (2006.01) |
| A61K 31/541 | (2006.01) |
| C07D 295/092 | (2006.01) |
| C07D 403/06 | (2006.01) |
| C07D 403/12 | (2006.01) |
| C07D 407/12 | (2006.01) |
| C07D 413/06 | (2006.01) |
| C07D 487/10 | (2006.01) |
| C07D 491/107 | (2006.01) |
| A61K 31/4164 | (2006.01) |
| A61K 31/4178 | (2006.01) |
| A61K 31/421 | (2006.01) |
| A61K 31/4439 | (2006.01) |
| A61K 31/454 | (2006.01) |
| A61K 31/4545 | (2006.01) |
| A61K 31/496 | (2006.01) |
| A61K 31/497 | (2006.01) |
| A61K 31/5355 | (2006.01) |
| A61K 45/06 | (2006.01) |
| C07D 405/12 | (2006.01) |
| C07D 409/12 | (2006.01) |

(52) U.S. Cl.
CPC ............ *A61K 45/06* (2013.01); *C07D 233/90* (2013.01); *C07D 263/34* (2013.01); *C07D 295/092* (2013.01); *C07D 401/12* (2013.01); *C07D 403/06* (2013.01); *C07D 403/12* (2013.01); *C07D 405/12* (2013.01); *C07D 407/12* (2013.01); *C07D 409/12* (2013.01); *C07D 413/06* (2013.01); *C07D 413/12* (2013.01); *C07D 487/10* (2013.01); *C07D 491/107* (2013.01)

(56) References Cited

FOREIGN PATENT DOCUMENTS

| | | |
|---|---|---|
| WO | WO-2006058630 | 6/2006 |
| WO | WO-2008042282 | 4/2008 |
| WO | WO-2008042283 | 4/2008 |
| WO | WO-2009059994 | 5/2009 |
| WO | WO-2011045292 | 4/2011 |
| WO | WO-2011133871 | 10/2011 |
| WO | WO-2012076898 | 6/2012 |
| WO | WO-2012123432 | 9/2012 |
| WO | WO-2013010092 | 1/2013 |
| WO | WO-2013012723 | 1/2013 |
| WO | WO-2013012915 | 1/2013 |
| WO | WO-2013012918 | 1/2013 |
| WO | WO-2013032591 | 3/2013 |
| WO | WO-2013093508 | 6/2013 |
| WO | WO-2013134079 | 9/2013 |
| WO | WO-2013154878 | 10/2013 |
| WO | WO-2013164061 | 11/2013 |
| WO | WO-2013177349 | 11/2013 |
| WO | WO-2013182546 | 12/2013 |
| WO | WO-2013189865 | 12/2013 |
| WO | WO-2013189905 | 12/2013 |
| WO | WO-2014023390 | 2/2014 |
| WO | WO-2014189128 | 11/2014 |
| WO | WO-2015062231 | 5/2015 |
| WO | WO-2016045587 | 3/2016 |
| WO | WO-2016177658 | 11/2016 |
| WO | WO-2017055313 | 4/2017 |
| WO | WO-2017055316 | 4/2017 |

OTHER PUBLICATIONS

Vostrova, L.N. et al. (1989). "Synthesis and antimicrobial activity of 5-nitrofurfural heteryl hydrazones," Translated from *Khimiko-farmatsevticheskii Zhurnal* 23(5):584-587.

Bregman, H. et al (2013). "Discovery of a Class of Novel Tankyrase Inhibitors that Bind to Both the Nicotinamide Pocket and the Induced Pocket," *J. Med. Chem.* 56: 1341-1345.

Bregman, H. et al (2013). "Discovery of Novel, Induced-Pocket Binding Oxazolidinones as Potent, Selective, and Orally Bioavailable Tankyrase Inhibitors," *J. Med. Chem.* 56: 4320-4342.

Haikarainen, T. et al. (2013). "para-Substituted 2-Phenyl-3,4-dihydroquinazolin-4-ones as Potent and Selective Tankyrase Inhibitors," *ChemMedChem* 8: 1987-1985.

Hua, Z. et al. (2013). "Development of Novel Dual Binders as Potent, Selective, and Orally Bioavailable Tankyrase Inhibitors," *J. Med. Chem.* 56: 10003-10015.

Huang, H. et al. (2013). "Structure-Based Design of 2-Aminopyridine Oxazolidinones as Potent and Selective Tankyrase Inhibitors," *ACS Medicinal Chemistry Letters* 4: 1218-1223.

Johannes, J.W. et al. (2015). "Pyrimidinone Nicotinamide Mimetics as Selective Tankyrase and Wnt Pathway Inhibitors Suitable for in Vivo Pharmacology," *ACS Medicinal Chemistry Letters* 6: 254-259.

Kirby, C.A. et al. (2012). "Structure of human tankyrase 1 in complex with small-molecule inhibitors PJ34 and XAV939," *Acta Crystallographica* F68(part 2): 115-118.

Lau, T. et al. (2013). "A Novel Tankyrase Small-Molecule Inhibitor Suppresses APC Mutation-Driven Colorectal Tumor Growth," *American Association for Cancer Research* 73(10): 3132-3144.

Narwal, M. et al. (2012). "Structural Basis of Selective Inhibition of Human Tankyrases," *Journal of Medicinal Chemistry* 55: 1360-1367.

Narwal, M. et al. (2013). "Discovery of Tankyrase Inhibiting Flavones with Increased Potency and Isoenzyme Selectivity," *Journal of Medicinal Chemistry* 56: 7880-7889.

Nathubhai, A. et al. (2013). "Design and Discovery of 2-Arylquinazolin-4-ones as Potent and Selective Inhibitors of Tankyrases," *ACS Medicinal Chemistry Letters* 4: 1173-1177.

Perchellet, E. M. (Jan. 2005). "Imidazole-4,5-dicarboxamide Derivatives with Antiproliferative Activity against HL-60 Cells," *J. Med. Chem.* 48: 5955-5965.

PubChem Compound Database Summary for CID=69228021, 5,10-dioxo-1-phenoxycarbonyldiimidazo[1,4-b:1',4'-e]pyrazine-6-carboxylic acid, *National Center for Biotechnology Information*, Nov. 30, 2012, XP-002744347.

Rush, J.R. et al (Jan. 2005). "Intramolecular Hydrogen Bond Strength and pKa Determination of N, N'—Disubstituted Imidazole-4,5-dicarboxamides", *Organic Letters* 7(1): 135-138.

Sekihachi, J. et al. (Sep. 1996). "Synthesis and Chromophoric Properties of Symmetrical bis-Heteroannelated Diketopiperazines: Diimidazo- and Dipyrazolo-Piperazinediones," *Dyes and Pigments*, 32(1): 43-58.

Serrao, E. et al. (Aug. 2013). "Discovery of a novel 5-carbonyl-1H-imidazole-4-carboxamide class of inhibitors of the HIV-1 integrase-LEDGF/p75 interac," *Bioorganic & Medicinal Chemistry* 21(19): 5963-5972.

Shultz, M.D. et al. (2013). "Identification of NVP-TNKS656: The Use of Structure-Efficiency Relationships to Generate a Highly Potent, Selective, and Orally Active Tankyrase Inhibitor," *Journal of Medicinal Chemistry* 56: 6495-6511.

Shultz, M.D. et al. (2013). "Structure-Efficiency Relationship of [1,2,4]Triazol-3-ylamines as Novel Nicotinamide Isosteres that Inhibit Tankyrases," *Journal of Medicinal Chemistry* 56: 7049-7059.

Voronkov, A. et al. (2013). "Structural Basis and SAR for G007-LK, a Lead Stage 1,2,4-Triazole Based Specific Tankyrase 1/2 Inhibitor," *Journal of Medicinal Chemistry* 56: 3012-3023.

Wiznycia, A. V. et al. (Nov. 2004). "Synthesis of Symmetric Bis(imidazole-4,5-dicarboxamides) Substituted with Amino Acids," *Journal of Organic Chemistry* 69: 8489-8491.

Xu, Z. et al. (Mar. 2010). "Parallel Synthesis of an Oligomeric Imidazole-4,5-dicarboxamide Library," *Journal of Combinatorial Chemisrty* 12(2): 248-254.

(56) References Cited

OTHER PUBLICATIONS

Xu, Z. et al. (May 2012). "Parallel Synthesis of Peptide-Like Macrocycles Containing Imidazole-4,5-dicarboxylic Acid," *Molecules* 17(12): 5346-5362.

Yasuda, N. (Jan. 1985). "Synthesis of Novel Imidazole-4,5-dicarboxylic Acid Derivatives," *Journal of Heterocyclic Chemistry* 22: 413-416.

* cited by examiner

AMIDO-SUBSTITUTED AZOLE COMPOUNDS

CROSS REFERENCE TO RELATED APPLICATIONS

This application is a National Phase application under 35 U.S.C. § 371 of International Application No. PCT/EP2015/057167, filed Apr. 1, 2015, which claims the benefit of U.S. Provisional Application No. 61/973,925, filed Apr. 2, 2014, and also claims the benefit of European Application No. 14163261.2, filed Apr. 2, 2014.

The present invention relates to amido-substituted azole compounds of general formula (I) as described and defined herein, to methods of preparing said compounds, to intermediate compounds useful for preparing said compounds, to pharmaceutical compositions and combinations comprising said compounds and to the use of said compounds for manufacturing a pharmaceutical composition for the treatment or prophylaxis of a disease, in particular of neoplasms, as a sole agent or in combination with other active ingredients.

BACKGROUND OF THE INVENTION

Cancer is the leading cause of death in developed countries and the second leading cause of death in developing countries. Deaths from cancer worldwide are projected to continue rising, with an estimated 12 million deaths in 2030. While substantial progress has been made in developing effective therapies, there is a need for additional therapeutic modalities that target cancer and related diseases.

The complexity of cancer disease arises after a selection process for cells with acquired functional capabilities to enhance survival and/or resistance towards apoptosis and a limitless proliferative potential. In addition, bi-direction interaction of cancer cells and stromal cells provides further advantage of cancer cell survival and distant metastasis to the secondary organs and tissues [Liotta L A, Kohn E C. *The microenvironment of the tumour-host interface. Nature* 411: 375, 2001]. Furthermore, cancer stem cells (CSCs) represent the apex in the hierarchical model of tumor genesis, heterogeneity and metastasis. CSCs possess the capacity for unlimited selfrenewal, the ability to give rise to progeny cells, and also an innate resistance to cytotoxic therapeutics [Corbin E. Meacham and Sean J. Morrison. *Tumour heterogeneity and cancer cell plasticity. [Nature* 501:328, 2013]. Thus, there is need to develop drugs for cancer therapy addressing distinct features of established tumors.

The discovery that *Drosophila* segment polarity gene Wingless had a common origin with the murine oncogene Int-1 led to intensive studies on Wnt signalling pathway and identification of 19 mammalian Wnts and 10 Wnt receptors [Rijsewijk F, Schuermann M, Wagenaar E, Parren P, Weigel D, Nusse R. *The Drosophila homolog of the mouse mammary oncogene int-1 is identical to the segment polarity gene wingless. Cell.* 1987; 50: 649-57.]. Wnts are secreted glycoproteins which bind to cell surface receptors to initiate signaling cascades. Wnt signaling cascades have classified into two categories: canonical and non-canonical, differentiated by their dependence on β-catenin. Non-canonical Wnt pathways, such as the planar cell polarity (PCP) and Ca2+ pathway, function through β-catenin independent mechanisms. Canonical Wnt signalling is initiated when a Wnt ligand engages co-receptors of the Frizzled (Fzd) and low-density lipoprotein receptor related protein (LRP) families, ultimately leading to β-catenin stabilization, nuclear translocation and activation of target genes [Angers S, Moon R T. *Proximal events in Wnt signal transduction. Nat Rev Mol Cell Biol.* 2009; 10: 468-77. 68. Cadigan K M, Liu Y I. *Wnt signaling: complexity at the surface. J Cell Sci.* 2006; 119: 395-402. 69. Gordon M D, Nusse R. *Wnt signaling: multiple pathways, multiple receptors, and multiple transcription factors. J Biol Chem.* 2006; 281: 22429-33. 70. Huang H, He X. *Wnt/beta-catenin signaling: new (and old) players and new insights. Curr Opin Cell Biol.* 2008; 20: 119-25. 71. Polakis P. *The many ways of Wnt in cancer. Curr Opin Genet Dev.* 2007; 17: 45-51. 72. Rao T P, Kuhl M. *An updated overview on Wnt signaling pathways: a prelude for more. Circ Res.* 2010; 106: 1798-806].

In the absence of Wnt stimulus, β-catenin is held in an inactive state by a multimeric "destruction" complex comprised of adenomatous polyposis coli (APC), Axin, glycogen synthase kinase 3β (GSK3β) and casein kinase 1α (CK1α). APC and Axin function as a scaffold, permitting GSK3β- and CK1α-mediated phosphorylation of critical residues within β-catenin. These phosphorylation events mark β-catenin for ubiquitination recognition by the E3 ubiquitin ligase β-transducin-repeat-containing protein and lead to subsequent proteasomal degradation [He X, Semenov M, Tamai K, Zeng X. *LDL receptor-related proteins 5 and 6 in Wnt/beta-catenin signaling: arrows point the way. Development.* 131:1663, 2004. Kimelman D, Xu W. *beta-catenin destruction complex: insights and questions from a structural perspective. Oncogene* 25: 7482, 2006.].

In the presence of Wnt stimulus, Axin, GSK3β and Dvl are recruited to the co-receptor complex Fzd and LRP5/6 and lead to disruption of the β-catenin destruction complex. Therefore, β-catenin is stabilized and translocated to nucleus. Once in the nucleus, β-catenin forms a complex with members of the T-cell factor/lymphoid enhancer factor (TCF/LEF) family of transcription factors, recruiting co-factors such as CBP, p300, TNIK, Bcl9 and Pygopus, and ultimately driving transcription of target genes including c-myc, Oct4, cyclin D, survivin. [Joshua C. Curtin and Matthew V. Lorenzi. *Drug Discovery Approaches to Target Wnt Signaling in Cancer Stem Cells. Oncotarget* 1: 552, 2010].

Tankyrases play a key role in the destruction complex by regulating the stability of the rate-limiting AXIN proteins, RNF146 and tankyrase itself. The E3 ubiquitin ligase RNF146 recognizes tankyrase-mediated PARsylation and eartags AXIN, tankyrase and itself for proteasome-mediated degradation. Thus, tankyrases control the protein stability and turnover of key components of the destruction complex, and consequently the cellular levels of β-catenin [Shih-Min A. Huang, Yuji M. Mishina, Shanming Liu, Atwood Cheung, Frank Stegmeier, et al. *Tankyrase inhibition stabilizes axin and antagonizes Wnt signalling. Nature* 461:614, 2009, Yue Zhang, Shanming Liu, Craig Mickanin, Yan Feng, Olga Charlat, et al. *RNF146 is a poly(ADP-ribose)-directed E3 ligase that regulates axin degradation and Wnt signalling. Nature Cell Biology* 13:623-629, 2011].

Aberrant regulation of the Wnt/β-catenin signaling pathway is a common feature across a broad spectrum of human cancers and evolves as a central mechanism in cancer biology. First of all, Wnt overexpression could lead to malignant transformation of mouse mammary tissue [Klaus A, Birchmeier W. *Wnt signalling and its impact on development and cancer. Nat Rev Cancer* 8: 387-398, 2008]. Second, tumor genome sequencing discovered the mutations in Wnt/β-catenin pathway components as well as epigenetic mechanisms that altered the expression of genes relevant to Wnt/β-catenin pathway [Ying, Y. et al. *Epigenetic disruption*

*of the WNT/beta-catenin signaling pathway in human cancers. Epigenetics* 4:307, 2009]. Third, Wnt/β-catenin pathway also cooperates with other oncogenic signaling pathways in cancer and regulates tumorigenesis, growth, and metastasis [Klaus A, Birchmeier W. *Wnt signalling and its impact on development and cancer. Nat Rev Cancer* 8: 387-398, 2008]. In addition, there is an additional role of WNT signaling between tumor and stromal cell interaction leading to tumorigenesis and metastasis [Shahi P, Park D, Pond A C, Seethammagari M, Chiou S-H, Cho K, et al. *Activation of Wnt signaling by chemically induced dimerization of LRP5 disrupts cellular homeostasis. PLoS ONE* 7: e30814, 2012]. Furthermore, growing body of evidence indicates a critical role of β-catenin in CSCs [Eaves C J, Humphries R K. *Acute myeloid leukemia and the Wnt pathway. N Engl J Med.* 362: 2326-7, 2010; Nusse R, Fuerer C, Ching W, Harnish K, Logan C, Zeng A, ten Berge D, Kalani Y. *Wnt signaling and stem cell control. Cold Spring Harb Symp Quant Biol.* 73: 59-66, 2008; Reya T, Clevers H. *Wnt signalling in stem cells and cancer. Nature* 434: 843-50, 2005]. For example, stem-like colon cells with a high level of β-catenin signaling have a much greater tumorigenic potential than counterpart cells with low β-catenin signaling [Vermeulen L, De Sousa E M F, van der Heijden M, Cameron K, de Jong J H, Borovski T, Tuynman J B, Todaro M, Merz C, Rodermond H, Sprick M R, Kemper K, Richel D J, Stassi G, Medema J P. *Wnt activity defines colon cancer stem cells and is regulated by the microenvironment. Nat Cell Biol.* 12: 468-76, 2010]. Finally, activation of Wnt/β-catenin signalling pathway is also one of the major mechanism causing tumor recurrence and drug resistance. All these provide clear rationale to develop therapeutics targeting Wnt/β-catenin signaling pathway for the treatment of cancer.

One of the approaches to inhibit Wnt/β-catenin signaling pathway is to target druggable tankyrases. Tankyrase 1 (TNKS1) and tankyrase 2 (TNKS2) are poly(ADP-ribosyl) ases that are distinguishable from other members of the enzyme family by the structural features of the catalytic domain, and the presence of a sterile a-motif multimerization domain and an ankyrin repeat protein-interaction domain. Inhibition of TNKS blocks PARsylation of AXIN1 and AXIN2 and prevents their proteasomal degradation. As the consequence, TNKS inhibition enhances the activity of the β-catenin destruction complex and suppresses β-catenin nuclear transclocation and the expression of β-catenin target genes.

In addition to its function in Wnt signaling through modulation of β-catenin destruction, tankyrases are also implicated in other cellular functions, including telomere homeostasis, mitotic spindle formation, vesicle transport linked to glucose metabolism, and viral replication. In these processes, tankyrases interact with target proteins, catalyze poly (ADP-ribosyl)ation, and regulate protein interactions and stability. For example, TNKS1 controls telomere homeostasis, which promotes telomeric extension by PARsylating TRF1. TRF1 is then targeted for proteasomal degradation by the E3 ubiquitin ligases F-box only protein 4 and/or RING finger LIM domain-binding protein (RLIM/RNF12), which facilitates telomere maintenance [Donigian J R and de Lange T. *The role of the poly(ADP-ribose) polymerase tankyrase1 in telomere length control by the TRF1 component of the shelterin complex. J Biol Chem* 282:22662, 2007]. In addition, telomeric end-capping also requires canonical DNA repair proteins such as DNA-dependent protein kinase (DNAPK) TNKS1 stabilizes the catalytic subunit of DNAPK (DNAPKcs) by PARsylation [Dregalla R C, Zhou J, Idate R R, Battaglia C L, Liber H L, Bailey S M. *Regulatory roles of tankyrase 1 at telomeres and in DNA repair: suppression of T-SCE and stabilization of DNA-PKcs. Aging* 2(10):691, 2010]. Altered expression of TNKS1 and/or TNKS2, as well as genetic alterations in the tankyrase locus, have been detected in multiple tumors, e.g. fibrosarcoma, ovarian cancer, glioblastoma, pancreatic adenocarcinoma, breast cancer, astrocytoma, lung cancer, gastric cancer, and colon cancer [Lari Lehti, Nai-Wen Chi and Stefan Krauss. *Tankyrases as drug targets. FEBS Journal* 280: 3576, 2013]. In addition, tankyrases appear to have impact on viral infections. For example, HSV infection, it was shown that the virus cannot replicate efficiently in cells that with depletion of both TNKS1 and TNKS2.

Furthermore, a connection between tankyrases and glucose metabolism has been indicated. Thus, DNA polymorphism in a chromosomal region encoding tankyrase/methionine sulfoxide reductase A is robustly associated with early-onset obesity. TNKS1 knockout mice appeared to have reduced fat pads, suggesting a potential connection of TNKS and obesity. TNKS may also play a role in tissue fibrosis.

In summary, tankyrases are promising drug targets in regulating WNT signalling, telomere length (e.g. telomere shortening and DNA damage induced cell death), lung fibrogenesis, myelination and viral infection. The invention presented here describes a novel class of tankyrase inhibitors and their potential clinical utility for the treatment of various diseases, such as cancer, aging, metabolic diseases (e.g. diabetes and obesity), fibrosis (e.g. lung fibrogenesis) and viral infection.

The following list of selected references relates to inhibitors of TNKS1 and/or TNKS2 described in the literature or in patents. However, the chemical structures and compound classes of the inhibitors described in these references are completely different from the chemical structures of the present invention:

Cancer Research 2013, 73 (10): 3132, J Med Chem 2013, 56 (16): 6495, J Med Chem 2013, 56(3): 1341, J Med Chem 2013, 56(17): 7049, J Med Chem 2013, 56(24): 10003, J Med Chem 2013, 56(7): 3012, J Med Chem 2013, 56(20): 7880, J Med Chem 2013, 56(11): 4320, ChemMedChem 2013, 8(12): 1978, ACS Med Chem Lett 2013, 4(12): 1173, ACS Med Chem Lett 2013, 4(12): 1218, Acta Crystallogr Sect F Struct Biol Cryst Commun 2012, 68 (Part 2): 115, J Med Chem 2012, 55(3): 1360, WO 2009059994, WO2013164061, WO2014023390, WO 2012076898, WO 2013093508, WO 2013010092, WO 2013189905, WO 2013189865, WO 2013177349, WO 2013012723, WO 2013134079, WO 2013182546.

WO 2008/042283 (Exelixis) discloses imidazole-4,5-dicarboxamide derivatives as JAK2 modulators.

WO 2001/000575 discloses heterocyclic dicarboxylic acid diamide derivatives as insecticides, including amido-substituted azole compounds.

However, the state of the art described above does not describe the specific substituted amido-substituted azole compounds of general formula (I) of the present invention as defined herein, i.e. an imidazole or an oxazole moiety, bearing:

in its 4-position, a group of structure:

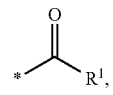

wherein:
* indicates the point of attachment of said groups with the rest of the molecule, and
R¹ represents —OR⁹, or —N(R¹⁰)R¹¹, which are as defined herein, and
in its 5-position, a group of structure:

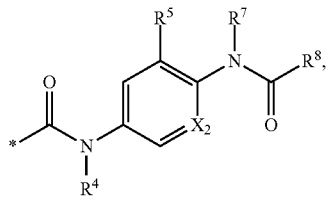

wherein:
* indicates the point of attachment of said groups with the rest of the molecule, and
X₂ represents CR⁶ or N, and R⁴, R⁵, R⁶, R⁷ and R⁸ are as defined herein, and
in its 2-position, a substituent R²,
wherein:
R² represents a group selected from hydrogen, C₁-C₃-alkyl, or C₃-C₄-cycloalkyl;

or a stereoisomer, a tautomer, an N-oxide, a hydrate, a solvate, or a salt thereof, or a mixture of same, as described and defined herein, and as hereinafter referred to as "compounds of the present invention", or their pharmacological activity.

It has now been found, and this constitutes the basis of the present invention, that said compounds of the present invention have surprising and advantageous properties.

In particular, said compounds of the present invention have surprisingly been found to effectively inhibit TNKS1 and/or TNKS2 and may therefore be used for the treatment or prophylaxis of diseases of uncontrolled cell growth, proliferation and/or survival, inappropriate cellular immune responses, or inappropriate cellular inflammatory responses or diseases which are accompanied with uncontrolled cell growth, proliferation and/or survival, inappropriate cellular immune responses, or inappropriate cellular inflammatory responses mediated by TNKS1 and/or TNKS2 and/or mediated by the Wnt pathway, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof. Compounds of the present invention may additionally show improved selectivity for TNKS1 and/or TNKS2 (e.g. over other PARP (poly(ADP-ribose)-polymerase) enzymes), for the treatment of TNKS1 and/or TNKS2 driven diseases, by reaching sufficient efficacious dose without inducing toxicity driven by, for example, other PARPs inhibition.

DESCRIPTION OF THE INVENTION

In accordance with a first aspect, the present invention covers compounds of general formula (I):

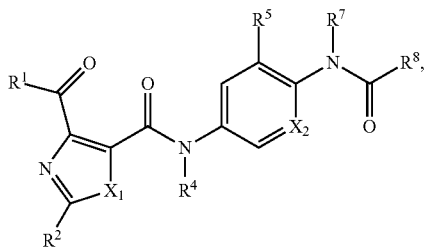

in which:
X¹ represents NR³ or O,
X² represents a CR⁶ or N,
R¹ represents a group selected from:
  —OR⁹, and —N(R¹⁰)R¹¹,
R² represents a group selected from:
  hydrogen, C₁-C₃-alkyl, and C₃-C₄-cycloalkyl,
R³ represents a hydrogen atom,
R⁴ represents a hydrogen atom,
R⁵ represents a group selected from:
  hydrogen, C₁-C₃-alkyl, C₁-C₃-alkoxy, C₁-C₃-haloalkyl, C₁-C₃-haloalkoxy, and halogen,
R⁶ represents a group selected from:
  hydrogen, and halogen,
R⁷ represents a hydrogen atom,
R⁸ represents a group selected from:
  aryl, and heteroaryl,
    wherein aryl and heteroaryl groups are optionally substituted with one, two or three substituents, which are independently of each other selected from:
    C₁-C₆-alkyl, C₁-C₃-alkoxy, C₃-C₆-cycloalkyl, C₃-C₆-cycloalkoxy, C₁-C₃-haloalkyl, C₁-C₃-haloalkoxy, halogen, cyano, nitro, hydroxy, (C₁-C₆-alkyl)-S—, (C₁-C₆-alkyl)-S(═O)—, (C₁-C₆-alkyl)-S(═O)₂—, —S(═O)(═NR¹⁵)R¹⁶, —N(R¹⁰)R¹¹, R¹⁰(R¹¹)N—(C₁-C₆-alkyl)-, R¹⁰(R¹¹)N—(C₂-C₆-alkoxy)-, phenyl, phenoxy, —N(R¹²)C(═O)R¹³, —C(═O)OH, —C(═O)OR⁹, and —C(═O)N(R¹²)₂,
    whereby two substituents of said aryl group, if they are in ortho-position to one another, can be linked to one another in such a way that they jointly form methanediylbisoxy, ethane-1,2-diylbisoxy, propane-1,3-diyl, or butane-1,4-diyl,
R⁹ represents a group selected from:
  C₁-C₆-alkyl, C₃-C₆-cycloalkyl, C₂-C₆-hydroxyalkyl-, and (C₁-C₃-alkoxy)-(C₁-C₆-alkyl)-,
R¹⁰ and R¹¹ are independently of each other selected from:
  hydrogen, C₁-C₆-alkyl, C₃-C₆-cycloalkyl, (C₃-C₆-cycloalkyl)-C₁-C₆-alkyl)-, C₂-C₆-hydroxyalkyl, (C₁-C₃-alkoxy)-(C₂-C₆-alkyl)-, C₁-C₆-haloalkyl, H₂N—(C₂-C₆-alkyl)-, (C₁-C₃-alkyl)N(H)(C₂-C₆-alkyl)-, (C₁-C₃-alkyl)₂N(C₂-C₆-alkyl)-, HOC(═O)—(C₁-C₆-alkyl)-, R⁹OC(═O)—(C₁-C₆-alkyl)-, 4-6 membered heterocycloalkyl, (4-6 membered heterocycloalkyl)-(C₂-C₆-alkyl)-, aryl, heteroaryl, aryl-(C₁-C₆-alkyl)-, and heteroaryl-(C₁-C₆-alkyl),
  wherein 4-6-membered heterocycloalkyl groups are optionally substituted with one or two substituents, which are independently of each other selected from:

C$_1$-C$_3$-alkyl, C$_1$-C$_3$-haloalkyl, C$_1$-C$_3$-alkoxy, C$_1$-C$_3$-haloalkoxy, C$_3$-C$_4$-cycloalkyl, C$_3$-C$_4$-cycloalkoxy, amino, hydroxy, a halogen atom, and cyano,
and,
wherein aryl and heteroaryl groups are optionally substituted with one or two substituents, which are independently of each other selected from:
C$_1$-C$_3$-alkyl, C$_3$-C$_6$-cycloalkyl, C$_1$-C$_3$-alkoxy, C$_3$-C$_6$-cycloalkoxy, C$_1$-C$_3$-haloalkyl, C$_1$-C$_3$-haloalkoxy, halogen, cyano, —C(=O)OH, —C(=O)OR$^9$, and —C(=O)N(R$^{12}$)$_2$, or,
R$^{10}$ and R$^{11}$ together with the nitrogen atom to which they are attached form a 4-6-membered heterocycloalkyl group, in which one carbon atom is optionally replaced by a further heteroatom-containing group selected from NR$^{14}$, O, S, S(=O) and S(=O)$_2$, in which heterocycloalkyl group one additional ring atom is optionally replaced by C(=O),
said 4-6-membered heterocycloalkyl group being optionally substituted with one or two substituents, which are independently of each other selected from:
C$_1$-C$_3$-alkyl, C$_1$-C$_3$-haloalkyl, C$_1$-C$_3$-alkoxy, C$_1$-C$_3$-haloalkoxy, C$_3$-C$_4$-cycloalkyl, C$_3$-C$_4$-cycloalkoxy, amino, hydroxy, a halogen atom, and cyano,
or,
R$^{10}$ and R$^{11}$ together with the nitrogen atom to which they are attached form a group selected from:

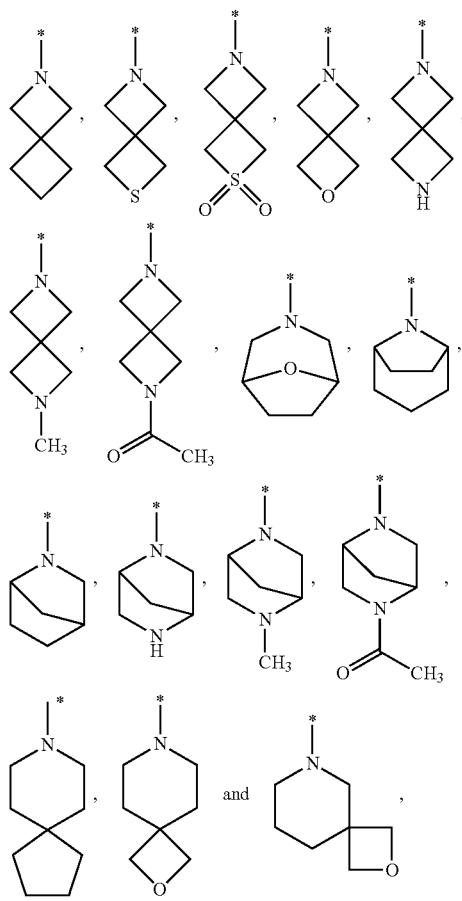

wherein * indicates the point of attachment of said group with the rest of the molecule, R$^{12}$ represents a group selected from:
hydrogen, and C$_1$-C$_3$-alkyl,
R$^{13}$ represents a group selected from:
hydrogen, C$_1$-C$_6$-alkyl, C$_1$-C$_6$-hydroxyalkyl, C$_3$-C$_6$-cycloalkyl, C$_1$-C$_6$-haloalkyl, (C$_1$-C$_3$-alkoxy)-(C$_1$-C$_6$-alkyl)-, aryl, and heteroaryl,
wherein aryl and heteroaryl groups are optionally substituted with one or two substituents, which are independently of each other selected from:
C$_1$-C$_3$-alkyl, C$_3$-C$_6$-cycloalkyl, C$_1$-C$_3$-alkoxy, C$_3$-C$_6$-cycloalkoxy, C$_1$-C$_3$-haloalkyl, C$_1$-C$_3$-haloalkoxy, halogen, cyano, and hydroxy,
R$^{14}$ represents a group selected from:
hydrogen, C$_1$-C$_3$-alkyl, C$_1$-C$_3$-haloalkyl, and C$_3$-C$_4$-cycloalkyl,
R$^{15}$ represents a group selected from:
hydrogen, cyano, (C$_1$-C$_3$-alkyl)-C(=O)—, and (C$_1$-C$_3$-haloalkyl)-C(=O)—,
R$^{16}$ represents a group selected from:
C$_1$-C$_4$-alkyl, and C$_3$-C$_4$-cycloalkyl,
or a stereoisomer, a tautomer, an N-oxide, a hydrate, a solvate, or a salt thereof, or a mixture of same.

Definitions

Constituents which are optionally substituted as stated herein, may be substituted, unless otherwise noted, one or more times, independently from one another at any possible position. When any variable occurs more than one time in any constituent, each definition is independent.

When any variable occurs more than one time in any compound of general formula (I) as described herein, each definition is independent. For example, when R$^9$, R$^{10}$, R$^{11}$, R$^{12}$ and/or R$^{13}$ occur more than one time in any compound of formula (I) each definition of R$^9$, R$^{10}$, R$^{11}$, R$^{12}$ and R$^{13}$ is independent.

A hyphen at the beginning or at the end of the constituent marks the point of attachment to the rest of the molecule. Should a ring be substituted the substituent could be at any suitable position of the ring, also on a ring nitrogen atom if suitable.

The terms as mentioned in the present text have preferably the following meanings:

The term "comprising" when used in the specification includes "consisting of".

If it is referred to "as mentioned above" or "mentioned above" within the description it is referred to any of the disclosures made within the specification in any of the preceding pages.

If it is referred to "as mentioned herein", "described herein", "provided herein" or "stated herein" within the description it is referred to any of the disclosures made within the specification in any of the preceding or subsequent pages.

The term "halogen", "halogen atom", "halo-" or "Hal-" is to be understood as meaning a fluorine, chlorine, bromine or iodine atom.

The term "C$_1$-C$_6$-alkyl" is to be understood as preferably meaning a linear or branched, saturated, monovalent hydrocarbon group having 1, 2, 3, 4, 5, or 6 carbon atoms, e.g. a methyl, ethyl, propyl, butyl, pentyl, hexyl, iso-propyl, iso-butyl, sec-butyl, tert-butyl, iso-pentyl, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl group, or an isomer thereof. Particularly, said group has 1, 2, 3 or 4 carbon atoms ("$C_1$-$C_4$-alkyl"), e.g. a methyl, ethyl, propyl, butyl, iso-propyl, iso-butyl, sec-butyl, tert-butyl group, more particularly 1, 2 or 3 carbon atoms ("$C_1$-$C_3$-alkyl"), e.g. a methyl, ethyl, n-propyl- or iso-propyl group, even more particularly 1 or 2 carbon atoms ("$C_1$-$C_2$-alkyl"), e.g. a methyl, ethyl group.

The term "$C_1$-$C_6$-hydroxyalkyl" is to be understood as preferably meaning a linear or branched, saturated, monovalent hydrocarbon group in which the term "$C_1$-$C_6$-alkyl" is defined supra, and in which one or more hydrogen atoms is replaced by a hydroxy group, e.g. a hydroxymethyl, 1-hydroxyethyl, 2-hydroxyethyl, 1,2-dihydroxyethyl, 3-hydroxypropyl, 2-hydroxypropyl, 2,3-dihydroxypropyl, 1,3-dihydroxypropan-2-yl, 3-hydroxy-2-methyl-propyl, 2-hydroxy-2-methyl-propyl, 1-hydroxy-2-methyl-propyl group.

The term "$C_1$-$C_6$-haloalkyl" is to be understood as preferably meaning a linear or branched, saturated, monovalent hydrocarbon group in which the term "$C_1$-$C_6$-alkyl" is defined supra, and in which one or more hydrogen atoms is replaced by a halogen atom, in identically or differently, i.e. one halogen atom being independent from another. Particularly, said halogen atom is F. Said $C_1$-$C_6$-haloalkyl group is, for example, —$CF_3$, —$CHF_2$, —$CH_2F$, —$CF_2CF_3$, —$CH_2CH_2F$, —$CH_2CHF_2$, —$CH_2CF_3$, or —$CH_2CH_2CF_3$.

The term "$C_1$-$C_6$-alkoxy" is to be understood as preferably meaning a linear or branched, saturated, monovalent, hydrocarbon group of formula —O-alkyl having 1, 2, 3, 4, 5, or 6 carbon atoms, in which the term "alkyl" is defined supra, e.g. a methoxy, ethoxy, n-propoxy, iso-propoxy, n-butoxy, iso-butoxy, tert-butoxy, sec-butoxy, pentoxy, iso-pentoxy, or n-hexoxy group, or an isomer thereof.

The term "$C_1$-$C_6$-haloalkoxy" is to be understood as preferably meaning a linear or branched, saturated, monovalent $C_1$-$C_6$-alkoxy group, as defined supra, in which one or more of the hydrogen atoms is replaced, in identically or differently, by a halogen atom. Particularly, said halogen atom is F. Said $C_1$-$C_6$-haloalkoxy group is, for example, —$OCF_3$, —$OCHF_2$, —$OCH_2F$, —$OCF_2CF_3$, or —$OCH_2CF_3$.

The term "$C_3$-$C_6$-cycloalkyl" is to be understood as meaning a saturated, monovalent, monocyclic hydrocarbon ring which contains 3, 4, 5 or 6 carbon atoms ("$C_3$-$C_6$-cycloalkyl"). Said $C_3$-$C_6$-cycloalkyl group is for example, a monocyclic hydrocarbon ring, e.g. a cyclopropyl, cyclobutyl, cyclopentyl or cyclohexyl ring.

The term "$C_3$-$C_6$-cycloalkoxy" is to be understood as preferably meaning a saturated, monovalent, hydrocarbon ring which contains 3, 4, 5 or 6 carbon atoms of formula —O-cycloalkyl, in which the term "cycloalkyl" is defined supra, e.g. a cyclopropyloxy, cyclobutyloxy, cyclopentyloxy or cyclohexyloxy.

The term "4- to 6-membered heterocycloalkyl", is to be understood as meaning a saturated, monovalent, monocyclic hydrocarbon ring which contains 3, 4 or 5 carbon atoms and a heteroatom-containing group selected from N, $NR^{14}$, O, S, S(=O) and S(=O)$_2$, wherein one carbon atom is optionally replaced by a further heteroatom-containing group selected from $NR^{14}$, O, S, S(=O) and S(=O)$_2$, in which $R^{14}$ represents a hydrogen atom, or a $C_1$-$C_3$-alkyl-, $C_1$-$C_3$-haloalkyl-, or a $C_3$-$C_4$-cycloalkyl-group, and in which heterocycloalkyl group one additional ring atom is optionally replaced by C(=O); it being possible for said heterocycloalkyl group to be attached to the rest of the molecule via any one of the carbon atoms or, if present, the nitrogen atom. A heteroatom-containing group as defined herein is to be understood as meaning a group containing a heteroatom, such as $NR^{14}$, S(=O) and S(=O)$_2$, or a single heteroatom such as N, O and S.

Particularly, without being limited thereto, said heterocycloalkyl can be a 4-membered ring, such as an azetidinyl, oxetanyl, or a 5-membered ring, such as tetrahydrofuranyl, dioxolinyl, pyrrolidinyl, imidazolidinyl, pyrazolidinyl, or a 6-membered ring, such as tetrahydropyranyl, piperidinyl, morpholinyl, dithianyl, thiomorpholinyl, piperazinyl, or N-methylpiperazinyl. Optionally, said heterocycloalkyl can be benzo fused. Particularly, without being limited thereto, 4- to 6-membered heterocycloalkyl can be selected from piperazinyl, tetrahydro-2H-pyranyl, tetrahydrofuranyl, pyrrolidinyl, piperidinyl, morpholinyl, azetidinyl, 2-oxoimidazolidinyl, 2-oxopyrrolidinyl and 1,1-dioxidothiomorpholinyl. More particularly, without being limited thereto, 4- to 6-membered heterocycloalkyl can be selected from piperazin-1-yl, tetrahydro-2H-pyran-4-yl, tetrahydrofuran-3-yl, pyrrolidin-1-yl, pyrrolidin-2-yl, pyrrolidin-3-yl, piperidin-4-yl, piperidin-1-yl, piperidin-2-yl, piperidin-3-yl, morpholin-4-yl, azetidin-1-yl, tetrahydrofuran-2-yl, 2-oxoimidazolidin-1-yl, 2-oxopyrrolidin-1-yl and 1,1-dioxidothiomorpholin-4-yl.

The term "aryl" is to be understood as preferably meaning a monovalent, aromatic or partially aromatic, mono- or bicyclic hydrocarbon ring having 6, 7, 8, 9 or 10 carbon atoms (a "$C_6$-$C_{10}$-aryl" group), particularly a ring having 6 carbon atoms (a "$C_6$-aryl" group), e.g. a phenyl group; or a ring having 9 carbon atoms (a "$C_9$-aryl" group), e.g. an indanyl or indenyl group, or a ring having 10 carbon atoms (a "$C_{10}$-aryl" group), e.g. a tetralinyl, dihydronaphthyl, or naphthyl group.

The term "heteroaryl" is understood as preferably meaning a monovalent, monocyclic aromatic ring system having 5 or 6 ring atoms (a "5- to 6-membered heteroaryl" group), which contains at least one heteroatom which may be identical or different, said heteroatom being such as oxygen, nitrogen or sulfur. Particularly, heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl etc., or pyridyl, pyridazinyl, pyrimidinyl, pyrazinyl, triazinyl, etc. More particularly, without being limited thereto, heteroaryl can be selected from pyrazolyl, thienyl, pyridyl, furanyl, thiazolyl, oxazolyl, and pyrazinyl.

In general, and unless otherwise mentioned, the heteroarylic or heteroarylenic radicals include all the possible isomeric forms thereof, e.g. the positional isomers thereof. Thus, for some illustrative non-restricting example, the term pyridinyl or pyridinylene includes pyridin-2-yl, pyridin-2-ylene, pyridin-3-yl, pyridin-3-ylene, pyridin-4-yl and pyridin-4-ylene; or the term thienyl or thienylene includes thien-2-yl, thien-2-ylene, thien-3-yl and thien-3-ylene.

In general, and unless otherwise mentioned, the heteroarylic radicals include all the possible isomeric forms thereof, e.g. the positional isomers thereof. Thus, for some illustrative non-restricting example, the term pyridinyl includes pyridin-2-yl, pyridin-3-yl and pyridin-4-yl.

In general, and unless otherwise mentioned, aromatic and non-aromatic (hetero)cyclic groups, may optionally be substituted as defined herein. The substituents may be present both when said aromatic and non-aromatic (hetero)cyclic groups exist as a (unitary) constituent, such as, for example, $C_3$-$C_6$-cycloalkyl, 4-6-membered heterocycloalkyl, aryl and heteroaryl groups, or as part of a constituent composed of more than one part, such as, for example, ($C_3$-$C_6$-cycloalkyl)-$C_1$-$C_6$-alkyl-, (4-6 membered heterocycloalkyl)-($C_2$-$C_6$-alkyl)-, aryl-($C_1$-$C_6$-alkyl)-, and heteroaryl-($C_1$-$C_6$- alkyl)-, for example. The present invention includes all suitably substituted aromatic and non-aromatic (hetero)cyclic groups both as a (unitary) constituent, or as part of a constituent composed of more than one part. In this context "suitably" is to be understood as meaning chemically possible to be made by methods within the knowledge of a skilled person.

The term "$C_1$-$C_6$", as used throughout this text, e.g. in the context of the definition of "$C_1$-$C_6$-alkyl", "$C_1$-$C_6$-haloalkyl", "$C_1$-$C_6$-hydroxyalkyl", "$C_1$-$C_6$-alkoxy", or "$C_1$-$C_6$-haloalkoxy" is to be understood as meaning an alkyl group having a finite number of carbon atoms of 1 to 6, i.e. 1, 2, 3, 4, 5, or 6 carbon atoms. It is to be understood further that said term "$C_1$-$C_6$" is to be interpreted as any sub-range comprised therein, e.g. $C_1$-$C_6$, $C_2$-$C_5$, $C_3$-$C_4$, $C_1$-$C_2$, $C_1$-$C_3$, $C_1$-$C_4$, $C_1$-$C_5$; particularly $C_1$-$C_2$, $C_1$-$C_3$, $C_1$-$C_4$, $C_1$-$C_5$, $C_1$-$C_6$; more particularly $C_1$-$C_4$; in the case of "$C_1$-$C_6$-haloalkyl" or "$C_1$-$C_6$-haloalkoxy" even more particularly $C_1$-$C_2$.

Similarly, as used herein, the term "$C_2$-$C_6$", as used throughout this text, e.g. in the context of the definitions of "$C_2$-$C_6$-alkyl", and "$C_2$-$C_6$-hydroxyalkyl" is to be understood as meaning an alkyl group or a hydroxyalkyl group having a finite number of carbon atoms of 2 to 6, i.e. 2, 3, 4, 5, or 6 carbon atoms. It is to be understood further that said term "$C_2$-$C_6$" is to be interpreted as any sub-range comprised therein, e.g. $C_2$-$C_6$, $C_3$-$C_5$, $C_3$-$C_4$, $C_2$-$C_3$, $C_2$-$C_4$, $C_2$-$C_5$; particularly $C_2$-$C_3$.

Further, as used herein, the term "$C_3$-$C_6$", as used throughout this text, e.g. in the context of the definition of "$C_3$-$C_6$-cycloalkyl", is to be understood as meaning a cycloalkyl group having a finite number of carbon atoms of 3 to 6, i.e. 3, 4, 5 or 6 carbon atoms. It is to be understood further that said term "$C_3$-$C_6$" is to be interpreted as any sub-range comprised therein, e.g. $C_3$-$C_6$, $C_4$-$C_5$, $C_3$-$C_5$, $C_3$-$C_4$, $C_4$-$C_6$, $C_5$-$C_6$; particularly $C_3$-$C_6$.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

The term "optionally substituted" means optional substitution with the specified groups, radicals or moieties.

Ring system substituent means a substituent attached to an aromatic or nonaromatic ring system which, for example, replaces an available hydrogen on the ring system.

As used herein, the term "one or more", e.g. in the definition of the substituents of the compounds of the general formulae of the present invention, is understood as meaning "one, two, three, four or five, particularly one, two, three or four, more particularly one, two or three, even more particularly one or two".

The invention also includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulphur, fluorine, chlorine, bromine and iodine, such as $^2H$ (deuterium), $^3H$ (tritium), $^{11}C$, $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{125}I$, $^{129}I$ and $^{131}I$, respectively. Certain isotopic variations of a compound of the invention, for example, those in which one or more radioactive isotopes such as $^3H$ or $^{14}C$ are incorporated, are useful in drug and/or substrate tissue distribution studies. Tritiated and carbon-14, i.e., $^{14}C$, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence is preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

Where the plural form of the word compounds, salts, polymorphs, hydrates, solvates and the like, is used herein, this is taken to mean also a single compound, salt, polymorph, isomer, hydrate, solvate or the like.

By "stable compound' or "stable structure" is meant a compound that is sufficiently robust to survive isolation to a useful degree of purity from a reaction mixture, and formulation into an efficacious therapeutic agent.

The compounds of this invention optionally contain one or more asymmetric centre, depending upon the location and nature of the various substituents desired. Asymmetric carbon atoms is present in the (R) or (S) configuration, resulting in racemic mixtures in the case of a single asymmetric centre, and diastereomeric mixtures in the case of multiple asymmetric centres. In certain instances, asymmetry may also be present due to restricted rotation about a given bond, for example, the central bond adjoining two substituted aromatic rings of the specified compounds.

The compounds of the present invention optionally contain sulphur atoms which are asymmetric, such as an asymmetric sulfoxide, of structure:

for example,
in which * indicates atoms to which the rest of the molecule can be bound.

Substituents on a ring may also be present in either cis or trans form. It is intended that all such configurations (including enantiomers and diastereomers), are included within the scope of the present invention.

Preferred compounds are those which produce the more desirable biological activity. Separated, pure or partially purified isomers and stereoisomers or racemic or diastereomeric mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., chiral HPLC columns), with or without conventional derivatisation, optimally chosen to maximise the separation of the enantiomers. Suitable chiral HPLC columns are manufactured by Daicel, e.g., Chiracel OD and Chiracel OJ among many others, all routinely selectable. Enzymatic separations, with or without derivatisation, are also useful. The optically active compounds of this invention can likewise be obtained by chiral syntheses utilizing optically active starting materials.

In order to limit different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. R- or S-isomers, or E- or Z-isomers, in any ratio. Isolation of a single stereoisomer, e.g. a single enantiomer or a single diastereomer, of a compound of the present invention is achieved by any suitable state of the art method, such as chromatography, especially chiral chromatography, for example.

Further, the compounds of the present invention may exist as tautomers. For example, any compound of the present invention which contains a pyrazole moiety as a heteroaryl group for example can exist as a 1H tautomer, or a 2H tautomer, or even a mixture in any amount of the two tautomers, namely:

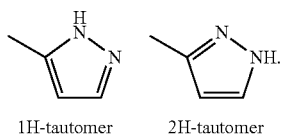

1H-tautomer    2H-tautomer

Particularly, when $X^1$ represents $NR^3$, wherein $R^3$ represents a hydrogen atom, the present invention can exist as one of the below tautomers, or even in a mixture in any amount of the two tautomers, namely:

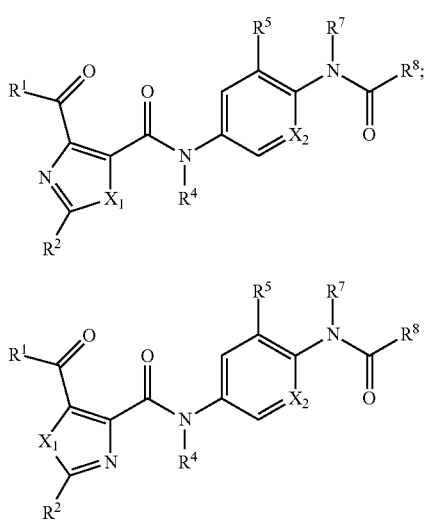

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also relates to useful forms of the compounds as disclosed herein, such as metabolites, hydrates, solvates, prodrugs, salts, in particular pharmaceutically acceptable salts, and co-precipitates.

The compounds of the present invention can exist as a hydrate, or as a solvate, wherein the compounds of the present invention contain polar solvents, in particular water, methanol or ethanol for example as structural element of the crystal lattice of the compounds. The amount of polar solvents, in particular water, may exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, the compounds of the present invention can exist in free form, e.g. as a free base, or as a free acid, or as a zwitterion, or can exist in the form of a salt. Said salt may be any salt, either an organic or inorganic addition salt, particularly any pharmaceutically acceptable organic or inorganic addition salt, customarily used in pharmacy.

The term "pharmaceutically acceptable salt" refers to a relatively non-toxic, inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, such as hydrochloric, hydrobromic, hydroiodic, sulfuric, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethanesulfonic, benzenesulfonic, para-toluenesulfonic, methansulfonic, 2-naphthalenesulfonic, naphthalenedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium or magnesium salt, an ammonium salt or a salt with an organic base which affords a physiologically acceptable cation, for example a salt with N-methyl-glucamine, dimethyl-glucamine, ethyl-glucamine, lysine, dicyclohexylamine, 1,6-hexadiamine, ethanolamine, glucosamine, sarcosine, serinol, tris-hydroxy-methyl-aminomethane, aminopropandiol, sovak-base, 1-amino-2,3,4-butantriol.

Additionally, basic nitrogen containing groups may be quaternised with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and stearyl chlorides, bromides and iodides, aralkyl halides like benzyl and phenethyl bromides and others.

Those skilled in the art will further recognise that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

The present invention includes all possible salts of the compounds of the present invention as single salts, or as any mixture of said salts, in any ratio.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae such as "hydrochloride", "trifluoroacetate", "sodium salt", or "x HO", "x CF$_3$COOH", "x Na$^+$", for example, are to be understood as not a stoichiometric specification, but solely as a salt form.

This applies analogously to cases in which synthesis intermediates or example compounds or salts thereof have been obtained, by the preparation and/or purification processes described, as solvates, such as hydrates with (if defined) unknown stoichiometric composition.

As used herein, the term "in vivo hydrolysable ester" is understood as meaning an in vivo hydrolysable ester of a compound of the present invention containing a carboxy or hydroxy group, for example, a pharmaceutically acceptable ester which is hydrolysed in the human or animal body to produce the parent acid or alcohol. Suitable pharmaceutically acceptable esters for carboxy include for example alkyl, cycloalkyl and optionally substituted phenylalkyl, in particular benzyl esters, $C_1$-$C_6$ alkoxymethyl esters, e.g. methoxymethyl, $C_1$-$C_6$ alkanoyloxymethyl esters, e.g. pivaloyloxymethyl, phthalidyl esters, $C_3$-$C_8$ cycloalkoxy-carbonyloxy-$C_1$-$C_6$ alkyl esters, e.g. 1-cyclohexylcarbonyloxyethyl; 1,3-dioxolen-2-onylmethyl esters, e.g. 5-methyl-1,3-dioxolen-2-onylmethyl; and $C_1$-$C_6$-alkoxycarbonyloxyethyl esters, e.g. 1-methoxycarbonyloxyethyl, and may be formed at any carboxy group in the compounds of this invention.

An in vivo hydrolysable ester of a compound of the present invention containing a hydroxy group includes inorganic esters such as phosphate esters and [alpha]-acyloxyalkyl ethers and related compounds which as a result of the in vivo hydrolysis of the ester breakdown to give the parent hydroxy group. Examples of [alpha]-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. The present invention covers all such esters.

Furthermore, the present invention includes all possible crystalline forms, or polymorphs, of the compounds of the present invention, either as single polymorph, or as a mixture of more than one polymorph, in any ratio.

In accordance with a second embodiment of the first aspect, the present invention covers compounds of general formula (I), supra, in which:
$X^1$ represents $NR^3$ or O,
$X^2$ represents $CR^6$ or N,
$R^1$ represents a group selected from:
—$OR^9$, and —$N(R^{10})R^{11}$,
$R^2$ represents a group selected from:
hydrogen, and $C_1$-$C_3$-alkyl,
$R^3$ represents a hydrogen atom,
$R^4$ represents a hydrogen atom,
$R^5$ represents a group selected from:
hydrogen, $C_1$-$C_3$-alkyl, $C_1$-$C_3$-alkoxy and $C_1$-$C_3$-haloalkoxy,
$R^6$ represents a group selected from:
hydrogen, and halogen,
$R^7$ represents a hydrogen atom,
$R^8$ represents a group selected from:
aryl, and heteroaryl,
wherein aryl and heteroaryl groups are optionally substituted with one, two or three substituents, which are independently of each other selected from:
$C_1$-$C_6$-alkyl, $C_1$-$C_3$-alkoxy, $C_3$-$C_6$-cycloalkyl, $C_3$-$C_6$-cycloalkoxy, $C_1$-$C_3$-haloalkyl, $C_1$-$C_3$-haloalkoxy, halogen, cyano, nitro, hydroxy, ($C_1$-$C_6$-alkyl)-S—, ($C_1$-$C_6$-alkyl)-S(=O)—, ($C_1$-$C_6$-alkyl)-S(=O)$_2$—, —S(=O)(=NR$^{15}$)R$^{16}$, —N(R$^{10}$)R$^{11}$, R$^{10}$(R$^{11}$)N—($C_1$-$C_6$-alkyl)-, R$^{10}$(R$^{11}$)N—($C_2$-$C_6$-alkoxy)-, phenyl, phenoxy, —N(R$^{12}$)C(=O)R$^{13}$, —C(=O)OH, —C(=O)OR$^9$, and —C(=O)N(R$^{12}$)$_2$,
whereby two substituents of said aryl group, if they are in ortho-position to one another, can be linked to one another in such a way that they jointly form methanediylbisoxy, ethane-1,2-diylbisoxy, propane-1,3-diyl, or butane-1,4-diyl,
$R^9$ represents a group selected from:
$C_1$-$C_6$-alkyl, $C_3$-$C_6$-cycloalkyl, $C_2$-$C_6$-hydroxyalkyl-, and ($C_1$-$C_3$-alkoxy)-($C_1$-$C_6$-alkyl)-,
$R^{10}$ and $R^{11}$ are independently of each other selected from:
hydrogen, $C_1$-$C_6$-alkyl, $C_3$-$C_6$-cycloalkyl, ($C_3$-$C_6$-cycloalkyl)-($C_1$-$C_6$-alkyl)-, $C_2$-$C_6$-hydroxyalkyl, ($C_1$-$C_3$-alkoxy)-($C_2$-$C_6$-alkyl)-, $C_1$-$C_6$-haloalkyl, H$_2$N—($C_2$-$C_6$-alkyl)-, ($C_1$-$C_3$-alkyl)N(H)($C_2$-$C_6$-alkyl)-, ($C_1$-$C_3$-alkyl)$_2$N($C_2$-$C_6$-alkyl)-, HOC(=O)—($C_1$-$C_6$-alkyl)-, R$^9$OC(=O)—($C_1$-$C_6$-alkyl)-, 4-6 membered heterocycloalkyl, (4-6 membered heterocycloalkyl)-($C_2$-$C_6$-alkyl)-, aryl, heteroaryl, aryl-($C_1$-$C_6$-alkyl)-, and heteroaryl-($C_1$-$C_6$-alkyl),
wherein 4-6-membered heterocycloalkyl groups are optionally substituted with one or two substituents, which are independently of each other selected from:
$C_1$-$C_3$-alkyl, $C_1$-$C_3$-haloalkyl, $C_1$-$C_3$-alkoxy, $C_1$-$C_3$-haloalkoxy, $C_3$-$C_4$-cycloalkyl, $C_3$-$C_4$-cycloalkoxy, amino, hydroxy, a halogen atom, and cyano,
and,
wherein aryl and heteroaryl groups are optionally substituted with one or two substituents, which are independently of each other selected from:
$C_1$-$C_3$-alkyl, $C_3$-$C_6$-cycloalkyl, $C_1$-$C_3$-alkoxy, $C_3$-$C_6$-cycloalkoxy, $C_1$-$C_3$-haloalkyl, $C_1$-$C_3$-haloalkoxy, halogen, cyano, —C(=O)OH, —C(=O)OR$^9$, and —C(=O)N(R$^{12}$)$_2$,
or,
$R^{10}$ and $R^{11}$ together with the nitrogen atom to which they are attached form a 4-6-membered heterocycloalkyl group, in which one carbon atom is optionally replaced by a further heteroatom-containing group selected from $NR^{14}$, O, S, S(=O) and S(=O)$_2$, in which heterocycloalkyl group one additional ring atom is optionally replaced by C(=O), said 4-6-membered heterocycloalkyl group being optionally substituted with one or two substituents, which are independently of each other selected from:

$C_1$-$C_3$-alkyl, $C_1$-$C_3$-haloalkyl, $C_1$-$C_3$-alkoxy, $C_1$-$C_3$-haloalkoxy, $C_3$-$C_4$-cycloalkyl, $C_3$-$C_4$-cycloalkoxy, amino, hydroxy, a halogen atom, and cyano, or, $R^{10}$ and $R^{11}$ together with the nitrogen atom to which they are attached form a group selected from:

wherein * indicates the point of attachment of said group with the rest of the molecule, $R^{12}$ represents a group selected from:
hydrogen, and $C_1$-$C_3$-alkyl, $R^{13}$ represents a group selected from:
hydrogen, $C_1$-$C_6$-alkyl, $C_1$-$C_6$-hydroxyalkyl, $C_3$-$C_6$-cycloalkyl, $C_1$-$C_6$-haloalkyl, ($C_1$-$C_3$-alkoxy)-($C_1$-$C_6$-alkyl)-, aryl, and heteroaryl,
wherein aryl and heteroaryl groups are optionally substituted with one or two substituents, which are independently of each other selected from:
$C_1$-$C_3$-alkyl, $C_3$-$C_6$-cycloalkyl, $C_1$-$C_3$-alkoxy, $C_3$-$C_6$-cycloalkoxy, $C_1$-$C_3$-haloalkyl, $C_1$-$C_3$-haloalkoxy, halogen, cyano, and hydroxy, $R^{14}$ represents a group selected from:
hydrogen, $C_1$-$C_3$-alkyl, $C_1$-$C_3$-haloalkyl, and $C_3$-$C_4$-cycloalkyl, $R^{15}$ represents a group selected from:
hydrogen, cyano, ($C_1$-$C_3$-alkyl)-C(=O)—, and ($C_1$-$C_3$-haloalkyl)-C(=O)—, $R^{16}$ represents a group selected from:
$C_1$-$C_4$-alkyl, and $C_3$-$C_4$-cycloalkyl, or a stereoisomer, a tautomer, an N-oxide, a hydrate, a solvate, or a salt thereof, or a mixture of same.

In accordance with a third embodiment of the first aspect, the present invention covers compounds of general formula (I), supra, in which:

$X^1$ represents $NR^3$ or O, $X^2$ represents $CR^6$ or N, $R^1$ represents a group selected from:
—$OR^9$, and —$N(R^{10})R^{11}$, $R^2$ represents a group selected from:
hydrogen, and $C_1$-$C_3$-alkyl, $R^3$ represents a hydrogen atom, $R^4$ represents a hydrogen atom, $R^5$ represents a group selected from:
hydrogen, and $C_1$-$C_3$-alkyl, $R^6$ represents a group selected from:
hydrogen, and halogen, $R^7$ represents a hydrogen atom, $R^8$ represents a group selected from:
aryl, and heteroaryl, wherein aryl and heteroaryl groups are optionally substituted with one, two or three substituents, which are independently of each other selected from:
$C_1$-$C_6$-alkyl, $C_1$-$C_3$-alkoxy, $C_3$-$C_6$-cycloalkyl, $C_3$-$C_6$-cycloalkoxy, $C_1$-$C_3$-haloalkyl, $C_1$-$C_3$-haloalkoxy, halogen, cyano, nitro, hydroxy, ($C_1$-$C_6$-alkyl)-S—, ($C_1$-$C_6$-alkyl)-S(=O)—, ($C_1$-$C_6$-alkyl)-S(=O)$_2$—, —S(=O)(=$NR^{15}$)$R^{16}$, —$N(R^{10})R^{11}$, $R^{10}(R^{11})$N—($C_1$-$C_6$-alkyl)-, $R^{10}(R^{11})$N—($C_2$-$C_6$-alkoxy)-, phenyl, phenoxy, —$N(R^{12})$C(=O)$R^{13}$, —C(=O)OH, —C(=O)$OR^9$, and —C(=O)$N(R^{12})_2$, whereby two substituents of said aryl group, if they are in ortho-position to one another, can be linked to one another in such a way that they jointly form methanediylbisoxy, ethane-1,2-diylbisoxy, propane-1,3-diyl, or butane-1,4-diyl, $R^9$ represents a group selected from:
$C_1$-$C_6$-alkyl, $C_3$-$C_6$-cycloalkyl, $C_2$-$C_6$-hydroxyalkyl-, and ($C_1$-$C_3$-alkoxy)-($C_1$-$C_6$-alkyl)-, $R^{10}$ and $R^{11}$ are independently of each other selected from:
hydrogen, $C_1$-$C_6$-alkyl, $C_3$-$C_6$-cycloalkyl, ($C_3$-$C_6$-cycloalkyl)-($C_1$-$C_6$-alkyl)-, $C_2$-$C_6$-hydroxyalkyl, ($C_1$-$C_3$-alkoxy)-($C_2$-$C_6$-alkyl)-, $C_1$-$C_6$-haloalkyl, $H_2$N—($C_2$-$C_6$-alkyl)-, ($C_1$-$C_3$-alkyl)N(H)($C_2$-$C_6$-alkyl)-, ($C_1$-$C_3$-alkyl)$_2$N($C_2$-$C_6$-alkyl)-, HOC(=O)—($C_1$-$C_6$-alkyl)-, $R^9$OC(=O)—($C_1$-$C_6$-alkyl)-, 4-6 membered heterocycloalkyl, (4-6 membered heterocycloalkyl)-($C_2$-$C_6$-alkyl)-, aryl, heteroaryl, aryl-($C_1$-$C_6$-alkyl)-, and heteroaryl-($C_1$-$C_6$-alkyl)-, wherein 4-6-membered heterocycloalkyl groups are optionally substituted with one or two substituents, which are independently of each other selected from:
$C_1$-$C_3$-alkyl, $C_1$-$C_3$-haloalkyl, $C_1$-$C_3$-alkoxy, $C_1$-$C_3$-haloalkoxy, $C_3$-$C_4$-cycloalkyl, $C_3$-$C_4$-cycloalkoxy, amino, hydroxy, a halogen atom, and cyano, and, wherein aryl and heteroaryl groups are optionally substituted with one or two substituents, which are independently of each other selected from:

$C_1$-$C_3$-alkyl, $C_3$-$C_6$-cycloalkyl, $C_1$-$C_3$-alkoxy, $C_3$-$C_6$-cycloalkoxy, $C_1$-$C_3$-haloalkyl, $C_1$-$C_3$-haloalkoxy, halogen, cyano, —C(=O)OH, —C(=O)OR$^9$, and —C(=O)N(R$^{12}$)$_2$, or, R$^{10}$ and R$^{11}$ together with the nitrogen atom to which they are attached form a 4-6-membered heterocycloalkyl group, in which one carbon atom is optionally replaced by a further heteroatom-containing group selected from NR$^{14}$, O, S, S(=O) and S(=O)$_2$, in which heterocycloalkyl group one additional ring atom is optionally replaced by C(=O), said 4-6-membered heterocycloalkyl group being optionally substituted with one or two substituents, which are independently of each other selected from:

$C_1$-$C_3$-alkyl, $C_1$-$C_3$-haloalkyl, $C_1$-$C_3$-alkoxy, $C_1$-$C_3$-haloalkoxy, $C_3$-$C_4$-cycloalkyl, $C_3$-$C_4$-cycloalkoxy, amino, hydroxy, a halogen atom, and cyano, or, R$^{10}$ and R$^{11}$ together with the nitrogen atom to which they are attached form a group selected from:

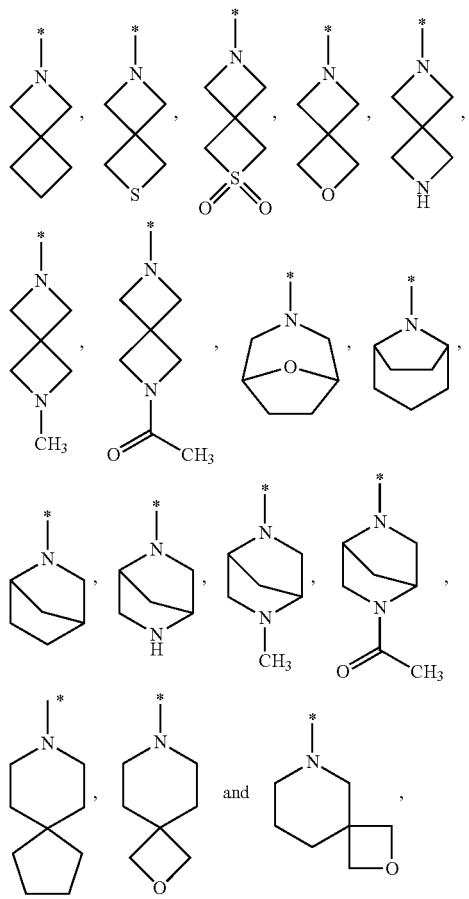

wherein * indicates the point of attachment of said group with the rest of the molecule, R$^{12}$ represents a group selected from:
hydrogen, and $C_1$-$C_3$-alkyl, R$^{13}$ represents a group selected from:
hydrogen, $C_1$-$C_6$-alkyl, $C_1$-$C_6$-hydroxyalkyl, $C_3$-$C_6$-cycloalkyl, $C_1$-$C_6$-haloalkyl, ($C_1$-$C_3$-alkoxy)-($C_1$-$C_6$-alkyl)-, aryl, and heteroaryl, wherein aryl and heteroaryl groups are optionally substituted with one or two substituents, which are independently of each other selected from:

$C_1$-$C_3$-alkyl, $C_3$-$C_6$-cycloalkyl, $C_1$-$C_3$-alkoxy, $C_3$-$C_6$-cycloalkoxy, $C_1$-$C_3$-haloalkyl, $C_1$-$C_3$-haloalkoxy, halogen, cyano, and hydroxy, R$^{14}$ represents a group selected from:
hydrogen, $C_1$-$C_3$-alkyl, $C_1$-$C_3$-haloalkyl, and $C_3$-$C_4$-cycloalkyl, R$^{15}$ represents a group selected from:
hydrogen, cyano, ($C_1$-$C_3$-alkyl)-C(=O)—, and ($C_1$-$C_3$-haloalkyl)-C(=O)—, R$^{16}$ represents a group selected from:
$C_1$-$C_4$-alkyl, and $C_3$-$C_4$-cycloalkyl, or a stereoisomer, a tautomer, an N-oxide, a hydrate, a solvate, or a salt thereof, or a mixture of same.

In accordance with a fourth embodiment of the first aspect, the present invention covers compounds of general formula (I), supra, in which:

X$^1$ represents NR$^3$ or O,

X$^2$ represents CR$^6$ or N,

R$^1$ represents a group selected from:
—OR$^9$, and —N(R$^{10}$)R$^{11}$,

R$^2$ represents a group selected from:
hydrogen, and $C_1$-$C_3$-alkyl,

R$^3$ represents a hydrogen atom,

R$^4$ represents a hydrogen atom,

R$^5$ represents a group selected from:
hydrogen, $C_1$-$C_3$-alkyl, $C_1$-$C_3$-alkoxy and $C_1$-$C_3$-haloalkoxy, R$^6$ represents a group selected from:
hydrogen, and halogen, R$^7$ represents a hydrogen atom, R$^8$ represents a group selected from:
aryl, and heteroaryl, wherein aryl and heteroaryl groups are optionally substituted with one, two or three substituents, which are independently of each other selected from:

$C_1$-$C_6$-alkyl, $C_1$-$C_3$-alkoxy, $C_3$-$C_6$-cycloalkyl, $C_3$-$C_6$-cycloalkoxy, $C_1$-$C_3$-haloalkyl, $C_1$-$C_3$-haloalkoxy, halogen, cyano, nitro, hydroxy, ($C_1$-$C_6$-alkyl)-S—, ($C_1$-$C_6$-alkyl)-S(=O)—, ($C_1$-$C_6$-alkyl)-S(=O)$_2$—, —S(=O)(=NR$^{15}$)R$^{16}$, —N(R$^{10}$)R$^{11}$, R$^{10}$(R$^{11}$)N—($C_1$-$C_6$-alkyl)-, R$^{10}$(R$^{11}$)N—($C_2$-$C_6$-alkoxy)-, phenyl, phenoxy, —N(R$^{12}$)C(=O)R$^{13}$, —C(=O)OH, —C(=O)OR$^9$, and —C(=O)N(R$^{12}$)$_2$, whereby two substituents of said aryl group, if they are in ortho-position to one another, can be linked to one another in such a way that they jointly form methanediylbisoxy, ethane-1,2-diylbisoxy, propane-1,3-diyl, or butane-1,4-diyl, R$^9$ represents a $C_1$-$C_6$-alkyl group, R$^{10}$ and R$^{11}$ are independently of each other selected from:
hydrogen, $C_1$-$C_6$-alkyl, $C_3$-$C_6$-cycloalkyl, ($C_3$-$C_6$-cycloalkyl)-($C_1$-$C_6$-alkyl)-, $C_2$-$C_6$-hydroxyalkyl, ($C_1$-$C_3$-alkoxy)-($C_2$-$C_6$-alkyl)-, $C_1$-$C_6$-haloalkyl, H$_2$N—($C_2$-$C_6$-alkyl)-, ($C_1$-$C_3$-alkyl)N(H)($C_2$-$C_6$-alkyl)-, ($C_1$-$C_3$-alkyl)$_2$N($C_2$-$C_6$-alkyl)-, 4-6 membered heterocycloalkyl, (4-6 membered heterocycloalkyl)-($C_2$-$C_6$-alkyl)-, aryl-($C_1$-$C_6$-alkyl)- and heteroaryl-($C_1$-$C_6$-alkyl)-, wherein 4-6-membered heterocycloalkyl groups are optionally substituted with one or two substituents, which are independently of each other selected from:
$C_1$-$C_3$-alkyl, $C_1$-$C_3$-haloalkyl, $C_1$-$C_3$-alkoxy, $C_1$-$C_3$-haloalkoxy, $C_3$-$C_4$-cycloalkyl, $C_3$-$C_4$-cycloalkoxy, amino, hydroxy, a halogen atom, and cyano, and, wherein aryl groups are optionally substituted with one or two substituents, which are independently of each other selected from:
$C_1$-$C_3$-alkyl, $C_3$-$C_6$-cycloalkyl, $C_1$-$C_3$-alkoxy, $C_3$-$C_6$-cycloalkoxy, $C_1$-$C_3$-haloalkyl, $C_1$-$C_3$-haloalkoxy, halogen, cyano, —C(=O)OH, —C(=O)OR$^9$, and —C(=O)N(R$^{12}$)$_2$, or, $R^{10}$ and $R^{11}$ together with the nitrogen atom to which they are attached form a 4-6-membered heterocycloalkyl group, in which one carbon atom is optionally replaced by a further heteroatom-containing group selected from NR$^{14}$, O, S, S(=O) and S(=O)$_2$, in which heterocycloalkyl group one additional ring atom is optionally replaced by C(=O), said 4-6-membered heterocycloalkyl group being optionally substituted with one or two substituents, which are independently of each other selected from:
$C_1$-$C_3$-alkyl, $C_1$-$C_3$-haloalkyl, $C_1$-$C_3$-alkoxy, $C_1$-$C_3$-haloalkoxy, $C_3$-$C_4$-cycloalkyl, $C_3$-$C_4$-cycloalkoxy, amino, hydroxy, a halogen atom, and cyano, or, $R^{10}$ and $R^{11}$ together with the nitrogen atom to which they are attached form a group selected from:

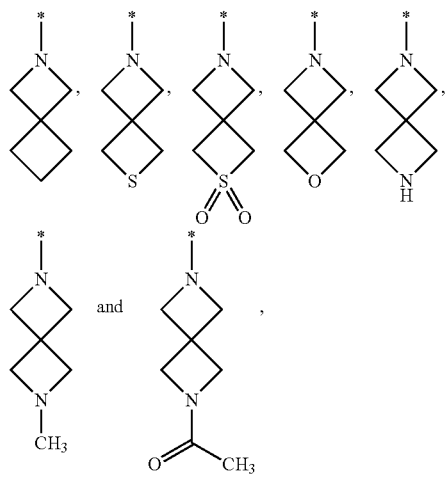

wherein * indicates the point of attachment of said group with the rest of the molecule, $R^{12}$ represents a group selected from:
hydrogen, and $C_1$-$C_3$-alkyl, $R^{13}$ represents a group selected from:
hydrogen, $C_1$-$C_6$-alkyl, $C_1$-$C_6$-hydroxyalkyl, $C_3$-$C_6$-cycloalkyl, $C_1$-$C_6$-haloalkyl, ($C_1$-$C_3$-alkoxy)-($C_1$-$C_6$-alkyl)-, aryl, and heteroaryl,
wherein aryl and heteroaryl groups are optionally substituted with one or two substituents, which are independently of each other selected from:
$C_1$-$C_3$-alkyl, $C_3$-$C_6$-cycloalkyl, $C_1$-$C_3$-alkoxy, $C_3$-$C_6$-cycloalkoxy, $C_1$-$C_3$-haloalkyl, $C_1$-$C_3$-haloalkoxy, halogen, cyano, and hydroxy, $R^{14}$ represents a group selected from:
hydrogen, $C_1$-$C_3$-alkyl, $C_1$-$C_3$-haloalkyl, and $C_3$-$C_4$-cycloalkyl, $R^{15}$ represents a group selected from:
hydrogen, cyano, ($C_1$-$C_3$-alkyl)-C(=O)—, and ($C_1$-$C_3$-haloalkyl)-C(=O)—, $R^{16}$ represents a group selected from:
$C_1$-$C_4$-alkyl, and $C_3$-$C_4$-cycloalkyl, or a stereoisomer, a tautomer, an N-oxide, a hydrate, a solvate, or a salt thereof, or a mixture of same.

In accordance with a fifth embodiment of the first aspect, the present invention covers compounds of general formula (I), supra, in which:
$X^1$ represents NR$^3$ or O,
$X^2$ represents CR$^6$ or N,
$R^1$ represents a group selected from:
—OR$^9$, and —N(R$^{10}$)R$^{11}$,
$R^2$ represents a group selected from:
hydrogen, and $C_1$-$C_3$-alkyl,
$R^3$ represents a hydrogen atom,
$R^4$ represents a hydrogen atom,
$R^5$ represents a group selected from:
hydrogen, and $C_1$-$C_3$-alkyl,
$R^6$ represents a group selected from:
hydrogen, and halogen,
$R^7$ represents a hydrogen atom,
$R^8$ represents a group selected from:
aryl, and heteroaryl,
wherein aryl and heteroaryl groups are optionally substituted with one, two or three substituents, which are independently of each other selected from:
$C_1$-$C_6$-alkyl, $C_1$-$C_3$-alkoxy, $C_3$-$C_6$-cycloalkyl, $C_3$-$C_6$-cycloalkoxy, $C_1$-$C_3$-haloalkyl, $C_1$-$C_3$-haloalkoxy, halogen, cyano, nitro, hydroxy, ($C_1$-$C_6$-alkyl)-S—, ($C_1$-$C_6$-alkyl)-S(=O)—, ($C_1$-$C_6$-alkyl)-S(=O)$_2$—, —S(=O)(=NR$^{15}$)R$^{16}$, —N(R$^{10}$)R$^{11}$, R$^{10}$(R$^{11}$)N—($C_1$-$C_6$-alkyl)-, R$^{10}$(R$^{11}$)N—($C_2$-$C_6$-alkoxy)-, phenyl, phenoxy, —N(R$^{12}$)C(=O)R$^{13}$, —C(=O)OH, —C(=O)OR$^9$, and —C(=O)N(R$^{12}$)$_2$,
whereby two substituents of said aryl group, if they are in ortho-position to one another, can be linked to one another in such a way that they jointly form methanediylbisoxy, ethane-1,2-diylbisoxy, propane-1,3-diyl, or butane-1,4-diyl,
$R^9$ represents a $C_1$-$C_6$-alkyl group,
$R^{10}$ and $R^{11}$ are independently of each other selected from:
hydrogen, $C_1$-$C_6$-alkyl, $C_3$-$C_6$-cycloalkyl, ($C_3$-$C_6$-cycloalkyl)-($C_1$-$C_6$-alkyl)-, $C_2$-$C_6$-hydroxyalkyl, ($C_1$-$C_3$-alkoxy)-($C_2$-$C_6$-alkyl)-, $C_1$-$C_6$-haloalkyl, ($C_1$-$C_3$-alkyl)$_2$N($C_2$-$C_6$-alkyl)-, (4-6 membered heterocycloalkyl)-($C_2$-$C_6$-alkyl)-, and aryl-($C_1$-$C_6$-alkyl)-,
wherein 4-6-membered heterocycloalkyl groups are optionally substituted with one or two substituents, which are independently of each other selected from:
$C_1$-$C_3$-alkyl, $C_1$-$C_3$-haloalkyl, $C_1$-$C_3$-alkoxy, $C_1$-$C_3$-haloalkoxy, $C_3$-$C_4$-cycloalkyl, $C_3$-$C_4$-cycloalkoxy, amino, hydroxy, a halogen atom, and cyano, and, wherein aryl groups are optionally substituted with one or two substituents, which are independently of each other selected from:
$C_1$-$C_3$-alkyl, $C_3$-$C_6$-cycloalkyl, $C_1$-$C_3$-alkoxy, $C_3$-$C_6$-cycloalkoxy, $C_1$-$C_3$-haloalkyl, $C_1$-$C_3$-haloalkoxy, halogen, cyano, —C(=O)OH, —C(=O)OR$^9$, and —C(=O)N(R$^{12}$)$_2$, or, $R^{10}$ and $R^{11}$ together with the nitrogen atom to which they are attached form a 4-6-membered heterocycloalkyl group, in which one carbon atom is optionally replaced by a further heteroatom-containing group selected from $NR^{14}$, O, S, S(=O) and S(=O)$_2$, in which heterocycloalkyl group one additional ring atom is optionally replaced by C(=O), said 4-6-membered heterocycloalkyl group being optionally substituted with one or two substituents, which are independently of each other selected from:

$C_1$-$C_3$-alkyl, $C_1$-$C_3$-haloalkyl, $C_1$-$C_3$-alkoxy, $C_1$-$C_3$-haloalkoxy, $C_3$-$C_4$-cycloalkyl, $C_3$-$C_4$-cycloalkoxy, amino, hydroxy, a halogen atom, and cyano, or, $R^{10}$ and $R^{11}$ together with the nitrogen atom to which they are attached form a group selected from:

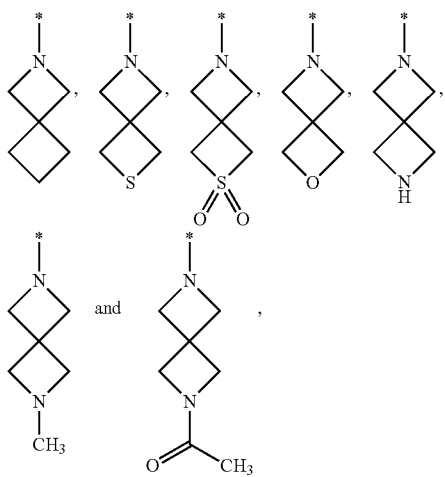

wherein * indicates the point of attachment of said group with the rest of the molecule, $R^{12}$ represents a group selected from:
hydrogen, and $C_1$-$C_3$-alkyl, $R^{13}$ represents a group selected from:
hydrogen, $C_1$-$C_6$-alkyl, $C_1$-$C_6$-hydroxyalkyl, $C_3$-$C_6$-cycloalkyl, $C_1$-$C_6$-haloalkyl, ($C_1$-$C_3$-alkoxy)-($C_1$-$C_6$-alkyl)-, aryl, and heteroaryl, wherein aryl and heteroaryl groups are optionally substituted with one or two substituents, which are independently of each other selected from:

$C_1$-$C_3$-alkyl, $C_3$-$C_6$-cycloalkyl, $C_1$-$C_3$-alkoxy, $C_3$-$C_6$-cycloalkoxy, $C_1$-$C_3$-haloalkyl, $C_1$-$C_3$-haloalkoxy, halogen, cyano, and hydroxy, $R^{14}$ represents a group selected from:
hydrogen, $C_1$-$C_3$-alkyl, $C_1$-$C_3$-haloalkyl, and $C_3$-$C_4$-cycloalkyl, $R^{15}$ represents a group selected from:
hydrogen, cyano, ($C_1$-$C_3$-alkyl)-C(=O)—, and ($C_1$-$C_3$-haloalkyl)-C(=O)—, $R^{16}$ represents a group selected from:
$C_1$-$C_4$-alkyl, and $C_3$-$C_4$-cycloalkyl, or a stereoisomer, a tautomer, an N-oxide, a hydrate, a solvate, or a salt thereof, or a mixture of same.

In accordance with a sixth embodiment of the first aspect, the present invention covers compounds of general formula (I), supra, in which:

$X^1$ represents $NR^3$ or O, $X^2$ represents $CR^6$ or N, $R^1$ represents a group selected from:
—$OR^9$, and —N($R^{10}$)$R^{11}$, $R^2$ represents a group selected from:
hydrogen, and $C_1$-$C_3$-alkyl, $R^3$ represents a hydrogen atom, $R^4$ represents a hydrogen atom, $R^5$ represents a group selected from:
hydrogen, $C_1$-$C_3$-alkyl, $C_1$-$C_3$-alkoxy and $C_1$-$C_3$-haloalkoxy, $R^6$ represents a group selected from:
hydrogen, and halogen, $R^7$ represents a hydrogen atom, $R^8$ represents a group selected from:
aryl, and heteroaryl,
wherein aryl and heteroaryl groups are optionally substituted with one, two or three substituents, which are independently of each other selected from:
$C_1$-$C_6$-alkyl, $C_1$-$C_3$-alkoxy, $C_1$-$C_3$-haloalkyl, $C_1$-$C_3$-haloalkoxy, halogen, cyano, nitro, hydroxy, ($C_1$-$C_6$-alkyl)-S(=O)$_2$—, —S(=O)(=N$R^{15}$)$R^{16}$, —N($R^{10}$)$R^{11}$,
$R^{10}$($R^{11}$)N—($C_2$-$C_6$-alkoxy)-, phenyl, phenoxy, and —N($R^{12}$)C(=O)$R^{13}$,
whereby two substituents of said aryl group, if they are in ortho-position to one another, can be linked to one another in such a way that they jointly form methanediylbisoxy, ethane-1,2-diylbisoxy, propane-1,3-diyl, or butane-1,4-diyl, $R^9$ represents a $C_1$-$C_6$-alkyl group, $R^{10}$ and $R^{11}$ are independently of each other selected from:
hydrogen, $C_1$-$C_6$-alkyl, $C_3$-$C_6$-cycloalkyl, ($C_3$-$C_6$-cycloalkyl)-($C_1$-$C_6$-alkyl)-, $C_2$-$C_6$-hydroxyalkyl, ($C_1$-$C_3$-alkoxy)-($C_2$-$C_6$-alkyl)-, $C_1$-$C_6$-haloalkyl, $H_2N$—($C_2$-$C_6$-alkyl)-, ($C_1$-$C_3$-alkyl)N(H)($C_2$-$C_6$-alkyl)-, ($C_1$-$C_3$-alkyl)$_2$N($C_2$-$C_6$-alkyl)-, 4-6 membered heterocycloalkyl, (4-6 membered heterocycloalkyl)-($C_2$-$C_6$-alkyl)-, aryl-($C_1$-$C_6$-alkyl)- and heteroaryl-($C_1$-$C_6$-alkyl)-,
wherein 4-6-membered heterocycloalkyl groups are optionally substituted with one or two substituents, which are independently of each other selected from:
$C_1$-$C_3$-alkyl, $C_1$-$C_3$-haloalkyl, $C_1$-$C_3$-alkoxy, $C_1$-$C_3$-haloalkoxy, $C_3$-$C_4$-cycloalkyl, $C_3$-$C_4$-cycloalkoxy, amino, hydroxy, a halogen atom, and cyano,
and,
wherein aryl groups are optionally substituted with one or two substituents, which are independently of each other selected from:
$C_1$-$C_3$-alkyl, $C_3$-$C_6$-cycloalkyl, $C_1$-$C_3$-alkoxy, $C_3$-$C_6$-cycloalkoxy, $C_1$-$C_3$-haloalkyl, $C_1$-$C_3$-haloalkoxy, halogen, cyano, —C(=O)OH, —C(=O)O$R^9$, and —C(=O)N($R^{12}$)$_2$, or, $R^{10}$ and $R^{11}$ together with the nitrogen atom to which they are attached form a 4-6-membered heterocycloalkyl group, in which one carbon atom is optionally replaced by a further heteroatom-containing group selected from $NR^{14}$, O, S, S(=O) and S(=O)$_2$, in which heterocycloalkyl group one additional ring atom is optionally replaced by C(=O),
said 4-6-membered heterocycloalkyl group being optionally substituted with one or two substituents, which are independently of each other selected from:
$C_1$-$C_3$-alkyl, $C_1$-$C_3$-haloalkyl, $C_1$-$C_3$-alkoxy, $C_1$-$C_3$-haloalkoxy, $C_3$-$C_4$-cycloalkyl, $C_3$-$C_4$-cycloalkoxy, amino, hydroxy, a halogen atom, and cyano, or, $R^{10}$ and $R^{11}$ together with the nitrogen atom to which they are attached form a group selected from:

wherein * indicates the point of attachment of said group with the rest of the molecule, $R^{12}$ represents a hydrogen atom, $R^{13}$ represents a group selected from:
hydrogen, and $C_1$-$C_6$-alkyl, $R^{14}$ represents a group selected from:
hydrogen, $C_1$-$C_3$-alkyl, $C_1$-$C_3$-haloalkyl, and $C_3$-$C_4$-cycloalkyl, $R^{15}$ represents a group selected from:
hydrogen, cyano, methyl-C(=O)—, and trifluoromethyl-C(=O)—, $R^{16}$ represents a group selected from:
$C_1$-$C_4$-alkyl, or a stereoisomer, a tautomer, an N-oxide, a hydrate, a solvate, or a salt thereof, or a mixture of same.

In accordance with a seventh embodiment of the first aspect, the present invention covers compounds of general formula (I), supra, in which:

$X^1$ represents $NR^3$ or O, $X^2$ represents $CR^6$ or N, $R^1$ represents a group selected from:
—$OR^9$, and —$N(R^{10})R^{11}$, $R^2$ represents a group selected from:
hydrogen, and $C_1$-$C_3$-alkyl, $R^3$ represents a hydrogen atom, $R^4$ represents a hydrogen atom, $R^5$ represents a group selected from:
hydrogen, and $C_1$-$C_3$-alkyl, $R^6$ represents a hydrogen atom, $R^7$ represents a hydrogen atom, $R^8$ represents a group selected from:
aryl, and heteroaryl, wherein aryl and heteroaryl groups are optionally substituted with one, two or three substituents, which are independently of each other selected from:
$C_1$-$C_6$-alkyl, $C_1$-$C_3$-alkoxy, $C_1$-$C_3$-haloalkyl, halogen, nitro, ($C_1$-$C_6$-alkyl)-S(=O)$_2$—, —S(=O)(=$NR^{15}$)$R^{16}$, —N($R^{10}$)$R^{11}$, $R^{10}$($R^{11}$)N—($C_2$-$C_6$-alkoxy)-, phenyl, phenoxy, and —N($R^{12}$)C(=O)$R^{13}$, whereby two substituents of said aryl group, if they are in ortho-position to one another, can be linked to one another in such a way that they jointly form methanediylbisoxy, ethane-1,2-diylbisoxy, propane-1,3-diyl, or butane-1,4-diyl, $R^9$ represents a $C_1$-$C_6$-alkyl group, $R^{10}$ and $R^{11}$ are independently of each other selected from: hydrogen, $C_1$-$C_6$-alkyl, $C_3$-$C_6$-cycloalkyl, ($C_3$-$C_6$-cycloalkyl)-($C_1$-$C_6$-alkyl)-, $C_2$-$C_6$-hydroxyalkyl, ($C_1$-$C_3$-alkoxy)-($C_2$-$C_6$-alkyl)-, $C_1$-$C_6$-haloalkyl, ($C_1$-$C_3$-alkyl)$_2$N($C_2$-$C_6$-alkyl)-, (4-6 membered heterocycloalkyl)-($C_2$-$C_6$-alkyl)-, and aryl-($C_1$-$C_6$-alkyl)-, wherein 4-6-membered heterocycloalkyl groups are optionally substituted with one or two substituents, which are independently of each other selected from:
$C_1$-$C_3$-alkyl, $C_1$-$C_3$-haloalkyl, $C_1$-$C_3$-alkoxy, $C_1$-$C_3$-haloalkoxy, $C_3$-$C_4$-cycloalkyl, $C_3$-$C_4$-cycloalkoxy, amino, hydroxy, a halogen atom, and cyano, and, wherein aryl groups are optionally substituted with one or two substituents, which are independently of each other selected from:
$C_1$-$C_3$-alkyl, $C_3$-$C_6$-cycloalkyl, $C_1$-$C_3$-alkoxy, $C_3$-$C_6$-cycloalkoxy, $C_1$-$C_3$-haloalkyl, $C_1$-$C_3$-haloalkoxy, halogen, cyano, —C(=O)OH, —C(=O)$OR^9$, and —C(=O)N($R^{12}$)$_2$, or, $R^{10}$ and $R^{11}$ together with the nitrogen atom to which they are attached form a 4-6-membered heterocycloalkyl group, in which one carbon atom is optionally replaced by a further heteroatom-containing group selected from $NR^{14}$, O, S, S(=O) and S(=O)$_2$, in which heterocycloalkyl group one additional ring atom is optionally replaced by C(=O), said 4-6-membered heterocycloalkyl group being optionally substituted with one or two substituents, which are independently of each other selected from:
$C_1$-$C_3$-alkyl, $C_1$-$C_3$-haloalkyl, $C_1$-$C_3$-alkoxy, $C_1$-$C_3$-haloalkoxy, $C_3$-$C_4$-cycloalkyl, $C_3$-$C_4$-cycloalkoxy, amino, hydroxy, a halogen atom, and cyano, or, $R^{10}$ and $R^{11}$ together with the nitrogen atom to which they are attached form a group selected from:

wherein * indicates the point of attachment of said group with the rest of the molecule, $R^{12}$ represents a hydrogen atom, $R^{13}$ represents a group selected from:
hydrogen, and $C_1$-$C_6$-alkyl, $R^{14}$ represents a group selected from:
hydrogen, $C_1$-$C_3$-alkyl, $C_1$-$C_3$-haloalkyl, and $C_3$-$C_4$-cycloalkyl, R$^{15}$ represents a group selected from:
hydrogen, cyano, methyl-C(=O)—, and trifluoromethyl-C(=O)—,
R$^{16}$ represents a group selected from:
C$_1$-C$_4$-alkyl,
or a stereoisomer, a tautomer, an N-oxide, a hydrate, a solvate, or a salt thereof, or a mixture of same.

In accordance with a eighth embodiment of the first aspect, the present invention covers compounds of general formula (I), supra, in which:
X$^1$ represents NR$^3$ or O,
X$^2$ represents CR$^6$ or N,
R$^1$ represents a group selected from:
—OR$^9$, and —N(R$^{10}$)R$^{11}$,
R$^2$ represents a group selected from:
hydrogen, and C$_1$-C$_3$-alkyl,
R$^3$ represents a hydrogen atom,
R$^4$ represents a hydrogen atom,
R$^5$ represents a group selected from:
hydrogen, methoxy, trifluoromethoxy and methyl,
R$^6$ represents a hydrogen or a fluorine atom,
R$^7$ represents a hydrogen atom,
R$^8$ represents a group selected from:
Phenyl, pyrazolyl, thienyl, pyridyl, furanyl, thiazolyl, oxazolyl, and pyrazinyl
wherein said groups are optionally substituted with one, two or three substituents, which are independently of each other selected from:
C$_1$-C$_5$-alkyl, C$_1$-C$_3$-alkoxy, C$_1$-haloalkyl, C$_1$-haloalkoxy, fluorine, chlorine, bromine, iodine, hydroxy, cyano, nitro, methyl-S(=O)$_2$—, —S(=O)(=NR$^{15}$)R$^{16}$, —N(R$^{10}$)R$^{11}$,
R$^{10}$(R$^{11}$)N—(C$_2$-alkoxy)-, phenyl, phenoxy, and —N(R$^{12}$)C(=O)R$^{13}$,
whereby two substituents of said phenyl group, if they are in ortho-position to one another, can be linked to one another in such a way that they jointly form methanediylbisoxy,
R$^9$ represents a C$_1$-C$_2$-alkyl group,
R$^{10}$ and R$^{11}$ are independently of each other selected from:
hydrogen, C$_1$-C$_5$-alkyl, cyclopropyl, (C$_3$-C$_5$-cycloalkyl)-(C$_1$-C$_2$-alkyl)-, C$_2$-C$_5$-hydroxyalkyl, (C$_1$-C$_3$-alkoxy)-(C$_2$-C$_3$-alkyl)-, C$_1$-C$_2$-haloalkyl, H$_2$N—(C$_2$-C$_5$-alkyl)-, (C$_1$-C$_3$-alkyl)N(H)(C$_2$-alkyl)-, (C$_1$-C$_3$-alkyl)$_2$N(C$_2$-C$_5$-alkyl)-, piperazin-1-yl, tetrahydro-2H-pyran-4-yl, tetrahydrofuran-3-yl, pyrrolidin-3-yl, piperidin-4-yl, (piperidin-1-yl)-(C$_2$-alkyl)-, (piperidin-1-yl)-(C$_3$-C$_4$-alkyl)-, (piperidin-2-yl)-(C$_1$-alkyl)-, (piperidin-3-yl)-(C$_1$-alkyl)-, (piperidin-4-yl)-(C$_1$-alkyl)-, (morpholin-4-yl)-(C$_2$-C$_4$-alkyl)-, (piperazin-1-yl)-(C$_2$-C$_5$-alkyl)-, (pyrrolidin-1-yl)-(C$_2$-C$_5$-alkyl)-, (pyrrolidin-2-yl)-(C$_1$-C$_2$-alkyl), (pyrrolidin-3-yl)-(C$_1$-alkyl), (azetidin-1-yl)-(C$_2$-alkyl), (tetrahydro-2H-pyran-4-yl)-(C$_1$-alkyl)-, (tetrahydrofuran-3-yl)-(C$_1$-alkyl)-, (tetrahydrofuran-2-yl)-(C$_1$-alkyl)-, (2-oxoimidazolidin-1-yl)-(C$_2$-alkyl)-, (2-oxopyrrolidin-1-yl)-(C$_2$-C$_3$-alkyl)-, (1,1-dioxidothiomorpholin-4-yl)-(C$_2$-alkyl)-, phenyl-(C$_1$-C$_2$-alkyl)- and pyridinyl-(C$_2$-alkyl),
wherein 4-6-membered heterocycloalkyl groups are optionally substituted with one or two substituents, which are independently of each other selected from:
C$_1$-C$_2$-alkyl, methoxy, hydroxy and fluorine,
or,
R$^{10}$ and R$^{11}$ together with the nitrogen atom to which they are attached form a:

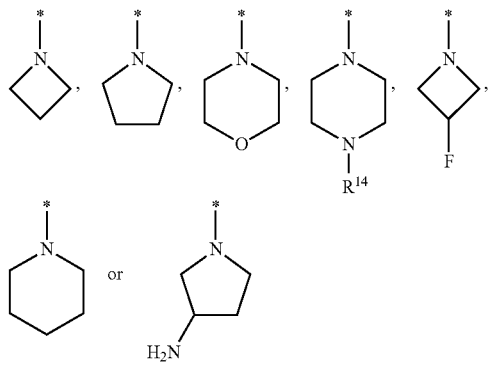

group,
wherein * indicates the point of attachment of said group with the rest of the molecule,
or
R$^{10}$ and R$^{11}$ together with the nitrogen atom to which they are attached form a:

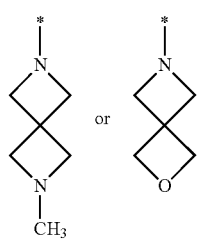

group,
wherein * indicates the point of attachment of said group with the rest of the molecule,
R$^{12}$ represents a hydrogen atom,
R$^{13}$ represents a methyl group,
R$^{14}$ represents hydrogen or a methyl group,
R$^{15}$ represents a hydrogen atom,
R$^{16}$ represents an ethyl group,
or a stereoisomer, a tautomer, an N-oxide, a hydrate, a solvate, or a salt thereof, or a mixture of same.

In accordance with a ninth embodiment of the first aspect, the present invention covers compounds of general formula (I), supra, in which:
X$^1$ represents NR$^3$ or O,
X$^2$ represents CR$^6$ or N,
R$^1$ represents a group selected from:
—OR$^9$, and —N(R$^{10}$)R$^{11}$,
R$^2$ represents a group selected from:
hydrogen, and C$_1$-C$_2$-alkyl,
R$^3$ represents a hydrogen atom,
R$^4$ represents a hydrogen atom,
R$^5$ represents a group selected from:
hydrogen, methoxy, trifluoromethoxy and methyl,
R$^6$ represents a hydrogen or a fluorine atom,
R$^7$ represents a hydrogen atom,
R$^8$ represents a group selected from:
Phenyl, pyridyl wherein said groups are optionally substituted with one, two or three substituents, which are independently of each other selected from:
C$_1$-alkyl, C$_1$-C$_2$-alkoxy, C$_1$-haloalkyl (preferably CF$_3$), C$_1$-haloalkoxy (preferably —OCF$_3$), fluorine, chlorine, bromine, iodine, hydroxy, cyano, methyl-S (=O)$_2$—, —S(=O)(=NH)Et, —N(CH$_3$)$_2$, (piperidin-1-yl)-(C$_2$-alkoxy)-, and (CH$_3$)$_2$N—(C$_2$-alkoxy)-,
R$^9$ represents a C$_1$-C$_2$-alkyl group,
R$^{10}$ and R$^{11}$ are independently of each other selected from:
hydrogen, C$_1$-C$_5$-alkyl, cyclopropyl, C$_2$-C$_5$-hydroxyalkyl, CH$_3$OCH$_2$CH$_2$—, C$_1$-C$_2$-haloalkyl, H$_2$N—(C$_2$-C$_5$-alkyl)-, (C$_1$-C$_3$-alkyl)N(H)(C$_2$-alkyl)-, (C$_1$-C$_3$-alkyl)$_2$N(C$_2$-C$_4$-alkyl)-, piperazin-1-yl, tetrahydro-2H-pyran-4-yl, tetrahydrofuran-3-yl, pyrrolidin-3-yl, piperidin-4-yl, (piperidin-1-yl)-(C$_2$-alkyl)-, (piperidin-1-yl)-(C$_3$-C$_4$-alkyl)-, (piperidin-2-yl)-(C$_1$-alkyl)-, (piperidin-3-yl)-(C$_1$-alkyl)-, (piperidin-4-yl)-(C$_1$-alkyl)-, (morpholin-4-yl)-(C$_2$-C$_4$-alkyl)-, (piperazin-1-yl)-(C$_2$-C$_5$-alkyl)-, (pyrrolidin-1-yl)-(C$_2$-C$_5$-alkyl)-, (pyrrolidin-2-yl)-(C$_1$-C$_2$-alkyl), (pyrrolidin-3-yl)-(C$_1$-alkyl), (azetidin-1-yl)-(C$_2$-alkyl), (tetrahydro-2H-pyran-4-yl)-(C$_1$-alkyl)-, (tetrahydrofuran-3-yl)-(C$_1$-alkyl)-, (tetrahydrofuran-2-yl)-(C$_1$-alkyl)-, (1,1-dioxidothiomorpholin-4-yl)-(C$_2$-alkyl)-, phenyl-(C$_1$-alkyl)- and pyridinyl-(C$_2$-alkyl),
wherein 4-6-membered heterocycloalkyl groups are optionally substituted with one or two substituents, which are independently of each other selected from:
C$_1$-C$_2$-alkyl, methoxy, hydroxy and fluorine,
or,
R$^{10}$ and R$^{11}$ together with the nitrogen atom to which they are attached form a:

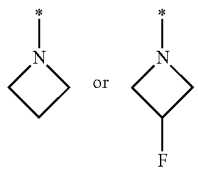

group,
wherein * indicates the point of attachment of said group with the rest of the molecule,
or
R$^{10}$ and R$^{11}$ together with the nitrogen atom to which they are attached form a:

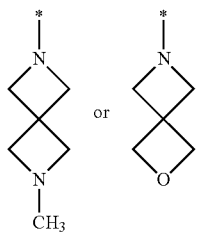

group,
wherein * indicates the point of attachment of said group with the rest of the molecule,
or a stereoisomer, a tautomer, an N-oxide, a hydrate, a solvate, or a salt thereof, or a mixture of same.

In accordance with a tenth embodiment of the first aspect, the present invention covers compounds of general formula (I), supra, in which:
X$^1$ represents NR$^3$ or O,
X$^2$ represents CR$^6$ or N, R$^1$ represents a group selected from:
—OR$^9$, and —N(R$^{10}$)R$^{11}$,
R$^2$ represents a group selected from:
hydrogen, and C$_1$-C$_3$-alkyl,
R$^3$ represents a hydrogen atom,
R$^4$ represents a hydrogen atom,
R$^5$ represents a group selected from:
hydrogen, and methyl,
R$^6$ represents a hydrogen atom,
R$^7$ represents a hydrogen atom,
R$^8$ represents a group selected from:
phenyl, pyrazolyl, thienyl, and pyridyl,
wherein said groups are optionally substituted with one, two or three substituents, which are independently of each other selected from:
C$_1$-C$_5$-alkyl, C$_1$-C$_3$-alkoxy, C$_1$-haloalkyl, fluorine, chlorine, bromine, nitro, methyl-S(=O)$_2$—, —S(=O)(=NR$^{15}$)R$^{16}$, —N(R$^{10}$)R$^{11}$, R$^{10}$(R$^{11}$)N—(C$_2$-alkoxy)-, phenyl, phenoxy, and —N(R$^{12}$)C(=O)R$^{13}$,
whereby two substituents of said phenyl group, if they are in ortho-position to one another, can be linked to one another in such a way that they jointly form methanediylbisoxy,
R$^9$ represents a C$_1$-C$_2$-alkyl group,
R$^{10}$ and R$^{11}$ are independently of each other selected from:
hydrogen, C$_1$-C$_5$-alkyl, cyclopropyl, cyclopropylmethyl-, C$_2$-hydroxyalkyl, methoxy-(C$_2$-alkyl)-, C$_1$-C$_2$-haloalkyl, (methyl)$_2$N(C$_2$-C$_3$-alkyl)-, (piperidin-1-yl)-(C$_2$-alkyl)-, and phenyl-(C$_1$-C$_2$-alkyl)-,
or,
R$^{10}$ and R$^{11}$ together with the nitrogen atom to which they are attached form a:

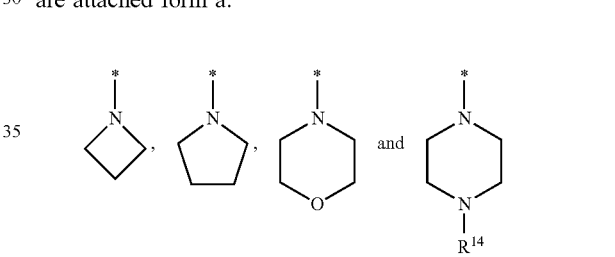

group,
wherein * indicates the point of attachment of said group with the rest of the molecule,
or
R$^{10}$ and R$^{11}$ together with the nitrogen atom to which they are attached form a:

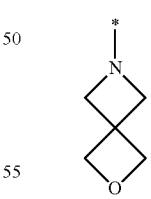

group,
wherein * indicates the point of attachment of said group with the rest of the molecule,
R$^{12}$ represents a hydrogen atom,
R$^{13}$ represents a methyl group,
R$^{14}$ represents a methyl group,
R$^{15}$ represents a hydrogen atom,
R$^{16}$ represents an ethyl group,
or a stereoisomer, a tautomer, an N-oxide, a hydrate, a solvate, or a salt thereof, or a mixture of same.

In accordance with a eleventh embodiment of the first aspect, the present invention covers a compound of general formula (I), supra, which is selected from the group consisting of:

$N^5$-{4-[(2,3-dichlorobenzoyl)amino]phenyl}-$N^4$-methyl-1H-imidazole-4,5-dicarboxamide $N^5$-(4-{[(2-chloropyridin-3-yl)carbonyl]amino}phenyl)-$N^4$-methyl-1H-imidazole-4,5-dicarboxamide $N^5$-(4-{[2-fluoro-4-(pyrrolidin-1-yl)benzoyl]amino}phenyl)-$N^4$-methyl-1H-imidazole-4,5-dicarboxamide $N^5$-(4-{[2-chloro-4-(dimethylamino)benzoyl]amino}phenyl)-$N^4$-methyl-1H-imidazole-4,5-dicarboxamide $N^5$-{4-[(2-chloro-4-fluorobenzoyl)amino]-3-methylphenyl}-$N^4$-methyl-1H-imidazole-4,5-dicarboxamide $N^5$-{4-[(3-chloroisonicotinoyl)amino]phenyl}-$N^4$-methyl-1H-imidazole-4,5-dicarboxamide $N^4$-sec-butyl-$N^5$-{4-[(2-chloro-4-fluorobenzoyl)amino]phenyl}-1,3-oxazole-4,5-dicarboxamide $N^5$-{4-[(2-chloro-4-fluorobenzoyl)amino]phenyl}-$N^4$-(1-phenylethyl)-1,3-oxazole-4,5-dicarboxamide $N^5$-{4-[(2,4-dichlorobenzoyl)amino]phenyl}-$N^4$-methyl-1H-imidazole-4,5-dicarboxamide $N^4$-{4-[(2-chloro-4-fluorobenzoyl)amino]phenyl}-$N^5$-isopropyl-1H-imidazole-4,5-dicarboxamide $N^5$-{4-[(2-chloro-4-fluorobenzoyl)amino]phenyl}-$N^4$-methyl-1,3-oxazole-4,5-dicarboxamide $N^4$-{4-[(2-chloro-4-fluorobenzoyl)amino]phenyl}-$N^5$-methyl-1H-imidazole-4,5-dicarboxamide methyl 5-({4-[(2-chloro-4-fluorobenzoyl)amino]phenyl}carbamoyl)-1H-imidazole-4-carboxylate methyl 5-({4-[(2-chloro-4-fluorobenzoyl)amino]phenyl}carbamoyl)-1,3-oxazole-4-carboxylate $N^5$-{4-[(2-chloro-4-fluorobenzoyl)amino]phenyl}-$N^4$-isopropyl-1,3-oxazole-4, 5-dicarboxamide $N^5$-{6-[(2-chloro-4-fluorobenzoyl)amino]pyridin-3-yl}-$N^4$-methyl-1H-imidazole-4,5-dicarboxamide $N^5$-(4-{[(5-chloro-1-methyl-3-phenyl-1H-pyrazol-4-yl)carbonyl]amino}phenyl)-$N^4$-methyl-1H-imidazole-4,5-dicarboxamide $N^5$-benzyl-$N^4$-{4-[(2-chloro-4-fluorobenzoyl)amino]phenyl}-1H-imidazole-4,5-dicarboxamide $N^4$-methyl-$N^5$-{4[(2-methylbenzoyl)amino]phenyl}-1H-imidazole-4,5-dicarboxamide $N^5$-{4[(4-fluorobenzoyl)amino]phenyl}-$N^4$-methyl-1H-imidazole-4,5-dicarboxamide $N^5$-[4-(benzoylamino)phenyl]-$N^4$-methyl-1H-imidazole-4, 5-dicarboxamide $N^4$-{4-[(2-chloro-4-fluorobenzoyl)amino]phenyl}-$N^5$-[2-(dimethylamino)ethyl]-1H-imidazole-4,5-dicarboxamide $N^5$-{4-[(4-fluoro-2,6-dimethylbenzoyl)amino]phenyl}-$N^4$-methyl-1H-imidazole-4,5-dicarboxamide $N^4$-{4-[(2-chloro-4-fluorobenzoyl)amino]phenyl}-$N^5$,$N^5$-dimethyl-1H-imidazole-4,5-dicarboxamide $N^5$-[4-({2-chloro-4-[2-(dimethylamino)ethoxy]benzoyl}amino)phenyl]-$N^4$-methyl-1H-imidazole-4,5-dicarboxamide $N^5$-{4-[(2,6-dichlorobenzoyl)amino]phenyl}-$N^4$-methyl-1H-imidazole-4,5-dicarboxamide $N^5$-{4[(2-chlorobenzoyl)amino]phenyl}-$N^4$-methyl-1H-imidazole-4,5-dicarboxamide $N^5$-[4-({2-chloro-4-[2-(4-methylpiperazin-1-yl)ethoxy]benzoyl}amino)phenyl]-$N^4$-methyl-1H-imidazole-4,5-dicarboxamide N-{4-[(2-chloro-4-fluorobenzoyl)amino]phenyl}-5-(morpholin-4-ylcarbonyl)-1H-imidazole-4-carboxamide $N^4$-{4-[(2-chloro-4-fluorobenzoyl)amino]phenyl}-$N^5$-(2,2,2-trifluoroethyl)-1H-imidazole-4,5-dicarboxamide $N^5$-{4-[(2-chloro-4-fluorobenzoyl)amino]phenyl}-$N^4$-[2-(dimethylamino)ethyl]-1,3-oxazole-4,5-dicarboxamide $N^4$-{4-[(2-chloro-4-fluorobenzoyl)amino]phenyl}-$N^5$-[2-(piperidin-1-yl)ethyl]-1H-imidazole-4,5-dicarboxamide $N^4$-{4-[(4-fluorobenzoyl)amino]phenyl}-$N^5$-[2-(piperidin-1-yl)ethyl]-1H-imidazole-4,5-dicarboxamide N-{4-[(4-fluorobenzoyl)amino]phenyl}-5-(2-oxa-6-azaspiro[3.3]hept-6-ylcarbonyl)-1H-imidazole-4-carboxamide $N^5$-{4-[(mesitylcarbonyl)amino]phenyl}-$N^4$-methyl-1H-imidazole-4,5-dicarboxamide $N^5$-(4-{[2-chloro-6-(trifluoromethyl)benzoyl]amino}phenyl)-$N^4$-methyl-1H-imidazole-4,5-dicarboxamide $N^5$-{4[(2-bromobenzoyl)amino]phenyl}-$N^4$-methyl-1H-imidazole-4,5-dicarboxamide $N^5$-{4-[(2,6-difluorobenzoyl)amino]phenyl}-$N^4$-methyl-1H-imidazole-4,5-dicarboxamide $N^5$-{4[(2-ethylbenzoyl)amino]phenyl}-$N^4$-methyl-1H-imidazole-4,5-dicarboxamide $N^4$-methyl-$N^5$-{4-[(2,3,4-trimethoxybenzoyl)amino]phenyl}-1H-imidazole-4,5-dicarboxamide N-{4-[(2-chloro-4-fluorobenzoyl)amino]phenyl}-4-[(3-fluoroazetidin-1-yl)carbonyl]-1H-imidazole-5-carboxamide $N^5$-{4-[(2-chloro-4-fluorobenzoyl)amino]phenyl}-$N^4$-(2-cyclopentylethyl)-1H-imidazole-4,5-dicarboxamide, $N^5$-{4-[(2-chloro-4-fluorobenzoyl)amino]phenyl}-$N^4$-(2-cyclopropylethyl)-1H-imidazole-4,5-dicarboxamide, $N^5$-{4-[(2-chloro-4-fluorobenzoyl)amino]phenyl}-$N^4$-cyclopropyl-1H-imidazole-4,5-dicarboxamide, N-{4-[(2-chloro-4-fluorobenzoyl)amino]phenyl}-4-[(6-methyl-2,6-diazaspiro[3.3]hept-2-yl)carbonyl]-1H-imidazole-5-carboxamide, N-{4-[(2-chloro-4,5-difluorobenzoyl)amino]phenyl}-4-[(3-fluoroazetidin-1-yl)carbonyl]-1H-imidazole-5-carboxamide, $N^5$-{4-[(2-chloro-4,5-difluorobenzoyl)amino]phenyl}-$N^4$-(2-cyclopentylethyl)-1H-imidazole-4,5-dicarboxamide, $N^5$-{4-[(2-chloro-4,5-difluorobenzoyl)amino]phenyl}-$N^4$-(2-cyclopropylethyl)-1H-imidazole-4,5-dicarboxamide, N-{4-[(2-chloro-4,5-difluorobenzoyl)amino]phenyl}-4-[(6-methyl-2,6-diazaspiro[3.3]hept-2-yl)carbonyl]-1H-imidazole-5-carboxamide, $N^5$-{4-[(2-chloro-4,5-difluorobenzoyl)amino]phenyl}-$N^4$-cyclopropyl-1H-imidazole-4,5-dicarboxamide, N-{4-[(2-chloro-4,5-difluorobenzoyl)amino]phenyl}-4-(2-oxa-6-azaspiro[3.3]hept-6-ylcarbonyl)-1H-imidazole-5-carboxamide, $N^5$-(4-{[2-chloro-4-(methylsulfonyl)benzoyl]amino}phenyl)-$N^4$-[2-(piperidin-1-yl)ethyl]-1H-imidazole-4,5-dicarboxamide, $N^5$-(4-{[2-chloro-4-(methylsulfonyl)benzoyl]amino}phenyl)-$N^4$-[2-(dimethylamino)ethyl]-1H-imidazole-4,5-dicarboxamide, $N^5$-(4-{[2-chloro-4-(methylsulfonyl)benzoyl]amino}phenyl)-$N^4$-methyl-1H-imidazole-4,5-dicarboxamide, $N^5$-{4-[(2-bromo-4-fluorobenzoyl)amino]phenyl}-$N^4$-methyl-1H-imidazole-4,5-dicarboxamide, $N^5$-{4-[(2,6-dimethoxybenzoyl)amino]phenyl}-$N^4$-methyl-1H-imidazole-4,5-dicarboxamide, $N^4$-methyl-$N^5$-(4-{[2-(trifluoromethyl)benzoyl]amino}phenyl)-1H-imidazole-4,5-dicarboxamide, $N^4$-methyl-$N^5$-{4-[(2,4,6-trichlorobenzoyl)amino]phenyl}-1H-imidazole-4,5-dicarboxamide,
$N^5$-{4-[(2-methoxybenzoyl)amino]phenyl}-$N^4$-methyl-1H-imidazole-4,5-dicarboxamide,
$N^5$-{4-[(4-fluoro-2-iodobenzoyl)amino]phenyl}-$N^4$-methyl-1H-imidazole-4,5-dicarboxamide,
$N^5$-{4-[(4-fluoro-2-iodobenzoyl)amino]phenyl}-$N^4$-[2-(piperidin-1-yl)ethyl]-1H-imidazole-4,5-dicarboxamide,
$N^5$-(4-{[2-bromo-5-(trifluoromethoxy)benzoyl]amino}phenyl)-$N^4$-[2-(piperidin-1-yl)ethyl]-1H-imidazole-4,5-dicarboxamide,
$N^5$-(4-{[2-bromo-5-(trifluoromethoxy)benzoyl]amino}phenyl)-$N^4$-methyl-1H-imidazole-4,5-dicarboxamide,
$N^5$-{4-[(2-chloro-4-fluorobenzoyl)amino]phenyl}-$N^4$,2-dimethyl-1H-imidazole-4,5-dicarboxamide,
$N^4$-{4-[(2-chloro-4-fluorobenzoyl)amino]phenyl}-$N^5$-[2-(dimethylamino)ethyl]-2-methyl-1H-imidazole-4,5-dicarboxamide,
$N^5$-{4-[(2-chloro-4-fluorobenzoyl)amino]phenyl}-2-methyl-$N^4$-[2-(piperidin-1-yl)ethyl]-1H-imidazole-4,5-dicarboxamide,
$N^5$-{4-[(2-chloro-4-fluorobenzoyl)amino]phenyl}-2-ethyl-$N^4$-methyl-1H-imidazole-4,5-dicarboxamide,
$N^4$-{4-[(2-chloro-4-fluorobenzoyl)amino]phenyl}-$N^5$-[2-(dimethylamino)ethyl]-2-ethyl-1H-imidazole-4,5-dicarboxamide,
$N^4$-{4-[(2-chloro-4-fluorobenzoyl)amino]phenyl}-2-ethyl-$N^5$-[2-(piperidin-1-yl)ethyl]-1H-imidazole-4,5-dicarboxamide,
methyl 5-({4-[(2-chloro-4-fluorobenzoyl)amino]-3-fluorophenyl}carbamoyl)-1H-imidazole-4-carboxylate,
$N^5$-{4-[(2-chloro-4-fluorobenzoyl)amino]-3-fluorophenyl}-$N^4$-methyl-1H-imidazole-4,5-dicarboxamide,
$N^5$-{4-[(2-chloro-4-fluorobenzoyl)amino]-3-fluorophenyl}-$N^4$-[2-(dimethylamino)ethyl]-1H-imidazole-4,5-dicarboxamide,
$N^5$-{4-[(2-chloro-4-fluorobenzoyl)amino]-3-fluorophenyl}-$N^4$-[2-(piperidin-1-yl)ethyl]-1H-imidazole-4,5-dicarboxamide,
methyl 5-({3-fluoro-4-[(4-fluorobenzoyl)amino]phenyl}carbamoyl)-1H-imidazole-4-carboxylate,
$N^5$-{3-fluoro-4-[(4-fluorobenzoyl)amino]phenyl}-$N^4$-methyl-1H-imidazole-4,5-dicarboxamide,
$N^4$-[2-(dimethylamino)ethyl]-$N^5$-{3-fluoro-4-[(4-fluorobenzoyl)amino]phenyl}-1H-imidazole-4,5-dicarboxamide,
$N^5$-{3-fluoro-4-[(4-fluorobenzoyl)amino]phenyl}-$N^4$-[2-(piperidin-1-yl)ethyl]-1H-imidazole-4,5-dicarboxamide,
methyl 5-({4-[(2-chlorobenzoyl)amino]-3-fluorophenyl}carbamoyl)-1H-imidazole-4-carboxylate,
$N^5$-{4-[(2-chlorobenzoyl)amino]-3-fluorophenyl}-$N^4$-methyl-1H-imidazole-4,5-dicarboxamide,
$N^5$-{4-[(2-chlorobenzoyl)amino]-3-fluorophenyl}-$N^4$-[2-(dimethylamino)ethyl]-1H-imidazole-4,5-dicarboxamide,
$N^5$-{4-[(2-chlorobenzoyl)amino]-3-fluorophenyl}-$N^4$-[2-(piperidin-1-yl)ethyl]-1H-imidazole-4,5-dicarboxamide,
methyl 5-({4-[(2-chloro-4-fluorobenzoyl)amino]-3-methylphenyl}carbamoyl)-1H-imidazole-4-carboxylate,
$N^5$-{4-[(2-chloro-4-fluorobenzoyl)amino]-3-methylphenyl}-$N^4$-[2-(dimethylamino)ethyl]-1H-imidazole-4,5-dicarboxamide,
$N^5$-{4-[(2-chloro-4-fluorobenzoyl)amino]-3-methylphenyl}-$N^4$-[2-(piperidin-1-yl)ethyl]-1H-imidazole-4,5-dicarboxamide,
methyl 5-({4-[(2-chlorobenzoyl)amino]-3-methylphenyl}carbamoyl)-1H-imidazole-4-carboxylate,
$N^5$-{4-[(2-chlorobenzoyl)amino]-3-methylphenyl}-$N^4$-methyl-1H-imidazole-4,5-dicarboxamide,
$N^5$-{4-[(2-chlorobenzoyl)amino]-3-methylphenyl}-$N^4$-[2-(dimethylamino)ethyl]-1H-imidazole-4,5-dicarboxamide,
$N^5$-{4-[(2-chlorobenzoyl)amino]-3-methylphenyl}-$N^4$-[2-(piperidin-1-yl)ethyl]-1H-imidazole-4,5-dicarboxamide,
methyl 5-({4-[(4-fluorobenzoyl)amino]-3-methylphenyl}carbamoyl)-1H-imidazole-4-carboxylate,
$N^5$-{4-[(4-fluorobenzoyl)amino]-3-methylphenyl}-$N^4$-methyl-1H-imidazole-4,5-dicarboxamide,
$N^4$-[2-(dimethylamino)ethyl]-$N^5$-{4-[(4-fluorobenzoyl)amino]-3-methylphenyl}-1H-imidazole-4,5-dicarboxamide,
$N^5$-{4-[(4-fluorobenzoyl)amino]-3-methylphenyl}-$N^4$-[2-(piperidin-1-yl)ethyl]-1H-imidazole-4,5-dicarboxamide,
methyl 5-({4-[(2-chloro-4-fluorobenzoyl)amino]-3-methoxyphenyl}carbamoyl)-1H-imidazole-4-carboxylate,
$N^5$-{4-[(2-chloro-4-fluorobenzoyl)amino]-3-methoxyphenyl}-$N^4$-methyl-1H-imidazole-4,5-dicarboxamide,
$N^5$-{4-[(2-chloro-4-fluorobenzoyl)amino]-3-methoxyphenyl}-$N^4$-[2-(dimethylamino)ethyl]-1H-imidazole-4,5-dicarboxamide,
$N^5$-{4-[(2-chloro-4-fluorobenzoyl)amino]-3-methoxyphenyl}-$N^4$-[2-(piperidin-1-yl)ethyl]-1H-imidazole-4,5-dicarboxamide,
methyl 5-({4-[(2-chlorobenzoyl)amino]-3-methoxyphenyl}carbamoyl)-1H-imidazole-4-carboxylate,
$N^5$-{4-[(2-chlorobenzoyl)amino]-3-methoxyphenyl}-$N^4$-methyl-1H-imidazole-4,5-dicarboxamide,
$N^5$-{4-[(2-chlorobenzoyl)amino]-3-methoxyphenyl}-$N^4$-[2-(dimethylamino)ethyl]-1H-imidazole-4,5-dicarboxamide,
$N^5$-{4-[(2-chlorobenzoyl)amino]-3-methoxyphenyl}-$N^4$-[2-(piperidin-1-yl)ethyl]-1H-imidazole-4,5-dicarboxamide,
methyl 5-({4-[(4-fluorobenzoyl)amino]-3-methoxyphenyl}carbamoyl)-1H-imidazole-4-carboxylate,
$N^5$-{4-[(4-fluorobenzoyl)amino]-3-methoxyphenyl}-$N^4$-methyl-1H-imidazole-4,5-dicarboxamide,
$N^4$-[2-(dimethylamino)ethyl]-$N^5$-{4-[(4-fluorobenzoyl)amino]-3-methoxyphenyl}-1H-imidazole-4,5-dicarboxamide,
$N^5$-{4-[(4-fluorobenzoyl)amino]-3-methoxyphenyl}-$N^4$-[2-(piperidin-1-yl)ethyl]-1H-imidazole-4,5-dicarboxamide,
$N^5$-{4-[(2-chloro-4-fluorobenzoyl)amino]phenyl}-2-isopropyl-$N^4$-methyl-1H-imidazole-4,5-dicarboxamide,
$N^4$-{4-[(2-chloro-4-fluorobenzoyl)amino]phenyl}-$N^5$-[2-(dimethylamino)ethyl]-2-isopropyl-1H-imidazole-4,5-dicarboxamide,
$N^4$-{4-[(2-chloro-4-fluorobenzoyl)amino]phenyl}-2-isopropyl-$N^5$-[2-(piperidin-1-yl)ethyl]-1H-imidazole-4,5-dicarboxamide,
$N^5$-{6-[(2-chloro-4-fluorobenzoyl)amino]pyridin-3-yl}-$N^4$-[2-(dimethylamino)ethyl]-1H-imidazole-4,5-dicarboxamide,
$N^5$-{6-[(2-chloro-4-fluorobenzoyl)amino]pyridin-3-yl}-$N^4$-[2-(piperidin-1-yl)ethyl]-1H-imidazole-4,5-dicarboxamide,
methyl 5-({6-[(2-chlorobenzoyl)amino]pyridin-3-yl}carbamoyl)-1H-imidazole-4-carboxylate,
$N^5$-{6-[(2-chlorobenzoyl)amino]pyridin-3-yl}-$N^4$-methyl-1H-imidazole-4,5-dicarboxamide,
$N^5$-{6-[(2-chlorobenzoyl)amino]pyridin-3-yl}-$N^4$-[2-(dimethylamino)ethyl]-1H-imidazole-4,5-dicarboxamide,
$N^5$-{6-[(2-chlorobenzoyl)amino]pyridin-3-yl}-$N^4$-[2-(piperidin-1-yl)ethyl]-1H-imidazole-4,5-dicarboxamide, $N^5$-{6-[(4-fluorobenzoyl)amino]pyridin-3-yl}-$N^4$-methyl-1H-imidazole-4,5-dicarboxamide, $N^4$-[2-(dimethylamino)ethyl]-$N^5$-{6-[(4-fluorobenzoyl)amino]pyridin-3-yl}-1H-imidazole-4,5-dicarboxamide, $N^5$-{6-[(4-fluorobenzoyl)amino]pyridin-3-yl}-$N^4$-[2-(piperidin-1-yl)ethyl]-1H-imidazole-4,5-dicarboxamide, $N^5$-{4-[(2-chloro-4,6-difluorobenzoyl)amino]phenyl}-$N^4$-methyl-1H-imidazole-4,5-dicarboxamide, $N^5$-{4-[(2-chloro-4,6-difluorobenzoyl)amino]phenyl}-$N^4$-[2-(piperidin-1-yl)ethyl]-1H-imidazole-4,5-dicarboxamide, $N^5$-{4[(2-chlorobenzoyl)amino]phenyl}-1H-imidazole-4,5-dicarboxamide, $N^5$-{4-[(2-chloro-4-fluorobenzoyl)amino]phenyl}-1H-imidazole-4,5-dicarboxamide, $N^5$-{4-[(2-chloro-4-hydroxybenzoyl)amino]phenyl}-$N^4$-methyl-1H-imidazole-4,5-dicarboxamide, $N^5$-{4-[(2-chloro-5-hydroxybenzoyl)amino]phenyl}-$N^4$-methyl-1H-imidazole-4,5-dicarboxamide, $N^5$-[4-({2-chloro-5-[2-(4-methylpiperazin-1-yl)ethoxy]benzoyl}amino)phenyl]-$N^4$-methyl-1H-imidazole-4,5-dicarboxamide, $N^5$-[4-({2-chloro-5-[2-(piperidin-1-yl)ethoxy]benzoyl}amino)phenyl]-$N^4$-methyl-1H-imidazole-4,5-dicarboxamide, $N^4$-{4-[(2-chloro-4-fluorobenzoyl)amino]phenyl}-$N^5$-[2-(4-methylpiperidin-1-yl)ethyl]-1H-imidazole-4,5-dicarboxamide, $N^4$-{4-[(2-chloro-4-fluorobenzoyl)amino]phenyl}-$N^5$-[2-(piperidin-1-yl)ethyl]-1H-imidazole-4,5-dicarboxamide hydrochloric acid salt, $N^4$-{4-[(2-chloro-4-fluorobenzoyl)amino]phenyl}-$N^5$-(cyclopropylmethyl)-1H-imidazole-4,5-dicarboxamide, $N^5$-tert-butyl-$N^4$-{4-[(4-fluorobenzoyl)amino]phenyl}-1H-imidazole-4,5-dicarboxamide, $N^4$-{4-[(2-chlorobenzoyl)amino]phenyl}-$N^5$-(2-methoxyethyl)-1H-imidazole-4,5-dicarboxamide, $N^5$-cyclopropyl-$N^4$-{4-[(4-fluorobenzoyl)amino]phenyl}-1H-imidazole-4,5-dicarboxamide, $N^4$-{4-[(2-chloro-4-fluorobenzoyl)amino]phenyl}-$N^5$-(2-hydroxyethyl)-1H-imidazole-4,5-dicarboxamide, $N^5$-tert-butyl-$N^4$-{4-[(2-chloro-4-fluorobenzoyl)amino]phenyl}-1H-imidazole-4,5-dicarboxamide, $N^4$-{4-[(2-chloro-4-fluorobenzoyl)amino]phenyl}-$N^5$-[(2R)-3-methylbutan-2-yl]-1H-imidazole-4,5-dicarboxamide, $N^4$-{4-[(4-fluorobenzoyl)amino]phenyl}-$N^5$-[(2R)-3-methylbutan-2-yl]-1H-imidazole-4,5-dicarboxamide, $N^4$-{4-[(4-fluorobenzoyl)amino]phenyl}-$N^5$-(2-hydroxyethyl)-1H-imidazole-4,5-dicarboxamide, $N^5$-ethyl-$N^4$-{4[(4-fluorobenzoyl)amino]phenyl}-1H-imidazole-4,5-dicarboxamide, $N^4$-{4-[(2-chloro-4-fluorobenzoyl)amino]phenyl}-$N^5$-ethyl-1H-imidazole-4,5-dicarboxamide, $N^4$-{4-[(2-chloro-4-fluorobenzoyl)amino]phenyl}-$N^5$-(2,2-difluoroethyl)-1H-imidazole-4,5-dicarboxamide, $N^4$-{4-[(4-fluorobenzoyl)amino]phenyl}-$N^5$-(2-methoxyethyl)-1H-imidazole-4,5-dicarboxamide, $N^5$-(2,2-difluoroethyl)-$N^4$-{4-[(4-fluorobenzoyl)amino]phenyl}-1H-imidazole-4,5-dicarboxamide, 5-(azetidin-1-ylcarbonyl)-N-{4-[(2-chloro-4-fluorobenzoyl)amino]phenyl}-1H-imidazole-4-carboxamide, 5-(azetidin-1-ylcarbonyl)-N-{4-[(4-fluorobenzoyl)amino]phenyl}-1H-imidazole-4-carboxamide, $N^4$-{4-[(4-fluorobenzoyl)amino]phenyl}-$N^5$,$N^5$-dimethyl-1H-imidazole-4,5-dicarboxamide, N-{4-[(2-chloro-4-fluorobenzoyl)amino]phenyl}-5-(2-oxa-6-azaspiro[3.3]hept-6-ylcarbonyl)-1H-imidazole-4-carboxamide, $N^4$-{4-[(4-fluorobenzoyl)amino]phenyl}-$N^5$-isobutyl-1H-imidazole-4,5-dicarboxamide, $N^4$-{4-[(2-chloro-4-fluorobenzoyl)amino]phenyl}-$N^5$-isobutyl-1H-imidazole-4,5-dicarboxamide, $N^4$-{4-[(2-chlorobenzoyl)amino]phenyl}-$N^5$-(2,2-dimethylpropyl)-1H-imidazole-4,5-dicarboxamide, $N^5$-(2,2-dimethylpropyl)-$N^4$-{4-[(4-fluorobenzoyl)amino]phenyl}-1H-imidazole-4,5-dicarboxamide, $N^5$-(1,3-dihydroxypropan-2-yl)-$N^4$-{4-[(4-fluorobenzoyl)amino]phenyl}-1H-imidazole-4,5-dicarboxamide, $N^4$-{4-[(4-fluorobenzoyl)amino]phenyl}-$N^5$-[2-(morpholin-4-yl)ethyl]-1H-imidazole-4,5-dicarboxamide, $N^4$-{4-[(2-chlorobenzoyl)amino]phenyl}-$N^5$-[2-(3-hydroxypiperidin-1-yl)ethyl]-1H-imidazole-4,5-dicarboxamide, $N^4$-{4-[(2-chlorobenzoyl)amino]phenyl}-$N^5$-[2-(2-methylpiperidin-1-yl)ethyl]-1H-imidazole-4,5-dicarboxamide, $N^4$-{4-[(2-chlorobenzoyl)amino]phenyl}-$N^5$-[2-methyl-1-(morpholin-4-yl)propan-2-yl]-1H-imidazole-4,5-dicarboxamide, $N^4$-{4-[(2-chloro-4-fluorobenzoyl)amino]phenyl}-$N^5$-[2-methyl-1-(4-methylpiperidin-1-yl)propan-2-yl]-1H-imidazole-4,5-dicarboxamide, $N^4$-{4-[(4-fluorobenzoyl)amino]phenyl}-$N^5$-[2-methyl-1-(piperidin-1-yl)propan-2-yl]-1H-imidazole-4,5-dicarboxamide, $N^4$-{4-[(2-chlorobenzoyl)amino]phenyl}-$N^5$-(1,3-dihydroxypropan-2-yl)-1H-imidazole-4,5-dicarboxamide, $N^4$-{4-[(2-chlorobenzoyl)amino]phenyl}-$N^5$-[2-methyl-1-(4-methylpiperidin-1-yl)propan-2-yl]-1H-imidazole-4,5-dicarboxamide, $N^4$-{4-[(2-chlorobenzoyl)amino]phenyl}-$N^5$-[2-methyl-2-(piperidin-1-yl)propyl]-1H-imidazole-4,5-dicarboxamide, $N^4$-{4-[(2-chlorobenzoyl)amino]phenyl}-$N^5$-[2-(4-methylpiperazin-1-yl)ethyl]-1H-imidazole-4,5-dicarboxamide, $N^4$-{4-[(4-fluorobenzoyl)amino]phenyl}-$N^5$-[2-(4-methylpiperazin-1-yl)ethyl]-1H-imidazole-4,5-dicarboxamide, $N^4$-{4-[(2-chlorobenzoyl)amino]phenyl}-$N^5$-[1-(morpholin-4-yl)propan-2-yl]-1H-imidazole-4,5-dicarboxamide, $N^4$-{4-[(2-chlorobenzoyl)amino]phenyl}-$N^5$-[2-(4-methylpiperidin-1-yl)ethyl]-1H-imidazole-4,5-dicarboxamide, $N^4$-{4-[(4-fluorobenzoyl)amino]phenyl}-$N^5$-[2-(4-methylpiperidin-1-yl)ethyl]-1H-imidazole-4,5-dicarboxamide, $N^4$-{4-[(2-chlorobenzoyl)amino]phenyl}-$N^5$-[2-methyl-2-(piperidin-1-yl)propyl]-1H-imidazole-4,5-dicarboxamide, $N^4$-{4-[(2-chlorobenzoyl)amino]phenyl}-$N^5$-(2-fluoroethyl)-1H-imidazole-4,5-dicarboxamide, $N^4$-{4-[(4-fluorobenzoyl)amino]phenyl}-$N^5$-[2-(3-hydroxypiperidin-1-yl)ethyl]-1H-imidazole-4,5-dicarboxamide, $N^4$-{4[(2-chlorobenzoyl)amino]phenyl}-$N^5$-[2-(pyrrolidin-1-yl)ethyl]-1H-imidazole-4,5-dicarboxamide, $N^4$-{4-[(4-fluorobenzoyl)amino]phenyl}-$N^5$-[2-(2-methylpiperidin-1-yl)ethyl]-1H-imidazole-4,5-dicarboxamide, $N^4$-{4-[(2-chloro-4-fluorobenzoyl)amino]phenyl}-$N^5$-[2-(piperidin-1-yl)propyl]-1H-imidazole-4,5-dicarboxamide, $N^4$-{4-[(2-chlorobenzoyl)amino]phenyl}-$N^5$-[2-methyl-1-(piperidin-1-yl)propan-2-yl]-1H-imidazole-4,5-dicarboxamide, N⁴-{4-[(2-chloro-4-fluorobenzoyl)amino]phenyl}-N⁵-(1,3-dihydroxypropan-2-yl)-1H-imidazole-4,5-dicarboxamide, N⁴-{4-[(2-chloro-4-fluorobenzoyl)amino]phenyl}-N⁵-(2-fluoroethyl)-1H-imidazole-4,5-dicarboxamide, N⁴-{4[(4-fluorobenzoyl)amino]phenyl}-N⁵-(2-fluoroethyl)-1H-imidazole-4, 5-dicarboxamide, N⁴-{4-[(4-fluorobenzoyl)amino]phenyl}-N⁵-[2-methyl-1-(4-methylpiperidin-1-yl)propan-2-yl]-1H-imidazole-4,5-dicarboxamide, N⁴-{4-[(4-fluorobenzoyl)amino]phenyl}-N⁵-[2-(pyrrolidin-1-yl)ethyl]-1H-imidazole-4,5-dicarboxamide, N⁴-{4-[(2-chloro-4-fluorobenzoyl)amino]phenyl}-N⁵-(4-methylpiperazin-1-yl)-1H-imidazole-4,5-dicarboxamide, N⁴-{4-[(4-fluorobenzoyl)amino]phenyl}-N⁵-[2-(4-hydroxypiperidin-1-yl)ethyl]-1H-imidazole-4,5-dicarboxamide, N⁴-{4-[(4-fluorobenzoyl)amino]phenyl}-N⁵-[2-methyl-1-(morpholin-4-yl)propan-2-yl]-1H-imidazole-4,5-dicarboxamide, N⁴-{4-[(4-fluorobenzoyl)amino]phenyl}-N⁵-[3-(4-methylpiperazin-1-yl)propyl]-1H-imidazole-4,5-dicarboxamide, N⁴-{4[(2-chlorobenzoyl)amino]phenyl}-N⁵-[2-(piperidin-1-yl)propyl]-1H-imidazole-4,5-dicarboxamide, N⁴-{4-[(4-fluorobenzoyl)amino]phenyl}-N⁵-[2-(piperidin-1-yl)propyl]-1H-imidazole-4,5-dicarboxamide, N⁴-{4-[(2-chloro-4-fluorobenzoyl)amino]phenyl}-N⁵-[2-methyl-1-(piperidin-1-yl)propan-2-yl]-1H-imidazole-4,5-dicarboxamide, N⁴-{4-[(2-chloro-4-fluorobenzoyl)amino]phenyl}-N⁵-[2-(4-methylpiperazin-1-yl)propyl]-1H-imidazole-4,5-dicarboxamide, N⁴-{4-[(2-chlorobenzoyl)amino]phenyl}-N⁵-[2-(4-methylpiperazin-1-yl)propyl]-1H-imidazole-4,5-dicarboxamide, N⁴-{4-[(2-chlorobenzoyl)amino]phenyl}-N⁵-[2-methyl-2-(4-methylpiperazin-1-yl)propyl]-1H-imidazole-4,5-dicarboxamide, N⁴-{4-[(4-fluorobenzoyl)amino]phenyl}-N⁵-[2-methyl-2-(4-methylpiperazin-1-yl)propyl]-1H-imidazole-4,5-dicarboxamide, N⁴-{4-[(2-chlorobenzoyl)amino]phenyl}-N⁵-[4-(piperidin-1-yl)butyl]-1H-imidazole-4,5-dicarboxamide, N⁵-[2-(azetidin-1-yl)ethyl]-N⁴-{4-[(2-chlorobenzoyl)amino]phenyl}-1H-imidazole-4,5-dicarboxamide, N⁴-{4-[(2-chloro-4-fluorobenzoyl)amino]phenyl}-N⁵-[2-(2-methylpiperidin-1-yl)ethyl]-1H-imidazole-4,5-dicarboxamide, N⁴-{4-[(2-chlorobenzoyl)amino]phenyl}-N⁵-[3-(4-methylpiperazin-1-yl)propyl]-1H-imidazole-4,5-dicarboxamide, N⁴-{4-[(4-fluorobenzoyl)amino]phenyl}-N⁵-(4-methylpiperazin-1-yl)-1H-imidazole-4,5-dicarboxamide, N⁴-{4-[(2-chlorobenzoyl)amino]phenyl}-N⁵-[2-methyl-1-(4-methylpiperazin-1-yl)propan-2-yl]-1H-imidazole-4,5-dicarboxamide, N⁴-{4-[(4-fluorobenzoyl)amino]phenyl}-N⁵-[2-methyl-1-(4-methylpiperazin-1-yl)propan-2-yl]-1H-imidazole-4,5-dicarboxamide, N⁴-{4-[(2-chlorobenzoyl)amino]phenyl}-N⁵-[4-(piperidin-1-yl)butyl]-1H-imidazole-4,5-dicarboxamide, N⁴-{4-[(2-chlorobenzoyl)amino]phenyl}-N⁵-[2-(4-hydroxypiperidin-1-yl)ethyl]-1H-imidazole-4,5-dicarboxamide, N⁵-[2-(azetidin-1-yl)ethyl]-N⁴-{4-[(2-chloro-4-fluorobenzoyl)amino]phenyl}-1H-imidazole-4,5-dicarboxamide, N⁵-[2-(azetidin-1-yl)ethyl]-N⁴-{4-[(4-fluorobenzoyl)amino]phenyl}-1H-imidazole-4,5-dicarboxamide, N⁴-{4-[(2-chlorobenzoyl)amino]phenyl}-N⁵-[3-(morpholin-4-yl)propyl]-1H-imidazole-4,5-dicarboxamide, N⁴-{4-[(4-fluorobenzoyl)amino]phenyl}-N⁵-[4-(piperidin-1-yl)butyl]-1H-imidazole-4,5-dicarboxamide, N⁴-{4-[(2-chlorobenzoyl)amino]phenyl}-N⁵-[2-methyl-2-(4-methylpiperazin-1-yl)propyl]-1H-imidazole-4,5-dicarboxamide, N⁴-{4-[(2-chlorobenzoyl)amino]phenyl}-N⁵-[2-methyl-1-(4-methylpiperazin-1-yl)propan-2-yl]-1H-imidazole-4,5-dicarboxamide, N⁴-{4-[(2-chloro-4-fluorobenzoyl)amino]phenyl}-N⁵-[3-(morpholin-4-yl)propyl]-1H-imidazole-4,5-dicarboxamide, N⁴-{4-[(4-fluorobenzoyl)amino]phenyl}-N⁵-[2-(4-methylpiperazin-1-yl)propyl]-1H-imidazole-4,5-dicarboxamide, N⁴-{4-[(4-fluorobenzoyl)amino]phenyl}-N⁵-[3-(morpholin-4-yl)propyl]-1H-imidazole-4,5-dicarboxamide, N⁴-{4-[(2-chloro-4-fluorobenzoyl)amino]phenyl}-N⁵-[2-methyl-1-(morpholin-4-yl)propan-2-yl]-1H-imidazole-4,5-dicarboxamide, N⁴-{4-[(2-chloro-4-fluorobenzoyl)amino]phenyl}-N⁵-[2-(3-methylpiperidin-1-yl)ethyl]-1H-imidazole-4,5-dicarboxamide, N⁴-{4-[(4-fluorobenzoyl)amino]phenyl}-N⁵-[2-methyl-2-(piperidin-1-yl)propyl]-1H-imidazole-4,5-dicarboxamide, N⁴-{4-[(2-chlorobenzoyl)amino]phenyl}-N⁵-[2-(3-methylpiperidin-1-yl)ethyl]-1H-imidazole-4,5-dicarboxamide, N⁴-{4-[(4-fluorobenzoyl)amino]phenyl}-N⁵-[2-(3-methylpiperidin-1-yl)ethyl]-1H-imidazole-4,5-dicarboxamide, N⁴-{4-[(2-chloro-4-fluorobenzoyl)amino]phenyl}-N⁵-[2-(4-hydroxypiperidin-1-yl)ethyl]-1H-imidazole-4,5-dicarboxamide, N⁵-(4-{[(2,5-dichloro-3-thienyl)carbonyl]amino}phenyl)-N⁴-methyl-1H-imidazole-4,5-dicarboxamide, N⁴-{4-[(2-chlorobenzoyl)amino]phenyl}-N⁵-[2-(4,4-difluoropiperidin-1-yl)ethyl]-1H-imidazole-4,5-dicarboxamide, N⁴-{4-[(2-bromo-4-fluorobenzoyl)amino]phenyl}-N⁵-[2-(4,4-difluoropiperidin-1-yl)ethyl]-1H-imidazole-4,5-dicarboxamide, N⁴-{4-[(2-bromo-4-fluorobenzoyl)amino]phenyl}-N⁵-[2-(piperidin-1-yl)ethyl]-1H-imidazole-4,5-dicarboxamide, N⁴-{4-[(2-bromo-4-fluorobenzoyl)amino]phenyl}-N⁵-[2-(dimethylamino)ethyl]-1H-imidazole-4,5-dicarboxamide, N⁵-{4-[(2-chloro-4-fluorobenzoyl)amino]phenyl}-N⁴-[2-(4,4-difluoropiperidin-1-yl)ethyl]-1,3-oxazole-4,5-dicarboxamide, N⁴-(2-amino-2-methylpropyl)-N⁵-{4-[(2-chloro-4-fluorobenzoyl)amino]phenyl}-1,3-oxazole-4,5-dicarboxamide, N⁵-{4-[(2-chloro-4-fluorobenzoyl)amino]phenyl}-N⁴-[2-(3-fluoropiperidin-1-yl)ethyl]-1,3-oxazole-4,5-dicarboxamide, N⁵-{4-[(2-chloro-4-fluorobenzoyl)amino]phenyl}-N⁴-{2-[(3S)-3-fluoropyrrolidin-1-yl]ethyl}-1,3-oxazole-4,5-dicarboxamide, N⁵-{4-[(2-chloro-4-fluorobenzoyl)amino]phenyl}-N⁴-{2-[(3R)-3-fluoropyrrolidin-1-yl]ethyl}-1,3-oxazole-4,5-dicarboxamide, N⁴-{4-[(2-chloro-4-fluorobenzoyl)amino]phenyl}-N⁵-(2-hydroxy-2-methylpropyl)-1H-imidazole-4,5-dicarboxamide, N⁴-{4-[(2-chloro-4-fluorobenzoyl)amino]phenyl}-N⁵-[2-(4,4-difluoropiperidin-1-yl)ethyl]-1H-imidazole-4,5-dicarboxamide, N⁴-{4-[(2-chloro-4-fluorobenzoyl)amino]phenyl}-N⁵-[2-(3,3-difluoropiperidin-1-yl)ethyl]-1H-imidazole-4,5-dicarboxamide,
N⁴-{4-[(2-chloro-4-fluorobenzoyl)amino]phenyl}-N⁵-[2-(3-fluoropiperidin-1-yl)ethyl]-1H-imidazole-4,5-dicarboxamide,
N⁴-{4-[(2-chloro-4-fluorobenzoyl)amino]phenyl}-N⁵-[2-(morpholin-4-yl)ethyl]-1H-imidazole-4,5-dicarboxamide,
N⁴-{4-[(2-chloro-4-fluorobenzoyl)amino]phenyl}-N⁵-[2-(pyrrolidin-1-yl)ethyl]-1H-imidazole-4,5-dicarboxamide,
N⁴-{4-[(2-chloro-4-fluorobenzoyl)amino]phenyl}-N⁵-[2-(3-hydroxypiperidin-1-yl)ethyl]-1H-imidazole-4,5-dicarboxamide,
N⁴-{4-[(2-chloro-4-fluorobenzoyl)amino]phenyl}-N⁵-[2-(4-fluoropiperidin-1-yl)ethyl]-1H-imidazole-4,5-dicarboxamide,
N⁴-{4-[(2-chloro-4-fluorobenzoyl)amino]phenyl}-N⁵-{2-[(3R)-3-fluoropyrrolidin-1-yl]ethyl}-1H-imidazole-4,5-dicarboxamide,
N⁴-{4-[(2-chloro-4-fluorobenzoyl)amino]phenyl}-N⁵-{2-[(3S)-3-fluoropyrrolidin-1-yl]ethyl}-1H-imidazole-4,5-dicarboxamide,
N⁴-{4-[(2-chloro-4-fluorobenzoyl)amino]phenyl}-N⁵-(tetrahydro-2H-pyran-4-ylmethyl)-1H-imidazole-4,5-dicarboxamide,
N⁴-{4-[(2-chloro-4-fluorobenzoyl)amino]phenyl}-N⁵-(tetrahydro-2H-pyran-4-yl)-1H-imidazole-4,5-dicarboxamide,
N⁴-{4-[(2-chloro-4-fluorobenzoyl)amino]phenyl}-N⁵-(tetrahydrofuran-3-ylmethyl)-1H-imidazole-4,5-dicarboxamide,
N⁴-{4-[(2-chloro-4-fluorobenzoyl)amino]phenyl}-N⁵-(tetrahydrofuran-3-yl)-1H-imidazole-4,5-dicarboxamide,
N⁴-{4-[(2-chloro-4-fluorobenzoyl)amino]phenyl}-N⁵-(tetrahydrofuran-2-ylmethyl)-1H-imidazole-4,5-dicarboxamide,
N⁴-{4-[(2-chloro-4-fluorobenzoyl)amino]phenyl}-N⁵-[2-(4-methylpiperazin-1-yl)ethyl]-1H-imidazole-4,5-dicarboxamide,
N⁵-{4-[(2-hydroxybenzoyl)amino]phenyl}-N⁴-methyl-1H-imidazole-4,5-dicarboxamide,
N⁵-{4-[(2-chloro-4,5-dimethoxybenzoyl)amino]phenyl}-N⁴-methyl-1H-imidazole-4,5-dicarboxamide,
N⁵-(4-{[2-(difluoromethyl)benzoyl]amino}phenyl)-N⁴-methyl-1H-imidazole-4,5-dicarboxamide,
N⁵-{4-[(2-chloro-4,5-difluorobenzoyl)amino]phenyl}-N⁴-methyl-1H-imidazole-4,5-dicarboxamide,
N⁴-methyl-N⁵-(4-{[2-(trifluoromethoxy)benzoyl]amino}phenyl)-1H-imidazole-4,5-dicarboxamide,
N⁵-{4-[(2-chloro-4-methylbenzoyl)amino]phenyl}-N⁴-methyl-1H-imidazole-4,5-dicarboxamide,
N⁵-{4-[(4-fluoro-2-hydroxybenzoyl)amino]phenyl}-N⁴-methyl-1H-imidazole-4,5-dicarboxamide,
N⁵-{4-[(2-chloro-4-methoxybenzoyl)amino]phenyl}-N⁴-methyl-1H-imidazole-4,5-dicarboxamide,
N⁵-(4-{[(3-chloropyridin-2-yl)carbonyl]amino}phenyl)-N⁴-methyl-1H-imidazole-4,5-dicarboxamide,
N⁵-{4-[(2-chloro-5-methoxybenzoyl)amino]phenyl}-N⁴-methyl-1H-imidazole-4,5-dicarboxamide,
N⁴-methyl-N⁵-(4-{[2-(methylsulfonyl)benzoyl]amino}phenyl)-1H-imidazole-4,5-dicarboxamide,
N⁵-{4-[(2-chloro-4-ethoxybenzoyl)amino]phenyl}-N⁴-methyl-1H-imidazole-4,5-dicarboxamide,
N⁵-(4-{[4-(difluoromethoxy)-2-fluorobenzoyl]amino}phenyl)-N⁴-methyl-1H-imidazole-4,5-dicarboxamide,
N⁵-{4-[(2-chloro-3-methoxybenzoyl)amino]phenyl}-N⁴-methyl-1H-imidazole-4,5-dicarboxamide,
N⁵-(4-{[2-fluoro-4-(trifluoromethoxy)benzoyl]amino}phenyl)-N⁴-methyl-1H-imidazole-4,5-dicarboxamide,
N⁵-(4-{[(4-chloropyridin-3-yl)carbonyl]amino}phenyl)-N⁴-methyl-1H-imidazole-4,5-dicarboxamide,
N⁵-(4-{[2-chloro-4-(S-ethylsulfonimidoyl)benzoyl]amino}phenyl)-N⁴-methyl-1H-imidazole-4,5-dicarboxamide,
N⁵-(4-{[2-chloro-4-(S-ethylsulfonimidoyl)benzoyl]amino}phenyl)-N⁴-[2-(piperidin-1-yl)ethyl]-1H-imidazole-4,5-dicarboxamide,
N⁴-ethyl-N⁵-(4-{[2-(methylsulfonyl)benzoyl]amino}phenyl)-1H-imidazole-4,5-dicarboxamide,
N⁵-(4-{[4-(difluoromethoxy)-2-fluorobenzoyl]amino}phenyl)-N⁴-ethyl-1H-imidazole-4,5-dicarboxamide,
N⁵-{4-[(2-chloro-4-ethoxybenzoyl)amino]phenyl}-N⁴-ethyl-1H-imidazole-4,5-dicarboxamide,
N⁵-{4-[(2-chloro-3-methoxybenzoyl)amino]phenyl}-N⁴-ethyl-1H-imidazole-4,5-dicarboxamide,
N⁵-(4-{[(3-chloropyridin-2-yl)carbonyl]amino}phenyl)-N⁴-ethyl-1H-imidazole-4,5-dicarboxamide,
N⁴-ethyl-N⁵-(4-{[2-fluoro-4-(trifluoromethoxy)benzoyl]amino}phenyl)-1H-imidazole-4,5-dicarboxamide,
N⁵-(4-{[(4-chloropyridin-3-yl)carbonyl]amino}phenyl)-N⁴-ethyl-1H-imidazole-4,5-dicarboxamide,
N⁵-{4-[(2-chloro-5-methoxybenzoyl)amino]phenyl}-N⁴-ethyl-1H-imidazole-4,5-dicarboxamide,
N⁴-{4-[(2-chloro-4-fluorobenzoyl)amino]phenyl}-N⁵-[2-(3-methoxypyrrolidin-1-yl)ethyl]-1H-imidazole-4,5-dicarboxamide,
N⁴-{4-[(2-chloro-4-fluorobenzoyl)amino]phenyl}-N⁵-{2-[(2S)-2-methylpiperidin-1-yl]ethyl}-1H-imidazole-4,5-dicarboxamide,
N⁴-{4-[(2-chloro-4-fluorobenzoyl)amino]phenyl}-N⁵-{2-[(2S)-2-methylpiperidin-1-yl]ethyl}-1H-imidazole-4,5-dicarboxamide formic acid salt,
N⁴-{4-[(2-chloro-4-fluorobenzoyl)amino]phenyl}-N⁵-{2-[(2R)-2-methylpiperidin-1-yl]ethyl}-1H-imidazole-4,5-dicarboxamide,
N⁴-{4-[(2-chloro-4-fluorobenzoyl)amino]phenyl}-N⁵-[1-(morpholin-4-yl)propan-2-yl]-1H-imidazole-4,5-dicarboxamide,
N⁴-{4-[(2-chloro-4-fluorobenzoyl)amino]phenyl}-N⁵-[1-(morpholin-4-yl)propan-2-yl]-1H-imidazole-4,5-dicarboxamide,
N⁴-{4-[(2-chloro-4-fluorobenzoyl)amino]phenyl}-N⁵-[1-(morpholin-4-yl)propan-2-yl]-1H-imidazole-4,5-dicarboxamide,
N⁴-{4-[(2-chloro-4-fluorobenzoyl)amino]phenyl}-N⁵-{2-[(3S)-3-hydroxypiperidin-1-yl]ethyl}-1H-imidazole-4,5-dicarboxamide,
N⁴-{4-[(2-chloro-4-fluorobenzoyl)amino]phenyl}-N⁵-{2-[(3R)-3-hydroxypiperidin-1-yl]ethyl}-1H-imidazole-4,5-dicarboxamide,
N⁴-{4-[(2-chloro-4-fluorobenzoyl)amino]phenyl}-N⁵-[3-(3-hydroxypiperidin-1-yl)propyl]-1H-imidazole-4,5-dicarboxamide,
N⁴-{4-[(2-chloro-4-fluorobenzoyl)amino]phenyl}-N⁵-[3-(pyrrolidin-1-yl)propyl]-1H-imidazole-4,5-dicarboxamide,
N⁴-{4-[(2-chloro-4-fluorobenzoyl)amino]phenyl}-N⁵-[3-(4-hydroxypiperidin-1-yl)propyl]-1H-imidazole-4,5-dicarboxamide, N⁴-{4-[(2-chloro-4-fluorobenzoyl)amino]phenyl}-N⁵-{2-[(3S)-3-fluoropiperidin-1-yl]ethyl}-1H-imidazole-4,5-dicarboxamide,
N⁴-{4-[(2-chloro-4-fluorobenzoyl)amino]phenyl}-N⁵-{2-[(3R)-3-fluoropiperidin-1-yl]ethyl}-1H-imidazole-4,5-dicarboxamide,
N⁴-{4-[(2-chloro-4-fluorobenzoyl)amino]phenyl}-N⁵-{2-[(3R)-3-methylpiperidin-1-yl]ethyl}-1H-imidazole-4,5-dicarboxamide,
N⁴-{4-[(2-chloro-4-fluorobenzoyl)amino]phenyl}-N⁵-[2-(3,3-difluoropyrrolidin-1-yl)ethyl]-1H-imidazole-4,5-dicarboxamide,
N⁵-(2-amino-2-methylpropyl)-N⁴-{4-[(2-chloro-4-fluorobenzoyl)amino]phenyl}-1H-imidazole-4,5-dicarboxamide,
N⁴-{4-[(2-chloro-4-fluorobenzoyl)amino]phenyl}-N⁵-[(3S)-pyrrolidin-3-yl]-1H-imidazole-4,5-dicarboxamide,
N⁴-{4-[(2-chloro-4-fluorobenzoyl)amino]phenyl}-N⁵-[(3R)-pyrrolidin-3-yl]-1H-imidazole-4,5-dicarboxamide,
N⁴-{4-[(2-chloro-4-fluorobenzoyl)amino]phenyl}-N⁵-[(3R)-pyrrolidin-3-yl]-1H-imidazole-4,5-dicarboxamide hydrochloric acid salt,
N⁵-(3-amino-3-methylbutyl)-N⁴-{4-[(2-chlorobenzoyl)amino]phenyl}-1H-imidazole-4,5-dicarboxamide,
N⁵-(3-amino-3-methylbutyl)-N⁴-{4-[(2-chlorobenzoyl)amino]phenyl}-1H-imidazole-4,5-dicarboxamide hydrochloric acid salt,
N⁴-{4-[(2-chloro-4-fluorobenzoyl)amino]phenyl}-N⁵-(pyrrolidin-2-ylmethyl)-1H-imidazole-4,5-dicarboxamide,
N⁴-{4-[(2-chloro-4-fluorobenzoyl)amino]phenyl}-N⁵-(pyrrolidin-2-ylmethyl)-1H-imidazole-4,5-dicarboxamide hydrochloric acid salt,
5-[(3-aminopyrrolidin-1-yl)carbonyl]-N-{4-[(2-chloro-4-fluorobenzoyl)amino]phenyl}-1H-imidazole-4-carboxamide,
5-[(3-aminopyrrolidin-1-yl)carbonyl]-N-{4-[(2-chloro-4-fluorobenzoyl)amino]phenyl}-1H-imidazole-4-carboxamide hydrochloric acid salt,
N⁵-(3-amino-3-methylbutyl)-N⁴-{4-[(2-chloro-4-fluorobenzoyl)amino]phenyl}-1H-imidazole-4,5-dicarboxamide,
N⁴-{4-[(2-chloro-4-fluorobenzoyl)amino]phenyl}-N⁵-[2-(methylamino)ethyl]-1H-imidazole-4,5-dicarboxamide,
N⁴-{4-[(2-chloro-4-fluorobenzoyl)amino]phenyl}-N⁵-[2-(isopropylamino)ethyl]-1H-imidazole-4,5-dicarboxamide,
N-{4-[(2-chloro-4-fluorobenzoyl)amino]phenyl}-5-(piperazin-1-ylcarbonyl)-1H-imidazole-4-carboxamide,
N-{4-[(2-chloro-4-fluorobenzoyl)amino]phenyl}-5-(piperazin-1-ylcarbonyl)-1H-imidazole-4-carboxamide hydrochloric acid salt,
N⁵-(2-aminoethyl)-N⁴-{4-[(2-chloro-4-fluorobenzoyl)amino]phenyl}-1H-imidazole-4,5-dicarboxamide,
N⁴-{4-[(2-chloro-4-fluorobenzoyl)amino]-3-(trifluoromethoxy)phenyl}-N⁵-methyl-1H-imidazole-4,5-dicarboxamide,
N⁴-{4-[(2-chloro-4-fluorobenzoyl)amino]-3-(trifluoromethoxy)phenyl}-N⁵-(2,2,2-trifluoroethyl)-1H-imidazole-4,5-dicarboxamide,
N⁴-{4-[(2-chloro-4-fluorobenzoyl)amino]-3-(trifluoromethoxy)phenyl}-N⁵-[2-(piperidin-1-yl)ethyl]-1H-imidazole-4,5-dicarboxamide,
N⁴-{4-[(4-fluorobenzoyl)amino]phenyl}-N⁵-[1-(morpholin-4-yl)propan-2-yl]-1H-imidazole-4,5-dicarboxamide,
N⁴-{4-[(4-fluorobenzoyl)amino]phenyl}-N⁵-[1-(morpholin-4-yl)propan-2-yl]-1H-imidazole-4,5-dicarboxamide,
N⁴-{4-[(4-fluorobenzoyl)amino]phenyl}-N⁵-[1-(morpholin-4-yl)propan-2-yl]-1H-imidazole-4,5-dicarboxamide,
N⁴-{4-[(2-chloro-4-fluorobenzoyl)amino]phenyl}-N⁵-[3-(piperidin-1-yl)propyl]-1H-imidazole-4,5-dicarboxamide,
N⁴-{4-[(2-chloro-4-fluorobenzoyl)amino]phenyl}-N⁵-[(1-methylpiperidin-3-yl)methyl]-1H-imidazole-4,5-dicarboxamide,
N⁴-{4-[(2-chloro-4-fluorobenzoyl)amino]phenyl}-N⁵-[3-(2-oxopyrrolidin-1-yl)propyl]-1H-imidazole-4,5-dicarboxamide,
N⁴-{4-[(2-chlorobenzoyl)amino]phenyl}-N⁵-[2-(2,6-dimethylmorpholin-4-yl)ethyl]-1H-imidazole-4,5-dicarboxamide,
N⁴-{4-[(2-4-fluorochlorobenzoyl)amino]phenyl}-N⁵-[2-(2,6-dimethylmorpholin-4-yl)ethyl]-1H-imidazole-4,5-dicarboxamide,
N⁴-{4-[(2-chlorobenzoyl)amino]phenyl}-N⁵-(4-methylpiperazin-1-yl)-1H-imidazole-4,5-dicarboxamide,
N⁵-{4-[(2-chloro-4-fluorobenzoyl)amino]phenyl}-N⁴-[2-(piperidin-1-yl)ethyl]-1,3-oxazole-4,5-dicarboxamide,
N⁵-{4-[(4-methoxybenzoyl)amino]phenyl}-N⁴-methyl-1H-imidazole-4,5-dicarboxamide,
N⁵-{4-[(3-methoxybenzoyl)amino]phenyl}-N⁴-methyl-1H-imidazole-4,5-dicarboxamide,
N⁵-{4[(4-chlorobenzoyl)amino]phenyl}-N⁴-methyl-1H-imidazole-4,5-dicarboxamide,
N⁵-{4-[(2,5-dimethylbenzoyl)amino]phenyl}-N⁴-methyl-1H-imidazole-4,5-dicarboxamide,
N⁵-{4-[(3,4-dichlorobenzoyl)amino]phenyl}-N⁴-methyl-1H-imidazole-4,5-dicarboxamide,
N⁵-{4-[(2,5-dichlorobenzoyl)amino]phenyl}-N⁴-methyl-1H-imidazole-4,5-dicarboxamide,
N⁵-{4-[(4-chloro-2-methoxybenzoyl)amino]phenyl}-N⁴-methyl-1H-imidazole-4,5-dicarboxamide,
N⁵-{4[(3-cyanobenzoyl)amino]phenyl}-N⁴-methyl-1H-imidazole-4,5-dicarboxamide,
N⁵-[4-(3-furoylamino)phenyl]-N⁴-methyl-1H-imidazole-4,5-dicarboxamide,
N⁵-{4-[(5-bromo-2-chlorobenzoyl)amino]phenyl}-N⁴-methyl-1H-imidazole-4,5-dicarboxamide,
N⁴-methyl-N⁵-(4-{[3-(trifluoromethyl)benzoyl]amino}phenyl)-1H-imidazole-4,5-dicarboxamide,
N⁵-(4-{[4-(dimethylamino)benzoyl]amino}phenyl)-N⁴-methyl-1H-imidazole-4,5-dicarboxamide,
N⁴-methyl-N⁵-(4-{[4-(trifluoromethyl)benzoyl]amino}phenyl)-1H-imidazole-4,5-dicarboxamide,
N⁵-(4-{[3-(dimethylamino)benzoyl]amino}phenyl)-N⁴-methyl-1H-imidazole-4,5-dicarboxamide,
N⁵-{4-[(2,5-difluorobenzoyl)amino]phenyl}-N⁴-methyl-1H-imidazole-4,5-dicarboxamide,
N⁵-{4-[(2,3-difluorobenzoyl)amino]phenyl}-N⁴-methyl-1H-imidazole-4,5-dicarboxamide,
N⁵-{4-[(3,4-difluorobenzoyl)amino]phenyl}-N⁴-methyl-1H-imidazole-4,5-dicarboxamide,
N⁵-{4-[(3,5-difluorobenzoyl)amino]phenyl}-N⁴-methyl-1H-imidazole-4,5-dicarboxamide,
N⁵-{4[(4-cyanobenzoyl)amino]phenyl}-N⁴-methyl-1H-imidazole-4,5-dicarboxamide,
N⁴-methyl-N⁵-{4-[(2,3,6-trifluorobenzoyl)amino]phenyl}-1H-imidazole-4,5-dicarboxamide,
N⁵-{4-[(3-fluoro-2-methylbenzoyl)amino]phenyl}-N⁴-methyl-1H-imidazole-4,5-dicarboxamide,
N⁵-{4[(3-chlorobenzoyl)amino]phenyl}-N⁴-methyl-1H-imidazole-4,5-dicarboxamide,
N⁵-{4[(2-fluorobenzoyl)amino]phenyl}-N⁴-methyl-1H-imidazole-4,5-dicarboxamide,
N⁵-{4-[(3,5-dichlorobenzoyl)amino]phenyl}-N⁴-methyl-1H-imidazole-4,5-dicarboxamide, $N^5$-{4-[(3-fluoro-4-methylbenzoyl)amino]phenyl}-$N^4$-methyl-1H-imidazole-4,5-dicarboxamide,
$N^5$-[4-(2-furoylamino)phenyl]-$N^4$-methyl-1H-imidazole-4,5-dicarboxamide,
$N^5$-{4[(3-fluorobenzoyl)amino]phenyl}-$N^4$-methyl-1H-imidazole-4,5-dicarboxamide,
$N^4$-methyl-$N^5$-(4-{[(1-methyl-1H-pyrazol-3-yl)carbonyl]amino}phenyl)-1H-imidazole-4,5-dicarboxamide,
$N^5$-{4-[(4-chloro-2-fluorobenzoyl)amino]phenyl}-$N^4$-methyl-1H-imidazole-4,5-dicarboxamide,
$N^5$-{4-[(4-bromo-2-chlorobenzoyl)amino]phenyl}-$N^4$-methyl-1H-imidazole-4,5-dicarboxamide,
$N^5$-{4-[(3,5-dimethylbenzoyl)amino]phenyl}-$N^4$-methyl-1H-imidazole-4,5-dicarboxamide,
$N^4$-methyl-$N^5$-{4-[(3-methylbenzoyl)amino]phenyl}-1H-imidazole-4,5-dicarboxamide,
$N^4$-methyl-$N^5$-{4-[(4-methylbenzoyl)amino]phenyl}-1H-imidazole-4,5-dicarboxamide,
$N^5$-{4-[(3-fluoro-4-methoxybenzoyl)amino]phenyl}-$N^4$-methyl-1H-imidazole-4,5-dicarboxamide,
$N^5$-(4-{[2-(dimethylamino)benzoyl]amino}phenyl)-$N^4$-methyl-1H-imidazole-4,5-dicarboxamide,
$N^5$-{4-[(3-chloro-4-fluorobenzoyl)amino]phenyl}-$N^4$-methyl-1H-imidazole-4,5-dicarboxamide,
$N^5$-{4-[(3-chloro-2-methylbenzoyl)amino]phenyl}-$N^4$-methyl-1H-imidazole-4,5-dicarboxamide,
$N^4$-methyl-$N^5$-{4-[(2,4,6-trifluorobenzoyl)amino]phenyl}-1H-imidazole-4,5-dicarboxamide,
$N^5$-{4-[(2-chloro-6-methylbenzoyl)amino]phenyl}-$N^4$-methyl-1H-imidazole-4,5-dicarboxamide,
$N^5$-{4-[(3-chloro-4-methylbenzoyl)amino]phenyl}-$N^4$-methyl-1H-imidazole-4,5-dicarboxamide,
$N^4$-methyl-$N^5$-{4-[(1,3-thiazol-5-ylcarbonyl)amino]phenyl}-1H-imidazole-4,5-dicarboxamide,
$N^5$-{4-[(2-chloro-3-methylbenzoyl)amino]phenyl}-$N^4$-methyl-1H-imidazole-4,5-dicarboxamide,
$N^4$-methyl-$N^5$-{4-[(2,3,5-trifluorobenzoyl)amino]phenyl}-1H-imidazole-4,5-dicarboxamide,
$N^5$-{4-[(2-chloro-3,4-dimethoxybenzoyl)amino]phenyl}-$N^4$-methyl-1H-imidazole-4,5-dicarboxamide,
$N^5$-{4-[(5-cyano-2-fluorobenzoyl)amino]phenyl}-$N^4$-methyl-1H-imidazole-4,5-dicarboxamide,
$N^5$-{4-[(4-cyano-3-fluorobenzoyl)amino]phenyl}-$N^4$-methyl-1H-imidazole-4,5-dicarboxamide,
$N^5$-{4-[(2-chloroisonicotinoyl)amino]phenyl}-$N^4$-methyl-1H-imidazole-4,5-dicarboxamide,
$N^5$-(4-{[2-chloro-5-(trifluoromethyl)benzoyl]amino}phenyl)-$N^4$-methyl-1H-imidazole-4,5-dicarboxamide,
$N^5$-(4-{[(6-chloropyridin-2-yl)carbonyl]amino}phenyl)-$N^4$-methyl-1H-imidazole-4,5-dicarboxamide,
$N^4$-methyl-$N^5$-{4-[(1,2-oxazol-5-ylcarbonyl)amino]phenyl}-1H-imidazole-4,5-dicarboxamide,
$N^5$-{4-[(4-methoxy-3-methylbenzoyl)amino]phenyl}-$N^4$-methyl-1H-imidazole-4,5-dicarboxamide,
$N^4$-methyl-$N^5$-(4-{[(3-methylpyridin-2-yl)carbonyl]amino}phenyl)-1H-imidazole-4,5-dicarboxamide,
$N^4$-methyl-$N^5$-(4-{[(5-methylpyridin-2-yl)carbonyl]amino}phenyl)-1H-imidazole-4,5-dicarboxamide,
$N^5$-(4-{[2-chloro-3-(trifluoromethyl)benzoyl]amino}phenyl)-$N^4$-methyl-1H-imidazole-4,5-dicarboxamide,
$N^5$-{4-[(3-chloro-2,4-difluorobenzoyl)amino]phenyl}-$N^4$-methyl-1H-imidazole-4,5-dicarboxamide,
$N^5$-{4-[(3-chloro-5-fluorobenzoyl)amino]phenyl}-$N^4$-methyl-1H-imidazole-4,5-dicarboxamide,
$N^5$-{4-[(2-chloro-5-fluorobenzoyl)amino]phenyl}-$N^4$-methyl-1H-imidazole-4,5-dicarboxamide,
$N^5$-{4-[(3-chloro-4,5-difluorobenzoyl)amino]phenyl}-$N^4$-methyl-1H-imidazole-4,5-dicarboxamide,
$N^4$-methyl-$N^5$-(4-{[(4-methylpyridin-2-yl)carbonyl]amino}phenyl)-1H-imidazole-4,5-dicarboxamide,
$N^5$-{4-[(5-fluoro-2-methoxybenzoyl)amino]phenyl}-$N^4$-methyl-1H-imidazole-4,5-dicarboxamide,
$N^5$-{4-[(2-fluoro-3-methoxybenzoyl)amino]phenyl}-$N^4$-methyl-1H-imidazole-4,5-dicarboxamide,
$N^4$-methyl-$N^5$-(4-{[(5-methylpyridin-3-yl)carbonyl]amino}phenyl)-1H-imidazole-4,5-dicarboxamide,
$N^5$-{4-[(3-fluoro-2-methoxybenzoyl)amino]phenyl}-$N^4$-methyl-1H-imidazole-4,5-dicarboxamide,
$N^5$-{4-[(4-cyano-2-fluorobenzoyl)amino]phenyl}-$N^4$-methyl-1H-imidazole-4,5-dicarboxamide,
$N^5$-{4-[(2-chloro-3-fluorobenzoyl)amino]phenyl}-$N^4$-methyl-1H-imidazole-4,5-dicarboxamide,
$N^5$-{4-[(3-cyano-5-fluorobenzoyl)amino]phenyl}-$N^4$-methyl-1H-imidazole-4,5-dicarboxamide,
$N^5$-(4-{[(3-chloropyrazin-2-yl)carbonyl]amino}phenyl)-$N^4$-methyl-1H-imidazole-4,5-dicarboxamide,
$N^5$-{4-[(4-fluoro-3-methylbenzoyl)amino]phenyl}-$N^4$-methyl-1H-imidazole-4,5-dicarboxamide,
$N^5$-{4-[(2-chloro-3,6-difluorobenzoyl)amino]phenyl}-$N^4$-methyl-1H-imidazole-4,5-dicarboxamide,
$N^5$-{4-[(2-fluoro-6-methylbenzoyl)amino]phenyl}-$N^4$-methyl-1H-imidazole-4,5-dicarboxamide,
$N^4$-methyl-$N^5$-{4-[(1,2-oxazol-3-ylcarbonyl)amino]phenyl}-1H-imidazole-4,5-dicarboxamide,
$N^5$-{4-[(4,5-difluoro-2-methylbenzoyl)amino]phenyl}-$N^4$-methyl-1H-imidazole-4,5-dicarboxamide,
$N^5$-{4-[(2-chloro-4-fluorobenzoyl)amino]phenyl}-$N^4$-[5-(dimethylamino)pentyl]-1H-imidazole-4,5-dicarboxamide,
$N^5$-{4-[(2-chloro-4-fluorobenzoyl)amino]phenyl}-$N^4$-[(2S)-1-hydroxy-3-methylbutan-2-yl]-1H-imidazole-4,5-dicarboxamide,
$N^5$-{4-[(2-chloro-4-fluorobenzoyl)amino]phenyl}-$N^4$-[5-(diethylamino)pentan-2-yl]-1H-imidazole-4,5-dicarboxamide,
$N^4$-{4-[(2-chlorobenzoyl)amino]phenyl}-$N^5$-[2-(piperidin-1-yl)ethyl]-1H-imidazole-4,5-dicarboxamide,
$N^5$-{4-[(2-chloro-4-fluorobenzoyl)amino]phenyl}-$N^4$-[2-(diethylamino)ethyl]-1H-imidazole-4,5-dicarboxamide,
$N^5$-{4-[(2-chloro-4-fluorobenzoyl)amino]phenyl}-$N^4$-(3-isopropoxypropyl)-1H-imidazole-4,5-dicarboxamide,
$N^5$-{4-[(2-chloro-4-fluorobenzoyl)amino]phenyl}-$N^4$-(2-phenylethyl)-1H-imidazole-4,5-dicarboxamide,
$N^5$-{4-[(2-chloro-4-fluorobenzoyl)amino]phenyl}-$N^4$-[2-(1-methylpyrrolidin-2-yl)ethyl]-1H-imidazole-4,5-dicarboxamide,
$N^5$-{4-[(2-chloro-4-fluorobenzoyl)amino]phenyl}-$N^4$-[3-(2-methylpiperidin-1-yl)propyl]-1H-imidazole-4,5-dicarboxamide,
$N^5$-{4-[(2-chloro-4-fluorobenzoyl)amino]phenyl}-$N^4$-[2-(pyridin-2-yl)ethyl]-1H-imidazole-4,5-dicarboxamide,
$N^5$-{4-[(2-chloro-4-fluorobenzoyl)amino]phenyl}-$N^4$-[3-(diethylamino)propyl]-1H-imidazole-4,5-dicarboxamide,
$N^5$-{4-[(2-chloro-4-fluorobenzoyl)amino]phenyl}-$N^4$-[2-(diisopropylamino)ethyl]-1H-imidazole-4,5-dicarboxamide,
$N^5$-{4-[(2-chloro-4-fluorobenzoyl)amino]phenyl}-$N^4$-[(1-ethylpyrrolidin-2-yl)methyl]-1H-imidazole-4,5-dicarboxamide, N$^5$-{4-[(2-chloro-4-fluorobenzoyl)amino]phenyl}-N$^4$-(2,2-dimethyltetrahydro-2H-pyran-4-yl)-1H-imidazole-4,5-dicarboxamide, N$^5$-{4-[(2-chloro-4-fluorobenzoyl)amino]phenyl}-N$^4$-[3-(4-methylpiperazin-1-yl)propyl]-1H-imidazole-4,5-dicarboxamide, N$^5$-{4-[(2-chloro-4-fluorobenzoyl)amino]phenyl}-N$^4$-[4-(diethylamino)butyl]-1H-imidazole-4,5-dicarboxamide, N$^5$-{4-[(2-chloro-4-fluorobenzoyl)amino]phenyl}-N$^4$-[2-(pyridin-4-yl)ethyl]-1H-imidazole-4,5-dicarboxamide, N$^5$-{4-[(2-chloro-4-fluorobenzoyl)amino]phenyl}-N$^4$-[3-(dimethylamino)-2,2-dimethylpropyl]-1H-imidazole-4,5-dicarboxamide, N$^5$-{4-[(2-chloro-4-fluorobenzoyl)amino]phenyl}-N$^4$-(tetrahydro-2H-pyran-4-ylmethyl)-1H-imidazole-4,5-dicarboxamide, N$^5$-{4-[(2-chloro-4-fluorobenzoyl)amino]phenyl}-N$^4$-[2-(2-oxopyrrolidin-1-yl)ethyl]-1H-imidazole-4,5-dicarboxamide, N$^5$-{4-[(2-chloro-4-fluorobenzoyl)amino]phenyl}-N$^4$-[2-(2-oxoimidazolidin-1-yl)ethyl]-1H-imidazole-4,5-dicarboxamide, N$^5$-{4-[(2-chloro-4-fluorobenzoyl)amino]phenyl}-N$^4$-[3-(4-methylpiperidin-1-yl)propyl]-1H-imidazole-4,5-dicarboxamide, N$^5$-{4-[(2-chloro-4-fluorobenzoyl)amino]phenyl}-N$^4$-[2-(2,6-dimethylpiperidin-1-yl)ethyl]-1H-imidazole-4,5-dicarboxamide, N$^5$-{4-[(2-chloro-4-fluorobenzoyl)amino]phenyl}-N$^4$-[2-(1,1-dioxidothiomorpholin-4-yl)ethyl]-1H-imidazole-4,5-dicarboxamide, N$^5$-{4-[(2-chloro-4-fluorobenzoyl)amino]phenyl}-N$^4$-{[(2S)-1-ethylpyrrolidin-2-yl]methyl}-1H-imidazole-4,5-dicarboxamide, N$^5$-{4-[(2-chloro-4-fluorobenzoyl)amino]phenyl}-N$^4$-[2-(pyridin-3-yl)ethyl]-1H-imidazole-4,5-dicarboxamide, N$^5$-{4-[(2-chloro-4-fluorobenzoyl)amino]phenyl}-N$^4$-[5-(pyrrolidin-1-yl)pentyl]-1H-imidazole-4,5-dicarboxamide, N$^5$-{4-[(2-chloro-4-fluorobenzoyl)amino]phenyl}-N$^4$-[(1-methylpyrrolidin-3-yl)methyl]-1H-imidazole-4,5-dicarboxamide, N$^5$-{4-[(2-chloro-4-fluorobenzoyl)amino]phenyl}-N$^4$-[(1-methylpiperidin-4-yl)methyl]-1H-imidazole-4,5-dicarboxamide, N$^5$-{4-[(2-chloro-4-fluorobenzoyl)amino]phenyl}-N$^4$-[(1-ethylpiperidin-4-yl)methyl]-1H-imidazole-4,5-dicarboxamide, N$^5$-{4-[(2-chloro-4-fluorobenzoyl)amino]phenyl}-N$^4$-[(1-methylpiperidin-2-yl)methyl]-1H-imidazole-4,5-dicarboxamide, N$^5$-{4-[(2-chloro-4-fluorobenzoyl)amino]phenyl}-N$^4$-[(1-ethylpyrrolidin-3-yl)methyl]-1H-imidazole-4,5-dicarboxamide, N$^5$-{4-[(2-chloro-4-fluorobenzoyl)amino]phenyl}-N$^4$-[2-(dimethylamino)-2-methylpropyl]-1H-imidazole-4,5-dicarboxamide, N$^5$-{4-[(2-chloro-4-fluorobenzoyl)amino]phenyl}-N$^4$-{[(2R)-1-ethylpyrrolidin-2-yl]methyl}-1H-imidazole-4,5-dicarboxamide, N$^5$-{4-[(2-chloro-4-fluorobenzoyl)amino]phenyl}-N$^4$-(1-methylpiperidin-4-yl)-1H-imidazole-4,5-dicarboxamide, N$^5$-{4-[(2-chloro-4-fluorobenzoyl)amino]phenyl}-N$^4$-[2,2-dimethyl-3-(4-methylpiperazin-1-yl)propyl]-1H-imidazole-4,5-dicarboxamide, or a stereoisomer, a tautomer, an N-oxide, a hydrate, a solvate, or a salt thereof, or a mixture of same.

In accordance with a twelfth embodiment of the first aspect, the present invention covers a compound of general formula (I), supra, which is selected from the group consisting of:

N$^5$-{4-[(2,3-dichlorobenzoyl)amino]phenyl}-N$^4$-methyl-1H-imidazole-4,5-dicarboxamide, N$^5$-(4-{[(2-chloropyridin-3-yl)carbonyl]amino}phenyl)-N$^4$-methyl-1H-imidazole-4,5-dicarboxamide, N$^5$-(4-{[2-fluoro-4-(pyrrolidin-1-yl)benzoyl]amino}phenyl)-N$^4$-methyl-1H-imidazole-4,5-dicarboxamide, N$^5$-(4-{[2-chloro-4-(dimethylamino)benzoyl]amino}phenyl)-N$^4$-methyl-1H-imidazole-4,5-dicarboxamide, N$^5$-{4-[(2-chloro-4-fluorobenzoyl)amino]-3-methylphenyl}-N$^4$-methyl-1H-imidazole-4,5-dicarboxamide, N$^5$-{4-[(3-chloroisonicotinoyl)amino]phenyl}-N$^4$-methyl-1H-imidazole-4,5-dicarboxamide, N$^4$-sec-butyl-N$^5$-{4-[(2-chloro-4-fluorobenzoyl)amino]phenyl}-1,3-oxazole-4,5-dicarboxamide, N$^5$-{4-[(2-chloro-4-fluorobenzoyl)amino]phenyl}-N$^4$-(1-phenylethyl)-1,3-oxazole-4,5-dicarboxamide, N$^5$-{4-[(2,4-dichlorobenzoyl)amino]phenyl}-N$^4$-methyl-1H-imidazole-4,5-dicarboxamide, N$^5$-{4-[(2-chloro-4-fluorobenzoyl)amino]phenyl}-N$^4$-isopropyl-1H-imidazole-4,5-dicarboxamide, N$^5$-{4-[(2-chloro-4-fluorobenzoyl)amino]phenyl}-N$^4$-methyl-1,3-oxazole-4,5-dicarboxamide, N$^5$-{4-[(2-chloro-4-fluorobenzoyl)amino]phenyl}-N$^4$-methyl-1H-imidazole-4,5-dicarboxamide, methyl 5-({4-[(2-chloro-4-fluorobenzoyl)amino]phenyl}carbamoyl)-1H-imidazole-4-carboxylate, methyl 5-({4-[(2-chloro-4-fluorobenzoyl)amino]phenyl}carbamoyl)-1,3-oxazole-4-carboxylate, N$^5$-{4-[(2-chloro-4-fluorobenzoyl)amino]phenyl}-N$^4$-isopropyl-1,3-oxazole-4,5-dicarboxamide, N$^5$-{6-[(2-chloro-4-fluorobenzoyl)amino]pyridin-3-yl}-N$^4$-methyl-1H-imidazole-4,5-dicarboxamide, N$^5$-(4-{[(5-chloro-1-methyl-3-phenyl-1H-pyrazol-4-yl)carbonyl]amino}phenyl)-N$^4$-methyl-1H-imidazole-4,5-dicarboxamide, N$^4$-benzyl-N$^5$-{4-[(2-chloro-4-fluorobenzoyl)amino]phenyl}-1H-imidazole-4,5-dicarboxamide, N$^4$-methyl-N$^5$-{4-[(2-methylbenzoyl)amino]phenyl}-1H-imidazole-4,5-dicarboxamide, N$^5$-{4-[(4-fluorobenzoyl)amino]phenyl}-N$^4$-methyl-1H-imidazole-4,5-dicarboxamide, N$^5$-[4-(benzoylamino)phenyl]-N$^4$-methyl-1H-imidazole-4,5-dicarboxamide, N$^4$-{4-[(2-chloro-4-fluorobenzoyl)amino]phenyl}-N$^5$-[2-(dimethylamino)ethyl]-1H-imidazole-4,5-dicarboxamide, N$^5$-{4-[(4-fluoro-2,6-dimethylbenzoyl)amino]phenyl}-N$^4$-methyl-1H-imidazole-4,5-dicarboxamide, N$^5$-{4-[(2-chloro-4-fluorobenzoyl)amino]phenyl}-N$^4$,N$^4$-dimethyl-1H-imidazole-4,5-dicarboxamide, N$^5$-[4-({2-chloro-4-[2-(dimethylamino)ethoxy]benzoyl}amino)phenyl]-N$^4$-methyl-1H-imidazole-4,5-dicarboxamide, N$^5$-{4-[(2,6-dichlorobenzoyl)amino]phenyl}-N$^4$-methyl-1H-imidazole-4,5-dicarboxamide, N$^5$-{4[(2-chlorobenzoyl)amino]phenyl}-N$^4$-methyl-1H-imidazole-4,5-dicarboxamide, N$^5$-[4-({2-chloro-4-[2-(4-methylpiperazin-1-yl)ethoxy]benzoyl}amino)phenyl]-N$^4$-methyl-1H-imidazole-4,5-dicarboxamide, N-{4-[(2-chloro-4-fluorobenzoyl)amino]phenyl}-5-(morpholin-4-ylcarbonyl)-1H-imidazole-4-carboxamide, N⁴-{4-[(2-chloro-4-fluorobenzoyl)amino]phenyl}-N⁵-(2,2,2-trifluoroethyl)-1H-imidazole-4,5-dicarboxamide, N⁵-{4-[(2-chloro-4-fluorobenzoyl)amino]phenyl}-N⁴-[2-(dimethylamino)ethyl]-1,3-oxazole-4,5-dicarboxamide, N⁴-{4-[(2-chloro-4-fluorobenzoyl)amino]phenyl}-N⁵-[2-(piperidin-1-yl)ethyl]-1H-imidazole-4,5-dicarboxamide, N⁴-{4-[(4-fluorobenzoyl)amino]phenyl}-N⁵-[2-(piperidin-1-yl)ethyl]-1H-imidazole-4,5-dicarboxamide, N-{4-[(4-fluorobenzoyl)amino]phenyl}-5-(2-oxa-6-azaspiro[3.3]hept-6-ylcarbonyl)-1H-imidazole-4-carboxamide N⁵-{4-[(mesitylcarbonyl)amino]phenyl}-N⁴-methyl-1H-imidazole-4,5-dicarboxamide, N⁵-(4-{[2-chloro-6-(trifluoromethyl)benzoyl]amino}phenyl)-N⁴-methyl-1H-imidazole-4,5-dicarboxamide, N⁵-{4-[(2-bromobenzoyl)amino]phenyl}-N⁴-methyl-1H-imidazole-4,5-dicarboxamide, N⁵-{4-[(2,6-difluorobenzoyl)amino]phenyl}-N⁴-methyl-1H-imidazole-4,5-dicarboxamide, N⁵-{4[(2-ethylbenzoyl)amino]phenyl}-N⁴-methyl-1H-imidazole-4,5-dicarboxamide, and N⁴-methyl-N⁵-{4-[(2,3,4-trimethoxybenzoyl)amino]phenyl}-1H-imidazole-4,5-dicarboxamide, or a stereoisomer, a tautomer, an N-oxide, a hydrate, a solvate, or a salt thereof, or a mixture of same.

In accordance with a thirteenth embodiment of the first aspect, the present invention covers a compound of general formula (I), supra, which is selected from the group consisting of:

N⁵-{4-[(2,3-dichlorobenzoyl)amino]phenyl}-N⁴-methyl-1H-imidazole-4,5-dicarboxamide;

N⁵-(4-{[(2-chloropyridin-3-yl)carbonyl]amino}phenyl)-N⁴-methyl-1H-imidazole-4,5-dicarboxamide;

N⁵-(4-{[2-fluoro-4-(pyrrolidin-1-yl)benzoyl]amino}phenyl)-N⁴-methyl-1H-imidazole-4,5-dicarboxamide;

N⁵-(4-{[2-chloro-4-(dimethylamino)benzoyl]amino}phenyl)-N⁴-methyl-1H-imidazole-4,5-dicarboxamide;

N⁵-{4-[(2-chloro-4-fluorobenzoyl)amino]-3-methylphenyl}-N⁴-methyl-1H-imidazole-4,5-dicarboxamide;

N⁵-{4-[(3-chloroisonicotinoyl)amino]phenyl}-N⁴-methyl-1H-imidazole-4,5-dicarboxamide;

N⁴-sec-butyl-N⁵-{4-[(2-chloro-4-fluorobenzoyl)amino]phenyl}-1,3-oxazole-4,5-dicarboxamide;

N⁵-{4-[(2-chloro-4-fluorobenzoyl)amino]phenyl}-N⁴-(1-phenylethyl)-1,3-oxazole-4,5-dicarboxamide;

N⁵-{4-[(2,4-dichlorobenzoyl)amino]phenyl}-N⁴-methyl-1H-imidazole-4,5-dicarboxamide;

N⁴-{4-[(2-chloro-4-fluorobenzoyl)amino]phenyl}-N⁵-isopropyl-1H-imidazole-4,5-dicarboxamide;

N⁵-{4-[(2-chloro-4-fluorobenzoyl)amino]phenyl}-N⁴-methyl-1,3-oxazole-4,5-dicarboxamide;

N⁴-{4-[(2-chloro-4-fluorobenzoyl)amino]phenyl}-N⁵-methyl-1H-imidazole-4,5-dicarboxamide;

methyl 5-({4-[(2-chloro-4-fluorobenzoyl)amino]phenyl}carbamoyl)-1H-imidazole-4-carboxylate;

methyl 5-({4-[(2-chloro-4-fluorobenzoyl)amino]phenyl}carbamoyl)-1,3-oxazole-4-carboxylate;

N⁵-{4-[(2-chloro-4-fluorobenzoyl)amino]phenyl}-N⁴-isopropyl-1,3-oxazole-4,5-dicarboxamide;

N⁵-{6-[(2-chloro-4-fluorobenzoyl)amino]pyridin-3-yl}-N⁴-methyl-1H-imidazole-4,5-dicarboxamide;

N⁵-(4-{[(5-chloro-1-methyl-3-phenyl-1H-pyrazol-4-yl)carbonyl]amino}phenyl)-N⁴-methyl-1H-imidazole-4,5-dicarboxamide;

N⁵-benzyl-N⁴-{4-[(2-chloro-4-fluorobenzoyl)amino]phenyl}-1H-imidazole-4,5-dicarboxamide;

N⁴-methyl-N⁵-{4[(2-methylbenzoyl)amino]phenyl}-1H-imidazole-4,5-dicarboxamide;

N⁴-{4-[(2-chloro-4-fluorobenzoyl)amino]phenyl}-N⁵-[2-(dimethylamino)ethyl]-1H-imidazole-4,5-dicarboxamide;

N⁵-{4-[(4-fluoro-2,6-dimethylbenzoyl)amino]phenyl}-N⁴-methyl-1H-imidazole-4,5-dicarboxamide;

N⁴-{4-[(2-chloro-4-fluorobenzoyl)amino]phenyl}-N⁵,N⁵-dimethyl-1H-imidazole-4,5-dicarboxamide;

N⁵-[4-({2-chloro-4-[2-(dimethylamino)ethoxy]benzoyl}amino)phenyl]-N⁴-methyl-1H-imidazole-4,5-dicarboxamide;

N⁵-{4-[(2,6-dichlorobenzoyl)amino]phenyl}-N⁴-methyl-1H-imidazole-4,5-dicarboxamide;

N⁵-{4[(2-chlorobenzoyl)amino]phenyl}-N⁴-methyl-1H-imidazole-4,5-dicarboxamide;

N⁵-[4-({2-chloro-4-[2-(4-methylpiperazin-1-yl)ethoxy]benzoyl}amino)phenyl]-N⁴-methyl-1H-imidazole-4,5-dicarboxamide;

N-{4-[(2-chloro-4-fluorobenzoyl)amino]phenyl}-5-(morpholin-4-ylcarbonyl)-1H-imidazole-4-carboxamide;

N⁴-{4-[(2-chloro-4-fluorobenzoyl)amino]phenyl}-N⁵-(2,2,2-trifluoroethyl)-1H-imidazole-4,5-dicarboxamide;

N⁵-{4-[(2-chloro-4-fluorobenzoyl)amino]phenyl}-N⁴-[2-(dimethylamino)ethyl]-1,3-oxazole-4,5-dicarboxamide;

N⁴-{4-[(2-chloro-4-fluorobenzoyl)amino]phenyl}-N⁵-[2-(piperidin-1-yl)ethyl]-1H-imidazole-4,5-dicarboxamide;

N⁴-{4-[(4-fluorobenzoyl)amino]phenyl}-N⁵-[2-(piperidin-1-yl)ethyl]-1H-imidazole-4,5-dicarboxamide;

N⁵-{4-[(mesitylcarbonyl)amino]phenyl}-N⁴-methyl-1H-imidazole-4,5-dicarboxamide;

N⁵-(4-{[2-chloro-6-(trifluoromethyl)benzoyl]amino}phenyl)-N⁴-methyl-1H-imidazole-4,5-dicarboxamide;

N⁵-{4-[(2-bromobenzoyl)amino]phenyl}-N⁴-methyl-1H-imidazole-4,5-dicarboxamide;

N⁵-{4-[(2,6-difluorobenzoyl)amino]phenyl}-N⁴-methyl-1H-imidazole-4,5-dicarboxamide;

N⁵-{4-[(2-ethylbenzoyl)amino]phenyl}-N⁴-methyl-1H-imidazole-4,5-dicarboxamide;

N-{4-[(2-chloro-4-fluorobenzoyl)amino]phenyl}-4-[(3-fluoroazetidin-1-yl)carbonyl]-1H-imidazole-5-carboxamide;

N⁵-{4-[(2-chloro-4-fluorobenzoyl)amino]phenyl}-N⁴-(2-cyclopentylethyl)-1H-imidazole-4,5-dicarboxamide;

N⁵-{4-[(2-chloro-4-fluorobenzoyl)amino]phenyl}-N⁴-(2-cyclopropylethyl)-1H-imidazole-4,5-dicarboxamide;

N⁵-{4-[(2-chloro-4-fluorobenzoyl)amino]phenyl}-N⁴-cyclopropyl-1H-imidazole-4,5-dicarboxamide;

N-{4-[(2-chloro-4-fluorobenzoyl)amino]phenyl}-4-[(6-methyl-2,6-diazaspiro[3.3]hept-2-yl)carbonyl]-1H-imidazole-5-carboxamide;

N-{4-[(2-chloro-4,5-difluorobenzoyl)amino]phenyl}-4-[(3-fluoroazetidin-1-yl)carbonyl]-1H-imidazole-5-carboxamide;

N⁵-{4-[(2-chloro-4,5-difluorobenzoyl)amino]phenyl}-N⁴-(2-cyclopentylethyl)-1H-imidazole-4,5-dicarboxamide;

N⁵-{4-[(2-chloro-4,5-difluorobenzoyl)amino]phenyl}-N⁴-(2-cyclopropylethyl)-1H-imidazole-4,5-dicarboxamide;

N-{4-[(2-chloro-4,5-difluorobenzoyl)amino]phenyl}-4-[(6-methyl-2,6-diazaspiro[3.3]hept-2-yl)carbonyl]-1H-imidazole-5-carboxamide;

$N^5$-{4-[(2-chloro-4,5-difluorobenzoyl)amino]phenyl}-$N^4$-cyclopropyl-1H-imidazole-4,5-dicarboxamide;

N-{4-[(2-chloro-4,5-difluorobenzoyl)amino]phenyl}-4-(2-oxa-6-azaspiro[3.3]hept-6-ylcarbonyl)-1H-imidazole-5-carboxamide;

$N^5$-(4-{[2-chloro-4-(methylsulfonyl)benzoyl]amino}phenyl)-$N^4$-[2-(piperidin-1-yl)ethyl]-1H-imidazole-4,5-dicarboxamide;

$N^5$-(4-{[2-chloro-4-(methylsulfonyl)benzoyl]amino}phenyl)-$N^4$-[2-(dimethylamino)ethyl]-1H-imidazole-4,5-dicarboxamide;

$N^5$-(4-{[2-chloro-4-(methylsulfonyl)benzoyl]amino}phenyl)-$N^4$-methyl-1H-imidazole-4,5-dicarboxamide;

$N^5$-{4-[(2-bromo-4-fluorobenzoyl)amino]phenyl}-$N^4$-methyl-1H-imidazole-4,5-dicarboxamide;

$N^4$-methyl-$N^5$-(4-{[2-(trifluoromethyl)benzoyl]amino}phenyl)-1H-imidazole-4,5-dicarboxamide;

$N^4$-methyl-$N^5$-{4-[(2,4,6-trichlorobenzoyl)amino]phenyl}-1H-imidazole-4,5-dicarboxamide;

$N^5$-{4-[(4-fluoro-2-iodobenzoyl)amino]phenyl}-$N^4$-methyl-1H-imidazole-4,5-dicarboxamide;

$N^5$-{4-[(4-fluoro-2-iodobenzoyl)amino]phenyl}-$N^4$-[2-(piperidin-1-yl)ethyl]-1H-imidazole-4,5-dicarboxamide;

$N^5$-(4-{[2-bromo-5-(trifluoromethoxy)benzoyl]amino}phenyl)-$N^4$-[2-(piperidin-1-yl)ethyl]-1H-imidazole-4,5-dicarboxamide;

$N^5$-(4-{[2-bromo-5-(trifluoromethoxy)benzoyl]amino}phenyl)-$N^4$-methyl-1H-imidazole-4,5-dicarboxamide;

$N^5$-{4-[(2-chloro-4-fluorobenzoyl)amino]phenyl}-$N^4$,2-dimethyl-1H-imidazole-4,5-dicarboxamide;

$N^4$-{4-[(2-chloro-4-fluorobenzoyl)amino]phenyl}-$N^5$-[2-(dimethylamino)ethyl]-2-methyl-1H-imidazole-4,5-dicarboxamide;

$N^5$-{4-[(2-chloro-4-fluorobenzoyl)amino]phenyl}-2-methyl-$N^4$-[2-(piperidin-1-yl)ethyl]-1H-imidazole-4,5-dicarboxamide;

$N^5$-{4-[(2-chloro-4-fluorobenzoyl)amino]phenyl}-2-ethyl-$N^4$-methyl-1H-imidazole-4,5-dicarboxamide;

$N^4$-{4-[(2-chloro-4-fluorobenzoyl)amino]phenyl}-$N^5$-[2-(dimethylamino)ethyl]-2-ethyl-1H-imidazole-4,5-dicarboxamide;

$N^4$-{4-[(2-chloro-4-fluorobenzoyl)amino]phenyl}-2-ethyl-$N^5$-[2-(piperidin-1-yl)ethyl]-1H-imidazole-4,5-dicarboxamide;

methyl 5-({4-[(2-chloro-4-fluorobenzoyl)amino]-3-fluorophenyl}carbamoyl)-1H-imidazole-4-carboxylate;

$N^5$-{4-[(2-chloro-4-fluorobenzoyl)amino]-3-fluorophenyl}-$N^4$-methyl-1H-imidazole-4,5-dicarboxamide;

$N^5$-{4-[(2-chloro-4-fluorobenzoyl)amino]-3-fluorophenyl}-$N^4$-[2-(dimethylamino)ethyl]-1H-imidazole-4,5-dicarboxamide;

$N^5$-{4-[(2-chloro-4-fluorobenzoyl)amino]-3-fluorophenyl}-$N^4$-[2-(piperidin-1-yl)ethyl]-1H-imidazole-4,5-dicarboxamide;

$N^4$-[2-(dimethylamino)ethyl]-$N^5$-{3-fluoro-4-[(4-fluorobenzoyl)amino]phenyl}-1H-imidazole-4,5-dicarboxamide;

$N^5$-{3-fluoro-4-[(4-fluorobenzoyl)amino]phenyl}-$N^4$-[2-(piperidin-1-yl)ethyl]-1H-imidazole-4,5-dicarboxamide;

methyl 5-({4-[(2-chlorobenzoyl)amino]-3-fluorophenyl}carbamoyl)-1H-imidazole-4-carboxylate;

$N^5$-{4-[(2-chlorobenzoyl)amino]-3-fluorophenyl}-$N^4$-methyl-1H-imidazole-4,5-dicarboxamide;

$N^5$-{4-[(2-chlorobenzoyl)amino]-3-fluorophenyl}-$N^4$-[2-(dimethylamino)ethyl]-1H-imidazole-4,5-dicarboxamide;

$N^5$-{4-[(2-chlorobenzoyl)amino]-3-fluorophenyl}-$N^4$-[2-(piperidin-1-yl)ethyl]-1H-imidazole-4,5-dicarboxamide;

methyl 5-({4-[(2-chloro-4-fluorobenzoyl)amino]-3-methylphenyl}carbamoyl)-1H-imidazole-4-carboxylate;

$N^5$-{4-[(2-chloro-4-fluorobenzoyl)amino]-3-methylphenyl}-$N^4$-[2-(dimethylamino)ethyl]-1H-imidazole-4,5-dicarboxamide;

$N^5$-{4-[(2-chloro-4-fluorobenzoyl)amino]-3-methylphenyl}-$N^4$-[2-(piperidin-1-yl)ethyl]-1H-imidazole-4,5-dicarboxamide;

methyl 5-({4-[(2-chlorobenzoyl)amino]-3-methylphenyl}carbamoyl)-1H-imidazole-4-carboxylate;

$N^5$-{4-[(2-chlorobenzoyl)amino]-3-methylphenyl}-$N^4$-methyl-1H-imidazole-4,5-dicarboxamide;

$N^5$-{4-[(2-chlorobenzoyl)amino]-3-methylphenyl}-$N^4$-[2-(dimethylamino)ethyl]-1H-imidazole-4,5-dicarboxamide;

$N^5$-{4-[(2-chlorobenzoyl)amino]-3-methylphenyl}-$N^4$-[2-(piperidin-1-yl)ethyl]-1H-imidazole-4,5-dicarboxamide;

methyl 5-({4-[(4-fluorobenzoyl)amino]-3-methylphenyl}carbamoyl)-1H-imidazole-4-carboxylate;

$N^4$-[2-(dimethylamino)ethyl]-$N^5$-{4-[(4-fluorobenzoyl)amino]-3-methylphenyl}-1H-imidazole-4,5-dicarboxamide;

$N^5$-{4-[(4-fluorobenzoyl)amino]-3-methylphenyl}-$N^4$-[2-(piperidin-1-yl)ethyl]-1H-imidazole-4,5-dicarboxamide;

$N^5$-{4-[(2-chloro-4-fluorobenzoyl)amino]-3-methoxyphenyl}-$N^4$-methyl-1H-imidazole-4,5-dicarboxamide;

$N^5$-{4-[(2-chloro-4-fluorobenzoyl)amino]-3-methoxyphenyl}-$N^4$-[2-(dimethylamino)ethyl]-1H-imidazole-4,5-dicarboxamide;

$N^5$-{4-[(2-chloro-4-fluorobenzoyl)amino]-3-methoxyphenyl}-$N^4$-[2-(piperidin-1-yl)ethyl]-1H-imidazole-4,5-dicarboxamide;

$N^5$-{4-[(2-chlorobenzoyl)amino]-3-methoxyphenyl}-$N^4$-methyl-1H-imidazole-4,5-dicarboxamide;

$N^5$-{4-[(2-chlorobenzoyl)amino]-3-methoxyphenyl}-$N^4$-[2-(dimethylamino)ethyl]-1H-imidazole-4,5-dicarboxamide;

$N^5$-{4-[(2-chlorobenzoyl)amino]-3-methoxyphenyl}-$N^4$-[2-(piperidin-1-yl)ethyl]-1H-imidazole-4,5-dicarboxamide;

$N^4$-[2-(dimethylamino)ethyl]-$N^5$-{4-[(4-fluorobenzoyl)amino]-3-methoxyphenyl}-1H-imidazole-4,5-dicarboxamide;

$N^5$-{4-[(4-fluorobenzoyl)amino]-3-methoxyphenyl}-$N^4$-[2-(piperidin-1-yl)ethyl]-1H-imidazole-4,5-dicarboxamide;

$N^4$-{4-[(2-chloro-4-fluorobenzoyl)amino]phenyl}-$N^5$-[2-(dimethylamino)ethyl]-2-isopropyl-1H-imidazole-4,5-dicarboxamide;

$N^4$-{4-[(2-chloro-4-fluorobenzoyl)amino]phenyl}-2-isopropyl-$N^5$-[2-(piperidin-1-yl)ethyl]-1H-imidazole-4,5-dicarboxamide;

$N^5$-{6-[(2-chloro-4-fluorobenzoyl)amino]pyridin-3-yl}-$N^4$-[2-(dimethylamino)ethyl]-1H-imidazole-4,5-dicarboxamide;

$N^5$-{6-[(2-chloro-4-fluorobenzoyl)amino]pyridin-3-yl}-$N^4$-[2-(piperidin-1-yl)ethyl]-1H-imidazole-4,5-dicarboxamide;

methyl 5-({6-[(2-chlorobenzoyl)amino]pyridin-3-yl}carbamoyl)-1H-imidazole-4-carboxylate;

$N^5$-{6-[(2-chlorobenzoyl)amino]pyridin-3-yl}-$N^4$-methyl-1H-imidazole-4,5-dicarboxamide;

$N^5$-{6-[(2-chlorobenzoyl)amino]pyridin-3-yl}-$N^4$-[2-(dimethylamino)ethyl]-1H-imidazole-4,5-dicarboxamide;

$N^5$-{6-[(2-chlorobenzoyl)amino]pyridin-3-yl}-$N^4$-[2-(piperidin-1-yl)ethyl]-1H-imidazole-4,5-dicarboxamide;
$N^5$-{6-[(4-fluorobenzoyl)amino]pyridin-3-yl}-$N^4$-methyl-1H-imidazole-4,5-dicarboxamide;
$N^5$-{4-[(2-chloro-4,6-difluorobenzoyl)amino]phenyl}-$N^4$-methyl-1H-imidazole-4,5-dicarboxamide;
$N^5$-{4-[(2-chloro-4,6-difluorobenzoyl)amino]phenyl}-$N^4$-[2-(piperidin-1-yl)ethyl]-1H-imidazole-4,5-dicarboxamide;
$N^5$-{4[(2-chlorobenzoyl)amino]phenyl}-1H-imidazole-4,5-dicarboxamide;
$N^5$-{4-[(2-chloro-4-fluorobenzoyl)amino]phenyl}-1H-imidazole-4,5-dicarboxamide;
$N^5$-{4-[(2-chloro-4-hydroxybenzoyl)amino]phenyl}-$N^4$-methyl-1H-imidazole-4,5-dicarboxamide;
$N^5$-{4-[(2-chloro-5-hydroxybenzoyl)amino]phenyl}-$N^4$-methyl-1H-imidazole-4,5-dicarboxamide;
$N^5$-[4-({2-chloro-5-[2-(piperidin-1-yl)ethoxy]benzoyl}amino)phenyl]-$N^4$-methyl-1H-imidazole-4,5-dicarboxamide;
$N^4$-{4-[(2-chloro-4-fluorobenzoyl)amino]phenyl}-$N^5$-[2-(4-methylpiperidin-1-yl)ethyl]-1H-imidazole-4,5-dicarboxamide;
$N^4$-{4-[(2-chloro-4-fluorobenzoyl)amino]phenyl}-$N^5$-[2-(piperidin-1-yl)ethyl]-1H-imidazole-4,5-dicarboxamide hydrochloric acid salt;
$N^4$-{4-[(2-chloro-4-fluorobenzoyl)amino]phenyl}-$N^5$-(cyclopropylmethyl)-1H-imidazole-4,5-dicarboxamide;
$N^5$-tert-butyl-$N^4$-{4-[(4-fluorobenzoyl)amino]phenyl}-1H-imidazole-4,5-dicarboxamide;
$N^4$-{4-[(2-chloro-4-fluorobenzoyl)amino]phenyl}-$N^5$-(2-methoxyethyl)-1H-imidazole-4,5-dicarboxamide;
$N^5$-cyclopropyl-$N^4$-{4-[(4-fluorobenzoyl)amino]phenyl}-1H-imidazole-4,5-dicarboxamide;
$N^4$-{4-[(2-chloro-4-fluorobenzoyl)amino]phenyl}-$N^5$-(2-hydroxyethyl)-1H-imidazole-4,5-dicarboxamide;
$N^5$-tert-butyl-$N^4$-{4-[(2-chloro-4-fluorobenzoyl)amino]phenyl}-1H-imidazole-4,5-dicarboxamide;
$N^4$-{4-[(2-chloro-4-fluorobenzoyl)amino]phenyl}-$N^5$-[(2R)-3-methylbutan-2-yl]-1H-imidazole-4,5-dicarboxamide;
$N^4$-{4-[(4-fluorobenzoyl)amino]phenyl}-$N^5$-[(2R)-3-methylbutan-2-yl]-1H-imidazole-4,5-dicarboxamide;
$N^4$-{4-[(4-fluorobenzoyl)amino]phenyl}-$N^5$-(2-hydroxyethyl)-1H-imidazole-4,5-dicarboxamide;
$N^5$-ethyl-$N^4$-{4[(4-fluorobenzoyl)amino]phenyl}-1H-imidazole-4,5-dicarboxamide;
$N^4$-{4-[(2-chloro-4-fluorobenzoyl)amino]phenyl}-$N^5$-ethyl-1H-imidazole-4,5-dicarboxamide;
$N^4$-{4-[(2-chloro-4-fluorobenzoyl)amino]phenyl}-$N^5$-(2,2-difluoroethyl)-1H-imidazole-4,5-dicarboxamide;
$N^4$-{4-[(4-fluorobenzoyl)amino]phenyl}-$N^5$-(2-methoxyethyl)-1H-imidazole-4,5-dicarboxamide;
$N^5$-(2,2-difluoroethyl)-$N^4$-{4-[(4-fluorobenzoyl)amino]phenyl}-1H-imidazole-4,5-dicarboxamide;
5-(azetidin-1-ylcarbonyl)-N-{4-[(2-chloro-4-fluorobenzoyl)amino]phenyl}-1H-imidazole-4-carboxamide;
N-{4-[(2-chloro-4-fluorobenzoyl)amino]phenyl}-5-(2-oxa-6-azaspiro[3.3]hept-6-ylcarbonyl)-1H-imidazole-4-carboxamide;
$N^4$-{4-[(4-fluorobenzoyl)amino]phenyl}-$N^5$-isobutyl-1H-imidazole-4,5-dicarboxamide;
$N^4$-{4-[(2-chloro-4-fluorobenzoyl)amino]phenyl}-$N^5$-isobutyl-1H-imidazole-4,5-dicarboxamide;
$N^4$-{4-[(2-chlorobenzoyl)amino]phenyl}-$N^5$-(2,2-dimethylpropyl)-1H-imidazole-4,5-dicarboxamide;
$N^5$-(2,2-dimethylpropyl)-$N^4$-{4-[(4-fluorobenzoyl)amino]phenyl}-1H-imidazole-4,5-dicarboxamide;
$N^4$-{4-[(4-fluorobenzoyl)amino]phenyl}-$N^5$-[2-(morpholin-4-yl)ethyl]-1H-imidazole-4,5-dicarboxamide;
$N^4$-{4-[(2-chlorobenzoyl)amino]phenyl}-$N^5$-[2-(3-hydroxypiperidin-1-yl)ethyl]-1H-imidazole-4,5-dicarboxamide;
$N^4$-{4-[(2-chlorobenzoyl)amino]phenyl}-$N^5$-[2-(2-methylpiperidin-1-yl)ethyl]-1H-imidazole-4,5-dicarboxamide;
$N^4$-{4-[(2-chlorobenzoyl)amino]phenyl}-$N^5$-[2-methyl-1-(morpholin-4-yl)propan-2-yl]-1H-imidazole-4,5-dicarboxamide;
$N^4$-{4-[(2-chloro-4-fluorobenzoyl)amino]phenyl}-$N^5$-[2-methyl-1-(4-methylpiperidin-1-yl)propan-2-yl]-1H-imidazole-4,5-dicarboxamide;
$N^4$-{4-[(4-fluorobenzoyl)amino]phenyl}-$N^5$-[2-methyl-1-(piperidin-1-yl)propan-2-yl]-1H-imidazole-4,5-dicarboxamide;
$N^4$-{4-[(2-chlorobenzoyl)amino]phenyl}-$N^5$-(1,3-dihydroxypropan-2-yl)-1H-imidazole-4,5-dicarboxamide;
$N^4$-{4-[(2-chlorobenzoyl)amino]phenyl}-$N^5$-[2-methyl-1-(4-methylpiperidin-1-yl)propan-2-yl]-1H-imidazole-4,5-dicarboxamide;
$N^4$-{4-[(2-chloro-4-fluorobenzoyl)amino]phenyl}-$N^5$-[2-methyl-2-(piperidin-1-yl)propyl]-1H-imidazole-4,5-dicarboxamide;
$N^4$-{4-[(2-chlorobenzoyl)amino]phenyl}-$N^5$-[2-(4-methylpiperazin-1-yl)ethyl]-1H-imidazole-4,5-dicarboxamide;
$N^4$-{4-[(2-chlorobenzoyl)amino]phenyl}-$N^5$-[1-(morpholin-4-yl)propan-2-yl]-1H-imidazole-4,5-dicarboxamide;
$N^4$-{4-[(2-chlorobenzoyl)amino]phenyl}-$N^5$-[2-(4-methylpiperidin-1-yl)ethyl]-1H-imidazole-4,5-dicarboxamide;
$N^4$-{4-[(4-fluorobenzoyl)amino]phenyl}-$N^5$-[2-(4-methylpiperidin-1-yl)ethyl]-1H-imidazole-4,5-dicarboxamide;
$N^4$-{4-[(2-chlorobenzoyl)amino]phenyl}-$N^5$-[2-methyl-2-(piperidin-1-yl)propyl]-1H-imidazole-4,5-dicarboxamide;
$N^4$-{4-[(2-chlorobenzoyl)amino]phenyl}-$N^5$-(2-fluoroethyl)-1H-imidazole-4,5-dicarboxamide;
$N^4$-{4-[(4-fluorobenzoyl)amino]phenyl}-$N^5$-[2-(3-hydroxypiperidin-1-yl)ethyl]-1H-imidazole-4,5-dicarboxamide;
$N^4$-{4[(2-chlorobenzoyl)amino]phenyl}-$N^5$-[2-(pyrrolidin-1-yl)ethyl]-1H-imidazole-4,5-dicarboxamide;
$N^4$-{4-[(4-fluorobenzoyl)amino]phenyl}-$N^5$-[2-(2-methylpiperidin-1-yl)ethyl]-1H-imidazole-4,5-dicarboxamide;
$N^4$-{4-[(2-chloro-4-fluorobenzoyl)amino]phenyl}-$N^5$-[2-(piperidin-1-yl)propyl]-1H-imidazole-4,5-dicarboxamide;
$N^4$-{4-[(2-chlorobenzoyl)amino]phenyl}-$N^5$-[2-methyl-1-(piperidin-1-yl)propan-2-yl]-1H-imidazole-4,5-dicarboxamide;
$N^4$-{4-[(2-chloro-4-fluorobenzoyl)amino]phenyl}-$N^5$-(1,3-dihydroxypropan-2-yl)-1H-imidazole-4,5-dicarboxamide;
$N^4$-{4-[(2-chloro-4-fluorobenzoyl)amino]phenyl}-$N^5$-(2-fluoroethyl)-1H-imidazole-4,5-dicarboxamide;
$N^4$-{4[(4-fluorobenzoyl)amino]phenyl}-$N^5$-(2-fluoroethyl)-1H-imidazole-4, 5-dicarboxamide;
$N^4$-{4[(4-fluorobenzoyl)amino]phenyl}-$N^5$-[2-methyl-1-(4-methylpiperidin-1-yl)propan-2-yl]-1H-imidazole-4,5-dicarboxamide;
$N^4$-{4-[(4-fluorobenzoyl)amino]phenyl}-$N^5$-[2-(pyrrolidin-1-yl)ethyl]-1H-imidazole-4,5-dicarboxamide;
$N^4$-{4-[(2-chloro-4-fluorobenzoyl)amino]phenyl}-$N^5$-(4-methylpiperazin-1-yl)-1H-imidazole-4,5-dicarboxamide;

N⁴-{4-[(4-fluorobenzoyl)amino]phenyl}-N⁵-[2-(4-hydroxypiperidin-1-yl)ethyl]-1H-imidazole-4,5-dicarboxamide;

N⁴-{4-[(4-fluorobenzoyl)amino]phenyl}-N⁵-[2-methyl-1-(morpholin-4-yl)propan-2-yl]-1H-imidazole-4,5-dicarboxamide;

N⁴-{4-[(4-fluorobenzoyl)amino]phenyl}-N⁵-[3-(4-methylpiperazin-1-yl)propyl]-1H-imidazole-4,5-dicarboxamide;

N⁴-{4-[(2-chlorobenzoyl)amino]phenyl}-N⁵-[2-(piperidin-1-yl)propyl]-1H-imidazole-4,5-dicarboxamide;

N⁴-{4-[(4-fluorobenzoyl)amino]phenyl}-N⁵-[2-(piperidin-1-yl)propyl]-1H-imidazole-4,5-dicarboxamide;

N⁴-{4-[(2-chloro-4-fluorobenzoyl)amino]phenyl}-N⁵-[2-methyl-1-(piperidin-1-yl)propan-2-yl]-1H-imidazole-4,5-dicarboxamide;

N⁴-{4-[(2-chloro-4-fluorobenzoyl)amino]phenyl}-N⁵-[2-(4-methylpiperazin-1-yl)propyl]-1H-imidazole-4,5-dicarboxamide;

N⁴-{4-[(2-chlorobenzoyl)amino]phenyl}-N⁵-[2-(4-methylpiperazin-1-yl)propyl]-1H-imidazole-4,5-dicarboxamide;

N⁴-{4-[(2-chloro-4-fluorobenzoyl)amino]phenyl}-N⁵-[2-methyl-2-(4-methylpiperazin-1-yl)propyl]-1H-imidazole-4,5-dicarboxamide;

N⁴-{4-[(4-fluorobenzoyl)amino]phenyl}-N⁵-[2-methyl-2-(4-methylpiperazin-1-yl)propyl]-1H-imidazole-4,5-dicarboxamide;

N⁴-{4-[(2-chlorobenzoyl)amino]phenyl}-N⁵-[4-(piperidin-1-yl)butyl]-1H-imidazole-4,5-dicarboxamide;

N⁵-[2-(azetidin-1-yl)ethyl]-N⁴-{4-[(2-chlorobenzoyl)amino]phenyl}-1H-imidazole-4,5-dicarboxamide;

N⁴-{4-[(2-chloro-4-fluorobenzoyl)amino]phenyl}-N⁵-[2-(2-methylpiperidin-1-yl)ethyl]-1H-imidazole-4,5-dicarboxamide;

N⁴-{4-[(2-chlorobenzoyl)amino]phenyl}-N⁵-[3-(4-methylpiperazin-1-yl)propyl]-1H-imidazole-4,5-dicarboxamide;

N⁴-{4-[(4-fluorobenzoyl)amino]phenyl}-N⁵-(4-methylpiperazin-1-yl)-1H-imidazole-4,5-dicarboxamide;

N⁴-{4-[(2-chloro-4-fluorobenzoyl)amino]phenyl}-N⁵-[2-methyl-1-(4-methylpiperazin-1-yl)propan-2-yl]-1H-imidazole-4,5-dicarboxamide;

N⁴-{4-[(4-fluorobenzoyl)amino]phenyl}-N⁵-[2-methyl-1-(4-methylpiperazin-1-yl)propan-2-yl]-1H-imidazole-4,5-dicarboxamide;

N⁴-{4-[(2-chloro-4-fluorobenzoyl)amino]phenyl}-N⁵-[4-(piperidin-1-yl)butyl]-1H-imidazole-4,5-dicarboxamide;

N⁴-{4-[(2-chlorobenzoyl)amino]phenyl}-N⁵-[2-(4-hydroxypiperidin-1-yl)ethyl]-1H-imidazole-4,5-dicarboxamide;

N⁵-[2-(azetidin-1-yl)ethyl]-N⁴-{4-[(2-chloro-4-fluorobenzoyl)amino]phenyl}-1H-imidazole-4,5-dicarboxamide;

N⁵-[2-(azetidin-1-yl)ethyl]-N⁴-{4-[(4-fluorobenzoyl)amino]phenyl}-1H-imidazole-4,5-dicarboxamide;

N⁴-{4-[(2-chlorobenzoyl)amino]phenyl}-N⁵-[3-(morpholin-4-yl)propyl]-1H-imidazole-4,5-dicarboxamide;

N⁴-{4-[(4-fluorobenzoyl)amino]phenyl}-N⁵-[4-(piperidin-1-yl)butyl]-1H-imidazole-4,5-dicarboxamide;

N⁴-{4-[(2-chlorobenzoyl)amino]phenyl}-N⁵-[2-methyl-2-(4-methylpiperazin-1-yl)propyl]-1H-imidazole-4,5-dicarboxamide;

N⁴-{4-[(2-chlorobenzoyl)amino]phenyl}-N⁵-[2-methyl-1-(4-methylpiperazin-1-yl)propan-2-yl]-1H-imidazole-4,5-dicarboxamide;

N⁴-{4-[(2-chloro-4-fluorobenzoyl)amino]phenyl}-N⁵-[3-(morpholin-4-yl)propyl]-1H-imidazole-4,5-dicarboxamide;

N⁴-{4-[(4-fluorobenzoyl)amino]phenyl}-N⁵-[2-(4-methylpiperazin-1-yl)propyl]-1H-imidazole-4,5-dicarboxamide;

N⁴-{4-[(4-fluorobenzoyl)amino]phenyl}-N⁵-[3-(morpholin-4-yl)propyl]-1H-imidazole-4,5-dicarboxamide;

N⁴-{4-[(2-chloro-4-fluorobenzoyl)amino]phenyl}-N⁵-[2-methyl-1-(morpholin-4-yl)propan-2-yl]-1H-imidazole-4,5-dicarboxamide;

N⁴-{4-[(2-chloro-4-fluorobenzoyl)amino]phenyl}-N⁵-[2-(3-methylpiperidin-1-yl)ethyl]-1H-imidazole-4,5-dicarboxamide;

N⁴-{4-[(4-fluorobenzoyl)amino]phenyl}-N⁵-[2-methyl-2-(piperidin-1-yl)propyl]-1H-imidazole-4,5-dicarboxamide;

N⁴-{4-[(2-chlorobenzoyl)amino]phenyl}-N⁵-[2-(3-methylpiperidin-1-yl)ethyl]-1H-imidazole-4,5-dicarboxamide;

N⁴-{4-[(4-fluorobenzoyl)amino]phenyl}-N⁵-[2-(3-methylpiperidin-1-yl)ethyl]-1H-imidazole-4,5-dicarboxamide;

N⁴-{4-[(2-chloro-4-fluorobenzoyl)amino]phenyl}-N⁵-[2-(4-hydroxypiperidin-1-yl)ethyl]-1H-imidazole-4,5-dicarboxamide;

N⁵-(4-{[(2,5-dichloro-3-thienyl)carbonyl]amino}phenyl)-N⁴-methyl-1H-imidazole-4,5-dicarboxamide;

N⁴-{4-[(2-chlorobenzoyl)amino]phenyl}-N⁵-[2-(4,4-difluoropiperidin-1-yl)ethyl]-1H-imidazole-4,5-dicarboxamide;

N⁴-{4-[(2-bromo-4-fluorobenzoyl)amino]phenyl}-N⁵-[2-(4,4-difluoropiperidin-1-yl)ethyl]-1H-imidazole-4,5-dicarboxamide;

N⁴-{4-[(2-bromo-4-fluorobenzoyl)amino]phenyl}-N⁵-[2-(piperidin-1-yl)ethyl]-1H-imidazole-4,5-dicarboxamide;

N⁴-{4-[(2-bromo-4-fluorobenzoyl)amino]phenyl}-N⁵-[2-(dimethylamino)ethyl]-1H-imidazole-4,5-dicarboxamide;

N⁵-{4-[(2-chloro-4-fluorobenzoyl)amino]phenyl}-N⁴-[2-(4,4-difluoropiperidin-1-yl)ethyl]-1,3-oxazole-4,5-dicarboxamide;

N⁴-(2-amino-2-methylpropyl)-N⁵-{4-[(2-chloro-4-fluorobenzoyl)amino]phenyl}-1,3-oxazole-4,5-dicarboxamide;

N⁵-{4-[(2-chloro-4-fluorobenzoyl)amino]phenyl}-N⁴-[2-(3-fluoropiperidin-1-yl)ethyl]-1,3-oxazole-4,5-dicarboxamide;

N⁵-{4-[(2-chloro-4-fluorobenzoyl)amino]phenyl}-N⁴-{2-[(3S)-3-fluoropyrrolidin-1-yl]ethyl}-1,3-oxazole-4,5-dicarboxamide;

N⁵-{4-[(2-chloro-4-fluorobenzoyl)amino]phenyl}-N⁴-{2-[(3R)-3-fluoropyrrolidin-1-yl]ethyl}-1,3-oxazole-4,5-dicarboxamide;

N⁴-{4-[(2-chloro-4-fluorobenzoyl)amino]phenyl}-N⁵-(2-hydroxy-2-methylpropyl)-1H-imidazole-4,5-dicarboxamide;

N⁴-{4-[(2-chloro-4-fluorobenzoyl)amino]phenyl}-N⁵-[2-(4,4-difluoropiperidin-1-yl)ethyl]-1H-imidazole-4,5-dicarboxamide;

N⁴-{4-[(2-chloro-4-fluorobenzoyl)amino]phenyl}-N⁵-[2-(3,3-difluoropiperidin-1-yl)ethyl]-1H-imidazole-4,5-dicarboxamide;

N⁴-{4-[(2-chloro-4-fluorobenzoyl)amino]phenyl}-N⁵-[2-(3-fluoropiperidin-1-yl)ethyl]-1H-imidazole-4,5-dicarboxamide;

N⁴-{4-[(2-chloro-4-fluorobenzoyl)amino]phenyl}-N⁵-[2-(morpholin-4-yl)ethyl]-1H-imidazole-4,5-dicarboxamide;

N⁴-{4-[(2-chloro-4-fluorobenzoyl)amino]phenyl}-N⁵-[2-(pyrrolidin-1-yl)ethyl]-1H-imidazole-4,5-dicarboxamide;

N⁴-{4-[(2-chloro-4-fluorobenzoyl)amino]phenyl}-N⁵-[2-(3-hydroxypiperidin-1-yl)ethyl]-1H-imidazole-4,5-dicarboxamide;

N⁴-{4-[(2-chloro-4-fluorobenzoyl)amino]phenyl}-N⁵-[2-(4-fluoropiperidin-1-yl)ethyl]-1H-imidazole-4,5-dicarboxamide;

N⁴-{4-[(2-chloro-4-fluorobenzoyl)amino]phenyl}-N⁵-{2-[(3R)-3-fluoropyrrolidin-1-yl]ethyl}-1H-imidazole-4,5-dicarboxamide;

N⁴-{4-[(2-chloro-4-fluorobenzoyl)amino]phenyl}-N⁵-{2-[(3S)-3-fluoropyrrolidin-1-yl]ethyl}-1H-imidazole-4,5-dicarboxamide;

N⁴-{4-[(2-chloro-4-fluorobenzoyl)amino]phenyl}-N⁵-(tetrahydro-2H-pyran-4-ylmethyl)-1H-imidazole-4,5-dicarboxamide;

N⁴-{4-[(2-chloro-4-fluorobenzoyl)amino]phenyl}-N⁵-(tetrahydro-2H-pyran-4-yl)-1H-imidazole-4,5-dicarboxamide;

N⁴-{4-[(2-chloro-4-fluorobenzoyl)amino]phenyl}-N⁵-(tetrahydrofuran-3-ylmethyl)-1H-imidazole-4,5-dicarboxamide;

N⁴-{4-[(2-chloro-4-fluorobenzoyl)amino]phenyl}-N⁵-(tetrahydrofuran-3-yl)-1H-imidazole-4,5-dicarboxamide;

N⁴-{4-[(2-chloro-4-fluorobenzoyl)amino]phenyl}-N⁵-(tetrahydrofuran-2-ylmethyl)-1H-imidazole-4,5-dicarboxamide;

N⁴-{4-[(2-chloro-4-fluorobenzoyl)amino]phenyl}-N⁵-[2-(4-methylpiperazin-1-yl)ethyl]-1H-imidazole-4,5-dicarboxamide;

N⁵-{4-[(2-chloro-4,5-dimethoxybenzoyl)amino]phenyl}-N⁴-methyl-1H-imidazole-4,5-dicarboxamide;

N⁵-(4-{[2-(difluoromethyl)benzoyl]amino}phenyl)-N⁴-methyl-1H-imidazole-4,5-dicarboxamide;

N⁵-{4-[(2-chloro-4,5-difluorobenzoyl)amino]phenyl}-N⁴-methyl-1H-imidazole-4,5-dicarboxamide;

N⁵-{4-[(2-chloro-4-methylbenzoyl)amino]phenyl}-N⁴-methyl-1H-imidazole-4,5-dicarboxamide;

N⁵-{4-[(2-chloro-4-methoxybenzoyl)amino]phenyl}-N⁴-methyl-1H-imidazole-4,5-dicarboxamide;

N⁵-(4-{[(3-chloropyridin-2-yl)carbonyl]amino}phenyl)-N⁴-methyl-1H-imidazole-4,5-dicarboxamide;

N⁵-{4-[(2-chloro-5-methoxybenzoyl)amino]phenyl}-N⁴-methyl-1H-imidazole-4,5-dicarboxamide;

N⁴-methyl-N⁵-(4-{[2-(methylsulfonyl)benzoyl]amino}phenyl)-1H-imidazole-4,5-dicarboxamide;

N⁵-{4-[(2-chloro-4-ethoxybenzoyl)amino]phenyl}-N⁴-methyl-1H-imidazole-4,5-dicarboxamide;

N⁵-(4-{[4-(difluoromethoxy)-2-fluorobenzoyl]amino}phenyl)-N⁴-methyl-1H-imidazole-4,5-dicarboxamide;

N⁵-{4-[(2-chloro-3-methoxybenzoyl)amino]phenyl}-N⁴-methyl-1H-imidazole-4,5-dicarboxamide;

N⁵-(4-{[(4-chloropyridin-3-yl)carbonyl]amino}phenyl)-N⁴-methyl-1H-imidazole-4,5-dicarboxamide;

N⁵-(4-{[2-chloro-4-(S-ethylsulfonimidoyl)benzoyl]amino}phenyl)-N⁴-methyl-1H-imidazole-4,5-dicarboxamide;

N⁵-(4-{[2-chloro-4-(S-ethylsulfonimidoyl)benzoyl]amino}phenyl)-N⁴-[2-(piperidin-1-yl)ethyl]-1H-imidazole-4,5-dicarboxamide;

N⁴-ethyl-N⁵-(4-{[2-(methylsulfonyl)benzoyl]amino}phenyl)-1H-imidazole-4,5-dicarboxamide;

N⁵-(4-{[4-(difluoromethoxy)-2-fluorobenzoyl]amino}phenyl)-N⁴-ethyl-1H-imidazole-4,5-dicarboxamide;

N⁵-{4-[(2-chloro-4-ethoxybenzoyl)amino]phenyl}-N⁴-ethyl-1H-imidazole-4,5-dicarboxamide;

N⁵-{4-[(2-chloro-3-methoxybenzoyl)amino]phenyl}-N⁴-ethyl-1H-imidazole-4,5-dicarboxamide;

N⁴-ethyl-N⁵-(4-{[2-fluoro-4-(trifluoromethoxy)benzoyl]amino}phenyl)-1H-imidazole-4,5-dicarboxamide;

N⁵-(4-{[(4-chloropyridin-3-yl)carbonyl]amino}phenyl)-N⁴-ethyl-1H-imidazole-4,5-dicarboxamide;

N⁵-{4-[(2-chloro-5-methoxybenzoyl)amino]phenyl}-N⁴-ethyl-1H-imidazole-4,5-dicarboxamide;

N⁴-{4-[(2-chloro-4-fluorobenzoyl)amino]phenyl}-N⁵-[2-(3-methoxypyrrolidin-1-yl)ethyl]-1H-imidazole-4,5-dicarboxamide;

N⁴-{4-[(2-chloro-4-fluorobenzoyl)amino]phenyl}-N⁵-{2-[(2S)-2-methylpiperidin-1-yl]ethyl}-1H-imidazole-4,5-dicarboxamide, N⁴-{4-[(2-chloro-4-fluorobenzoyl)amino]phenyl}-N⁵-{2-[(2S)-2-methylpiperidin-1-yl]ethyl}-1H-imidazole-4,5-dicarboxamide formic acid salt;

N⁴-{4-[(2-chloro-4-fluorobenzoyl)amino]phenyl}-N⁵-{2-[(2R)-2-methylpiperidin-1-yl]ethyl}-1H-imidazole-4,5-dicarboxamide;

N⁴-{4-[(2-chloro-4-fluorobenzoyl)amino]phenyl}-N⁵-[1-(morpholin-4-yl)propan-2-yl]-1H-imidazole-4,5-dicarboxamide;

N⁴-{4-[(2-chloro-4-fluorobenzoyl)amino]phenyl}-N⁵-[1-(morpholin-4-yl)propan-2-yl]-1H-imidazole-4,5-dicarboxamide;

N⁴-{4-[(2-chloro-4-fluorobenzoyl)amino]phenyl}-N⁵-[1-(morpholin-4-yl)propan-2-yl]-1H-imidazole-4,5-dicarboxamide;

N⁴-{4-[(2-chloro-4-fluorobenzoyl)amino]phenyl}-N⁵-{2-[(3S)-3-hydroxypiperidin-1-yl]ethyl}-1H-imidazole-4,5-dicarboxamide;

N⁴-{4-[(2-chloro-4-fluorobenzoyl)amino]phenyl}-N⁵-{2-[(3R)-3-hydroxypiperidin-1-yl]ethyl}-1H-imidazole-4,5-dicarboxamide;

N⁴-{4-[(2-chloro-4-fluorobenzoyl)amino]phenyl}-N⁵-[3-(3-hydroxypiperidin-1-yl)propyl]-1H-imidazole-4,5-dicarboxamide;

N⁴-{4-[(2-chloro-4-fluorobenzoyl)amino]phenyl}-N⁵-[3-(pyrrolidin-1-yl)propyl]-1H-imidazole-4,5-dicarboxamide;

N⁴-{4-[(2-chloro-4-fluorobenzoyl)amino]phenyl}-N⁵-[3-(4-hydroxypiperidin-1-yl)propyl]-1H-imidazole-4,5-dicarboxamide;

N⁴-{4-[(2-chloro-4-fluorobenzoyl)amino]phenyl}-N⁵-{2-[(3S)-3-fluoropiperidin-1-yl]ethyl}-1H-imidazole-4,5-dicarboxamide;

N⁴-{4-[(2-chloro-4-fluorobenzoyl)amino]phenyl}-N⁵-{2-[(3R)-3-fluoropiperidin-1-yl]ethyl}-1H-imidazole-4,5-dicarboxamide;

N⁴-{4-[(2-chloro-4-fluorobenzoyl)amino]phenyl}-N⁵-{2-[(3R)-3-methylpiperidin-1-yl]ethyl}-1H-imidazole-4,5-dicarboxamide;

N⁴-{4-[(2-chloro-4-fluorobenzoyl)amino]phenyl}-N⁵-[2-(3,3-difluoropyrrolidin-1-yl)ethyl]-1H-imidazole-4,5-dicarboxamide;

N⁵-(2-amino-2-methylpropyl)-N⁴-{4-[(2-chloro-4-fluorobenzoyl)amino]phenyl}-1H-imidazole-4,5-dicarboxamide;

N⁴-{4-[(2-chloro-4-fluorobenzoyl)amino]phenyl}-N⁵-[(3S)-pyrrolidin-3-yl]-1H-imidazole-4,5-dicarboxamide;

N⁴-{4-[(2-chloro-4-fluorobenzoyl)amino]phenyl}-N⁵-[(3R)-pyrrolidin-3-yl]-1H-imidazole-4,5-dicarboxamide;

N⁴-{4-[(2-chloro-4-fluorobenzoyl)amino]phenyl}-N⁵-[(3R)-pyrrolidin-3-yl]-1H-imidazole-4,5-dicarboxamide hydrochloric acid salt;

N⁵-(3-amino-3-methylbutyl)-N⁴-{4-[(2-chlorobenzoyl)amino]phenyl}-1H-imidazole-4,5-dicarboxamide;

$N^5$-(3-amino-3-methylbutyl)-$N^4$-{4-[(2-chlorobenzoyl)amino]phenyl}-1H-imidazole-4,5-dicarboxamide hydrochloric acid salt;

$N^4$-{4-[(2-chloro-4-fluorobenzoyl)amino]phenyl}-$N^5$-(pyrrolidin-2-ylmethyl)-1H-imidazole-4,5-dicarboxamide;

$N^4$-{4-[(2-chloro-4-fluorobenzoyl)amino]phenyl}-$N^5$-(pyrrolidin-2-ylmethyl)-1H-imidazole-4,5-dicarboxamide hydrochloric acid salt;

5-[(3-aminopyrrolidin-1-yl)carbonyl]-N-{4-[(2-chloro-4-fluorobenzoyl)amino]phenyl}-1H-imidazole-4-carboxamide;

5-[(3-aminopyrrolidin-1-yl)carbonyl]-N-{4-[(2-chloro-4-fluorobenzoyl)amino]phenyl}-1H-imidazole-4-carboxamide hydrochloric acid salt;

$N^5$-(3-amino-3-methylbutyl)-$N^4$-{4-[(2-chloro-4-fluorobenzoyl)amino]phenyl}-1H-imidazole-4,5-dicarboxamide;

$N^4$-{4-[(2-chloro-4-fluorobenzoyl)amino]phenyl}-$N^5$-[2-(methylamino)ethyl]-1H-imidazole-4,5-dicarboxamide;

$N^4$-{4-[(2-chloro-4-fluorobenzoyl)amino]phenyl}-$N^5$-[2-(isopropylamino)ethyl]-1H-imidazole-4,5-dicarboxamide;

N-{4-[(2-chloro-4-fluorobenzoyl)amino]phenyl}-5-(piperazin-1-ylcarbonyl)-1H-imidazole-4-carboxamide;

N-{4-[(2-chloro-4-fluorobenzoyl)amino]phenyl}-5-(piperazin-1-ylcarbonyl)-1H-imidazole-4-carboxamide hydrochloric acid salt;

$N^5$-(2-aminoethyl)-$N^4$-{4-[(2-chloro-4-fluorobenzoyl)amino]phenyl}-1H-imidazole-4,5-dicarboxamide;

$N^4$-{4-[(2-chloro-4-fluorobenzoyl)amino]-3-(trifluoromethoxy)phenyl}-$N^5$-[2-(piperidin-1-yl)ethyl]-1H-imidazole-4,5-dicarboxamide;

$N^4$-{4-[(4-fluorobenzoyl)amino]phenyl}-$N^5$-[1-(morpholin-4-yl)propan-2-yl]-1H-imidazole-4,5-dicarboxamide;

$N^4$-{4-[(4-fluorobenzoyl)amino]phenyl}-$N^5$-[1-(morpholin-4-yl)propan-2-yl]-1H-imidazole-4,5-dicarboxamide;

$N^4$-{4-[(4-fluorobenzoyl)amino]phenyl}-$N^5$-[1-(morpholin-4-yl)propan-2-yl]-1H-imidazole-4,5-dicarboxamide;

$N^4$-{4-[(2-chloro-4-fluorobenzoyl)amino]phenyl}-$N^5$-[3-(piperidin-1-yl)propyl]-1H-imidazole-4,5-dicarboxamide;

$N^4$-{4-[(2-chloro-4-fluorobenzoyl)amino]phenyl}-$N^5$-[(1-methylpiperidin-3-yl)methyl]-1H-imidazole-4,5-dicarboxamide;

$N^4$-{4-[(2-chloro-4-fluorobenzoyl)amino]phenyl}-$N^5$-[3-(2-oxopyrrolidin-1-yl)propyl]-1H-imidazole-4,5-dicarboxamide;

$N^4$-{4-[(2-chlorobenzoyl)amino]phenyl}-$N^5$-[2-(2,6-dimethylmorpholin-4-yl)ethyl]-1H-imidazole-4,5-dicarboxamide;

$N^4$-{4-[(2-4-fluorochlorobenzoyl)amino]phenyl}-$N^5$-[2-(2,6-dimethylmorpholin-4-yl)ethyl]-1H-imidazole-4,5-dicarboxamide;

$N^4$-{4-[(2-chlorobenzoyl)amino]phenyl}-$N^5$-(4-methylpiperazin-1-yl)-1H-imidazole-4,5-dicarboxamide;

$N^5$-{4-[(2-chloro-4-fluorobenzoyl)amino]phenyl}-$N^4$-[2-(piperidin-1-yl)ethyl]-1,3-oxazole-4,5-dicarboxamide;

$N^5$-{4[(4-chlorobenzoyl)amino]phenyl}-$N^4$-methyl-1H-imidazole-4,5-dicarboxamide;

$N^5$-{4-[(2,5-dimethylbenzoyl)amino]phenyl}-$N^4$-methyl-1H-imidazole-4,5-dicarboxamide;

$N^5$-{4-[(3,4-dichlorobenzoyl)amino]phenyl}-$N^4$-methyl-1H-imidazole-4,5-dicarboxamide;

$N^5$-{4-[(2,5-dichlorobenzoyl)amino]phenyl}-$N^4$-methyl-1H-imidazole-4,5-dicarboxamide;

$N^5$-{4-[(5-bromo-2-chlorobenzoyl)amino]phenyl}-$N^4$-methyl-1H-imidazole-4,5-dicarboxamide;

$N^4$-methyl-$N^5$-(4-{[3-(trifluoromethyl)benzoyl]amino}phenyl)-1H-imidazole-4,5-dicarboxamide;

$N^5$-{4-[(2,5-difluorobenzoyl)amino]phenyl}-$N^4$-methyl-1H-imidazole-4,5-dicarboxamide;

$N^5$-{4-[(2,3-difluorobenzoyl)amino]phenyl}-$N^4$-methyl-1H-imidazole-4,5-dicarboxamide;

$N^5$-{4-[(3,4-difluorobenzoyl)amino]phenyl}-$N^4$-methyl-1H-imidazole-4,5-dicarboxamide;

$N^5$-{4[(4-cyanobenzoyl)amino]phenyl}-$N^4$-methyl-1H-imidazole-4,5-dicarboxamide;

$N^4$-methyl-$N^5$-{4-[(2,3,6-trifluorobenzoyl)amino]phenyl}-1H-imidazole-4,5-dicarboxamide;

$N^5$-{4-[(3-fluoro-2-methylbenzoyl)amino]phenyl}-$N^4$-methyl-1H-imidazole-4,5-dicarboxamide;

$N^5$-{4[(3-chlorobenzoyl)amino]phenyl}-$N^4$-methyl-1H-imidazole-4,5-dicarboxamide;

$N^5$-{4-[(2-fluorobenzoyl)amino]phenyl}-$N^4$-methyl-1H-imidazole-4,5-dicarboxamide;

$N^5$-{4-[(3-fluoro-4-methylbenzoyl)amino]phenyl}-$N^4$-methyl-1H-imidazole-4,5-dicarboxamide;

$N^5$-{4[(3-fluorobenzoyl)amino]phenyl}-$N^4$-methyl-1H-imidazole-4,5-dicarboxamide;

$N^4$-methyl-$N^5$-(4-{[(1-methyl-1H-pyrazol-3-yl)carbonyl]amino}phenyl)-1H-imidazole-4,5-dicarboxamide;

$N^5$-{4-[(4-chloro-2-fluorobenzoyl)amino]phenyl}-$N^4$-methyl-1H-imidazole-4,5-dicarboxamide;

$N^5$-{4-[(4-bromo-2-chlorobenzoyl)amino]phenyl}-$N^4$-methyl-1H-imidazole-4,5-dicarboxamide;

$N^5$-{4-[(3-fluoro-4-methoxybenzoyl)amino]phenyl}-$N^4$-methyl-1H-imidazole-4,5-dicarboxamide;

$N^5$-{4-[(3-chloro-4-fluorobenzoyl)amino]phenyl}-$N^4$-methyl-1H-imidazole-4,5-dicarboxamide;

$N^5$-{4-[(3-chloro-2-methylbenzoyl)amino]phenyl}-$N^4$-methyl-1H-imidazole-4,5-dicarboxamide;

$N^4$-methyl-$N^5$-{4-[(2,4,6-trifluorobenzoyl)amino]phenyl}-1H-imidazole-4,5-dicarboxamide;

$N^5$-{4-[(2-chloro-6-methylbenzoyl)amino]phenyl}-$N^4$-methyl-1H-imidazole-4,5-dicarboxamide;

$N^5$-{4-[(2-chloro-3-methylbenzoyl)amino]phenyl}-$N^4$-methyl-1H-imidazole-4,5-dicarboxamide;

$N^5$-{4-[(2-chloro-3,4-dimethoxybenzoyl)amino]phenyl}-$N^4$-methyl-1H-imidazole-4,5-dicarboxamide;

$N^5$-{4-[(5-cyano-2-fluorobenzoyl)amino]phenyl}-$N^4$-methyl-1H-imidazole-4,5-dicarboxamide;

$N^5$-{4-[(4-cyano-3-fluorobenzoyl)amino]phenyl}-$N^4$-methyl-1H-imidazole-4,5-dicarboxamide;

$N^5$-(4-{[2-chloro-5-(trifluoromethyl)benzoyl]amino}phenyl)-$N^4$-methyl-1H-imidazole-4,5-dicarboxamide;

$N^4$-methyl-$N^5$-(4-{[(3-methylpyridin-2-yl)carbonyl]amino}phenyl)-1H-imidazole-4,5-dicarboxamide;

$N^5$-(4-{[2-chloro-3-(trifluoromethyl)benzoyl]amino}phenyl)-$N^4$-methyl-1H-imidazole-4,5-dicarboxamide;

$N^5$-{4-[(3-chloro-2,4-difluorobenzoyl)amino]phenyl}-$N^4$-methyl-1H-imidazole-4,5-dicarboxamide;

$N^5$-{4-[(2-chloro-5-fluorobenzoyl)amino]phenyl}-$N^4$-methyl-1H-imidazole-4,5-dicarboxamide;

$N^5$-{4-[(4-cyano-2-fluorobenzoyl)amino]phenyl}-$N^4$-methyl-1H-imidazole-4,5-dicarboxamide;

$N^5$-{4-[(2-chloro-3-fluorobenzoyl)amino]phenyl}-$N^4$-methyl-1H-imidazole-4,5-dicarboxamide;

$N^5$-(4-{[(3-chloropyrazin-2-yl)carbonyl]amino}phenyl)-$N^4$-methyl-1H-imidazole-4,5-dicarboxamide;

$N^5$-{4-[(4-fluoro-3-methylbenzoyl)amino]phenyl}-$N^4$-methyl-1H-imidazole-4,5-dicarboxamide;

N⁵-{4-[(2-chloro-3,6-difluorobenzoyl)amino]phenyl}-N⁴-methyl-1H-imidazole-4,5-dicarboxamide;
N⁵-{4-[(2-fluoro-6-methylbenzoyl)amino]phenyl}-N⁴-methyl-1H-imidazole-4,5-dicarboxamide;
N⁵-{4-[(4,5-difluoro-2-methylbenzoyl)amino]phenyl}-N⁴-methyl-1H-imidazole-4,5-dicarboxamide;
N⁵-{4-[(2-chloro-4-fluorobenzoyl)amino]phenyl}-N⁴-[5-(dimethylamino)pentyl]-1H-imidazole-4,5-dicarboxamide;
N⁵-{4-[(2-chloro-4-fluorobenzoyl)amino]phenyl}-N⁴-[(2S)-1-hydroxy-3-methylbutan-2-yl]-1H-imidazole-4,5-dicarboxamide;
N⁵-{4-[(2-chloro-4-fluorobenzoyl)amino]phenyl}-N⁴-[5-(diethylamino)pentan-2-yl]-1H-imidazole-4,5-dicarboxamide;
N⁴-{4-[(2-chlorobenzoyl)amino]phenyl}-N⁵-[2-(piperidin-1-yl)ethyl]-1H-imidazole-4,5-dicarboxamide;
N⁵-{4-[(2-chloro-4-fluorobenzoyl)amino]phenyl}-N⁴-[2-(diethylamino)ethyl]-1H-imidazole-4,5-dicarboxamide;
N⁵-{4-[(2-chloro-4-fluorobenzoyl)amino]phenyl}-N⁴-(2-phenylethyl)-1H-imidazole-4,5-dicarboxamide;
N⁵-{4-[(2-chloro-4-fluorobenzoyl)amino]phenyl}-N⁴-[2-(1-methylpyrrolidin-2-yl)ethyl]-1H-imidazole-4,5-dicarboxamide;
N⁵-{4-[(2-chloro-4-fluorobenzoyl)amino]phenyl}-N⁴-[3-(2-methylpiperidin-1-yl)propyl]-1H-imidazole-4,5-dicarboxamide;
N⁵-{4-[(2-chloro-4-fluorobenzoyl)amino]phenyl}-N⁴-[2-(pyridin-2-yl)ethyl]-1H-imidazole-4,5-dicarboxamide;
N⁵-{4-[(2-chloro-4-fluorobenzoyl)amino]phenyl}-N⁴-[3-(diethylamino)propyl]-1H-imidazole-4,5-dicarboxamide;
N⁵-{4-[(2-chloro-4-fluorobenzoyl)amino]phenyl}-N⁴-[2-(diisopropylamino)ethyl]-1H-imidazole-4,5-dicarboxamide;
N⁵-{4-[(2-chloro-4-fluorobenzoyl)amino]phenyl}-N⁴-[(1-ethylpyrrolidin-2-yl)methyl]-1H-imidazole-4,5-dicarboxamide;
N⁵-{4-[(2-chloro-4-fluorobenzoyl)amino]phenyl}-N⁴-(2,2-dimethyltetrahydro-2H-pyran-4-yl)-1H-imidazole-4,5-dicarboxamide;
N⁵-{4-[(2-chloro-4-fluorobenzoyl)amino]phenyl}-N⁴-[3-(4-methylpiperazin-1-yl)propyl]-1H-imidazole-4,5-dicarboxamide;
N⁵-{4-[(2-chloro-4-fluorobenzoyl)amino]phenyl}-N⁴-[4-(diethylamino)butyl]-1H-imidazole-4,5-dicarboxamide;
N⁵-{4-[(2-chloro-4-fluorobenzoyl)amino]phenyl}-N⁴-[2-(pyridin-4-yl)ethyl]-1H-imidazole-4,5-dicarboxamide;
N⁵-{4-[(2-chloro-4-fluorobenzoyl)amino]phenyl}-N⁴-[3-(dimethylamino)-2,2-dimethylpropyl]-1H-imidazole-4,5-dicarboxamide;
N⁵-{4-[(2-chloro-4-fluorobenzoyl)amino]phenyl}-N⁴-(tetrahydro-2H-pyran-4-ylmethyl)-1H-imidazole-4,5-dicarboxamide;
N⁵-{4-[(2-chloro-4-fluorobenzoyl)amino]phenyl}-N⁴-[2-(2-oxopyrrolidin-1-yl)ethyl]-1H-imidazole-4,5-dicarboxamide;
N⁵-{4-[(2-chloro-4-fluorobenzoyl)amino]phenyl}-N⁴-[2-(2-oxoimidazolidin-1-yl)ethyl]-1H-imidazole-4,5-dicarboxamide;
N⁵-{4-[(2-chloro-4-fluorobenzoyl)amino]phenyl}-N⁴-[3-(4-methylpiperidin-1-yl)propyl]-1H-imidazole-4,5-dicarboxamide;
N⁵-{4-[(2-chloro-4-fluorobenzoyl)amino]phenyl}-N⁴-[2-(2,6-dimethylpiperidin-1-yl)ethyl]-1H-imidazole-4,5-dicarboxamide;
N⁵-{4-[(2-chloro-4-fluorobenzoyl)amino]phenyl}-N⁴-[2-(1,1-dioxidothiomorpholin-4-yl)ethyl]-1H-imidazole-4,5-dicarboxamide;
N⁵-{4-[(2-chloro-4-fluorobenzoyl)amino]phenyl}-N⁴-{[(2S)-1-ethylpyrrolidin-2-yl]methyl}-1H-imidazole-4,5-dicarboxamide;
N⁵-{4-[(2-chloro-4-fluorobenzoyl)amino]phenyl}-N⁴-[2-(pyridin-3-yl)ethyl]-1H-imidazole-4,5-dicarboxamide;
N⁵-{4-[(2-chloro-4-fluorobenzoyl)amino]phenyl}-N⁴-[5-(pyrrolidin-1-yl)pentyl]-1H-imidazole-4,5-dicarboxamide;
N⁵-{4-[(2-chloro-4-fluorobenzoyl)amino]phenyl}-N⁴-[(1-methylpyrrolidin-3-yl)methyl]-1H-imidazole-4,5-dicarboxamide;
N⁵-{4-[(2-chloro-4-fluorobenzoyl)amino]phenyl}-N⁴-[(1-methylpiperidin-4-yl)methyl]-1H-imidazole-4,5-dicarboxamide;
N⁵-{4-[(2-chloro-4-fluorobenzoyl)amino]phenyl}-N⁴-[(1-ethylpiperidin-4-yl)methyl]-1H-imidazole-4,5-dicarboxamide;
N⁵-{4-[(2-chloro-4-fluorobenzoyl)amino]phenyl}-N⁴-[(1-methylpiperidin-2-yl)methyl]-1H-imidazole-4,5-dicarboxamide;
N⁵-{4-[(2-chloro-4-fluorobenzoyl)amino]phenyl}-N⁴-[(1-ethylpyrrolidin-3-yl)methyl]-1H-imidazole-4,5-dicarboxamide;
N⁵-{4-[(2-chloro-4-fluorobenzoyl)amino]phenyl}-N⁴-[2-(dimethylamino)-2-methylpropyl]-1H-imidazole-4,5-dicarboxamide;
N⁵-{4-[(2-chloro-4-fluorobenzoyl)amino]phenyl}-N⁴-{[(2R)-1-ethylpyrrolidin-2-yl]methyl}-1H-imidazole-4,5-dicarboxamide;
N⁵-{4-[(2-chloro-4-fluorobenzoyl)amino]phenyl}-N⁴-(1-methylpiperidin-4-yl)-1H-imidazole-4,5-dicarboxamide;
N⁵-{4-[(2-chloro-4-fluorobenzoyl)amino]phenyl}-N⁴-[2,2-dimethyl-3-(4-methylpiperazin-1-yl)propyl]-1H-imidazole-4,5-dicarboxamide;

In a further embodiment of the above-mentioned aspects, the invention relates to compounds of formula (I), wherein: X¹ represents NR³.

In a further embodiment of the above-mentioned aspects, the invention relates to compounds of formula (I), wherein: X¹ represents O.

In a further embodiment of the above-mentioned aspects, the invention relates to compounds of formula (I), wherein: X² represents CR⁶, preferably CH.

In a further embodiment of the above-mentioned aspects, the invention relates to compounds of formula (I), wherein: X² represents N.

In a further embodiment of the above-mentioned aspects, the invention relates to compounds of formula (I), wherein:
X¹ represents NR³, and
X² represents CR⁶, preferably CH.

In a further embodiment of the above-mentioned aspects, the invention relates to compounds of formula (I), wherein:
R¹ represents a group selected from:
—OR⁹, and —N(R¹⁰)R¹¹.

In a further embodiment of the above-mentioned aspects, the invention relates to compounds of formula (I), wherein:
R¹ represents —OR⁹.

In a further embodiment of the above-mentioned aspects, the invention relates to compounds of formula (I), wherein:
R¹ represents —N(R¹⁰)R¹¹.

In a further embodiment of the above-mentioned aspects, the invention relates to compounds of formula (I), wherein:
R² represents a group selected from:

hydrogen, $C_1$-$C_3$-alkyl, and $C_3$-$C_4$-cycloalkyl, preferably hydrogen and $C_1$-$C_3$-alky.

In a further embodiment of the above-mentioned aspects, the invention relates to compounds of formula (I), wherein:
$R^2$ represents hydrogen.

In a further embodiment of the above-mentioned aspects, the invention relates to compounds of formula (I), wherein:
$R^2$ represents $C_1$-$C_3$-alkyl.

In a further embodiment of the above-mentioned aspects, the invention relates to compounds of formula (I), wherein:
$R^2$ represents $C_1$-$C_2$-alkyl.

In a further embodiment of the above-mentioned aspects, the invention relates to compounds of formula (I), wherein:
$R^3$ represents a hydrogen atom, In a further embodiment of the above-mentioned aspects, the invention relates to compounds of formula (I), wherein:
$R^4$ represents a hydrogen atom, In a further embodiment of the above-mentioned aspects, the invention relates to compounds of formula (I), wherein:
$R^5$ represents a group selected from:
hydrogen, $C_1$-$C_3$-alkyl, $C_1$-$C_3$-alkoxy, $C_1$-$C_3$-haloalkyl, $C_1$-$C_3$-haloalkoxy, and halogen, preferably hydrogen, $C_1$-$C_3$-alkyl, more preferably hydrogen, and methyl.

In a further embodiment of the above-mentioned aspects, the invention relates to compounds of formula (I), wherein:
$R^5$ represents a group selected from:
hydrogen, $C_1$-$C_3$-alkyl, $C_1$-$C_3$-alkoxy and $C_1$-$C_3$-haloalkoxy.

In a further embodiment of the above-mentioned aspects, the invention relates to compounds of formula (I), wherein:
$R^5$ represents a group selected from:
hydrogen, methoxy, trifluoromethoxy and methyl.

In a further embodiment of the above-mentioned aspects, the invention relates to compounds of formula (I), wherein:
$R^5$ represents a group selected from:
$C_1$-$C_3$-alkoxy and $C_1$-$C_3$-haloalkoxy, preferably a group selected from methoxy and trifluoromethoxy.

In a further embodiment of the above-mentioned aspects, the invention relates to compounds of formula (I), wherein:
$R^5$ represents hydrogen.

In a further embodiment of the above-mentioned aspects, the invention relates to compounds of formula (I), wherein:
$R^6$ represents a group selected from:
hydrogen, and halogen, preferably hydrogen.

In a further embodiment of the above-mentioned aspects, the invention relates to compounds of formula (I), wherein:
$R^6$ represents halogen, preferably a fluorine atom.

In a further embodiment of the above-mentioned aspects, the invention relates to compounds of formula (I), wherein:
$R^7$ represents a hydrogen atom, In a further embodiment of the above-mentioned aspects, the invention relates to compounds of formula (I), wherein:
$R^8$ represents a group selected from:
aryl, and heteroaryl,
wherein aryl and heteroaryl groups are optionally substituted with one, two or three substituents, which are independently of each other selected from:
$C_1$-$C_6$-alkyl, $C_1$-$C_3$-alkoxy, $C_3$-$C_6$-cycloalkyl, $C_3$-$C_6$-cycloalkoxy, $C_1$-$C_3$-haloalkyl, $C_1$-$C_3$-haloalkoxy, halogen, cyano, nitro, hydroxy, ($C_1$-$C_6$-alkyl)-S—, ($C_1$-$C_6$-alkyl)-S(=O)—, ($C_1$-$C_6$-alkyl)-S(=O)$_2$—, —S(=O)(=NR$^{15}$)R$^{16}$, —N(R$^{10}$)R$^{11}$, R$^{10}$(R$^{11}$)N—($C_1$-$C_6$-alkyl)-, R$^{10}$(R$^{11}$)N—($C_2$-$C_6$-alkoxy)-, phenyl, phenoxy, —N(R$^{12}$)C(=O)R$^{13}$, —C(=O)OH, —C(=O)OR$^9$, and —C(=O)N(R$^{12}$)$_2$,
whereby two substituents of said aryl group, if they are in ortho-position to one another, can be linked to one another in such a way that they jointly form methanediylbisoxy, ethane-1,2-diylbisoxy, propane-1,3-diyl, or butane-1,4-diyl.

In a further embodiment of the above-mentioned aspects, the invention relates to compounds of formula (I), wherein:
$R^8$ represents a group selected from:
aryl, and heteroaryl,
wherein aryl and heteroaryl groups are optionally substituted with one, two or three substituents, which are independently of each other selected from:
$C_1$-$C_6$-alkyl, $C_1$-$C_3$-alkoxy, $C_1$-$C_3$-haloalkyl, halogen, nitro, ($C_1$-$C_6$-alkyl)-S(=O)$_2$—, —S(=O)(=NR$^{15}$)R$^{16}$, —N(R$^{10}$)R$^{11}$, R$^{10}$(R$^{11}$)N—($C_2$-$C_6$-alkoxy)-, phenyl, phenoxy and —N(R$^{12}$)C(=O)R$^{13}$.
whereby two substituents of said aryl group, if they are in ortho-position to one another, can be linked to one another in such a way that they jointly form methanediylbisoxy.

In a further embodiment of the above-mentioned aspects, the invention relates to compounds of formula (I), wherein:
$R^8$ represents a group selected from:
phenyl, pyrazolyl, thienyl, and pyridyl,
wherein said groups are optionally substituted with one, two or three substituents, which are independently of each other selected from:
$C_1$-$C_5$-alkyl, $C_1$-$C_3$-alkoxy, $C_1$-haloalkyl, fluorine, chlorine, bromine, nitro, methyl-S(=O)$_2$—, —S(=O)(=NR$^{15}$)R$^{16}$, —N(R$^{10}$)R$^{11}$, R$^{10}$(R$^{11}$)N—($C_2$-alkoxy)-, phenyl, phenoxy, and —N(R$^{12}$)C(=O)R$^{13}$,
whereby two substituents of said phenyl group, if they are in ortho-position to one another, can be linked to one another in such a way that they jointly form methanediylbisoxy.

In a further embodiment of the above-mentioned aspects, the invention relates to compounds of formula (I), wherein:
$R^8$ represents a group selected from:
phenyl, pyrazolyl, and pyridyl,
wherein said groups are optionally substituted with one, two or three substituents, which are independently of each other selected from:
$C_1$-$C_5$-alkyl, $C_1$-$C_3$-alkoxy, $C_1$-haloalkyl, fluorine, chlorine, bromine, —N(R$^{10}$)R$^{11}$, R$^{10}$(R$^{11}$)N—($C_2$-alkoxy)- and phenyl.

In a further embodiment of the above-mentioned aspects, the invention relates to compounds of formula (I), wherein:
$R^8$ represents an aryl group, preferably phenyl, optionally substituted with one, two or three substituents, which are independently of each other selected from:
$C_1$-$C_6$-alkyl, $C_1$-$C_3$-alkoxy, $C_1$-$C_3$-haloalkyl, halogen, nitro, ($C_1$-$C_6$-alkyl)-S(=O)$_2$—, —S(=O)(=NR$^{15}$)R$^{16}$, —N(R$^{10}$)R$^{11}$, R$^{10}$(R$^{11}$)N—($C_2$-$C_6$-alkoxy)-, phenyl, phenoxy and —N(R$^{12}$)C(=O)R$^{13}$,
whereby two substituents of said aryl group, if they are in ortho-position to one another, can be linked to one another in such a way that they jointly form methanediylbisoxy.

In a further embodiment of the above-mentioned aspects, the invention relates to compounds of formula (I), wherein:
$R^8$ represents an aryl group, preferably phenyl, optionally substituted with one, two or three substituents, which are independently of each other selected from:
$C_1$-$C_6$-alkyl, $C_1$-$C_3$-alkoxy, $C_1$-$C_3$-haloalkyl, halogen, —N(R$^{10}$)R$^{11}$ and R$^{10}$(R$^{11}$)N—($C_2$-$C_6$-alkoxy)-.

In a further embodiment of the above-mentioned aspects, the invention relates to compounds of formula (I), wherein:
$R^8$ represents a heteroaryl group, preferably pyrazolyl or pyridyl, optionally substituted with one, two or three substituents, which are independently of each other selected from:
$C_1$-$C_6$-alkyl, $C_1$-$C_3$-alkoxy, $C_1$-$C_3$-haloalkyl, halogen, nitro, ($C_1$-$C_6$-alkyl)-S(=O)$_2$—, —S(=O)(=NR$^{15}$)R$^{16}$, —N($R^{10}$)$R^{11}$, $R^{10}$($R^{11}$)N—($C_2$-$C_6$-alkoxy)-, phenyl, phenoxy and —N($R^{12}$)C(=O)$R^{13}$.

In a further embodiment of the above-mentioned aspects, the invention relates to compounds of formula (I), wherein:
$R^8$ represents a heteroaryl group, preferably pyrazolyl or pyridyl, optionally substituted with one, two or three substituents, which are independently of each other selected from:
$C_1$-$C_6$-alkyl, halogen and phenyl, preferably $C_1$-$C_3$-alkyl, chlorine and phenyl.

In a further embodiment of the above-mentioned aspects, the invention relates to compounds of formula (I), wherein:
$R^8$ represents a group selected from:
aryl, and heteroaryl,
wherein aryl and heteroaryl groups are optionally substituted with one, two or three substituents, which are independently of each other selected from:
$C_1$-$C_6$-alkyl, $C_1$-$C_3$-alkoxy, $C_1$-$C_3$-haloalkyl, $C_1$-$C_3$-haloalkoxy, halogen, cyano, nitro, hydroxy, ($C_1$-$C_6$-alkyl)-S(=O)$_2$—, —S(=O)(=N$R^{15}$)$R^{16}$, —N($R^{10}$)$R^{11}$,
$R^{10}$($R^{11}$)N—($C_2$-$C_6$-alkoxy)-, phenyl, phenoxy, and —N($R^{12}$)C(=O)$R^{13}$,
whereby two substituents of said aryl group, if they are in ortho-position to one another, can be linked to one another in such a way that they jointly form methanediylbisoxy, ethane-1,2-diylbisoxy, propane-1,3-diyl, or butane-1,4-diyl.

In a further embodiment of the above-mentioned aspects, the invention relates to compounds of formula (I), wherein:
$R^8$ represents a group selected from:
aryl, and heteroaryl,
wherein aryl and heteroaryl groups are substituted with one substituent, which is selected from:
$C_1$-$C_3$-haloalkoxy, iodine, cyano and hydroxy, and
wherein aryl and heteroaryl groups are optionally further substituted with one or two substituents, which are independently of each other selected from:
$C_1$-$C_6$-alkyl, $C_1$-$C_3$-alkoxy, $C_1$-$C_3$-haloalkyl, $C_1$-$C_3$-haloalkoxy, halogen, cyano, nitro, hydroxy, ($C_1$-$C_6$-alkyl)-S(=O)$_2$—, —S(=O)(=N$R^{15}$)$R^{16}$, —N($R^{10}$)$R^{11}$,
$R^{10}$($R^{11}$)N—($C_2$-$C_6$-alkoxy)-, phenyl, phenoxy, and —N($R^{12}$)C(=O)$R^{13}$,
whereby two substituents of said aryl group, if they are in ortho-position to one another, can be linked to one another in such a way that they jointly form methanediylbisoxy, ethane-1,2-diylbisoxy, propane-1,3-diyl, or butane-1,4-diyl.

In a further embodiment of the above-mentioned aspects, the invention relates to compounds of formula (I), wherein:
$R^8$ represents a group selected from:
Phenyl, pyrazolyl, thienyl, pyridyl, furanyl, thiazolyl, oxazolyl, and pyrazinyl
wherein said groups are optionally substituted with one, two or three substituents, which are independently of each other selected from:
$C_1$-$C_5$-alkyl, $C_1$-$C_3$-alkoxy, $C_1$-haloalkyl, $C_1$-haloalkoxy, fluorine, chlorine, bromine, iodine, hydroxy, cyano, nitro, methyl-S(=O)$_2$—, —S(=O)(=N$R^{15}$)$R^{16}$, —N($R^{10}$)$R^{11}$,
$R^{10}$($R^{11}$)N—($C_2$-alkoxy)-, phenyl, phenoxy, and —N($R^{12}$)C(=O)$R^{13}$,
whereby two substituents of said phenyl group, if they are in ortho-position to one another, can be linked to one another in such a way that they jointly form methanediylbisoxy.

In a further embodiment of the above-mentioned aspects, the invention relates to compounds of formula (I), wherein:
$R^8$ represents:
Phenyl
wherein said phenyl is optionally substituted with one, two or three substituents, which are independently of each other selected from:
$C_1$-$C_5$-alkyl, $C_1$-$C_3$-alkoxy, $C_1$-haloalkyl, $C_1$-haloalkoxy, fluorine, chlorine, bromine, iodine, hydroxy, cyano, nitro, methyl-S(=O)$_2$—, —S(=O)(=N$R^{15}$)$R^{16}$, —N($R^{10}$)$R^{11}$,
$R^{10}$($R^{11}$)N—($C_2$-alkoxy)-, phenyl, phenoxy, and —N($R^{12}$)C(=O)$R^{13}$,
whereby two substituents of said phenyl group, if they are in ortho-position to one another, can be linked to one another in such a way that they jointly form methanediylbisoxy.

In a further embodiment of the above-mentioned aspects, the invention relates to compounds of formula (I), wherein:
$R^8$ represents:
Phenyl
wherein said phenyl is substituted with one substituent, which is selected from:
$C_1$-$C_3$-haloalkoxy, iodine, hydroxy and cyano, and
wherein said phenyl is optionally further substituted with one or two substituents, which are independently of each other selected from:
$C_1$-$C_5$-alkyl, $C_1$-$C_3$-alkoxy, $C_1$-haloalkyl, $C_1$-haloalkoxy, fluorine, chlorine, bromine, iodine, hydroxy, cyano, nitro, methyl-S(=O)$_2$—, —S(=O)(=N$R^{15}$)$R^{16}$, —N($R^{10}$)$R^{11}$,
$R^{10}$($R^{11}$)N—($C_2$-alkoxy)-, phenyl, phenoxy, and —N($R^{12}$)C(=O)$R^{13}$,
whereby two substituents of said phenyl group, if they are in ortho-position to one another, can be linked to one another in such a way that they jointly form methanediylbisoxy.

In a further embodiment of the above-mentioned aspects, the invention relates to compounds of formula (I), wherein:
$R^8$ represents a group selected from:
pyrazolyl, thienyl, pyridyl, furanyl, thiazolyl, oxazolyl, and pyrazinyl
wherein said groups are optionally substituted with one, two or three substituents, which are independently of each other selected from:
$C_1$-$C_5$-alkyl, $C_1$-$C_3$-alkoxy, $C_1$-haloalkyl, $C_1$-haloalkoxy, fluorine, chlorine, bromine, iodine, hydroxy, cyano, nitro, methyl-S(=O)$_2$—, —S(=O)(=N$R^{15}$)$R^{16}$, —N($R^{10}$)$R^{11}$,
$R^{10}$($R^{11}$)N—($C_2$-alkoxy)-, phenyl, phenoxy, and —N($R^{12}$)C(=O)$R^{13}$.

In a further embodiment of the above-mentioned aspects, the invention relates to compounds of formula (I), wherein:
$R^8$ represents a group selected from:
pyrazolyl, thienyl, pyridyl, furanyl, thiazolyl, oxazolyl, and pyrazinyl
wherein said groups are substituted with one substituent, which is selected from:
$C_1$-$C_3$-haloalkoxy, iodine, hydroxy and cyano, and
wherein said groups are optionally further substituted with one or two substituents, which are independently of each other selected from:
$C_1$-$C_5$-alkyl, $C_1$-$C_3$-alkoxy, $C_1$-haloalkyl, $C_1$-haloalkoxy, fluorine, chlorine, bromine, iodine, hydroxy, cyano, nitro, methyl-S(=O)$_2$—, —S(=O)(=N$R^{15}$)$R^{16}$, —N($R^{10}$)$R^{11}$,
$R^{10}$($R^{11}$)N—($C_2$-alkoxy)-, phenyl, phenoxy, and —N($R^{12}$)C(=O)$R^{13}$.

In a further embodiment of the above-mentioned aspects, the invention relates to compounds of formula (I), wherein:
R$^8$ represents a group selected from:
Phenyl, pyrazolyl, thienyl, pyridyl, furanyl, thiazolyl, oxazolyl, and pyrazinyl
wherein said groups are substituted with one substituent, which is selected from:
C$_1$-C$_3$-haloalkoxy, iodine, hydroxy and cyano, and
wherein said groups are optionally further substituted with one or two substituents, which are independently of each other selected from:
C$_1$-C$_5$-alkyl, C$_1$-C$_3$-alkoxy, C$_1$-haloalkyl, C$_1$-haloalkoxy, fluorine, chlorine, bromine, iodine, hydroxy, cyano, nitro, methyl-S(=O)$_2$—, —S(=O)(=NR$^{15}$)R$^{16}$, —N(R$^{10}$)R$^{11}$,
R$^{10}$(R$^{11}$)N—(C$_2$-alkoxy)-, phenyl, phenoxy, and —N(R$^{12}$)C(=O)R$^{13}$,
whereby two substituents of said phenyl group, if they are in ortho-position to one another, can be linked to one another in such a way that they jointly form methanediylbisoxy.

In a further embodiment of the above-mentioned aspects, the invention relates to compounds of formula (I), wherein:
R$^8$ represents a heteroaryl group, preferably pyrazolyl, thienyl, pyridyl, furanyl, thiazolyl, oxazolyl or pyrazinyl, optionally substituted with one, two or three substituents, which are independently of each other selected from:
C$_1$-C$_6$-alkyl, C$_1$-C$_3$-alkoxy, C$_1$-C$_3$-haloalkyl, C$_1$-C$_3$-haloalkoxy, halogen, cyano, nitro, hydroxy, (C$_1$-C$_6$-alkyl)-S(=O)$_2$—, —S(=O)(=NR$^{15}$)R$^{16}$, —N(R$^{10}$)R$^{11}$,
R$^{10}$(R$^{11}$)N—(C$_2$-C$_6$-alkoxy)-, phenyl, phenoxy, and —N(R$^{12}$)C(=O)R$^{13}$.

In a further embodiment of the above-mentioned aspects, the invention relates to compounds of formula (I), wherein:
R$^8$ represents a heteroaryl group, preferably furanyl, thiazolyl, oxazolyl or pyrazinyl, optionally substituted with one, two or three substituents, which are independently of each other selected from:
C$_1$-C$_6$-alkyl, C$_1$-C$_3$-alkoxy, C$_1$-C$_3$-haloalkyl, C$_1$-C$_3$-haloalkoxy, halogen, cyano, nitro, hydroxy, (C$_1$-C$_6$-alkyl)-S(=O)$_2$—, —S(=O)(=NR$^{15}$)R$^{16}$, —N(R$^{10}$)R$^{11}$,
R$^{10}$(R$^{11}$)N—(C$_2$-C$_6$-alkoxy)-, phenyl, phenoxy, and —N(R$^{12}$)C(=O)R$^{13}$.

In a further embodiment of the above-mentioned aspects, the invention relates to compounds of formula (I), wherein:
R$^8$ represents a heteroaryl group, preferably pyrazolyl, thienyl or pyridyl substituted with one substituent, which is selected from:
C$_1$-C$_3$-haloalkoxy, iodine, cyano, and hydroxyl,
said heteroaryl being optionally further substituted with one or two substituents, which are independently of each other selected from:
C$_1$-C$_6$-alkyl, C$_1$-C$_3$-alkoxy, C$_1$-C$_3$-haloalkyl, C$_1$-C$_3$-haloalkoxy, halogen, cyano, nitro, hydroxy, (C$_1$-C$_6$-alkyl)-S(=O)$_2$—, —S(=O)(=NR$^{15}$)R$^{16}$, —N(R$^{10}$)R$^{11}$,
R$^{10}$(R$^{11}$)N—(C$_2$-C$_6$-alkoxy)-, phenyl, phenoxy, and —N(R$^{12}$)C(=O)R$^{13}$.

In a further embodiment of the above-mentioned aspects, the invention relates to compounds of formula (I), wherein:
R$^8$ represents
aryl,
wherein aryl is optionally substituted with one, two or three substituents, which are independently of each other selected from:
C$_1$-C$_6$-alkyl, C$_1$-C$_3$-alkoxy, C$_1$-C$_3$-haloalkyl, C$_1$-C$_3$-haloalkoxy, halogen, cyano, nitro, hydroxy, (C$_1$-C$_6$-alkyl)-S(=O)$_2$—, —S(=O)(=NR$^{15}$)R$^{16}$, —N(R$^{10}$)R$^{11}$,
R$^{10}$(R$^{11}$)N—(C$_2$-C$_6$-alkoxy)-, phenyl, phenoxy, and —N(R$^{12}$)C(=O)R$^{13}$,
whereby two substituents of said aryl group, if they are in ortho-position to one another, can be linked to one another in such a way that they jointly form methanediylbisoxy, ethane-1,2-diylbisoxy, propane-1,3-diyl, or butane-1,4-diyl.

In a further embodiment of the above-mentioned aspects, the invention relates to compounds of formula (I), wherein:
R$^8$ represents aryl,
wherein aryl is substituted with one substituent, which is selected from:
C$_1$-C$_3$-haloalkoxy, iodine, cyano and hydroxy, and
wherein aryl is optionally further substituted with one or two substituents, which are independently of each other selected from:
C$_1$-C$_6$-alkyl, C$_1$-C$_3$-alkoxy, C$_1$-C$_3$-haloalkyl, C$_1$-C$_3$-haloalkoxy, halogen, cyano, nitro, hydroxy, (C$_1$-C$_6$-alkyl)-S(=O)$_2$—, —S(=O)(=NR$^{15}$)R$^{16}$, —N(R$^{10}$)R$^{11}$,
R$^{10}$(R$^{11}$)N—(C$_2$-C$_6$-alkoxy)-, phenyl, phenoxy, and —N(R$^{12}$)C(=O)R$^{13}$,
whereby two substituents of said aryl group, if they are in ortho-position to one another, can be linked to one another in such a way that they jointly form methanediylbisoxy, ethane-1,2-diylbisoxy, propane-1,3-diyl, or butane-1,4-diyl.

In a further embodiment of the above-mentioned aspects, the invention relates to compounds of formula (I), wherein:
R$^8$ represents a heteroaryl group, preferably pyrazolyl, thienyl, pyridyl, furanyl, thiazolyl, oxazolyl or pyrazinyl, optionally substituted with one, two or three substituents, which are independently of each other selected from:
C$_1$-C$_6$-alkyl, halogen and phenyl, preferably C$_1$-C$_3$-alkyl, chlorine and phenyl.

In a preferred embodiment of all aspects of the invention described herein, the invention relates to compounds of formula (I), wherein:
R$^8$ represents a group selected from aryl and heteroaryl, preferably selected from phenyl, pyrazolyl, thienyl, pyridyl, furanyl, thiazolyl, oxazolyl, and pyrazinyl,
wherein aryl and heteroaryl groups are substituted with one halogen atom, preferably fluorine, chlorine or bromine, more preferably chlorine and bromine, at a ring carbon atom adjacent (e.g. ortho) to the point of attachment of said group with the rest of the molecule,
wherein aryl and heteroaryl groups are optionally further substituted with one or two substituents, which are independently of each other selected from:
C$_1$-C$_6$-alkyl, C$_1$-C$_3$-alkoxy, C$_1$-C$_3$-haloalkyl, C$_1$-C$_3$-haloalkoxy, halogen, cyano, nitro, hydroxy, (C$_1$-C$_6$-alkyl)-S(=O)$_2$—, —S(=O)(=NR$^{15}$)R$^{16}$, —N(R$^{10}$)R$^{11}$,
R$^{10}$(R$^{11}$)N—(C$_2$-C$_6$-alkoxy)-, phenyl, phenoxy, and —N(R$^{12}$)C(=O)R$^{13}$,
whereby two substituents of said aryl group, if they are in ortho-position to one another, can be linked to one another in such a way that they jointly form methanediylbisoxy, ethane-1,2-diylbisoxy, propane-1,3-diyl, or butane-1,4-diyl.

In a preferred embodiment of all aspects of the invention described herein, the invention relates to compounds of formula (I), wherein:

$R^8$ represents a group selected from:
aryl, and heteroaryl,
wherein aryl and heteroaryl groups are optionally substituted with one, two or three substituents, as defined for all the above-mentioned aspects,
wherein when said aryl and heteroaryl groups are substituted with a halogen atom, said halogen atom is attached to a ring carbon atom adjacent (e.g. ortho) to the point of attachment of said group with the rest of the molecule.

Preferably said halogen atom is selected from fluorine, chlorine and bromine, more preferably said halogen atom is chlorine or bromine. It is understood that said aryl and heteroaryl groups may optionally be further substituted with one or two substituents, which are independently of each other selected from the substituents defined for the above-mentioned aspects, including one or two further halogen atoms. For example, said aryl and heteroaryl groups may optionally be further substituted with one or two substituents, which are independently of each other selected from:
$C_1$-$C_6$-alkyl, $C_1$-$C_3$-alkoxy, $C_1$-$C_3$-haloalkyl, $C_1$-$C_3$-haloalkoxy, halogen, cyano, nitro, hydroxy, ($C_1$-$C_6$-alkyl)-S(=O)$_2$—, —S(=O)(=NR$^{15}$)R$^{16}$, —N(R$^{10}$)R$^{11}$, R$^{10}$(R$^{11}$)N—($C_2$-$C_6$-alkoxy)-, phenyl, phenoxy, and —N(R$^{12}$)C(=O)R$^{13}$.

In a further embodiment of the above-mentioned aspects, the invention relates to compounds of formula (I), wherein:
$R^8$ represents a group selected from:
Phenyl, pyridyl,
wherein said groups are optionally substituted with one, two or three substituents, which are independently of each other selected from:
$C_1$-alkyl, $C_1$-$C_2$-alkoxy, $C_1$-haloalkyl (preferably CF$_3$), $C_1$-haloalkoxy (preferably —OCF$_3$), fluorine, chlorine, bromine, iodine, hydroxy, cyano, methyl-S(=O)$_2$—, —S(=O)(=NH)Et, —N(CH$_3$)$_2$, (piperidin-1-yl)-(C$_2$-alkoxy)-, and (CH$_3$)$_2$N—(C$_2$-alkoxy)-.

In a further embodiment of the above-mentioned aspects, the invention relates to compounds of formula (I), wherein:
$R^9$ represents a group selected from:
$C_1$-$C_6$-alkyl, $C_3$-$C_6$-cycloalkyl, $C_2$-$C_6$-hydroxyalkyl-, and ($C_1$-$C_3$-alkoxy)-($C_1$-$C_6$-alkyl)-.

In a further embodiment of the above-mentioned aspects, the invention relates to compounds of formula (I), wherein:
$R^9$ represents $C_1$-$C_6$-alkyl, preferably $C_1$-$C_2$-alkyl group.

In a further embodiment of the above-mentioned aspects, the invention relates to compounds of formula (I), wherein:
$R^{10}$ and $R^{11}$ are independently of each other selected from:
hydrogen, $C_1$-$C_6$-alkyl, $C_3$-$C_6$-cycloalkyl, ($C_3$-$C_6$-cycloalkyl)-$C_1$-$C_6$-alkyl)-, $C_2$-$C_6$-hydroxyalkyl, ($C_1$-$C_3$-alkoxy)-($C_2$-$C_6$-alkyl)-, $C_1$-$C_6$-haloalkyl, H$_2$N—($C_2$-$C_6$-alkyl)-, ($C_1$-$C_3$-alkyl)N(H)($C_2$-$C_6$-alkyl)-, ($C_1$-$C_3$-alkyl)$_2$N($C_2$-$C_6$-alkyl)-, HOC(=O)—($C_1$-$C_6$-alkyl)-, R$^9$OC(=O)—($C_1$-$C_6$-alkyl)-, 4-6 membered heterocycloalkyl, (4-6 membered heterocycloalkyl)-($C_2$-$C_6$-alkyl)-, aryl, heteroaryl, aryl-($C_1$-$C_6$-alkyl)-, and heteroaryl-($C_1$-$C_6$-alkyl)-, wherein 4-6-membered heterocycloalkyl groups are optionally substituted with one or two substituents, which are independently of each other selected from:
$C_1$-$C_3$-alkyl, $C_1$-$C_3$-haloalkyl, $C_1$-$C_3$-alkoxy, $C_1$-$C_3$-haloalkoxy, $C_3$-$C_4$-cycloalkyl, $C_3$-$C_4$-cycloalkoxy, amino, hydroxy, a halogen atom, and cyano,
and,
wherein aryl and heteroaryl groups are optionally substituted with one or two substituents, which are independently of each other selected from:
$C_1$-$C_3$-alkyl, $C_3$-$C_6$-cycloalkyl, $C_1$-$C_3$-alkoxy, $C_3$-$C_6$-cycloalkoxy, $C_1$-$C_3$-haloalkyl, $C_1$-$C_3$-haloalkoxy, halogen, cyano, —C(=O)OH, —C(=O)OR$^9$, and —C(=O)N(R$^{12}$)$_2$,
or,
$R^{10}$ and $R^{11}$ together with the nitrogen atom to which they are attached form a 4-6-membered heterocycloalkyl group, in which one carbon atom is optionally replaced by a further heteroatom-containing group selected from NR$^{14}$, O, S, S(=O) and S(=O)$_2$, in which heterocycloalkyl group one additional ring atom is optionally replaced by C(=O),
said 4-6-membered heterocycloalkyl group being optionally substituted with one or two substituents, which are independently of each other selected from:
$C_1$-$C_3$-alkyl, $C_1$-$C_3$-haloalkyl, $C_1$-$C_3$-alkoxy, $C_1$-$C_3$-haloalkoxy, $C_3$-$C_4$-cycloalkyl, $C_3$-$C_4$-cycloalkoxy, amino, hydroxy, a halogen atom, and cyano,
or,
$R^{10}$ and $R^{11}$ together with the nitrogen atom to which they are attached form a group selected from:

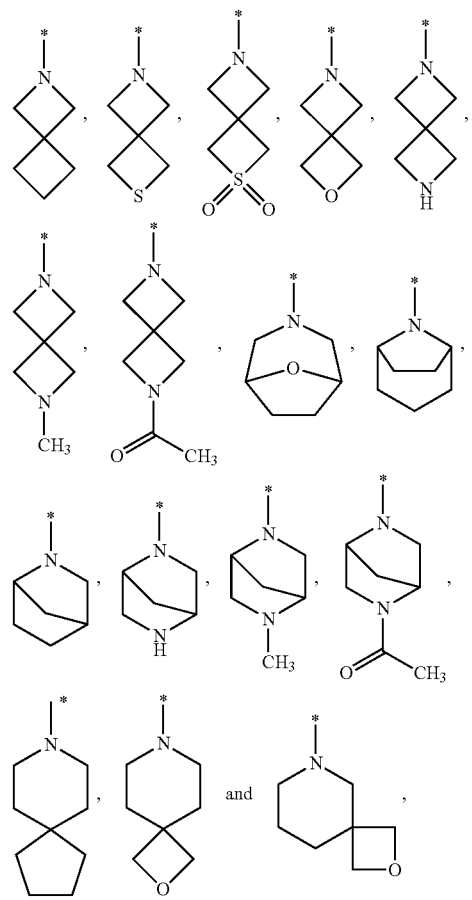

wherein * indicates the point of attachment of said group with the rest of the molecule.

In a further embodiment of the above-mentioned aspects, the invention relates to compounds of formula (I), wherein:
$R^{10}$ and $R^{11}$ are independently of each other selected from:
hydrogen, $C_1$-$C_6$-alkyl, $C_3$-$C_6$-cycloalkyl, ($C_3$-$C_6$-cycloalkyl)-$C_1$-$C_6$-alkyl)-, $C_2$-$C_6$-hydroxyalkyl-, ($C_1$-$C_3$-alkoxy)-($C_2$-$C_6$-alkyl)-, $C_1$-$C_6$-haloalkyl, H$_2$N—($C_2$-$C_6$-alkyl)-, ($C_1$-$C_3$-alkyl)N(H)($C_2$-$C_6$-alkyl)-, ($C_1$-$C_3$-alkyl)$_2$N ($C_2$-$C_6$-alkyl)-, HOC(=O)—($C_1$-$C_6$-alkyl)-, $R^9$OC(=O)—($C_1$-$C_6$-alkyl)-, 4-6 membered heterocycloalkyl, (4-6 membered heterocycloalkyl)-($C_2$-$C_6$-alkyl)-, aryl, heteroaryl, aryl-($C_1$-$C_6$-alkyl)-, and heteroaryl-($C_1$-$C_6$-alkyl)-, wherein 4-6-membered heterocycloalkyl groups are optionally substituted with one or two substituents, which are independently of each other selected from:
$C_1$-$C_3$-alkyl, $C_1$-$C_3$-haloalkyl, $C_1$-$C_3$-alkoxy, $C_1$-$C_3$-haloalkoxy, $C_3$-$C_4$-cycloalkyl, $C_3$-$C_4$-cycloalkoxy, amino, hydroxy, a halogen atom, and cyano,
and,
wherein aryl and heteroaryl groups are optionally substituted with one or two substituents, which are independently of each other selected from:
$C_1$-$C_3$-alkyl, $C_3$-$C_6$-cycloalkyl, $C_1$-$C_3$-alkoxy, $C_3$-$C_6$-cycloalkoxy, $C_1$-$C_3$-haloalkyl, $C_1$-$C_3$-haloalkoxy, halogen, cyano, —C(=O)OH, —C(=O)O$R^9$, and —C(=O)N($R^{12}$)$_2$.

In a further embodiment of the above-mentioned aspects, the invention relates to compounds of formula (I), wherein:
$R^{10}$ and $R^{11}$ are independently of each other selected from: hydrogen, $C_1$-$C_6$-alkyl, $C_3$-$C_6$-cycloalkyl, ($C_3$-$C_6$-cycloalkyl)-$C_1$-$C_6$-alkyl)-, $C_2$-$C_6$-hydroxyalkyl, ($C_1$-$C_3$-alkoxy)-($C_2$-$C_6$-alkyl)-, $C_1$-$C_6$-haloalkyl, ($C_1$-$C_3$-alkyl)$_2$N($C_2$-$C_6$-alkyl)-, (4-6 membered heterocycloalkyl)-($C_2$-$C_6$-alkyl)- and aryl-($C_1$-$C_6$-alkyl)-.

In a further embodiment of the above-mentioned aspects, the invention relates to compounds of formula (I), wherein:
$R^{10}$ and $R^{11}$ are independently of each other selected from: hydrogen, $C_1$-$C_6$-alkyl, $C_1$-$C_6$-haloalkyl, ($C_1$-$C_3$-alkyl)$_2$N($C_2$-$C_6$-alkyl)-, (4-6 membered heterocycloalkyl)-($C_2$-$C_6$-alkyl)- and aryl-($C_1$-$C_6$-alkyl)-.

In a further embodiment of the above-mentioned aspects, the invention relates to compounds of formula (I), wherein $R^{10}$ and $R^{11}$ are independently of each other selected from:
hydrogen, $C_1$-$C_6$-alkyl, $C_3$-$C_6$-cycloalkyl, ($C_3$-$C_6$-cycloalkyl)-($C_1$-$C_6$-alkyl)-, $C_2$-$C_6$-hydroxyalkyl, ($C_1$-$C_3$-alkoxy)-($C_2$-$C_6$-alkyl)-, $C_1$-$C_6$-haloalkyl, $H_2$N—($C_2$-$C_6$-alkyl)-, ($C_1$-$C_3$-alkyl)N(H)($C_2$-$C_6$-alkyl)-, ($C_1$-$C_3$-alkyl)$_2$N($C_2$-$C_6$-alkyl)-, 4-6 membered heterocycloalkyl, (4-6 membered heterocycloalkyl)-($C_2$-$C_6$-alkyl)-, aryl-($C_1$-$C_6$-alkyl)- and heteroaryl-($C_1$-$C_6$-alkyl)-,
wherein 4-6-membered heterocycloalkyl groups are optionally substituted with one or two substituents, which are independently of each other selected from:
$C_1$-$C_3$-alkyl, $C_1$-$C_3$-haloalkyl, $C_1$-$C_3$-alkoxy, $C_1$-$C_3$-haloalkoxy, $C_3$-$C_4$-cycloalkyl, $C_3$-$C_4$-cycloalkoxy, amino, hydroxy, a halogen atom, and cyano,
and,
wherein aryl groups are optionally substituted with one or two substituents, which are independently of each other selected from:
$C_1$-$C_3$-alkyl, $C_3$-$C_6$-cycloalkyl, $C_1$-$C_3$-alkoxy, $C_3$-$C_6$-cycloalkoxy, $C_1$-$C_3$-haloalkyl, $C_1$-$C_3$-haloalkoxy, halogen, cyano, —C(=O)OH, —C(=O)O$R^9$, and —C(=O)N($R^{12}$)$_2$,
or,
$R^{10}$ and $R^{11}$ together with the nitrogen atom to which they are attached form a 4-6-membered heterocycloalkyl group, in which one carbon atom is optionally replaced by a further heteroatom-containing group selected from N$R^{14}$, O, S, S(=O) and S(=O)$_2$, in which heterocycloalkyl group one additional ring atom is optionally replaced by C(=O),
said 4-6-membered heterocycloalkyl group being optionally substituted with one or two substituents, which are independently of each other selected from:
$C_1$-$C_3$-alkyl, $C_1$-$C_3$-haloalkyl, $C_1$-$C_3$-alkoxy, $C_1$-$C_3$-haloalkoxy, $C_3$-$C_4$-cycloalkyl, $C_3$-$C_4$-cycloalkoxy, amino, hydroxy, a halogen atom, and cyano,
or,
$R^{10}$ and $R^{11}$ together with the nitrogen atom to which they are attached form a group selected from:

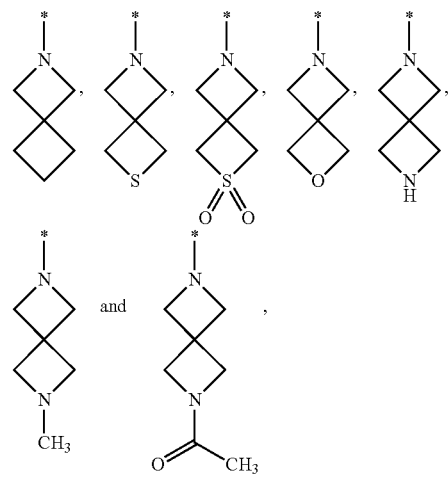

wherein * indicates the point of attachment of said group with the rest of the molecule.

In a further embodiment of the above-mentioned aspects, the invention relates to compounds of formula (I), wherein $R^{10}$ and $R^{11}$ are independently of each other selected from:
hydrogen, $C_1$-$C_6$-alkyl, $C_3$-$C_6$-cycloalkyl, ($C_3$-$C_6$-cycloalkyl)-($C_1$-$C_6$-alkyl)-, $C_2$-$C_6$-hydroxyalkyl, ($C_1$-$C_3$-alkoxy)-($C_2$-$C_6$-alkyl)-, $C_1$-$C_6$-haloalkyl, $H_2$N—($C_2$-$C_6$-alkyl)-, ($C_1$-$C_3$-alkyl)N(H)($C_2$-$C_6$-alkyl)-, ($C_1$-$C_3$-alkyl)$_2$N($C_2$-$C_6$-alkyl)-, 4-6 membered heterocycloalkyl, (4-6 membered heterocycloalkyl)-($C_2$-$C_6$-alkyl)-, aryl-($C_1$-$C_6$-alkyl)- and heteroaryl-($C_1$-$C_6$-alkyl)-,
wherein 4-6-membered heterocycloalkyl groups are optionally substituted with one or two substituents, which are independently of each other selected from:
$C_1$-$C_3$-alkyl, $C_1$-$C_3$-haloalkyl, $C_1$-$C_3$-alkoxy, $C_1$-$C_3$-haloalkoxy, $C_3$-$C_4$-cycloalkyl, $C_3$-$C_4$-cycloalkoxy, amino, hydroxy, a halogen atom, and cyano,
and,
wherein aryl groups are optionally substituted with one or two substituents, which are independently of each other selected from:
$C_1$-$C_3$-alkyl, $C_3$-$C_6$-cycloalkyl, $C_1$-$C_3$-alkoxy, $C_3$-$C_6$-cycloalkoxy, $C_1$-$C_3$-haloalkyl, $C_1$-$C_3$-haloalkoxy, halogen, cyano, —C(=O)OH, —C(=O)O$R^9$, and —C(=O)N($R^{12}$)$_2$.

In a further embodiment of the above-mentioned aspects, the invention relates to compounds of formula (I), wherein $R^{10}$ is, independently of each other, selected from:
hydrogen, $C_1$-$C_6$-alkyl, $C_3$-$C_6$-cycloalkyl, ($C_3$-$C_6$-cycloalkyl)-($C_1$-$C_6$-alkyl)-, $C_2$-$C_6$-hydroxyalkyl, ($C_1$-$C_3$-alkoxy)-($C_2$-$C_6$-alkyl)-, $C_1$-$C_6$-haloalkyl, $H_2$N—($C_2$-$C_6$-alkyl)-, ($C_1$-$C_3$-alkyl)N(H)($C_2$-$C_6$-alkyl)-, ($C_1$-$C_3$-alkyl)$_2$N($C_2$-$C_6$-alkyl)-, 4-6 membered heterocycloalkyl, (4-6 membered heterocycloalkyl)-($C_2$-$C_6$-alkyl)-, aryl-($C_1$-$C_6$-alkyl)- and heteroaryl-($C_1$-$C_6$-alkyl)-,
  wherein 4-6-membered heterocycloalkyl groups are optionally substituted with one or two substituents, which are independently of each other selected from:
  $C_1$-$C_3$-alkyl, $C_1$-$C_3$-haloalkyl, $C_1$-$C_3$-alkoxy, $C_1$-$C_3$-haloalkoxy, $C_3$-$C_4$-cycloalkyl, $C_3$-$C_4$-cycloalkoxy, amino, hydroxy, a halogen atom, and cyano,
  and,
  wherein aryl groups are optionally substituted with one or two substituents, which are independently of each other selected from:
  $C_1$-$C_3$-alkyl, $C_3$-$C_6$-cycloalkyl, $C_1$-$C_3$-alkoxy, $C_3$-$C_6$-cycloalkoxy, $C_1$-$C_3$-haloalkyl, $C_1$-$C_3$-haloalkoxy, halogen, cyano, —C(=O)OH, —C(=O)OR$^9$, and —C(=O)N(R$^{12}$)$_2$.

In a further embodiment of the above-mentioned aspects, the invention relates to compounds of formula (I), wherein R$^{11}$ is, independently of each other, selected from:
  hydrogen, $C_1$-$C_6$-alkyl, $C_3$-$C_6$-cycloalkyl, ($C_3$-$C_6$-cycloalkyl)-($C_1$-$C_6$-alkyl)-, $C_2$-$C_6$-hydroxyalkyl, ($C_1$-$C_3$-alkoxy)-($C_2$-$C_6$-alkyl)-, $C_1$-$C_6$-haloalkyl, H$_2$N—($C_2$-$C_6$-alkyl)-, ($C_1$-$C_3$-alkyl)N(H)($C_2$-$C_6$-alkyl)-, ($C_1$-$C_3$-alkyl)$_2$N($C_2$-$C_6$-alkyl)-, 4-6 membered heterocycloalkyl, (4-6 membered heterocycloalkyl)-($C_2$-$C_6$-alkyl)-, aryl-($C_1$-$C_6$-alkyl)- and heteroaryl-($C_1$-$C_6$-alkyl)-,
  wherein 4-6-membered heterocycloalkyl groups are optionally substituted with one or two substituents, which are independently of each other selected from:
  $C_1$-$C_3$-alkyl, $C_1$-$C_3$-haloalkyl, $C_1$-$C_3$-alkoxy, $C_1$-$C_3$-haloalkoxy, $C_3$-$C_4$-cycloalkyl, $C_3$-$C_4$-cycloalkoxy, amino, hydroxy, a halogen atom, and cyano,
  and,
  wherein aryl groups are optionally substituted with one or two substituents, which are independently of each other selected from:
  $C_1$-$C_3$-alkyl, $C_3$-$C_6$-cycloalkyl, $C_1$-$C_3$-alkoxy, $C_3$-$C_6$-cycloalkoxy, $C_1$-$C_3$-haloalkyl, $C_1$-$C_3$-haloalkoxy, halogen, cyano, —C(=O)OH, —C(=O)OR$^9$, and —C(=O)N(R$^{12}$)$_2$.

In a further embodiment of the above-mentioned aspects, the invention relates to compounds of formula (I), wherein R$^{10}$ is, independently of each other, selected from:
  hydrogen, $C_1$-$C_6$-alkyl, $C_3$-$C_6$-cycloalkyl, ($C_3$-$C_6$-cycloalkyl)-($C_1$-$C_6$-alkyl)-, $C_2$-$C_6$-hydroxyalkyl, ($C_1$-$C_3$-alkoxy)-($C_2$-$C_6$-alkyl)-, $C_1$-$C_6$-haloalkyl, H$_2$N—($C_2$-$C_6$-alkyl)-, ($C_1$-$C_3$-alkyl)N(H)($C_2$-$C_6$-alkyl)-, ($C_1$-$C_3$-alkyl)$_2$N($C_2$-$C_6$-alkyl)-, 4-6 membered heterocycloalkyl, (4-6 membered heterocycloalkyl)-($C_2$-$C_6$-alkyl)-, aryl-($C_1$-$C_6$-alkyl)- and heteroaryl-($C_1$-$C_6$-alkyl)-,
  wherein 4-6-membered heterocycloalkyl groups are optionally substituted with one or two substituents, which are independently of each other selected from:
  $C_1$-$C_3$-alkyl, $C_1$-$C_3$-haloalkyl, $C_1$-$C_3$-alkoxy, $C_1$-$C_3$-haloalkoxy, $C_3$-$C_4$-cycloalkyl, $C_3$-$C_4$-cycloalkoxy, amino, hydroxy, a halogen atom, and cyano,
  and,
  wherein aryl groups are optionally substituted with one or two substituents, which are independently of each other selected from:
  $C_1$-$C_3$-alkyl, $C_3$-$C_6$-cycloalkyl, $C_1$-$C_3$-alkoxy, $C_3$-$C_6$-cycloalkoxy, $C_1$-$C_3$-haloalkyl, $C_1$-$C_3$-haloalkoxy, halogen, cyano, —C(=O)OH, —C(=O)OR$^9$, and —C(=O)N(R$^{12}$)$_2$, and R$^{11}$ is, independently of each other, selected from:
  ($C_3$-$C_6$-cycloalkyl)-($C_1$-$C_6$-alkyl)- with the proviso that it is not cyclopropylmethyl-, ($C_1$-$C_3$-alkoxy)-($C_2$-$C_6$-alkyl)- with the proviso that it is not methoxy-($C_2$-alkyl)-, H$_2$N—($C_2$-$C_6$-alkyl)-, ($C_1$-$C_3$-alkyl)N(H)($C_2$-$C_6$-alkyl)-, 4-6 membered heterocycloalkyl, (4-6 membered heterocycloalkyl)-($C_2$-$C_6$-alkyl)-, and heteroaryl-($C_1$-$C_6$-alkyl)-,
  wherein 4-6-membered heterocycloalkyl groups are optionally substituted with one or two substituents, which are independently of each other selected from:
  $C_1$-$C_3$-alkyl, $C_1$-$C_3$-haloalkyl, $C_1$-$C_3$-alkoxy, $C_1$-$C_3$-haloalkoxy, $C_3$-$C_4$-cycloalkyl, $C_3$-$C_4$-cycloalkoxy, amino, hydroxy, a halogen atom, and cyano,
  with the proviso that when (4-6 membered heterocycloalkyl)-($C_2$-$C_6$-alkyl)- is a (piperidin-1-yl)-($C_2$-alkyl)- group the piperidin-1-yl ring of said group is substituted with one or two substituents, which are independently of each other selected from:
  $C_1$-$C_3$-alkyl, $C_1$-$C_3$-haloalkyl, $C_1$-$C_3$-alkoxy, $C_1$-$C_3$-haloalkoxy, $C_3$-$C_4$-cycloalkyl, $C_3$-$C_4$-cycloalkoxy, amino, hydroxy, a halogen atom, and cyano,
  and,
  wherein aryl groups are optionally substituted with one or two substituents, which are independently of each other selected from:
  $C_1$-$C_3$-alkyl, $C_3$-$C_6$-cycloalkyl, $C_1$-$C_3$-alkoxy, $C_3$-$C_6$-cycloalkoxy, $C_1$-$C_3$-haloalkyl, $C_1$-$C_3$-haloalkoxy, halogen, cyano, —C(=O)OH, —C(=O)OR$^9$, and —C(=O)N(R$^{12}$)$_2$.

In a further embodiment of the above-mentioned aspects, the invention relates to compounds of formula (I), wherein R$^{10}$ and R$^{11}$ are independently of each other selected from:
  hydrogen, $C_1$-$C_5$-alkyl, cyclopropyl, ($C_3$-$C_5$-cycloalkyl)-($C_1$-$C_2$-alkyl)-, $C_2$-$C_5$-hydroxyalkyl, ($C_1$-$C_3$-alkoxy)-($C_2$-$C_3$-alkyl)-, $C_1$-$C_2$-haloalkyl, H$_2$N—($C_2$-$C_5$-alkyl)-, ($C_1$-$C_3$-alkyl)N(H)($C_2$-alkyl)-, ($C_1$-$C_3$-alkyl)$_2$N($C_2$-$C_5$-alkyl)-, piperazin-1-yl, tetrahydro-2H-pyran-4-yl, tetrahydrofuran-3-yl, pyrrolidin-3-yl, piperidin-4-yl, (piperidin-1-yl)-($C_2$-alkyl)-, (piperidin-1-yl)-($C_3$-$C_4$-alkyl)-, (piperidin-2-yl)-($C_1$-alkyl)-, (piperidin-3-yl)-($C_1$-alkyl)-, (piperidin-4-yl)-($C_1$-alkyl)-, (morpholin-4-yl)-($C_2$-$C_4$-alkyl)-, (piperazin-1-yl)-($C_2$-$C_5$-alkyl)-, (pyrrolidin-1-yl)-($C_2$-$C_5$-alkyl)-, (pyrrolidin-2-yl)-($C_1$-$C_2$-alkyl), (pyrrolidin-3-yl)-($C_1$-alkyl), (azetidin-1-yl)-($C_2$-alkyl), (tetrahydro-2H-pyran-4-yl)-($C_1$-alkyl)-, (tetrahydrofuran-3-yl)-($C_1$-alkyl)-, (tetrahydrofuran-2-yl)-($C_1$-alkyl)-, (2-oxoimidazolidin-1-yl)-($C_2$-alkyl)-, (2-oxopyrrolidin-1-yl)-($C_2$-$C_3$-alkyl)-, (1,1-dioxidothiomorpholin-4-yl)-($C_2$-alkyl)-, phenyl-($C_1$-$C_2$-alkyl)- and pyridinyl-($C_2$-alkyl),
  wherein 4-6-membered heterocycloalkyl groups are optionally substituted with one or two substituents, which are independently of each other selected from:
  $C_1$-$C_2$-alkyl, methoxy, hydroxy and fluorine,
  wherein said optionally substituted 4-6-membered heterocycloalkyl groups is selected from piperazin-1-yl, tetrahydro-2H-pyran-4-yl, tetrahydrofuran-3-yl, pyrrolidin-1-yl, pyrrolidin-2-yl, pyrrolidin-3-yl, piperidin-4-yl, piperidin-1-yl, piperidin-2-yl, piperidin-3-yl, morpholin-4-yl, azetidin-1-yl, tetrahydrofuran-2-yl, 2-oxoimidazolidin-1-yl, 2-oxopyrrolidin-1-yl and 1,1-dioxidothiomorpholin-4-yl.

In a further embodiment of the above-mentioned aspects, the invention relates to compounds of formula (I), wherein $R^{10}$ and $R^{11}$ are independently of each other selected from:

hydrogen, $C_1$-$C_5$-alkyl, cyclopropyl, ($C_3$-$C_5$-cycloalkyl)-($C_1$-$C_2$-alkyl)-, $C_2$-$C_5$-hydroxyalkyl, ($C_1$-$C_3$-alkoxy)-($C_2$-$C_3$-alkyl)-, $C_1$-$C_2$-haloalkyl, $H_2N$—($C_2$-$C_5$-alkyl)-, ($C_1$-$C_3$-alkyl)N(H)($C_2$-alkyl)-, ($C_1$-$C_3$-alkyl)$_2$N($C_2$-$C_5$-alkyl)-, piperazinyl, tetrahydro-2H-pyranyl, tetrahydrofuranyl, pyrrolidinyl, piperidinyl, (piperidinyl)-($C_2$-alkyl)-, (piperidinyl)-($C_3$-$C_4$-alkyl)-, (piperidinyl)-($C_1$-alkyl)-, (morpholinyl)-($C_2$-$C_4$-alkyl)-, (piperazinyl)-($C_2$-$C_5$-alkyl)-, (pyrrolidinyl)-($C_2$-$C_5$-alkyl)-, (pyrrolidinyl)-($C_1$-$C_2$-alkyl), (azetidinyl)-($C_2$-alkyl), (tetrahydro-2H-pyranyl)-($C_1$-alkyl)-, (tetrahydrofuranyl)-($C_1$-alkyl)-, (2-oxoimidazolidinyl)-($C_2$-alkyl)-, (2-oxopyrrolidinyl)-($C_2$-$C_3$-alkyl)-, (1,1-dioxidothiomorpholinyl)-($C_2$-alkyl)-, phenyl-($C_1$-$C_2$-alkyl)- and pyridinyl-($C_2$-alkyl),
  wherein 4-6-membered heterocycloalkyl groups are optionally substituted with one or two substituents, which are independently of each other selected from: $C_1$-$C_2$-alkyl, methoxy, hydroxy and fluorine,
  wherein said optionally substituted 4-6-membered heterocycloalkyl groups is selected from piperazinyl, tetrahydro-2H-pyranyl, tetrahydrofuranyl, pyrrolidinyl, piperidinyl, morpholinyl, azetidinyl, 2-oxoimidazolidinyl, 2-oxopyrrolidinyl and 1,1-dioxidothiomorpholinyl.

In a further embodiment of the above-mentioned aspects, the invention relates to compounds of formula (I), wherein $R^{10}$ is, independently of each other, selected from:

hydrogen, $C_1$-$C_5$-alkyl, cyclopropyl, ($C_3$-$C_5$-cycloalkyl)-($C_1$-$C_2$-alkyl)-, $C_2$-$C_5$-hydroxyalkyl, ($C_1$-$C_3$-alkoxy)-($C_2$-$C_3$-alkyl)-, $C_1$-$C_2$-haloalkyl, $H_2N$—($C_2$-$C_5$-alkyl)-, ($C_1$-$C_3$-alkyl)N(H)($C_2$-alkyl)-, ($C_1$-$C_3$-alkyl)$_2$N($C_2$-$C_5$-alkyl)-, piperazinyl, tetrahydro-2H-pyranyl, tetrahydrofuranyl, pyrrolidinyl, piperidinyl, (piperidinyl)-($C_2$-alkyl)-, (piperidinyl)-($C_3$-$C_4$-alkyl)-, (piperidinyl)-($C_1$-alkyl)-, (morpholinyl)-($C_2$-$C_4$-alkyl)-, (piperazinyl)-($C_2$-$C_5$-alkyl)-, (pyrrolidinyl)-($C_2$-$C_5$-alkyl)-, (pyrrolidinyl)-($C_1$-$C_2$-alkyl), (azetidinyl)-($C_2$-alkyl), (tetrahydro-2H-pyranyl)-($C_1$-alkyl)-, (tetrahydrofuranyl)-($C_1$-alkyl)-, (2-oxoimidazolidinyl)-($C_2$-alkyl)-, (2-oxopyrrolidinyl)-($C_2$-$C_3$-alkyl)-, (1,1-dioxidothiomorpholinyl)-($C_2$-alkyl)-, phenyl-($C_1$-$C_2$-alkyl)- and pyridinyl-($C_2$-alkyl),
  wherein 4-6-membered heterocycloalkyl groups are optionally substituted with one or two substituents, which are independently of each other selected from: $C_1$-$C_2$-alkyl, methoxy, hydroxy and fluorine.

In a further embodiment of the above-mentioned aspects, the invention relates to compounds of formula (I), wherein $R^{11}$ is, independently of each other, selected from:

hydrogen, $C_1$-$C_5$-alkyl, cyclopropyl, ($C_3$-$C_5$-cycloalkyl)-($C_1$-$C_2$-alkyl)-, $C_2$-$C_5$-hydroxyalkyl, ($C_1$-$C_3$-alkoxy)-($C_2$-$C_3$-alkyl)-, $C_1$-$C_2$-haloalkyl, $H_2N$—($C_2$-$C_5$-alkyl)-, ($C_1$-$C_3$-alkyl)N(H)($C_2$-alkyl)-, ($C_1$-$C_3$-alkyl)$_2$N($C_2$-$C_5$-alkyl)-, piperazinyl, tetrahydro-2H-pyranyl, tetrahydrofuranyl, pyrrolidinyl, piperidinyl, (piperidinyl)-($C_2$-alkyl)-, (piperidinyl)-($C_3$-$C_4$-alkyl)-, (piperidinyl)-($C_1$-alkyl)-, (morpholinyl)-($C_2$-$C_4$-alkyl)-, (piperazinyl)-($C_2$-$C_5$-alkyl)-, (pyrrolidinyl)-($C_2$-$C_5$-alkyl)-, (pyrrolidinyl)-($C_1$-$C_2$-alkyl), (azetidinyl)-($C_2$-alkyl), (tetrahydro-2H-pyranyl)-($C_1$-alkyl)-, (tetrahydrofuranyl)-($C_1$-alkyl)-, (2-oxoimidazolidinyl)-($C_2$-alkyl)-, (2-oxopyrrolidinyl)-($C_2$-$C_3$-alkyl)-, (1,1-dioxidothiomorpholinyl)-($C_2$-alkyl)-, phenyl-($C_1$-$C_2$-alkyl)- and pyridinyl-($C_2$-alkyl),
  wherein 4-6-membered heterocycloalkyl groups are optionally substituted with one or two substituents, which are independently of each other selected from: $C_1$-$C_2$-alkyl, methoxy, hydroxy and fluorine.

In a further embodiment of the above-mentioned aspects, the invention relates to compounds of formula (I), wherein $R^{10}$ is, independently of each other, selected from:

hydrogen, $C_1$-$C_5$-alkyl, cyclopropyl, ($C_3$-$C_5$-cycloalkyl)-($C_1$-$C_2$-alkyl)-, $C_2$-$C_5$-hydroxyalkyl, ($C_1$-$C_3$-alkoxy)-($C_2$-$C_3$-alkyl)-, $C_1$-$C_2$-haloalkyl, $H_2N$—($C_2$-$C_5$-alkyl)-, ($C_1$-$C_3$-alkyl)N(H)($C_2$-alkyl)-, ($C_1$-$C_3$-alkyl)$_2$N($C_2$-$C_5$-alkyl)-piperazin-1-yl, tetrahydro-2H-pyran-4-yl, tetrahydrofuran-3-yl, pyrrolidin-3-yl, piperidin-4-yl, (piperidin-1-yl)-($C_2$-alkyl)-, (piperidin-1-yl)-($C_3$-$C_4$-alkyl)-(piperidin-2-yl)-($C_1$-alkyl)-, (piperidin-3-yl)-($C_1$-alkyl)-, (piperidin-4-yl)-($C_1$-alkyl)-, (morpholin-4-yl)-($C_2$-$C_4$-alkyl)-, (piperazin-1-yl)-($C_2$-$C_5$-alkyl)-, (pyrrolidin-1-yl)-($C_2$-$C_5$-alkyl)-, (pyrrolidin-2-yl)-($C_1$-$C_2$-alkyl)-, (pyrrolidin-3-yl)-($C_1$-alkyl)-, (azetidin-1-yl)-($C_2$-alkyl)-, (tetrahydro-2H-pyran-4-yl)-($C_1$-alkyl)-, (tetrahydrofuran-3-yl)-($C_1$-alkyl)-, (tetrahydrofuran-2-yl)-($C_1$-alkyl)-, (2-oxoimidazolidin-1-yl)-($C_2$-alkyl)-, (2-oxopyrrolidin-1-yl)-($C_2$-$C_3$-alkyl)-, (1,1-dioxidothiomorpholin-4-yl)-($C_2$-alkyl)-, phenyl-($C_1$-$C_2$-alkyl)- and pyridinyl-($C_2$-alkyl)-,
  wherein 4-6-membered heterocycloalkyl groups are optionally substituted with one or two substituents, which are independently of each other selected from: $C_1$-$C_2$-alkyl, methoxy, hydroxy and fluorine, and $R^{11}$ is, independently of each other, selected from:
  ($C_3$-$C_5$-cycloalkyl)-($C_1$-$C_2$-alkyl)- with the proviso that it is not cyclopropylmethyl-, $C_3$-$C_5$-hydroxyalkyl, ($C_1$-$C_3$-alkoxy)-($C_2$-$C_3$-alkyl)- with the proviso that it is not methoxy-($C_2$-alkyl), $H_2N$—($C_2$-$C_5$-alkyl)-, ($C_1$-$C_3$-alkyl)N(H)($C_2$-alkyl)-, ($C_1$-$C_3$-alkyl)$_2$N($C_2$-$C_5$-alkyl)- with the proviso that it is not (methyl)$_2$N($C_2$-$C_3$-alkyl)-, piperazin-1-yl, tetrahydro-2H-pyran-4-yl, tetrahydrofuran-3-yl, pyrrolidin-3-yl, piperidin-4-yl, (piperidin-1-yl)-($C_2$-alkyl)-, (piperidin-1-yl)-($C_3$-$C_4$-alkyl)-, (piperidin-2-yl)-($C_1$-alkyl), (piperidin-3-yl)-($C_1$-alkyl)-, (piperidin-4-yl)-($C_1$-alkyl)-, (morpholin-4-yl)-($C_2$-$C_4$-alkyl)-, (piperazin-1-yl)-($C_2$-$C_5$-alkyl)-, (pyrrolidin-1-yl)-($C_2$-$C_5$-alkyl)-, (pyrrolidin-2-yl)-($C_1$-$C_2$-alkyl)-, (pyrrolidin-3-yl)-($C_1$-alkyl)-, (azetidin-1-yl)-($C_2$-alkyl), (tetrahydro-2H-pyran-4-yl)-($C_1$-alkyl)-, (tetrahydrofuran-3-yl)-($C_1$-alkyl)-, (tetrahydrofuran-2-yl)-($C_1$-alkyl)-, (2-oxoimidazolidin-1-yl)-($C_2$-alkyl)-, (2-oxopyrrolidin-1-yl)-($C_2$-$C_3$-alkyl)-, (1,1-dioxidothiomorpholin-4-yl)-($C_2$-alkyl)-, and pyridinyl-($C_2$-alkyl)-,
    wherein 4-6-membered heterocycloalkyl groups are optionally substituted with one or two substituents, which are independently of each other selected from: $C_1$-$C_2$-alkyl, methoxy, hydroxy and fluorine.
    with the proviso that (piperidin-1-yl)-($C_2$-alkyl)- is substituted at the piperidin-1-yl ring with one or two substituents, which are independently of each other selected from $C_1$-$C_2$-alkyl, methoxy, hydroxy and fluorine.

In a further embodiment of the above-mentioned aspects, the invention relates to compounds of formula (I), wherein $R^{10}$ is, independently of each other, selected from:

hydrogen, $C_1$-$C_5$-alkyl, cyclopropyl, ($C_3$-$C_5$-cycloalkyl)-($C_1$-$C_2$-alkyl)-, $C_2$-$C_5$-hydroxyalkyl, ($C_1$-$C_3$-alkoxy)-

($C_2$-$C_3$-alkyl)-, $C_1$-$C_2$-haloalkyl, $H_2N$—($C_2$-$C_5$-alkyl)-, ($C_1$-$C_3$-alkyl)N(H)($C_2$-alkyl)-, ($C_1$-$C_3$-alkyl)$_2$N($C_2$-$C_5$-alkyl)-, piperazinyl, tetrahydro-2H-pyranyl, tetrahydrofuranyl, pyrrolidinyl, piperidinyl, (piperidinyl)-($C_2$-alkyl)-, (piperidinyl)-($C_3$-$C_4$-alkyl)-, (piperidinyl)-($C_1$-alkyl)-, (morpholinyl)-($C_2$-$C_4$-alkyl)-, (piperazinyl)-($C_2$-$C_5$-alkyl)-, (pyrrolidinyl)-($C_2$-$C_5$-alkyl)-, (pyrrolidinyl)-($C_1$-$C_2$-alkyl)-, (azetidinyl)-($C_2$-alkyl)-, (tetrahydro-2H-pyranyl)-($C_1$-alkyl)-, (tetrahydrofuranyl)-($C_1$-alkyl)-, (2-oxoimidazolidinyl)-($C_2$-alkyl)-, (2-oxopyrrolidinyl)-($C_2$-$C_3$-alkyl)-, (1,1-dioxidothiomorpholinyl)-($C_2$-alkyl)-, phenyl-($C_1$-$C_2$-alkyl)- and pyridinyl-($C_2$-alkyl)-,
  wherein 4-6-membered heterocycloalkyl groups are optionally substituted with one or two substituents, which are independently of each other selected from: $C_1$-$C_2$-alkyl, methoxy, hydroxy and fluorine,
and $R^{11}$ is, independently of each other, selected from:
  ($C_3$-$C_5$-cycloalkyl)-($C_1$-$C_2$-alkyl)- with the proviso that it is not cyclopropylmethyl-, $C_3$-$C_5$-hydroxyalkyl, ($C_1$-$C_3$-alkoxy)-($C_2$-$C_3$-alkyl)- with the proviso that it is not methoxy-($C_2$-alkyl), $H_2N$—($C_2$-$C_5$-alkyl)-, ($C_1$-$C_3$-alkyl)N(H)($C_2$-alkyl)-, ($C_1$-$C_3$-alkyl)$_2$N($C_2$-$C_5$-alkyl)- with the proviso that it is not (methyl)$_2$N($C_2$-$C_3$-alkyl)-, piperazinyl, tetrahydro-2H-pyranyl, tetrahydrofuranyl, pyrrolidinyl, piperidinyl, (piperidinyl)-($C_2$-alkyl)-, (piperidinyl)-($C_3$-$C_4$-alkyl)-, (piperidinyl)-($C_1$-alkyl)-, (morpholinyl)-($C_2$-$C_4$-alkyl)-, (piperazinyl)-($C_2$-$C_5$-alkyl)-, (pyrrolidinyl)-($C_2$-$C_5$-alkyl)-, (pyrrolidinyl)-($C_1$-$C_2$-alkyl), (azetidinyl)-($C_2$-alkyl), (tetrahydro-2H-pyranyl)-($C_1$-alkyl)-, (tetrahydrofuranyl)-($C_1$-alkyl)-, (2-oxoimidazolidinyl)-($C_2$-alkyl)-, (2-oxopyrrolidinyl)-($C_2$-$C_3$-alkyl)-, (1,1-dioxidothiomorpholinyl)-($C_2$-alkyl)-, phenyl-($C_1$-$C_2$-alkyl)- and pyridinyl-($C_2$-alkyl),
  wherein 4-6-membered heterocycloalkyl groups are optionally substituted with one or two substituents, which are independently of each other selected from: $C_1$-$C_2$-alkyl, methoxy, hydroxy and fluorine,
with the proviso that when (piperidinyl)-($C_2$-alkyl)- is a (piperidin-1-yl)-($C_2$-alkyl)- group the piperidin-1-yl ring of said group is substituted with one or two substituents, which are independently of each other selected from $C_1$-$C_2$-alkyl, methoxy, hydroxy and fluorine.

In a further embodiment of the above-mentioned aspects, the invention relates to compounds of formula (I), wherein $R^{10}$ is hydrogen.

In a further embodiment of the above-mentioned aspects, the invention relates to compounds of formula (I), wherein $R^{11}$ is hydrogen.

In a further embodiment of the above-mentioned aspects, the invention relates to compounds of formula (I), wherein: $R^{10}$ and $R^{11}$ are independently of each other selected from:
  hydrogen, $C_1$-$C_5$-alkyl, cyclopropyl, $C_2$-$C_5$-hydroxyalkyl, $CH_3OCH_2CH_2$—, $C_1$-$C_2$-haloalkyl, $H_2N$—($C_2$-$C_5$-alkyl)-, ($C_1$-$C_3$-alkyl)N(H)($C_2$-alkyl)-, ($C_1$-$C_3$-alkyl)$_2$N($C_2$-$C_4$-alkyl)-, piperazin-1-yl, tetrahydro-2H-pyran-4-yl, tetrahydrofuran-3-yl, pyrrolidin-3-yl, piperidin-4-yl, (piperidin-1-yl)-($C_2$-alkyl)-, (piperidin-1-yl)-($C_3$-$C_4$-alkyl)-, (piperidin-2-yl)-($C_1$-alkyl)-, (piperidin-3-yl)-($C_1$-alkyl)-, (piperidin-4-yl)-($C_1$-alkyl)-, (morpholin-4-yl)-($C_2$-$C_4$-alkyl)-, (piperazin-1-yl)-($C_2$-$C_5$-alkyl)-, (pyrrolidin-1-yl)-($C_2$-$C_5$-alkyl)-, (pyrrolidin-2-yl)-($C_1$-$C_2$-alkyl), (pyrrolidin-3-yl)-($C_1$-alkyl), (azetidin-1-yl)-($C_2$-alkyl), (tetrahydro-2H-pyran-4-yl)-($C_1$-alkyl)-, (tetrahydrofuran-3-yl)-($C_1$-alkyl)-, (tetrahydrofuran-2-yl)-($C_1$-alkyl)-, (1,1-dioxidothiomorpholin-4-yl)-($C_2$-alkyl), phenyl-($C_1$-alkyl)- and pyridinyl-($C_2$-alkyl),
  wherein 4-6-membered heterocycloalkyl groups are optionally substituted with one or two substituents, which are independently of each other selected from: $C_1$-$C_2$-alkyl, methoxy, hydroxy and fluorine.

In a further embodiment of the above-mentioned aspects, the invention relates to compounds of formula (I), wherein: $R^{10}$ and $R^{11}$ together with the nitrogen atom to which they are attached form a 4-6-membered heterocycloalkyl group, in which one carbon atom is optionally replaced by a further heteroatom-containing group selected from $NR^{14}$, O, S, S(=O) and S(=O)$_2$, in which heterocycloalkyl group one additional ring atom is optionally replaced by C(=O), said 4-6-membered heterocycloalkyl group being optionally substituted with one or two substituents, which are independently of each other selected from:
$C_1$-$C_3$-alkyl, $C_1$-$C_3$-haloalkyl, $C_1$-$C_3$-alkoxy, $C_1$-$C_3$-haloalkoxy, $C_3$-$C_4$-cycloalkyl, $C_3$-$C_4$-cycloalkoxy, amino, hydroxy, a halogen atom, and cyano.

In a further embodiment of the above-mentioned aspects, the invention relates to compounds of formula (I), wherein: $R^{10}$ and $R^{11}$ together with the nitrogen atom to which they are attached form a 4-6-membered heterocycloalkyl group, in which one carbon atom is optionally replaced by a further heteroatom-containing group selected from $NR^{14}$ and O.

In a further embodiment of the above-mentioned aspects, the invention relates to compounds of formula (I), wherein: $R^{10}$ and $R^{11}$ together with the nitrogen atom to which they are attached form a 4-6-membered heterocycloalkyl group, in which one carbon atom is optionally replaced by a further heteroatom-containing group selected from $NR^{14}$ and O, said 4-6-membered heterocycloalkyl group being optionally substituted with one or two substituents, which are independently of each other selected from:
$C_1$-$C_3$-alkyl, $C_1$-$C_3$-haloalkyl, $C_1$-$C_3$-alkoxy, $C_1$-$C_3$-haloalkoxy, $C_3$-$C_4$-cycloalkyl, $C_3$-$C_4$-cycloalkoxy, amino, hydroxy, a halogen atom, and cyano.

In a further embodiment of the above-mentioned aspects, the invention relates to compounds of formula (I), wherein: $R^{10}$ and $R^{11}$ together with the nitrogen atom to which they are attached form a 4-6-membered heterocycloalkyl group, in which one carbon atom is optionally replaced by a further heteroatom-containing group selected from $NR^{14}$ and O, said 4-6-membered heterocycloalkyl group being optionally substituted with one or two substituents, which are independently of each other selected from:
$C_1$-$C_3$-alkyl, $C_1$-$C_3$-haloalkyl, $C_1$-$C_3$-alkoxy, $C_1$-$C_3$-haloalkoxy, $C_3$-$C_4$-cycloalkyl, $C_3$-$C_4$-cycloalkoxy, amino, hydroxy, a halogen atom, and cyano,
with the proviso that said 4-6-membered heterocycloalkyl group is not unsubstituted

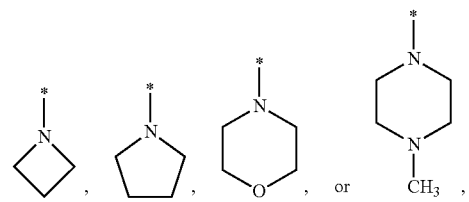

group,
wherein * indicates the point of attachment of said group with the rest of the molecule.

In a further embodiment of the above-mentioned aspects, the invention relates to compounds of formula (I), wherein: $R^{10}$ and $R^{11}$ together with the nitrogen atom to which they are attached form a 4-6-membered heterocycloalkyl group, in which one carbon atom is optionally replaced by a further heteroatom-containing group selected from $NR^{14}$ and O, said 4-6-membered heterocycloalkyl group being substituted with one or two substituents, which are independently of each other selected from:

amino and a halogen atom, such as fluorine.

In a further embodiment of the above-mentioned aspects, the invention relates to compounds of formula (I), wherein: $R^{10}$ and $R^{11}$ together with the nitrogen atom to which they are attached form a:

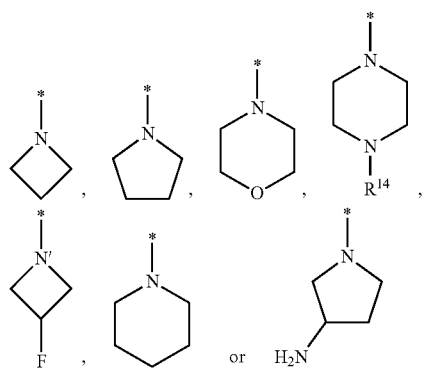

group,
wherein * indicates the point of attachment of said group with the rest of the molecule.

In a further embodiment of the above-mentioned aspects, the invention relates to compounds of formula (I), wherein: $R^{10}$ and $R^{11}$ together with the nitrogen atom to which they are attached form a:

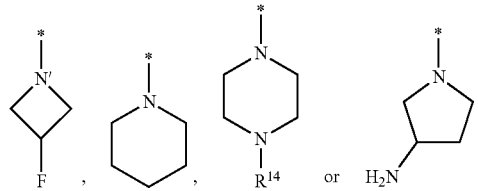

group,
wherein * indicates the point of attachment of said group with the rest of the molecule.
wherein $R^{14}$ represents hydrogen.

In a further embodiment of the above-mentioned aspects, the invention relates to compounds of formula (I), wherein: $R^{10}$ and $R^{11}$ together with the nitrogen atom to which they are attached form a:

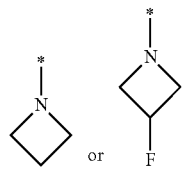 [SMILES: *N1CCC1 ; *N1CC(F)C1]

group,
wherein * indicates the point of attachment of said group with the rest of the molecule.

In a further embodiment of the above-mentioned aspects, the invention relates to compounds of formula (I), wherein: $R^{10}$ and $R^{11}$ together with the nitrogen atom to which they are attached form a 6-membered heterocycloalkyl group, in which one carbon atom is optionally replaced by a further heteroatom-containing group selected from $NR^{14}$ and O.

In a further embodiment of the above-mentioned aspects, the invention relates to compounds of formula (I), wherein: $R^{10}$ and $R^{11}$ together with the nitrogen atom to which they are attached form a:

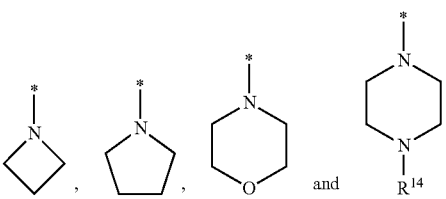

group,
wherein * indicates the point of attachment of said group with the rest of the molecule.

In a further embodiment of the above-mentioned aspects, the invention relates to compounds of formula (I), wherein: $R^{10}$ and $R^{11}$ together with the nitrogen atom to which they are attached form a group selected from:

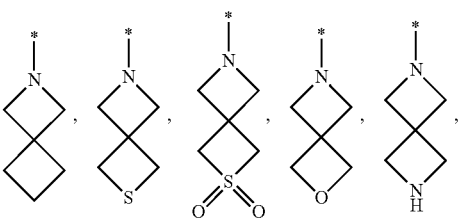

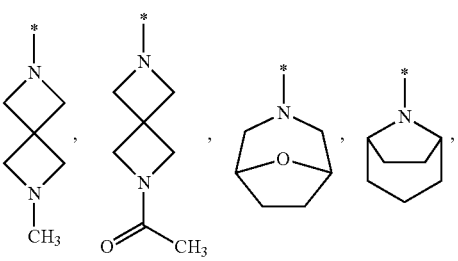

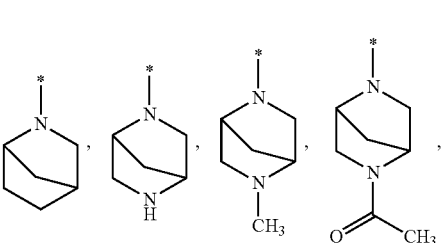

-continued

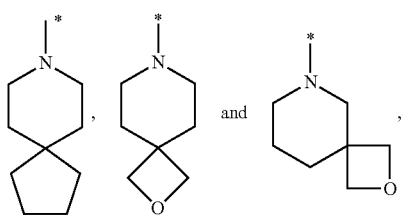

wherein * indicates the point of attachment of said group with the rest of the molecule.

In a further embodiment of the above-mentioned aspects, the invention relates to compounds of formula (I), wherein:
$R^{10}$ and $R^{11}$ together with the nitrogen atom to which they are attached form a group selected from:

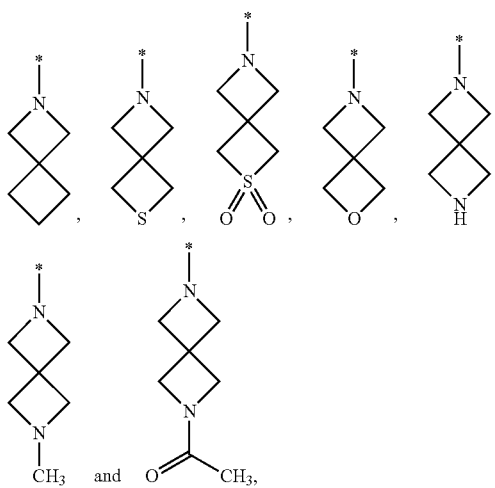

wherein * indicates the point of attachment of said group with the rest of the molecule.

In a further embodiment of the above-mentioned aspects, the invention relates to compounds of formula (I), wherein:
$R^{10}$ and $R^{11}$ together with the nitrogen atom to which they are attached form a group selected from:

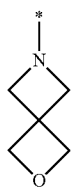

wherein * indicates the point of attachment of said group with the rest of the molecule.

In a further embodiment of the above-mentioned aspects, the invention relates to compounds of formula (I), wherein:
$R^{10}$ and $R^{11}$ together with the nitrogen atom to which they are attached form a:

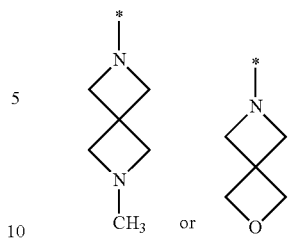

group.

In a further embodiment of the above-mentioned aspects, the invention relates to compounds of formula (I), wherein:
$R^{10}$ and $R^{11}$ together with the nitrogen atom to which they are attached form a:

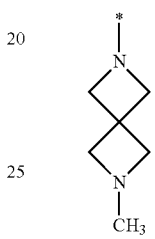

group.

In a further embodiment of the above-mentioned aspects, the invention relates to compounds of formula (I), wherein:
$R^{12}$ represents a group selected from:
hydrogen, and $C_1$-$C_3$-alkyl, preferably hydrogen.

In a further embodiment of the above-mentioned aspects, the invention relates to compounds of formula (I), wherein:
$R^{13}$ represents a group selected from:
hydrogen, $C_1$-$C_6$-alkyl, $C_1$-$C_6$-hydroxyalkyl, $C_3$-$C_6$-cycloalkyl, $C_1$-$C_6$-haloalkyl, ($C_1$-$C_3$-alkoxy)-($C_1$-$C_6$-alkyl)-, aryl, and heteroaryl,
wherein aryl and heteroaryl groups are optionally substituted with one or two substituents, which are independently of each other selected from:
$C_1$-$C_3$-alkyl, $C_3$-$C_6$-cycloalkyl, $C_1$-$C_3$-alkoxy, $C_3$-$C_6$-cycloalkoxy, $C_1$-$C_3$-haloalkyl, $C_1$-$C_3$-haloalkoxy, halogen, cyano, and hydroxy.

In a further embodiment of the above-mentioned aspects, the invention relates to compounds of formula (I), wherein:
$R^{13}$ represents a group selected from hydrogen and $C_1$-$C_6$-alkyl, preferably $C_1$-$C_6$-alkyl, more preferably a methyl group.

In a further embodiment of the above-mentioned aspects, the invention relates to compounds of formula (I), wherein:
$R^{14}$ represents a group selected from:
hydrogen, $C_1$-$C_3$-alkyl, $C_1$-$C_3$-haloalkyl, and $C_3$-$C_4$-cycloalkyl, preferably hydrogen, $C_1$-$C_3$-alkyl, more preferably a methyl group.

In a further embodiment of the above-mentioned aspects, the invention relates to compounds of formula (I), wherein:
$R^{14}$ represents hydrogen.

In a further embodiment of the above-mentioned aspects, the invention relates to compounds of formula (I), wherein:
$R^{15}$ represents a group selected from:
hydrogen, cyano, ($C_1$-$C_3$-alkyl)-C(=O)—, and ($C_1$-$C_3$-haloalkyl)-C(=O)—.

In a further embodiment of the above-mentioned aspects, the invention relates to compounds of formula (I), wherein:
$R^{15}$ represents a group selected from:
hydrogen, cyano, methyl-C(=O)—, and trifluoromethyl-C(=O)—, preferably a hydrogen atom.

In a further embodiment of the above-mentioned aspects, the invention relates to compounds of formula (I), wherein:
$R^{16}$ represents a group selected from:
$C_1$-$C_4$-alkyl, and $C_3$-$C_4$-cycloalkyl.

In a further embodiment of the above-mentioned aspects, the invention relates to compounds of formula (I), wherein:
$R^{16}$ represents $C_1$-$C_4$-alkyl, preferably an ethyl group.

In a further embodiment of the above-mentioned aspects, the invention relates to compounds of formula (I), wherein:
$X^1$ represents $NR^3$ or O,
$X^2$ represents a $CR^6$ or N,
$R^1$ represents a group selected from:
—$OR^9$, and —$N(R^{10})R^{11}$,
$R^2$ represents a group selected from:
Hydrogen and $C_1$-$C_3$-alkyl,
$R^3$ represents a hydrogen atom,
$R^4$ represents a hydrogen atom,
$R^5$ represents a group selected from:
Hydrogen and $C_1$-$C_3$-alkyl,
$R^6$ represents hydrogen,
$R^7$ represents a hydrogen atom,
$R^8$ represents a group selected from:
aryl, and heteroaryl,
wherein aryl and heteroaryl groups are optionally substituted with one, two or three substituents, which are independently of each other selected from:
$C_1$-$C_6$-alkyl, $C_1$-$C_3$-alkoxy, $C_1$-$C_3$-haloalkyl, halogen, nitro, ($C_1$-$C_6$-alkyl)-S(=O)$_2$—, —S(=O)(=$NR^{15}$)$R^{16}$, —$N(R^{10})R^{11}$, $R^{10}(R^{11})N$—($C_2$-$C_6$-alkoxy)-, phenyl, phenoxy and —$N(R^{12})C(=O)R^{13}$,
whereby two substituents of said aryl group, if they are in ortho-position to one another, can be linked to one another in such a way that they jointly form methanediylbisoxy,
$R^9$ represents $C_1$-$C_6$-alkyl,
$R^{10}$ and $R^{11}$ are independently of each other selected from:
hydrogen, $C_1$-$C_6$-alkyl, $C_3$-$C_6$-cycloalkyl, ($C_3$-$C_6$-cycloalkyl)-$C_1$-$C_6$-alkyl)-, $C_2$-$C_6$-hydroxyalkyl, ($C_1$-$C_3$-alkoxy)-($C_2$-$C_6$-alkyl)-, $C_1$-$C_6$-haloalkyl, ($C_1$-$C_3$-alkyl)$_2$N($C_2$-$C_6$-alkyl)-, (4-6 membered heterocycloalkyl)-($C_2$-$C_6$-alkyl)- and aryl-($C_1$-$C_6$-alkyl)-,
or,
$R^{10}$ and $R^{11}$ together with the nitrogen atom to which they are attached form a 4-6-membered heterocycloalkyl group, in which one carbon atom is optionally replaced by a further heteroatom-containing group selected from $NR^{14}$, O,
or,
$R^{10}$ and $R^{11}$ together with the nitrogen atom to which they are attached form a group selected from:

wherein * indicates the point of attachment of said group with the rest of the molecule,
$R^{12}$ represents hydrogen,
$R^{13}$ represents $C_1$-$C_6$-alkyl,
$R^{14}$ represents $C_1$-$C_3$-alkyl,
$R^{15}$ represents hydrogen,
$R^{16}$ represents $C_1$-$C_4$-alkyl.

In a further embodiment of the above-mentioned aspects, the invention relates to compounds of formula (I), wherein:
$X^1$ represents $NR^3$ or O,
$X^2$ represents a $CR^6$ or N,
$R^1$ represents a group selected from:
—$OR^9$, and —$N(R^{10})R^{11}$,
$R^2$ represents Hydrogen,
$R^3$ represents a hydrogen atom,
$R^4$ represents a hydrogen atom,
$R^5$ represents a group selected from:
Hydrogen and $C_1$-$C_3$-alkyl,
$R^6$ represents hydrogen,
$R^7$ represents a hydrogen atom,
$R^8$ represents a group selected from:
aryl, and heteroaryl,
wherein aryl and heteroaryl groups are optionally substituted with one, two or three substituents, which are independently of each other selected from:
$C_1$-$C_6$-alkyl, $C_1$-$C_3$-alkoxy, $C_1$-$C_3$-haloalkyl, halogen, nitro, —$N(R^{10})R^{11}$, $R^{10}(R^{11})N$—($C_2$-$C_6$-alkoxy)-, phenyl, phenoxy and
—$N(R^{12})C(=O)R^{13}$,
whereby two substituents of said aryl group, if they are in ortho-position to one another, can be linked to one another in such a way that they jointly form methanediylbisoxy,
$R^9$ represents $C_1$-$C_6$-alkyl,
$R^{10}$ and $R^{11}$ are independently of each other selected from:
hydrogen, $C_1$-$C_6$-alkyl, $C_1$-$C_6$-haloalkyl, ($C_1$-$C_3$-alkyl)$_2$N($C_2$-$C_6$-alkyl)-, (4-6 membered heterocycloalkyl)-($C_2$-$C_6$-alkyl)- and aryl-($C_1$-$C_6$-alkyl)-,
or,
$R^{10}$ and $R^{11}$ together with the nitrogen atom to which they are attached form a 6-membered heterocycloalkyl group, in which one carbon atom is optionally replaced by a further heteroatom-containing group selected from $NR^{14}$, O,
or,
$R^{10}$ and $R^{11}$ together with the nitrogen atom to which they are attached form a group selected from:

wherein * indicates the point of attachment of said group with the rest of the molecule,
$R^{12}$ represents hydrogen,
$R^{13}$ represents $C_1$-$C_6$-alkyl,
$R^{14}$ represents $C_1$-$C_3$-alkyl.

In a further embodiment of the above-mentioned aspects, the invention relates to compounds of formula (I), wherein:
$X^1$ represents $NR^3$ or O,
$X^2$ represents a $CR^6$ or N,
$R^1$ represents a group selected from:
—$OR^9$, and —$N(R^{10})R^{11}$,
$R^2$ represents Hydrogen,
$R^3$ represents a hydrogen atom,
$R^4$ represents a hydrogen atom, $R^5$ represents a group selected from:
Hydrogen and $C_1$-$C_3$-alkyl,
$R^6$ represents hydrogen,
$R^7$ represents a hydrogen atom,
$R^8$ represents a group selected from:
aryl, and heteroaryl,
wherein aryl and heteroaryl groups are optionally substituted with one, two or three substituents, which are independently of each other selected from:
$C_1$-$C_6$-alkyl, $C_1$-$C_3$-alkoxy, $C_1$-$C_3$-haloalkyl, halogen, —N($R^{10}$)$R^{11}$, $R^{10}$($R^{11}$)N—($C_2$-$C_6$-alkoxy)- and phenyl,
$R^9$ represents $C_1$-$C_6$-alkyl,
$R^{10}$ and $R^{11}$ are independently of each other selected from: hydrogen, $C_1$-$C_6$-alkyl, $C_1$-$C_6$-haloalkyl, ($C_1$-$C_3$-alkyl)$_2$N($C_2$-$C_6$-alkyl)-, (4-6 membered heterocycloalkyl)-($C_2$-$C_6$-alkyl)- and aryl-($C_1$-$C_6$-alkyl)-,
or,
$R^{10}$ and $R^{11}$ together with the nitrogen atom to which they are attached form a 6-membered heterocycloalkyl group, in which one carbon atom is optionally replaced by a further heteroatom-containing group selected from $NR^{14}$, O,
or,
$R^{10}$ and $R^{11}$ together with the nitrogen atom to which they are attached form a group selected from:

wherein * indicates the point of attachment of said group with the rest of the molecule,
$R^{14}$ represents $C_1$-$C_3$-alkyl.

In a further embodiment of the above-mentioned aspects, the invention relates to compounds of formula (I), according to any of the above-mentioned embodiments, in the form of or a stereoisomer, a tautomer, an N-oxide, a hydrate, a solvate, or a salt thereof, or a mixture of same.

It is to be understood that the present invention relates to any sub-combination within any embodiment or aspect of the present invention of compounds of general formula (I), supra.

More particularly still, the present invention covers compounds of general formula (I) which are disclosed in the Example section of this text, infra.

In accordance with another aspect, the present invention covers methods of preparing compounds of the present invention, said methods comprising the steps as described in the Experimental Section herein.

Another aspect of the invention is intermediate (II):

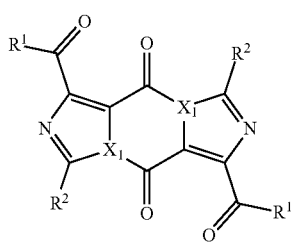

(II)

in which $X_1$ represents N, and $R^1$ and $R^2$ are as defined for the compound of general formula (I) supra.

Another aspect of the invention is intermediate (IV):

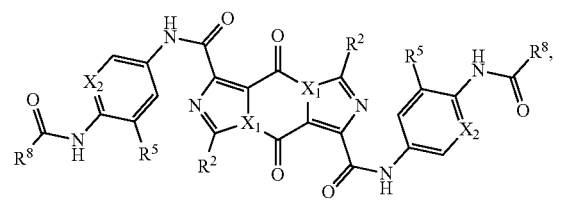

(IV)

in which $X_1$ represents N, and $X_2$, $R^2$, $R^5$ and $R^8$ are as defined for the compound of general formula (I) supra.

Another aspect of the invention is intermediate (VI):

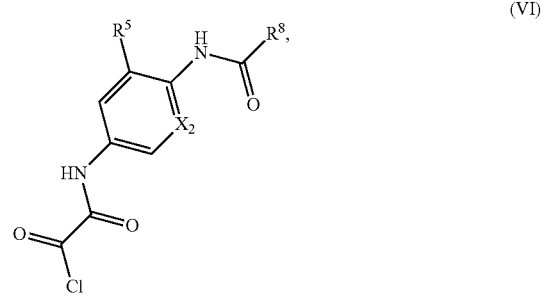

(VI)

in which $X_2$, $R^5$ and $R^8$ are as defined for the compound of general formula (I) supra.

Another aspect of the invention is intermediate (VIII):

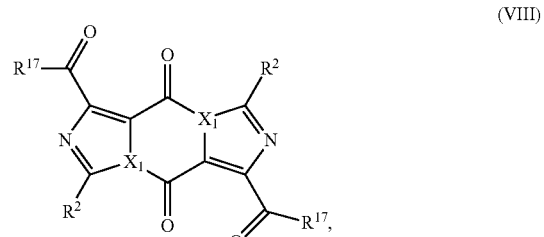

(VIII)

in which:
$X_1$ represents N,
$R^{17}$ represents $OR^{18}$,
$R^{18}$ represents hydrogen or phenyl, and
$R^2$ is as defined for the compound of general formula (I) supra.

Another aspect of the invention is intermediate (IX):

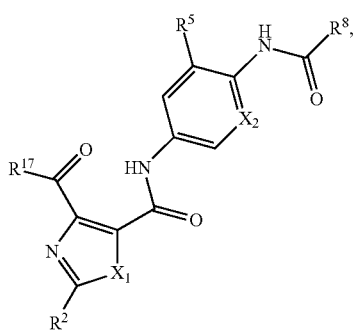
(IX)

in which:
X$_1$ represents NR$^3$,
R$^{17}$ represents OR$^{18}$,
R$^{18}$ represents hydrogen or phenyl, and
X$_2$, R$^2$, R$^3$, R$^5$ and R$^8$ are as defined for the compound of general formula (I) supra.

In accordance with a further aspect, the present invention covers the use of the intermediate compounds of general formula (II):

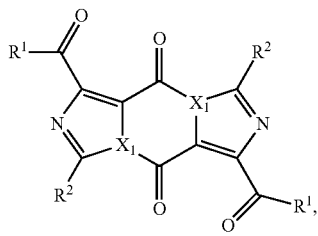
(II)

in which X$_1$ represents N, and R$^1$ and R$^2$ are as defined for the compound of general formula (I) supra, for the preparation of a compound of general formula (I) as defined supra, or an N-oxide, a salt, a tautomer or a stereoisomer of said compound, or a salt of said N-oxide, tautomer or stereoisomer.

In accordance with further aspect, the present invention covers the use of the intermediate compounds of general formula (IV):

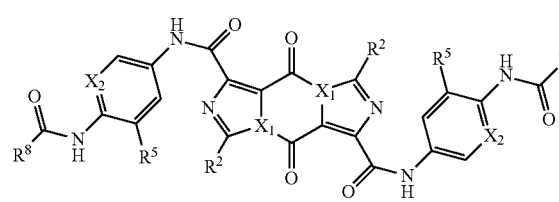
(IV)

in which X$_1$ represents N, and X$_2$, R$^2$, R$^5$ and R$^8$ are as defined for the compound of general formula (I) supra, for the preparation of a compound of general formula (I) as defined supra, or an N-oxide, a salt, a tautomer or a stereoisomer of said compound, or a salt of said N-oxide, tautomer or stereoisomer.

In accordance with further aspect, the present invention covers the use of the intermediate compounds of general formula (VI):

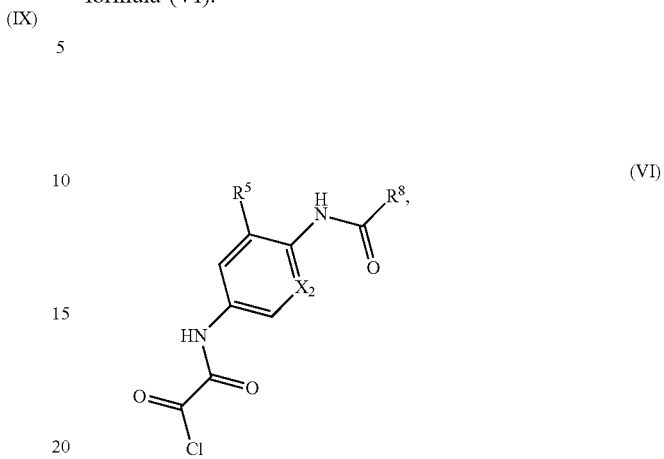
(VI)

in which X$_2$, R$^5$ and R$^8$ are as defined for the compound of general formula (I) supra, for the preparation of a compound of general formula (I) as defined supra, or an N-oxide, a salt, a tautomer or a stereoisomer of said compound, or a salt of said N-oxide, tautomer or stereoisomer.

In accordance with a further aspect, the present invention covers the use of the intermediate compounds of general formula (VIII):

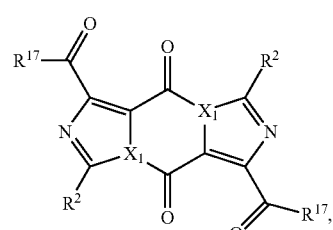
(VIII)

in which:
X$_1$ represents N,
R$^{17}$ represents OR$^{18}$,
R$^{18}$ represents hydrogen or phenyl, and
R$^2$ is as defined for the compound of general formula (I) supra,
for the preparation of a compound of general formula (I) as defined supra, or an N-oxide, a salt, a tautomer or a stereoisomer of said compound, or a salt of said N-oxide, tautomer or stereoisomer.

In accordance with a further aspect, the present invention covers the use of the intermediate compounds of general formula (IX):

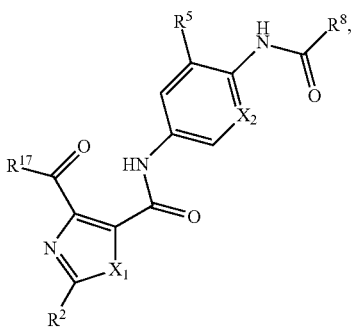

(IX)

in which:
X$_1$ represents NR$^3$,
R$^{17}$ represents OR$^{18}$,
R$^{18}$ represents hydrogen or phenyl, and
X$_2$ and R$^2$, R$^3$, R$^5$, R$^8$ are as defined for the compound of general formula (I) supra, for the preparation of a compound of general formula (I) as defined supra, or an N-oxide, a salt, a tautomer or a stereoisomer of said compound, or a salt of said N-oxide, tautomer or stereoisomer.

Another aspect of the invention relates to the intermediates described herein and their use for preparing a compound of formula (I) as defined supra or an N-oxide, a salt, a tautomer or a stereoisomer of said compound, or a salt of said N-oxide, tautomer or stereoisomer.

The intermediates used for the synthesis of the compounds of claims 1-6 as described below, as well as their use for the synthesis of the compounds of claims 1-6, are one further aspect of the present invention. Preferred intermediates are the Intermediate Examples as disclosed below.

EXPERIMENTAL SECTION

The following table lists the abbreviations used in this paragraph and in the Intermediate Examples and Examples section as far as they are not explained within the text body. NMR peak forms are stated as they appear in the spectra, possible higher order effects have not been considered. Chemical names were generated using Chemical names were generated using ACD/Name Batch Version 12.01./Batch Version 12.02. In some cases generally accepted names of commercially available reagents were used in place of ICS naming tool generated names.

| Abbreviation | Meaning |
|---|---|
| BOC | tert-butoxycarbonyl- |
| br. | broad signal (NMR) |
| DCM | dichloromethane |
| d | doublet |
| dd | doublet of doublet |
| DMF | N,N-dimethylformamide |
| DMSO | dimethylsulfoxide |
| EDTA | ethylenediaminetetraacetic acid |
| ESI | electrospray (ES) ionisation |
| h | hour(s) |
| HATU | 1-[bis(dimethylamino)methylene]-1H-1,2,3-triazolo[4,5-b]-pyridinium 3-oxid hexafluorophosphate |
| HCl | hydrochloric acid |
| HPLC | high performance liquid chromatography |
| HRP | horseradish peroxidase |
| LCMS | liquid chromatography-mass spectrometry |
| m | multiplet |
| min | minute(s) |

-continued

| Abbreviation | Meaning |
|---|---|
| MS | mass spectrometry |
| MTP | microtiter plate |
| NMR | nuclear magnetic resonance spectroscopy: chemical shifts (δ) are given in ppm. The chemical shifts were corrected by setting the DMSO signal to 2.50 ppm using unless otherwise stated. |
| NAD$^+$ | nicotinamide adenine dinucleotide |
| PBS | Phosphate buffered saline |
| PG | protecting group |
| PyBOP | Benzotriazol-1-yl-oxytripyrrolidinophosphonium hexafluorophosphate |
| q | quartet |
| s | singulet |
| SPA | Scintillation proximity assay |
| t | triplet |
| td | triplet of doublet |
| TFA | trifluoro acetic acid |
| THF | tetrahydrufuran |
| [$^3$H]- | Tritium |
| δ | chemical shift |

Other abbreviations have their meanings customary per se to the skilled person. The various aspects of the invention described in this application are illustrated by the following examples which are not meant to limit the invention in any way.

1. SYNTHESES OF COMPOUNDS (OVERVIEW)

The compounds of the present invention can be prepared as described in the following section. Schemes 1 to 5 and the procedures described below illustrate general synthetic routes to the compounds of general formula (I) of the invention and are not intended to be limiting. It is clear to the person skilled in the art that the order of transformations as exemplified in Schemes 1 to 5 can be modified in various ways. The order of transformations as exemplified in the Schemes 1 to 5 are therefore not intended to be limiting. In addition, interconversion of any of the substituents, R$^1$, R$^2$, R$^5$ and R$^8$ can be achieved before and/or after the exemplified transformations. These modifications can be such as the introduction of protecting groups, cleavage of protecting groups, exchange, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in Protective Groups in Organic Synthesis, 3rd edition, Wiley 1999). Specific examples are described in the subsequent paragraphs. Further, it is possible that two or more successive steps may be performed without work-up being performed between said steps, e.g. a "one-pot" reaction, as is well-known to the person skilled in the art.

All reagents used for the preparation of the compounds of the invention are either commercially available or can be prepared as described.

1.1 Synthesis of Aromatic Amines

Aromatic amines as intermediates for the synthesis of compounds of the invention are either commercially available or can be synthesized as depicted in scheme 1.

89

Scheme 1

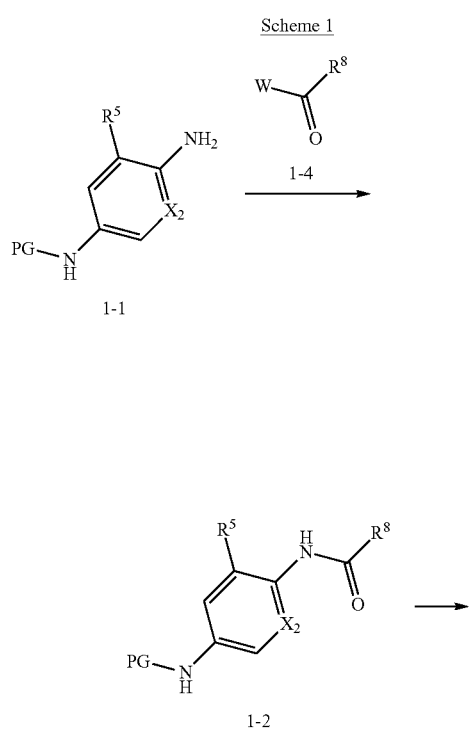

Scheme 1: Synthesis of aromatic amines, wherein $X_2$, $R^5$ and $R^8$ as defined for the compound of general formula (I) supra, and in which PG represents a protecting group, such as a BOC group, and W represents a hydroxy group or a chlorine atom.

Starting from an aromatic amine of type 1-1, where the para position of the amino function is a second protected amino function bearing a protecting group such as, for example, a BOC group or a nitro group as a precursor of a second amino function, upon a standard amide bond forming reaction, for example with a carboxylic acid of the type 1-4 in presence of a coupling agent such as, for example, HATU or the corresponding acid chloride of type 1-4, results in compounds of type 1-2.

Deprotection of the protected amine, in the case of a BOC-protecting group for example employing TFA or hydrochloric acid, or reduction of the nitro-moiety, for example using tin(II)chloride or a palladium on charcoal catalyst with hydrogen gas results in compounds of general formula (III), which can then be transformed further as described, for example, in scheme 3.

90

1.2 Synthesis of Imidazole Derivatives

One possible synthesis route for the compounds of this invention is depicted in schemes 2 and 3.

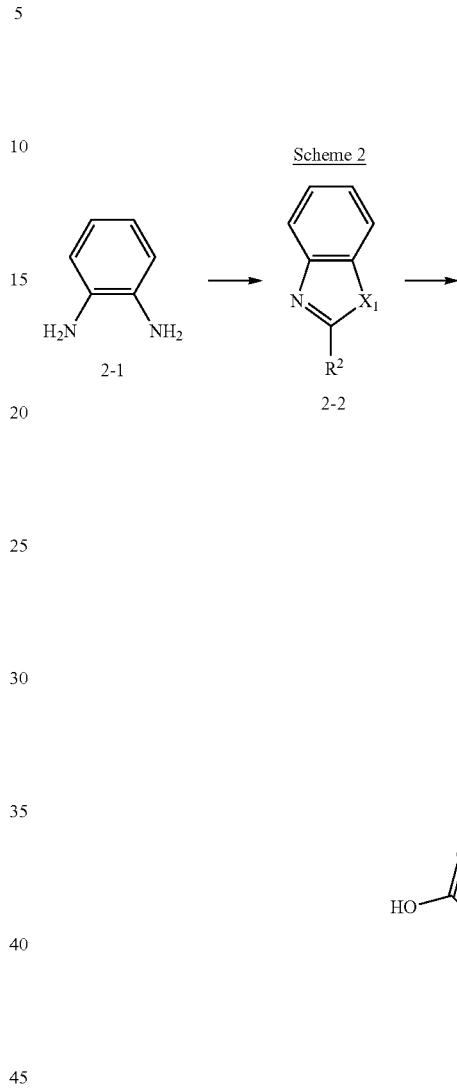

Scheme 2: Synthesis of 3,4 dicarboxylic acid substituted imidazoles, wherein $X_1$ represents $NR^3$, and $R^2$ and $R^3$ are as defined for the compounds of general formula (I) supra.

Commercially available benzene-1,2-diamine 2-1 can be reacted with carboxyclic acids at elevated temperatures to give compounds of type 2-2.

Treatment of compound 2-2, for example with hydrogen-peroxide under acidic conditions and elevated temperature, yields compound 2-3.

The synthesis of some of the compounds claimed in this invention employs the dicarboxylic acids of type 2-3 as depicted in scheme 3.

Scheme 3

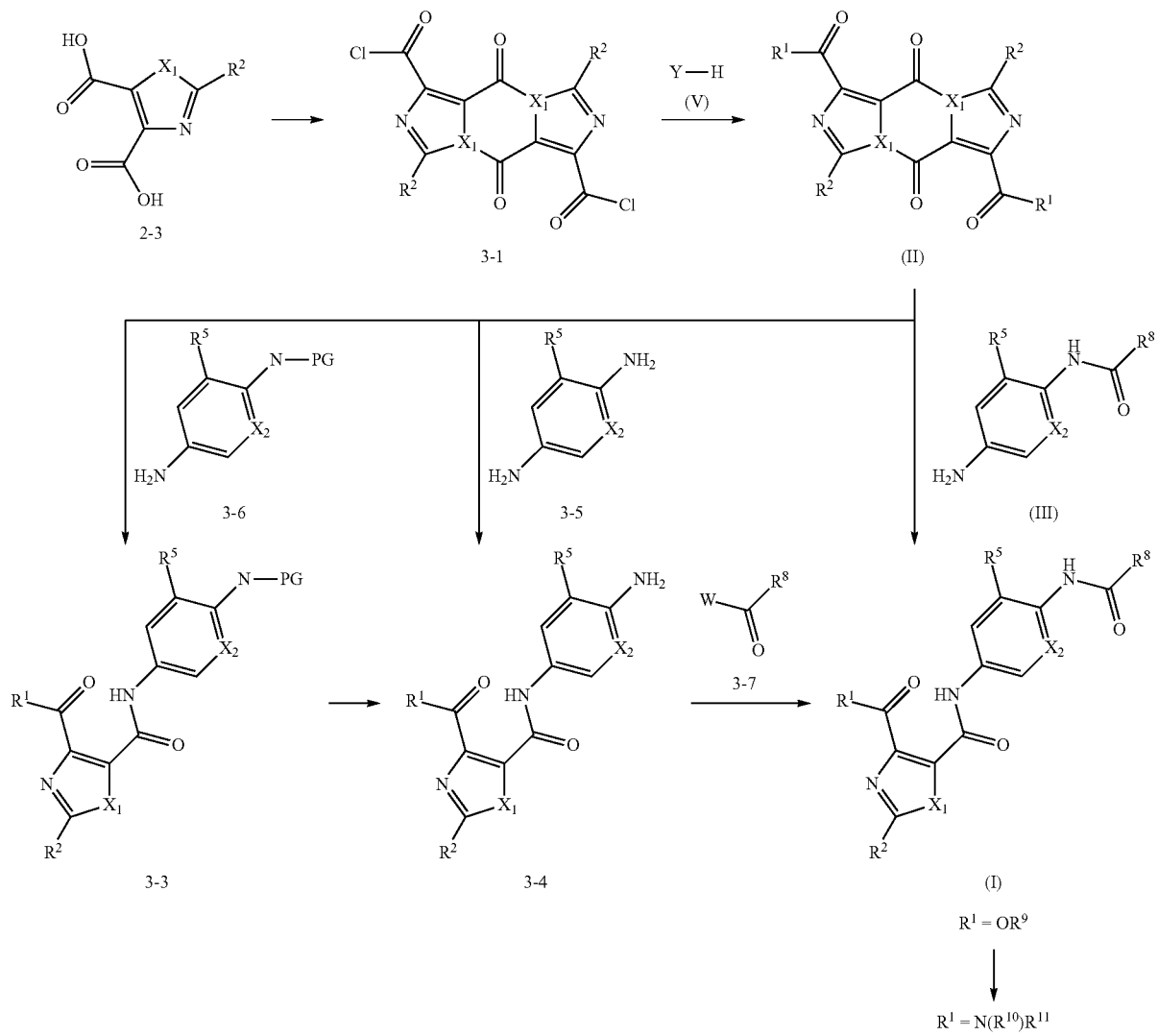

Scheme 3: Synthesis of compounds starting from dicarboxylic acid precursors, wherein $X_1$ represents $NR^3$, except for compounds 3-1 and (II) wherein $X_1$ represents N, and $X_2$, and $R^1$, $R^2$, $R^3$, $R^5$, $R^8$, $R^9$, $R^{10}$ and $R^{11}$ are as defined for the compound of general formula (I) supra, and in which PG represents a protecting group, such as a BOC group, and in which YH represents an alcohol $R^9OH$ or an amine $R^{11}(R^{10})NH_2$, wherein $R^9$, $R^{10}$ and $R^{11}$ are as defined for the compound of general formula (I) supra, and W represents a hydroxy group or a chlorine atom.

Starting from the corresponding 1H-imidazole-4,5-dicarboxylic acid derivative 2-3, after treatment with thionylchloride at elevated temperature 5,10-dioxo-5H,10H-diimidazo[1,5-a:1',5'-d]pyrazine-1,6-dicarbonyl dichlorides of type 3-1 are obtained.

Compounds of type 3-1 can be reacted with suitable nucleophiles, such as, for example, amines or alcohols of general formula (V) in presence of a suitable base, for example N-ethyl-N-isopropylpropan-2-amine, to give a compound of general formula (II).

Compounds of type (II) may serve as starting materials for several transformations:

Compounds of general formula (I) can be obtained directly by reacting compounds of general formula (II) with a fully decorated aromatic amine of general formula (III) at elevated temperatures.

Alternatively, an intermediate of type 3-4 can be obtained by reacting a compound of general formula (II) with a suitably substituted aromatic diamine of type 3-5 at elevated temperatures followed by standard amide bond forming reactions, for example with a carboxylic acid of the type 3-7 in presence of a coupling agent such as, for example, HATU or the corresponding acid chloride of type 3-7, to give compounds of type (I).

Another alternative synthesis route employs compounds of general formula (II) in presence of an aromatic amines of the type 3-6 with a suitably protected second amine function, such as, for example a BOC-protecting group, or a nitro group as a precursor for the second amine function (N-PG) at elevated temperatures to give compounds of type 3-3.

Deprotection of the protected amine, in the case of a BOC-protecting group for example employing TEA or hydrochloric acid, or reduction of the nitro-moiety, for example using tin(II)chloride or a palladium on charcoal catalyst with hydrogen gas results in compounds of type 3-4, which can then be transformed further as described above.

Esters of general formula (I) ($R^1$=$OR^9$) can be transformed into amides of general formula (I), ($R^1$=$N(R^{10})R^{11}$), according to the invention, for example by treatment with different amines, optionally in presence of a base, such as, for example, N-ethyl-N-isopropylpropan-2-amine, or alternatively in a two step procedure consisting of ester hydrolysis, for example using sodium hydroxide followed by standard amide bond formation in presence of amines and coupling agents such as HATU or alternatively in a three step procedure after hydrolysis of the ester, generation of corresponding acid chloride, for example using thionylchloride and reaction with amines under basic conditions in presence of, for example, N-ethyl-N-isopropylpropan-2-amine.

An alternative synthesis route of imidazole derivatives of the present invention is depicted in scheme 4.

Scheme 4: Alternative Synthesis of imidazole derivatives, wherein $X_1$ represents $NR^3$, except for compounds 3-1 and (IV) wherein $X_1$ represents N, and $X_2$, $R^1$, $R^2$, $R^3$, $R^5$ and $R^8$ are as defined for the compound of general formula (I) supra, and in which YH represents an alcohol $R^9OH$ or an amine $R^{11}(R^{10})NH_2$, wherein $R^9$, $R^{10}$ and $R^{11}$ are as defined for the compound of general formula (I) supra.

Starting from compounds of type 3-1, upon reaction with aromatic amines of general formula (III) in the presence of a base such as, for example N-ethyl-N-isopropylpropan-2-amine, compounds of general formula (IV) can be obtained.

Compounds of general formula (IV) can be transformed to compounds of general formula (I) by reaction with nucleophiles of general formula (V), such as, for example,

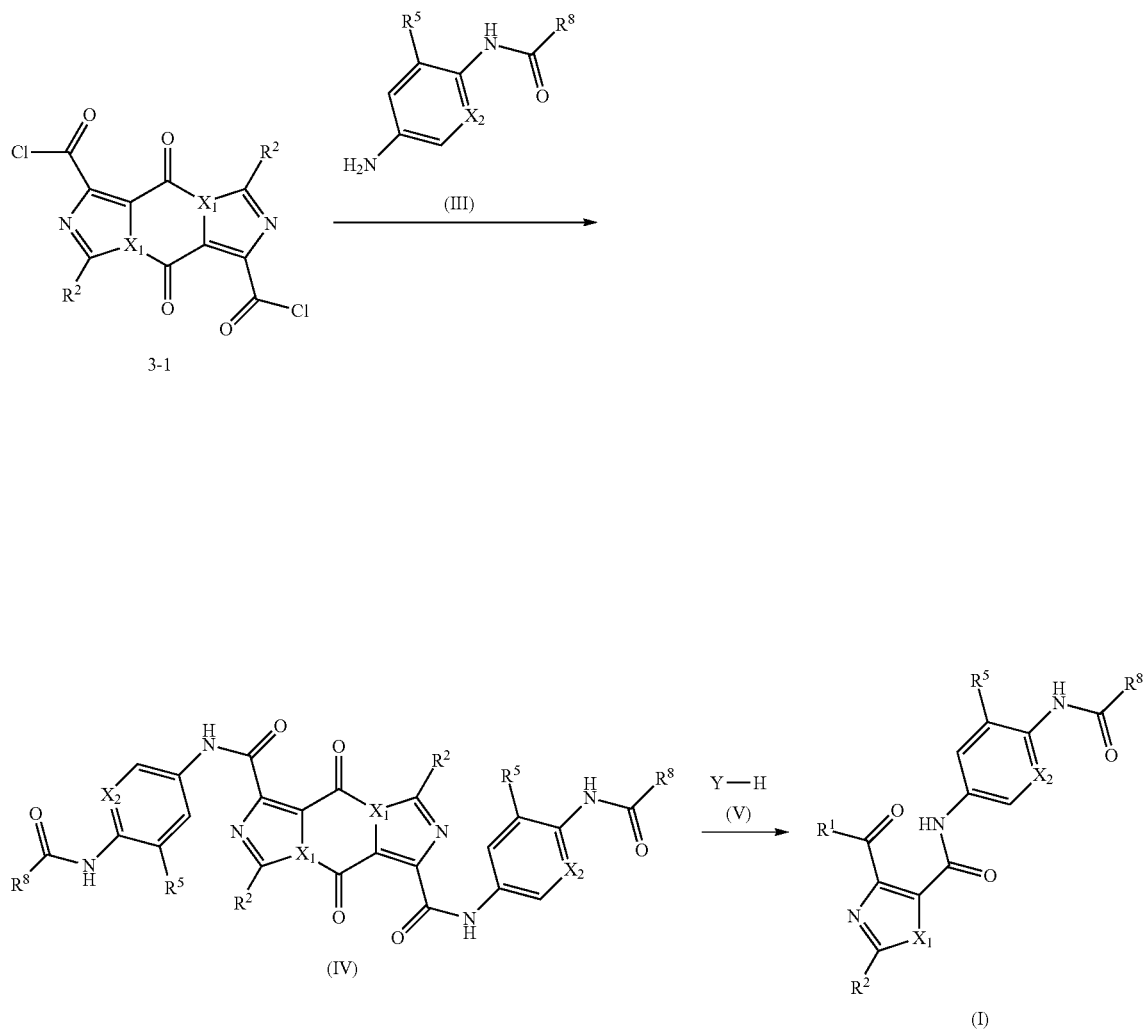

amines or alcohols, optionally in the presence of a base, such as, for example N-ethyl-N-isopropylpropan-2-amine.

1.3 Synthesis of Oxazole Derivatives

Yet another possible synthesis route for the compounds of this invention is depicted in scheme 5.

Scheme 5

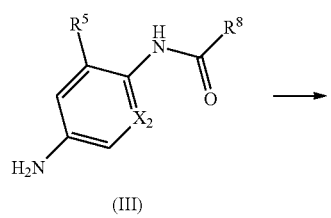

(III)

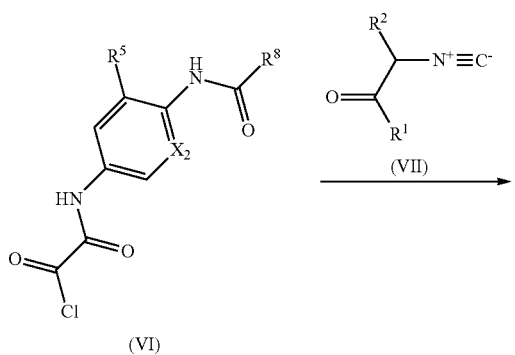

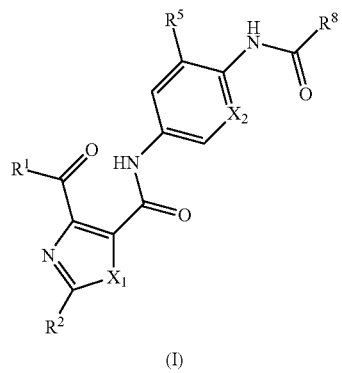

(I)

$R^1 = OR^9$

↓

$R^1 = N(R^{10})R^{11}$

Scheme 5: Synthesis of oxazole derivatives of the present invention, wherein $X_1$ represents O, and, $X_2$, $R^1$, $R^2$, $R^5$, $R^8$, $R^9$, $R^{10}$ and $R^{11}$ as defined for the compound of general formula (I) supra.

Compounds of type (III) can be transformed into compounds of type (VI) by reaction with oxalyl chloride.

Reaction of general formula (VI) with alkyl isocyanoacetates of general formula (VII) in presence of, for example, imidazole and triethylamine yields esters of general formula as claimed in this invention.

Esters of general formula (I) ($R^1=OR^9$) can be transformed into amides of general formula (I), ($R^1=N(R^{10})R^{11}$), according to the invention, for example by treatment with different amines, optionally in presence of a base, such as, for example, N-ethyl-N-isopropylpropan-2-amine, or alternatively in a two step procedure consisting of ester hydrolysis, for example using sodium hydroxide followed by standard amide bond formation in presence of amines and coupling agents such as HATU or alternatively in a three step procedure after hydrolysis of the ester, generation of corresponding acid chloride, for example using thionylchloride and reaction with amines under basic conditions in presence of, for example, N-ethyl-N-isopropylpropan-2-amine.

Scheme 6

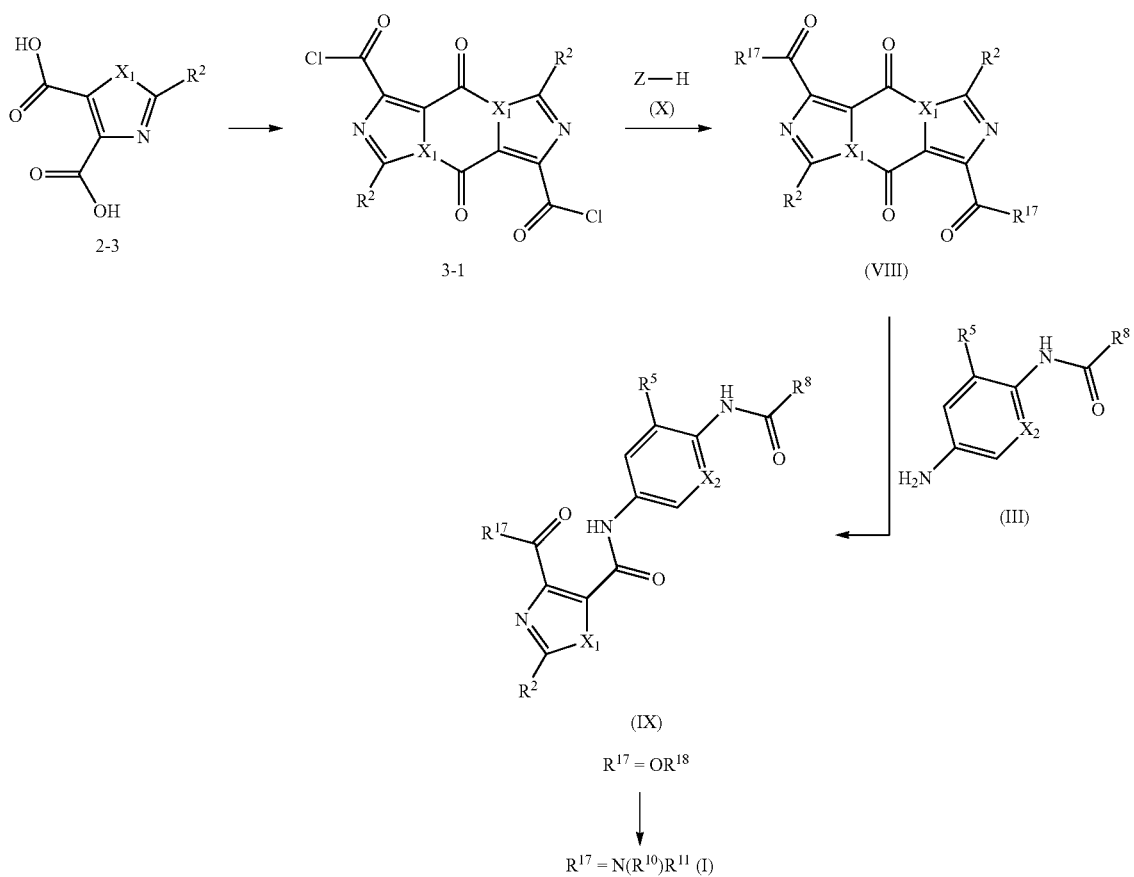

Scheme 6: Synthesis of compounds starting from dicarboxylic acid precursors, wherein $X_1$ represents $NR^3$, except for compounds 3-1 and (VIII) wherein $X_1$ represents N, $R^{17}$ represents $OR^{18}$, wherein $R^{18}$ represents hydrogen or phenyl and $X_2$ and $R^2$, $R^3$, $R^5$, $R^8$, $R^{10}$ and $R^{11}$ are as defined for the compound of general formula (I) supra, and in which ZH represents an alcohol $R^{18}OH$ or a carbamate, such as tert-butyl carbamat. Starting from the corresponding 1H-imidazole-4,5-dicarboxylic acid derivative 2-3, after treatment with thionylchloride at elevated temperature 5,10-dioxo-5H,10H-diimidazo[1,5-a:1',5'-d]pyrazine-1,6-dicarbonyl dichlorides of type 3-1 are obtained.

Compounds of type 3-1 can be reacted with suitable nucleophiles, such as, for example, carbamates (tert butyl carbamate) or alcohols of general formula (X) in presence of a suitable base, for example N-ethyl-N-isopropylpropan-2-amine, to give a compound of general formula (VIII).

Compounds of type (VIII) can react with a fully decorated aromatic amine of general formula (III) at room temperature or elevated temperature to give compounds of the general formula (IX).

Compounds of general formula (IX) ($R^{17}$=$OR^{18}$) can be transformed into amides of general formula (I), ($R^{17}$=N($R^{10}$)($R^{11}$)), according to the invention, for example by treatment with different amines of formula HN($R^{10}$)($R^{11}$), optionally in presence of a base, such as, for example, N-ethyl-N-isopropylpropan-2-amine, or alternatively if $R^{18}$ is hydrogen by standard amide bond formation in presence of amines of formula HN($R^{10}$)$R^{11}$) and coupling agents such as HATU.

In accordance with an embodiment, the present invention also relates to a method of preparing a compound of general formula (I) as defined supra, said method comprising the step of allowing an intermediate compound of general formula (II):

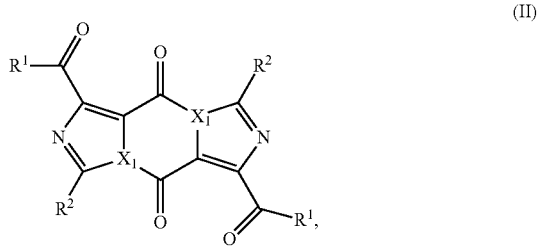

in which $X_1$ represents N, and $R^1$ and $R^2$ are as defined for the compound of general formula (I) supra, to react with a compound of general formula (III):

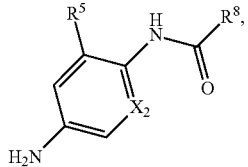

(III)

in which $X_2$, $R^5$ and $R^8$ are as defined for the compound of general formula (I) supra,
thereby giving a compound of general formula (I):

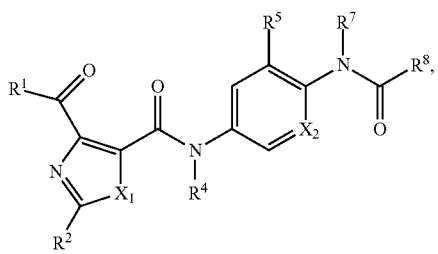

(I)

in which $X_1$ represents $NR^3$, and $X_2$, $R^1$, $R^2$, $R^3$, $R^4$, $R^5$, $R^7$, and $R^8$ are as defined for the compound of general formula (I) supra.

In accordance with another embodiment, the present invention also relates to a method of preparing a compound of general formula (I) as defined supra, said method comprising the step of allowing an intermediate compound of general formula (IV):

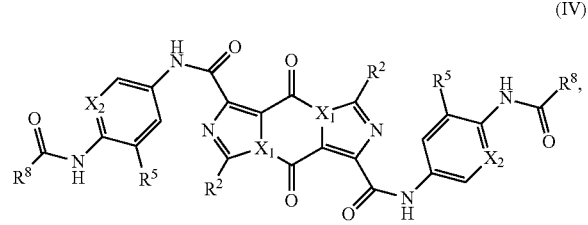

(IV)

in which $X_1$ represents N, and $X_2$, $R^2$, $R^5$ and $R^8$ are as defined for the compound of general formula (I) supra,
to react with a compound of general formula (V):

YH    (V), in which YH represents an alcohol $R^9OH$ or an amine $R^{11}(R^{10})NH_2$, wherein $R^9$, $R^{10}$ and $R^{11}$ are as defined for the compound of general formula (I) supra, thereby giving a compound of general formula (I):

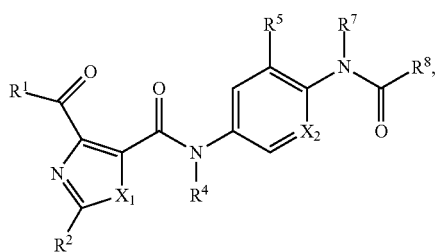

(I)

in which $X_1$ represents $NR^3$, and $X_2$, $R^1$, $R^2$, $R^3$, $R^4$, $R^5$, $R^7$, and $R^8$ are as defined for the compound of general formula (I) supra.

In accordance with yet another embodiment, the present invention also relates to a method of preparing a compound of general formula (I) as defined supra, said method comprising the step of allowing an intermediate compound of general formula (VI):

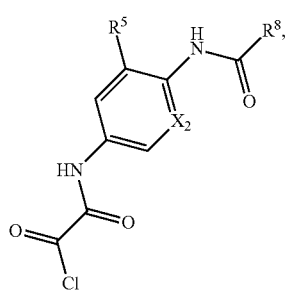

(VI)

in which $X_2$, $R^5$ and $R^8$ are as defined for the compound of general formula (I) supra,
to react with a compound of general formula (VII):

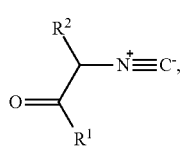

(VII)

in which $R^1$ and $R^2$ are as defined for the compound of general formula (I) supra, thereby giving a compound of general formula (I):

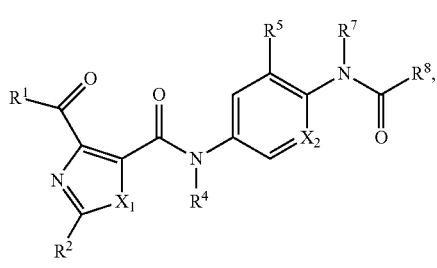

(I)

in which $X_1$ represents O, and $X_2$, $R^1$, $R^2$, $R^4$, $R^5$, $R^7$, and $R^8$ are as defined for the compound of general formula (I) supra.

In accordance with yet another embodiment, the present invention also relates to a method of preparing a compound of general formula (I) supra, said method comprising the step of allowing an intermediate compound of general formula (IX):

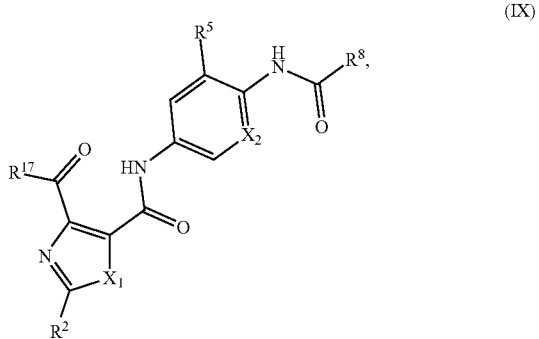

in which $X_1$ represents $NR^3$,
$R^{17}$ represents $OR^{18}$,
$R^{18}$ represents hydrogen or phenyl,
$X_2$ and $R^2$, $R^3$, $R^5$, $R^8$, $R^9$ are as defined for the compound of general formula (I) according to any one of claims 1 to 6, to react with a compound of formula $HN(R^{10})(R^{11})$ in which:
$R^{10}$, $R^{11}$ are as defined for the compound of general formula (I) supra, thereby giving a compound of general formula (I):

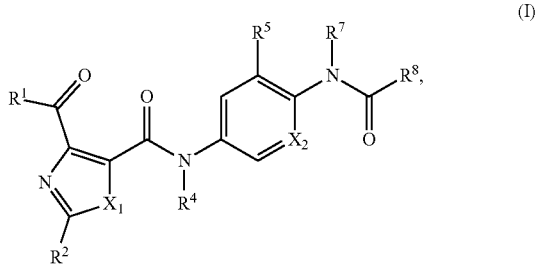

in which $X_1$ represents $NR^3$, $R^1$ represents $-NR^{10}R^{11}$, and $X_2$, $R^2$, $R^4$, $R^5$, $R^7$, and $R^8$ are as defined for the compound of general formula (I) supra.

2. GENERAL PART

HPLC Methods:
Method 1:
Instrument: Waters Acquity UPLCMS; Column: Acquity UPLC BEH C18 1.7 μm, 50×2.1 mm; eluent A: water+0.1 vol % formic acid (99%), Eluent B: acetonitrile; gradient: 0-1.6 min 1-99% B, 1.6-2.0 min 99% B; flow 0.8 ml/min; temperature: 60° C.; injection: 2 μL.
Method 2:
Instrument: Waters Acquity UPLCMS; column: Acquity UPLC BEH C18 1.7 μm, 50×2.1 mm; eluent A: water+0.1 vol % formic acid (99%), eluent B: acetonitrile; gradient: 0-1.6 min 1-99% B, 1.6-2.0 min 99% B; flow 0.8 ml/min; temperature: 60° C.; injection: 2 μL.
Method 3:
Instrument: Waters Acquity UPLCMS; column: Acquity UPLC BEH C18 1.7 μm, 50×2.1 mm; eluent A: water+0.1 vol % formic acid (99%), eluent B: acetonitrile; gradient: 0-1.6 min 1-99% B, 1.6-2.0 min 99% B; flow 0.8 ml/min; temperature: 60° C.; injection: 2 μL.
Method 4:
Instrument: Waters Acquity UPLCMS; column: Acquity UPLC BEH C18 1.7 μm, 50×2.1 mm; eluent A: water+0.1 vol % formic acid (99%), eluent B: acetonitrile; gradient: 0-1.6 min 1-99% B, 1.6-2.0 min 99% B; flow 0.8 ml/min; temperature: 60° C.; injection: 1 μL.
Method 5:
Instrument: Waters Acquity UPLCMS; column: Acquity UPLC BEH C18 1.7 μm, 50×2.1 mm; eluent A: water+0.2 vol % aqueous ammonia (32%), eluent B: acetonitrile; gradient: 0-1.6 min 1-99% B, 1.6-2.0 min 99% B; flow 0.8 ml/min; temperature: 60° C.; injection: 1 μL.
Method 6:
Instrument: Agilent LC-MS 1200 rapid Resolution with MSD6140; Column: Ascentis Express C18 2.7 μm, 30×2.1 mm; eluent A: water+0.1 vol % formic acid (95%), eluent B: methanol+0.1 vol % formic acid; gradient: 0-1.0 min 5% B, 1.0-4.0 min 5-100% B; 4.0-6.0 100-5% B, flow 0.8 ml/min; temperature: 30° C.; injection: 1 μL.
Method 7
Instrument: Waters Acquity UPLCMS SingleQuad; Column: Acquity UPLC BEH C18 1.7 μm, 50×2.1 mm; eluent A: water+0.1 vol % formic acid (99%), eluent B: acetonitrile; gradient: 0-1.6 min 1-99% B, 1.6-2.0 min 99% B; flow 0.8 ml/min; temperature: 60° C.; DAD scan: 210-400 nm.
Method 8
Instrument: Waters Acquity UPLCMS SingleQuad; Column: Acquity UPLC BEH C18 1.7 μm, 50×2.1 mm; eluent A: water+0.2 vol % aqueous ammonia (32%), eluent B: acetonitrile; gradient: 0-1.6 min 1-99% B, 1.6-2.0 min 99% B; flow 0.8 ml/min; temperature: 60° C.; DAD scan: 210-400 nm.
Method 9
Instrument: Waters Acquity UPLCMS SingleQuad; Column: Acquity UPLC BEH C18 1.7 50×2.1 mm; eluent A: water+0.1 vol % formic acid (99%), eluent B: acetonitrile; gradient: 0-1.6 min 1-99% B, 1.6-2.0 min 99% B; flow 0.8 ml/min; temperature: 60° C.; DAD scan: 210-400 nm.
Method 10
Instrument: Waters Acquity UPLCMS SingleQuad; Column: Acquity UPLC BEH C18 1.7 50×2.1 mm; eluent A: water+0.2 vol % aqueous ammonia (32%), eluent B: acetonitrile; gradient: 0-1.6 min 1-99% B, 1.6-2.0 min 99% B; flow 0.8 ml/min; temperature: 60° C.; DAD scan: 210-400 nm.
Method 11
Instrument: Waters Acquity UPLCMS Tof; column: Kinetex C18 (Phenomenex) 2.6 μm, 50×2.1 mm; eluent A: water+0.05 Vol-% formic acid (99%), eluent B: acetonitrile+0.05% formic acid; gradient: 0-0.2 min 98% A, 0.2-1.7 min 98-10% A, 1.7-1.9 min 10% A, 1.9-2.0 min 10-98% A, 2.0-2.5 min 98% A; flow 1.3 ml/min; temperature: 60° C.; DAD scan: 210-400 nm
Method 12
Instrument: Agilent 1290 UHPLCMS Tof; column: BEH C18 (Waters) 1.7 μm, 50×2.1 mm; eluent A: water+0.05 Vol-% formic acid (99%), eluent B: acetonitrile+0.05% formic acid; gradient: 0-1.7 min 98-10% A, 1.7-2.0 min 10% A, 2.0-2.5 min 10-98% A, flow 1.2 ml/min; temperature: 60° C.; DAD scan: 210-400 nm
Method 13
Instrument: Waters Acquity UPLC-SQD; column: Acquity UPLC BEH C18 1.7 50×2.1 mm; eluent A: water+0.2% Vol. aqueous ammonia (32%), eluent B: methanol; gradient: 0-1.6 min 1-99% B, 1.6-2.0 min 99% B; flow 0.8 ml/min; temperature: 60° C.; injection: 2 µl; DAD scan: 210-400 nm; ELSD MS ESI-pos/neg., scan range 160-1000 m/z.

Method 14

Instrument: Waters Acquity UPLC-SQD; column: Acquity UPLC BEH C18 1.7 50×2.1 mm; eluent A: water+ 0.2% Vol. aqueous ammonia (32%), eluent B: acetonitrile; gradient: 0-1.6 min 1-99% B, 1.6-2.0 min 99% B; flow 0.8 ml/min; temperature: 60° C.; Injection: 2 µl; DAD scan: 210-400 nm; ELSD MS ESI-pos/neg., scan range 160-1000 m/z.

Method 15

Instrument MS: Waters ZQ; Instrument HPLC: Waters UPLC Acquity; Column: Acquity BEH C18 (Waters), 50 mm×2.1 mm, 1.7 µm; eluent A: water+0.1 vol % formic acid, eluent B: acetonitrile (Lichrosolv Merck); gradient: 0.0 min 99% A—1.6 min 1% A—1.8 min 1% A—1.81 min 99% A—2.0 min 99% A; temperature: 60° C.; flow: 0.8 mL/min; UV-Detection PDA 210-400 nm.

Optical Rotation:

Instrument: JASCO P2000 Polarimeter; wavelength 589 nm; temperature: 20° C.; integration time 10 s; path length 100 mm.

NMR Data:

The $^1$H-NMR data of selected examples are listed in the form of $^1$H-NMR peaklists. For each signal peak the δ value in ppm is given, followed by the signal intensity, reported in round brackets. The δ value-signal intensity pairs from different peaks are separated by commas. Therefore, a peaklist is described by the general form: $\delta_1$ (intensity$_1$), $\delta_2$ (intensity$_2$), . . . , $\delta_i$ (intensity$_i$), . . . , $\delta_n$ (intensity$_n$).

The intensity of a sharp signal correlates with the height (in cm) of the signal in a printed NMR spectrum. When compared with other signals, this data can be correlated to the real ratios of the signal intensities. In the case of broad signals, more than one peak, or the center of the signal along with their relative intensity, compared to the most intense signal displayed in the spectrum, are shown. A $^1$H-NMR peaklist is similar to a classical $^1$H-NMR readout, and thus usually contains all the peaks listed in a classical NMR interpretation. Moreover, similar to classical $^1$H-NMR printouts, peaklists can show solvent signals, signals derived from stereoisomers of target compounds (also the subject of the invention), and/or peaks of impurities. The peaks of stereoisomers, and/or peaks of impurities are typically displayed with a lower intensity compared to the peaks of the target compounds (e.g., with a purity of >90%). Such stereoisomers and/or impurities may be typical for the particular manufacturing process, and therefore their peaks may help to identify the reproduction of our manufacturing process on the basis of "by-product fingerprints". An expert who calculates the peaks of the target compounds by known methods (MestReC, ACD simulation, or by use of empirically evaluated expectation values), can isolate the peaks of target compounds as required, optionally using additional intensity filters. Such an operation would be similar to peak-picking in classical $^1$H-NMR interpretation. A detailed description of the reporting of NMR data in the form of peaklists can be found in the publication "Citation of NMR Peaklist Data within Patent Applications" (cf. Research Disclosure Database Number 605005, 2014, 1 Aug. 2014, or researchdisclosure.com/searching-disclosures). In the peak picking routine, as described in the Research Disclosure Database Number 605005, the parameter "MinimumHeight" can be adjusted between 1% and 4%. Depending on the chemical structure and/or depending on the concentration of the measured compound it may be reasonable to set the parameter "MinimumHeight"<1%.

3. INTERMEDIATES

Intermediate 001

5,10-dioxo-5H,10H-diimidazo[1,5-a:1',5'-d]pyrazine-1,6-dicarbonyl dichloride

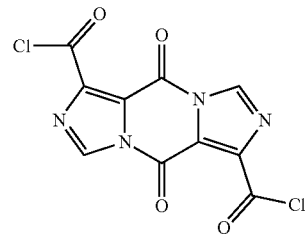 [SMILES: O=C(Cl)c1ncn2c(=O)c3c(C(=O)Cl)ncn3c(=O)c12]

In a dried flask, to 25 g (157 mmol) 1H-imidazole-4,5-dicarboxylic acid in 334 mL of toluene, 12.1 mL DMF and 94 mL (1.29 mol) thionyl chloride were added. The mixture was stirred for 24 h at 80° C.

The mixture was concentrated under reduced pressure. 100 mL toluene were added and the mixture was concentrated under reduced pressure to give 35.5 g of the title compound as crude material which was used at the same day without further purification for subsequent steps.

Intermediate 002

N,N'-dimethyl-5,10-dioxo-5H,10H-diimidazo[1,5-a:1',5'-d]pyrazine-1,6-dicarboxamide

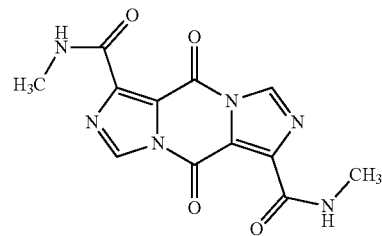

To 35 g (crude product) of 5,10-dioxo-5H,10H-diimidazo [1,5-a:1',5'-d]pyrazine-1,6-dicarbonyl dichloride (Intermediate 001) in 460 mL THF were added dropwise 153 mL (307 mmol) of a 2M solution of methyl amine in THF and 68 mL (391 mmol) N-ethyl-N-isopropylpropan-2-amine. The resulting mixture was stirred for 20 h at room temperature.

The precipitate was filtered off and washed with dichloromethame. The obtained solid material was digested in methanol and dried in vacuum to give 15.2 g of the tittle compound as a crude product which was used without further purification in the subsequent steps.

Intermediate 003

N[5]-(4-aminophenyl)-N[4]-methyl-1H-imidazole-4,5-dicarboxamide

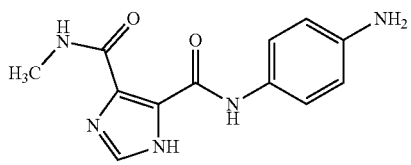 [SMILES: CNC(=O)c1nc[nH]c1C(=O)Nc1ccc(N)cc1]

To 5.31 g (47.6 mmol) benzene-1,4-diamine in 260 mL THF were added 12 g (crude product) N,N'-dimethyl-5,10-dioxo-5H,10H-diimidazo[1,5-a:1',5'-d]pyrazine-1,6-dicarboxamide (Intermediate 002) and 6.64 mL (47.6 mmol) triethylamine. The mixture was stirred for 30 min at room temperature.

Insoluble material was filtered off and washed with THF. The combined organic layers were concentrated. The obtained solid material was digested in dichloromethane and dried in vacuum to give 10.2 g of the title compound as solid material, which was used without further purification in the subsequent step.

LCMS (Method 3): $R_t$=0.57 min; MS (ESIpos) m/z=260 [M+H]$^+$.

Intermediate 004

N-(4-aminophenyl)-2-chloro-4-fluorobenzamide

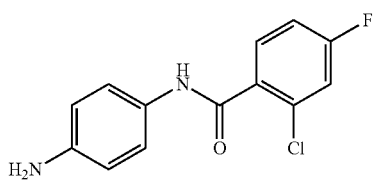 [SMILES: Nc1ccc(NC(=O)c2ccc(F)cc2Cl)cc1]

Step 1: To 10 g (48 mmol) tert-butyl (4-aminophenyl)carbamate in 81 mL DMF were added 21.7 mL (125 mmol) N-ethyl-N-isopropylpropan-2-amine, 9.64 g (55.2 mmol) 2-chloro-4-fluoro-benzoic acid and 34.3 mL (57.6 mmol) of a 50% solution of 2,4,6-tripropyl-1,3,5,2,4,6-trioxatriphosphinane 2,4,6-trioxide in DMF. The resulting mixture was stirred for 23 h at room temperature.

The mixture was poured into water. The precipitate was filtered off, washed with water and lyophilized. The BOC-protected title compound was obtained as a crude product which was used in step 2 without further purification.

Step 2: To the crude material from step 1 in 214 mL dichloromethane were added 107 mL trifluoro acetic acid. The mixture was stirred for 30 min at room temperature.

Water was added. 110 mL of a 25% aqueous ammonia solution were added. The obtained solution was extracted with dichloromethane. The organic layer was dried over sodium sulfate to give 9.2 g of the title compound as solid material.

$^1$H-NMR (400 MHz, DMSO-d$_6$): δ [ppm]=10.02 (s, 1H), 7.59 (dd, 1H), 7.53 (dd, 1H), 7.35-7.28 (m, 3H), 6.56-6.47 (m, 2H), 4.92 (s, 2H).

LCMS (Method 1): $R_t$=0.69 min; MS (ESIpos) m/z=265 [M+H]$^+$.

Intermediate 005

N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide

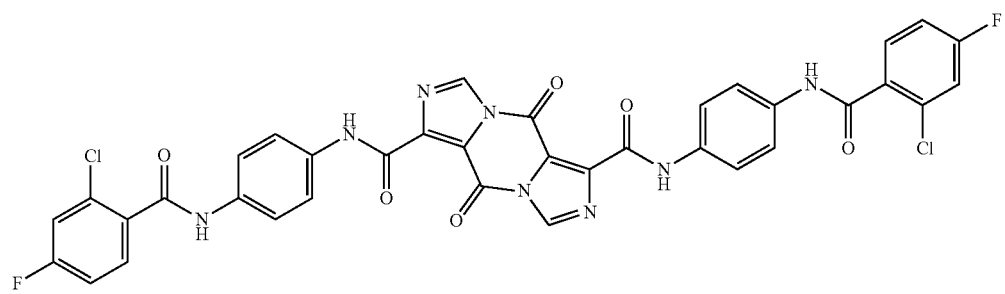 [SMILES: O=C(Nc1ccc(NC(=O)c2ncn3c(=O)c4c(C(=O)Nc5ccc(NC(=O)c6ccc(F)cc6Cl)cc5)ncn4c(=O)c23)cc1)c1ccc(F)cc1Cl]

To 150 mg (0.48 mmol) 5,10-Dioxo-5H,10H-diimidazo[1,5-a; 1',5'-d]pyrazin-1,6-dicarbonyl-dichloride (Intermediate 001) in 2 ml THF were added 254 mg (0.96 mmol) N-(4-aminophenyl)-2-chloro-4-fluorobenzamide (Intermediate 004) and 200 μL (1.44 mmol) triethylamine. The resulting mixture was stirred for 30 min at room temperature.

The obtained reaction mixture was used without workup in the next reaction.

Intermediate 006

({4-[(2-chloro-4-fluorobenzoyl)amino]phenyl}amino)(oxo)acetyl chloride

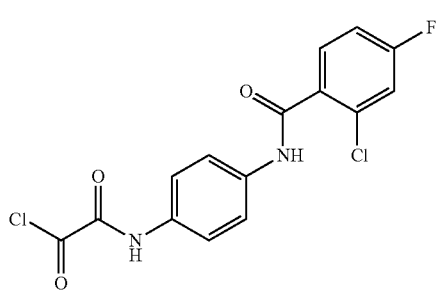 [SMILES: O=C(Cl)C(=O)Nc1ccc(NC(=O)c2ccc(F)cc2Cl)cc1]

A mixture of 1.50 mL (17.47 mmol) oxalyl chloride and 300 mg (1.13 mmol) N-(4-aminophenyl)-2-chloro-4-fluorobenzamide (Intermediate 004) in 4 mL trichloromethane was stirred for 2 hours at room temperature. The reaction mixture was then concentrated in vacuo to give 400 mg of the title compound as a solid material which was used without further purification.

Intermediate 007

4-fluoro-2,6-dimethylbenzoyl chloride

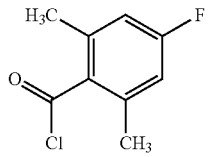

To a solution of 169 mg (1.00 mmol) 4-fluoro-2,6-dimethylbenzoic acid and 112 µL (1.30 mmol) oxalylchloride in 5 mL dry dichloromethane, a few drops of DMF were added under an argon atmosphere. After stirring for 2 hours at room temperature the reaction mixture was concentrated in vacuo to give 187 mg of the title compound which was used without further purification.

Intermediate 008

3-chloroisonicotinoyl chloride

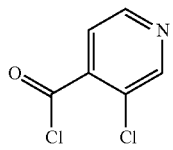

To a solution of 121 mg (0.77 mmol) 3-chloroisonicotinic acid and 349 µL (9.77 mmol) oxalyl chloride in 4 mL dry dichloromethane, a few drops of DMF were added under an argon atmosphere. After stirring for 3 hours at room temperature the reaction mixture was concentrated in vacuo to give 136 mg of the title compound as a solid material which was used without further purification.

Intermediate 009

2-chloro-4-[2-(dimethylamino)ethoxy]benzoyl chloride

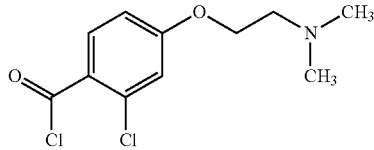 [SMILES: CN(C)CCOc1ccc(C(=O)Cl)c(Cl)c1]

Step 1:

640 mg (3.43 mmol) methyl 2-chloro-4-hydroxybenzoate, 739 mg (5.14 mmol) 2-chloro-N,N-dimethylethanamine hydrochloride and 2.31 g (16.7 mmol) potassium carbonate were suspended in 12 mL DMF. After stirring for 2 days at room temperature 15 mL water were added and the mixture was extracted twice with ethyl acetate. The combined organic phases were dried over magnesium sulfate, and the solvent was removed under reduced pressure. The crude product was purified by flash chromatography to give 523 mg of the title compound as oil.

LC-MS (Method 6): $R_t$=2.05 min; MS (ESIpos) m/z=258.3 [M+H]$^+$.

Step 2:

To a solution of 517 mg (2.01 mmol) methyl 2-chloro-4-[2-(dimethylamino)ethoxy]benzoate in 2 mL methanol 3.01 mL (3.01 mmol) of a 1N sodium hydroxid solution were added. After stirring for 2.5 h at room temperature 3.01 mL (3.01 mmol) of an 1N aqueous hydrochloric acid were added and the solvents were removed under reduced pressure to give 654 mg of the title compound (contains 27% sodium chloride) as a solid material which was used without further purification.

LC-MS (Method 6): $R_t$=0.25 min; MS (ESIpos) m/z=244.3 [M+H]$^+$.

Step 3:

To a solution of 200 mg (0.82 mmol) 2-chloro-4-[2-(dimethylamino)ethoxy]benzoic acid (contains 27% sodium chloride) and 112 µL (1.30 mmol) oxalyl chloride in 2 mL dry tetrahydrofuran, a few drops of DMF were added under an argon atmosphere. After stirring for 3 hours at room temperature the reaction mixture was concentrated in vacuo to give the title compound which was used without further purification LC-MS (Method 6): $R_t$=2.0 min; MS (ESIpos) m/z=258.3 [M+H]$^+$ (methyl ester).

Intermediate 010

2-chloro-4-[2-(4-methylpiperazin-1-yl)ethoxy]benzoyl chloride

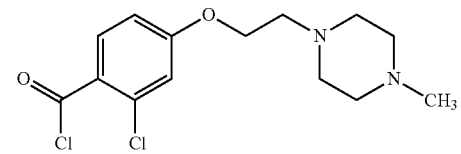 [SMILES: CN1CCN(CCOc2ccc(C(=O)Cl)c(Cl)c2)CC1]

Step 1:

740 mg (3.97 mmol) methyl 2-chloro-4-hydroxybenzoate, 1.40 g (5.94 mmol) 1-(2-chloroethyl)-4-methylpiperazine and 2.68 g (19.4 mmol) potassium carbonate were suspended in 14 mL DMF. After stirring for 2 days at room temperature 15 mL water were added and the mixture was extracted twice with ethyl acetate. The combined organic phases were dried over magnesium sulfate, and the solvent was removed under reduced pressure. The crude product was purified by flash chromatography to give 400 mg of the title compound as oil.

LC-MS (Method 6): $R_t$=2.3 min; MS (ESIpos) m/z=313.3 [M+H]$^+$.

Step 2:

To a solution of 391 mg (1.25 mmol) methyl 2-chloro-4-[2-(4-methylpiperazin-1-yl)ethoxy]benzoate in 2 mL methanol 1.88 mL (1.88 mmol) of a 1N sodium hydroxid solution were added. After stirring for 2.5 h at room temperature 1.88 mL (1.88 mmol) of an 1N aqueous hydrochloric acid were added and the solvents were removed under reduced pressure to give 454 mg of the title compound (contains 32% sodium chloride) as a solid material which was used without further purification.

LC-MS (Method 6): $R_t$=0.4 min; MS (ESIpos) m/z=299.3 [M+H]$^+$.

Step 3:

To a solution of 200 mg (0.67 mmol) 2-chloro-4-[2-(4-methylpiperazin-1-yl)-ethoxy]benzoic acid and 86 µL (1.00 mmol) oxalyl chloride in 2 mL dry tetrahydrofuran, a few drops of DMF were added under an argon atmosphere. After stirring for 3 hours at room temperature the reaction mixture was concentrated in vacuo to give the title compound as a solid material which was used without further purification LC-MS (Method 6): $R_t$=2.35 min; MS (ESIpos) m/z=313.3 [M+H](methyl ester).

Intermediate 013

$N^4$-methyl-$N^5$-(3-methyl-4-nitrophenyl)-1H-imidazole-4,5-dicarboxamide

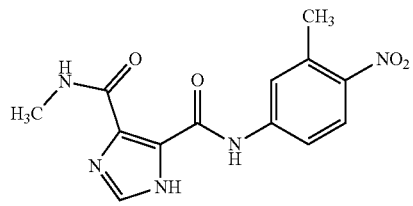

A mixture of 392 mg (2.573 mmol) 3-methyl-4-nitroaniline, 500 mg (70% pure, 1.158 mmol) N,N'-dimethyl-5,10-dioxo-5H,10H-diimidazo[1,5-a:1',5'-d]pyrazine-1,6-dicarboxamide (Intermediate 002) and 0.54 mL (3.860 mmol) triethylamine in 14.1 mL dichloromethane was subsequently stirred for 1 h at room temperature, for 2 h at 45° C. and at room temperature again overnight. The resulting precipitate was filtered off and washed with dichloromethane to yield 497 mg of the title compound as a solid material which was used without further purification.

LC-MS (Method 4): $R_t$=1.04 min; MS (ESIpos) m/z=304 [M+H]$^+$.

Intermediate 014

$N^5$-(4-amino-3-methylphenyl)-$N^4$-methyl-1H-imidazole-4,5-dicarboxamide

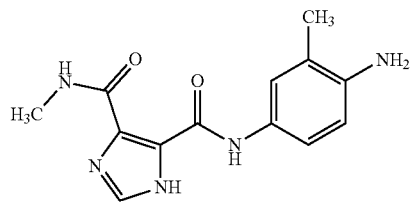 [SMILES: CNC(=O)c1nc[nH]c1C(=O)Nc1ccc([N+](=O)[O-])c(C)c1]

To 490 mg (1.616 mmol) $N^4$-methyl-$N^5$-(3-methyl-4-nitrophenyl)-1H-imidazole-4,5-dicarboxamide (Intermediate 013) in 50 mL ethylacetate, 50 mg palladium on charcoal (10% w/w) were added and the mixture was stirred under hydrogen atmosphere for 3 h at room temperature. Then, 10 mL of methanol were added and the mixture was further stirred under hydrogen atmosphere for 17 h at room temperature. 50 mg palladium on charcoal (10% w/w) were again added and the mixture was stirred under hydrogen atmosphere for 5 h at room temperature. The solids were filtered off, washed with ethylacetate and the combined filtrate was concentrated in vacuo to give 490 mg of the title compound as a solid material which was used without further purification.

LC-MS (Method 3): $R_t$=0.62 min; MS (ESIpos) m/z=274 [M+H]$^+$.

Intermediate 015 methyl 5-[(4-aminophenyl)carbamoyl]-1H-imidazole-4-carboxylate

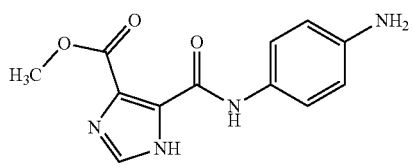 [SMILES: COC(=O)c1nc[nH]c1C(=O)Nc1ccc(N)cc1]

To a mixture of 257 mg (2.301 mmol) benzene-1,4-diamine in 13 mL dichloromethane, 350 mg (1.150 mmol) dimethyl 5,10-dioxo-5H,10H-diimidazo[1,5-a:1',5'-d]pyrazine-1,6-dicarboxylate [described in WO2006/58630 A1, Page 34-35] and 0.32 mL (2.301 mmol) triethylamine were subsequently added and the mixture was stirred for 3 h at 40° C. The reaction mixture was then concentrated in vacuo and the residue was purified by flash column chromatography (dichloromethan/methanol-gradient) to give the crude product which was further purified by flash column chromatography (dichloromethane/2-propanol-gradient) to give 281 mg of the title compound as a solid material.

LC-MS (Method 5): $R_t$=0.49 min; MS (ESIpos) m/z=261 [M+H]$^+$.

Intermediate 016

$N^5$-(6-aminopyridin-3-yl)-$N^4$-methyl-1H-imidazole-4,5-dicarboxamide

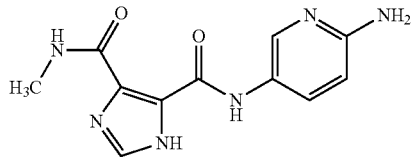 [SMILES: CNC(=O)c1nc[nH]c1C(=O)Nc1ccc(N)nc1]

To a mixture of 152 mg (1.390 mmol) pyridine-2,5-diamine in 8 mL dichloromethane, 300 mg (70% pure, 0.70 mmol) N,N'-dimethyl-5,10-dioxo-5H,10H-diimidazo[1,5-a: 1',5'-d]pyrazine-1,6-dicarboxamide (Intermediate 002) and 0.19 mL (1.390 mmol) triethylamine were subsequently added and the mixture was stirred for 3 h at 40° C. The reaction mixture was then concentrated in vacuo and the residue was washed with methanol to give 165 mg of the title compound as a solid material which was used without further purification.

LCMS (Method 5): $R_t$=0.48 min; MS (ESIpos) m/z=261 [M+H]$^+$.

Intermediate 017

N-(4-aminophenyl)-4-fluorobenzamide

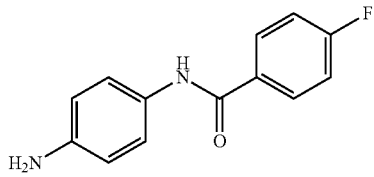 [SMILES: Nc1ccc(NC(=O)c2ccc(F)cc2)cc1]

Step 1: To 10 g (48 mmol) tert-butyl (4-aminophenyl) carbamate in 80 mL DMF were added 21.7 mL (125 mmol) N-ethyl-N-isopropylpropan-2-amine, 7.74 g (55.2 mmol) 4-fluoro-benzoic acid and 34.3 mL (57.6 mmol) of a 50% solution of 2,4,6-tripropyl-1,3,5,2,4,6-trioxatriphosphinane 2,4,6-trioxide in DMF. The resulting mixture was stirred for 20 h at room temperature.

The mixture was poured into water. The precipitate was filtered off, washed with water and lyophilized. The BOC-protected title compound was obtained as a crude product which was used in step 2 without further purification.

Step 2: To the crude material from step 1 in 300 mL dichloromethane were added 150 mL trifluoro acetic acid. The mixture was stirred for 30 min at room temperature.

Water was added. 150 mL of a 25% aqueous ammonia solution were added. The obtained solution was extracted with dichloromethane. The organic layer was dried over sodium sulfate to give 9.9 g of the title compound as solid material.

$^1$H-NMR (300 MHz, DMSO-d$_6$): δ [ppm]=9.87 (s, 1H), 7.98 (dd, 2H), 7.38-7.28 (m, 4H), 6.53 (d, 2H), 4.99 (br. s., 2H).

LCMS (Method 2): R$_t$=0.69 min; MS (ESIpos) m/z=231 [M+H]$^+$.

Intermediate 018

N,N'-bis{4-[(4-fluorobenzoyl)amino]phenyl}-5,10-dioxo-5H,10H-diimidazo[1,5-a:1',5'-d]pyrazine-1,6-dicarboxamide To 62 mg (0.2 mmol) 5,10-dioxo-5H,10H-diimidazo[1,5-a; 1',5'-d]pyrazin-1,6-dicarbonyl-dichloride (Intermediate 001) in 3 ml THF were added 96 mg (0.4 mmol) N-(4-aminophenyl)-4-fluorobenzamide (Intermediate 017) and 84 μL (0.6 mmol) triethylamine. The resulting mixture was stirred for 30 min at room temperature.

The obtained reaction mixture was used without workup in the next reaction.

Intermediate 019 dimethyl 5,10-dioxo-5H,10H-diimidazo[1,5-a:1',5'-d]pyrazine-1,6-dicarboxylate

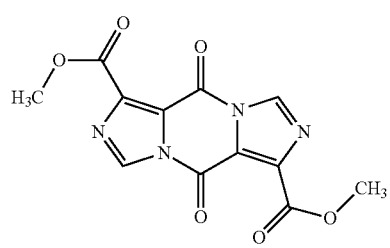

2.00 g (crude product) of 5,10-dioxo-5H,10H-diimidazo[1,5-a:1',5'-d]pyrazine-1,6-dicarbonyl dichloride (Intermediate 001) were suspended in 10 mL methanol. The resulting mixture was stirred for 3 h at room temperature. The precipitate was filtered off and washed with methanol. The obtained solid material was dried under vacuum at 50° C. to give 1.98 g of the title compound as a crude product which was used without further purification in the subsequent steps.

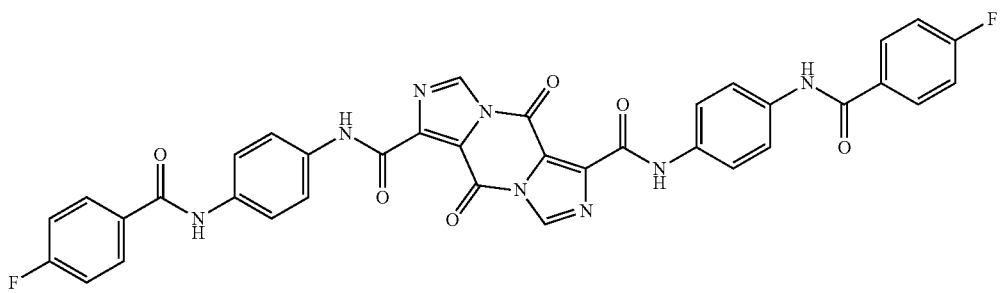 [SMILES: O=C(Nc1ccc(NC(=O)c2ncn3c(=O)c4c(C(=O)Nc5ccc(NC(=O)c6ccc(F)cc6)cc5)ncn4c(=O)c23)cc1)c1ccc(F)cc1]

Intermediate 020 diphenyl 5,10-dioxo-5H,10H-diimidazo[1,5-a:1',5'-d]pyrazine-1,6-dicarboxylate

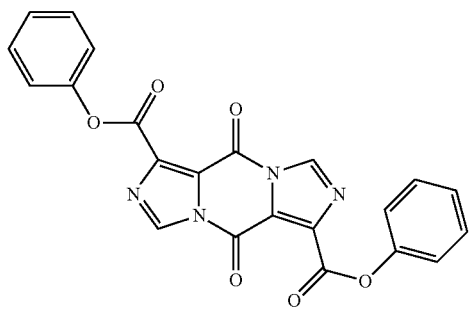 [SMILES: O=C(Oc1ccccc1)c1ncn2c(=O)c3c(C(=O)Oc4ccccc4)ncn3c(=O)c12]

20.0 g (crude product) of 5,10-dioxo-5H,10H-diimidazo[1,5-a:1',5'-d]pyrazine-1,6-dicarbonyl dichloride (Intermediate 001) and 12.6 g (0.13 mol) phenol were suspended in 380 mL dichloromethane. The resulting mixture was cooled to 0° C. and 10.8 mL (0.13 mol) pyridine were added dropwise. The reaction was stirred for 3 h at room temperature. The precipitate was filtered off and washed with dichloromethane. The obtained solid material was dried under vacuum at 50° C. to give 21.6 g of the title compound as a crude product which was used without further purification in the subsequent steps.

Intermediate 021 phenyl-5-({4-[(2-chloro-4-fluorobenzoyl)amino]phenyl}carbamoyl)-1H-imidazole-4-carboxylate

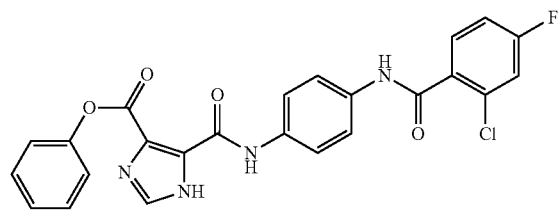 [SMILES: O=C(Nc1ccc(NC(=O)c2[nH]cnc2C(=O)Oc2ccccc2)cc1)c1ccc(F)cc1Cl]

To a suspension of 476 mg (1.80 mmol) N-(4-aminophenyl)-2-chloro-4-fluorobenzamide (Intermediate 004) and 385 mg (0.90 mmol) diphenyl 5,10-dioxo-5H,10H-diimidazo[1,5-a:1',5'-d]pyrazine-1,6-dicarboxylate (Intermediate 020) in 30 mL tetrahydrofuran were added 0.75 mL (5.40 mmol) triethylamine. The mixture was stirred for 2 h at 50° C. The reaction mixture was divided in six portions and each portion was used without further purification in the subsequent steps.

LCMS (Method 1): $R_t$=1.15 min; MS (ESIpos) m/z=478.8 [M+H]$^+$.

Intermediate 022 phenyl 5-({4-[(2-chloro-4,5-difluorobenzoyl)amino]phenyl}carbamoyl)-1H-imidazole-4-carboxylate

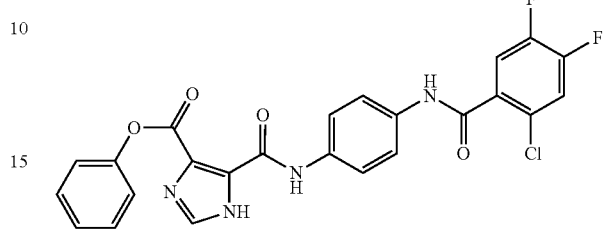

To a suspension of 1.13 g (4.00 mmol) N-(4-aminophenyl)-2-chloro-4,5-difluorobenzamide (Intermediate 004) and 856 mg (2.00 mmol) diphenyl 5,10-dioxo-5H,10H-diimidazo[1,5-a:1',5'-d]pyrazine-1,6-dicarboxylate (Intermediate 020) in 50 mL tetrahydrofuran were added 1.67 mL (12.0 mmol) triethylamine. The mixture was stirred for 2 h at 50° C. The reaction mixture was divided in ten portions and each portion was used without further purification in the subsequent steps.

LCMS (Method 1): $R_t$=0.95 min; MS (ESIpos) m/z=497.1 [M+H]$^+$.

Intermediate 023

3,8-dimethyl-5,10-dioxo-5H,10H-diimidazo[1,5-a:1',5'-d]pyrazine-1,6-dicarbonyl dichloride

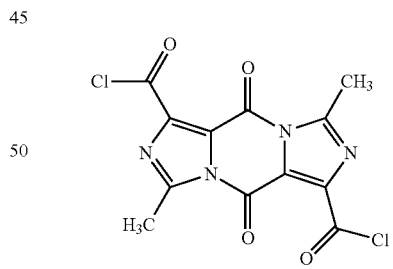

To 128 mg (0.75 mmol) of 5 2-methyl-1H-imidazole-4,5-dicarboxylic acid suspended in 1.5 mL chloroform were added 1.50 mL (20.7 mmol) thionylchloride and 1 µL DMF. The resulting mixture was stirred for 20 minutes at 65° C. and 2 hours at 75° C. The reaction mixture was concentrated under reduced pressure to give the title compound as a crude product which was used without further purification in the subsequent steps.

Intermediate 024

2-ethyl-1H-benzimidazole

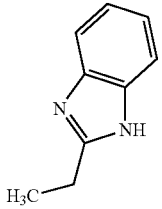

To a suspension of 5.50 g (50.8 mmol) benzol-1,2-diamine in 8 mL (107.2 mmol) propionic acid were added 0.1 mL (1.8 mmol) sulphuric acid (96% ig). The resulting mixture was warmed to 200° C. and stirred for 3 hours to distil off the volatile components. After cooling down to room temperature 50 mL water were added. The precipitate was filtered off and was recrystallised from 20 ml methanol and 40 mL water to give 4.20 g of the title compound as a solid material LC-MS (Method 6): $R_t$=0.32 min; MS (ESIpos) m/z=147 [M+H]$^+$.

Intermediate 025

2-ethyl-1H-imidazole-4,5-dicarboxylic acid

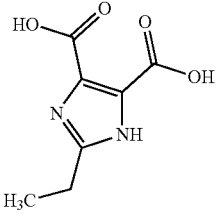

To 4.00 g (50.8 mmol) 2-ethyl-1H-benzimidazole (Intermediate 024) were added 60 mL sulphuric acid (96% ig). The resulting mixture was cooled down with an icebad and 20 mL of hydrogenperoxide solution (35%) were added dropwise. The resulting mixture was warmed to 120° C. and was stirred for 3 hours. After cooling down with an icebad 500 mL icewater were added in portions. The precipitate was filtered off and was washed five times with 10 mL water. The precipitate was dried in vacuo to give 3.86 g of the title compound as a solid material $^1$H-NMR (300 MHz, DMSO-d$_6$), δ [ppm]=1.27 (t, 3H), 2.81-2.88 (q, 2H).

LC-MS (Method 6): $R_t$=0.20 min; MS (ESIpos) m/z=185.3 [M+H]$^+$.

Intermediate 026

3,8-diethyl-5,10-dioxo-5H,10H-diimidazo[1,5-a:1',5'-d]pyrazine-1,6-dicarbonyl dichloride

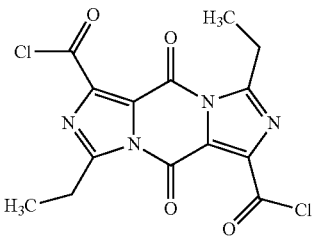 [SMILES: CCc1nc(C(=O)Cl)c2c(=O)n3c(CC)nc(C(=O)Cl)c3c(=O)n12]

To 185 mg (1.00 mmol) of 2-ethyl-1H-imidazole-4,5-dicarboxylic acid (Intermediate 025) suspended in 1.5 mL chloroform were added 1.50 mL (20.7 mmol) thionylchloride and 2 µL DMF. The resulting mixture was stirred for 20 minutes at 65° C. and 2 hours at 75° C. The reaction mixture was concentrated in vacuo to give the title compound as a crude product which was used without further purification in the subsequent steps.

Intermediate 027 methyl 5-[(4-{[2-chloro-4-(methylsulfonyl)benzoyl]amino}phenyl)carbamoyl]-1H-imidazole-4-carboxylate To 1.59 g (6.76 mmol) 2-chloro-4-(methylsulfonyl)benzoic acid in 160 mL DMF were added 2.57 g (6.76 mmol) HATU and 3.21 mL N,N-diisopropylethylamine. After stirring for 5 minutes 1.60 g (6.15 mmol) methyl 5-[(4-aminophenyl)carbamoyl]-1H-imidazole-4-carboxylate (Intermediate 015) were added and the mixture was stirred for 4 hours at room temperature. The reaction was poured into water and the aqueous solution was extracted three times with DCM/2-propanole (8:2). The combined organic layers were washed with sat. sodium carbonate solution and sat. sodium chloride-solution. The organic phase was dried over sodium sulphate, and the solvent was removed under reduced pressure to afford the crude material which was triturated in methanol to give 2.25 g (93% ig) of the title compound as solid material.

LCMS (Method 5) (: $R_t$=0.69 min; MS (ESIpos) m/z=477.0 [M+H]$^+$.

Intermediate 028 methyl 5-({4-[(4-fluoro-2-iodobenzoyl)amino]phenyl}carbamoyl)-1H-imidazole-4-carboxylate

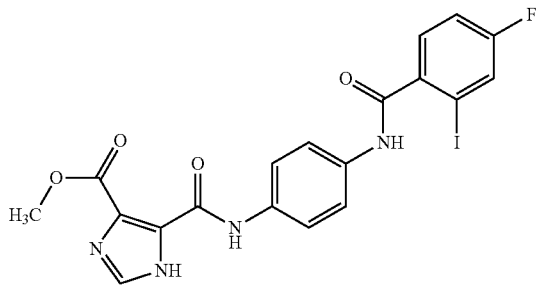 [SMILES: COC(=O)c1nc[nH]c1C(=O)Nc1ccc(NC(=O)c2ccc(F)cc2I)cc1]

To 341 mg (1.24 mmol) 4-fluoro-2-iodobenzoic acid in 10 mL DMF were added 472 mg (1.24 mmol) HATU and 590 µL (3.40 mmol) N,N-diisopropylethylamine. After stirring for 5 minutes 300 mg (1.13 mmol) methyl 5-[(4-aminophenyl)carbamoyl]-1H-imidazole-4-carboxylate (Intermediate 015) were added and the mixture was stirred for 8 hours at room temperature. The reaction was poured into water and the aqueous solution was extracted three times with DCM/2-propanole (8:2). The combined organic layers were washed with sat. sodium carbonate solution and sat. sodiumchloride solution. The organic phase was dried over sodium sulphate, and the solvent was removed under reduced pressure to afford the crude material which was purified by flash column chromatography to give 518 mg of the title compound as a solid material.

Intermediate 029 methyl 5-[(4-{[2-bromo-5-(trifluoromethoxy)benzoyl]amino}phenyl)carbamoyl]-1H-imidazole-4-carboxylate

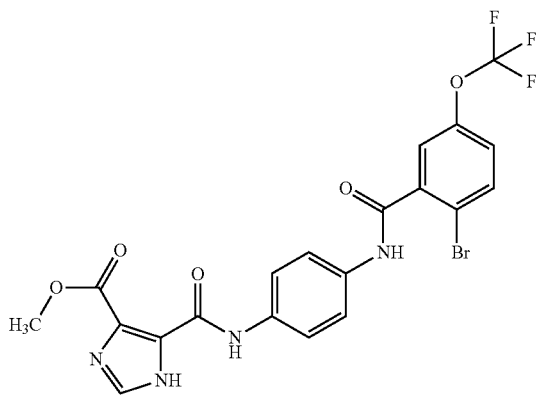 [SMILES: COC(=O)c1nc[nH]c1C(=O)Nc1ccc(NC(=O)c2cc(OC(F)(F)F)ccc2Br)cc1]

To 365 mg (1.24 mmol) 2-bromo-5-(trifluoromethoxy)benzoic acid in 10 mL DMF were added 472 mg (1.24 mmol) HATU and 590 µL (3.40 mmol) N,N-diisopropylethylamine. After stirring for 5 minutes 300 mg (1.13 mmol) methyl 5-[(4-aminophenyl)carbamoyl]-1H-imidazole-4-carboxylate (Intermediate 015) were added and the mixture was stirred for 8 hours at room temperature. The reaction was poured into water and the aqueous solution was extracted three times with DCM/2-propanole (8:2). The combined organic layers were washed with sat. sodium carbonate solution and sat. sodiumchloride solution. The organic phase was dried over sodium sulphate, and the solvent was removed under reduced pressure to afford the crude material which was purified by flash column chromatography to give 584 mg of the title compound as a solid material.

LC-MS (Method 5): $R_t$=0.95 min; MS (ESIpos) m/z=528.8 [M+H]$^+$.

Intermediate 030 methyl 5-[(3-fluoro-4-nitrophenyl)carbamoyl]-1H-imidazole-4-carboxylate

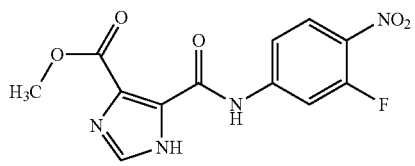 [SMILES: COC(=O)c1nc[nH]c1C(=O)Nc1ccc([N+](=O)[O-])c(F)c1]

Step A:
To 1.81 g (5.77 mmol) of 5,10-dioxo-5H,10H-diimidazo[1,5-a:1',5'-d]pyrazine-1,6-dicarbonyl dichloride (Intermediate 001) in 18 mL THF were added dropwise 1.80 g (11.53 mmol) 3-fluoro-4-nitroaniline and 2.21 mL N,N-diisopropylethylamine. The resulting mixture was stirred for 30 minutes at room temperature under an argon atmosphere.
Step B
2 mL methanol were added to the mixture and the reaction was stirred for 1 hour at 70° C. The precipitate was filtered off and was washed three times with methanol (3 mL). The obtained solid material was dried in vacuo to give 3.20 g of the title compound.

$^1$H-NMR (300 MHz, DMSO-d$_6$), δ [ppm]=13.72 (s, 1H), 12.12 (s, 1H), 8.22 (t, 1H), 8.04-7.96 (m, 2H), 7.58 (s, 1H), 3.89 (s, 3H).

LC-MS (Method 6): $R_t$=3.35 min; MS (ESIpos) m/z=309.2 [M+H]$^+$.

Intermediate 031 methyl 5-[(4-amino-3-fluorophenyl)carbamoyl]-1H-imidazole-4-carboxylate

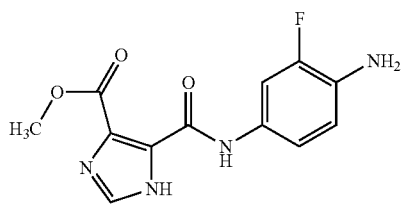 [SMILES: COC(=O)c1nc[nH]c1C(=O)Nc1ccc(N)c(F)c1]

To a solution of 3.41 g (11.06 mmol) methyl 5-[(3-fluoro-4-nitrophenyl)carbamoyl]-1H-imidazole-4-carboxylate (Intermediate 030) in 40 mL dichloromethane and 20 mL ethylacetate were added 1.00 g palladium on charcoal (10% w/w) and the mixture was stirred under an hydrogen atmosphere (4 bar) for 2 h at room temperature and 1 hour at 4.5 bar. The solids were filtered off washed four times with tetrahydrofuran (15 mL) and the combined filtrate was concentrated in vacuo to give 2.89 g of the title compound as a solid material which was used without further purification.

¹H-NMR (300 MHz, DMSO-d₆), δ [ppm]=13.54 (s, 1H), 11.69 (s, 1H), 7.89 (s, 1H), 7.63-7.51 (d, 1H), 7.08-6.99 (m, 1H), 6.79 (t, 1H), 5.05 (s, 1H), 3.91 (s, 3H).

LC-MS (Method 6): $R_t$=2.65 min; MS (ESIpos) m/z=279.3 [M+H]⁺.

Intermediate 032 methyl 5-[(3-methyl-4-nitrophenyl)carbamoyl]-1H-imidazole-4-carboxylate

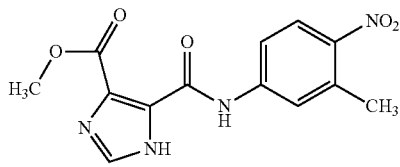 [SMILES: COC(=O)c1nc[nH]c1C(=O)Nc1ccc([N+](=O)[O-])c(C)c1]

Step A:

To 1.50 g (4.79 mmol) 5,10-dioxo-5H,10H-diimidazo[1,5-a:1',5'-d]pyrazine-1,6-dicarbonyl dichloride (Intermediate 001) in 15 mL tetrahydrofuran were added dropwise 1.32 g (9.58 mmol) 3-methyl-4-nitroaniline and 1.84 mL N,N-diisopropylethylamine. The resulting mixture was stirred for 1 hour at room temperature under an argon atmosphere.

Step B:

5 mL methanol were added to the mixture and the reaction was stirred for 1 hour at 70° C. The precipitate was filtered off and washed with three times with methanol (3 mL). The obtained solid material was dried under vacuum to give 2.39 g of the title compound.

LC-MS (Method 6): $R_t$=3.50 min; MS (ESIpos) m/z=305.3 [M+H]⁺.

Intermediate 033 methyl 5-[(4-amino-3-methylphenyl)carbamoyl]-1H-imidazole-4-carboxylate

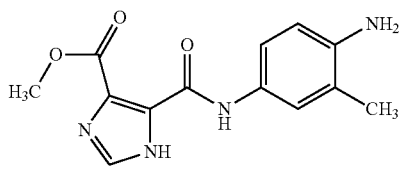

To 2.39 g (7.85 mmol) methyl 5-[(3-methyl-4-nitrophenyl)carbamoyl]-1H-imidazole-4-carboxylate (Intermediate 032) in 40 mL dichloromethane and 20 mL ethylacetate were added 750 mg palladium on charcoal (10% w/w) and the mixture was stirred under hydrogen atmosphere (4 bar) for 2 h at room temperature. The solids were filtered off and washed with tetrahydrofuran/methanol (3:1, 1 L). The combined filtrate was concentrated under reduced pressure to give 1.90 g of the title compound as a solid material which was used without further purification.

LC-MS (Method 6): $R_t$=2.17 min; MS (ESIpos) m/z=275.3 [M+H]⁺.

Intermediate 034 tert-butyl (2-methoxy-4-nitrophenyl)carbamate

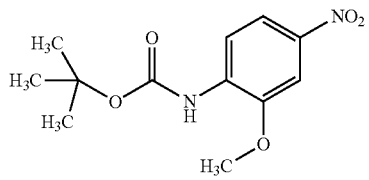 [SMILES: COc1cc([N+](=O)[O-])ccc1NC(=O)OC(C)(C)C]

To a suspension of 15.0 g (89.2 mmol) 2-methoxy-4-nitroaniline in 150 mL dichloromethan were added 20.4 g (93.5 mmol) di-tert-butyldicarbonate and 30 mg (0.2 mmol) 4-methylaminopyridine and the mixture was refluxed for 2 hours. The reaction mixture was concentrated in vacuo and the residue was purified by flash column chromatography (dichloromethane/cyclohexane) to give 11.6 g of the title compound as a solid material.

LC-MS (Method 6): $R_t$=3.80 min; MS (ESIpos) m/z=267.2 [M+H]⁺.

Intermediate 035 methyl 4-({4-[(tert-butoxycarbonyl)amino]-3-methoxyphenyl}carbamoyl)-1H-imidazole-5-carboxylate

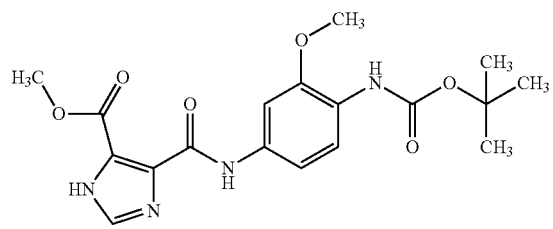 [SMILES: COC(=O)c1[nH]cnc1C(=O)Nc1ccc(NC(=O)OC(C)(C)C)c(OC)c1]

Step A:

To a solution of 11.5 g (42.9 mmol) tert-butyl (2-methoxy-4-nitrophenyl)carbamate (Intermediate 034) in 170 mL ethylacetate were added 1.70 g palladium on charcoal (10% w/w) and the mixture was stirred under an hydrogen atmosphere (3 bar) for 1 h at room temperature. The solids were filtered off and washed three times with ethylacetate (30 mL). The filtrate was used without further purification.

Step B:

6.60 g (21.1 mmol) of 5,10-dioxo-5H,10H-diimidazo[1,5-a:1',5'-d]pyrazine-1,6-dicarbonyl dichloride (Intermediate 001) and 10 mL (57.4 mmol) N,N-diisopropylethylamine were added and the resulting mixture was stirred for 1 hour at room temperature. The reaction mixture was concentrated under reduced pressure to give the crude product as a solid material which was used without further purification.

Step C:

To the residue of step B were added 200 mL tetrahydrofuran and 50 mL methanol and the mixture was refluxed for 1 hour. 400 ml trichloromethane were added and the suspension was filtered through a pad of celite. The filtrate was concentrated under reduced pressure and the residue was suspended in 100 mL methanol. The precipitate was filtered off to give after washing with methanol (three times, 10 mL) and drying under vacuum 10.3 g of the title compound as a solid material.

LC-MS (Method 6): $R_t$=3.74 min; MS (ESIpos) m/z=391.3 [M+H]$^+$.

Intermediate 036 methyl 4-[(4-amino-3-methoxyphenyl)carbamoyl]-1H-imidazole-5-carboxylate trifluoroacetate

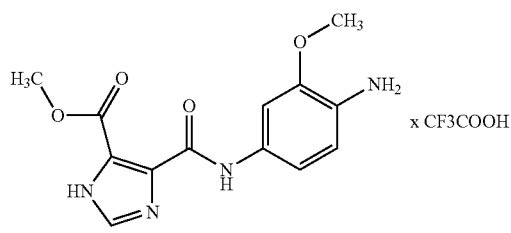 [SMILES: COC(=O)c1[nH]cnc1C(=O)Nc1ccc(N)c(OC)c1]

To a suspension of 10.3 g (26.4 mmol) methyl 4-({4-[(tert-butoxycarbonyl)amino]-3-methoxyphenyl}carbamoyl)-1H-imidazole-5-carboxylate (Intermediate 035) in 50 mL dichloromethane were added 25 mL (324 mmol) trifluoroacetic acid and the mixture was stirred for 3 hours at room temperature. The reaction was concentrated under reduced pressure and the residue was suspended in 200 mL diethylether and stirred for 1 hour. The precipitate was filtered off to give after washing with diethylether (three times, 25 mL) and drying under vacuum 10.6 g of the title compound as a solid material.

LC-MS (Method 6): $R_t$=2.14 min; MS (ESIpos) m/z=291.3 [M+H]$^+$.

Intermediate 037 methyl 4-[(4-amino-3-methoxyphenyl)carbamoyl]-1H-imidazole-5-carboxylate

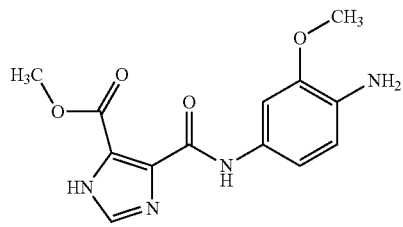 [SMILES: COC(=O)c1[nH]cnc1C(=O)Nc1ccc(N)c(OC)c1]

To 5.00 g (12.4 mmol) 2-methoxy-4-({[5-(methoxycarbonyl)-1H-imidazol-4-yl]carbonyl}amino) anilinium trifluoroacetate (Intermediate 036) were added 200 mL chloroform and 300 mL of a saturated sodiumbicarbonate-solution. The phases were separated and the aqueous phase was extracted four times with 400 mL chloroform/methanol (98:2). The combined organic phases were washed with 20 mL of a saturated sodium chloride solution. The organic layer was dried over sodium sulfate and the solution was concentrated in vacuo. After standing at 0° C. overnight the resulting precipitate was filtered off. The solid was washed twice with methanol (5 mL) to give after drying under vacuum 2.76 g of the title compound as a solid material.

$^1$H-NMR (400 MHz, DMSO-d$_6$): δ [ppm]=13.47 (s, 1H), 11.61 (s, 1H), 7.89 (s, 1H), 7.31 (m, 1H), 6.96 (m, 1H), 6.64 (m, 1H), 4.66 (s, 2H), 3.91 (s, 3H), 3.78 (s, 3H).

LC-MS (Method 6): $R_t$=2.18 min; MS (ESIpos) m/z=291.3 [M+H]$^+$.

Intermediate 038

2-isopropyl-1H-benzimidazole

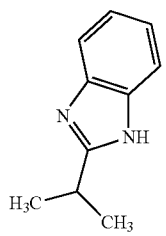

To a suspension of 5.50 g (50.8 mmol) benzol-1,2-diamine in 50 mL toluene were added 5.5 mL (1.8 mmol) 2-methylpropanal. The resulting mixture was stirred for 18 hours at room temperature in an open flask. The precipitate was filtered off and the solid was washed three times with toluene (10 mL) to give after drying under vacuum 6.50 g of the title compound as a solid material.

LC-MS (Method 6): $R_t$=0.41 min; MS (ESIpos) m/z=161 [M+H]$^+$.

Intermediate 039

2-isopropyl-1H-imidazole-4,5-dicarboxylic acid

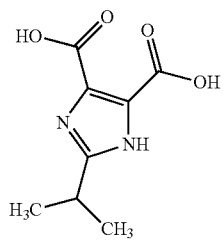

To 4.40 g (27.5 mmol) 2-isopropyl-1H-benzimidazole (Intermediate 038) were added 60 mL sulphuric acid (96% ig). The resulting mixture was cooled down with an icebad and 20 mL of a hydrogenperoxide solution (35%) were added dropwise. The resulting mixture was warmed to 120° C. and the reaction was stirred for 3 hours. After cooling down with an icebad 500 mL icewater were added in portions. The precipitate was filtered off and washed five times with 10 mL water. The precipitate was dried in vacuo to give 1.12 g of the title compound as a solid material

Intermediate 040

3,8-diisopropyl-5,10-dioxo-5H,10H-diimidazo[1,5-a:1',5'-d]pyrazine-1,6-dicarbonyl dichloride

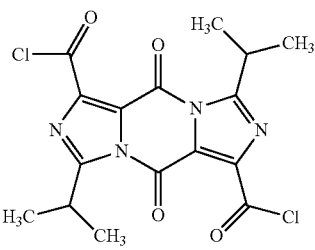 [SMILES: CC(C)c1nc(C(=O)Cl)c2c(=O)n3c(C(C)C)nc(C(=O)Cl)c3c(=O)n12]

To 149 mg (1.00 mmol) of 2-isopropyl-1H-imidazole-4,5-dicarboxylic acid (Intermediate 039) suspended in 1.5 mL chloroform were added 1.50 mL (20.7 mmol) thionylchloride and 1 μL DMF. The resulting mixture was stirred for 3 hours at 75° C. The reaction mixture was concentrated in vacuo to give the title compound as a crude product which was used without further purification in the subsequent steps.

Intermediate 041 methyl 5-[(6-nitropyridin-3-yl)carbamoyl]-1H-imidazole-4-carboxylate

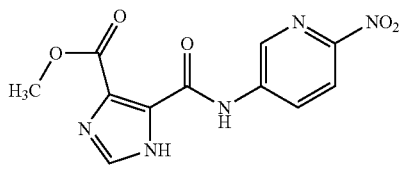 [SMILES: COC(=O)c1nc[nH]c1C(=O)Nc1ccc([N+](=O)[O-])nc1]

Step A:

To a solution of 3.50 g (11.2 mmol) 5,10-dioxo-5H,10H-diimidazo[1,5-a:1',5'-d]pyrazine-1,6-dicarbonyl dichloride (Intermediate 001) in 60 mL THE were added 3.10 g (22.4 mmol) 6-nitropyridin-3-amine and 5.00 mL N,N-diisopropylethylamine. The resulting mixture was stirred for 1 hour at room temperature under an argon atmosphere.

Step B 10 mL methanol were added to the mixture and the reaction was refluxed for 1 hour. After cooling down to room temperature the precipitate was filtered off and the solid was washed three times with methanol (25 mL) and diethylether. The obtained solid material was dried under vacuum to give 5.12 g of the title compound.

LC-MS (Method 6): $R_t$=2.90 min; MS (ESIpos) m/z=292.0 [M+H]$^+$.

Intermediate 042 methyl 5-[(6-aminopyridin-3-yl)carbamoyl]-1H-imidazole-4-carboxylate

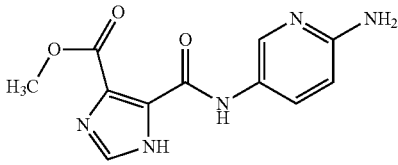

To a solution of 5.00 g (17.1 mmol) methyl 5-[(6-nitropyridin-3-yl)carbamoyl]-1H-imidazole-4-carboxylate (Intermediate 041) in 200 mL dichloromethane/methanol (1:1) and 5 mL trifluoroacetic acid were added 1.00 g palladium on charcoal (10% w/w). The mixture was stirred under a hydrogen atmosphere (3 bar) for 19 hours at room temperature. The solids were filtered off and were washed three times with methanol (20 mL). The combined filtrate was concentrated in vacuo and the residue was treated with 80 mL saturated sodiuchloride solution and 20 mL saturated sodiumbicarbonate solution. The mixture was extracted three times with tetrahydrofuran (250 mL) and the combined organic phases were dried over sodium sulphate. The solvent was removed under reduced pressure to give 2.30 g (89% ig) of the title compound as solid material.

LC-MS (Method 6): $R_t$=1.30 min; MS (ESIpos) m/z=262.3 [M+H]$^+$.

Intermediate 043 methyl 5-({6-[(2-chloro-4-fluorobenzoyl)amino]pyridin-3-yl}carbamoyl)-1H-imidazole-4-carboxylate

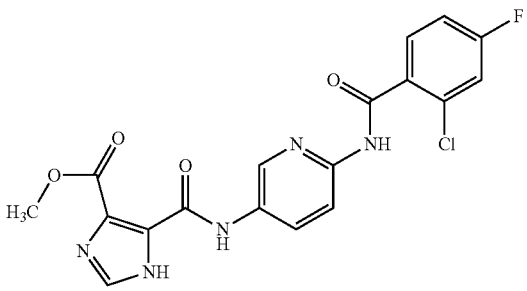 [SMILES: COC(=O)c1nc[nH]c1C(=O)Nc1ccc(NC(=O)c2ccc(F)cc2Cl)nc1]

496 mg (1.90 mmol) methyl 5-[(6-aminopyridin-3-yl)carbamoyl]-1H-imidazole-4-carboxylate (Intermediate 42) and 1.65 mL (9.5 mmol) N-ethyl-N,N-diisopropylamine were suspended in 300 mL tetrahydrofuran. During 30 minutes 279 μL (2.09 mmol) 2-chloro-4-fluorobenzoyl chloride diluted in 5 mL were added dropwise at 50° C. and the mixture was stirred at 50° C. for 1 hour. The solvent was removed under reduced pressure and 20 mL water were added to the residue. The precipitate was filtered off and the solid was washed with water and methanol to give after drying under vacuum 600 mg of the title compound as a solid material (contains 20% of the bisacylated product).

$^1$H-NMR (400 MHz, DMSO-d$_6$), δ [ppm]=13.6 (s, 1H), 11.05 (s, 1H), 8.74-8.66 (m, 1H), 8.29-8.13 (m, 2H), 7.96 (s, 1H), 7.67-7.63 (m, 1H), 7.57-7.50 (m, 1H), 7.35-7.20 (m, 1H), 3.91 (s, 3H).

LC-MS (Method 6): $R_t$=3.44 min; MS (ESIpos) m/z=418.2 [M+H]$^+$.

Intermediate 044 methyl 5-({6-[(4-fluorobenzoyl)amino]pyridin-3-yl}carbamoyl)-1H-imidazole-4-carboxylate

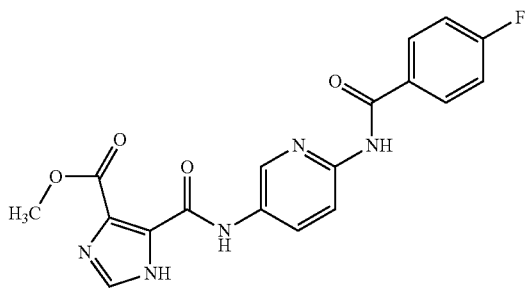 [SMILES: COC(=O)c1nc[nH]c1C(=O)Nc1ccc(NC(=O)c2ccc(F)cc2)nc1]

714 mg (2.70 mmol) methyl 5-[(6-aminopyridin-3-yl)carbamoyl]-1H-imidazole-4-carboxylate (Intermediate 042) and 2.50 mL (13.6 mmol) N-ethyl-N,N-diisopropylamine were suspended in 400 mL dry tetrahydrofuran. During 30 minutes 335 µL (3.00 mmol) 4-fluorobenzoyl chloride diluted in 5 mL tetrahydrofuran were added dropwise at 50° C. and the mixture was stirred at 50° C. for 1 hour. 120 µL (1.00 mmol) 4-fluorobenzoyl chloride diluted with 4 mL tetrahydrofuran were added dropwise over a period of 30 minutes and the mixture was stirred for 2 hours at 50° C. The solvent was removed under reduced pressure and 20 mL water were added to the residue. The precipitate was filtered off and the solid was washed with water and methanol to give 803 mg of the title compound as a solid material (contains 20% of the bisacylated product).

$^1$H-NMR (400 MHz, DMSO-d$_6$), δ [ppm]=13.6 (s, 1H), 11.9 (s, 1H), 10.9 (s, 1H), 8.74 (s, 1H), 8.24-8.09 (m, 4H), 7.96 (s, 1H), 7.37-7.27 (m, 2H), 3.91 (s, 3H).

LC-MS (Method 6): $R_t$=3.44 min; MS (ESIpos) m/z=384.2 [M+H]$^+$.

Intermediate 045 methyl 5-({4-[(2-chloro-4,6-difluorobenzoyl)amino]phenyl}carbamoyl)-1H-imidazole-4-carboxylate

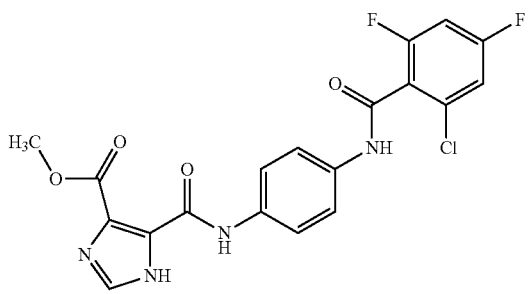 [SMILES: COC(=O)c1nc[nH]c1C(=O)Nc1ccc(NC(=O)c2c(F)cc(F)cc2Cl)cc1]

To 227 mg (1.18 mmol) 2-chloro-4,6-difluorobenzoic acid in 20 mL DMF were added 448 mg (1.18 mmol) HATU and 560 µL N,N-diisopropylethylamine. After stirring for 5 minutes 300 mg (1.07 mmol) methyl 5-[(4-aminophenyl)carbamoyl]-1H-imidazole-4-carboxylate (Intermediate 015) were added and the mixture was stirred for 24 hours at room temperature. The reaction was poured into water and the aqueous solution was extracted three times with DCM/2-propanole (8:2). The combined organic layers were washed with sat. sodium carbonate solution and sat. sodium chloride solution. The organic phase was dried over sodium sulphate, and the solvent was removed under reduced pressure to afford the crude material which was triturated in diethylether to give 450 mg of the title compound as solid material.

LCMS (Method 4): $R_t$=1.01 min; MS (ESIpos) m/z=435.1 [M+H]$^+$.

Intermediate 047

5-({4-[(2-chlorobenzoyl)amino]phenyl}carbamoyl)-1H-imidazole-4-carboxylic acid

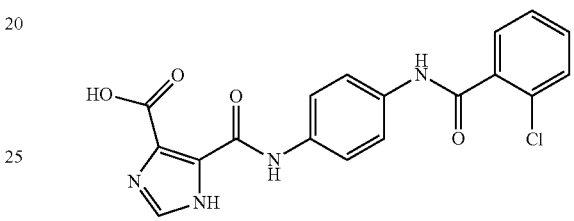

Step 1:
To a solution of 234 mg (2.00 mmol) tert-butyl carbamate in 10 mL tetrahydrofuran were added 871 µL (5 mmol) N,N diisopropylethyl amine and 447 mg (1 mmol 70% ig) of the crude 5,10-dioxo-5H,10H-diimidazo[1,5-a:1',5'-d]pyrazine-1,6-dicarbonyl dichloride (Intermediate 001). The resulting mixture was stirred for 5 h at room temperature. The reaction mixture was divided in two portions and each portion was used without further purification in the subsequent steps.
Step 2:
To the crude reaction mixture was added 378 mg (1.53 mmol) N-(4-aminophenyl)-2-chloro-benzamide (Intermediate 51) and the mixture was stirred for 30 minutes. The precipitate was filtered off and the obtained solution was purified by HPLC chromatography to give 77 mg of the title compound as a solid material.

LC-MS (Method 5): $R_t$=0.54 min; MS (ESIpos) m/z=385.1 [M+H]$^+$.

Intermediate 048

5-({4-[(2-chloro-4-fluorobenzoyl)amino]phenyl}carbamoyl)-1H-imidazole-4-carboxylic acid

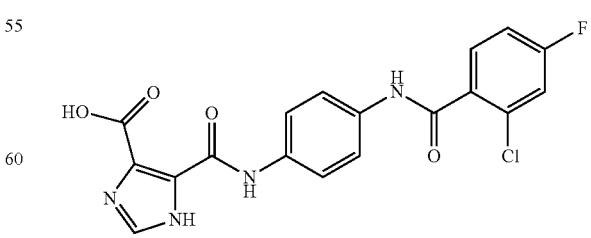

Step 1:
To a solution of 234 mg (2.00 mmol) tert-butyl carbamate in 10 mL tetrahydrofuran were added 871 µL (5 mmol) N,N diisopropylethyl amine and 447 mg (1 mmol 70% ig) of the crude 5,10-dioxo-5H,10H-diimidazo[1,5-a:1',5'-d]pyrazine-1,6-dicarbonyl dichloride (Intermediate 001). The resulting mixture was stirred for 5 h at room temperature. The reaction mixture was divided in two portions and each portion was used without further purification in the subsequent steps.

Step 2:

To the crude reaction mixture was added 265 mg (1 mmol) N-(4-aminophenyl)-2-chloro-4-fluorobenzamide (Intermediate 004) and the mixture was stirred for 30 minutes. The solvent was removed under reduced pressure and the residue was suspended in 10 mL of 4 M solution of HCl in dioxane. The mixture was stirred for 90 minutes. The reaction mixture was concentrated under reduced pressure and the residue was purified by flash column chromatography to give 274 mg of the title compound as a solid material.

LCMS (Method 5): $R_t$=0.56 min; MS (ESIpos) m/z=403.1 [M+H]$^+$.

Intermediate 049

2-chloro-4-hydroxybenzoyl chloride

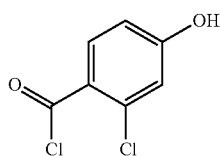 [SMILES: O=C(Cl)c1ccc(O)cc1Cl]

To a solution of 1.30 g (7.38 mmol) 2-chloro-4-hydroxybenzoic acid in 15 mL dry dichloromethane, were added two drops of DMF and 9.23 mL (18.45 mmol) oxalylchloride (2M solution in dichloromethane) under an argon atmosphere. After stirring for 3 hours at 40° C. the reaction mixture was concentrated in vacuo to give the title compound which was used without further purification.

Intermediate 050

2-chloro-5-hydroxybenzoyl chloride

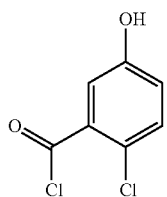 [SMILES: O=C(Cl)c1cc(O)ccc1Cl]

To a solution of 1.00 g (5.80 mmol) 2-chloro-5-hydroxybenzoic acid in 30 mL dry dichloromethane, were added 0.1 mL DMF and 7.24 mL (14.5 mmol) oxalylchloride (2M solution in dichloromethane) under an argon atmosphere. After stirring for 3 hours at 40° C. the reaction mixture was concentrated in vacuo to give 1.15 g of the title compound which was used without further purification.

Intermediate 051

N-(4-aminophenyl)-2-chlorobenzamide

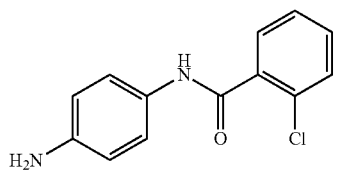 [SMILES: Nc1ccc(NC(=O)c2ccccc2Cl)cc1]

Step 1: To 10.5 g (50.7 mmol) tert-butyl (4-aminophenyl) carbamate in 81 mL DMF were added 22.9 mL (131 mmol) N-ethyl-N-isopropylpropan-2-amine, 9.12 g (58.2 mmol) 2-chloro-benzoic acid and 36.2 mL (60.8 mmol) of a 50% solution of 2,4,6-tripropyl-1,3,5,2,4,6-trioxatriphosphinane 2,4,6-trioxide in DMF. The resulting mixture was stirred for 18 h at room temperature.

The mixture was poured into 350 mL water. The precipitate was filtered off, washed with water and lyophilized. The BOC-protected title compound was obtained as a crude product which was used in step 2 without further purification.

Step 2: To the crude material from step 1 in 238 mL dichloromethane were added 119 mL trifluoro acetic acid. The mixture was stirred for 30 min at room temperature.

Water was added. 170 mL of a 25% aqueous ammonia solution were added. The obtained solution was extracted with dichloromethane and the organic layer was dried over sodium sulfat. The reaction mixture was concentrated under reduced pressure and the residue was purified by flash column chromatography to give 3.98 g of the title compound as a solid material.

$^1$H-NMR (400 MHz, DMSO-d$_6$): δ [ppm]=10.03 (s, 1H), 7.56-7.47 (m, 2H), 7.47-7.40 (m, 2H), 7.34 (d, 2H), 6.52 (d, 2H), 4.92 (s, 2H).

LCMS (Method 1): $R_t$=0.63 min; MS (ESIpos) m/z=246.9 [M+H]$^+$.

Intermediate 052

N,N'-bis{4-[(2-chlorobenzoyl)amino]phenyl}-5,10-dioxo-5H,10H-diimidazo[1,5-a:1',5'-d]pyrazine-1,6-dicarboxamide

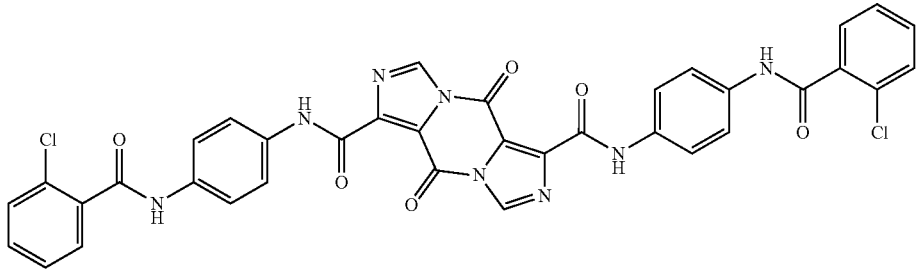 [SMILES: O=C(Nc1ccc(NC(=O)c2ncn3c(=O)c4c(C(=O)Nc5ccc(NC(=O)c6ccccc6Cl)cc5)ncn4c(=O)c23)cc1)c1ccccc1Cl]

To 62 mg (0.2 mmol) 5,10-dioxo-5H,10H-diimidazo[1,5-a; 1',5'-d]pyrazin-1,6-dicarbonyl-dichloride (Intermediate 001) in 3 ml THF were added 103 mg (0.4 mmol) N-(4-aminophenyl)-2-chlorobenzamide (Intermediate 051) and 84 μL (0.6 mmol) triethylamine. The resulting mixture was stirred for 30 min at room temperature.

The obtained reaction mixture was used without workup in the next reaction.

Intermediate 053

N-(4-aminophenyl)-2-chloro-4,5-difluorobenzamide

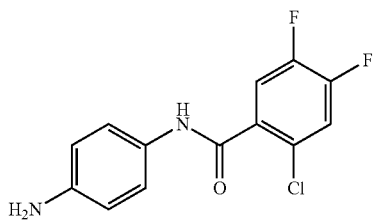 [SMILES: Nc1ccc(NC(=O)c2cc(F)c(F)cc2Cl)cc1]

To 2.00 g (10.4 mmol) 2-chloro-4,6-difluorobenzoic acid in 125 mL DMF were added 4.34 g (11.4 mmol) HATU and 5.4 mL N,N-diisopropylethylamine. After stirring for 5 minutes 5.62 g (51.9 mmol) benzene-1,4-diamine were added and the mixture was stirred for 18 hours at room temperature. The reaction mixture was concentrated under reduced pressure. Water was added to the remaining material and the precipitate was filtered off to afford after drying 1.9 g of the title compound as solid material.

LCMS (Method 5): $R_t$=0.95 min; MS (ESIpos) m/z=283.0 [M+H]$^+$.

Intermediate 054

N-(4-aminophenyl)-2-bromo-4-fluorobenzamide hydrochloride salt

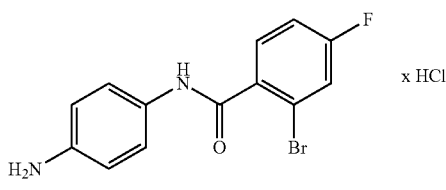 [SMILES: Nc1ccc(NC(=O)c2ccc(F)cc2Br)cc1]

Step 1: To 1.32 g (6.16 mmol) tert-butyl (4-aminophenyl)carbamate (CAS No. 71026-66-9) and 1.35 g (6.16 mmol) 2-bromo-4-fluorobenzoic acid (CAS No. 1006-41-3) in 39 mL DMF were added 3.22 mL (18.5 mmol) N-ethyl-N-isopropylpropan-2-amine and 3.05 g (8.01 mmol) HATU. The mixture was stirred for 3 h at room temperature and then poured into 100 mL water. The precipitate thus formed was collected by filtration and dried overnight at 50° C. under vacuum to give tert-butyl {4[(2-bromo-4-fluorobenzoyl)amino]phenyl}carbamate (2.44 g).

$^1$H-NMR (300 MHz, DMSO-d$_6$): δ [ppm]=10.34 (s, 1H), 9.30 (s, 1H), 7.48-7.81 (m, 4H), 7.24-7.48 (m, 3H), 1.46 (s, 9H).

Step 2: 22 mL (88 mmol) 4 M hydrochloric acid in dioxane were added to a suspension of 2.40 g (5.86 mmol) tert-butyl {4-[(2-bromo-4-fluorobenzoyl)amino]phenyl}carbamate in a mixture of 50 mL dichloromethane and 50 mL ethanol under cooling and the mixture was stirred for 3 days at room temperature. The precipitate was collected by filtration and dried at 50° C. under vacuum to give 1.9 g of the title compound.

$^1$H-NMR (300 MHz, DMSO-d$_6$): δ [ppm]=10.56 (s, 1H), 7.77-7.60 (m, 4H), 7.44-7.33 (m, 1H), 7.20 (d, 2H).

LC-MS (OA01a01): $R_t$=0.72 min; MS (ESIpos) m/z=309.0 [M+H]$^+$.

Intermediate 055

N-[4-amino-2-(trifluoromethoxy)phenyl]-2-chloro-4-fluorobenzamide

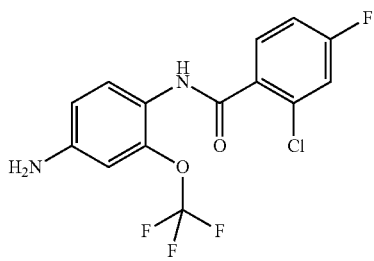 [SMILES: Nc1ccc(NC(=O)c2ccc(F)cc2Cl)c(OC(F)(F)F)c1]

Step 1: A mixture of 1.17 g (5.27 mmol) 4-nitro-2-(trifluoromethoxy)aniline (CAS No. 1261753-88-1) and 1.02 g (5.27 mmol) 2-chloro-4-fluorobenzoyl chloride (CAS No. 21900-54-9) in 12 mL o-xylene was heated in a microwave reactor for 8 h at 160° C. Upon cooling, the precipitate was collected by filtration and washed with toluene. The filtrate was concentrated and the residue was stirred with methanol. The precipitate formed was collected by filtration, washed with ethanol and dried to give 2-chloro-4-fluoro-N-[4-nitro-2-(trifluoromethoxy)phenyl]benzamide (325 mg).
$^1$H-NMR (400 MHz, DMSO-$d_6$): δ [ppm]=10.93 (s, 1H), 8.51-8.31 (m, 2H), 8.25 (d, 1H), 7.71-7.58 (m, 2H), 7.39 (td, 1H).
LC-MS (Method 8): $R_t$=1.31 min; MS (ESIpos) m/z=377.0 [M+H]$^+$.

Step 2: 4.0 mL (8.0 mmol) 2M hydrochloric acid was added under ice-cooling to a mixture of 304 mg (0.803 mmol) 2-chloro-4-fluoro-N-[4-nitro-2-(trifluoromethoxy)phenyl]benzamide and 262 mg (4.01 mmol) zinc powder in 9.1 mL ethanol. The resulting mixture was stirred for 12 h at room temperature and the filtrated through a pad of cilite which was washed with a mixture of ethanol and ethyl acetate. Water and saturated sodium bicarbonate solution was added to the filtrate and the precipitate was collected by filtration. The precipitate was dissolved in dichloromethane and the organic phase was washed with water (3×), filtrated through a silicone filter and concentrated to give the title compound (276 mg) which was used without further purification.
$^1$H-NMR (400 MHz, DMSO-$d_6$): δ [ppm]=9.82 (s, 1H), 7.57-7.48 (m, 2H), 7.38-7.29 (m, 1H), 7.21 (d, 1H), 6.61-6.52 (m, 2H), 5.49 (s, 2H).
LC-MS (Method 7): $R_t$=1.09 min; MS (ESIpos) m/z=349.1 [M+H]$^+$.

Intermediate 056

N$^5$-(4-aminophenyl)-N$^4$-ethyl-1H-imidazole-4,5-dicarboxamide

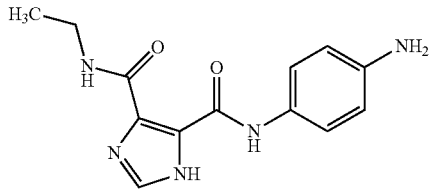 [SMILES: CCNC(=O)c1nc[nH]c1C(=O)Nc1ccc(N)cc1]

2.50 g (9.61 mmol) methyl 5-[(4-aminophenyl)carbamoyl]-1H-imidazole-4-carboxylate (intermediate 015,) were stirred in 144 mL (288 mmol) 2M solution of ethylamine in THF in a sealed tube over night at room temperature. The mixture was then concentrated under reduced pressure and the residue was recrystallized from methanol to give the title compound (0.73 g).
$^1$H-NMR (400 MHz, DMSO-$d_6$): δ [ppm]=13.00-12.50 (m 2H), 9.04-8.38 (m, 1H), 7.87 (s, 1H), 7.38 (d, 2H), 6.57 (d, 2H), 4.98 (br. s., 2H), 3.47-3.21 (m, 2H), 1.15 (t, 3H).
LC-MS (Method 8): $R_t$=0.71 min; MS (ESIpos) m/z=274.1 [M+H]$^+$.

Intermediate 057

2-(4,4-difluoropiperidin-1-yl)ethanamine

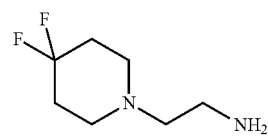

Step 1: A mixture of 1.50 g (9.52 mmol) 4,4-difluoropiperidine hydrochloride (CAS No. 144230-52-4), 0.698 mL (10.5 mmol) bromoacetonitrile and 3.29 g (23.8 mmol) potassium carbonate in acetonitrile were stirred at 60° C. over night. Solids were filtered off and the filtrate was concentrated and the residue was purified by flash chromatography (Snap cartridge, hexanes/ethylacetate 1:1) to give 1.23 g of (4,4-difluoropiperidin-1-yl)acetonitrile
$^1$H-NMR (400 MHz, CDCl$_3$): δ [ppm]=3.58 (s, 2H), 2.77-2.69 (m, 4H), 2.16-2.01 (m, 4H).

Step 2: A solution of 1.23 g (7.65 mmol) (4,4-difluoropiperidin-1-yl)acetonitrile in 30 mL 7M solution of ammonia in methanol was hydrogenated in an autoclave (20 bar hydrogen pressure) at room temperature for 16 h in the presence of 1.5 g Raney-Nickel catalyst (50% wet). For work-up, the catalyst was filtrated off and the filtrate was concentrated under reduced pressure to give 1.19 g of the title compound which was used without further purification.

Intermediate 058

2-[(2S)-2-methylpiperidin-1-yl]ethanamine

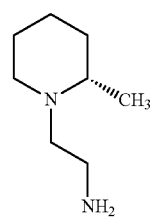

Was prepared in analogy to the synthesis of intermediate 057 using 1.00 g (10.1 mmol) (S)-(+)-2-methyl piperidine (CAS No. 3197-42-0) as starting material to give the title compound (1.01 g).
$^1$H-NMR (400 MHz, CDCl$_3$): δ [ppm]=2.95-2.82 (m, 2H), 2.82-2.67 (m, 2H), 2.39-2.24 (m, 2H), 2.13 (td, 1H), 1.74-1.47 (m, 6H), 1.39-1.25 (m, 2H), 1.08 (d, 3H).

Intermediate 059

2-[(2R)-2-methylpiperidin-1-yl]ethanamine

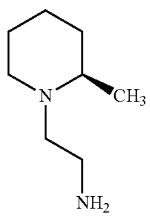

Was prepared in analogy to the synthesis of intermediate 057 using 1.00 g (10.1 mmol) (2R)-2-methylpiperidine (CAS No. 1722-95-7) as starting material to give the title compound (0.87 g).

$^1$H-NMR (400 MHz, CDCl$_3$): δ [ppm]=2.93-2.82 (m, 2H), 2.82-2.73 (m, 2H), 2.33-2.19 (m, 2H), 2.13 (t, 1H), 1.73-1.45 (m, 5H), 1.39-1.20 (m, 3H), 1.10 (d, 3H).

Intermediate 060

2-(3-fluoropiperidin-1-yl)ethanamine

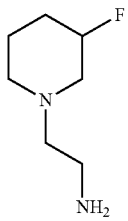

Was prepared in analogy to the synthesis of intermediate 057 using 2.00 g (14.2 mmol) 3-fluoropiperidine hydrochloride (CAS No. 737000-77-0) as starting material to give the title compound (1.70 g).

$^1$H-NMR (400 MHz, CDCl$_3$): δ [ppm]=4.76-4.54 (m, 1H), 2.89-2.71 (m, 3H), 2.56-2.35 (m, 4H), 2.34-2.19 (m, 1H), 1.98-1.75 (m, 2H), 1.69-1.49 (m, 2H).

Intermediate 061

2-[(3.5)-3-fluoropyrrolidin-1-yl]ethanamine

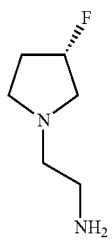

Was prepared in analogy to the synthesis of intermediate 057 using 1.00 g (7.96 mmol) (3S)-3-fluoropyrrolidine hydrochloride (CAS No. 136725-53-6) as starting material to give the title compound (0.85 g).

$^1$H-NMR (300 MHz, CDCl$_3$): δ [ppm]=5.42-4.99 (m, 1H), 3.01-2.53 (m, 7H), 2.46 (m, 1H), 2.32-1.94 (m, 2H).

Intermediate 062

2-[(3R)-3-fluoropyrrolidin-1-yl]ethanamine

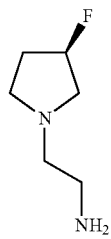

Was prepared in analogy to the synthesis of intermediate 057 using 1.00 g (7.96 mmol) (3R)-3-fluoropyrrolidine hydrochloride (CAS No. 136725-55-8) as starting material to give the title compound.

$^1$H-NMR (300 MHz, CDCl$_3$): δ [ppm]=5.39-5.01 (m, 1H), 3.01-2.52 (m, 7H), 2.52-2.39 (m, 1H), 2.30-1.93 (m, 2H).

Intermediate 063

2-(3,3-difluoropiperidin-1-yl)ethanamine

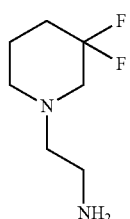

Was prepared in analogy to the synthesis of intermediate 057 using 1.01 g (6.2 mmol) 3,3-difluoropiperidine hydrochloride (CAS No. 496807-97-7) as starting material to give the title compound (0.94 g).

NMR of step 1 ((3,3-difluoropiperidin-1-yl)acetonitrile): $^1$H-NMR (400 MHz, DMSO-d$_6$): δ [ppm]=3.81 (s, 2H), 2.72 (t, 2H), 1.95-1.81 (m, 2H), 1.72-1.62 (m, 2H).

Intermediate 064

2-[(3S)-3-fluoropiperidin-1-yl]ethanamine

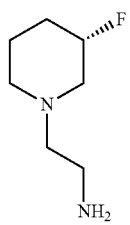

Step 1: A solution of 3.2 g (15.9 mmol) tert-butyl (3R)-3-hydroxypiperidine-1-carboxylate in 80 mL dichloromethane was cooled to −78° C. 2.5 mL g (19 mmol) N-ethyl-N-(trifluoro-λ⁴-sulfanyl)ethanamine (DAST) was added. The mixture was stirred 75 min at room temperature. The reaction mixture was poured into ice water and extracted with dichloromethane. The combined organic layers were filtrated through a silicone filter and concentrated under reduced pressure. The residue was purified by flash chromatography on silica gel (eluent: hexane/ethyl acetate 4:1) to give tert-butyl (3S)-3-fluoropiperidine-1-carboxylate (773 mg).

Step 2: To a suspension of 773 mg (3.80 mmol) tert-butyl (3S)-3-fluoropiperidine-1-carboxylate (step 1) in 45 mL dichloromethane was added 9.5 mL (38 mmol) 4 M hydrochloric acid in dioxane. The mixture stirred overnight at room temperature and was then concentrated under reduced pressure to give crude (3S)-3-fluoropiperidine hydrochloride (531 mg) which was used in the next step without purification.

Step 3 and 4: 2-[(3S)-3-fluoropiperidin-1-yl]ethanamine was then prepared in 2 steps from 476 mg (3.41 mmol) (3S)-3-fluoropiperidine hydrochloride (step 2) in analogy to the synthesis of intermediate 057 to give the title compound (255 mg).

¹H-NMR (400 MHz, CDCl₃): δ [ppm]=4.79-4.50 (m, 1H), 3.13-1.39 (m, 14H).

Intermediate 065

2-[(3R)-3-fluoropiperidin-1-yl]ethanamine

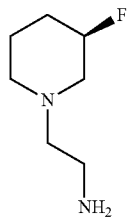

Was prepared in analogy to the synthesis of intermediate 068 using 3.2 g (15.9 mmol) tert-butyl (3S)-3-hydroxypiperidine-1-carboxylate (CAS No. 143900-44-1) as starting material to give the title compound (223 mg).

¹H-NMR (400 MHz, CDCl₃): δ [ppm]=4.81-4.48 (m, 1H), 2.90-2.71 (m, 3H), 2.56-2.38 (m, 4H), 2.38-2.24 (m, 1H), 1.96-1.77 (m, 2H), 1.65-1.48 (m, 4H).

Intermediate 066

(3S)-1-(2-aminoethyl)piperidin-3-ol

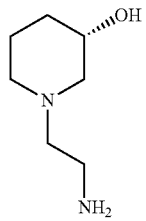

Was prepared in analogy to the synthesis of intermediate 057 using 2.00 g (14.5 mmol) (3S)-piperidin-3-ol hydrochloride (CAS No. 475058-41-4) as starting material to give the title compound (1.56 g).

¹H-NMR (300 MHz, CDCl₃): δ [ppm]=3.93-3.63 (m, 1H), 2.89-2.64 (m, 2H), 2.61-2.38 (m, 4H), 2.36-2.23 (m, 1H), 1.89-1.73 (m, 1H), 1.72-1.39 (m, 3H)

Intermediate 067

(3R)-1-(2-aminoethyl)piperidin-3-ol

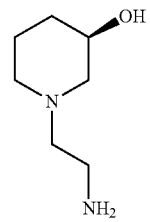

Was prepared in analogy to the synthesis of intermediate 057 using 2.00 g (14.5 mmol) (3R)-piperidin-3-ol hydrochloride (CAS No. 198976-43-1) as starting material and 5.02 g (36.3 mmol, 2.5 eq.) K₂CO₃ to give the title compound (1.38 g).

¹H-NMR (300 MHz, CDCl₃): δ [ppm]=3.92-3.66 (m, 1H), 2.89-2.65 (m, 2H), 2.60-2.38 (m, 4H), 2.36-2.20 (m, 1H), 1.90-1.73 (m, 1H), 1.72-1.44 (m, 3H)

Intermediate 068

2-(3,3-difluoropyrrolidin-1-yl)ethanamine

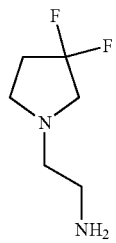

Was prepared in analogy to the synthesis of intermediate 057 using 1.02 g (7.1 mmol) 3,3-difluoropyrrolidine hydrochloride (CAS No. 163457-23-6) as starting material to give the title compound (0.78 g).

¹H-NMR (400 MHz, CDCl₃): δ [ppm]=2.92 (t, 2H), 2.86-2.71 (m, 4H), 2.57 (t, 2H), 2.37-2.18 (m, 2H).

Intermediate 069

2-[(3R)-3-methylpiperidin-1-yl]ethanamine

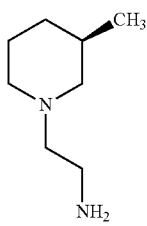

Was prepared in analogy to the synthesis of intermediate 057 using 1.62 g (16.3 mmol) (3R)-3-methylpiperidine (CAS No. 16078-25-4) to give the title compound (0.55 g).

$^1$H-NMR (400 MHz, CDCl$_3$): δ [ppm]=2.88-2.72 (m, 4H), 2.42-2.34 (m, 2H), 1.87 (td, 1H), 1.76-1.47 (m, 7H), 0.95-0.79 (m, 4H).

Intermediate 70

2-(4-fluoropiperidin-1-yl)ethanamine

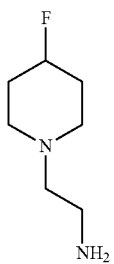

Was prepared in analogy to the synthesis of intermediate 057 using 338 mg (2.35 mmol) 4-fluoropiperidine hydrochloride (CAS No. 57395-89-8) as starting material to give the title compound (185 mg).

$^1$H-NMR (400 MHz, CDCl$_3$): δ [ppm]=4.82-4.49 (m, 1H), 3.00-2.11 (m, 8H), 2.02-1.76 (m, 2H), 1.74-1.32 (m, 4H).

Intermediate 071 tert-butyl (3S)-3-({[4-({4-[(2-chloro-4-fluorobenzoyl)amino]phenyl}carbamoyl)-1H-imidazol-5-yl]carbonyl}amino)pyrrolidine-1-carboxylate

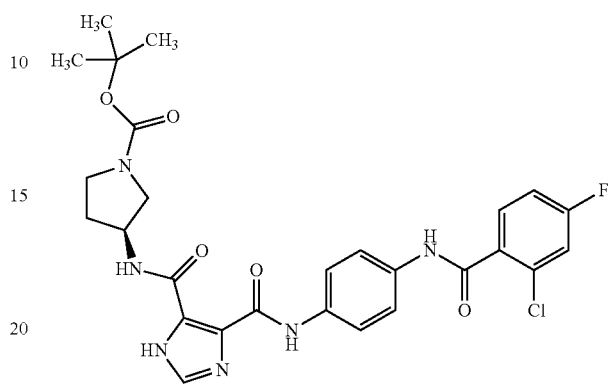

Step 1: 159 mg (0.60 mmol, 2.0 equiv.) N-(4-aminophenyl)-2-chloro-4-fluorobenzamide (intermediate 004) and 125 µL (0.90 mmol, 3.0 equiv.) triethylamine were added to a suspension of 93.9 mg (0.300 mmol, 1.0 equiv.) 5,10-dioxo-5H,10H-diimidazo[1, 5-a; 1',5'-d]pyrazin-1,6-dicarbonyl-dichloride (Intermediate 001) in 4.5 mL THF and the mixture was stirred for 2.5 h at room temperature to give N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide. The reaction mixture was used directly in the next step.

Step 2: 114 mg (0.600 mmol) tert-butyl (3S)-3-aminopyrrolidine-1-carboxylate and 125 µL (0.90 mmol, 3. equiv.) triethylamine were added to the reaction mixture of step 1 and the mixture was stirred over night at room temperature. The mixture was concentrated, and the residue was purified by preparative HPLC to give the title compound (86.0 mg).

LC-MS (Method 8): R$_t$=1.14 min; MS (ESIneg) m/z=569.3 [M−H]$^-$.

Intermediate 072 tert-butyl (3R)-3-({[4-({4-[(2-chloro-4-fluorobenzoyl)amino]phenyl}carbamoyl)-1H-imidazol-5-yl]carbonyl}amino)pyrrolidine-1-carboxylate

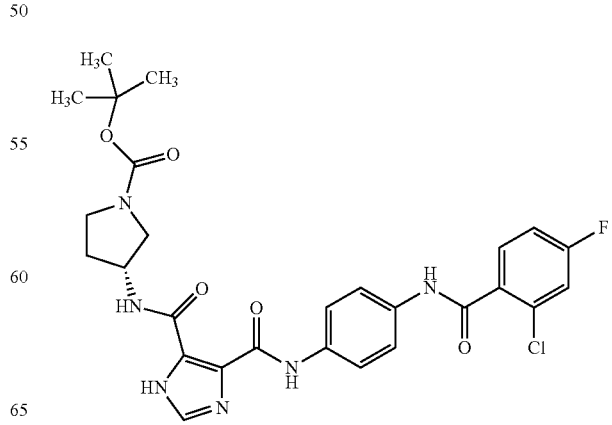

Was prepared in analogy to the synthesis of intermediate 71 using 114 mg (0.600 mmol) tert-butyl (3R)-3-aminopyrrolidine-1-carboxylate (CAS No. 147081-49-0) as starting material and 157 μL (0.900 mmol) N,N-diisopropylethylamine as base in the second step to give the title compound (120 mg).

¹H-NMR (400 MHz, DMSO-d₆): δ [ppm]=13.81-13.03 (m, 1H), 10.52 (s, 1H), 9.35-8.73 (m, 1H), 7.94 (s, 1H), 7.82-7.54 (m, 6H), 7.35 (td, 1H), 4.50 (br. s., 1H), 3.67-3.50 (m, 1H), 3.47-3.37 (m, 2H), 3.29-3.21 (m, 1H), 2.21-1.90 (m, 2H), 1.41 (s, 9H).

LC-MS (Method 8): $R_t$=1.15 min; MS (ESIpos) m/z=571.2 [M+H]⁺.

Intermediate 073 tert-butyl [4-({[4-({4-[(2-chlorobenzoyl)amino]phenyl}carbamoyl)-1H-imidazol-5-yl]carbonyl}amino)-2-methylbutan-2-yl]carbamate

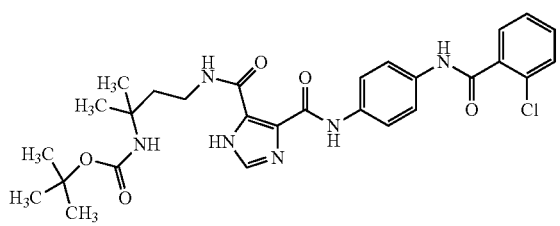 [SMILES: CC(C)(CCNC(=O)c1[nH]cnc1C(=O)Nc1ccc(NC(=O)c2ccccc2Cl)cc1)NC(=O)OC(C)(C)C]

148 mg (0.600 mmol) N-(4-aminophenyl)-2-chlorobenzamide (intermediate 051) and 157 μL (0.900 mmol) N,N-diisopropylethylamine were added to a suspension of 93.9 mg (0.300 mmol) 5,10-dioxo-5H,10H-diimidazo[1,5-a;1',5'-d]pyrazin-1,6-dicarbonyl-dichloride (Intermediate 001) in 4.5 mL THF and the mixture was stirred for 6 h at room temperature. 143 mg (0.600 mmol) tert-butyl (4-amino-2-methylbutan-2-yl)carbamate hydrochloride salt and 209 μL (1.2 mmol) N,N-diisopropylethylamine were added. The mixture was stirred overnight at room temperature. The mixture was concentrated and the residue was purified by preparative HPLC to give the title compound (97.0 mg).

¹H-NMR (400 MHz, DMSO-d₆): δ [ppm]=13.80-13.21 (m, 2H), 10.51 (s, 1H), 9.09-8.14 (m, 1H), 7.91 (s, 1H), 7.78-7.66 (m, 4H), 7.65-7.56 (m, 2H), 7.55-7.43 (m, 2H), 6.47 (br. s., 1H), 1.97-1.81 (m, 2H), 1.38 (s, 9H), 1.23 (s, 6H).

LC-MS (Method 8): $R_t$=1.19 min; MS (ESIpos) m/z=569.3 [M+H]⁺.

Intermediate 074 tert-butyl 2-[(({[4-({4-[(2-chloro-4-fluorobenzoyl)amino]phenyl}carbamoyl)-1H-imidazol-5-yl]carbonyl}amino)methyl]pyrrolidine-1-carboxylate

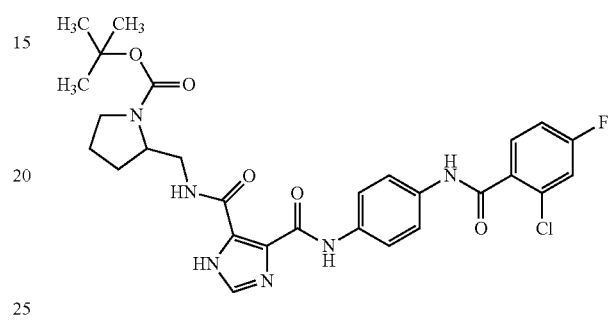

Was prepared in analogy to the synthesis of intermediate 071 using 120 mg (0.600 mmol) tert-butyl 2-(aminomethyl)pyrrolidine-1-carboxylate (CAS No. 177911-87-4) as starting material and 157 μL (0.900 mmol) N,N-diisopropylethylamine as base in the second step to give the title compound (106 mg).

¹H-NMR (400 MHz, DMSO-d₆): δ [ppm]=13.80-13.20 (m, 2H), 10.51 (s, 1H), 9.40-8.50 (m, 1H), 7.90 (s, 1H), 7.84-7.64 (m, 5H), 7.59 (dd, 1H), 7.35 (dt, 1H), 4.02-3.93 (m, 1H), 3.59-3.49 (m, 1H), 3.47-3.35 (m, 1H), 3.29-3.20 (m, 2H), 1.93-1.72 (m, 4H), 1.41 (s, 9H).

LC-MS (Method 8): $R_t$=1.24 min; MS (ESIpos) m/z=585.3 [M+H]⁺.

Intermediate 075 tert-butyl (1-{[4-({4-[(2-chloro-4-fluorobenzoyl)amino]phenyl}carbamoyl)-1H-imidazol-5-yl]carbonyl}pyrrolidin-3-yl)carbamate

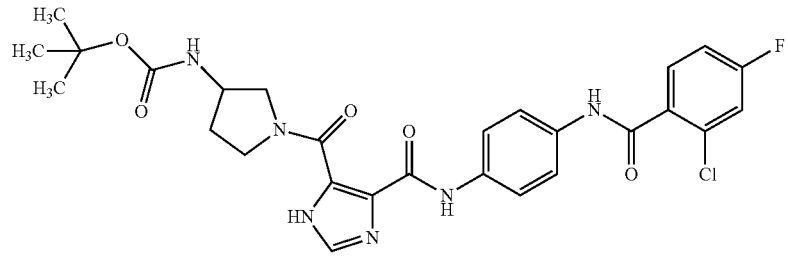 [SMILES: CC(C)(C)OC(=O)NC1CCN(C(=O)c2[nH]cnc2C(=O)Nc2ccc(NC(=O)c3ccc(F)cc3Cl)cc2)C1]

Was prepared in analogy to the synthesis of intermediate 071 using 112 mg (0.600 mmol) tert-butyl pyrrolidin-3-ylcarbamate (CAS No. 99724-19-3) as starting material and 157 μL (0.900 mmol) N,N-diisopropylethylamine as base in the second step to give the title compound (87.0 mg).

¹H-NMR (400 MHz, DMSO-d₆): δ [ppm]=13.69-12.89 (m, 2H), 10.62-10.29 (m, 1H), 8.00-7.86 (m, 1H), 7.75-7.63 (m, 5H), 7.62-7.53 (m, 1H), 7.40-7.30 (m, 1H), 7.29-7.12 (m, 1H), 4.22-3.94 (m, 2H), 3.92-3.45 (m, 3H), 2.16-1.96 (m, 1H), 1.92-1.77 (m, 1H), 1.46-1.32 (m, 9H).

LC-MS (Method 8): R$_t$=1.15 min; MS (ESIpos) m/z=571.2 [M+H]⁺.

Intermediate 076 tert-butyl [4-({[4-({4-[(2-chloro-4-fluorobenzoyl)amino]phenyl}carbamoyl)-1H-imidazol-5-yl]carbonyl}amino)-2-methylbutan-2-yl]carbamate

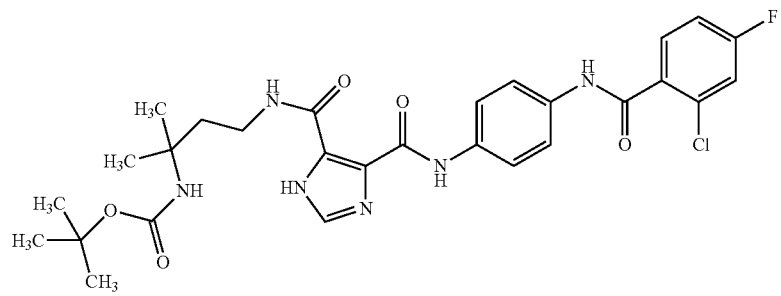 [SMILES: CC(C)(CCNC(=O)c1[nH]cnc1C(=O)Nc1ccc(NC(=O)c2ccc(F)cc2Cl)cc1)NC(=O)OC(C)(C)C]

Was prepared in analogy to intermediate 73 using 159 mg (0.600 mmol, 2.0 equiv.) N-(4-aminophenyl)-2-chloro-4-fluorobenzamide (intermediate 004) as starting material to give the title compound (33.0 mg).

¹H-NMR (400 MHz, DMSO-d₆): δ [ppm]=13.92-12.77 (m, 2H), 10.60-10.48 (m, 1H), 8.96-8.48 (m, 1H), 7.92 (s, 1H), 7.77-7.65 (m, 5H), 7.63-7.57 (m, 1H), 7.43-7.31 (m, 1H), 6.47 (br. s., 1H), 1.94-1.83 (m, 2H), 1.38 (s, 9H), 1.30-1.18 (m, 6H).

LC-MS (Method 8): R$_t$=1.26 min; MS (ESIpos) m/z=587.4 [M+H]⁺.

Intermediate 077 tert-butyl [2-({[4-({4-[(2-chloro-4-fluorobenzoyl)amino]phenyl}carbamoyl)-1H-imidazol-5-yl]carbonyl}amino)ethyl]methylcarbamate

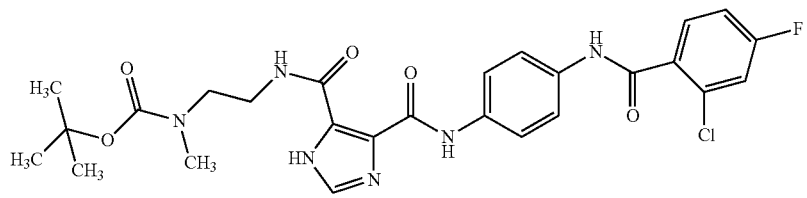 [SMILES: CN(CCNC(=O)c1[nH]cnc1C(=O)Nc1ccc(NC(=O)c2ccc(F)cc2Cl)cc1)C(=O)OC(C)(C)C]

Was prepared in analogy to intermediate 071 using 107 mg (0.600 mmol) tert-butyl (2-aminoethyl)methylcarbamate (CAS No. 121492-06-6) as starting material to give the title compound (62.0 mg).

¹H-NMR (400 MHz, DMSO-d₆): δ [ppm]=14.20-12.92 (m, 1H), 10.96-10.09 (m, 2H), 9.04-8.70 (m, 1H), 8.10-7.52 (m, 8H), 7.42-7.30 (m, 1H), 2.96-2.71 (m, 3H), 1.65-0.83 (m, 8H).

LC-MS (Method 8): R$_t$=1.15 min; MS (ESIpos) m/z=559.3 [M+H]⁺.

Intermediate 078 tert-butyl 4-{[4-({4-[(2-chloro-4-fluorobenzoyl)amino]phenyl}carbamoyl)-1H-imidazol-5-yl]carbonyl}piperazine-1-carboxylate

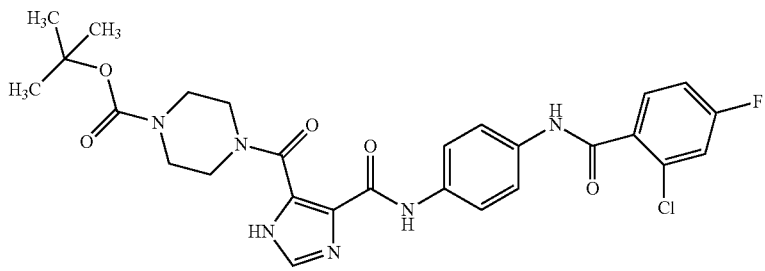 [SMILES: CC(C)(C)OC(=O)N1CCN(C(=O)c2[nH]cnc2C(=O)Nc2ccc(NC(=O)c3ccc(F)cc3Cl)cc2)CC1]

Was prepared in analogy to intermediate 071 using 113 mg (0.600 mmol) tert-butyl piperazine-1-carboxylate (CAS No. 5726-71-6) as starting material to give the title compound (12.0 mg).

$^1$H-NMR (400 MHz, DMSO-d$_6$): δ [ppm]=10.49 (s, 1H), 7.90-7.84 (m, 1H), 7.72-7.63 (m, 5H), 7.58 (dd, 1H), 7.35 (dt, 1H), 3.74-3.64 (m, 2H), 3.50-3.35 (m, 4H), 1.41 (s, 9H).

LC-MS (Method 8): R$_t$=1.01 min; MS (ESIneg) m/z=571.3 [M−H]⁻.

Intermediate 079 tert-butyl [2-({[4-({4-[(2-chloro-4-fluorobenzoyl)amino]phenyl}carbamoyl)-1H-imidazol-5-yl]carbonyl}amino)ethyl]carbamate Was prepared in analogy to intermediate 071 using 98.1 mg (0.60 mmol) tert-butyl (2-aminoethyl)carbamate (CAS No. 57260-73-8) as starting material to give the title compound (37.0 mg).

LC-MS (Method 8): R$_t$=1.05 min; MS (ESIpos) m/z=545.3 [M+H]⁺.

Intermediate 080

2-chloro-4-(S-ethylsulfonimidoyl)benzoic acid

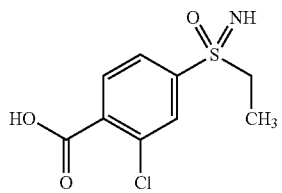

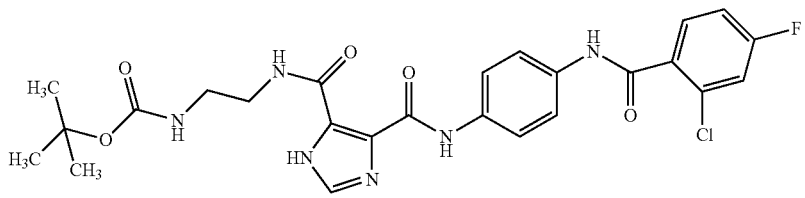 [SMILES: CC(C)(C)OC(=O)NCCNC(=O)c1[nH]cnc1C(=O)Nc1ccc(NC(=O)c2ccc(F)cc2Cl)cc1]

Step 1 (methyl 2-chloro-4-(ethylsulfanyl)benzoate)

3.30 g (15.2 mmol) 2-chloro-4-(ethylsulfanyl)benzoic acid (CAS No. 13205-49-7) in a mixture of 15 mL methanol and 16 μL concentrated sulfuric acid was heated at reflux overnight. The mixture was then concentrated, neutralized with saturated sodium bicarbonate solution and extracted with ethyl acetate. The organic phase was filtrated through a silicone filter and concentrated. The residue was purified by flash chromatography (25 g Snap cartridge, hexanes/ethyl acetate gradient) to give 1.40 g methyl 2-chloro-4-(ethylsulfanyl)benzoate.

$^1$H-NMR (300 MHz, CDCl$_3$): δ [ppm]=7.80 (d, 1H), 7.32 (s, 1H), 7.17 (d, 1H), 3.03 (q, 2H), 1.61 (s, 1H), 1.39 (t, 3H).

Step 2 (methyl 2-chloro-4-(ethylsulfinyl)benzoate)

1.77 (65% purity, 6.68 mmol) 3-chloroperoxybenzoic acid was added under cooling to a solution of 1.40 (6.07 mmol) methyl 2-chloro-4-(ethylsulfanyl)benzoate in 25 mL dichloromethane. The reaction mixture was stirred for 2 h at 4° C. The reaction mixture was then diluted with dichloromethane, washed with saturated sodium bicarbonate solution and filtrated through a silicone filter. The filtrate was concentrated and the residue was purified by flash chromatography (25 g Snap cartridge, hexanes/ethyl acetate gradient) to provide 0.71 g methyl 2-chloro-4-(ethylsulfinyl)benzoate.

$^1$H-NMR (400 MHz, CDCl$_3$): δ [ppm]=7.89 (d, 1H), 7.64 (d, 1H), 7.45 (dd, 1H), 3.90 (s, 3H), 2.97-2.83 (m, 1H), 2.75-2.64 (m, 1H), 1.16 (t, 3H)

LC-MS (Method 8): R$_t$=0.86 min; MS (ESIpos) m/z=247.0 [M+H]$^+$.

Step 3 (methyl 2-chloro-4-[S-ethyl-N-(trifluoroacetyl)sulfonimidoyl]benzoate)

1.43 g (4.34 mmol) bis(acetyloxy)(phenyl)-lambda3-iodane (CAS No. 3240-34-4) was added to a mixture of 713 mg (2.89 mmol) methyl 2-chloro-4-(ethylsulfinyl)benzoate, 674 mg (5.78 mmol) 2,2,2-trifluoroacetamide, 466 mg (11.6 mmol) magnesium oxide and rhodium(2+) diacetate (CAS No. 5503-41-3) in 30 mL dichloromethane and the mixture was stirred under and argon atmosphere at room temperature for 18 h. The mixture was then filtrated through a pad of celite and the filtrate was concentrated. The residue was purified by flash chromatography (25 g Snap cartridge, hexanes/ethyl acetate gradient) to yield 757 mg of methyl 2-chloro-4-[S-ethyl-N-(trifluoroacetyl)sulfonimidoyl]benzoate.

Step 4 (2-chloro-4-(S-ethylsulfonimidoyl)benzoic acid)

750 mg (2.10 mmol) methyl 2-chloro-4-[S-ethyl-N-(trifluoroacetyl)sulfonimidoyl]benzoate was stirred in a mixture of 5.2 mL 1 M aqueous lithium hydroxide solution, 3.8 mL tetrahydrofuran and 15.3 mL methanol for 2 h. The mixture was then concentrated, diluted with water, acidified with 2 M hydrochloric acid and extracted several times with a mixture of dichloromethane and 2-propanol (4:1). The combined organic phases were filtrated through a silicone filter and concentrated to give 523 mg of crude 2-chloro-4-(S-ethylsulfonimidoyl)benzoic acid which was used without further purification.

$^1$H-NMR (300 MHz, DMSO-d$_6$): δ [ppm]=8.08-7.83 (m, 3H), 3.30 (q, 2H), 1.08 (t, 3H).

LC-MS (Method 7): R$_t$=0.49 min; MS (ESIpos) m/z=248.0 [M+H]$^+$.

4. EXAMPLES

Example 1

N$^5$-{4-[(2,3-dichlorobenzoyl)amino]phenyl}-N$^4$-methyl-1H-imidazole-4,5-dicarboxamide

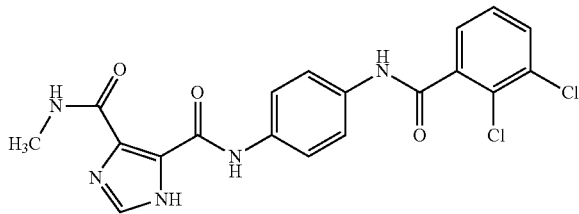 [SMILES: CNC(=O)c1nc[nH]c1C(=O)Nc1ccc(NC(=O)c2cccc(Cl)c2Cl)cc1]

To a mixture of 200 mg (80% pure, 0.617 mmol) N$^5$-(4-aminophenyl)-N$^4$-methyl-1H-imidazole-4,5-dicarboxamide (Intermediate 003) in 12.5 mL THF, 0.09 mL (0.617 mmol) triethylamine and 0.09 mL (0.617 mmol) 2,3-dichlorobenzoyl chloride were subsequently added and the mixture was stirred for additional 90 min. at room temperature. The reaction mixture was concentrated in vacuo and the residue was purified by flash column chromatography (dichloromethane/acetone-gradient). The product containing eluent was collected and concentrated in vacuo which resulted in a suspension. The precipitate was filtered, washed with dichloromethane and dried under high vacuum to give 120 mg of the title compound as a solid material.

$^1$H-NMR (300 MHz, DMSO-d$_6$), δ [ppm]=13.72-13.62 (m, 1H), 13.40 (br. s., 1H), 10.57 (s, 1H), 8.87-8.75 (m, 1H), 7.91 (s, 1H), 7.76 (dd, 1H), 7.70 (s, 4H), 7.59-7.53 (m, 1H), 7.52-7.44 (m, 1H), 2.86 (d, 3H).

LC-MS (Method 5): R$_t$=1.00 min; MS (ESIpos) m/z=432 [M+H]$^+$.

Example 2

N$^5$-(4-{[(2-chloropyridin-3-yl)carbonyl]amino}phenyl)-N$^4$-methyl-1H-imidazole-4,5-dicarboxamide

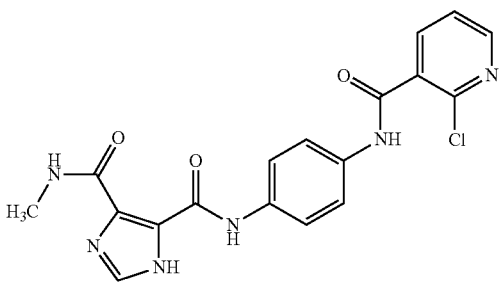 [SMILES: CNC(=O)c1nc[nH]c1C(=O)Nc1ccc(NC(=O)c2cccnc2Cl)cc1]

100 mg (0.39 mmol) N$^5$-(4-aminophenyl)-N$^4$-methyl-1H-imidazole-4,5-dicarboxamide (Intermediate 003) were suspended in 5 mL dry tetrahydrofuran. 53.8 μL (0.39 mmol) triethylamine and 67.9 mg (0.39 mmol) 2-chlornicotinyl chloride were added and the mixture was stirred at room temperature for 2 hours. The solvent was removed under reduced pressure and the crude product was purified by HPLC to give 61 mg of the title compound as a solid material.

$^1$H-NMR (300 MHz, DMSO-d$_6$), δ [ppm]=13.69 (s, 1H), 13.42 (br. s., 1H), 10.64 (s, 1H), 8.83 (d, 1H), 8.52 (dd, 1H), 8.08 (dd, 1H), 7.92 (s, 1H), 7.70 (s, 4H), 7.56 (dd, 1H), 2.86 (d, 3H).

LC-MS (Method 4): R$_t$=0.84 min; MS (ESIpos) m/z=399.2 [M+H]$^+$.

Example 3

N$^5$-(4-{[2-fluoro-4-(pyrrolidin-1-yl)benzoyl]amino}phenyl)-N$^4$-methyl-1H-imidazole-4,5-dicarboxamide

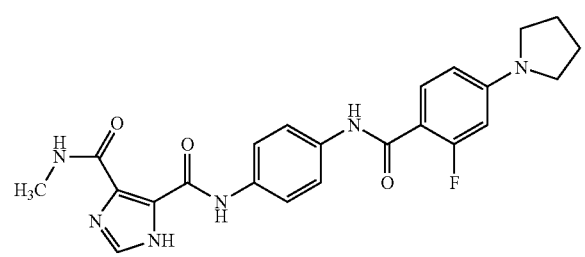 [SMILES: CNC(=O)c1nc[nH]c1C(=O)Nc1ccc(NC(=O)c2ccc(N3CCCC3)cc2F)cc1]

In 5.00 mL DMF, a mixture of 200 mg (0.771 mmol) N$^5$-(4-aminophenyl)-N$^4$-methyl-1H-imidazole-4,5-dicarboxamide (Intermediate 003), 161 mg (0.771 mmol) 2-fluoro-4-(pyrrolidin-1-yl)benzoic acid, 293 mg (0.771 mmol) HATU and 0.40 mL (2.314 mmol) N,N-diisopropylethylamine was stirred for 3 days at room temperature. The resulting precipitate was filtered off and the solids were subsequently treated with DMSO as well as water to give after filtration and drying in vacuo 109 mg of the title compound as a solid material.

$^1$H-NMR (300 MHz, DMSO-d$_6$), δ [ppm]=13.68-13.56 (m, 1H), 13.44-13.35 (m, 1H), 9.79-9.63 (m, 1H), 8.88-8.71 (m, 1H), 7.90 (s, 1H), 7.75-7.61 (m, 4H), 7.57 (t, 1H), 6.48-6.39 (m, 1H), 6.38-6.30 (m, 1H), 3.29-3.26 (m, 4H), 2.86 (d, 3H), 2.01-1.90 (m, 4H).

LC-MS (Method 4): R$_t$=1.20 min; MS (ESIpos) m/z=451 [M+H]$^+$.

Example 4

N$^5$-(4-{[2-chloro-4-(dimethylamino)benzoyl]amino}phenyl)-N$^4$-methyl-1H-imidazole-4,5-dicarboxamide

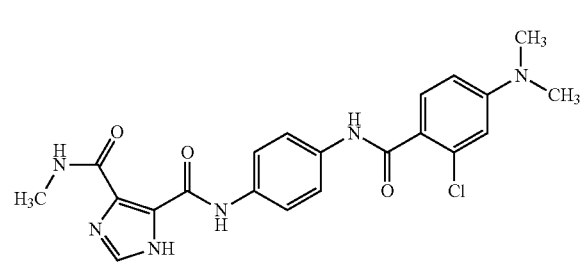

In 5.00 mL DMF, a mixture of 200 mg (0.771 mmol) N$^5$-(4-aminophenyl)-N$^4$-methyl-1H-imidazole-4,5-dicarboxamide (Intermediate 003), 154 mg (0.771 mmol) 2-chloro-4-(dimethylamino)benzoic acid, 293 mg (0.771 mmol) HATU and 0.40 mL (2.314 mmol) N,N-diisopropylethylamine was stirred for 3 days at room temperature. The resulting precipitate was filtered off and purified by preparative HPLC to yield 37 mg of the title compound as a solid material.

$^1$H-NMR (300 MHz, DMSO-d$_6$), δ [ppm]=13.71-13.54 (m, 1H), 13.41 (br. s., 1H), 10.17 (s, 1H), 8.95-8.71 (m, 1H), 7.91 (s, 1H), 7.77-7.59 (m, 4H), 7.41 (d, 1H), 6.78-6.64 (m, 2H), 2.96 (s, 6H), 2.86 (d, 3H).

LC-MS (Method 3): R$_t$=1.07 min; MS (ESIpos) m/z=441 [M+H]$^+$.

Example 5

N$^5$-{4-[(2-chloro-4-fluorobenzoyl)amino]-3-methylphenyl}-N$^4$-methyl-1H-imidazole-4,5-dicarboxamide

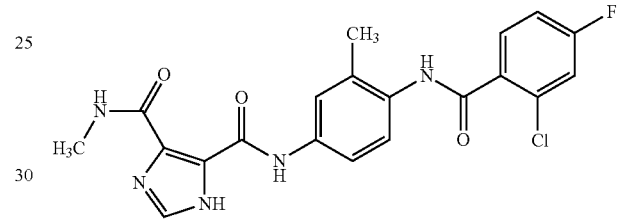

In 14.83 mL THF, a mixture of 200 mg (0.732 mmol) N$^5$-(4-amino-3-methylphenyl)-N$^4$-methyl-1H-imidazole-4,5-dicarboxamide (Intermediate 003), 0.10 mL (0.732 mmol) 2-chloro-4-fluorobenzoyl chloride and 0.10 mL (0.732 mmol) triethylamine was stirred for 3 days at room temperature. The resulting precipitate was filtered off and purified by preparative HPLC to yield 26 mg of the title compound as a solid material.

$^1$H-NMR (300 MHz, DMSO-d$_6$), δ [ppm]=13.75-13.51 (m, 1H), 13.43-13.33 (m, 1H), 9.92 (s, 1H), 8.96-8.68 (m, 1H), 7.91 (s, 1H), 7.75-7.65 (m, 1H), 7.64-7.52 (m, 3H), 7.43 (s, 2H), 2.87 (d, 3H), 2.29 (s, 3H).

LC-MS (Method 4): R$_t$=1.04 min; MS (ESIpos) m/z=430 [M+H]$^+$.

Example 6

N$^5$-{4-[(3-chloroisonicotinoyl)amino]phenyl}-N$^4$-methyl-1H-imidazole-4,5-dicarboxamide

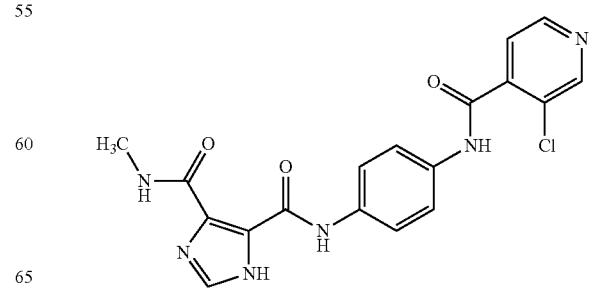

To a suspension of 200 mg (0.77 mmol) $N^5$-(4-aminophenyl)-$N^4$-methyl-1H-imidazole-4,5-dicarboxamide (Intermediate 003) in 6 mL dry tetrahydrofuran, 672 µL (3.85 mmol) N-ethyl-N,N-diisopropylamine and a solution of 136 mg (0.77 mmol) 3-chloroisonicotinoyl chloride in 5 mL dry THF were added. After stirring for 1 hour at room temperature 7 ml water and 7 mL of a saturated aqueous sodium carbonate solution was added to the reaction and the mixture was stirred for additional 10 minutes. The suspension was filtered to give 194 mg of the title compound as a solid material.

$^1$H-NMR (300 MHz, DMSO-$d_6$), δ [ppm]=2.86 (s, 3H), 7.63-7.86 (7H), 8.64-8.69 (d, 1H), 8.78 (s, 1H), 9.02 (s, 1H), 10.69 (s, 1H), 13.19 (s, 1H).

LC-MS (Method 6): $R_t$=3.2 min; MS (ESIpos) m/z=399.2 $[M+H]^+$.

Example 7

$N^4$-sec-butyl-$N^5$-{4-[(2-chloro-4-fluorobenzoyl)amino]phenyl}-1,3-oxazole-4,5-dicarboxamide

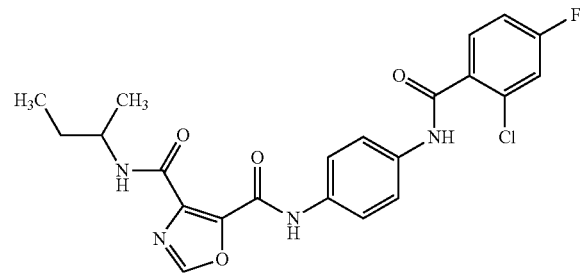 [SMILES: CCC(C)NC(=O)c1ncoc1C(=O)Nc1ccc(NC(=O)c2ccc(F)cc2Cl)cc1]

To a suspension of 80 mg (0.19 mmol) methyl 5-({4-[(2-chloro-4-fluorobenzoyl)amino]phenyl}carbamoyl)-1,3-oxazole-4-carboxylate (Example 14) in 1 mL methanol, 445 µL (3.45 mmol) butan-2-amine were added and the reaction was stirred for 5 hours at room temperature. The solvent was removed under reduced pressure and the residue was treated with 3 mL diethyl ether. The resulting precipitate was filtered to afford 33 mg of the title compound as a solid material.

$^1$H-NMR (300 MHz, DMSO-$d_6$), δ [ppm]=0.88 (t, 3H), 1.21 (d, 3H), 1.64 (m, 2H), 4.04 (m, 1H), 7.28-7.40 (m, 1H), 7.48-7.60 (m, 1H), 7.60-7.80 (m, 5H), 8.79 (s, 1H), 8.89 (d, 1H), 10.53 (s, 1H), 13.28 (s, 1H).

Example 8

$N^5$-{4-[(2-chloro-4-fluorobenzoyl)amino]phenyl}-$N^4$-(1-phenylethyl)-1,3-oxazole-4,5-dicarboxamide

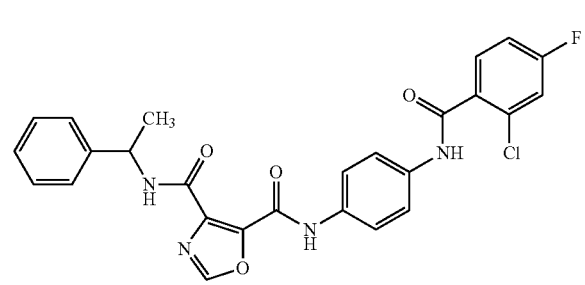 [SMILES: CC(NC(=O)c1ncoc1C(=O)Nc1ccc(NC(=O)c2ccc(F)cc2Cl)cc1)c1ccccc1]

To a suspension of 90 mg (0.22 mmol) methyl 5-({4-[(2-chloro-4-fluorobenzoyl)-amino]phenyl}carbamoyl)-1,3-oxazole-4-carboxylate (Example 14) in 1 mL methanol, 445 µL (3.45 mmol) 1-phenylethanamine were added and the reaction was stirred for 5 hours at room temperature. The reaction was diluted with 30 mL ethyl acetate and the organic layer was washed three times with 1N aqueous hydrochloric acid and once with sat. sodium carbonate solution. The organic phase was dried over magnesium sulfate, and the solvent was removed under reduced pressure to afford 66 mg of the title compound as a solid material.

$^1$H-NMR (300 MHz, DMSO-$d_6$), δ [ppm]=1.57 (d, 3H), 5.30 (t, 1H), 7.22-7.42 (4H), 7.42-7.53 (2H), 7.53-7.77 (6H), 8.81 (s, 1H), 9.53 (d, 1H), 10.52 (s, 1H), 13.07 (s, 1H).

Example 9

$N^5$-{4-[(2,4-dichlorobenzoyl)amino]phenyl}-$N^4$-methyl-1H-imidazole-4,5-dicarboxamide

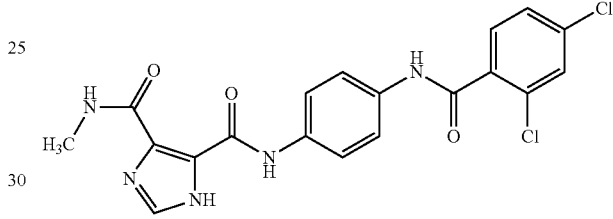

In 15.64 mL THF, a mixture of 200 mg (0.771 mmol) $N^5$-(4-amino-3-methylphenyl)-$N^4$-methyl-1H-imidazole-4,5-dicarboxamide (Intermediate 003), 0.11 mL (0.771 mmol) 2,4-dichlorobenzoyl chloride and 0.11 mL (0.771 mmol) triethylamine was stirred for 3 days at room temperature. The resulting precipitate was filtered off and purified by preparative HPLC to yield 135 mg of the title compound as a solid material.

$^1$H-NMR (300 MHz, DMSO-$d_6$), δ [ppm]=13.73-13.62 (m, 1H), 13.42 (br. s., 1H), 10.54 (s, 1H), 8.90-8.77 (m, 1H), 7.91 (s, 1H), 7.78-7.75 (m, 1H), 7.74-7.66 (m, 4H), 7.65-7.60 (m, 1H), 7.58-7.51 (m, 1H), 2.86 (d, 3H).

LC-MS (Method 4): $R_t$=1.10 min; MS (ESIpos) m/z=432 $[M+H]^+$.

Example 10

$N^5$-{4-[(2-chloro-4-fluorobenzoyl)amino]phenyl}-$N^4$-isopropyl-1H-imidazole-4, 5-dicarboxamide

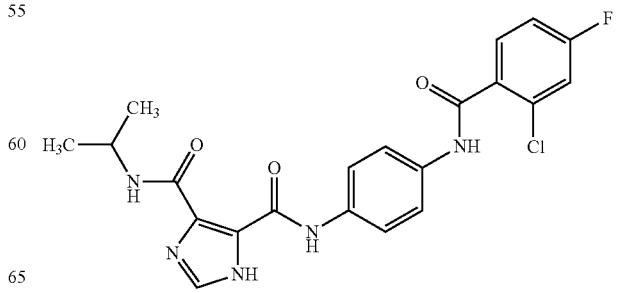

To the crude reaction mixture of N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide (Intermediate 005), 411 µL (4.80 mmol) isopropyl amine were added and the reaction was stirred for 48 hours at 60° C. The reaction mixture was adsorbed on silica and purified by flash chromatography to afford 49 mg of the title compound as a solid material.

$^1$H-NMR (300 MHz, DMSO-d$_6$), δ [ppm]=1.22 (d, 6H), 4.17 (m, 1H), 7.34 (m, 1H), 7.57 (m, 1H), 7.62-7.84 (5H), 7.91 (s, 1H), 8.50 (s, 1H), 10.50 (s, 1H), 13.34 (s, 1H), 13.59 (s, 1H).

Example 11

N$^5$-{4-[(2-chloro-4-fluorobenzoyl)amino]phenyl}-N$^4$-methyl-1,3-oxazole-4,5-dicarboxamide

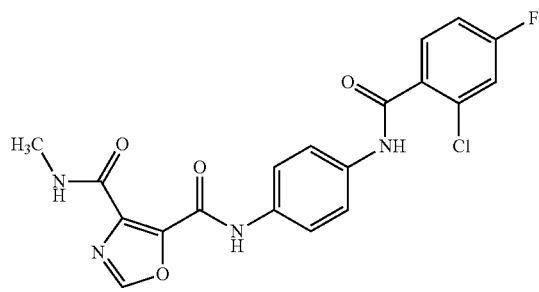

90 mg (0.22 mmol) methyl 5-({4-[(2-chloro-4-fluorobenzoyl)amino]phenyl}carbamoyl)-1,3-oxazole-4-carboxylate (Example 14) were suspended in 5 mL (10 mmol) of a 2M solution of methylamine in methanol and the reaction was stirred for 5 hours at room temperature. The precipitate was filtered and washed with methanol to afford 80 mg of the title compound as a solid material.

$^1$H-NMR (300 MHz, DMSO-d$_6$), δ [ppm]=2.89 (d, 3H), 7.35 (m, 1H), 7.56 (m, 1H), 7.61-7.83 (5H), 8.76 (s, 1H), 9.12 (s, 1H), 10.53 (s, 1H), 13.28 (s, 1H).

Example 12

N$^5$-{4-[(2-chloro-4-fluorobenzoyl)amino]phenyl}-N$^4$-methyl-1H-imidazole-4,5-dicarboxamide

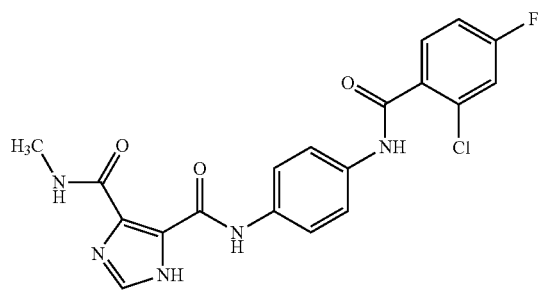 [SMILES: CNC(=O)c1nc[nH]c1C(=O)Nc1ccc(NC(=O)c2ccc(F)cc2Cl)cc1]

In 720 mL THF, a mixture of 8.09 g (40.7 mmol) N$^5$-(4-amino-phenyl)-N$^4$-methyl-1H-imidazole-4,5-dicarboxamide (Intermediate 003), 5.59 mL (40.7 mmol) 2-chloro-4-fluoro-benzoyl chloride and 5.15 mL (37 mmol) triethylamine was stirred for 2 h at room temperature.

300 mL THF, 3.6 mL triethylamine and 2.5 mL 2-chloro-4-fluoro-benzoyl chloride were added and stirring was continued to 1.5 h.

2.5 mL triethylamine and 2.5 mL 2chloro-4-fluoro-benzoyl chloride were added and stirring was continued for another 1.5 h.

The suspension was concentrated and dried in vacuo. The precipitate was suspended in a mixture of 500 mL 1N aqueous sodium hydroxide solution and 300 mL methanol and stirred for 30 min at 40° C. (water bath). The pH of the mixture was adjusted to 7 by addition of 3N aqueous hydrochloric acid. The precipitate was filtered off and washed with water and dried.

The crude material was purified by flash chromatography to give a material which was digested in methanol to give 7.59 g (49% yield) of the title compound as solid material.

$^1$H-NMR (500 MHz, DMSO-d$_6$): δ [ppm]=2.86 (d, 3H), 7.34 (td, 1H), 7.57 (dd, 1H), 7.64-7.74 (m, 5H), 7.91 (s, 1H), 8.81 (d, 1H), 10.49 (s, 1H), 13.40 (s, 1H), 13.66 (s, 1H).

LC-MS (Method 1): R$_t$=1.00 min; MS (ESIpos) m/z=416 [M+H]$^+$.

Example 13

Methyl 5-({4-[(2-chloro-4-fluorobenzoyl)amino]phenyl}carbamoyl)-1H-imidazole-4-carboxylate

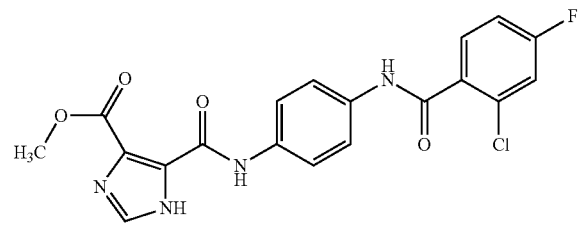 [SMILES: COC(=O)c1nc[nH]c1C(=O)Nc1ccc(NC(=O)c2ccc(F)cc2Cl)cc1]

To a mixture of 281 mg (1.079 mmol) methyl 5-[(4-aminophenyl)carbamoyl]-1H-imidazole-4-carboxylate (Intermediate 015) in 15.8 mL THF, 0.17 mL (1.187 mmol) triethylamine and 0.16 mL (1.187 mmol) 2-chloro-4-fluorobenzoyl chloride were subsequently added and the mixture was stirred for additional 2 h at room temperature. The reaction mixture was concentrated in vacuo and the residue was purified by flash column chromatography (dichloromethane/methanol-gradient) to give after washing with dichloromethane 69 mg of the title compound as a solid material.

$^1$H-NMR (300 MHz, DMSO-d$_6$), δ [ppm]=13.67-13.50 (m, 1H), 11.94-11.78 (m, 1H), 10.51 (br. s., 1H), 7.92 (s, 1H), 7.75-7.64 (m, 5H), 7.61-7.55 (m, 1H), 7.37-7.29 (m, 1H), 3.91 (br. s., 3H).

LC-MS (Method 5): R$_t$=0.99 min; MS (ESIpos) m/z=417 [M+H]$^+$.

Example 14

Methyl 5-({4-[(2-chloro-4-fluorobenzoyl)amino]phenyl}carbamoyl)-1,3-oxazole-4-carboxylate

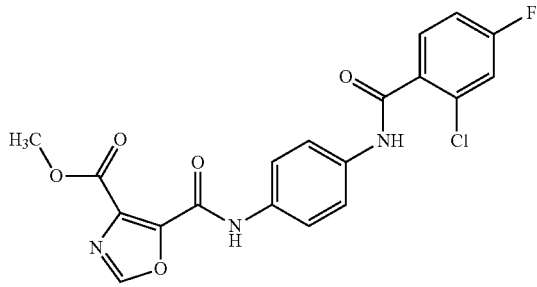 [SMILES: COC(=O)c1ncoc1C(=O)Nc1ccc(NC(=O)c2ccc(F)cc2Cl)cc1]

To a suspension of 400 mg (1.11 mmol) ({4-[(2-chloro-4-fluorobenzoyl)amino]-phenyl}amino)(oxo)acetyl chloride (Intermediate 006) in 5 mL dioxane, 90 mg (1.32 mmol) imidazole, 0.5 mL (3.60 mmol) triethylamine and 0.1 mL (1.11 mmol) methyl isocyanoacetate were subsequently added and the mixture was stirred for 2 hours at 90° C. The reaction was then cooled to room temperature and 50 mL water was added. The solids were filtered off and after washing with water (4 times) the residue was dissolved in 75 mL methanol and 75 mL dichloromethane. The suspension was filtered through a pad of celite. The filtrate was concentrated to 10 mL and the solids were filtered off to give after washing with methanol 128 mg of the title compound as a solid material.

$^1$H-NMR (300 MHz, DMSO-$d_6$), δ [ppm]=3.91 (s, 3H), 7.35 (m, 1H), 7.57 (m, 1H), 7.62-7.82 (5H), 8.72 (s, 1H), 10.54 (s, 1H), 11.16 (s, 1H).

Example 15

$N^5$-{4-[(2-chloro-4-fluorobenzoyl)amino]phenyl}-$N^4$-isopropyl-1,3-oxazole-4,5-dicarboxamide

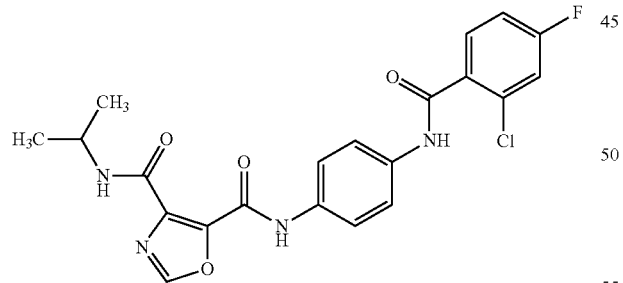

To a suspension of 60 mg (0.14 mmol) methyl 5-({4-[(2-chloro-4-fluorobenzoyl)amino]phenyl}carbamoyl)-1,3-oxazole-4-carboxylate (Example 14) in 1 mL methanol, 0.2 mL (2.33 mmol) isopropyl amine were added and the reaction was stirred for 8 hours at room temperature. The precipitate was filtered off and washed with methanol to afford 40 mg of the title compound as a solid material.

$^1$H-NMR (300 MHz, DMSO-$d_6$), δ [ppm]=1.23 (d, 6H), 4.24 (m, 1H), 7.29-7.40 (m, 1H), 7.53-7.61 (1H), 7.63-7.83 (m, 5H), 8.78 (s, 1H), 8.89-9.02 (m, 1H), 10.53 (s, 1H), 13.28 (s, 1H).

Example 16

$N^5$-{6-[(2-chloro-4-fluorobenzoyl)amino]pyridin-3-yl}-$N^4$-methyl-1H-imidazole-4,5-dicarboxamide

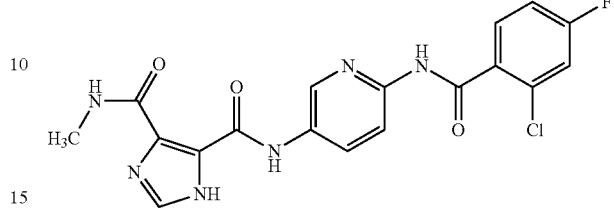

To a mixture of 180 mg (0.692 mmol) $N^5$-(6-aminopyridin-3-yl)-$N^4$-methyl-1H-imidazole-4,5-dicarboxamide (Intermediate 016) in 10.1 mL THF, 0.11 mL (0.761 mmol) triethylamine and 0.10 mL (0.761 mmol) 2-chloro-4-fluorobenzoyl chloride were subsequently added and the mixture was stirred for additional 3 h at room temperature. The reaction mixture was concentrated in vacuo and the residue was purified by flash column chromatography (dichloromethane/methanol-gradient) to give after washing with methanol 11 mg of the title compound as a solid material.

$^1$H-NMR (300 MHz, DMSO-$d_6$), δ [ppm]=13.93-13.80 (m, 1H), 13.58-13.40 (m, 1H), 11.13-10.98 (m, 1H), 8.94-8.84 (m, 1H), 8.77-8.63 (m, 1H), 8.32-8.06 (m, 2H), 7.95 (s, 1H), 7.69-7.61 (m, 1H), 7.59-7.50 (m, 1H), 7.36-7.23 (m, 1H), 2.90-2.83 (m, 3H).

LC-MS (Method 5): $R_t$=1.00 min; MS (ESIpos) m/z=417 [M+H]$^+$.

Example 17

$N^5$-(4-{[(5-chloro-1-methyl-3-phenyl-1H-pyrazol-4-yl)carbonyl]amino}phenyl)-$N^4$-methyl-1H-imidazole-4,5-dicarboxamide

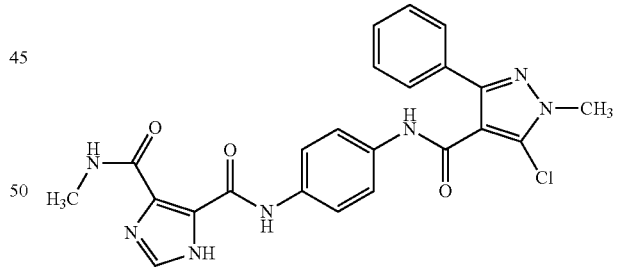

In 5.00 mL DMF, a mixture of 200 mg (0.771 mmol) $N^5$-(4-aminophenyl)-$N^4$-methyl-1H-imidazole-4,5-dicarboxamide (Intermediate 003), 183 mg (0.771 mmol) 5-chloro-1-methyl-3-phenyl-1H-pyrazole-4-carboxylic acid, 293 mg (0.771 mmol) HATU and 0.40 mL (2.314 mmol) N,N-diisopropylethylamine was stirred for 3 days at room temperature. The resulting precipitate was filtered off and purified by preparative HPLC to yield 117 mg of the title compound as a solid material.

$^1$H-NMR (300 MHz, DMSO-$d_6$), δ [ppm]=13.68-13.58 (m, 1H), 13.39 (br. s., 1H), 10.40 (s, 1H), 8.88-8.73 (m, 1H), 7.90 (s, 1H), 7.72-7.60 (m, 6H), 7.44-7.31 (m, 3H), 3.91 (s, 3H), 2.86 (d, 3H).

LC-MS (Method 3): $R_t$=1.03 min; MS (ESIpos) m/z=478 [M+H]$^+$.

Example 18

N$^4$-benzyl-N$^5$-{4-[(2-chloro-4-fluorobenzoyl)amino]phenyl}-1H-imidazole-4,5-dicarboxamide

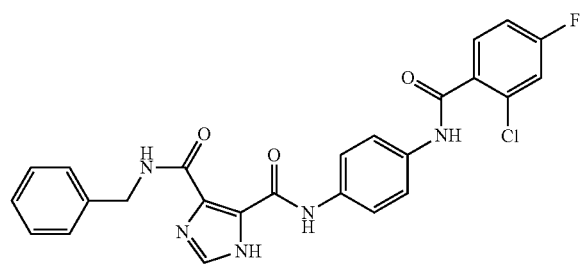 [SMILES: O=C(Nc1ccc(NC(=O)c2[nH]cnc2C(=O)NCc2ccccc2)cc1)c1ccc(F)cc1Cl]

To the crude reaction mixture of N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide (Intermediate 005) 210 µL (1.92 mmol) benzylamin were added and the reaction was stirred for 48 hours at room temperature. The reaction mixture was adsorbed on silica and purified by flash chromatography to afford 68 mg of the title compound as a solid material.

$^1$H-NMR (300 MHz, DMSO-d$_6$), δ [ppm]=4.57 (d, 2H), 7.25 (m, 1H), 7.30-7.45 (5H), 7.57 (m, 1H), 7.62-7.79 (5H) 7.95 (s, 1H), 9.50 (s, 1H), 10.49 (s, 3H), 13.38 (s, 1H).

Example 19

N$^4$-methyl-N$^5$-{4-[(2-methylbenzoyl)amino]phenyl}-1H-imidazole-4,5-dicarboxamide

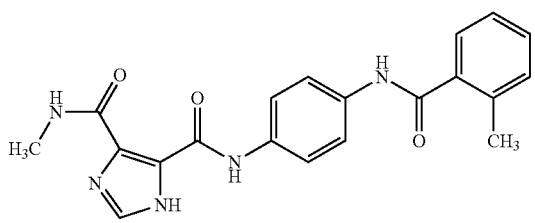 [SMILES: CNC(=O)c1nc[nH]c1C(=O)Nc1ccc(NC(=O)c2ccccc2C)cc1]

In 15.64 mL THF, a mixture of 200 mg (0.771 mmol) N$^5$-(4-amino-phenyl)-N$^4$-methyl-1H-imidazole-4,5-dicarboxamide (Intermediate 003), 0.10 mL (0.771 mmol) 2-methylbenzoyl chloride and 0.11 mL (0.771 mmol) triethylamine was stirred for 3 days at room temperature. The resulting precipitate was filtered off and purified by preparative HPLC to yield 60 mg of the title compound as a solid material.

$^1$H-NMR (300 MHz, DMSO-d$_6$), δ [ppm]=13.72-13.56 (m, 1H), 13.46-13.36 (m, 1H), 10.29 (s, 1H), 8.91-8.75 (m, 1H), 7.91 (s, 1H), 7.79-7.63 (m, 4H), 7.48-7.42 (m, 1H), 7.42-7.35 (m, 1H), 7.34-7.24 (m, 2H), 2.86 (d, 3H), 2.38 (s, 3H).

LC-MS (Method 4): $R_t$=0.99 min; MS (ESIpos) m/z=378 [M+H]$^+$.

Example 20

N$^5$-{4-[(4-fluorobenzoyl)amino]phenyl}-N$^4$-methyl-1H-imidazole-4,5-dicarboxamide

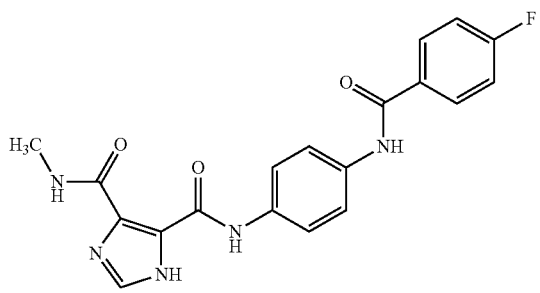 [SMILES: CNC(=O)c1nc[nH]c1C(=O)Nc1ccc(NC(=O)c2ccc(F)cc2)cc1]

260 mg (1.00 mmol) N$^5$-(4-aminophenyl)-N$^4$-methyl-1H-imidazole-4,5-dicarboxamide (Intermediate 003) were suspended in 10 mL dry tetrahydrofuran and 7.5 mL (45.5 mmol) N-ethyl-N,N-diisopropylamine were added. After stirring for 10 minutes at room temperature 476 mg (3.00 mmol) 4-fluorobenzoyl chloride were added and the reaction was stirred for 1 hour at room temperature. 10 mL of a 5N sodium hydroxide solution were added and the mixture was stirred for additional 30 minutes. The phases were separated and the aqueous phase was extracted three times with ethyl acetate. The combined organic phases were dried over sodium sulfate, and the solvent was removed under reduced pressure. The crude product was purified by flash chromatography to give 267 mg of the title compound as a solid material.

$^1$H-NMR (300 MHz, DMSO-d$_6$), δ [ppm]=2.87 (d, 3H), 7.34-7.39 (2H), 7.69 (d, 2H), 7.78 (d, 2H), 7.92 (s, 1H), 8.03-8-07 (2H), 8.84 (d, 1H), 10.29 (s, 1H), 13.43 (s, 1H), 13.69 (s, 1H).

Example 21

N$^5$-[4-(benzoylamino)phenyl]-N$^4$-methyl-1H-imidazole-4,5-dicarboxamide

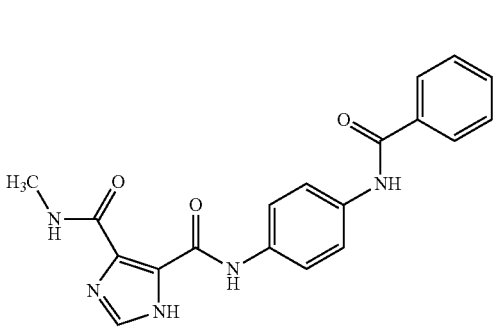 [SMILES: CNC(=O)c1nc[nH]c1C(=O)Nc1ccc(NC(=O)c2ccccc2)cc1]

260 mg (1.00 mmol) N$^5$-(4-aminophenyl)-N$^4$-methyl-1H-imidazole-4,5-dicarboxamide (Intermediate 003) were suspended in 10 mL dry tetrahydrofuran and 7.5 mL (45.5 mmol) N-ethyl-N,N-diisopropylamine were added. After stirring for 10 minutes at room temperature 248 µL (3.00 mmol) benzoyl chloride were added and the reaction was stirred for 1 hour at room temperature. 10 mL of a 5N sodium hydroxide solution were added and the mixture was stirred for additional 30 minutes, the phases were separated and the aqueous phase was extracted three times with ethyl acetate. The combined organic phases were dried over sodium sulfate, and the solvent was removed under reduced pressure. The crude product was purified by flash chromatography to give 310 mg of the title compound as a solid material.

¹H-NMR (300 MHz, DMSO-d₆), δ [ppm]=2.88 (d, 3H), 7.51-7.61 (3H), 7.70 (bd, 2H), 7.79 (d, 2H), 7.91 (s, 1H), 7.96-7.98 (2H), 8.81 (bs, 1H), 10.25 (s, 1H), 13.40 (bs, 1H), 13.66 (bs, 1H).

Example 22

N⁴-{4-[(2-chloro-4-fluorobenzoyl)amino]phenyl}-N⁵-[2-(dimethylamino)ethyl]-1H-imidazole-4,5-dicarboxamide

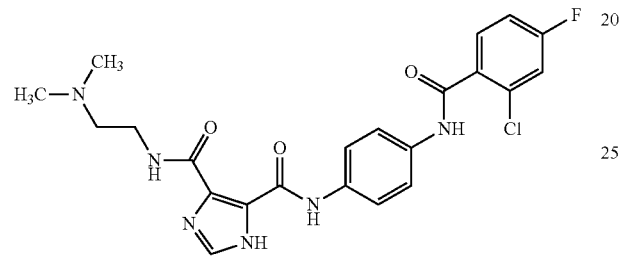

123 mg (0.16 mmol) N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide (Intermediate 005) were suspended in 174 µL (1.6 mmol) N,N-dimethyl-ethylendiamine. The mixture was stirred for 4 days at room temperature.

The reaction mixture was concentrated and the obtained crude material was purified by preparative HPLC to give 30 mg (39% yield) of the title compound as solid material.

¹H-NMR (300 MHz, DMSO-d₆): δ [ppm]=13.68-13.24 (m, 2H), 10.49 (s, 1H), 8.73-8.47 (m, 1H), 7.90 (s, 1H), 7.78-7.64 (m, 5H), 7.57 (dd, 1H), 7.34 (td, 1H), 3.43 (q, 2H), 2.19 (s, 6H), 1.23 (br. s., 2H).

LC-MS (Method 1): R_t=0.76 min; MS (ESIpos) m/z=473 [M+H]⁺.

Example 23

N⁵-{4-[(4-fluoro-2,6-dimethylbenzoyl)amino]phenyl}-N⁴-methyl-1H-imidazole-4,5-dicarboxamide

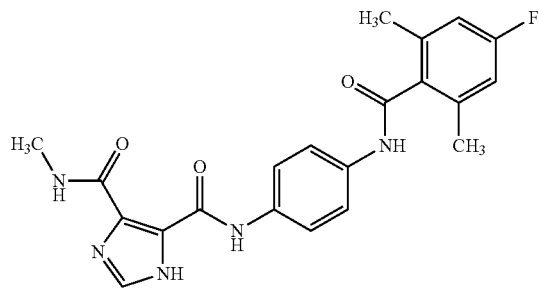 [SMILES: CNC(=O)c1nc[nH]c1C(=O)Nc1ccc(NC(=O)c2c(C)cc(F)cc2C)cc1]

260 mg (1.00 mmol) N⁵-(4-aminophenyl)-N⁴-methyl-1H-imidazole-4,5-dicarboxamide (Intermediate 003) were suspended in 10 mL dry tetrahydrofuran and 7.5 mL (45.5 mmol) N-ethyl-N,N-diisopropylamine were added. After stirring for 10 minutes at room temperature 187 mg (1.00 mmol) 4-fluoro-2,6-dimethylbenzoyl chloride were added and the reaction was stirred for 16 hours at room temperature. 10 mL of a 5N sodium hydroxide solution were added to the reaction and the mixture was stirred for additional 10 minutes, the phases were separated and the aqueous phase was extracted three times with ethyl acetate. The combined organic phases were dried over sodium sulfate, and the solvent was removed under reduced pressure. The crude product was purified by flash chromatography to give 60 mg of the title compound as a solid material.

¹H-NMR (300 MHz, DMSO-d₆), δ [ppm]=2.87 (d, 3H), 6.68 (d, 2H), 7.70-7.73 (4H), 7.91 (s, 1H), 8.80 (bs, 1H), 10.36 (s, 1H), 13.39 (bs, 1H), 13.65 (bs, 1H).

Example 24

N⁵-{4-[(2-chloro-4-fluorobenzoyl)amino]phenyl}-N⁴,N⁴-dimethyl-1H-imidazole-4,5-dicarboxamide

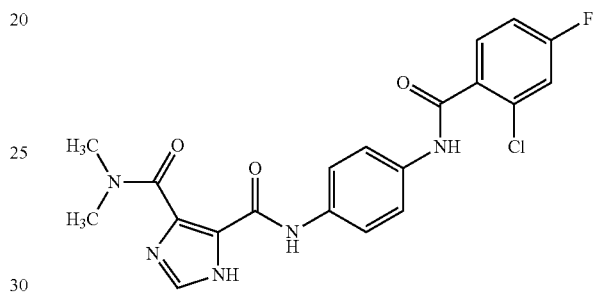

To the crude reaction mixture of N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide (Intermediate 005) 2.4 mL (4.8 mmol) of a 2M solution of dimethyl amine in tetrahydrofuran were added and the reaction was stirred for 18 hours at room temperature. The reaction mixture was adsorbed on silica and purified by flash chromatography to afford 106 mg of the title compound as a solid material.

¹H-NMR (300 MHz, DMSO-d₆), δ [ppm]=3.08 (s, 3H), 3.31 (s, 3H), 7.27-7.42 (m, 1H), 7.52-7.62 (m, 1H), 7.62-7.77 (m, 5H) 7.88 (s, 1H), 10.48 (s, 1H), 12.23 (s, 1H), 13.30 (s, 1H).

Example 25

N⁵-[4-({2-chloro-4-[2-(dimethylamino)ethoxy]benzoyl}amino)phenyl]-N⁴-methyl-1H-imidazole-4,5-dicarboxamide

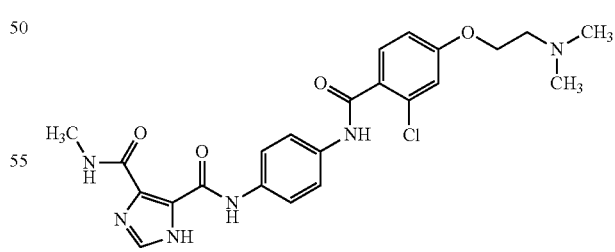

166 mg (0.64 mmol) N⁵-(4-aminophenyl)-N⁴-methyl-1H-imidazole-4,5-dicarboxamide (Intermediate 003) were suspended in 5 mL dry tetrahydrofuran. 402 µL (2.30 mmol) N-ethyl-N,N-diisopropylamine and a solution of 121 mg (0.64 mmol) 2-chloro-4-[2-(dimethylamino)ethoxy]benzoyl chloride in 5 mL dry tetrahydrofuran were added. After stirring for 16 hours at room temperature 7 ml water and 7 mL of a saturated sodium carbonate solution was added to the reaction and the mixture was stirred for additional 10 minutes. The phases were separated and the aqueous phase was extracted three times with ethyl acetate. The combined organic phases were dried over magnesium sulfate, and the solvent was removed under reduced pressure. The crude product was purified by flash chromatography to give 100 mg of the title compound as a solid material.

$^1$H-NMR (300 MHz, DMSO-$d_6$), δ [ppm]=2.21 (s, 5H), 2.61-2.67 (t, 2H), 2.84-2.91 (d, 3H), 3.24 (s, 2H), 4.40-4.17 (t, 2H), 6.99-7.05 (m, 1H), 7.12-7.16 (m, 1H), 7.50-7.56 (d, 1H), 7.67-7.80 (4H), 7.90 (s, 1H), 8.87 (s, 1H), 10.36 (s, 1H), 13.45 (s, 1H).

LC-MS (Method 6): $R_t$=2.9 min; MS (ESIpos) m/z=485.3 [M+H]$^+$.

Example 26

$N^5$-{4-[(2,6-dichlorobenzoyl)amino]phenyl}-$N^4$-methyl-1H-imidazole-4,5-dicarboxamide

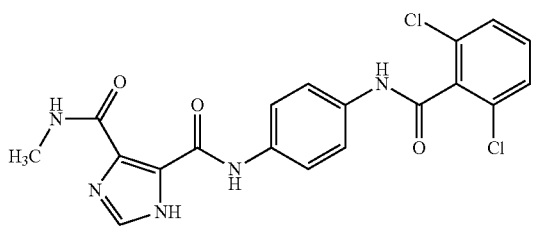 [SMILES: CNC(=O)c1nc[nH]c1C(=O)Nc1ccc(NC(=O)c2c(Cl)cccc2Cl)cc1]

To a mixture of 200 mg (80% pure, 0.617 mmol) $N^5$-(4-aminophenyl)-$N^4$-methyl-1H-imidazole-4,5-dicarboxamide (Intermediate 003) in 12.5 mL THF, 0.09 mL (0.617 mmol) triethylamine and 0.09 mL (0.617 mmol) 2,6-dichlorobenzoyl chloride were subsequently added and the mixture was stirred for additional 90 min. at room temperature. The reaction mixture was concentrated in vacuo and the residue was purified by flash column chromatography (dichloromethane/acetone-gradient). The product containing eluent was collected and concentrated in vacuo which resulted in a suspension. The precipitate was filtered, washed with dichloromethane and dried under high vacuum to give 92 mg of the title compound as a solid material.

$^1$H-NMR (300 MHz, DMSO-$d_6$), δ [ppm]=13.74-13.59 (m, 1H), 13.40 (br. s., 1H), 10.72 (s, 1H), 8.89-8.73 (m, 1H), 7.91 (s, 1H), 7.75-7.65 (m, 4H), 7.61-7.54 (m, 2H), 7.52-7.45 (m, 1H), 2.87 (d, 3H).

LC-MS (Method 5): $R_t$=0.93 min; MS (ESIpos) m/z=433 [M+H]$^+$.

Example 27

$N^5$-{4-[(2-chlorobenzoyl)amino]phenyl}-$N^4$-methyl-1H-imidazole-4,5-dicarboxamide

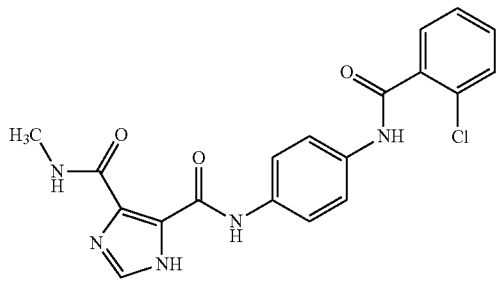 [SMILES: CNC(=O)c1nc[nH]c1C(=O)Nc1ccc(NC(=O)c2ccccc2Cl)cc1]

130 mg (0.50 mmol) $N^5$-(4-aminophenyl)-$N^4$-methyl-1H-imidazole-4,5-dicarboxamide (Intermediate 003) were suspended in 10 mL dry tetrahydrofuran and 3.75 mL (22.7 mmol) N-ethyl-N,N-diisopropylamine were added. After stirring for 10 minutes at room temperature 190 μL (1.50 mmol) 2-chlorobenzoyl chloride were added and the reaction was stirred for 1 hour at room temperature. 10 mL of a 5N sodium hydroxide solution were added to the reaction and the mixture was stirred for additional 30 minutes, the phases were separated and the aqueous phase was extracted three times with ethyl acetate. The combined organic phases were dried over sodium sulfate, and the solvent was removed under reduced pressure. The crude product was purified by flash chromatography to give 170 mg of the title compound as a solid material.

$^1$H-NMR (300 MHz, DMSO-$d_6$), δ [ppm]=2.87 (d, 3H), 7.47 (m, 1H), 7.49-7.49 (m, 1H), 7.56-7.60 2H), 7.69-7.74 (4H), 8.85 (bs, 1H), 10.52 (s, 1H), 13.41 (bs, 1H), 13.65 (bs, 1H).

Example 28

$N^5$-[4-({2-chloro-4-[2-(4-methylpiperazin-1-yl)ethoxy]benzoyl}amino)phenyl]-$N^4$-methyl-1H-imidazole-4,5-dicarboxamide

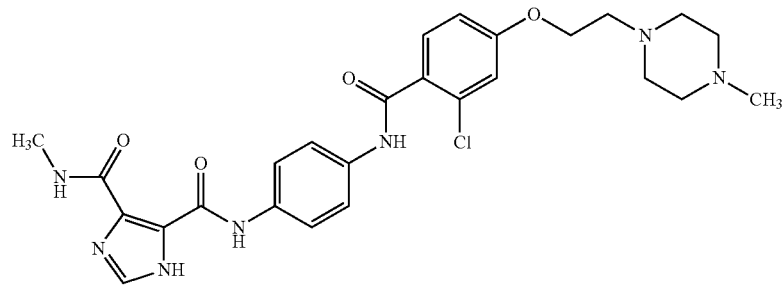

120 mg (0.46 mmol) $N^5$-(4-aminophenyl)-$N^4$-methyl-1H-imidazole-4,5-dicarboxamide (Intermediate 003) were suspended in 5 mL dry tetrahydrofuran. 402 μL (2.30 mmol) N-ethyl-N,N-diisopropylamine and a solution of 215 mg (0.46 mmol) 2-chloro-4-[2-(4-methylpiperazin-1-yl)ethoxy] benzoyl chloride (contains 32% sodiumchloride) in 5 mL dry DCM were added. After stirring for 16 hours at room temperature 7 mL water and 7 mL of a saturated sodium carbonate solution were added to the reaction and the mixture was stirred for additional 10 minutes. The phases were separated and the aqueous phase was extracted three times with ethyl acetate. The combined organic phases were dried over magnesium sulfate, and the solvent was removed under reduced pressure. The crude product was purified by flash chromatography to give 104 mg of the title compound as a solid material.

$^1$H-NMR (300 MHz, DMSO-d$_6$), δ [ppm]=2.14 (s, 3H), 2.31 (s, 4H), 2.48 (s, 2H), 2.65-2.73 (t, 2H), 2.84-2.91 (d, 3H), 3.13-3.28 (2H), 4.12-4.22 (t, 2H), 6.99-7.05 (m, 1H), 7.12-7.16 (m, 1H), 7.48-7.55 (d, 1H), 7.67-7.76 (4H), 7.89 (s, 1H), 9.05 (s, 1H), 10.34 (s, 1H), 13.18 (s, 1H).

LC-MS (Method 6): R$_t$=2.9 min; MS (ESIpos) m/z=540.3 [M+H]$^+$.

Example 29

N-{4-[(2-chloro-4-fluorobenzoyl)amino]phenyl}-5-(morpholin-4-ylcarbonyl)-1H-imidazole-4-carboxamide

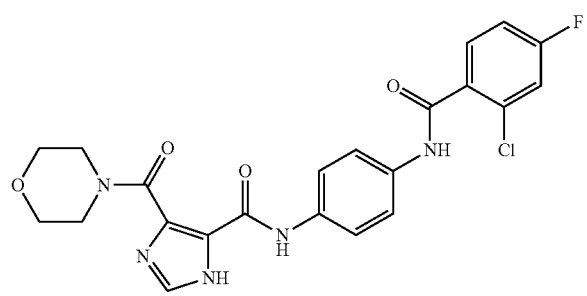 [SMILES: O=C(Nc1ccc(NC(=O)c2[nH]cnc2C(=O)N2CCOCC2)cc1)c1ccc(F)cc1Cl]

123 mg (0.16 mmol) N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide (Intermediate 005) were suspended in 27 µL (0.32 mmol) morpholine and 279 µL (1.6 mmol) N-ethyl-N-isopropylpropan-2-amine. The mixture was stirred for 4 days at room temperature.

The reaction mixture was concentrated and the obtained crude material was purified by preparative HPLC to give 38 mg (50% yield) of the title compound as solid material.

$^1$H-NMR (300 MHz, DMSO-d$_6$): δ [ppm]=13.41 (br. s., 1H), 12.44 (br. s., 1H), 10.48 (s, 1H), 7.89 (s, 1H), 7.78-7.51 (m, 6H), 7.41-7.22 (m, 1H), 4.12 (br. s., 1H), 3.70 (br. s., 6H).

LC-MS (Method 1): R$_t$=0.95 min; MS (ESIpos) m/z=472 [M+H]$^+$.

Example 30

N$^4$-{4-[(2-chloro-4-fluorobenzoyl)amino]phenyl}-N$^5$-(2,2,2-trifluoroethyl)-1H-imidazole-4,5-dicarboxamide

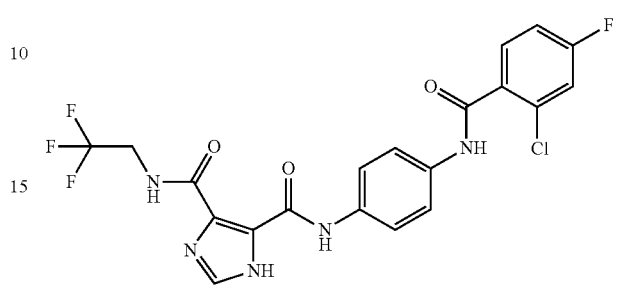

123 mg (0.16 mmol) N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide (Intermediate 005) were suspended in 25 µL (0.32 mmol) 2,2,2-trifluoroethylamine and 279 µL (1.6 mmol) N-ethyl-N-isopropylpropan-2-amine. The mixture was stirred for 4 days at room temperature.

The reaction mixture was concentrated and the obtained crude material was purified by preparative HPLC to give 41 mg (53% yield) of the title compound as solid material.

$^1$H-NMR (400 MHz, DMSO-d$_6$): δ [ppm]=13.55 (br. s., 1H), 10.51 (s, 1H), 7.98 (s, 1H), 7.74-7.64 (m, 5H), 7.57 (dd, 1H), 7.34 (td, 1H), 4.25-4.10 (m, 2H)

LC-MS (Method 1): R$_t$=1.16 min; MS (ESIpos) m/z=484 [M+H]$^+$.

Example 31

N$^5$-{4-[(2-chloro-4-fluorobenzoyl)amino]phenyl}-N$^4$-[2-(dimethylamino)ethyl]-1,3-oxazole-4,5-dicarboxamide

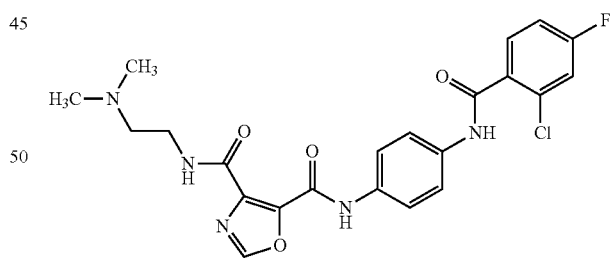

To 63 mg (0.112 mmol) methyl 5-({4-[(2-chloro-4-fluorobenzoyl)amino]phenyl}carbamoyl)-1,3-oxazole-4-carboxylate (Example 14) in 2 mL methanol were added 61 µL (0.56 mmol) N,N-dimethyl-ethylendiamine. The mixture was stirred for 18 h at room temperature.

The reaction mixture was concentrated and the obtained crude material was purified by preparative HPLC to give 18 mg (34% yield) of the title compound as solid material.

$^1$H-NMR (400 MHz, DMSO-d$_6$): δ [ppm]=13.26 (s, 1H), 10.56 (s, 1H), 8.96 (t, 1H), 8.79 (s, 1H), 7.77-7.72 (m, 2H), 7.72-7.65 (m, 3H), 7.60 (dd, 1H), 7.36 (td, 1H), 3.46 (q, 2H), 2.49-2.44 (m, 2H), 2.20 (s, 6H).

Example 32

N⁴-{4-[(2-chloro-4-fluorobenzoyl)amino]phenyl}-N⁵-[2-(piperidin-1-yl)ethyl]-1H-imidazole-4,5-dicarboxamide

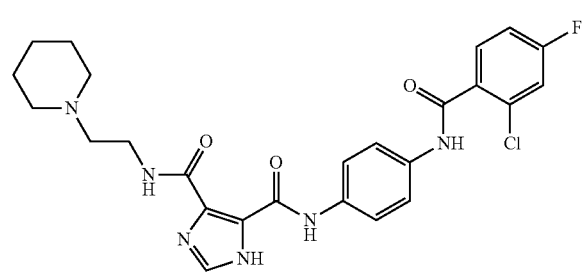 [SMILES: O=C(Nc1ccc(NC(=O)c2[nH]cnc2C(=O)NCCN2CCCCC2)cc1)c1ccc(F)cc1Cl]

123 mg (0.16 mmol) N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide (Intermediate 005) were suspended in 46 μL (0.32 mmol) 2-(piperidin-1-yl)ethanamine and 279 μL (1.6 mmol) N-ethyl-N-isopropylpropan-2-amine. The mixture was stirred for 5 d at room temperature.

The reaction mixture was concentrated and the obtained crude material was purified by preparative HPLC to give 22 mg (27% yield) of the title compound as solid material.

¹H-NMR (400 MHz, DMSO-d₆): δ [ppm]=13.59 (s, 1H), 13.46 (br. s., 1H), 10.52 (s, 1H), 8.67 (br. s., 1H), 7.94 (s, 1H), 7.75-7.65 (m, 5H), 7.60 (dd, 1H), 7.36 (td, 1H), 3.51-3.44 (m, 2H), 2.48-2.40 (m, 2H), 1.52 (br. s., 2H), 1.41 (d, 1H).

LC-MS (Method 1): R$_t$=0.81 min; MS (ESIpos) m/z=513 [M+H]⁺.

Example 33

N⁴-{4-[(4-fluorobenzoyl)amino]phenyl}-N⁵-[2-(piperidin-1-yl)ethyl]-1H-imidazole-4,5-dicarboxamide

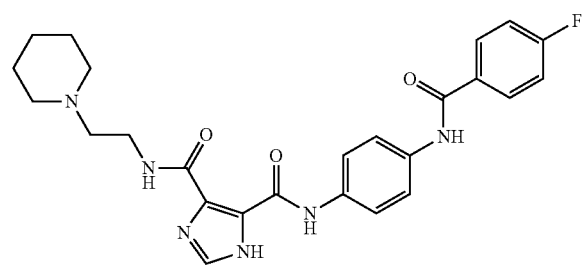 [SMILES: O=C(Nc1ccc(NC(=O)c2[nH]cnc2C(=O)NCCN2CCCCC2)cc1)c1ccc(F)cc1]

112 mg (0.16 mmol) N,N'-bis{4-[(4-fluorobenzoyl)amino]phenyl}-5,10-dioxo-5H,10H-diimidazo[1,5-a:1',5'-d]pyrazine-1,6-dicarboxamide (Intermediate 018) were suspended in 46 μL (0.32 mmol) 2-(piperidin-1-yl)ethanamine and 279 μL (1.6 mmol) N-ethyl-N-isopropylpropan-2-amine. The mixture was stirred for 5 days at room temperature.

The reaction mixture was concentrated and the obtained crude material was purified by preparative HPLC to give 77 mg (99% yield) of the title compound as solid material.

¹H-NMR (400 MHz, DMSO-d₆): δ [ppm]=13.51 (d, 2H), 10.41-10.23 (m, 1H), 8.17-7.90 (m, 3H), 7.85-7.63 (m, 4H), 7.38 (t, 2H), 3.54 (br. s., 2H), 1.78-1.33 (m, 6H).

LC-MS (Method 1): R$_t$=0.78 min; MS (ESIpos) m/z=479 [M+H]⁺.

Example 34

N-{4-[(4-fluorobenzoyl)amino]phenyl}-5-(2-oxa-6-azaspiro[3.3]hept-6-ylcarbonyl)-1H-imidazole-4-carboxamide

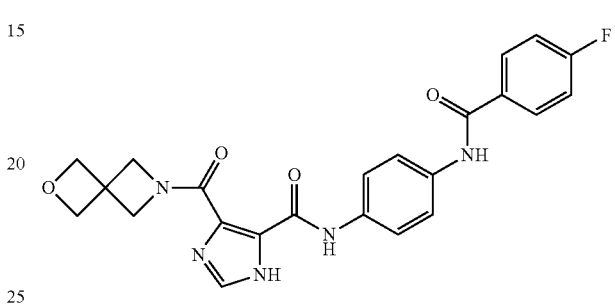

112 mg (0.16 mmol) N,N'-bis{4-[(4-fluorobenzoyl)amino]phenyl}-5,10-dioxo-5H,10H-diimidazo[1,5-a:1',5'-d]pyrazine-1,6-dicarboxamide (Intermediate 018) were suspended in 61 mg (0.32 mmol) 2-oxa-6-azaspiro[3.3]heptane and 279 μL (1.6 mmol) N-ethyl-N-isopropylpropan-2-amine. The mixture was stirred for 5 d at room temperature.

The reaction mixture was concentrated and the obtained crude material was purified by preparative HPLC to give 27 mg (37% yield) of the title compound as solid material.

¹H-NMR (400 MHz, DMSO-d₆): δ [ppm]=13.60 (s, 1H), 13.47 (s, 1H), 10.35-10.19 (m, 1H), 8.12-8.00 (m, 2H), 7.93 (s, 1H), 7.82-7.73 (m, 2H), 7.67 (d, 2H), 7.37 (t, 2H), 4.83 (s, 2H), 4.77-4.67 (m, 4H), 4.33 (s, 2H).

LC-MS (Method 1): R$_t$=0.94 min; MS (ESIpos) m/z=450 [M+H]⁺.

Example 35

N⁵-{4-[(mesitylcarbonyl)amino]phenyl}-N⁴-methyl-1H-imidazole-4,5-dicarboxamide

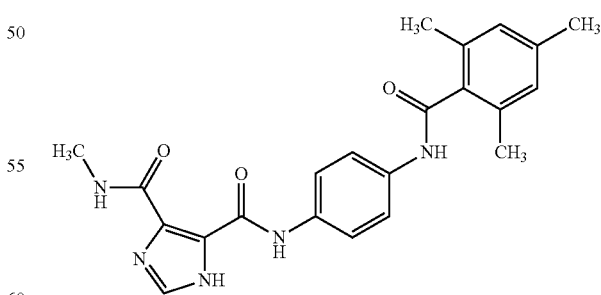

100 mg (0.39 mmol) N⁵-(4-aminophenyl)-N⁴-methyl-1H-imidazole-4,5-dicarboxamide (Intermediate 003) were suspended in 10 mL dry tetrahydrofuran. 53.8 μL (0.39 mmol) triethylamine and 64.3 μL (0.39 mmol) 2,4,6 trimethylbenzoyl chloride were added and the mixture was stirred at room temperature for 2 days. The solvent was removed under reduced pressure and the crude product was purified by HPLC to give 61 mg of the title compound as a solid material.

$^1$H-NMR (300 MHz, DMSO-$d_6$), δ [ppm]=13.76 (br. s., 1H), 13.41 (br. s., 1H), 10.29 (s, 1H), 8.83 (br. s., 1H), 7.91 (s, 1H), 7.77-7.58 (m, 4H), 6.91 (s, 2H), 2.86 (d, 3H), 2.26 (s, 3H) m, 2.23 (m, 6H).

LC-MS (Method 3): $R_t$=1.13 min; MS (ESIpos) m/z=406.3 [M+H]$^+$.

Example 36

$N^5$-(4-{[2-chloro-6-(trifluoromethyl)benzoyl]amino}phenyl)-$N^4$-methyl-1H-imidazole-4,5-dicarboxamide

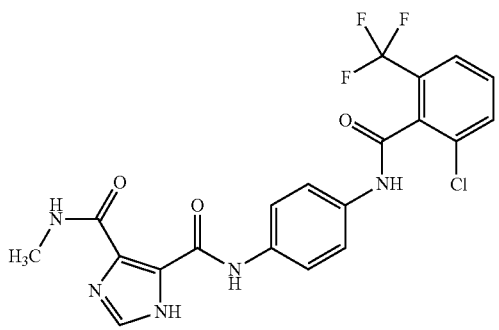 [SMILES: CNC(=O)c1nc[nH]c1C(=O)Nc1ccc(NC(=O)c2c(Cl)cccc2C(F)(F)F)cc1]

100 mg (0.39 mmol) $N^5$-(4-aminophenyl)-$N^4$-methyl-1H-imidazole-4,5-dicarboxamide (Intermediate 003) were suspended in 5 mL dry tetrahydrofuran. 53.8 μL (0.39 mmol) triethylamine and 93.7 mg (0.39 mmol) 2-chloro-6-(trifluormethyl)benzoyl chloride were added and the mixture was stirred at room temperature for 2 days. The solvent was removed under reduced pressure and the crude product was purified by HPLC to give 30 mg of the title compound as a solid material.

$^1$H-NMR (300 MHz, DMSO-$d_6$), δ [ppm]=13.69 (br. s., 1H), 13.43 (br. s., 1H), 10.74 (br. s., 1H), 8.88-8.80 (m, 1H), 7.95-7.93 (m, 2H), 7.89-7.83 (m, 1H), 7.69 (d, 5H), 2.88 (d, 3H).

LC-MS (Method 4): $R_t$=1.06 min; MS (ESIpos) m/z=466.1 [M+H]$^+$.

Example 37

$N^5$-{4-[(2-bromobenzoyl)amino]phenyl}-$N^4$-methyl-1H-imidazole-4,5-dicarboxamide

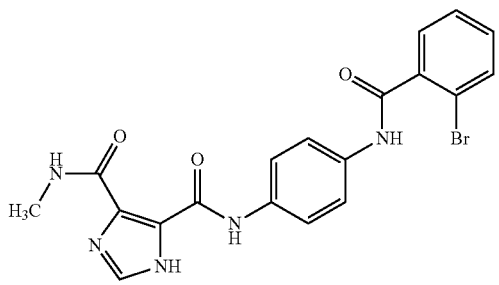

100 mg (0.39 mmol) $N^5$-(4-aminophenyl)-$N^4$-methyl-1H-imidazole-4,5-dicarboxamide (Intermediate 003) were suspended in 5 mL dry tetrahydrofuran. 53.8 μL (0.39 mmol) triethylamine and 84.7 mg (0.39 mmol) 2-bromobenzoyl chloride were subsequently added and the mixture was stirred at room temperature for 4 hours. The solvent was removed under reduced pressure and the crude product was purified by HPLC to give 72 mg of the title compound as a solid material.

$^1$H-NMR (300 MHz, DMSO-$d_6$), δ [ppm]=13.65 (br. s., 1H), 13.40 (br. s., 1H), 10.48 (s, 1H), 8.83 (br. s., 1H), 7.91 (s, 1H), 7.77-7.64 (m, 5H), 7.58-7.53 (m, 1H), 7.51-7.46 (m, 1H), 7.44-7.37 (m, 1H), 2.86 (d, 3H).

LC-MS (Method 1): $R_t$=0.97 min; MS (ESIpos) m/z=441.9 [M+H]$^+$.

Example 38

$N^5$-{4-[(2,6-difluorobenzoyl)amino]phenyl}-$N^4$-methyl-1H-imidazole-4,5-dicarboxamide

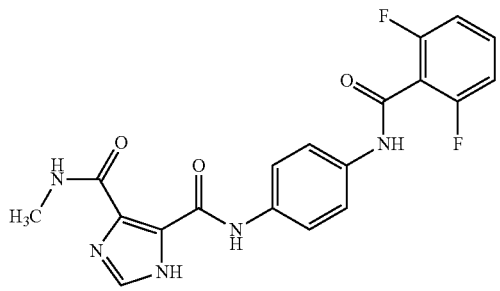 [SMILES: CNC(=O)c1nc[nH]c1C(=O)Nc1ccc(NC(=O)c2c(F)cccc2F)cc1]

100 mg (0.39 mmol) $N^5$-(4-aminophenyl)-$N^4$-methyl-1H-imidazole-4,5-dicarboxamide (Intermediate 003) were suspended in 5 mL dry tetrahydrofuran. 53.8 μL (0.39 mmol) triethylamine and 68.1 mg (0.39 mmol) 2,6-difluorobenzoyl chloride were added and the mixture was stirred at room temperature for 4 hours. The solvent was removed under reduced pressure and the crude product was purified by HPLC to give 45 mg of the title compound as a solid material.

$^1$H-NMR (300 MHz, DMSO-$d_6$), δ [ppm]=13.71 (s, 1H), 13.44 (br. s., 1H), 10.80 (s, 1H), 8.86-8.84 (m, 1H), 7.93 (s, 1H), 7.74-7.66 (m, 4H), 7.64-7.55 (m, 1H), 7.30-7.22 (m, 2H), 2.88 (d, 3H).

LC-MS (Method 4): $R_t$=0.95 min; MS (ESIpos) m/z=400.2 [M+H]$^+$.

Example 39

N⁵-{4-[(2-ethylbenzoyl)amino]phenyl}-N⁴-methyl-1H-imidazole-4,5-dicarboxamide

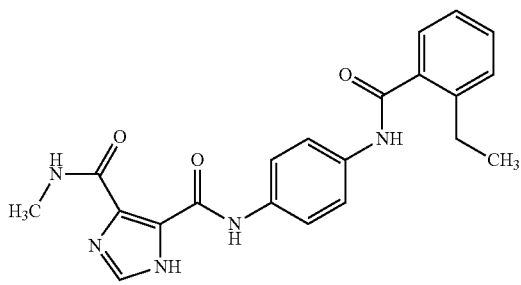 [SMILES: CCc1ccccc1C(=O)Nc1ccc(NC(=O)c2[nH]cnc2C(=O)NC)cc1]

100 mg (0.39 mmol) N⁵-(4-aminophenyl)-N⁴-methyl-1H-imidazole-4,5-dicarboxamide (Intermediate 003) were suspended in 5 mL dry tetrahydrofuran. 53.8 µL (0.39 mmol) triethylamine and 65.0 mg (0.39 mmol) 2-ethylbenzoyl chloride were added and the mixture was stirred at room temperature for 18 hours. The solvent was removed under reduced pressure and the crude product was purified by HPLC to give 51 mg of the title compound as a solid material.

¹H-NMR (300 MHz, DMSO-d₆), δ [ppm]=13.65 (s, 1H), 13.42 (s, 1H), 10.35 (s, 1H), 8.83 (d, 1H), 7.93 (s, 1H), 7.80-7.59 (m, 4H), 7.49-7.39 (m, 2H), 7.37-7.22 (m, 2H), 2.88 (d, 3H), 2.75 (q, 2H), 1.18 (t, 3H).

LC-MS (Method 4): $R_t$=1.07 min; MS (ESIpos) m/z=392.3 [M+H]⁺.

Example 40

N⁴-methyl-N⁵-{4-[(2,3,4-trimethoxybenzoyl)amino]phenyl}-1H-imidazole-4,5-dicarboxamide

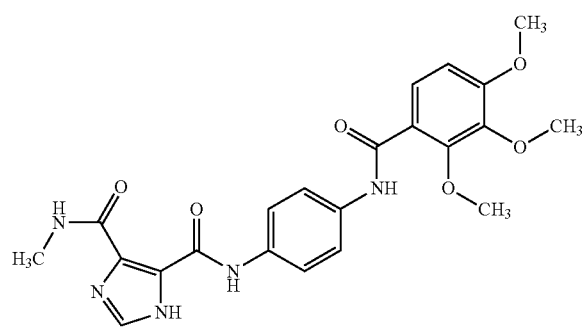

100 mg (0.39 mmol) N⁵-(4-aminophenyl)-N⁴-methyl-1H-imidazole-4,5-dicarboxamide (Intermediate 003) were suspended in 5 mL dry tetrahydrofuran. 53.8 µL (0.39 mmol) triethylamine and 88.9 mg (0.39 mmol) 2,3,4-trimethoxybenzoyl chloride were added and the mixture was stirred at room temperature for 4 hours. The solvent was removed under reduced pressure and the crude product was purified by HPLC to give 73 mg of the title compound as a solid material.

¹H-NMR (300 MHz, DMSO-d₆), δ [ppm]=13.64 (s, 1H), 13.40 (br. s., 1H), 10.08 (s, 1H), 8.80 (d, 1H), 7.91 (s, 1H), 7.77-7.62 (m, 4H), 7.42 (d, 1H), 6.93 (d, 1H), 3.90 (s, 3H), 3.85 (s, 3H), 3.79 (s, 3H), 2.86 (d, 3H).

LC-MS (Method 4): $R_t$=1.06 min; MS (ESIpos) m/z=454.2 [M+H]⁺.

Example 41

N-{4-[(2-chloro-4-fluorobenzoyl)amino]phenyl}-4-[(3-fluoroazetidin-1-yl)carbonyl]-1H-imidazole-5-carboxamide

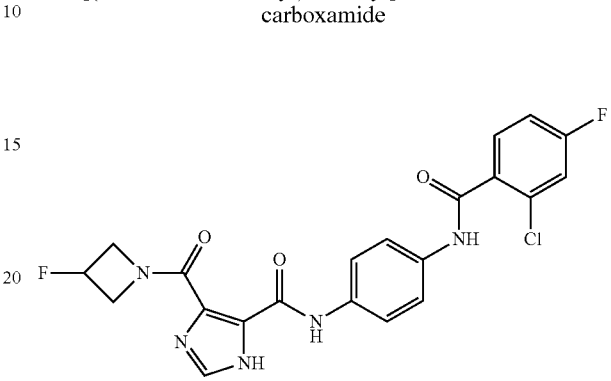

To the crude reaction mixture of phenyl-5-({4-[(2-chloro-4-fluorobenzoyl)amino]phenyl}carbamoyl)-1H-imidazole-4-carboxylate (0.28 mmol, Intermediate 021) were added 37.9 mg (0.34 mmol) 3-fluoroazetidine and 39 µL (0.28 mmol) triethylamine and the mixture was stirred for 36 hours at 50° C. The reaction mixture was concentrated in vacuo and the residue was purified by flash column chromatography (dichloromethane/methanol-gradient) to give after washing with methanol and diisopropylether (1:10) 47 mg of the title compound as a solid material.

¹H-NMR (400 MHz, DMSO-d₆), δ [ppm]=13.58-13.40 (m, 2H), 10.49 (s, 1H), 7.92 (s, 1H), 7.76-7.62 (m, 5H), 7.57 (dd, 1H), 7.34 (td, 1H), 5.53-5.38 (m, 1H), 5.04-4.92 (m, 1H), 4.74-4.62 (m, 1H), 4.55-4.44 (m, 1H), 4.25-4.13 (m, 1H).

LC-MS (Method 5): $R_t$=0.93 min; MS (ESIpos) m/z=459.9 [M+H]⁺.

Example 42

N⁵-{4-[(2-chloro-4-fluorobenzoyl)amino]phenyl}-N⁴-(2-cyclopentylethyl)-1H-imidazole-4,5-dicarboxamide

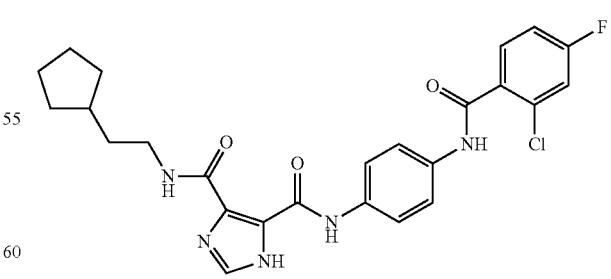

To the crude reaction mixture of phenyl-5-({4-[(2-chloro-4-fluorobenzoyl)amino]phenyl}carbamoyl)-1H-imidazole-4-carboxylate (0.28 mmol, Intermediate 021) were added 38.4 mg (0.34 mmol) 2-cyclopentylethanamine and the mixture was stirred for 36 hours at 50° C. The reaction mixture was concentrated in vacuo and the residue was purified by flash column chromatography (dichloromethane/methanol-gradient) to give 30 mg of the title compound as a solid material.

¹H-NMR (400 MHz, DMSO-d₆), δ [ppm]=13.64 (br. s., 1H), 13.42 (br. s., 1H), 10.52 (s, 1H), 8.97-8.70 (m, 1H), 7.92 (s, 1H), 7.76-7.65 (m, 5H), 7.60 (dd, 1H), 7.36 (td, 1H), 3.40-3.34 (m, 2H), 1.80 (br. s., 3H), 1.64-1.55 (m, 4H), 1.55-1.44 (m, 2H), 1.29-1.06 (m, 2H).

LC-MS (Method 11): $R_t$=1.42 min; MS (ESIpos) m/z=498 [M+H]⁺.

Example 43

N⁵-{4-[(2-chloro-4-fluorobenzoyl)amino]phenyl}-N⁴-(2-cyclopropylethyl)-1H-imidazole-4,5-dicarboxamide

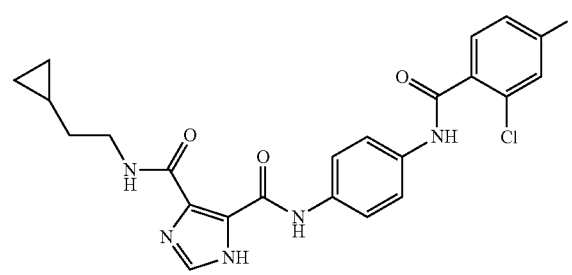

To the crude reaction mixture of phenyl-5-({4-[(2-chloro-4-fluorobenzoyl)amino]phenyl}carbamoyl)-1H-imidazole-4-carboxylate (0.30 mmol, Intermediate 021) were added 30.7 mg (0.36 mmol) 2-cyclopropylethanamine and 40 µL triethylamine and the mixture was stirred for 36 hours at 50° C. The reaction mixture was concentrated in vacuo and the residue was purified by flash column chromatography (dichloromethane/methanol-gradient) to give after drying 47 mg of the title compound as a solid material.

¹H-NMR (400 MHz, DMSO-d₆), δ [ppm]=13.65 (br. s., 1H), 13.43 (br. s., 1H), 10.52 (s, 1H), 8.79 (br. s., 1H), 7.93 (s, 1H), 7.78-7.64 (m, 5H), 7.60 (dd, 1H), 7.36 (td, 1H), 3.43 (q, 2H), 1.49 (q, 2H), 1.24 (br. s., 1H), 0.74 (br. s., 1H), 0.47-0.37 (m, 2H), 0.09 (d, 2H).

LC-MS (Method 2): $R_t$=1.19 min; MS (ESIpos) m/z=470.2 [M+H]⁺.

Example 44

N⁵-{4-[(2-chloro-4-fluorobenzoyl)amino]phenyl}-N⁴-cyclopropyl-1H-imidazole-4,5-dicarboxamide

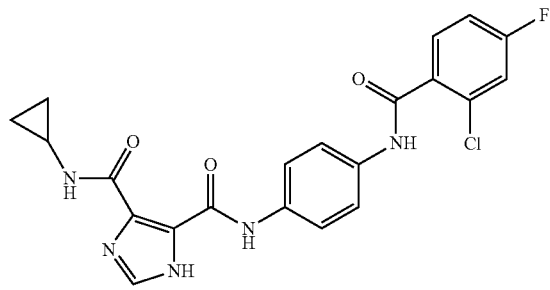 [SMILES: O=C(Nc1ccc(NC(=O)c2[nH]cnc2C(=O)NC2CC2)cc1)c1ccc(F)cc1Cl]

To the crude reaction mixture of phenyl-5-({4-[(2-chloro-4-fluorobenzoyl)amino]phenyl}carbamoyl)-1H-imidazole-4-carboxylate (0.30 mmol, Intermediate 021) were added 20.6 mg (0.36 mmol) cyclopropanamine and the mixture was stirred for 36 hours at 50° C. The reaction mixture was concentrated in vacuo and the residue was purified by flash column chromatography (dichloromethane/methanol-gradient) to give after drying under vacuum 64 mg of the title compound as a solid material.

¹H-NMR (400 MHz, DMSO-d₆), δ [ppm]=13.41 (br. s., 1H), 10.49 (s, 1H), 8.83 (br. s., 1H), 7.89 (s, 1H), 7.73-7.65 (m, 5H), 7.57 (dd, 1H), 7.34 (td, 1H), 2.93 (br. s., 1H), 2.51 (br. s., 1H), 0.80-0.60 (m, 4H).

LC-MS (Method 11): $R_t$=1.13 min; MS (ESIpos) m/z=442 [M+H]⁺.

Example 46

N-{4-[(2-chloro-4-fluorobenzoyl)amino]phenyl}-4-[(6-methyl-2,6-diazaspiro[3.3]hept-2-yl)carbonyl]-1H-imidazole-5-carboxamide

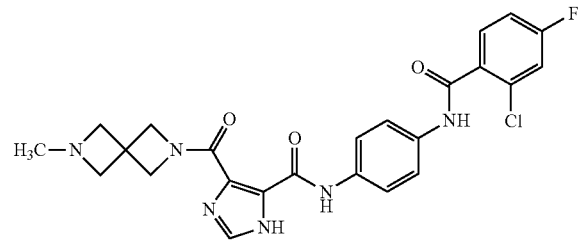 [SMILES: CN1CC2(C1)CN(C(=O)c1nc[nH]c1C(=O)Nc1ccc(NC(=O)c3ccc(F)cc3Cl)cc1)C2]

To the crude reaction mixture of phenyl-5-({4-[(2-chloro-4-fluorobenzoyl)amino]phenyl}carbamoyl)-1H-imidazole-4-carboxylate (0.30 mmol, Intermediate 21) were added 56.6 mg (0.18 mmol) 2-methyl-2,6-diazaspiro[3.3]heptane ethanedioate (2:1) and 84 µL (0.60 mmol) triethylamine. After stirring for 3 days at 50° C. 56.6 mg (0.18 mmol) 2-methyl-2,6-diazaspiro[3.3]heptane ethanedioate (2:1) and 84 µL triethlyamine were added and the mixture was stirred for 4 days at 70° C. The reaction mixture was concentrated under reduced pressure and the residue was purified by flash column chromatography (dichloromethane/methanol-gradient) to give after drying 12 mg of the title compound as a solid material.

¹H-NMR (400 MHz, DMSO-d₆), δ [ppm]=13.58 (s, 1H), 13.51-13.20 (m, 1H), 10.48 (s, 1H), 7.89 (s, 1H), 7.80-7.63 (m, 5H), 7.57 (dd, 1H), 7.34 (td, 1H), 4.69 (s, 2H), 4.19 (s, 2H), 3.28-3.17 (m, 4H), 2.16 (s, 3H).

LC-MS (Method 5): $R_t$=0.93 min; MS (ESIpos) m/z=497.1 [M+H]⁺.

Example 47

N-{4-[(2-chloro-4,5-difluorobenzoyl)amino]phenyl}-4-[(3-fluoroazetidin-1-yl)carbonyl]-1H-imidazole-5-carboxamide

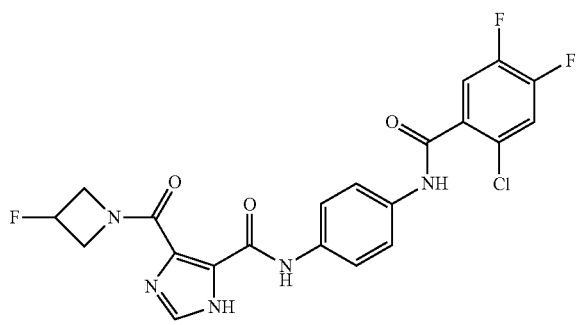 [SMILES: O=C(Nc1ccc(NC(=O)c2[nH]cnc2C(=O)N2CC(F)C2)cc1)c1cc(F)c(F)cc1Cl]

To the crude reaction mixture of phenyl 5-({4-[(2-chloro-4,5-difluorobenzoyl)amino]phenyl}carbamoyl)-1H-imidazole-4-carboxylate (0.40 mmol, Intermediate 022) were added 53.5 mg (0.48 mmol) 3-fluoroazetidine and the mixture was stirred for 2 hours at room temperature. The reaction was diluted with water and the resulting precipitate was filtered off and washed with water. The crude product was purified by flash column chromatography (dichloromethane/methanol-gradient) to give after washing with dichloromethane 46 mg of the title compound as a solid material.

$^1$H-NMR (400 MHz, DMSO-$d_6$), δ [ppm] 13.60-13.43 (m, 2H), 10.58 (s, 1H), 7.96-7.86 (m, 3H), 7.73-7.66 (m, 4H), 5.57-5.52 (m, 1H), 5.43-5.33 (m, 1H), 5.06-4.94 (m, 1H), 4.75-4.63 (m, 1H), 4.57-4.45 (m, 1H), 4.27-4.15 (m, 1H), 2.35-2.32 (m, 1H), 1.24 (br. s., 1H).

LC-MS (Method 2): $R_t$=1.01 min; MS (ESIpos) m/z=478.2 [M+H]$^+$.

Example 48

$N^5$-{4-[(2-chloro-4,5-difluorobenzoyl)amino]phenyl}-$N^4$-(2-cyclopentylethyl)-1H-imidazole-4,5-dicarboxamide

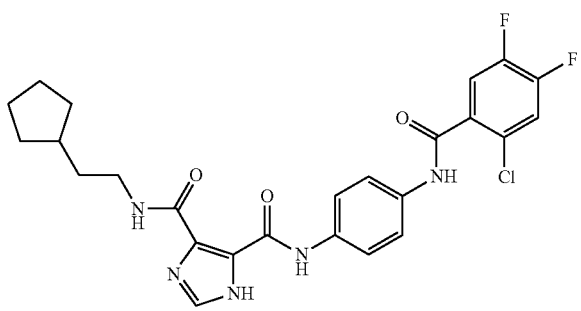 [SMILES: O=C(Nc1ccc(NC(=O)c2[nH]cnc2C(=O)NCCC2CCCC2)cc1)c1cc(F)c(F)cc1Cl]

To the crude reaction mixture of phenyl 5-({4-[(2-chloro-4,5-difluorobenzoyl)amino]phenyl}carbamoyl)-1H-imidazole-4-carboxylate (0.40 mmol, Intermediate 022) were added 54.3 mg (0.48 mmol) 2-cyclopentylethanamine and the mixture was stirred for 2 hours at room temperature. The reaction was diluted with water and the resulting precipitate was filtered off and was washed with water. The crude product was purified by flash column chromatography (dichloromethane/methanol-gradient) to give after washing with dichloromethane 52 mg of the title compound as a solid material.

$^1$H-NMR (400 MHz, DMSO-$d_6$), δ [ppm]=13.63 (br. s., 1H), 13.39 (br. s., 1H), 10.55 (s, 1H), 8.79 (br. s., 1H), 7.92-7.84 (m, 3H), 7.69 (s, 3H), 3.38-3.31 (m, 2H), 1.79 (br. s., 3H), 1.62-1.53 (m, 4H), 1.53-1.43 (m, 2H), 1.11 (br. s., 2H).

LC-MS (Method 5): $R_t$=1.41 min; MS (ESIpos) m/z=516.0 [M+H]$^+$.

Example 49

$N^5$-{4-[(2-chloro-4,5-difluorobenzoyl)amino]phenyl}-$N^4$-(2-cyclopropylethyl)-1H-imidazole-4,5-dicarboxamide

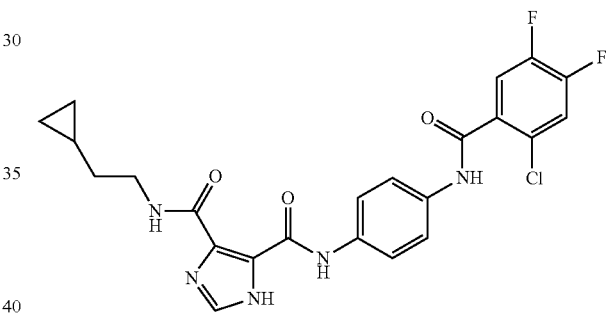

To the crude reaction mixture of phenyl 5-({4-[(2-chloro-4,5-difluorobenzoyl)amino]phenyl}carbamoyl)-1H-imidazole-4-carboxylate (0.40 mmol, Intermediate 022) were added 40.9 mg (0.48 mmol) 2-cyclopropylethanamine and the mixture was stirred for 2 hours at room temperature. The reaction was diluted with water and the resulting precipitate was filtered off and was washed with water. The crude product was purified by flash column chromatography (dichloromethane/methanol-gradient) to give after washing with dichloromethane 28 mg of the title compound as a solid material.

$^1$H-NMR (400 MHz, DMSO-$d_6$), δ [ppm]=13.63 (br. s., 1H), 13.40 (br. s., 1H), 10.55 (s, 1H), 8.79 (br. s., 1H), 7.92-7.84 (m, 3H), 7.69 (br. s., 4H), 3.41 (q, 2H), 1.50-1.44 (m, 2H), 0.72 (br. s., 1H), 0.43-0.38 (m, 2H), 0.07 (d, 2H).

LC-MS (Method 5): $R_t$=1.24 min; MS (ESIpos) m/z=488.0 [M+H]$^+$.

Example 50

N N-{4-[(2-chloro-4,5-difluorobenzoyl)amino]phenyl}-4-[(6-methyl-2,6-diazaspiro[3.3]hept-2-yl)carbonyl]-1H-imidazole-5-carboxamide

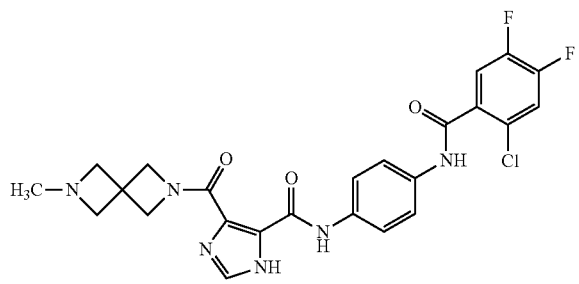 [SMILES: CN1CC2(C1)CN(C(=O)c1nc[nH]c1C(=O)Nc1ccc(NC(=O)c3cc(F)c(F)cc3Cl)cc1)C2]

To the crude reaction mixture of phenyl 5-({4-[(2-chloro-4,5-difluorobenzoyl)amino]phenyl}carbamoyl)-1H-imidazole-4-carboxylate (0.40 mmol, Intermediate 022) were added 125.8 mg (0.40 mmol) 2-methyl-2,6-diazaspiro[3.3]heptane ethanedioate (2:1) and the mixture was stirred for 2 days at 50° C. 125.8 mg (0.40 mmol) 2-methyl-2,6-diazaspiro[3.3]heptane ethanedioate (2:1) and 200 μL triethylamine were added and the mixture was stirred for 3 days at 70° C. The reaction mixture was concentrated in vacuo and the residue was purified by flash column chromatography (dichloromethane/methanol-gradient) to give after drying under vacuum at 50° C. 20 mg of the title compound as a solid material.

$^1$H-NMR (400 MHz, DMSO-$d_6$), δ [ppm]=$^1$H-NMR (400 MHz, DMSO-$d_6$): δ [ppm]=13.60 (s, 1H), 10.54 (s, 1H), 7.96-7.79 (m, 3H), 7.72-7.51 (m, 4H), 4.69 (s, 2H), 4.19 (s, 2H), 3.27-3.07 (m, 3H), 2.24-1.95 (m, 3H).

LC-MS (Method 8): $R_t$=0.92 min; MS (ESIpos) m/z=515.3 [M+H]$^+$.

Example 51

N$^5$-{4-[(2-chloro-4,5-difluorobenzoyl)amino]phenyl}-N$^4$-cyclopropyl-1H-imidazole-4,5-dicarboxamide

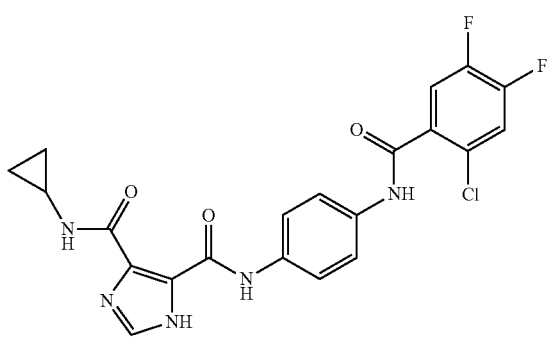 [SMILES: O=C(Nc1ccc(NC(=O)c2[nH]cnc2C(=O)NC2CC2)cc1)c1cc(F)c(F)cc1Cl]

To the crude reaction mixture of phenyl 5-({4-[(2-chloro-4,5-difluorobenzoyl)amino]phenyl}carbamoyl)-1H-imidazole-4-carboxylate (0.40 mmol, Intermediate 022) were added 27.4 mg (0.48 mmol) cyclopropanamine and the mixture was stirred for 2 hours at room temperature. The reaction was diluted with water and the resulting precipitate was filtered off and was washed with water. The crude product was purified by flash column chromatography (dichloromethane/methanol-gradient) to give after washing with dichloromethane and drying under vacuum at 50° C. 16 mg of the title compound as a solid material.

$^1$H-NMR (400 MHz, DMSO-$d_6$), δ [ppm]=13.59 (br. s., 1H), 13.42 (br. s., 1H), 10.55 (s, 1H), 8.77 (br. s., 1H), 7.99-7.80 (m, 3H), 7.77-7.60 (m, 4H), 2.93 (br. s., 1H), 0.74 (d, 4H).

LC-MS (Method 5): $R_t$=1.03 min; MS (ESIpos) m/z=460.0 [M+H]$^+$.

Example 52

N-{4-[(2-chloro-4,5-difluorobenzoyl)amino]phenyl}-4-(2-oxa-6-azaspiro[3.3]hept-6-ylcarbonyl)-1H-imidazole-5-carboxamide

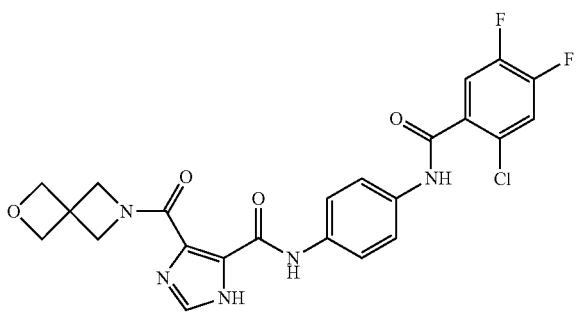 [SMILES: O=C(Nc1ccc(NC(=O)c2[nH]cnc2C(=O)N2CC3(COC3)C2)cc1)c1cc(F)c(F)cc1Cl]

To the crude reaction mixture of phenyl 5-({4-[(2-chloro-4,5-difluorobenzoyl)amino]phenyl}carbamoyl)-1H-imidazole-4-carboxylate (0.40 mmol, Intermediate 022) were added 69.1 mg (0.24 mmol) 2-oxa-6-azaspiro[3.3]heptane ethanedioate (2:1) and the mixture was stirred for 20 hours at room temperature. The reaction was diluted with water and the resulting precipitate was filtered off and was washed with water. The crude product was purified by flash column chromatography (dichloromethane/methanol-gradient) to give after washing with dichloromethane and drying under vacuum at 50° C. 40 mg of the title compound as a solid material.

$^1$H-NMR (400 MHz, DMSO-$d_6$), δ [ppm]=13.58 (s, 1H), 13.44 (br. s., 1H), 10.54 (s, 1H), 8.06-7.80 (m, 3H), 7.75-7.47 (m, 4H), 4.81 (s, 2H), 4.75-4.56 (m, 4H), 4.32 (s, 2H).

LC-MS (Method 5): $R_t$=0.92 min; MS (ESIpos) m/z=502.0 [M+H]$^+$.

Example 53

N⁵-(4-{[2-chloro-4-(methylsulfonyl)benzoyl]amino}phenyl)-N⁴-[2-(piperidin-1-yl)ethyl]-1H-imidazole-4,5-dicarboxamide

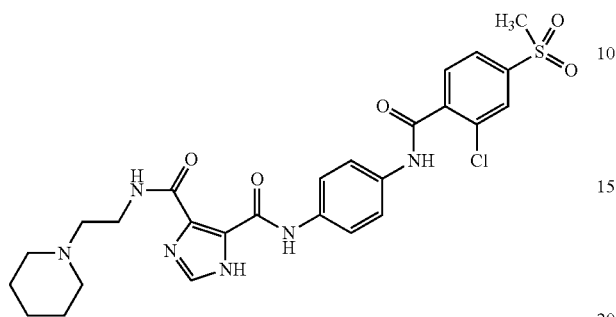

To a suspension of 500 mg (1.05 mmol) methyl 5-[(4-{[2-chloro-4-(methylsulfonyl)benzoyl]amino}phenyl)carbamoyl]-1H-imidazole-4-carboxylate (Intermediate 027) in 5.6 mL dioxane and 2.8 mL methanol, 0.9 mL (6.29 mmol) 2-(piperidin-1-yl)ethanamine were added and the mixture was stirred for 4 hours at 100° C. The reaction mixture was concentrated in vacuo and the residue was purified by flash column chromatography (dichloromethane/methanol-gradient) to give after washing with methanol 408 mg of the title compound as a solid material.

¹H-NMR (400 MHz, DMSO-d₆), δ [ppm]=13.61 (br. s., 1H), 13.19 (br. s., 1H), 10.70 (s, 1H), 8.66 (br. s., 1H), 8.13 (d, 1H), 8.00 (dd, 1H), 7.95-7.87 (m, 2H), 7.72 (s, 4H), 3.46 (q, 2H), 3.33 (s, 5H), 2.40 (br. s., 4H), 1.56-1.47 (m, 4H), 1.40 (d, 2H).

LC-MS (Method 5): $R_t$=1.01 min; MS (ESIpos) m/z=573.2 [M+H]⁺.

Example 54

N⁵-(4-{[2-chloro-4-(methylsulfonyl)benzoyl]amino}phenyl)-N⁴-[2-(dimethylamino)ethyl]-1H-imidazole-4,5-dicarboxamide

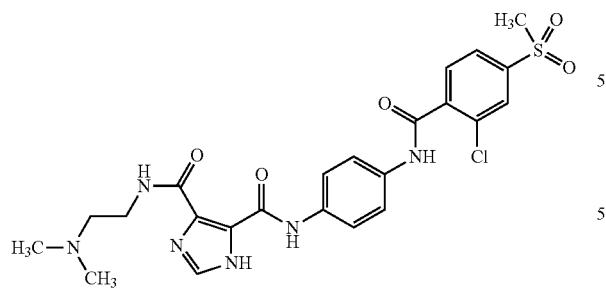

To a suspension of 500 mg (1.05 mmol) methyl 5-[(4-{[2-chloro-4-(methylsulfonyl)benzoyl]amino}phenyl)carbamoyl]-1H-imidazole-4-carboxylate (Intermediate 027) in 5.4 mL dioxane and 2.7 mL methanol, 0.7 mL (6.29 mmol) N,N-dimethylethane-1,2-diamine were added and the mixture was stirred for 4 hours at 100° C. The reaction mixture was concentrated under reduced pressure and the residue was purified by flash column chromatography (dichloromethane/methanol-gradient) to give after washing with methanol and dichloromethane 313 mg of the title compound as a solid material.

¹H-NMR (400 MHz, DMSO-d₆), δ [ppm]=13.62 (br. s., 1H), 13.41 (br. s., 1H), 10.71 (s, 1H), 8.64 (br. s., 1H), 8.13 (d, 1H), 8.00 (dd, 1H), 7.96-7.86 (m, 2H), 7.72 (s, 4H), 3.45 (q, 2H), 3.36 (s, 3H), 2.46 (t, 2H), 2.21 (s, 6H).

LC-MS (Method 5): $R_t$=0.83 min; MS (ESIpos) m/z=533.1 [M+H]⁺.

Example 55

N⁵-(4-{[2-chloro-4-(methylsulfonyl)benzoyl]amino}phenyl)-N⁴-methyl-1H-imidazole-4,5-dicarboxamide

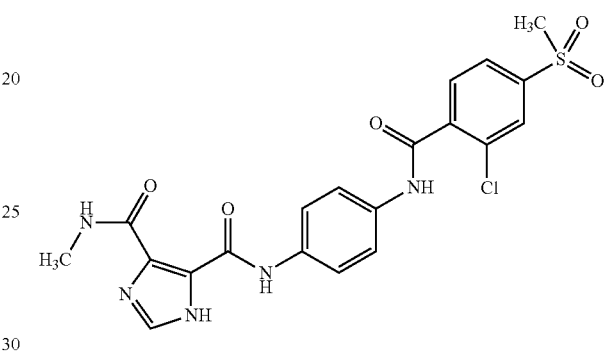

To 90.5 mg (0.39 mmol) 2-chloro-4-(methylsulfonyl)benzoic acid in 5 mL DMF were added 147 mg (0.39 mmol) HATU and 201 μL N,N-diisopropylethylamine. After stirring for 5 minutes 100 mg (0.39 mmol) N⁵-(4-aminophenyl)-N⁴-methyl-1H-imidazole-4,5-dicarboxamide (Intermediate 003) were added and the mixture was stirred for 4 days at room temperature. The solvent was removed under reduced pressure and the crude product was purified by HPLC to give 30 mg of the title compound as a solid material.

¹H-NMR (400 MHz, DMSO-d₆), δ [ppm]=13.71 (br. s., 1H), 13.43 (br. s., 1H), 10.70 (s, 1H), 8.85 (br. s., 1H), 8.13 (d, 1H), 8.00 (dd, 1H), 7.96-7.84 (m, 2H), 7.72 (s, 4H), 3.36 (s, 3H), 2.88 (d, 3H).

LC-MS (Method 4): $R_t$=0.89 min; MS (ESIpos) m/z=476.1 [M+H]⁺.

Example 56

N⁵-{4-[(2-bromo-4-fluorobenzoyl)amino]phenyl}-N⁴-methyl-1H-imidazole-4,5-dicarboxamide

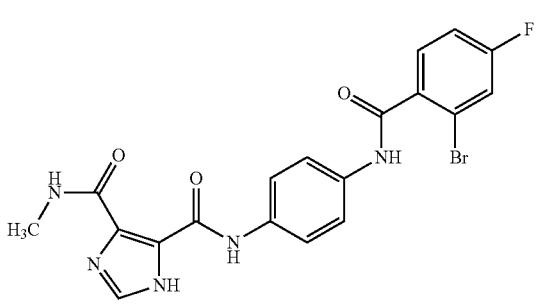

100 mg (0.39 mmol) $N^5$-(4-aminophenyl)-$N^4$-methyl-1H-imidazole-4,5-dicarboxamide (Intermediate 003) were suspended in 5 mL dry tetrahydrofuran. 53.8 µL (0.39 mmol) triethylamine and 91.6 mg (0.39 mmol) 2-bromo-6-(fluoro) benzoyl chloride were added and the mixture was stirred at room temperature for 1 day. The solvent was removed under reduced pressure and the crude product was purified by HPLC to give 61 mg of the title compound as a solid material.

$^1$H-NMR (400 MHz, DMSO-$d_6$), δ [ppm]=13.68 (s, 1H), 13.43 (s, 1H), 10.50 (s, 1H), 8.84 (d, 1H), 7.96-7.90 (m, 1H), 7.77-7.61 (m, 6H), 7.39 (td, 1H), 2.93-2.84 (m, 3H).

LC-MS (Method 4): $R_t$=1.03 min; MS (ESIpos) m/z=462.0 [M+H]$^+$.

Example 57

$N^5$-{4-[(2,6-dimethoxybenzoyl)amino]phenyl}-$N^4$-methyl-1H-imidazole-4,5-dicarboxamide

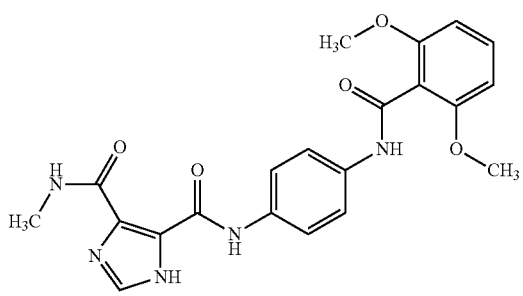

100 mg (0.39 mmol) $N^5$-(4-aminophenyl)-$N^4$-methyl-1H-imidazole-4,5-dicarboxamide (Intermediate 003) were suspended in 5 mL dry tetrahydrofuran. 53.8 µL (0.39 mmol) triethylamine and 77.4 mg (0.39 mmol) 2,6-dimethoxybenzoyl chloride were added and the mixture was stirred at room temperature for 2 days. The solvent was removed under reduced pressure and the crude product was purified by HPLC to give 43 mg of the title compound as a solid material.

$^1$H-NMR (400 MHz, DMSO-$d_6$), δ [ppm]=13.60 (s, 1H), 13.37 (br. s., 1H), 10.18 (s, 1H), 8.79 (d, 1H), 7.90 (s, 1H), 7.71 (d, 2H), 7.63 (d, 2H), 7.34 (t, 1H), 6.72 (d, 2H), 3.30 (s, 4H), 2.86 (d, 3H).

LC-MS (Method 4): $R_t$=0.91 min; MS (ESIpos) m/z=424.2 [M+H]$^+$.

Example 58

$N^4$-methyl-$N^5$-(4-{[2-(trifluoromethyl)benzoyl]amino}phenyl)-1H-imidazole-4,5-dicarboxamide

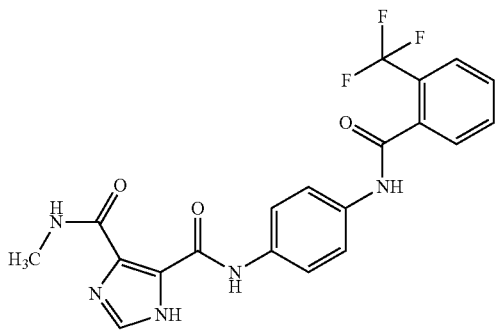 [SMILES: CNC(=O)c1nc[nH]c1C(=O)Nc1ccc(NC(=O)c2ccccc2C(F)(F)F)cc1]

100 mg (0.39 mmol) $N^5$-(4-aminophenyl)-$N^4$-methyl-1H-imidazole-4,5-dicarboxamide (Intermediate 003) were suspended in 5 mL dry tetrahydrofuran. 53.8 µL (0.39 mmol) triethylamine and 80.4 mg (0.39 mmol) 2-(trifluoromethyl) benzoyl chloride were added and the mixture was stirred at room temperature for 1 day. The solvent was removed under reduced pressure and the crude product was purified by HPLC to give 50 mg of the title compound as a solid material.

$^1$H-NMR (400 MHz, DMSO-$d_6$), δ [ppm]=13.65 (s, 1H), 13.40 (br. s., 1H), 10.54 (s, 1H), 8.80 (d, 1H), 7.91 (s, 1H), 7.86-7.82 (m, 1H), 7.81-7.76 (m, 1H), 7.73-7.66 (m, 6H), 2.86 (d, 3H).

LC-MS (Method 4): $R_t$=1.03 min; MS (ESIpos) m/z=432.2 [M+H]$^+$.

Example 59

$N^4$-methyl-$N^5$-{4-[(2,4,6-trichlorobenzoyl)amino]phenyl}-1H-imidazole-4,5-dicarboxamide

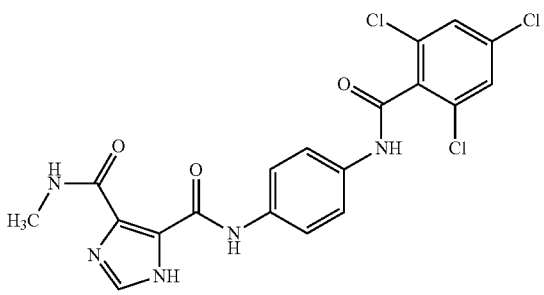 [SMILES: CNC(=O)c1nc[nH]c1C(=O)Nc1ccc(NC(=O)c2c(Cl)cc(Cl)cc2Cl)cc1]

100 mg (0.39 mmol) $N^5$-(4-aminophenyl)-$N^4$-methyl-1H-imidazole-4,5-dicarboxamide (Intermediate 003) were suspended in 5 mL dry tetrahydrofuran. 53.8 µL (0.39 mmol) triethylamine and 94.1 mg (0.39 mmol) 2,4,6-trichlorobenzoyl chloride were added and the mixture was stirred at room temperature for 4 hours. The solvent was removed under reduced pressure and the crude product was purified by HPLC to give 45 mg of the title compound as a solid material.

$^1$H-NMR (400 MHz, DMSO-$d_6$), δ [ppm]=13.69 (br. s., 1H), 13.42 (br. s., 1H), 10.76 (s, 1H), 8.84 (br. s., 1H), 7.92 (s, 1H), 7.83 (s, 2H), 7.78-7.63 (m, 4H), 2.86 (d, 3H).

Example 60

N$^5$-{4-[(2-methoxybenzoyl)amino]phenyl}-N$^4$-methyl-1H-imidazole-4,5-dicarboxamide

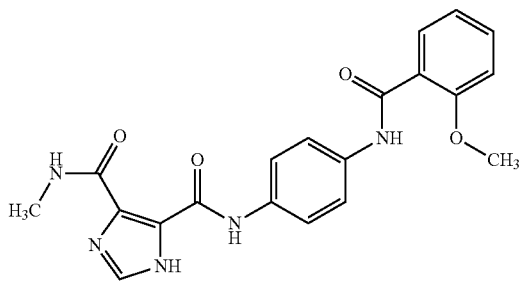

100 mg (0.39 mmol) N$^5$-(4-aminophenyl)-N$^4$-methyl-1H-imidazole-4,5-dicarboxamide (Intermediate 003) were suspended in 5 mL dry tetrahydrofuran. 53.8 µL (0.39 mmol) triethylamine and 65.8 mg (0.39 mmol) 2-methoxybenzoyl chloride were added and the mixture was stirred at room temperature for 4 hours. The solvent was removed under reduced pressure and the crude product was purified by HPLC to give 30 mg of the title compound as a solid material.

$^1$H-NMR (400 MHz, DMSO-d$_6$), δ [ppm]=13.66 (br. s., 1H), 13.42 (br. s., 1H), 10.13 (s, 1H), 8.84 (br. s., 1H), 7.93 (s, 1H), 7.82-7.72 (m, 2H), 7.72-7.63 (m, 3H), 7.58-7.47 (m, 1H), 7.19 (d, 1H), 7.08 (t, 1H), 3.91 (s, 3H), 2.88 (d, 3H).

LC-MS (Method 4): R$_t$=1.03 min; MS (ESIpos) m/z=394.2 [M+H]$^+$.

Example 61

N$^5$-{4-[(4-fluoro-2-iodobenzoyl)amino]phenyl}-N$^4$-methyl-1H-imidazole-4,5-dicarboxamide

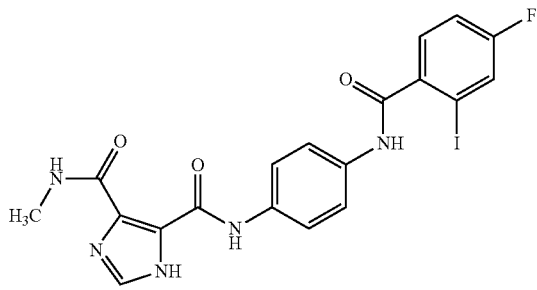

To 342 mg (1.25 mmol) 4-fluoro-2-iodobenzoic acid in 10 mL DMF were added 474 mg (1.25 mmol) HATU and 593 µL (3.40 mmol) N,N-diisopropylethylamine. After stirring for 5 minutes 300 mg (1.13 mmol) N$^5$-(4-aminophenyl)-N$^4$-methyl-1H-imidazole-4,5-dicarboxamide (Intermediate 003) were added and the mixture was stirred for 8 hours at room temperature. The reaction was poured into water and the aqueous solution was extracted three times with DCM/2-propanole (8:2). The combined organic layers were washed with sat. sodium carbonate solution and sat. sodiumchloride-solution. The organic phase was dried over sodium sulphate, and the solvent was removed under reduced pressure to afford the crude material which was purified twice by flash column chromatography to give after trituration with methanol 357 mg of the title compound as a solid material.

$^1$H-NMR (400 MHz, DMSO-d$_6$), δ [ppm]=13.67 (s, 1H), 13.43 (s, 1H), 10.43 (s, 1H), 8.84 (d, 1H), 7.93 (s, 1H), 7.85 (dd, 1H), 7.79-7.67 (m, 4H), 7.56 (dd, 1H), 7.38 (td, 1H), 2.88 (d, 3H).

LC-MS (Method 5): R$_t$=0.98 min; MS (ESIpos) m/z=507.9 [M+H]$^+$.

Example 62

N$^5$-{4-[(4-fluoro-2-iodobenzoyl)amino]phenyl}-N$^4$-[2-(piperidin-1-yl)ethyl]-1H-imidazole-4,5-dicarboxamide

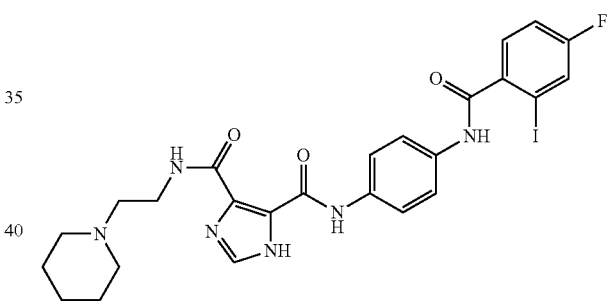

To a suspension of 518 mg (1.02 mmol) methyl 5-({4-[(4-fluoro-2-iodobenzoyl)amino]phenyl}carbamoyl)-1H-imidazole-4-carboxylate (Intermediate 028) in 6.0 mL dioxane and 3.0 mL methanol were added 0.9 mL (6.12 mmol) 2-(piperidin-1-yl)ethanamine and the mixture was stirred for 8 hours at 80° C. The reaction mixture was concentrated under reduced pressure and the residue was purified by flash column chromatography (dichloromethane/methanol-gradient) to give after trituration with dichloromethane and then with dioxan/methanol 153 mg (purity: 92%) of the title compound as a solid material.

$^1$H-NMR (400 MHz, DMSO-d$_6$), δ [ppm]=13.60 (br. s., 1H), 13.44 (br. s., 1H), 10.52-10.24 (m, 1H), 8.64 (br. s., 1H), 8.07-8.03 (m, 1H), 7.94 (s, 1H), 7.85 (dd, 1H), 7.79-7.65 (m, 4H), 7.56 (dd, 1H), 7.48-7.25 (m, 1H), 3.46 (q, 2H), 2.49-2.46 (m, 2H), 2.41 (br. s., 4H), 1.57-1.47 (m, 4H), 1.40 (d, 2H).

LC-MS (Method 5): R$_t$=1.21 min; MS (ESIpos) m/z=605.1 [M+H]$^+$.

Example 63

N⁵-(4-{[2-bromo-5-(trifluoromethoxy)benzoyl]amino}phenyl)-N⁴-[2-(piperidin-1-yl)ethyl]-1H-imidazole-4,5-dicarboxamide

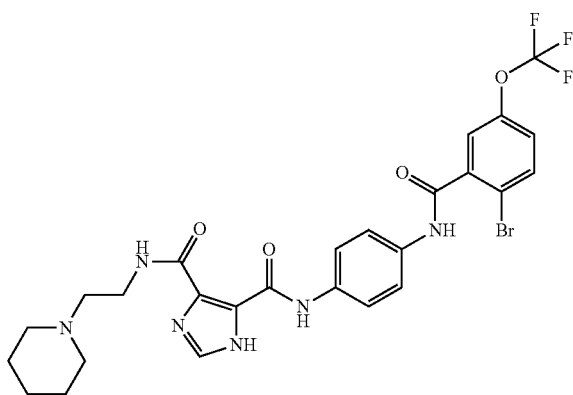 [SMILES: O=C(Nc1ccc(NC(=O)c2[nH]cnc2C(=O)NCCN2CCCCC2)cc1)c1cc(OC(F)(F)F)ccc1Br]

To a suspension of 584 mg (1.10 mmol) methyl 5-[(4-{[2-bromo-5-(trifluoromethoxy)benzoyl]amino}phenyl)carbamoyl]-1H-imidazole-4-carboxylate (Intermediate 029) in 6.0 mL dioxane and 3.0 mL methanol, 0.95 mL (6.65 mmol) 2-(piperidin-1-yl)ethanamine were added and the mixture was stirred for 7 hours at 80° C. The reaction mixture was concentrated in vacuo and the residue was purified by flash column chromatography (dichloromethane/methanol-gradient) to give after trituration with dichloromethane 53 mg of the title compound as a solid material.

¹H-NMR (400 MHz, DMSO-d₆), δ [ppm]=13.58 (br. s., 1H), 13.35 (br. s., 1H), 10.58 (s, 1H), 8.63 (br. s., 1H), 7.91 (s, 1H), 7.85 (d, 1H), 7.70 (br. s., 4H), 7.64 (d, 1H), 7.45 (ddd, 1H), 3.45 (q, 2H), 2.51-2.45 (br. s., 2H), 2.39 (br. s., 4H), 1.59-1.43 (m, 4H), 1.38 (d, 2H).

LC-MS (Method 12)): R$_t$=0.87 min; MS (ESIpos) m/z=625.1 [M+H]⁺.

Example 64

N⁵-(4-{[2-bromo-5-(trifluoromethoxy)benzoyl]amino}phenyl)-N⁴-methyl-1H-imidazole-4,5-dicarboxamide

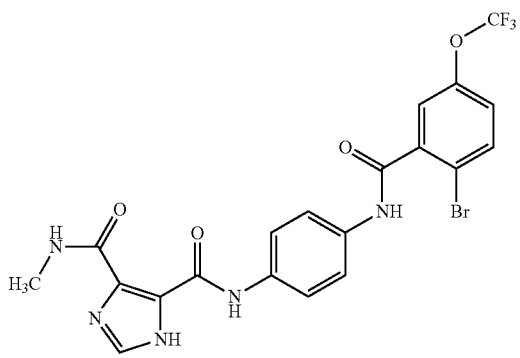 [SMILES: CNC(=O)c1nc[nH]c1C(=O)Nc1ccc(NC(=O)c2cc(OC(F)(F)F)ccc2Br)cc1]

To 366 mg (1.25 mmol) 2-bromo-5-(trifluoromethoxy)benzoic acid in 10 mL DMF were added 474 mg (1.25 mmol) HATU and 593 μL (3.40 mmol) N,N-diisopropylethylamine. After stirring for 5 minutes 300 mg (1.13 mmol) N⁵-(4-aminophenyl)-N⁴-methyl-1H-imidazole-4,5-dicarboxamide (Intermediate 003) were added and the mixture was stirred for 7 hours at room temperature. The reaction was poured into water and the aqueous solution was extracted three times with DCM/2-propanole (8:2). The combined organic layers were washed with sat. sodium carbonate solution and sodium chloride solution. The organic phase was dried over sodium sulphate, and the solvent was removed under reduced pressure to afford the crude material which was purified twice by flash column chromatography to give after trituration with methanol 317 mg of the title compound as a solid material.

¹H-NMR (400 MHz, DMSO-d₆), δ [ppm]=13.67 (s, 1H), 13.43 (s, 1H), 10.43 (s, 1H), 8.84 (d, 1H), 7.93 (s, 1H), 7.85 (dd, 1H), 7.79-7.67 (m, 4H), 7.56 (dd, 1H), 7.38 (td, 1H), 2.88 (d, 3H).

LC-MS (Method 5): R$_t$=1.10 min; MS (ESIpos) m/z=507.9 [M+H]⁺.

Example 65

N⁴-{4-[(2-chloro-4-fluorobenzoyl)amino]phenyl}-N⁵,2-dimethyl-1H-imidazole-4,5-dicarboxamide

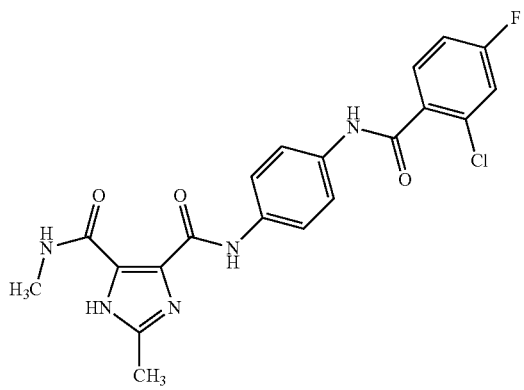 [SMILES: CNC(=O)c1[nH]c(C)nc1C(=O)Nc1ccc(NC(=O)c2ccc(F)cc2Cl)cc1]

Step A:

To 0.38 mmol (crude product, intermediate 23) of 3,8-dimethyl-5,10-dioxo-5H,10H-diimidazo[1,5-a:1',5'-d]pyrazine-1,6-dicarbonyl dichloride dissolved in 3 mL tetrahydrofuran were added 198 mg (0.75 mmol) N-(4-aminophenyl)-2-chloro-4-fluorobenzamide (Intermediate 004) and 157 μL (1.13 mmol) triethylamine. The resulting mixture was stirred for 30 minutes at room temperature.

Step B:

3.75 mL (7.50 mmol) of a 2 M solution of methylamine in tetrahydrofuran were added and the mixture was stirred for 30 minutes at room temperature. The solvent was removed under reduced pressure and the crude product was purified twice by flash column chromatography (first ethylacetate/cyclohexane then ethylacetate/tetrahydrofuran) to give 75 mg of the title compound as a solid material.

¹H-NMR (400 MHz, DMSO-d₆), δ [ppm]=2.36 (s, 3H), 2.81-2.90 (m, 3H), 7.30-7.38 (m, 1H), 7.54-7.61 (m, 1H), 7.64-7.82 (m, 5H), 8.72 (s, 1H), 10.48 (s, 1H), 13.03 (s, 1H), 13.63 (s, 1H).

LC-MS (Method 6): R$_t$=3.55 min; MS (ESIpos) m/z=430.2 [M+H]⁺.

Example 66

N⁴-{4-[(2-chloro-4-fluorobenzoyl)amino]phenyl}-N⁵-[2-(dimethylamino)ethyl]-2-methyl-1H-imidazole-4,5-dicarboxamide

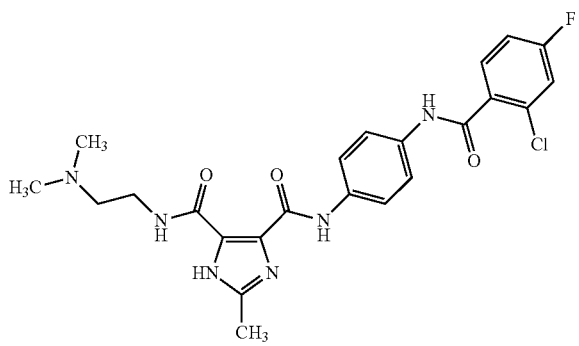 [SMILES: Cc1nc(C(=O)Nc2ccc(NC(=O)c3ccc(F)cc3Cl)cc2)c(C(=O)NCCN(C)C)[nH]1]

Step A:
To 0.38 mmol (crude product, intermediate 023) of 3,8-dimethyl-5,10-dioxo-5H,10H-diimidazo[1,5-a:1',5'-d]pyrazine-1,6-dicarbonyl dichloride dissolved in 3 mL tetrahydrofuran were added 198 mg (0.75 mmol) N-(4-aminophenyl)-2-chloro-4-fluorobenzamide (intermediate 004) and 157 μL (1.13 mmol) triethylamine. The resulting mixture was stirred for 30 minutes at room temperature.

Step B:
250 μL (2.25 mmol) of N,N-dimethylethane-1,2-diamine were added and the mixture was stirred for 30 minutes at room temperature. 50 mL water were added and the resulting precipitate was filtered off and was washed three times with water (3 mL). The crude product was dried under vacuum and the solid material was purified by flash column chromatography (tetrahydrofuran) to give 66 mg of the title compound as a solid material.

$^1$H-NMR (400 MHz, DMSO-d$_6$), δ [ppm]=13.59 (s, 1H), 13.11 (s, 1H), 10.54 (s, 1H), 8.53 (s, 1H), 7.90-7.56 (m, 6H), 7.47-7.32 (m, 1H), 3.59-3.29 (m, 2H), 2.63-2.45 (m, 2H), 2.41 (s, 3H), 2.25 (s, 6H).

LC-MS (Method 6): R$_t$=2.93 min; MS (ESIpos) m/z=487.2 [M+H]⁺.

Example 67

N⁴-{4-[(2-chloro-4-fluorobenzoyl)amino]phenyl}-2-methyl-N⁵-[2-(piperidin-1-yl)ethyl]-1H-imidazole-4,5-dicarboxamide

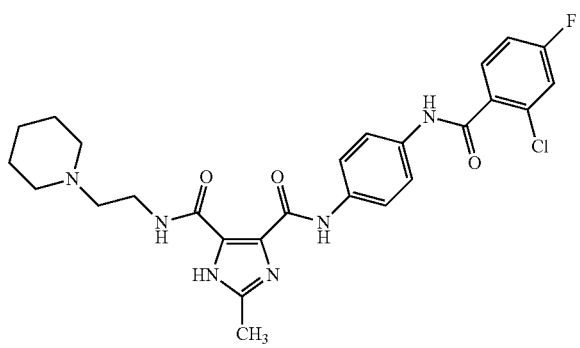 [SMILES: Cc1nc(C(=O)Nc2ccc(NC(=O)c3ccc(F)cc3Cl)cc2)c(C(=O)NCCN2CCCCC2)[nH]1]

Step A:
To 0.38 mmol (crude product, intermediate 023) of 3,8-dimethyl-5,10-dioxo-5H,10H-diimidazo[1,5-a:1',5'-d]pyrazine-1,6-dicarbonyl dichloride dissolved in 3 mL tetrahydrofuran were added 198 mg (0.75 mmol) N-(4-aminophenyl)-2-chloro-4-fluorobenzamide (Intermediate 004) and 157 μL (1.13 mmol) triethylamine. The resulting mixture was stirred for 30 minutes at room temperature.

Step B:
319 μL (2.25 mmol) of 2-(piperidin-1-yl)ethanamine were added and the mixture was stirred for 2 hours at room temperature. 50 mL water were added and the resulting precipitate was filtered off and was washed three times with water (3 mL). The obtained solid material was dried in vacuo and the crude product was purified by flash column chromatography (tetrahydrofuran) to give 61 mg of the title compound as a solid material.

$^1$H-NMR (400 MHz, DMSO-d$_6$), δ [ppm]=13.56 (s, 1H), 13.05 (s, 1H), 10.48 (s, 1H), 8.55 (t, 1H), 7.75-7.63 (m, 5H), 7.60-7.54 (m, 2H), 7.38-7.31 (m, 1H), 3.48-3.39 (m, 2H), 2.48-2.42 (m, 2H), 2.42-2.37 (m, 4H), 2.36 (s, 3H), 1.57-1.44 (m, 4H), 1.42-1.33 (m, 2H).

LC-MS (Method 6): R$_t$=3.05 min; MS (ESIpos) m/z=527.3 [M+H]⁺.

Example 68

N⁴-{4-[(2-chloro-4-fluorobenzoyl)amino]phenyl}-2-ethyl-N⁵-methyl-1H-imidazole-4,5-dicarboxamide

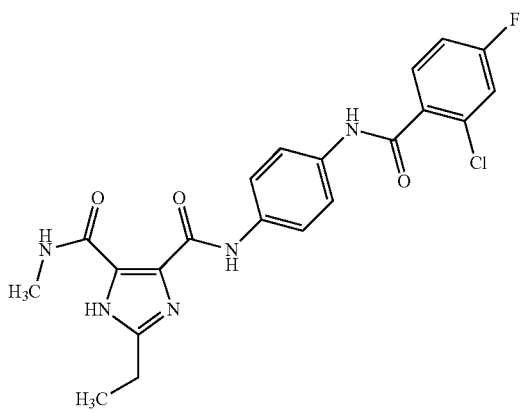 [SMILES: CCc1nc(C(=O)Nc2ccc(NC(=O)c3ccc(F)cc3Cl)cc2)c(C(=O)NC)[nH]1]

Step A:
To 184 mg (0.50 mmol, crude product, intermediate 026) of 3,8-diethyl-5,10-dioxo-5H,10H-diimidazo[1,5-a:1',5'-d]pyrazine-1,6-dicarbonyl dichloride dissolved in 2 mL tetrahydrofuran were added 265 mg (1.00 mmol) N-(4-aminophenyl)-2-chloro-4-fluorobenzamide (Intermediate 004) and 209 μL (1.50 mmol) triethylamine. The resulting mixture was stirred for 1 hour at room temperature.

Step B:
3.75 mL (7.50 mmol) of a 2 M solution of methylamine in tetrahydrofuran were added and the mixture was stirred for 30 minutes at room temperature. The solvent was removed under reduced pressure and the crude product was purified twice by flash column chromatography (first ethylacetate/cyclohexane then ethylacetate/tetrahydrofuran) to give 39 mg of the title compound as a solid material.

$^1$H-NMR (400 MHz, DMSO-d$_6$), δ [ppm]=13.63 (s, 1H), 13.02 (s, 1H), 10.48 (s, 1H), 8.69-8.61 (d, 1H), 7.81-7.62 (m, 5H), 7.60-7.53 (m, 1H), 7.38-7.30 (m, 1H), 2.89-2.84 (d, 3H), 2.75-2.65 (q, 2H), 1.28-1.22 (t, 3H).

LC-MS (Method 6): $R_t$=3.65 min; MS (ESIpos) m/z=444.2 [M+H]$^+$.

Example 69

N$^4$-{4-[(2-chloro-4-fluorobenzoyl)amino]phenyl}-N$^5$-[2-(dimethylamino)ethyl]-2-ethyl-1H-imidazole-4,5-dicarboxamide

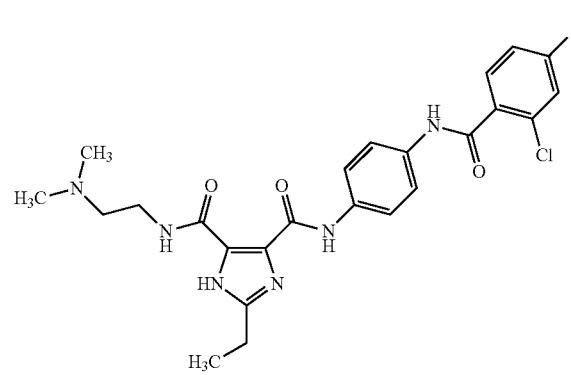

Step A:

To 184 mg (0.50 mmol, crude product, intermediate 026) of 3,8-diethyl-5,10-dioxo-5H,10H-diimidazo[1,5-a:1',5'-d]pyrazine-1,6-dicarbonyl dichloride dissolved in 2 mL tetrahydrofuran were added 265 mg (1.00 mmol) N-(4-aminophenyl)-2-chloro-4-fluorobenzamide (Intermediate 004) and 209 μL (1.50 mmol) triethylamine. The resulting mixture was stirred for 1 hour at room temperature.

Step B:

331 μL (3.00 mmol) N,N-dimethylethane-1,2-diamine were added and the mixture was stirred for 30 minutes at room temperature. 50 mL water were added and the resulting precipitate was filtered off and washed three times with water (2 mL). The obtained solid material was dried in vacuo and the crude product was purified by flash column chromatography (ethylacetate/tetrahydrofuran) to give 113 mg of the title compound as a solid material.

$^1$H-NMR (400 MHz, DMSO-d$_6$), δ [ppm]=13.56 (s, 1H), 13.05 (s, 1H), 10.49 (s, 1H), 8.46 (m, 1H), 7.83-7.62 (m, 5H), 7.62-7.52 (m, 1H), 7.41-7.26 (m, 1H), 3.53-3.37 (m, 2H), 2.78-2.63 (m, 2H), 2.54-2.37 (m, 2H), 2.20 (s, 6H), 1.33-1.17 (m, 3H).

LC-MS (Method 6): $R_t$=3.01 min; MS (ESIpos) m/z=501.2 [M+H]$^+$.

Example 70

N$^4$-{4-[(2-chloro-4-fluorobenzoyl)amino]phenyl}-2-ethyl-N$^5$-[2-(piperidin-1-yl)ethyl]-1H-imidazole-4,5-dicarboxamide

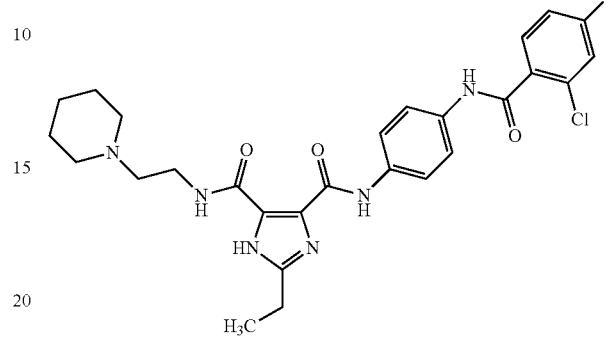

Step A:

To 184 mg (0.50 mmol, crude product, intermediate 026) of 3,8-diethyl-5,10-dioxo-5H,10H-diimidazo[1,5-a:1',5'-d]pyrazine-1,6-dicarbonyl dichloride dissolved in 2 mL tetrahydrofuran were added 265 mg (1.00 mmol) N-(4-aminophenyl)-2-chloro-4-fluorobenzamide (Intermediate 004) and 209 μL (1.50 mmol) triethylamine. The resulting mixture was stirred for 1 hour at room temperature.

Step B:

427 μL (3.00 mmol) 2-(piperidin-1-yl)ethanamine were added and the mixture was stirred for 30 minutes at room temperature. 50 mL water were added and the resulting precipitate was filtered off and was washed three times with water (3 mL). The obtained solid material was dried in vacuo and the crude product was purified by flash column chromatography (ethylacetate/tetrahydrofuran) to give 112 mg of the title compound as a solid material.

$^1$H-NMR (400 MHz, DMSO-d$_6$), δ [ppm]=13.56 (s, 1H), 13.04 (s, 1H), 10.48 (s, 1H), 8.54 (m, 1H), 7.87-7.62 (m, 5H), 7.62-7.52 (m, 1H), 7.39-7.29 (m, 1H), 3.51-3.38 (m, 2H), 2.77-2.65 (m, 2H), 2.55-2.44 (m, 2H), 2.40 (s, 4H), 1.51 (s, 4H), 1.43-1.33 (m, 2H), 1.25 (t, 3H).

LC-MS (Method 6): $R_t$=3.09 min; MS (ESIpos) m/z=541.3 [M+H]$^+$.

Example 71 methyl 5-({4-[(2-chloro-4-fluorobenzoyl)amino]-3-fluorophenyl}carbamoyl)-1H-imidazole-4-carboxylate

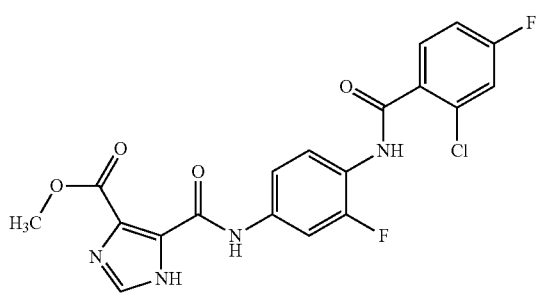 [SMILES: COC(=O)c1nc[nH]c1C(=O)Nc1ccc(NC(=O)c2ccc(F)cc2Cl)c(F)c1]

439 mg (1.58 mmol) methyl 5-[(4-amino-3-fluorophenyl) carbamoyl]-1H-imidazole-4-carboxylate (Intermediate 031) were suspended in 10 mL dry tetrahydrofuran. 1.37 mL (7.89 mmol) N-ethyl-N,N-diisopropylamine and 412 μL (3.16 mmol) 2-chloro-4-fluorobenzoyl chloride were added and the mixture was stirred at room temperature for 1 hour. 50 mL water were added and the precipitate was filtered off. The solid was washed twice with methanol (3 mL) and twice with diethylether (3 mL) to give 562 mg of the title compound as a solid material.

$^1$H-NMR (400 MHz, DMSO-$d_6$), δ [ppm]=13.62 (s, 1H), 11.80 (bs, 1H), 10.29 (s, 1H), 7.95 (s, 1H), 7.90-7.74 (m, 2H), 7.68 (t, 1H), 7.61-7.52 (m, 1H), 7.43-7.28 (m, 1H), 3.91 (s, 3H).

LC-MS (Method 6): $R_t$=3.50 min; MS (ESIpos) m/z=435.2 [M+H]$^+$.

Example 72

$N^5$-{4-[(2-chloro-4-fluorobenzoyl)amino]-3-fluorophenyl}-$N^4$-methyl-1H-imidazole-4,5-dicarboxamide

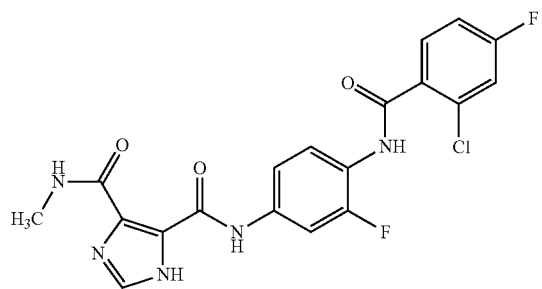 [SMILES: CNC(=O)c1nc[nH]c1C(=O)Nc1ccc(NC(=O)c2ccc(F)cc2Cl)c(F)c1]

To a suspension of 250 mg (0.58 mmol) methyl 5-({4-[(2-chloro-4-fluorobenzoyl)amino]-3-fluorophenyl}carbamoyl)-1H-imidazole-4-carboxylate (Example 71) in 2.5 mL methanol, 5.75 mL (2M solution in THF) methylamine were added and the mixture was stirred for 90 minutes at 50° C. and for 18 hours at 0° C. The precipitate was filtered off and was washed with cold methanol and with cold diethylether to give 159 mg of the title compound as a solid material.

$^1$H-NMR (400 MHz, DMSO-$d_6$), δ [ppm]=13.93 (s, 1H), 13.47 (s, 1H), 10.28 (s, 1H), 8.87 (s, 1H), 7.94 (s, 1H), 7.88 (m, 1H), 7.78 (t, 1H), 7.67 (m, 1H), 7.57 (m, 1H), 7.34 (m, 2H), 2.88 (d, 3H).

LC-MS (Method 6): $R_t$=3.50 min; MS (ESIpos) m/z=434.2 [M+H]$^+$.

Example 73

$N^5$-{4-[(2-chloro-4-fluorobenzoyl)amino]-3-fluorophenyl}-$N^4$-[2-(dimethylamino)ethyl]-1H-imidazole-4,5-dicarboxamide

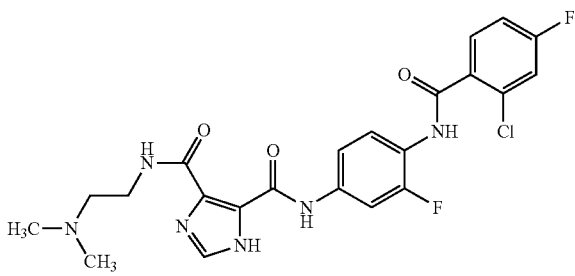 [SMILES: CN(C)CCNC(=O)c1nc[nH]c1C(=O)Nc1ccc(NC(=O)c2ccc(F)cc2Cl)c(F)c1]

A suspension of 200 mg (0.46 mmol) methyl 5-({4-[(2-chloro-4-fluorobenzoyl)amino]-3-fluorophenyl}carbamoyl)-1H-imidazole-4-carboxylate (Example 71) and 304 μL (2.76 mmol) N,N-dimethylethane-1,2-diamine in 2.5 mL dioxane and 1.25 mL methanol was stirred for 20 hours at 80° C. The precipitate was filtered off and was washed with methanol (2 mL) and twice with diethylether (2 mL) to give after drying under vacuum 176 mg of the title compound as a solid material.

$^1$H-NMR (400 MHz, DMSO-$d_6$), δ [ppm]=13.45 (s, 1H), 10.28 (s, 1H), 8.78 (s, 1H), 7.94 (s, 1H), 7.91-7.83 (m, 1H), 7.79 (t, 1H), 7.67 (t, 1H), 7.61-7.52 (m, 1H), 7.42-7.27 (m, 2H), 3.50-3.40 (m, 2H), 2.48-2.41 (m, 2H), 2.21 (s, 6H).

LC-MS (Method 6): $R_t$=2.87 min; MS (ESIpos) m/z=491.2 [M+H]$^+$.

Example 74

$N^5$-{4-[(2-chloro-4-fluorobenzoyl)amino]-3-fluorophenyl}-$N^4$-[2-(piperidin-1-yl)ethyl]-1H-imidazole-4,5-dicarboxamide

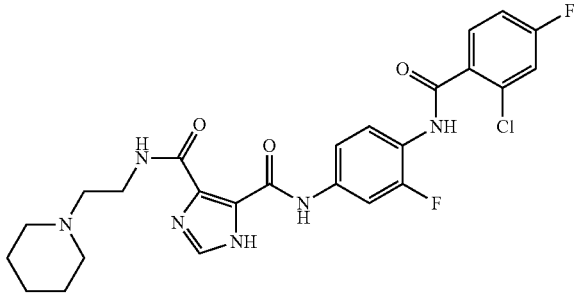 [SMILES: O=C(Nc1ccc(NC(=O)c2[nH]cnc2C(=O)NCCN2CCCCC2)cc1F)c1ccc(F)cc1Cl]

A suspension of 200 mg (0.46 mmol) methyl 5-({4-[(2-chloro-4-fluorobenzoyl)amino]-3-fluorophenyl}carbamoyl)-1H-imidazole-4-carboxylate (Example 71) and 392 μL (2.76 mmol) 2-(piperidin-1-yl) ethanamine in 2.5 mL dioxane and 1.25 mL methanol was stirred for 16 hours at 80° C. The solvent was removed under reduced pressure and the residue was suspended in 2 mL methanol. The precipitate was filtered off and was washed with methanol (2 mL) and twice with diethylether (2 mL) to give after drying under vacuum 115 mg of the title compound as a solid material.

$^1$H-NMR (400 MHz, DMSO-d$_6$), δ [ppm]=13.41 (s, 1H), 10.38 (s, 1H), 9.08 (s, 1H), 8.04 (s, 1H), 8.03-7.95 (m, 1H), 7.88 (t, 1H), 7.78 (q, 1H), 7.70-7.64 (m, 1H), 7.53-7.40 (m, 2H), 7.12 (q, 2H), 2.63-2.54 (m, 4H), 2.54-2.45 (m, 2H), 1.66-1.56 (m, 4H), 1.53-1.43 (m, 2H).

LC-MS (Method 6): R$_t$=2.95 min; MS (ESIpos) m/z=531.2 [M+H]$^+$.

Example 75 methyl-5-({3-fluoro-4-[(4-fluorobenzoyl)amino]phenyl}carbamoyl)-1H-imidazole-4-carboxylate

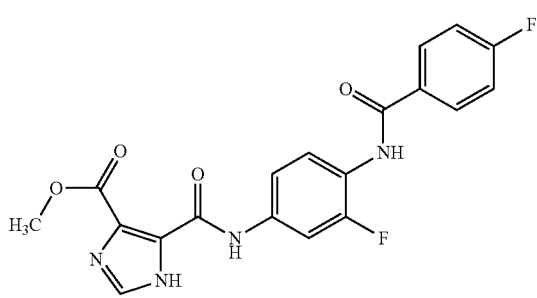 [SMILES: COC(=O)c1nc[nH]c1C(=O)Nc1ccc(NC(=O)c2ccc(F)cc2)c(F)c1]

800 mg (2.88 mmol) methyl 5-[(4-amino-3-fluorophenyl)carbamoyl]-1H-imidazole-4-carboxylate (Intermediate 031) and 2.50 mL (14.38 mmol) N-ethyl-N,N-diisopropylamine were suspended in 15 mL tetrahydrofuran. 679 μL (5.75 mmol) 4-fluorobenzoyl chloride were added and the mixture was stirred at room temperature for 1 hour. 10 mL water were added and the precipitate was filtered off. The solid was washed twice with methanol (5 mL) and twice with diethylether (5 mL) to give 797 mg of the title compound as a solid material.

$^1$H-NMR (400 MHz, DMSO-d$_6$), δ [ppm]=13.63 (s, 1H), 11.80 (s, 1H), 10.11 (s, 1H), 8.10-8.03 (m, 2H), 7.96 (s, 1H), 7.88-7.81 (m, 1H), 7.58 (t, 1H), 7.42-7.32 (m, 3H), 3.91 (s, 1H).

LC-MS (Method 6): R$_t$=3.45 min; MS (ESIpos) m/z=401.2 [M+H]$^+$.

Example 76

N$^5$-{3-fluoro-4-[(4-fluorobenzoyl)amino]phenyl}-N$^4$-methyl-1H-imidazole-4,5-dicarboxamide

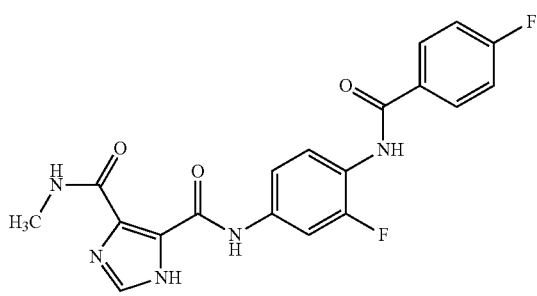 [SMILES: CNC(=O)c1nc[nH]c1C(=O)Nc1ccc(NC(=O)c2ccc(F)cc2)c(F)c1]

A suspension of 200 mg (0.50 mmol) methyl-5-({3-fluoro-4-[(4-fluorobenzoyl)amino]phenyl}carbamoyl)-1H-imidazole-4-carboxylate (Example 75) in 5.00 mL (2M solution in THF) methylamine was stirred for 4 hours at 90° C. The precipitate was filtered off and the solid was washed with methanol (2 mL) and twice with diethylether (2 mL) to give after drying under vacuum 163 mg of the title compound as a solid material.

$^1$H-NMR (400 MHz, DMSO-d$_6$), δ [ppm]=13.9 (s, 1H), 13.42 (s, 1H), 10.27 (s, 1H), 8.93 (s, 1H), 7.95 (s, 1H), 7.91-7.85 (m, 1H), 7.77 (t, 1H), 7.62-7.54 (m, 2H), 7.53-7.42 (m, 2H), 7.38 (s, 1H), 2.92-2.86 (d, 1H).

LC-MS (Method 6): R$_t$=3.45 min; MS (ESIpos) m/z=400.3 [M+H]$^+$.

Example 77

N$^4$-[2-(dimethylamino)ethyl]-N$^5$-{3-fluoro-4-[(4-fluorobenzoyl)amino]phenyl}-1H-imidazole-4,5-dicarboxamide

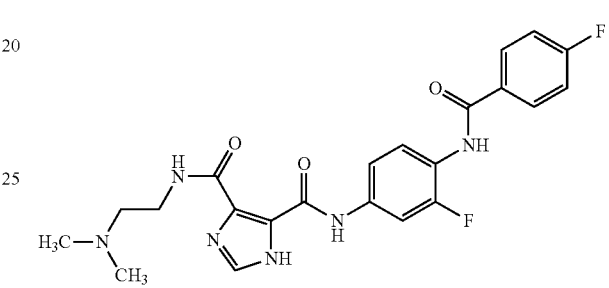

A suspension of 200 mg (0.50 mmol) methyl-5-({3-fluoro-4-[(4-fluorobenzoyl)amino]phenyl}carbamoyl)-1H-imidazole-4-carboxylate (Example 75) and 330 μL (3.00 mmol) N,N-dimethylethane-1,2-diamine in 2.5 mL dioxane and 1.25 mL methanol was stirred for 4 hours at 90° C. The precipitate was filtered off and the solid was washed with methanol (2 mL) and twice with diethylether (2 mL) to give after drying under vacuum 180 mg of the title compound as a solid material.

$^1$H-NMR (400 MHz, DMSO-d$_6$), δ [ppm]=13.47 (s, 1H), 10.10 (s, 1H), 8.84 (s, 1H), 8.06 (q, 2H), 7.94 (s, 1H), 7.90-7.82 (m, 1H), 7.58 (t, 1H), 7.36 (t, 3H), 3.50-3.40 (q, 2H), 2.46 (t, 2H), 2.20 (s, 1H).

LC-MS (Method 6): R$_t$=2.80 min; MS (ESIpos) m/z=457.3 [M+H]$^+$.

Example 78

N$^5$-{3-fluoro-4-[(4-fluorobenzoyl)amino]phenyl}-N$^4$-[2-(piperidin-1-yl)ethyl]-1H-imidazole-4,5-dicarboxamide

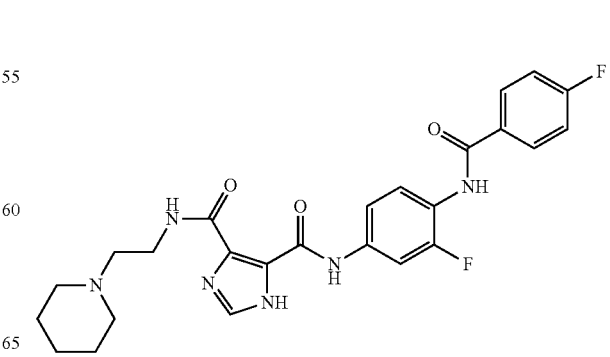

A suspension of 200 mg (0.5 mmol) methyl-5-({3-fluoro-4-[(4-fluorobenzoyl)amino]phenyl}carbamoyl)-1H-imidazole-4-carboxylate (Example 75) and 426 μL (3.00 mmol) 2-(piperidin-1-yl)ethanamine in 2.5 mL dioxane and 1.25 mL methanol was stirred for 4 hours at 90° C. The precipitate was filtered off and the solid was washed with methanol (2 mL) and twice with diethylether (2 mL) to give after drying under vacuum 199 mg of the title compound as a solid material.

$^1$H-NMR (400 MHz, DMSO-d$_6$), δ [ppm]=13.45 (s, 1H), 10.10 (s, 1H), 8.34 (s, 1H), 8.07 (q, 2H), 7.95 (s, 1H), 7.93-7.86 (m, 1H), 7.57 (t, 1H), 7.36 (t, 3H), 3.46 (q, 2H), 2.49-2.45 (m, 2H), 2.43-2.35 (m, 4H), 1.55-1.47 (m, 4H), 1.42-1.34 (m, 2H).

LC-MS (Method 6): R$_t$=2.85 min; MS (ESIpos) m/z=497.3 [M+H]$^+$.

Example 79 methyl-5-({4-[(2-chlorobenzoyl)amino]-3-fluorophenyl}carbamoyl)-1H-imidazole-4-carboxylate

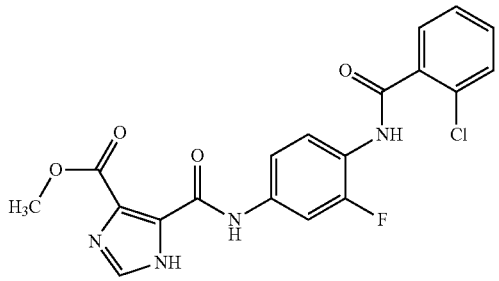 [SMILES: COC(=O)c1nc[nH]c1C(=O)Nc1ccc(NC(=O)c2ccccc2Cl)c(F)c1]

800 mg (2.88 mmol) methyl 5-[(4-amino-3-fluorophenyl)carbamoyl]-1H-imidazole-4-carboxylate (Intermediate 031) and 2.50 mL (14.38 mmol) N-ethyl-N,N-diisopropylamine were suspended in 15 mL tetrahydrofuran. 728 μL (5.75 mmol) 2-chlorobenzoyl chloride were added and the mixture was stirred at room temperature for 1 hour. 10 mL water were added and the precipitate was filtered off. The solid was washed twice with methanol (5 mL) and twice with diethylether (5 mL) to give 819 mg of the title compound as a solid material.

$^1$H-NMR (400 MHz, DMSO-d$_6$), δ [ppm]=13.63 (s, 1H), 11.73 (s, 1H), 10.28 (s, 1H), 7.95 (s, 1H), 7.88-7.82 (m, 1H), 7.78 (t, 1H), 7.62-7.54 (m, 2H), 7.54-7.42 (m, 2H), 7.42-7.35 (s, 1H), 3.91 (s, 3H).

LC-MS (Method 6): R$_t$=3.42 min; MS (ESIpos) m/z=417.2 [M+H]$^+$.

Example 80

N$^5$-{4-[(2-chlorobenzoyl)amino]-3-fluorophenyl}-N$^4$-methyl-1H-imidazole-4,5-dicarboxamide

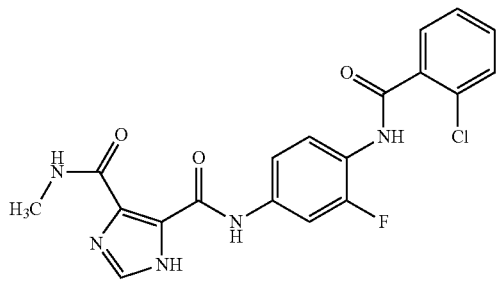 [SMILES: CNC(=O)c1nc[nH]c1C(=O)Nc1ccc(NC(=O)c2ccccc2Cl)c(F)c1]

A suspension of 200 mg (0.48 mmol) methyl-5-({4-[(2-chlorobenzoyl)amino]-3-fluorophenyl}carbamoyl)-1H-imidazole-4-carboxylate (Example 79) in 4.8 mL (2M solution in THF) methylamine was stirred for 90 minutes at 80° C. The solvent was removed under reduced pressure and the residue was suspended in 3 mL diethylether. The precipitate was filtered off to give after drying in vacuo 183 mg of the title compound as a solid material.

$^1$H-NMR (400 MHz, DMSO-d$_6$), δ [ppm]=13.80 (s, 1H), 13.42 (s, 1H), 10.27 (s, 1H), 8.93 (s, 1H), 7.95 (s, 1H), 7.91-7.85 (m, 1H), 7.77 (t, 1H), 7.62-7.54 (m, 2H), 7.53-7.42 (m, 2H), 7.38 (s, 1H), 2.92-2.86 (d, 1H).

LC-MS (Method 6): R$_t$=3.42 min; MS (ESIpos) m/z=416.2 [M+H]$^+$.

Example 81

N$^5$-{4-[(2-chlorobenzoyl)amino]-3-fluorophenyl}-N$^4$-[2-(dimethylamino)ethyl]-1H-imidazole-4,5-dicarboxamide

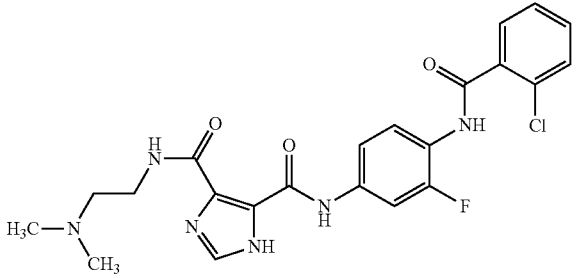 [SMILES: CN(C)CCNC(=O)c1nc[nH]c1C(=O)Nc1ccc(NC(=O)c2ccccc2Cl)c(F)c1]

A suspension of 200 mg (0.48 mmol) methyl-5-({4-[(2-chlorobenzoyl)amino]-3-fluorophenyl}carbamoyl)-1H-imidazole-4-carboxylate (Example 79) and 106 μL (0.96 mmol) N,N-dimethylethane-1,2-diamine in 2.0 mL dioxane and 2.0 mL methanol was stirred for 7 hours at 80° C. The precipitate was filtered off and the solid was washed with methanol (2 mL) and twice with diethylether (2 mL) to give after drying under vacuum 158 mg of the title compound as a solid material.

$^1$H-NMR (400 MHz, DMSO-d$_6$), δ [ppm]=13.48 (s, 1H), 10.27 (s, 1H), 8.81 (s, 1H), 7.94 (s, 1H), 7.91-7.84 (d, 1H), 7.77 (t, 1H), 7.64-7.53 (m, 2H), 7.53-7.42 (m, 2H), 7.41-7.32 (m, 1H), 3.50-3.41 (q, 2H), 2.47 (t, 2H), 2.21 (s, 6H).

LC-MS (Method 6): $R_t$=2.80 min; MS (ESIpos) m/z=473.3 [M+H]⁺.

Example 82

$N^5$-{4-[(2-chlorobenzoyl)amino]-3-fluorophenyl}-$N^4$-[2-(piperidin-1-yl)ethyl]-1H-imidazole-4,5-dicarboxamide

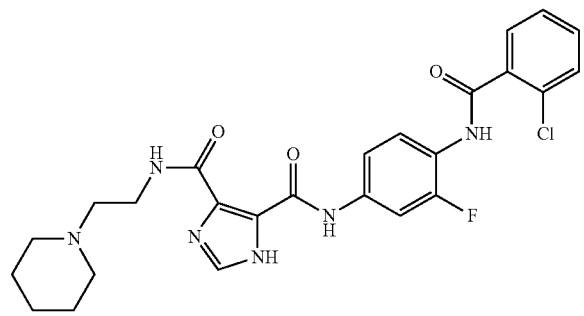 [SMILES: O=C(Nc1ccc(NC(=O)c2[nH]cnc2C(=O)NCCN2CCCCC2)cc1F)c1ccccc1Cl]

A suspension of 200 mg (0.48 mmol) methyl-5-({4-[(2-chlorobenzoyl)amino]-3-fluorophenyl}carbamoyl)-1H-imidazole-4-carboxylate (Example 79) and 136 µL (0.90 mmol) 2-(piperidin-1-yl)ethanamine in 2.0 mL dioxane and 2.0 mL methanol was stirred for 7 hours at 80° C. The solvent was removed under reduced pressure and the residue was suspended in 10 mL diethylether. The precipitate was filtered off and was washed with methanol (2 mL) and twice with diethylether (2 mL) to give after drying under vacuum 136 mg of the title compound as a solid material.

¹H-NMR (400 MHz, DMSO-$d_6$), δ [ppm]=13.18 (s, 1H), 10.27 (s, 1H), 9.06 (s, 1H), 7.93 (s, 1H), 7.92-7.86 (m, 1H), 7.76 (t, 1H), 7.63-7.42 (m, 4H), 7.42-7.36 (m, 1H), 2.52-2.45 (m, 2H), 2.44-2.35 (m, 4H), 1.56-1.45 (m, 5H), 1.43-1.34 (m, 2H).

LC-MS (Method 6): $R_t$=2.85 min; MS (ESIpos) m/z=513.3 [M+H]⁺.

Example 83 methyl 5-({4-[(2-chloro-4-fluorobenzoyl)amino]-3-methylphenyl}carbamoyl)-1H-imidazole-4-carboxylate

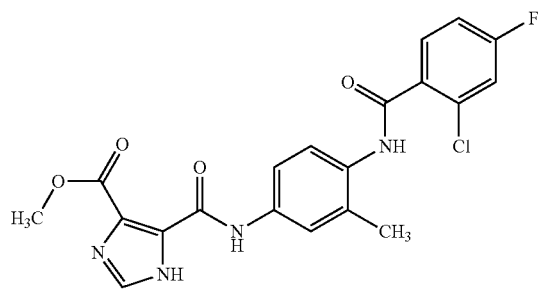 [SMILES: COC(=O)c1nc[nH]c1C(=O)Nc1ccc(NC(=O)c2ccc(F)cc2Cl)c(C)c1]

600 mg (2.19 mmol) methyl 5-[(4-amino-3-methylphenyl)carbamoyl]-1H-imidazole-4-carboxylate Intermediate 033) and 1.90 mL (10.94 mmol) N-ethyl-N,N-diisopropylamine were suspended in 12 mL tetrahydrofuran. 584 µL (4.38 mmol) 2-chloro-4-fluorobenzoyl chloride were added and the mixture was stirred at room temperature for 1 hour. 100 mL water were added and the precipitate was filtered off. The solid was washed three times with water, methanol and diethylether to give 704 mg of the title compound as a solid material.

¹H-NMR (400 MHz, DMSO-$d_6$), δ [ppm]=13.57 (s, 1H), 11.61 (s, 1H), 9.94 (s, 1H), 7.93 (s, 1H), 7.74-7.67 (m, 1H), 7.62-7.54 (m, 3H), 7.46-7.42 (m, 1H), 7.39-7.31 (m, 1H), 3.92 (s, 3H), 2.31 (s, 3H).

LC-MS (Method 6): $R_t$=3.44 min; MS (ESIpos) m/z=431.2 [M+H]⁺.

Example 84

$N^5$-{4-[(2-chloro-4-fluorobenzoyl)amino]-3-methylphenyl}-$N^4$-[2-(dimethyl amino)ethyl]-1H-imidazole-4,5-dicarboxamide

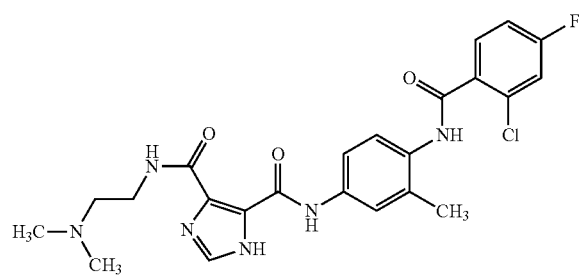

To a suspension of 150 mg (0.35 mmol) methyl 5-({4-[(2-chloro-4-fluorobenzoyl)amino]-3-methylphenyl}carbamoyl)-1H-imidazole-4-carboxylate (Example 83) in 2.5 mL dioxane and 1.25 mL methanol were added 230 µL (2.09 mmol) N,N-dimethylethane-1,2-diamine. The mixture was stirred for 72 hours at 80° C. The precipitate was filtered off and was washed five times with methanol (3 mL) and five times with diethylether (3 mL) to give after drying under vacuum 132 mg of the title compound as a solid material.

¹H-NMR (400 MHz, DMSO-$d_6$), δ [ppm]=13.44 (s, 1H), 9.93 (s, 1H), 8.71 (s, 1H), 7.92 (s, 1H), 7.75-7.66 (m, 1H), 7.58 (t, 3H), 7.43 (d, 1H), 7.39-7.31 (m, 1H), 3.49-3.41 (m, 2H), 3.31 (m, 1H), 2.46 (t, 2H), 2.30 (s, 3H) 2.20 (s, 6H).

LC-MS (Method 6): $R_t$=2.78 min; MS (ESIpos) m/z=487.2 [M+H]⁺.

Example 85

$N^5$-{4-[(2-chloro-4-fluorobenzoyl)amino]-3-methylphenyl}-$N^4$-[2-(piperidin-1-yl)ethyl]-1H-imidazole-4,5-dicarboxamide

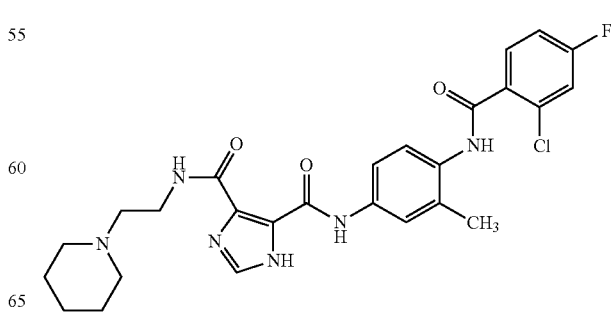

To a suspension of 150 mg (0.35 mmol) methyl 5-({4-[(2-chloro-4-fluorobenzoyl)amino]-3-methylphenyl}carbamoyl)-1H-imidazole-4-carboxylate (Example 83) in 2.5 mL dioxane and 1.25 mL methanol were added 300 μL (2.09 mmol) 2-(piperidin-1-yl)ethanamine. The reaction mixture was stirred for 18 hours at 80° C. The solvent was removed under reduced pressure and the residue was suspended in 5 mL methanol. The precipitate was filtered off and the solid was washed three times with water (3 mL), methanol (3 mL) and diethylether (3 mL) to give after drying under vacuum 152 mg of the title compound as a solid material.

$^1$H-NMR (400 MHz, DMSO-$d_6$), δ [ppm]=13.41 (s, 1H), 9.92 (s, 1H), 8.91 (s, 1H), 7.92 (s, 1H), 7.73-7.68 (m, 1H), 7.64-7.55 (m, 3H), 7.42 (d, 1H), 7.38-7.32 (m, 1H), 3.50-3.43 (m, 2H), 3.31 (m, 1H), 2.52-2.45 (m, 2H), 2.40 (s, 4H), 2.30 (s, 3H), 1.56-1.47 (m, 4H), 1.43-1.35 (m, 2H).

LC-MS (Method 6): $R_t$=2.86 min; MS (ESIpos) m/z=527.3 [M+H]$^+$.

Example 86 methyl-5-({4-[(2-chlorobenzoyl)amino]-3-methylphenyl}carbamoyl)-1H-imidazole-4-carboxylate

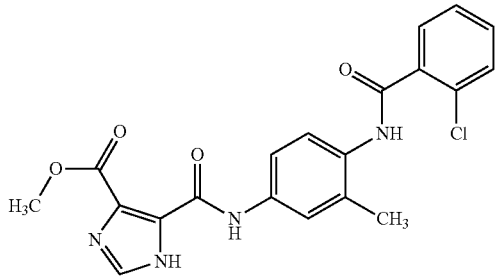 [SMILES: COC(=O)c1nc[nH]c1C(=O)Nc1ccc(NC(=O)c2ccccc2Cl)c(C)c1]

600 mg (2.19 mmol) methyl 5-[(4-amino-3-methylphenyl)carbamoyl]-1H-imidazole-4-carboxylate (Intermediate 033) and 1.90 mL (10.94 mmol) N-ethyl-N,N-diisopropylamine were suspended in 12 mL tetrahydrofuran. 554 μL (4.38 mmol) 2-chlorobenzoyl chloride were added and the mixture was stirred at room temperature for 1 hour. 100 mL water were added and the precipitate was filtered off. The solid was washed three times with water, methanol and diethylether (10 mL) to give 629 mg of the title compound as a solid material.

$^1$H-NMR (400 MHz, DMSO-$d_6$), δ [ppm]=13.58 (s, 1H), 11.61 (s, 1H), 9.94 (s, 1H), 7.93 (s, 1H), 7.65-7.54 (m, 4H), 7.53-7.41 (m, 3H), 3.92 (s, 3H), 2.31 (s, 3H).

LC-MS (Method 6): $R_t$=3.35 min; MS (ESIpos) m/z=413.2 [M+H]$^+$.

Example 87

$N^5$-{4-[(2-chlorobenzoyl)amino]-3-methylphenyl}-$N^4$-methyl-1H-imidazole-4,5-dicarboxamide

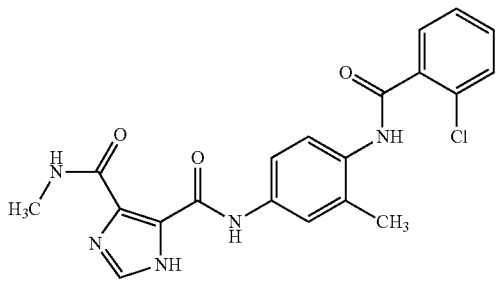 [SMILES: CNC(=O)c1nc[nH]c1C(=O)Nc1ccc(NC(=O)c2ccccc2Cl)c(C)c1]

A suspension of 150 mg (0.36 mmol) methyl-5-({4-[(2-chlorobenzoyl)amino]-3-methylphenyl}carbamoyl)-1H-imidazole-4-carboxylate (Example 86) in 3.6 mL (2M solution in THF) methylamine was stirred for 18 hours at 80° C. The precipitate was filtered off and the solid was washed five times with methanol (3 mL) and five times with diethylether (3 mL) to give after drying under vacuum 52 mg of the title compound as a solid material.

$^1$H-NMR (400 MHz, DMSO-$d_6$), δ [ppm]=13.37 (s, 2H), 9.92 (s, 1H), 8.89 (s, 1H), 7.92 (s, 1H), 7.65-7.54 (m, 4H), 7.53-7.39 (m, 3H), 2.88 (d, 3H), 2.31 (s, 3H).

LC-MS (Method 6): $R_t$=3.33 min; MS (ESIpos) m/z=412.3 [M+H]$^+$.

Example 88

$N^5$-{4-[(2-chlorobenzoyl)amino]-3-methylphenyl}-$N^4$-[2-(dimethylamino)ethyl]-1H-imidazole-4,5-dicarboxamide

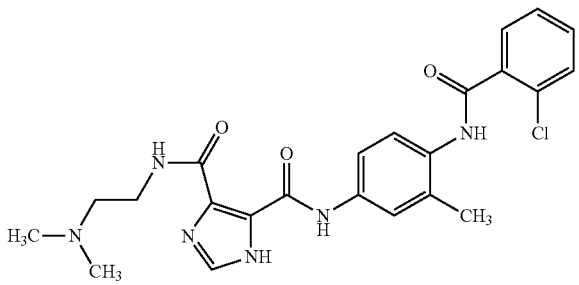

To a suspension of 150 mg (0.36 mmol) methyl-5-({4-[(2-chlorobenzoyl)amino]-3-methylphenyl}carbamoyl)-1H-imidazole-4-carboxylate (Example 86) in 2.5 mL dioxane and 1.25 mL methanol were added 240 μL (2.18 mmol) N,N-dimethylethane-1,2-diamine. The mixture was stirred for 24 hours at 80° C. The precipitate was filtered off and the solid was washed three times with water (3 mL), methanol (3 mL) and diethylether (3 mL) to give 125 mg of the title compound as a solid material.

$^1$H-NMR (400 MHz, DMSO-$d_6$), δ [ppm]=13.44 (s, 1H), 9.92 (s, 1H), 8.65 (s, 1H), 7.92 (s, 1H), 7.65-7.54 (m, 4H), 7.53-7.39 (m, 3H), 3.50-3.42 (m, 2H), 3.31 (m, 1H), 2.46 (t, 2H), 2.31 (s, 3H), 2.21 (s, 6H).

LC-MS (Method 6): $R_t$=2.70 min; MS (ESIpos) m/z=469.3 [M+H]$^+$.

Example 89

N$^5$-{4-[(2-chlorobenzoyl)amino]-3-methylphenyl}-N$^4$-[2-(piperidin-1-yl)ethyl]-1H-imidazole-4,5-dicarboxamide

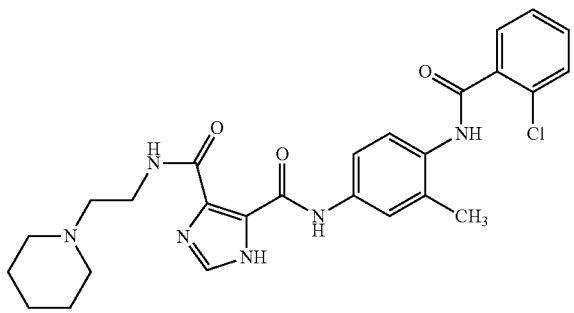 [SMILES: Cc1cc(NC(=O)c2[nH]cnc2C(=O)NCCN2CCCCC2)ccc1NC(=O)c1ccccc1Cl]

To a suspension of 150 mg (0.36 mmol) methyl-5-({4-[(2-chlorobenzoyl)amino]-3-methylphenyl}carbamoyl)-1H-imidazole-4-carboxylate (Example 86) in 2.5 mL dioxane and 1.25 mL methanol were added 310 µL (2.18 mmol) 2-(piperidin-1-yl)ethanamine. The reaction mixture was stirred for 18 hours at 80° C. The solvent was removed under reduced pressure and the residue was suspended in 25 mL water. The precipitate was filtered off and was washed three times with water (3 mL), methanol (3 mL) and diethylether (3 mL) to give 154 mg of the title compound as a solid material.

$^1$H-NMR (400 MHz, DMSO-d$_6$), δ [ppm]=13.42 (s, 2H), 9.92 (s, 1H), 8.81 (s, 1H), 7.93 (s, 1H), 7.66-7.54 (m, 4H), 7.53-7.39 (m, 3H), 3.47 (m, 2H), 3.31 (m, 2H), 2.45-2.35 (m, 4H), 2.35 (s, 3H), 1.56-1.45 (m, 4H), 1.44-1.34 (m, 2H).

LC-MS (Method 6): $R_t$=2.79 min; MS (ESIpos) m/z=509.3 [M+H]$^+$.

Example 90 methyl-5-({4-[(4-fluorobenzoyl)amino]-3-methylphenyl}carbamoyl)-1H-imidazole-4-carboxylate

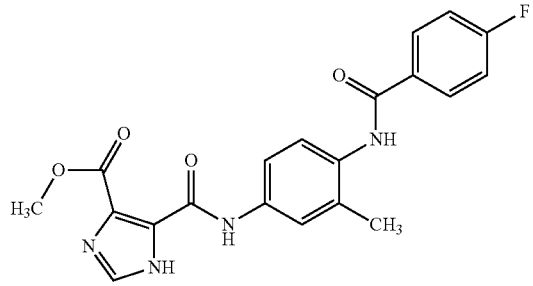 [SMILES: COC(=O)c1nc[nH]c1C(=O)Nc1ccc(NC(=O)c2ccc(F)cc2)c(C)c1]

600 mg (2.19 mmol) methyl 5-[(4-amino-3-methylphenyl)carbamoyl]-1H-imidazole-4-carboxylate (Intermediate 033) and 1.90 mL (10.94 mmol) N-ethyl-N,N-diisopropylamine were suspended in 12 mL tetrahydrofuran. 520 µL (4.38 mmol) 4-fluorobenzoyl chloride were added and the mixture was stirred at room temperature for 1 hour. 100 mL water were added and the precipitate was filtered off. The solid was washed three times with water, methanol and diethylether (10 mL) to give 642 mg of the title compound as a solid material.

$^1$H-NMR (400 MHz, DMSO-d$_6$), δ [ppm]=13.57 (s, 1H), 11.61 (s, 1H), 9.88 (s, 1H), 8.12-8.00 (m, 2H), 7.93 (s, 1H), 7.64-7.55 (m, 2H), 7.41-7.30 (m, 3H), 3.92 (s, 3H), 2.25 (s, 3H).

LC-MS (Method 6): $R_t$=3.37 min; MS (ESIpos) m/z=397.3 [M+H]$^+$.

Example 91

N$^5$-{4-[(4-fluorobenzoyl)amino]-3-methylphenyl}-N$^4$-methyl-1H-imidazole-4,5-dicarboxamide

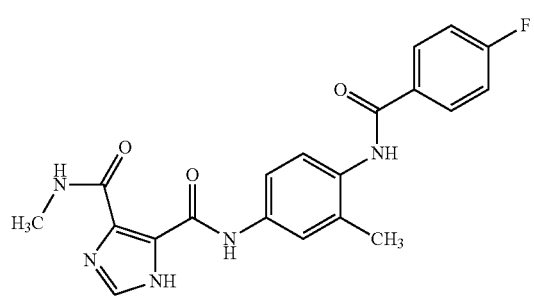 [SMILES: CNC(=O)c1nc[nH]c1C(=O)Nc1ccc(NC(=O)c2ccc(F)cc2)c(C)c1]

A suspension of 150 mg (0.38 mmol) methyl-5-({4-[(4-fluorobenzoyl)amino]-3-methylphenyl}carbamoyl)-1H-imidazole-4-carboxylate (Example 90) in 3.8 mL (2M solution in THF) methylamine was stirred for 90 minutes at 80° C. 2 mL methanol were added and the mixture was stirred for 24 hours at 80° C. The precipitate was filtered off and the solid was washed five times with methanol (3 mL) and five times with diethylether (3 mL) to give after drying under vacuum 125 mg of the title compound as a solid material.

$^1$H-NMR (400 MHz, DMSO-d$_6$), δ [ppm]=13.43 (s, 1H), 9.87 (s, 1H), 8.88 (s, 1H), 8.11-8.02 (m, 2H), 7.92 (s, 1H), 7.66-7.56 (m, 2H), 7.41-7.30 (m, 3H), 3.92 (s, 1H), 2.88 (d, 3H), 2.25 (s, 3H).

LC-MS (Method 6): $R_t$=3.35 min; MS (ESIpos) m/z=396.2 [M+H]$^+$.

Example 92

N$^4$-[2-(dimethylamino)ethyl]-N$^5$-{4-[(4-fluorobenzoyl)amino]-3-methylphenyl}-1H-imidazole-4,5-dicarboxamide

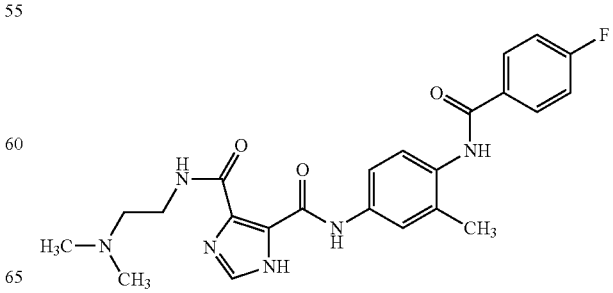

To a suspension of 150 mg (0.38 mmol) methyl 5-({4[(4-fluorobenzoyl)amino]-3-methylphenyl}carbamoyl)-1H-imidazole-4-carboxylate (Example 90) in 2.5 mL dioxane and 1.25 mL methanol were added 250 µL (2.27 mmol) N,N-dimethylethane-1,2-diamine. The mixture was stirred for 24 hours at 80° C. The precipitate was filtered off and the solid was washed five times with methanol (3 mL) and five times with diethylether (3 mL) to give after drying under vacuum 102 mg of the title compound as a solid material.

$^1$H-NMR (400 MHz, DMSO-$d_6$), δ [ppm]=13.45 (s, 1H), 9.88 (s, 1H), 8.73 (s, 1H), 8.11-8.02 (m, 2H), 7.92 (s, 1H), 7.64-7.56 (m, 2H), 7.40-7.30 (m, 3H), 3.49-3.41 (m, 2H), 3.31 (m, 1H), 2.49-2.44 (m, 2H), 2.25 (s, 3H), 2.20 (s, 6H).

LC-MS (Method 6): $R_t$=2.69 min; MS (ESIpos) m/z=453.3 [M+H]$^+$.

Example 93

$N^5$-{4-[(4-fluorobenzoyl)amino]-3-methylphenyl}-$N^4$-[2-(piperidin-1-yl)ethyl]-1H-imidazole-4,5-dicarboxamide

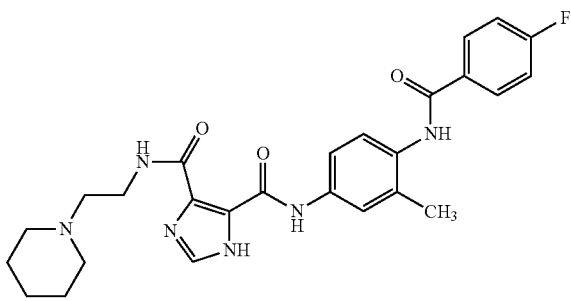 [SMILES: Cc1cc(NC(=O)c2[nH]cnc2C(=O)NCCN2CCCCC2)ccc1NC(=O)c1ccc(F)cc1]

To a suspension of 150 mg (0.38 mmol) methyl 5-({4-[(4-fluorobenzoyl)amino]-3-methylphenyl}carbamoyl)-1H-imidazole-4-carboxylate (Example 90) in 2.5 mL dioxane and 1.25 mL methanol were added 322 µL (2.27 mmol) 2-(piperidin-1-yl)ethanamine. The reaction mixture was stirred for 24 hours at 80° C. The precipitate was filtered off and the solid was washed five times with methanol (3 mL) and five times with diethylether (3 mL) to give after drying under vacuum 111 mg of the title compound as a solid material.

$^1$H-NMR (400 MHz, DMSO-$d_6$), δ [ppm]=13.44 (s, 2H), 9.87 (s, 1H), 8.79 (s, 1H), 8.10-8.03 (m, 2H), 7.93 (s, 1H), 7.61 (d, 2H), 7.40-7.30 (m, 3H), 3.50-3.43 (m, 2H), 2.52-2.45 (m, 2H), 2.40 (s, 4H), 2.25 (s, 3H), 1.55-1.47 (m, 4H), 1.43-1.34 (m, 2H).

LC-MS (Method 6): $R_t$=2.80 min; MS (ESIpos) m/z=493.3 [M+H]$^+$.

Example 94 methyl 5-({4-[(2-chloro-4-fluorobenzoyl)amino]-3-methoxyphenyl}carbamoyl)-1H-imidazole-4-carboxylate

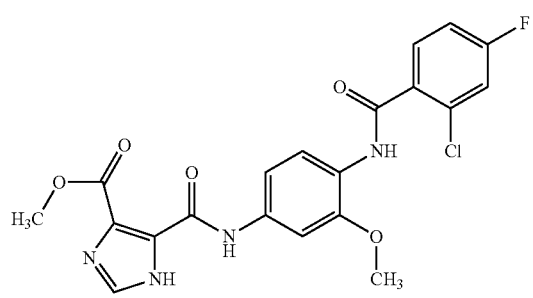 [SMILES: COC(=O)c1nc[nH]c1C(=O)Nc1ccc(NC(=O)c2ccc(F)cc2Cl)c(OC)c1]

500 mg (1.72 mmol) methyl 4-[(4-amino-3-methoxyphenyl)carbamoyl]-1H-imidazole-5-carboxylate (Intermediate 037) and 1.50 mL (8.61 mmol) N-ethyl-N,N-diisopropylamine were suspended in 20 mL tetrahydrofuran. 460 µL (3.45 mmol) 2-chloro-4-fluorobenzoyl chloride were added and the mixture was stirred at room temperature for 1 hour. 40 mL water were added and the organic solvent was removed under reduced pressure. The precipitate was filtered off and washed with water. After drying in vacuo the crude product was recrystallised to give 534 mg of the title compound as a solid material.

$^1$H-NMR (400 MHz, DMSO-$d_6$), δ [ppm]=13.58 (s, 1H), 11.87 (s, 1H), 9.66 (s, 1H), 7.95 (s, 1H), 7.90 (s, 1H), 7.67-7.61 (m, 2H), 7.54 (m, 1H), 7.32 (m, 1H), 7.21 (s, 1H), 3.93 (s, 3H), 3.84 (s, 3H).

LC-MS (Method 6): $R_t$=3.61 min; MS (ESIpos) m/z=447.2 [M+H]$^+$.

Example 95

$N^5$-{4-[(2-chloro-4-fluorobenzoyl)amino]-3-methoxyphenyl}-$N^4$-methyl-1H-imidazole-4,5-dicarboxamide

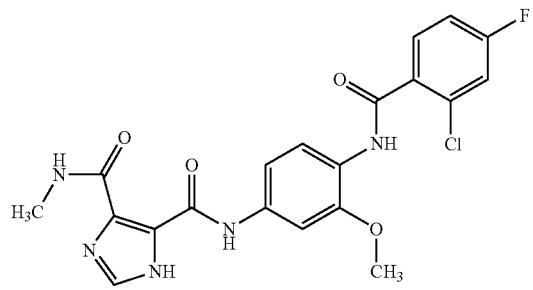 [SMILES: CNC(=O)c1nc[nH]c1C(=O)Nc1ccc(NC(=O)c2ccc(F)cc2Cl)c(OC)c1]

100 mg (0.22 mmol) methyl 5-({4-[(2-chloro-4-fluorobenzoyl)amino]-3-methoxyphenyl}carbamoyl)-1H-imidazole-4-carboxylate (Example 94) was dissolved in 670 µL of a 2M solution of methylamine in tetrahydrofuran. The mixture was stirred for 2 hours at 90° C. After standing overnight at 0° C. the precipitate was filtered off and the solid was washed with tetrahydrofuran (2 mL), methanol (2 mL) and diethylether (2 mL). The residue was dried under vacuum to give 68 mg of the title compound as a solid material.

¹H-NMR (400 MHz, DMSO-d₆), δ [ppm]=13.70 (s, 1H), 13.40 (s, 1H), 9.63 (s, 1H), 8.82 (s, 1H), 7.93 (s, 1H), 7.89 (m, 1H), 7.63 (m, 2H), 7.53 (m, 1H), 7.32 (s, 1H), 7.17 (m, 1H), 3.85 (s, 3H), 2.89 (s, 3H).

LC-MS (Method 6): $R_t$=3.60 min; MS (ESIpos) m/z=446.2 [M+H]⁺.

Example 96

N⁵-{4-[(2-chloro-4-fluorobenzoyl)amino]-3-methoxyphenyl}-N⁴-[2-(dimethylamino)ethyl]-1H-imidazole-4,5-dicarboxamide

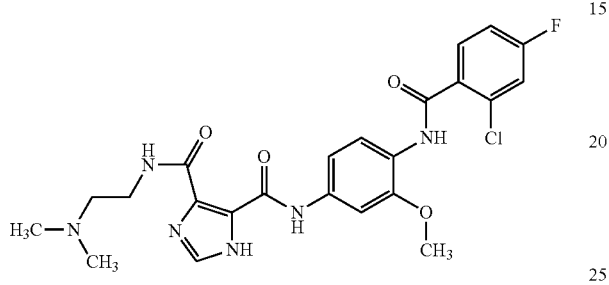

To a suspension of 150 mg (0.34 mmol) methyl 5-({4-[(2-chloro-4-fluorobenzoyl)amino]-3-methoxyphenyl}carbamoyl)-1H-imidazole-4-carboxylate (Example 94) in 1.00 mL methanol were added 280 μL (2.53 mmol) N,N-dimethylethane-1,2-diamine and 6 mL tetrahydrofuran. The mixture was stirred for 18 hours at 70° C. The reaction mixture was concentrated and the residue was recrystallised in methanol to give 134 mg of the title compound as a solid material.

¹H-NMR (400 MHz, DMSO-d₆), δ [ppm]=13.39 (s, 1H), 9.64 (s, 1H), 8.61 (s, 1H), 7.93 (s, 1H), 7.90 (m, 1H), 7.67 (m, 2H), 7.55 (m, 1H), 7.30 (m, 1H), 7.22 (m, 1H), 3.84 (s, 3H), 3.46 (m, 2H), 2.46 (m, 2H), 2.21 (s, 6H).

LC-MS (Method 6): $R_t$=2.931 min; MS (ESIpos) m/z=503.2 [M+H]⁺.

Example 97

N⁵-{4-[(2-chloro-4-fluorobenzoyl)amino]-3-methoxyphenyl}-N⁴-[2-(piperidin-1-yl)ethyl]-1H-imidazole-4,5-dicarboxamide

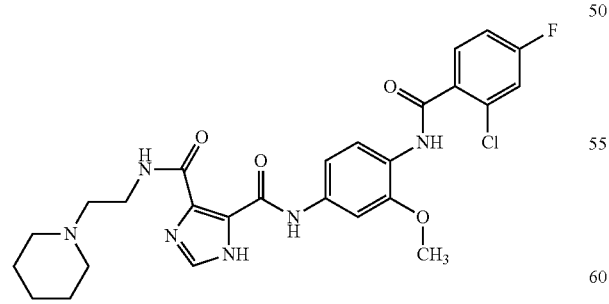

To a suspension of 150 mg (0.34 mmol) methyl 5-({4-[(2-chloro-4-fluorobenzoyl)amino]-3-methoxyphenyl}carbamoyl)-1H-imidazole-4-carboxylate (Example 94) in 1.00 mL methanol were added 365 μL (2.53 mmol) 2-(piperidin-1-yl)ethanamine and 3 mL tetrahydrofuran. The reaction mixture was stirred for 18 hours at 70° C. The reaction mixture was concentrated and the residue was recrystallised in methanol to give 124 mg of the title compound as a solid material.

¹H-NMR (400 MHz, DMSO-d₆), δ [ppm]=13.50 (s, 1H), 13.39 (s, 1H), 9.63 (s, 1H), 8.65 (s, 1H), 7.94 (s, 1H), 7.89 (m, 1H), 7.65 (m, 2H), 7.54 (m, 1H), 7.32 (s, 1H), 7.23 (m, 1H), 3.84 (s, 3H), 3.46 (m, 2H), 2.48 (m 2H), 2.40 (m, 4H), 1.51 (m, 4H) 1.39 (m, 2H).

LC-MS (Method 6): $R_t$=2.98 min; MS (ESIpos) m/z=543.2 [M+H]⁺.

Example 98 methyl 5-({4-[(2-chlorobenzoyl)amino]-3-methoxyphenyl}carbamoyl)-1H-imidazole-4-carboxylate

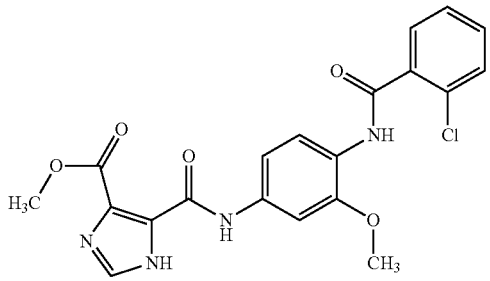 [SMILES: COC(=O)c1nc[nH]c1C(=O)Nc1ccc(NC(=O)c2ccccc2Cl)c(OC)c1]

700 mg (2.41 mmol) methyl 4-[(4-amino-3-methoxyphenyl)carbamoyl]-1H-imidazole-5-carboxylate (Intermediate 037) and 2.10 mL (12.06 mmol) N-ethyl-N,N-diisopropylamine were suspended in 20 mL tetrahydrofuran. 610 μL (4.82 mmol) 2-chlorobenzoyl chloride were added and the mixture was stirred at room temperature for 1 hour. 40 mL water were added and the organic solvent was removed under reduced pressure. The precipitate was filtered off and the solid was washed with water. After drying under vacuum the crude product was recrystallised to give 867 mg of the title compound as a solid material.

¹H-NMR (400 MHz, DMSO-d₆), δ [ppm]=13.57 (s, 1H), 11.69 (s, 1H), 9.60 (s, 1H), 7.94 (s, 1H), 7.90 (s, 1H), 7.61-7.44 (m, 5H), 7.21 (m, 1H), 3.92 (s, 3H), 3.84 (s, 3H).

LC-MS (Method 6): $R_t$=3.53 min; MS (ESIpos) m/z=429.2 [M+H]⁺.

Example 99

N⁵-{4-[(2-chlorobenzoyl)amino]-3-methoxyphenyl}-N⁴-methyl-1H-imidazole-4,5-dicarboxamide

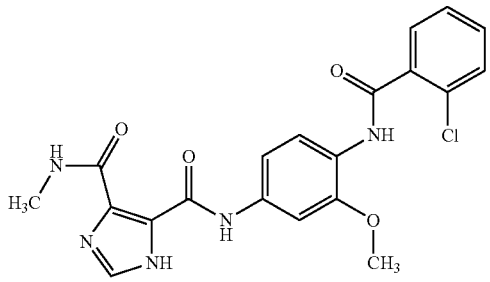 [SMILES: CNC(=O)c1nc[nH]c1C(=O)Nc1ccc(NC(=O)c2ccccc2Cl)c(OC)c1]

To a suspension of 200 mg (0.36 mmol) methyl 5-({4-[(2-chlorobenzoyl)amino]-3-methoxyphenyl}carbamoyl)-1H-imidazole-4-carboxylate (Example 98) in 1 mL tetrahydrofuran were added 4.7 mL (2M solution in THF) methylamine. The mixture was stirred for 4 hours at 70° C. The organic solvent was removed under reduced pressure and the precipitate was filtered off and was washed with methanol to give after drying under vacuum 157 mg of the title compound as a solid material.

$^1$H-NMR (400 MHz, DMSO-d$_6$), δ [ppm]=13.3 (s, 1H), 9.49 (s, 1H), 9.01 (s, 1H), 8.04 (m, 2H), 7.93 (s, 1H), 7.67 (m, 2H), 7.34 (m, 2H), 7.24 (m, 2H), 3.85 (s, 3H), 2.89 (s, 3H).

LC-MS (Method 6): R$_t$=3.53 min; MS (ESIpos) m/z=428.2 [M+H]$^+$.

Example 100

N$^5$-{4-[(2-chlorobenzoyl)amino]-3-methoxyphenyl}-N$^4$-[2-(dimethylamino)ethyl]-1H-imidazole-4,5-dicarboxamide

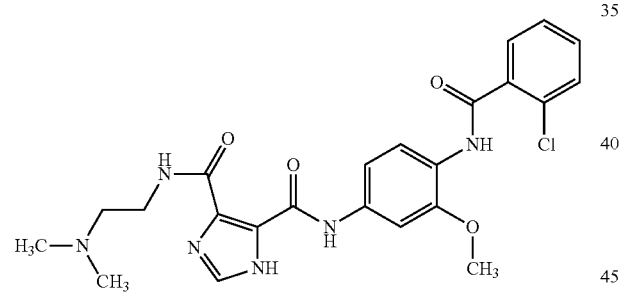

To a suspension of 150 mg (0.35 mmol) methyl 5-({4-[(2-chlorobenzoyl)amino]-3-methoxyphenyl}carbamoyl)-1H-imidazole-4-carboxylate (Example 98) in 1.00 mL methanol were added 280 μL (2.18 mmol) N,N-dimethylethane-1,2-diamine and 6 mL tetrahydrofuran. The mixture was stirred for 3 days at 70° C. The reaction mixture was concentrated and the residue was recrystallised in methanol to give 109 mg of the title compound as a solid material.

$^1$H-NMR (400 MHz, DMSO-d$_6$), δ [ppm]=13.50 (s, 1H), 13.40 (s, 1H), 9.58 (s, 1H), 7.93 (s, 1H), 7.89 (m, 1H), 7.65 (m, 1H), 7.60-7.42 (m, 4H), 7.21 (s, 1H), 3.84 (s, 3H), 3.47 (m, 2H), 2.49 (m, 2H), 2.21 (s, 6H).

LC-MS (Method 6): R$_t$=2.90 min; MS (ESIpos) m/z=485.3 [M+H]$^+$.

Example 101

N$^5$-{4-[(2-chlorobenzoyl)amino]-3-methoxyphenyl}-N$^4$-[2-(piperidin-1-yl)ethyl]-1H-imidazole-4,5-dicarboxamide

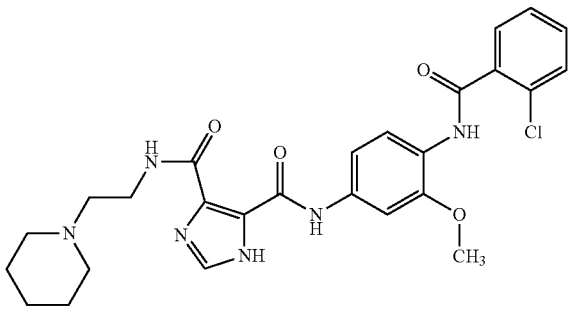 [SMILES: COc1cc(NC(=O)c2[nH]cnc2C(=O)NCCN2CCCCC2)ccc1NC(=O)c1ccccc1Cl]

To a suspension of 150 mg (0.35 mmol) methyl 5-({4-[(2-chlorobenzoyl)amino]-3-methoxyphenyl}carbamoyl)-1H-imidazole-4-carboxylate (Example 98) in 1.00 mL methanol were added 300 μL (2.10 mmol) 2-(piperidin-1-yl)ethanamine and 3 mL tetrahydrofuran. The reaction mixture was stirred for 18 hours at 70° C. The reaction mixture was concentrated and the residue was recrystallised in methanol to give 79 mg of the title compound as a solid material.

$^1$H-NMR (400 MHz, DMSO-d$_6$), δ [ppm]=13.50 (s, 1H), 13.31 (s, 1H), 9.58 (s, 1H), 8.77 (s, 1H), 7.94 (s, 1H), 7.89 (m, 1H), 7.65 (s, 1H), 7.60-7.44 (m, 4H), 7.23 (m, 1H), 3.84 (s, 3H), 3.46 (m, 2H), 2.47 (m, 2H), 2.40 (m, 4H), 1.51 (m, 4H), 1.39 (m, 2H).

LC-MS (Method 6): R$_t$=2.96 min; MS (ESIpos) m/z=525.3 [M+H]$^+$.

Example 102 methyl 5-({4-[(4-fluorobenzoyl)amino]-3-methoxyphenyl}carbamoyl)-1H-imidazole-4-carboxylate

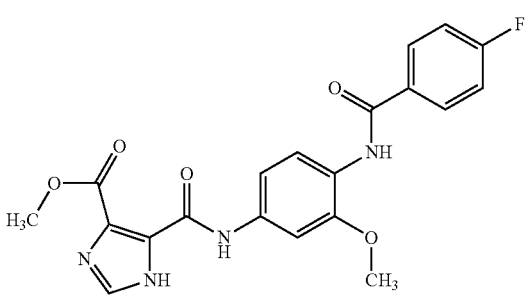 [SMILES: COC(=O)c1nc[nH]c1C(=O)Nc1ccc(NC(=O)c2ccc(F)cc2)c(OC)c1]

700 mg (2.41 mmol) methyl 4-[(4-amino-3-methoxyphenyl)carbamoyl]-1H-imidazole-5-carboxylate (intermediate 037) and 2.10 mL (12.06 mmol) N-ethyl-N,N-diisopropylamine were suspended in 20 mL tetrahydrofuran. 570 μL (4.82 mmol) 4-fluorobenzoyl chloride were added and the mixture was stirred at room temperature for 1 hour. 40 mL water were added and the organic solvent was removed under reduced pressure. The precipitate was filtered off and washed with water. After drying under vacuum the crude product was recrystallised from methanol to give 939 mg of the title compound as a solid material.

$^1$H-NMR (400 MHz, DMSO-d$_6$), δ [ppm]=δ [ppm]=13.58 (s, 1H), 11.81 (s, 1H), 9.50 (s, 1H), 8.05 (m, 2H), 7.95 (s, 1H), 7.68 (m, 1H), 7.61 (m 1H), 7.35 (m, 2H), 7.21 (m, 1H), 3.92 (s, 3H), 3.85 (s, 3H).

LC-MS (Method 6): R$_t$=3.54 min; MS (ESIpos) m/z=413. [M+H]$^+$.

Example 103

N$^5$-{4-[(4-fluorobenzoyl)amino]-3-methoxyphenyl}-N$^4$-methyl-1H-imidazole-4,5-dicarboxamide

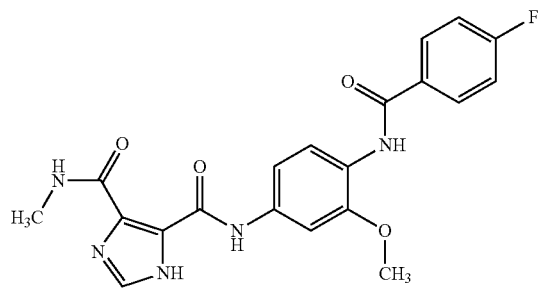 [SMILES: CNC(=O)c1nc[nH]c1C(=O)Nc1ccc(NC(=O)c2ccc(F)cc2)c(OC)c1]

To a suspension of 200 mg (0.49 mmol) methyl 5-({4-[(4-fluorobenzoyl)amino]-3-methoxyphenyl}carbamoyl)-1H-imidazole-4-carboxylate (Example 102) in 1 mL methanol were added 4.90 mL (2M solution in THF) methylamine. The mixture was stirred for 4 hours at 70° C. The tetrahydrofuran was removed under reduced pressure and the precipitate was filtered off and was washed with methanol to give after drying in vacuo 176 mg of the title compound as a solid material.

$^1$H-NMR (400 MHz, DMSO-d$_6$), δ [ppm]=13.70 (s, 1H), 13.40 (s, 1H), 9.58 (s, 1H), 8.82 (s, 1H), 7.93 (s, 1H), 7.90 (m, 1H), 7.64-7.42 (m, 5H), 7.19 (m, 1H), 3.85 (s, 3H), 2.89 (s, 3H).

LC-MS (Method 6): R$_t$=3.53 min; MS (ESIpos) m/z=412.3 [M+H]$^+$.

Example 104

N$^4$-[2-(dimethylamino)ethyl]-N$^5$-{4-[(4-fluorobenzoyl)amino]-3-methoxyphenyl}-1H-imidazole-4,5-dicarboxamide

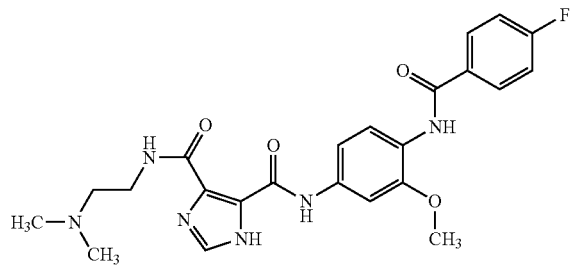

To a suspension of 150 mg (0.36 mmol) methyl 5-({4-[(4-fluorobenzoyl)amino]-3-methoxyphenyl}carbamoyl)-1H-imidazole-4-carboxylate (Example 102) in 1.00 mL methanol were added 280 μL (2.53 mmol) N,N-dimethylethane-1,2-diamine and 6 mL tetrahydrofuran. The mixture was stirred for 64 hours at 70° C. The reaction was concentrated in vacuo and the residue was recrystallised from methanol to give 134 mg of the title compound as a solid material.

$^1$H-NMR (400 MHz, DMSO-d$_6$), δ [ppm]=13.40 (s, 1H), 13.50 (s, 1H), 9.49 (s, 1H), 8.65 (s, 1H), 8.06 (m, 2H), 7.93 (s, 1H), 7.66 (m, 2H), 7.35 (m, 2H), 7.22 (m, 1H), 3.85 (s, 3H), 3.46 (m, 2H), 2.46 (m, 2H), 2.21 (s, 6H).

LC-MS (Method 6): R$_t$=2.90 min; MS (ESIpos) m/z=469.3 [M+H]$^+$.

Example 105

N$^5$-{4-[(4-fluorobenzoyl)amino]-3-methoxyphenyl}-N$^4$-[2-(piperidin-1-yl)ethyl]-1H-imidazole-4,5-dicarboxamide

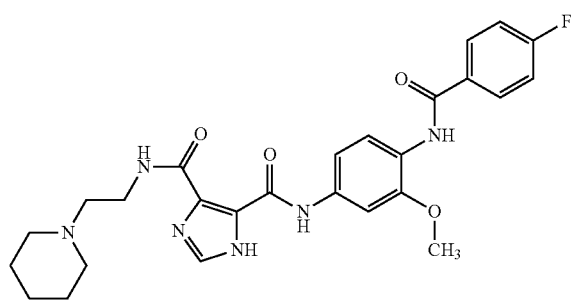

To a suspension of 150 mg (0.36 mmol) methyl 5-({4-[(4-fluorobenzoyl)amino]-3-methoxyphenyl}carbamoyl)-1H-imidazole-4-carboxylate (example 102) in 1.00 mL methanol were added 315 μL (2.18 mmol) 2-(piperidin-1-yl)ethanamine and 3 mL tetrahydrofuran. The reaction mixture was stirred for 18 hours at 70° C. The reaction was concentrated in vacuo and the residue was recrystallised from methanol to give 163 mg of the title compound as a solid material.

$^1$H-NMR (400 MHz, DMSO-d$_6$), δ [ppm]=13.59 (s, 1H), 13.40 (s, 1H), 9.49 (s, 1H), 8.85 (s, 1H), 8.05 (m, 2H), 7.94 (s, 1H), 7.66 (m, 2H), 7.37 (m, 2H), 7.23 (m, 1H), 3.85 (s, 3H), 3.47 (m, 2H), 2.49 (2H, m), 2.40 (m, 4H), 1.51 (m, 4H), 1.38 (m, 2H).

LC-MS (Method 6): R$_t$=2.92 min; MS (ESIpos) m/z=509.3 [M+H]$^+$.

Example 106

N⁴-{4-[(2-chloro-4-fluorobenzoyl)amino]phenyl}-2-isopropyl-N⁵-methyl-1H-imidazole-4,5-dicarboxamide

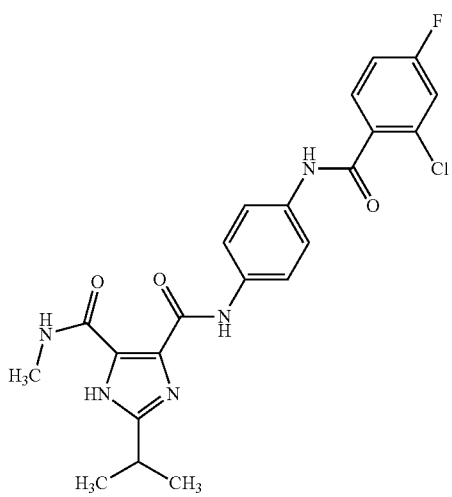 [SMILES: CNC(=O)c1[nH]c(C(C)C)nc1C(=O)Nc1ccc(NC(=O)c2ccc(F)cc2Cl)cc1]

Step A:

To 149 mg (0.38 mmol, crude product, intermediate 040) of 3,8-diisopropyl-5,10-dioxo-5H,10H-diimidazo[1,5-a:1',5'-d]pyrazine-1,6-dicarbonyl dichloride dissolved in 3 mL tetrahydrofuran were added 198 mg (1.00 mmol) N-(4-aminophenyl)-2-chloro-4-fluorobenzamide (Intermediate 004) and 157 µL (1.13 mmol) triethylamine. The resulting mixture was stirred for 30 minutes at room temperature.

Step B:

3.75 mL (7.50 mmol) of a 2 M solution of methylamine in tetrahydrofuran were added and the mixture was stirred for 30 minutes at room temperature. The solvent was removed under reduced pressure and the crude product was purified by flash column chromatography (ethylacetate) to give 98 mg of the title compound as a solid material.

¹H-NMR (400 MHz, DMSO-$d_6$), δ [ppm]=13.63 (s, 1H), 12.98 (s, 1H), 10.49 (s, 1H), 8.56 (s, 1H), 7.80-7.62 (m, 5H), 7.62-7.52 (m, 1H), 7.41-7.28 (m, 1H), 3.09 (m, 1H), 2.87 (d, 3H), 1.28 (d, 6H).

LC-MS (Method 6): $R_t$=3.74 min; MS (ESIpos) m/z=458.2 [M+H]⁺.

Example 107

N⁴-{4-[(2-chloro-4-fluorobenzoyl)amino]phenyl}-N⁵-[2-(dimethylamino)ethyl]-2-isopropyl-1H-imidazole-4,5-dicarboxamide

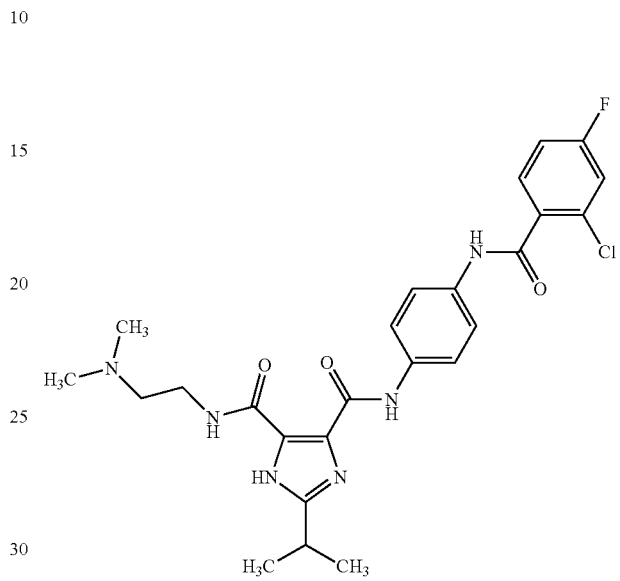

Step A:

To 149 mg (0.38 mmol, crude product, intermediate 040) of 3,8-diisopropyl-5,10-dioxo-5H,10H-diimidazo[1,5-a:1',5'-d]pyrazine-1,6-dicarbonyl dichloride dissolved in 3 mL tetrahydrofuran were added 198 mg (1.00 mmol) N-(4-aminophenyl)-2-chloro-4-fluorobenzamide (Intermediate 004) and 157 µL (1.13 mmol) triethylamine. The resulting mixture was stirred for 30 minutes at room temperature.

Step B:

99 µL (0.90 mmol) of N,N-dimethylethane-1,2-diamine were added and the mixture was stirred for 30 minutes at room temperature. 50 mL water were added and the resulting precipitate was filtered off and washed three times with water (3 mL). The obtained solid material was dried under vacuum and the crude product was purified by flash column chromatography (ethylacetate) to give 26.9 mg of the title compound as a solid material.

¹H-NMR (400 MHz, DMSO-$d_6$), δ [ppm]=12.64 (s, 1H), 11.70 (s, 1H), 10.28 (s, 1H), 7.56-7.38 (m, 5H), 7.38-7.30 (m, 1H), 7.16-7.05 (m, 1H), 3.85 (s, 1H), 3.05 (2H), 2.41 (s, 1H), 2.25 (s, 6H), 1.91 (s, 2H), 0.67 (d, 6H).

LC-MS (Method 6): $R_t$=3.51 min; MS (ESIpos) m/z=515.3 [M+H]⁺.

Example 108

N⁴-{4-[(2-chloro-4-fluorobenzoyl)amino]phenyl}-2-isopropyl-N⁵-[2-(piperidin-1-yl)ethyl]-1H-imidazole-4,5-dicarboxamide

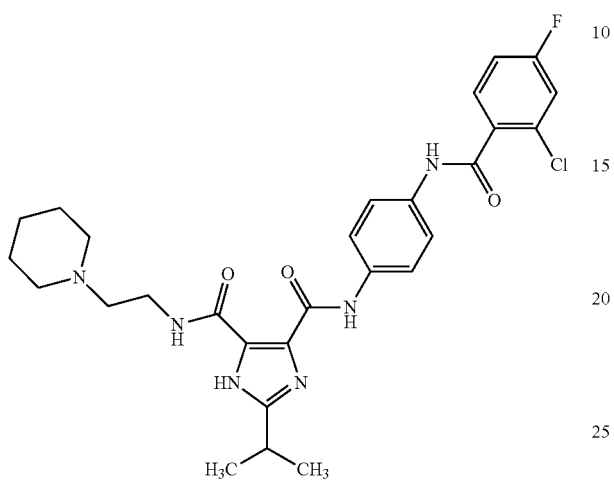

Step A:

To 149 mg (0.38 mmol, crude product, intermediate 040) 3,8-diisopropyl-5,10-dioxo-5H,10H-diimidazo[1,5-a:1',5'-d]pyrazine-1,6-dicarbonyl dichloride dissolved in 3 mL tetrahydrofuran were added 198 mg (1.00 mmol) N-(4-aminophenyl)-2-chloro-4-fluorobenzamide (Intermediate 004) and 157 µL (1.13 mmol) triethylamine. The resulting mixture was stirred for 30 minutes at room temperature.

Step B:

128 µL (0.90 mmol) 2-(piperidin-1-yl)ethanamine were added and the mixture was stirred for 30 minutes at room temperature. 50 mL water were added and the resulting precipitate was filtered off and the solids were washed three times with water (3 mL). The obtained solid material was dried in vacuo and the crude product was purified by flash column chromatography (ethylacetate/tetrahydrofuran/ethanol) to give 26.7 mg of the title compound as a solid material.

$^1$H-NMR (400 MHz, DMSO-d$_6$), δ [ppm]=12.56 (s, 1H), 11.93 (s, 1H), 10.27 (s, 1H), 7.54-7.38 (m, 5H), 7.37-7.29 (m, 1H), 7.14-7.05 (m, 1H), 3.87 (s, 1H), 3.05 (2H), 2.37 (s, 1H), 2.24 (m, 4H), 2.07 (m, 2H), 0.93-0.83 (m, 6H), 0.65 (d, 6H).

LC-MS (Method 6): R$_t$=3.57 min; MS (ESIpos) m/z=555.3 [M+H]⁺.

Example 109

N⁵-{6-[(2-chloro-4-fluorobenzoyl)amino]pyridin-3-yl}-N⁴-[2-(dimethylamino)ethyl]-1H-imidazole-4,5-dicarboxamide

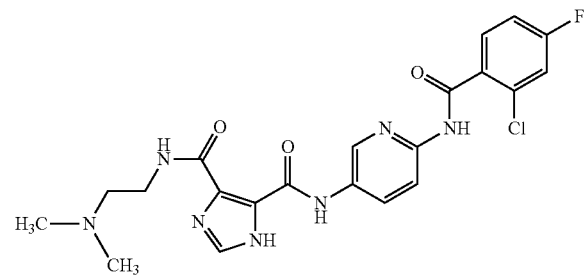 [SMILES: CN(C)CCNC(=O)c1nc[nH]c1C(=O)Nc1ccc(NC(=O)c2ccc(F)cc2Cl)nc1]

To a suspension of 162 mg (0.39 mmol) methyl 5-({6-[(2-chloro-4-fluorobenzoyl)amino]pyridin-3-yl}carbamoyl)-1H-imidazole-4-carboxylate (intermediate 043) in 1.00 mL methanol were added 256 µL (2.34 mmol) N,N-dimethylethane-1,2-diamine diluted with 10 mL tetrahydrofuran. The mixture was stirred for 18 hours at 70° C. The solvent was removed under reduced pressure and methanol were added to the residue. The precipitate was filtered off to give 81 mg of the title compound as a solid material.

$^1$H-NMR (400 MHz, DMSO-d$_6$), δ [ppm]=13.0 (br s, 1H); 11.0 (s, 1H), 9.00 (br s, 1H), 8.70 (d, 1H), 8.25-8.13 (m, 2H), 7.94 (s, 1H), 7.69-7.64 (m, 1H), 7.56-7.52 (m, 1H), 7.35-7.28 (m, 1H), 3.48-3.40 (m, 2H), 3.28 (br s, 1H), 2.48-2.43 (m, 2H), 2.20 (s, 6H).

LC-MS (Method 6): R$_t$=2.8 min; MS (ESIpos) m/z=474.1 [M+H]⁺.

Example 110

N⁵-{6-[(2-chloro-4-fluorobenzoyl)amino]pyridin-3-yl}-N⁴-[2-(piperidin-1-yl)ethyl]-1H-imidazole-4,5-dicarboxamide

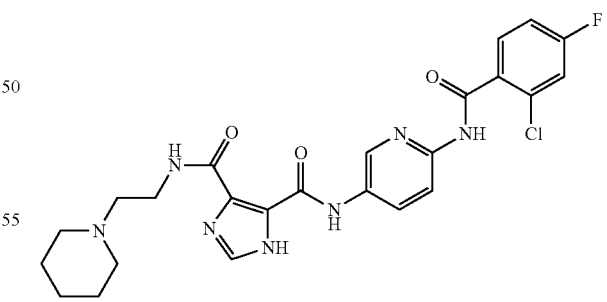

To a solution of 132 mg (0.36 mmol) methyl 5-({6-[(2-chloro-4-fluorobenzoyl)amino]pyridin-3-yl}carbamoyl)-1H-imidazole-4-carboxylate (Intermediate 043) in 1.00 mL methanol were added 273 µL (1.90 mmol) 2-(piperidin-1-yl)ethanamine diluted with 10 mL tetrahydrofuran. The reaction mixture was stirred for 18 hours at 70° C. The solvent was removed under reduced pressure and the residue was suspended in methanol. The precipitate was filtered off and the solid was washed with methanol to give after drying under vacuum 81 mg of the title compound as a solid material.

$^1$H-NMR (400 MHz, DMSO-$d_6$), δ [ppm]=14.0-13.0 (m, 2H); 11.0 (s, 1H), 8.72 (s, 1H), 8.26-8.10 (m, 2H), 7.95 (s, 1H), 7.69-7.63 (m, 1H), 7.57-7.56 (m, 1H), 7.35-7.28 (m, 1H), 3.50-3.42 (m, 2H), 2.49-2.45 (2H, m), 2.44-2.30 (m, 4H), 1.55-1.45 (m, 4H), 1.43-1.33 (m, 4H).

LC-MS (Method 6): $R_t$=2.9 min; MS (ESIpos) m/z=514.3 [M+H]$^+$.

Example 111 methyl 5-({6-[(2-chlorobenzoyl)amino]pyridin-3-yl}carbamoyl)-1H-imidazole-4-carboxylate

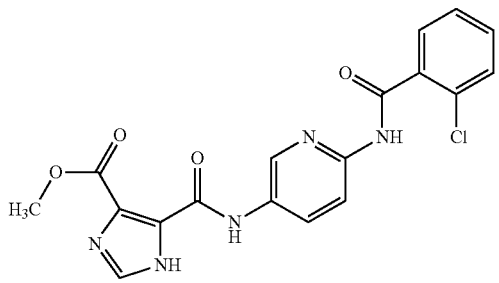 [SMILES: COC(=O)c1nc[nH]c1C(=O)Nc1ccc(NC(=O)c2ccccc2Cl)nc1]

470 mg (1.78 mmol) methyl 5-[(6-aminopyridin-3-yl)carbamoyl]-1H-imidazole-4-carboxylate (Intermediate 042) and 1.56 mL (3.83 mmol) N-ethyl-N,N-diisopropylamine were suspended in 300 mL dry tetrahydrofuran. During 30 minutes 250 μL (1.98 mmol) 2-chlorobenzoyl chloride diluted in 5 mL were added dropwise at 50° C. After stirring for 1 hour at 50° C. 120 μL (0.95 mmol) 2-chlorobenzoyl chloride diluted in 5 mL were added dropwise over a period of 30 minutes. The mixture was stirred at 50° C. for 1 hour. The solvent was removed under reduced pressure and 20 mL water were added to the residue. The precipitate was filtered off and the solid was washed with water and methanol to give after drying under vacuum 545 mg of the title compound as a solid material (contains 20% of the bisacylated product).

LC-MS (Method 6): $R_t$=3.3 min; MS (ESIpos) m/z=400.3 [M+H]$^+$.

Example 112

N$^5$-{6-[(2-chlorobenzoyl)amino]pyridin-3-yl}-N$^4$-methyl-1H-imidazole-4,5-dicarboxamide

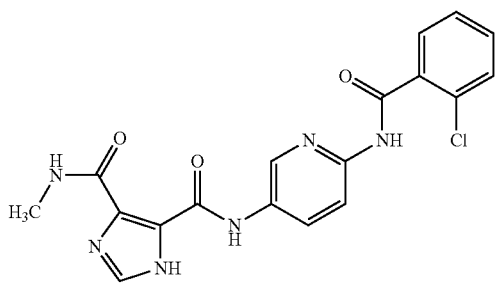

To a solution of 159 mg (0.40 mmol) methyl 5-({6-[(2-chlorobenzoyl)amino]pyridin-3-yl}carbamoyl)-1H-imidazole-4-carboxylate (Example 111) in 1 mL methanol were added 4 mL (2M solution in THF) methylamine and the mixture was stirred for 2 hours at 70° C. The solvent was removed under reduced pressure and the residue was suspended in methanol. The precipitate was filtered off to give after drying under vacuum 105 mg of the title compound as a solid material.

$^1$H-NMR (400 MHz, DMSO-$d_6$), δ [ppm]=13.3 (s, 1H); 11.0 (s, 1H), 9.0 (s, 1H), 8.71 (s, 1H), 8.25-8.12 (m, 2H), 7.95 (s, 1H), 7.60-7.40 (m, 4H), 2.92-2.84 (m, 3H).

LC-MS (Method 6): $R_t$=3.37 min; MS (ESIpos) m/z=399.2 [M+H]$^+$.

Example 113

N$^5$-{6-[(2-chlorobenzoyl)amino]pyridin-3-yl}-N$^4$-[2-(dimethylamino)ethyl]-1H-imidazole-4,5-dicarboxamide

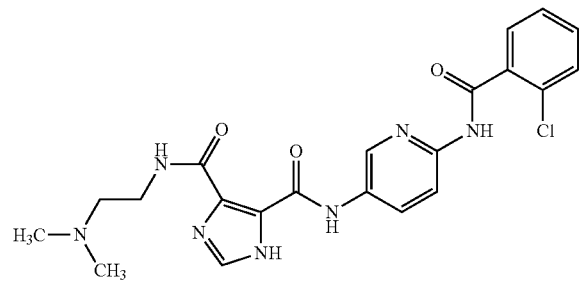 [SMILES: CN(C)CCNC(=O)c1nc[nH]c1C(=O)Nc1ccc(NC(=O)c2ccccc2Cl)nc1]

To a solution of 162 mg (0.40 mmol) methyl 5-({6-[(2-chlorobenzoyl)amino]pyridin-3-yl}carbamoyl)-1H-imidazole-4-carboxylate (Example 111) in 1.00 mL methanol were added 264 μL (2.40 mmol) N,N-dimethylethane-1,2-diamine diluted in 10 mL tetrahydrofuran. The mixture was stirred for 18 hours at 70° C. The solvent was removed under reduced pressure and the residue was suspended in methanol. The precipitate was filtered off to give 105 mg of the title compound as a solid material.

$^1$H-NMR (400 MHz, DMSO-$d_6$), δ [ppm]=13.0 (s, 1H), 11.0 (s, 1H), 8.70 (s, 1H), 8.24-8.13 (m, 2H), 7.94 (s, 1H), 7.60-7.40 (m, 4H), 3.45-3.40 (m, 2H), 2.49-2.40 (m, 2H), 2.20 (s, 6H).

LC-MS (Method 6): $R_t$=2.7 min; MS (ESIpos) m/z=456.3 [M+H]$^+$.

Example 114

N$^5$-{6-[(2-chlorobenzoyl)amino]pyridin-3-yl}-N$^4$-[2-(piperidin-1-yl)ethyl]-1H-imidazole-4,5-dicarboxamide

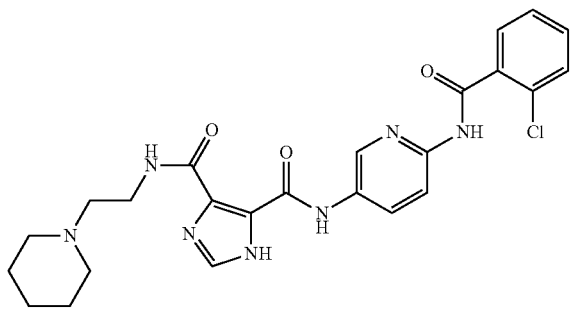

To a solution of 145 mg (0.36 mmol) methyl 5-({6-[(2-chlorobenzoyl)amino]pyridin-3-yl}carbamoyl)-1H-imidazole-4-carboxylate (Example 111) in 1.00 mL methanol were added 314 µL (2.18 mmol) 2-(piperidin-1-yl)ethanamine diluted in 10 mL tetrahydrofuran. The reaction mixture was stirred for 18 hours at 70° C. The solvent was removed under reduced pressure and the residue was suspended in methanol. The precipitate was filtered off to give 113 mg of the title compound as a solid material.

$^1$H-NMR (400 MHz, DMSO-d$_6$), δ [ppm]=11.0 (s, 1H), 8.72 (s, 1H), 8.24-8.14 (m, 2H), 7.94 (s, 1H), 7.60-7.40 (m, 4H), 3.50-3.42 (m, 2H), 2.49-2.37 (6H, m), 1.56-1.46 (4H, m), 1.43-1.35 (2H, m).

LC-MS (Method 6): R$_t$=2.9 min; MS (ESIpos) m/z=496.2 [M+H]$^+$.

Example 115

N$^5$-{6-[(4-fluorobenzoyl)amino]pyridin-3-yl}-N$^4$-methyl-1H-imidazole-4,5-dicarboxamide

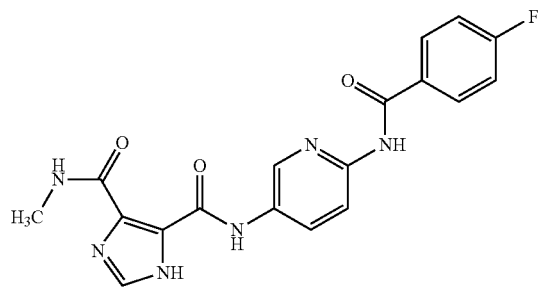 [SMILES: CNC(=O)c1nc[nH]c1C(=O)Nc1ccc(NC(=O)c2ccc(F)cc2)nc1]

To a solution of 158 mg (0.40 mmol) methyl 5-({6-[(4-fluorobenzoyl)amino]pyridin-3-yl}carbamoyl)-1H-imidazole-4-carboxylate (Intermediate 044) in 1 mL methanol were added 4 mL (2M solution in THF) methylamine. The mixture was stirred for 2 hours at 70° C. The precipitate was filtered off and the solids were washed with methanol to give after drying under vacuum 69 mg of the title compound as a solid material.

$^1$H-NMR (400 MHz, DMSO-d$_6$), δ [ppm]=13.3 (s, 1H), 13.4 (s, 1H); 10.9 (s, 1H), 9.18 (s, 1H), 8.73 (s, 1H), 8.23-8.10 (m, 4H), 7.94 (s, 1H), 7.40-7.31 (m, 2H), 2.88 (d, 3H).

LC-MS (Method 6): R$_t$=3.5 min; MS (ESIpos) m/z=383.3 [M+H]$^+$.

Example 116

N$^4$-[2-(dimethylamino)ethyl]-N$^5$-{6-[(4-fluorobenzoyl)amino]pyridin-3-yl}-1H-imidazole-4,5-dicarboxamide

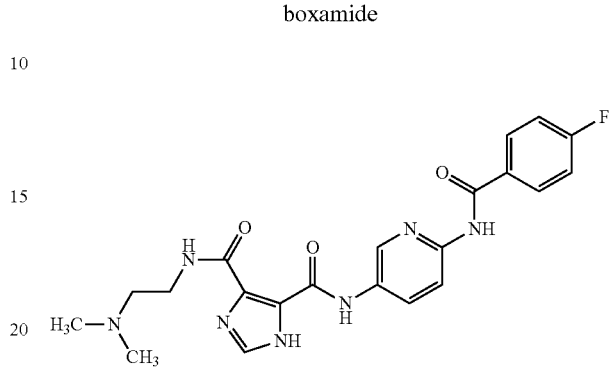

To a solution of 182 mg (0.47 mmol) methyl 5-({6-[(4-fluorobenzoyl)amino]pyridin-3-yl}carbamoyl)-1H-imidazole-4-carboxylate (Intermediate 044) in 1.00 mL methanol were added 312 µL (2.85 mmol) N,N-dimethylethane-1,2-diamine diluted in 10 mL tetrahydrofuran. The mixture was stirred for 18 hours at 70° C. The precipitate was filtered off and was washed with methanol to give after drying under vacuum 120 mg of the title compound as a solid material.

$^1$H-NMR (400 MHz, DMSO-d$_6$), δ [ppm]=13.7 (s, 1H), 13.5 (s, 1H); 10.9 (s, 1H), 8.73 (s, 1H), 8.23-8.05 (m, 4H), 7.95 (s, 1H), 7.40-7.30 (m, 2H), 3.50-3.41 (m, 2H), 2.50-2.41 (m, 2H), 2.20 (s, 6H).

LC-MS (Method 6): R$_t$=2.82 min; MS (ESIpos) m/z=440.3 [M+H]$^+$.

Example 117

N$^5$-{6-[(4-fluorobenzoyl)amino]pyridin-3-yl}-N$^4$-[2-(piperidin-1-yl)ethyl]-1H-imidazole-4,5-dicarboxamide

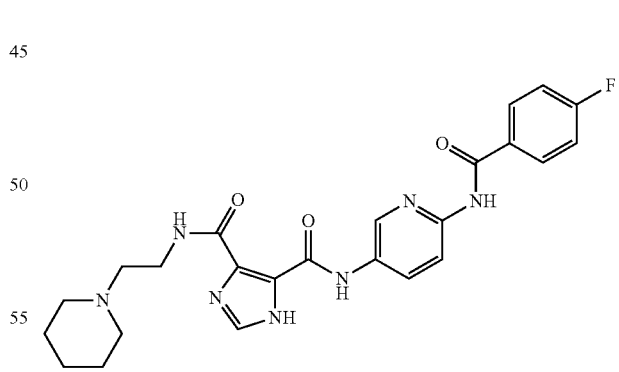

To a solution of 193 mg (0.36 mmol) methyl 5-({6-[(4-fluorobenzoyl)amino]pyridin-3-yl}carbamoyl)-1H-imidazole-4-carboxylate (Intermediate 044) in 1.00 mL methanol were added 453 µL (3.00 mmol) 2-(piperidin-1-yl)ethanamine diluted in 8 mL tetrahydrofuran. The reaction mixture was stirred for 18 hours at 70° C. The precipitate was filtered off and the solids were washed with methanol to give after drying under vacuum 158 mg of the title compound as a solid material.

¹H-NMR (400 MHz, DMSO-d₆), δ [ppm]=13.7 (s, 1H), 13.4 (s, 1H), 10.9 (s, 1H), 8.74 (s, 1H), 8.24-8.08 (m, 4H), 7.95 (s, 1H), 7.38-7.30 (m, 2H), 3.50-3.42 (m, 2H), 2.49-2.46 (m, 2H), 2.44-2.36 (m, 4H), 1.56-1.46 (m, 4H), 1.44-1.34 (m, 2H).

LC-MS (Method 6): $R_t$=2.87 min; MS (ESIpos) m/z=480.3 [M+H]⁺.

Example 118

N⁵-{4-[(2-chloro-4,6-difluorobenzoyl)amino]phenyl}-N⁴-methyl-1H-imidazole-4,5-dicarboxamide

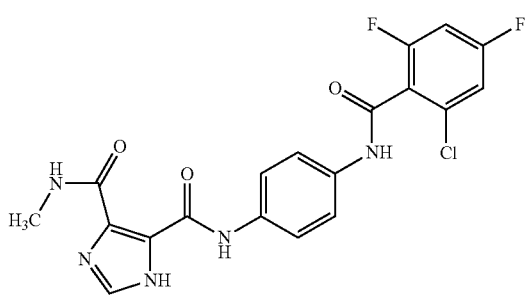 [SMILES: CNC(=O)c1nc[nH]c1C(=O)Nc1ccc(NC(=O)c2c(F)cc(F)cc2Cl)cc1]

To a suspension of 225 mg (0.52 mmol) methyl 5-({4-[(2-chloro-4,6-difluorobenzoyl)amino]phenyl}carbamoyl)-1H-imidazole-4-carboxylate (Intermediate 045) in 4 mL dioxane 2.0 mL of a 2 M methylamine solution in THF were added and the mixture was stirred for 8 hours at 100° C. The reaction mixture was concentrated in vacuo and the residue was purified by flash column chromatography (dichloromethane/methanol-gradient) to give after recrystallisation with methanol 45 mg of the title compound as a solid material.

¹H-NMR (400 MHz, DMSO-d₆), δ [ppm]=13.71 (br. s., 1H), 13.42 (br. s., 1H), 10.79 (s, 1H), 8.84 (br. s., 1H), 7.93 (s, 1H), 7.80-7.65 (m, 4H), 7.61-7.45 (m, 2H), 2.88 (d, 3H).

LC-MS (Method 12): $R_t$=0.94 min; MS (ESIpos) m/z=434.1 [M+H]⁺.

Example 119

N⁵-{4-[(2-chloro-4,6-difluorobenzoyl)amino]phenyl}-N⁴-[2-(piperidin-1-yl)ethyl]-1H-imidazole-4,5-dicarboxamide

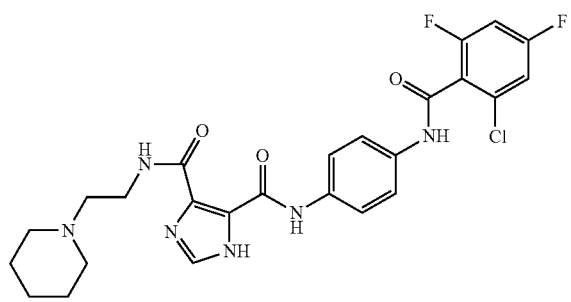 [SMILES: O=C(NCCN1CCCCC1)c1nc[nH]c1C(=O)Nc1ccc(NC(=O)c2c(F)cc(F)cc2Cl)cc1]

To a suspension of 225 mg (0.52 mmol) methyl 5-({4-[(2-chloro-4,6-difluorobenzoyl)amino]phenyl}carbamoyl)-1H-imidazole-4-carboxylate (Intermediate 045) in 4 mL dioxane and 2 mL methanol, 0.6 mL (0.40 mmol) 2-(piperidin-1-yl)ethanamine were added and the mixture was stirred for 8 hours at 100° C. The reaction mixture was concentrated in vacuo and the residue was purified by flash column chromatography (dichloromethane/methanol-gradient) to give after washing with methanol 103 mg of the title compound as a solid material.

¹H-NMR (400 MHz, DMSO-d₆), δ [ppm]=13.63 (br. s., 1H), 13.44 (br. s., 1H), 10.79 (s, 1H), 8.66 (br. s., 1H), 7.94 (s, 1H), 7.78-7.63 (m, 4H), 7.59-7.44 (m, 2H), 3.46 (q, 2H), 2.49-2.45 (m, 1H), 2.40 (br. s., 4H), 2.09 (s, 1H), 1.63-1.45 (m, 4H), 1.40 (d, 2H).

LC-MS (Method 5): $R_t$=1.16 min; MS (ESIpos) m/z=531.3 [M+H]⁺.

Example 120

N⁵-{4-[(2-chlorobenzoyl)amino]phenyl}-1H-imidazole-4,5-dicarboxamide

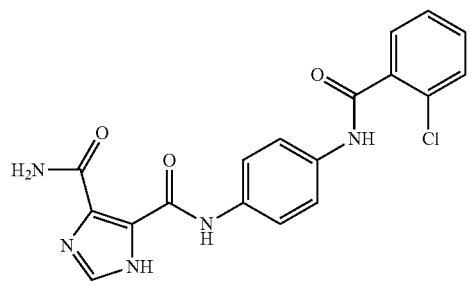 [SMILES: NC(=O)c1nc[nH]c1C(=O)Nc1ccc(NC(=O)c2ccccc2Cl)cc1]

To a suspension of 74 mg (0.19 mmol) 5-({4-[(2-chlorobenzoyl)amino]phenyl}carbamoyl)-1H-imidazole-4-carboxylicacid (Intermediate 047) in 3.3 mL DMF were added 64 mg (0.40 mmol) CDI and the mixture was stirred for 3 hours at room temperature. 2.3 mL (25% solution in water) ammonia were added. After stirring for additional 5 minutes 10 mL water were added and the mixture was stirred for 10 minutes. The precipitate was filtered off and washed with water to give 47 mg of crude product which was purified by HPLC chromatography to give 9 mg of the title compound as a solid material.

¹H-NMR (400 MHz, DMSO-d₆), δ [ppm]=13.42 (br. s., 1H), 10.50 (s, 1H), 8.48 (s, 1H), 8.31 (s, 1H), 8.00 (br. s., 1H), 7.89 (s, 1H), 7.82-7.63 (m, 4H), 7.62-7.55 (m, 2H), 7.51 (td, 1H), 7.48-7.42 (m, 1H).

LC-MS (Method 4): $R_t$=0.90 min; MS (ESIpos) m/z=384.1 [M+H]⁺.

Example 121

5-({4-[(2-chloro-4-fluorobenzoyl)amino]phenyl}carbamoyl)-1H-imidazole-4-carboxylic acid

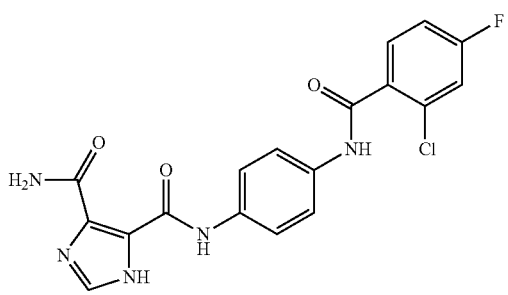 [SMILES: NC(=O)c1nc[nH]c1C(=O)Nc1ccc(NC(=O)c2ccc(F)cc2Cl)cc1]

To a suspension of 175 mg (0.43 mmol) 5-({4-[(2-chloro-4-fluorobenzoyl)amino]phenyl}carbamoyl)-1H-imidazole-4-carboxylicacid (Intermediate 048) in 7.5 mL DMF were added 144 mg (0.89 mmol) CDI and the mixture was stirred for 3 hours at room temperature. 5.17 mL (25% solution in water) ammonia were added. After stirring for additional 5 minutes 15 mL water was added and the mixture was stirred for 10 minutes. The precipitate was filtered off and was washed with water to give 86 mg of the title compound as a solid material.

$^1$H-NMR (400 MHz, DMSO-$d_6$), δ [ppm]=13.72 (br. s., 1H), 13.42 (br. s., 1H), 10.52 (s, 1H), 8.19 (br. s., 1H), 8.05 (br. s., 1H), 7.91 (s, 1H), 7.79-7.64 (m, 4H), 7.60 (dd, 1H), 7.36 (d, 1H).

LC-MS (Method 8): $R_t$=0.81 min; MS (ESIpos) m/z=402.1 [M+H]$^+$.

Example 122

$N^5$-{4-[(2-chloro-4-hydroxybenzoyl)amino]phenyl}-$N^4$-methyl-1H-imidazole-4,5-dicarboxamide

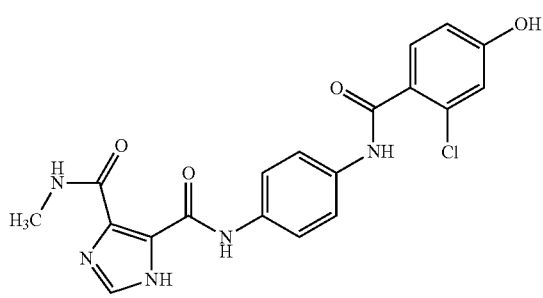 [SMILES: CNC(=O)c1nc[nH]c1C(=O)Nc1ccc(NC(=O)c2ccc(O)cc2Cl)cc1]

400 mg (1.54 mmol) $N^5$-(4-aminophenyl)-$N^4$-methyl-1H-imidazole-4,5-dicarboxamide (Intermediate 003) were suspended in 10 mL dry tetrahydrofuran. 0.43 mL (3.08 mmol) triethylamine and 324 mg (1.70 mmol) 2-chloro-4-hydroxybenzoyl chloride (Intermediate 049) diluted in 10 mL dry tetrahydrofuran were added and the mixture was stirred at room temperature for 1 day. The solvent was removed under reduced pressure and the crude product was purified by flash column chromatography (DCM/methanol) to give 450 mg of the title compound as a solid material.

$^1$H-NMR (400 MHz, DMSO-$d_6$), δ [ppm]=13.63 (br. s., 1H), 10.27 (s, 1H), 8.79 (br. s., 1H), 7.90 (s, 1H), 7.76-7.59 (m, 4H), 7.41 (d, 1H), 6.88 (d, 1H), 6.81 (dd, 1H), 2.86 (d, 3H), 2.51 (br. s., 1H), 2.07 (s, 1H).

LC-MS (Method 2): $R_t$=0.85 min; MS (ESIpos) m/z=414.2 [M+H]$^+$.

Example 123

$N^5$-{4-[(2-chloro-4-hydroxybenzoyl)amino]phenyl}-$N^4$-methyl-1H-imidazole-4,5-dicarboxamide

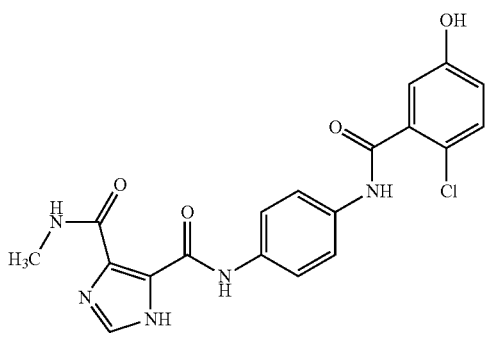 [SMILES: CNC(=O)c1nc[nH]c1C(=O)Nc1ccc(NC(=O)c2cc(O)ccc2Cl)cc1]

250 mg (0.96 mmol) $N^5$-(4-aminophenyl)-$N^4$-methyl-1H-imidazole-4,5-dicarboxamide (Intermediate 003) were suspended in 30 mL dry tetrahydrofuran. 0.27 mL (1.92 mmol) triethylamine and 221 mg (1.16 mmol) 2-chloro-5-hydroxybenzoyl chloride (Intermediate 050) diluted in 30 mL dry tetrahydrofuran were added and the mixture was stirred at room temperature for 4 hours. The solvent was removed under reduced pressure and the crude product was purified twice by flash column chromatography (DCM/methanol) to give 125 mg of the title compound as a solid material.

$^1$H-NMR (400 MHz, DMSO-$d_6$), δ [ppm]=13.67 (s, 1H), 13.43 (br. s., 1H), 10.44 (s, 1H), 9.99 (s, 1H), 8.83 (br. s., 1H), 7.93 (s, 1H), 7.70 (d, 4H), 7.33 (d, 1H), 6.95-6.83 (m, 2H), 2.88 (d, 3H).

LC-MS (Method 11): $R_t$=0.95 min; MS (ESIpos) m/z=414 [M+H]$^+$.

Example 124

$N^5$-[4-({2-chloro-5-[2-(4-methylpiperazin-1-yl)ethoxy]benzoyl}amino)phenyl]-$N^4$-methyl-1H-imidazole-4,5-dicarboxamide

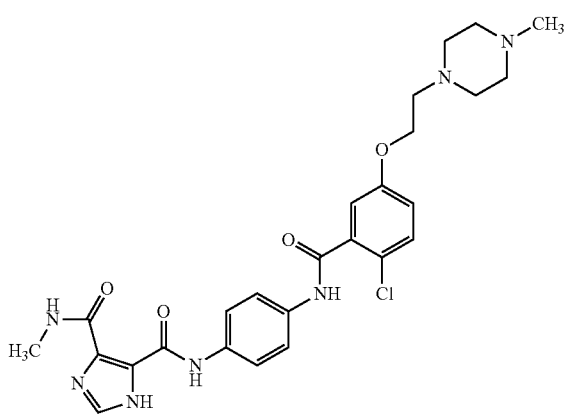

To a suspension of 553 mg (2.11 mmol) triphenylphosphine in 5 mL dry THF were added in portions and at 0° C. 537 mg (2.11 mmol) (E)-diazene-1,2-diylbis(piperidin-1-ylmethanone) and 310 mg (2.11 mmol) 2-(4-methylpiperazin-1-yl)ethanol. After stirring for 10 minuets 200 mg (0.47 mmol) $N^5$-{4-[(2-chloro-4-hydroxybenzoyl)amino]phenyl}-$N^4$-methyl-1H-imidazole-4,5-dicarboxamide (Example 123) were added to the reaction mixture and the mixture was stirred at room temperature for 24 hours. The solvent was removed under reduced pressure and the crude product was purified by flash column chromatography (DCM/methanol) to give after trituration with diethyether and drying 133 mg of the title compound as a solid material.

LC-MS (Method 4): $R_t$=0.82 min; MS (ESIpos) m/z=540.1 $[M+H]^+$.

Example 125

$N^5$-[4-({2-chloro-5-[2-(piperidin-1-yl)ethoxy]benzoyl}amino)phenyl]-$N^4$-methyl-1H-imidazole-4,5-dicarboxamide

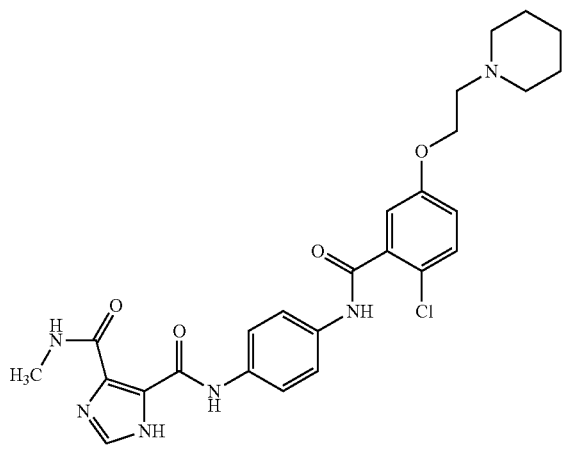 [SMILES: CNC(=O)c1nc[nH]c1C(=O)Nc1ccc(NC(=O)c2cc(OCCN3CCCCC3)ccc2Cl)cc1]

To a suspension of 276 mg (1.06 mmol) triphenylphosphine in 5 mL dry THF were added in portions and at 0° C. 269 mg (1.06 mmol) (E)-diazene-1,2-diylbis(piperidin-1-ylmethanone) then 138 mg (1.06 mmol) 2-(piperidin-1-yl)ethanol were added. After stirring for 10 minuets 100 mg (0.23 mmol) $N^5$-{4-[(2-chloro-4-hydroxybenzoyl)amino]phenyl}-$N^4$-methyl-1H-imidazole-4,5-dicarboxamide (Example 123) were added to the reaction mixture and the mixture was stirred at room temperature for 24 hours. The solvent was removed under reduced pressure and the crude product was combined with another batch. The combined crude product was purified by flash column chromatography (DCM/methanol) to give after trituration with diethyether/dichloromethan and drying 62.2 mg of the title compound as a solid material.

$^1$H-NMR (400 MHz, DMSO-$d_6$), δ [ppm]=13.76 (s, 1H), 10.40 (s, 1H), 9.96 (s, 1H), 8.84 (d, 1H), 7.96 (s, 1H), 7.80-7.57 (m, 4H), 7.31 (d, 1H), 6.93-6.80 (m, 2H), 4.58-4.51 (m, 2H), 2.90-2.75 (m, 3H), 2.65-2.52 (m, 2H), 2.43-2.29 (m, 4H), 1.48-1.38 (m, 4H), 1.35-1.33 (m, 2H).

LC-MS (Method 11): $R_t$=0.84 min; MS (ESIpos) m/z=525 $[M+H]^+$.

Example 126

$N^5$-{4-[(2-chloro-4-fluorobenzoyl)amino]phenyl}-$N^4$-[2-(4-methylpiperidin-1-yl)ethyl]-1H-imidazole-4,5-dicarboxamide

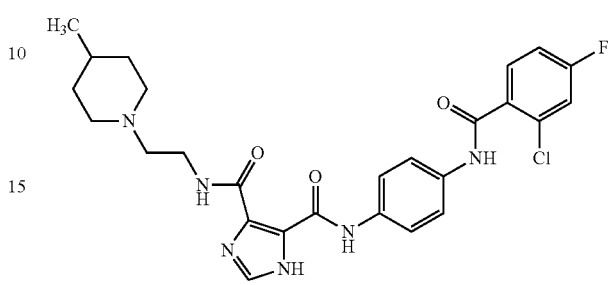

To the crude reaction mixture of N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide (0.90 mmol, Intermediate 005), 256 mg (1.80 mmol) 2-(4-methylpiperidin-1-yl)ethanamine and 470 μL (2.70 mmol) N-ethyl-N-isopropylpropan-2-amine were added and the reaction was stirred for 18 hours at room temperature. The reaction mixture was diluted with water and the mixture was extracted with a mixture of dichloromethane and iso-propanol (4:1). The combined organic phases were dried by filtration through a whatman filter. The solvent was removed under reduced pressure and the crude product was purified by preparative HPLC to give 100 mg of the title compound as a solid material.

$^1$H-NMR (400 MHz, DMSO-$d_6$), δ [ppm]=13.59 (br. s., 1H), 13.41 (br. s., 1H), 10.52 (s, 1H), 8.64 (br. s., 1H), 7.93 (s, 1H), 7.76-7.65 (m, 5H), 7.60 (dd, 1H), 7.36 (td, 1H), 3.46 (q, 2H), 2.88 (d, 2H), 2.53-2.48 (m., 2H), 1.95 (t, 2H), 1.59 (d, 2H), 1.39-1.26 (m, 1H), 1.22-1.09 (m, 2H), 0.90 (d, 3H).

LC-MS (Method 8): $R_t$=1.21 min; MS (ESIpos) m/z=527.3 $[M+H]^+$.

Example 127

$N^5$-{4-[(2-chloro-4-fluorobenzoyl)amino]phenyl}-$N^4$-[2-(piperidin-1-yl)ethyl]-1H-imidazole-4,5-dicarboxamide hydrochloride

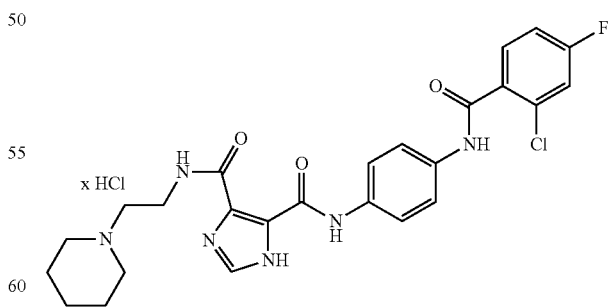

To a suspension of 103 mg (0.20 mmol) $N^5$-{4-[(2-chloro-4-fluorobenzoyl)amino]phenyl}-$N^4$-[2-(piperidin-1-yl)ethyl]-1H-imidazole-4,5-dicarboxamide (Example 32) in dichloromethane/ethanol were added 151 μL of a 4 M solution of acidic acid in dioxane. The resulting precipitate was filtered of and the solids were washed with dichloromethane to give after drying 110 mg of the title compound as a solid material.

¹H-NMR (400 MHz, DMSO-d₆), δ [ppm]=13.10 (br. s., 1H), 10.55 (s, 1H), 9.49 (br. s., 1H), 8.00 (s, 1H), 7.79-7.66 (m, 5H), 7.60 (dd, 1H), 7.36 (td, 1H), 3.75 (q, 2H), 3.65-3.53 (m, 2H), 3.36-3.23 (m, 2H), 3.03-2.81 (m, 2H), 1.92-1.79 (m, 2H), 1.78-1.63 (m, 3H), 1.39 (d, 1H).

LC-MS (Method 8): $R_t$=1.14 min; MS (ESIpos) m/z=513.3 [M+H]⁺.

Example 128

N⁴-{4-[(2-chloro-4-fluorobenzoyl)amino]phenyl}-N⁵-(cyclopropylmethyl)-1H-imidazole-4,5-dicarboxamide

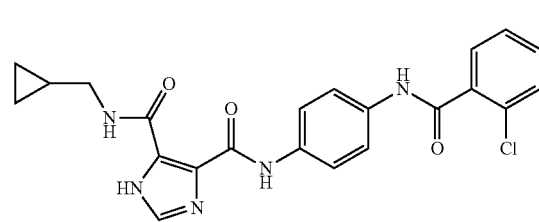

To the crude mixture of N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide (0.160 mmol, Intermediate 005), were added 0.028 mL (0.32 mmol) 1-cyclopropylmethanamine and 0.278 mL (1.6 mmol) N-ethyl-N-isopropylpropan-2-amine and the mixture was stirred for 20 h at room temperature. The reaction mixture was concentrated in vacuo and the residue was purified by preparative HPLC to give 4 mg of the title compound as a solid material.

¹H-NMR (400 MHz, DMSO-d₆): δ [ppm]=13.80-13.54 (m, 1H), 13.44 (br. s., 1H), 10.60-10.47 (m, 1H), 9.03-8.81 (m, 1H), 7.93 (s, 1H), 7.80-7.66 (m, 5H), 7.60 (dd, 1H), 7.36 (td, 1H), 3.23 (t, 2H), 1.11 (br. s., 1H), 0.51-0.43 (m, 2H), 0.33-0.24 (m, 2H).

LC-MS (Method 1): $R_t$=1.16 min; MS (ESIpos) m/z=456 [M+H]⁺.

Example 129

N⁵-tert-butyl-N⁴-{4-[(4-fluorobenzoyl)amino]phenyl}-1H-imidazole-4,5-dicarboxamide

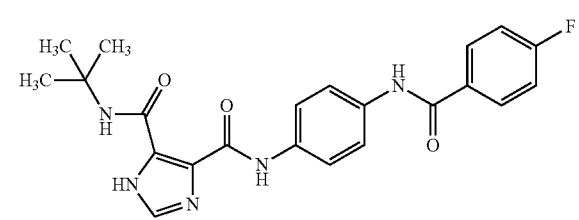 [SMILES: CC(C)(C)NC(=O)c1[nH]cnc1C(=O)Nc1ccc(NC(=O)c2ccc(F)cc2)cc1]

To the crude mixture of N,N'-bis{4-[(4-fluorobenzoyl)amino]phenyl}-5,10-dioxo-5H,10H-diimidazo[1,5-a:1',5'-d]pyrazine-1,6-dicarboxamide (0.160 mmol, Intermediate 018), were added 0.034 mL (0.32 mmol) tert.-butylamine and 0.278 mL (1.6 mmol) N-ethyl-N-isopropylpropan-2-amine and the mixture was stirred for 19 h at room temperature. The reaction mixture was concentrated in vacuo and the residue was purified by preparative HPLC to give 37 mg of the title compound as a solid material.

¹H-NMR (400 MHz, DMSO-d₆): δ [ppm]=13.45 (br. s., 1H), 13.29 (br. s., 1H), 10.73 (br. s., 1H), 10.39-10.25 (m, 1H), 8.13-8.00 (m, 2H), 7.91 (s, 1H), 7.85-7.63 (m, 4H), 7.46-7.31 (m, 2H), 1.45 (d, 9H).

LC-MS (Method 1): $R_t$=1.21 min; MS (ESIpos) m/z=424 [M+H]⁺.

Example 130

N⁴-{4-[(2-chloro-4-fluorobenzoyl)amino]phenyl}-N⁵-(2-methoxyethyl)-1H-imidazole-4,5-dicarboxamide

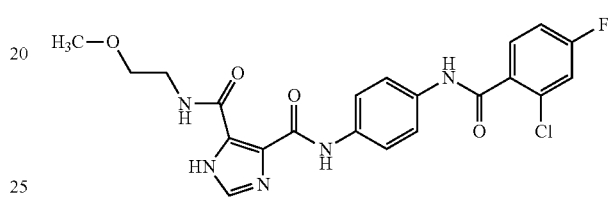

To the crude mixture of N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide (0.160 mmol, Intermediate 005), were added 0.028 mL (0.32 mmol) 2-methoxyethanamine and 0.278 mL (1.6 mmol) N-ethyl-N-isopropylpropan-2-amine and the mixture was stirred for 19 h at room temperature. The reaction mixture was concentrated in vacuo and the residue was purified by preparative HPLC to give 4 mg of the title compound as a solid material.

¹H-NMR (400 MHz, DMSO-d₆): δ [ppm]=13.55 (s, 1H), 13.47 (s, 1H), 10.52 (s, 1H), 8.72 (br. s., 1H), 7.94 (s, 1H), 7.83-7.63 (m, 6H), 7.60 (dd, 1H), 7.36 (td, 1H), 3.57-3.48 (m, 4H), 3.31-3.28 (m, 3H).

LC-MS (Method 1): $R_t$=1.03 min; MS (ESIpos) m/z=461 [M+H]⁺.

Example 131

N⁵-cyclopropyl-N⁴-{4-[(4-fluorobenzoyl)amino]phenyl}-1H-imidazole-4,5-dicarboxamide 4579

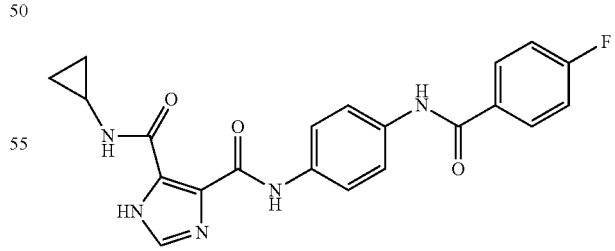

To the crude mixture of N,N'-bis{4-[(4-fluorobenzoyl)amino]phenyl}-5,10-dioxo-5H,10H-diimidazo[1,5-a:1',5'-d]pyrazine-1,6-dicarboxamide (0.160 mmol, Intermediate 018), were added 0.022 mL (0.32 mmol) cyclopropanamine and 0.278 mL (1.6 mmol) N-ethyl-N-isopropylpropan-2-amine and the mixture was stirred for 19 h at room temperature.

The reaction mixture was concentrated in vacuo and the residue was purified by preparative HPLC followed by flash chromatography to give 10 mg of the title compound as a solid material.

$^1$H-NMR (400 MHz, DMSO-$d_6$): δ [ppm]=10.37-10.26 (m, 2H), 8.12-8.01 (m, 3H), 7.95-7.90 (m, 1H), 7.83-7.68 (m, 5H), 7.38 (t, 3H), 3.03-2.92 (m, 1H), 0.78-0.71 (m, 4H).

LC-MS (Method 1): $R_t$=1.04 min; MS (ESIpos) m/z=408 [M+H]$^+$.

Example 132

N$^4$-{4-[(2-chloro-4-fluorobenzoyl)amino]phenyl}-N$^5$-(2-hydroxyethyl)-1H-imidazole-4,5-dicarboxamide

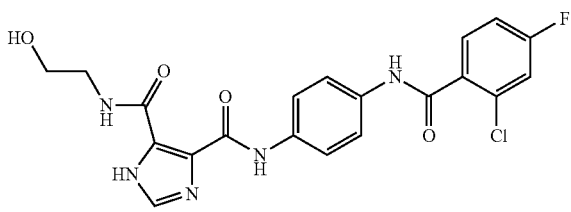 [SMILES: O=C(Nc1ccc(NC(=O)c2nc[nH]c2C(=O)NCCO)cc1)c1ccc(F)cc1Cl]

To the crude mixture of N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide (0.160 mmol, Intermediate 005), were added 0.019 mL (0.32 mmol) 2-aminoethanol and 0.278 mL (1.6 mmol) N-ethyl-N-isopropylpropan-2-amine and the mixture was stirred for 20 h at room temperature.

The reaction mixture was concentrated in vacuo and the residue was purified by preparative HPLC followed by flash chromatography to give 11 mg of the title compound as a solid material.

$^1$H-NMR (400 MHz, DMSO-$d_6$): δ [ppm]=13.66-13.39 (m, 2H), 10.52 (s, 1H), 8.69 (t, 1H), 7.96-7.90 (m, 1H), 7.83-7.50 (m, 7H), 7.36 (td, 1H), 4.85 (t, 1H), 3.56 (quin, 2H), 3.48-3.38 (m, 2H).

LC-MS (Method 1): $R_t$=0.91 min; MS (ESIpos) m/z=446 [M+H]$^+$.

Example 133

N$^5$-tert-butyl-N$^4$-{4-[(2-chloro-4-fluorobenzoyl)amino]phenyl}-1H-imidazole-4,5-dicarboxamide

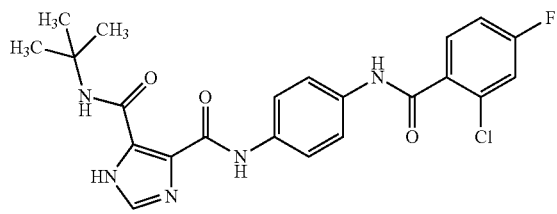 [SMILES: CC(C)(C)NC(=O)c1[nH]cnc1C(=O)Nc1ccc(NC(=O)c2ccc(F)cc2Cl)cc1]

To the crude mixture of N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide (0.160 mmol, Intermediate 005), were added 0.034 mL (0.32 mmol) tert.-butylamine and 0.278 mL (1.6 mmol) N-ethyl-N-isopropylpropan-2-amine and the mixture was stirred for 19 h at room temperature.

The reaction mixture was concentrated in vacuo and the residue was purified by preparative HPLC chromatography to give 15 mg of the title compound as a solid material.

$^1$H-NMR (400 MHz, DMSO-$d_6$): δ [ppm]=13.45 (s, 1H), 10.61-10.47 (m, 1H), 7.94-7.56 (m, 10H), 7.36 (td, 1H), 1.44 (d, 9H).

LC-MS (Method 1): $R_t$=1.24 min; MS (ESIpos) m/z=458 [M+H]$^+$.

Example 134

N$^4$-{4-[(2-chloro-4-fluorobenzoyl)amino]phenyl}-N$^5$-[(2R)-3-methylbutan-2-yl]-1H-imidazole-4,5-dicarboxamide

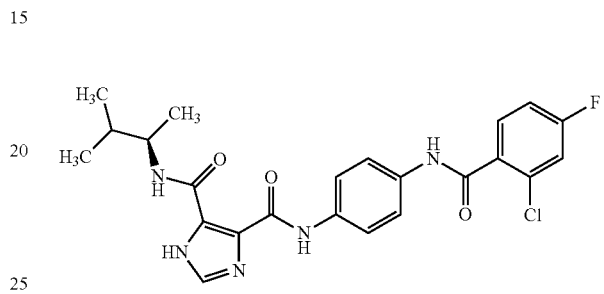

To the crude mixture of N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide (0.160 mmol, Intermediate 005), were added 0.038 mL (0.32 mmol) (2R)-3-methylbutan-2-amine and 0.278 mL (1.6 mmol) N-ethyl-N-isopropylpropan-2-amine and the mixture was stirred for 19 h at room temperature.

The reaction mixture was concentrated in vacuo and the residue was purified by preparative HPLC chromatography to give 48 mg of the title compound as a solid material.

$^1$H-NMR (400 MHz, DMSO-$d_6$): δ [ppm]=13.42 (br. s., 1H), 10.58-10.48 (m, 1H), 7.92 (s, 1H), 7.79-7.65 (m, 5H), 7.60 (dd, 1H), 7.36 (td, 1H), 3.90 (dt, 1H), 1.91-1.76 (m, 1H), 1.23-1.12 (m, 3H), 1.00-0.87 (m, 6H).

LC-MS (Method 1): $R_t$=1.27 min; MS (ESIpos) m/z=472 [M+H]$^+$.

Example 135

N$^4$-{4-[(4-fluorobenzoyl)amino]phenyl}-N$^5$-[(2R)-3-methylbutan-2-yl]-1H-imidazole-4,5-dicarboxamide

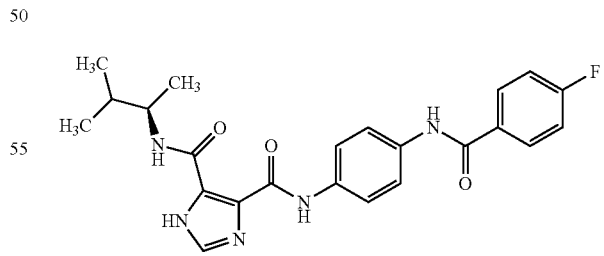

To the crude mixture of N,N'-bis{4-[(4-fluorobenzoyl)amino]phenyl}-5,10-dioxo-5H,10H-diimidazo[1,5-a:1',5'-d]pyrazine-1,6-dicarboxamide (0.160 mmol, Intermediate 018), were added 0.038 mL (0.32 mmol) (2R)-3-methylbutan-2-amine and 0.278 mL (1.6 mmol) N-ethyl-N-isopropylpropan-2-amine and the mixture was stirred for 19 h at room temperature.

The reaction mixture was concentrated in vacuo and the residue was purified by preparative HPLC chromatography to give 26 mg of the title compound as a solid material.

$^1$H-NMR (400 MHz, DMSO-d$_6$): δ [ppm]=13.43 (br. s., 1H), 10.29 (s, 1H), 8.09-8.02 (m, 2H), 7.93 (s, 1H), 7.80-7.67 (m, 4H), 7.41-7.34 (m, 2H), 3.90 (dt, 1H), 1.94-1.76 (m, 1H), 1.17 (d, 3H), 0.93 (d, 6H).

LC-MS (Method 1): R$_t$=1.24 min; MS (ESIpos) m/z=438 [M+H]$^+$.

Example 136

N$^4$-{4-[(4-fluorobenzoyl)amino]phenyl}-N$^5$-(2-hydroxyethyl)-1H-imidazole-4,5-dicarboxamide

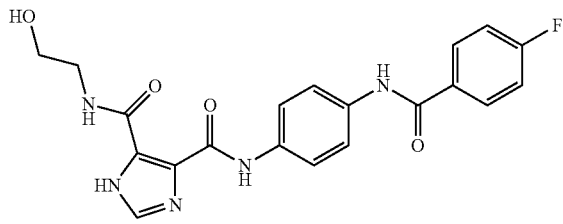 [SMILES: O=C(Nc1ccc(NC(=O)c2nc[nH]c2C(=O)NCCO)cc1)c1ccc(F)cc1]

To the crude mixture of N,N'-bis{4-[(4-fluorobenzoyl)amino]phenyl}-5,10-dioxo-5H,10H-diimidazo[1,5-a:1',5'-d]pyrazine-1,6-dicarboxamide (0.160 mmol, Intermediate 018), were added 0.019 mL (0.32 mmol) 2-aminoethanol and 0.278 mL (1.6 mmol) N-ethyl-N-isopropylpropan-2-amine and the mixture was stirred for 19 h at room temperature.

The reaction mixture was concentrated in vacuo and the residue was purified by preparative HPLC chromatography followed by flash chromatography to give 28 mg of the title compound as a solid material.

$^1$H-NMR (400 MHz, DMSO-d$_6$): δ [ppm]=13.64-13.38 (m, 1H), 10.36-10.27 (m, 1H), 8.69 (t, 1H), 8.10-8.02 (m, 3H), 7.94 (s, 1H), 7.83-7.66 (m, 5H), 7.38 (t, 3H), 4.89-4.79 (m, 1H), 3.61-3.52 (m, 2H), 3.48-3.40 (m, 2H).

LC-MS (Method 1): R$_t$=0.88 min; MS (ESIpos) m/z=412 [M+H]$^+$.

Example 137

N$^5$-ethyl-N$^4$-{4-[(4-fluorobenzoyl)amino]phenyl}-1H-imidazole-4,5-dicarboxamide

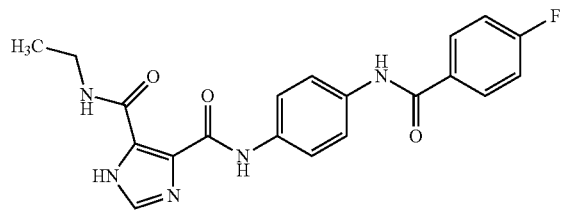 [SMILES: CCNC(=O)c1[nH]cnc1C(=O)Nc1ccc(NC(=O)c2ccc(F)cc2)cc1]

To the crude mixture of N,N'-bis{4-[(4-fluorobenzoyl)amino]phenyl}-5,10-dioxo-5H,10H-diimidazo[1,5-a:1',5'-d]pyrazine-1,6-dicarboxamide (0.160 mmol, Intermediate 018), were added 27 mg (0.32 mmol) ethanamine hydrochloride and 0.278 mL (1.6 mmol) N-ethyl-N-isopropylpropan-2-amine and the mixture was stirred for 19 h at room temperature.

The reaction mixture was concentrated in vacuo and the residue was purified by preparative HPLC chromatography to give 11 mg of the title compound as a solid material.

$^1$H-NMR (400 MHz, DMSO-d$_6$): δ [ppm]=13.68 (s, 1H), 13.43 (s, 1H), 10.37-10.26 (m, 1H), 8.88 (t, 1H), 8.10-8.02 (m, 2H), 7.93 (s, 1H), 7.82-7.66 (m, 5H), 7.42-7.34 (m, 2H), 3.43-3.36 (m, 2H), 1.21-1.13 (m, 3H).

LC-MS (Method 1): R$_t$=1.04 min; MS (ESIpos) m/z=396 [M+H]$^+$.

Example 138

N$^4$-{4-[(2-chloro-4-fluorobenzoyl)amino]phenyl}-N$^5$-ethyl-1H-imidazole-4,5-dicarboxamide

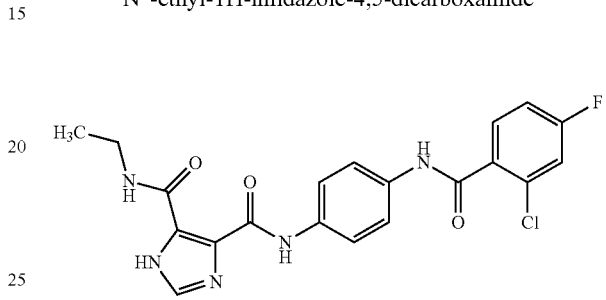

To the crude mixture of N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide (0.160 mmol, Intermediate 005), were added 27 mg (0.32 mmol) ethanamine hydrochloride and 0.278 mL (1.6 mmol) N-ethyl-N-isopropylpropan-2-amine and the mixture was stirred for 19 h at room temperature.

The reaction mixture was concentrated in vacuo and the residue was purified by preparative HPLC chromatography followed by flash chromatography to give 28 mg of the title compound as a solid material.

$^1$H-NMR (400 MHz, DMSO-d$_6$): δ [ppm]=13.68 (s, 1H), 13.43 (s, 1H), 10.62-10.48 (m, 1H), 8.88 (t, 1H), 7.99-7.88 (m, 1H), 7.83-7.56 (m, 6H), 7.36 (td, 1H), 3.46-3.36 (m, 2H), 1.26-1.12 (m, 3H).

LC-MS (Method 1): R$_t$=1.07 min; MS (ESIpos) m/z=430 [M+H]$^+$.

Example 139

N$^4$-{4-[(2-chloro-4-fluorobenzoyl)amino]phenyl}-N$^5$-(2,2-difluoroethyl)-1H-imidazole-4,5-dicarboxamide

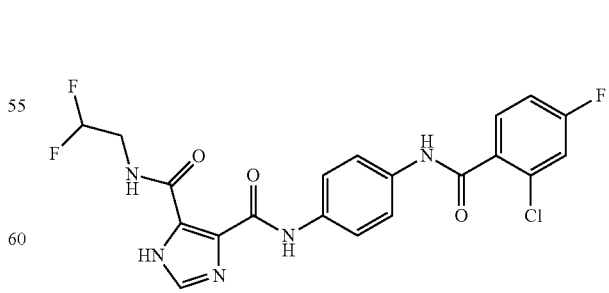

To the crude mixture of N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide (0.160 mmol, Intermediate 005), were added 0.023 mL (0.32 mmol) 2,2- difluoroethylamine and 0.278 mL (1.6 mmol) N-ethyl-N-isopropylpropan-2-amine and the mixture was stirred for 19 h at room temperature.

The reaction mixture was concentrated in vacuo and the residue was purified by preparative HPLC chromatography to give 50 mg of the title compound as a solid material.

$^1$H-NMR (400 MHz, DMSO-d$_6$): δ [ppm]=13.64-13.19 (m, 1H), 10.53 (s, 1H), 7.99 (s, 1H), 7.79-7.66 (m, 5H), 7.60 (dd, 1H), 7.36 (td, 1H), 6.38-6.05 (m, 1H), 3.79 (br. s., 2H).

LC-MS (Method 1): R$_t$=1.08 min; MS (ESIpos) m/z=466 [M+H]$^+$.

Example 140

N$^4$-{4-[(4-fluorobenzoyl)amino]phenyl}-N$^5$-(2-methoxyethyl)-1H-imidazole-4,5-dicarboxamide

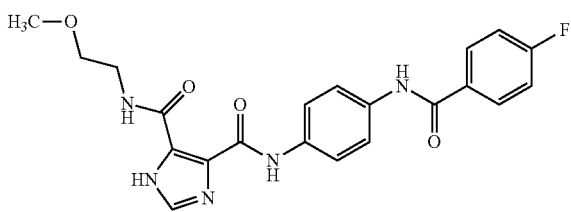 [SMILES: COCCNC(=O)c1[nH]cnc1C(=O)Nc1ccc(NC(=O)c2ccc(F)cc2)cc1]

To the crude mixture of N,N'-bis{4-[(4-fluorobenzoyl)amino]phenyl}-5,10-dioxo-5H,10H-diimidazo[1,5-a:1',5'-d]pyrazine-1,6-dicarboxamide (0.160 mmol, Intermediate 018), were added 0.028 mL (0.32 mmol) 2-methoxyethanamine and 0.278 mL (1.6 mmol) N-ethyl-N-isopropylpropan-2-amine and the mixture was stirred for 19 h at room temperature.

The reaction mixture was concentrated in vacuo and the residue was purified by preparative HPLC chromatography to give 14 mg of the title compound as a solid material.

$^1$H-NMR (400 MHz, DMSO-d$_6$): δ [ppm]=13.62-13.39 (m, 2H), 10.38-10.16 (m, 1H), 8.72 (br. s., 1H), 8.14-7.89 (m, 3H), 7.86-7.66 (m, 4H), 7.38 (t, 2H), 3.63-3.43 (m, 4H), 3.30 (s, 3H).

LC-MS (Method 1): R$_t$=1.01 min; MS (ESIpos) m/z=426 [M+H]$^+$.

Example 141

N$^5$-(2,2-difluoroethyl)-N$^4$-{4-[(4-fluorobenzoyl)amino]phenyl}-1H-imidazole-4,5-dicarboxamide

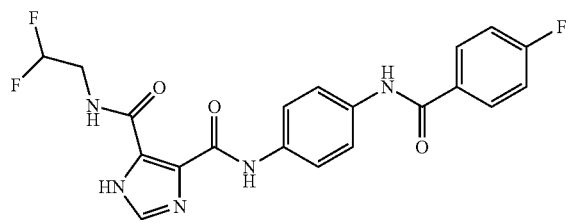 [SMILES: O=C(Nc1ccc(NC(=O)c2nc[nH]c2C(=O)NCC(F)F)cc1)c1ccc(F)cc1]

To the crude mixture of N,N'-bis{4-[(4-fluorobenzoyl)amino]phenyl}-5,10-dioxo-5H,10H-diimidazo[1,5-a:1',5'-d]pyrazine-1,6-dicarboxamide (0.160 mmol, Intermediate 018), were added 0.023 mL (0.32 mmol) 2,2-difluoroethylamine and 0.278 mL (1.6 mmol) N-ethyl-N-isopropylpropan-2-amine and the mixture was stirred for 19 h at room temperature.

The reaction mixture was concentrated in vacuo and the residue was purified by preparative HPLC chromatography to give 9 mg of the title compound as a solid material.

$^1$H-NMR (400 MHz, DMSO-d$_6$): δ [ppm]=13.59-13.26 (m, 1H), 10.46-10.26 (m, 1H), 9.11 (t, 1H), 8.10-7.97 (m, 3H), 7.84-7.67 (m, 4H), 7.44-7.32 (m, 2H), 6.40-6.05 (m, 1H), 3.91-3.71 (m, 2H).

LC-MS (Method 1): R$_t$=1.05 min; MS (ESIpos) m/z=432 [M+H]$^+$.

Example 142

5-(azetidin-1-ylcarbonyl)-N-{4-[(2-chloro-4-fluorobenzoyl)amino]phenyl}-1H-imidazole-4-carboxamide

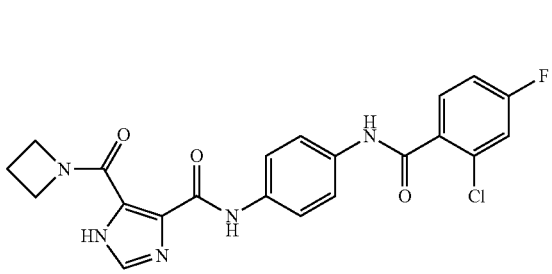 [SMILES: O=C(Nc1ccc(NC(=O)c2nc[nH]c2C(=O)N2CCC2)cc1)c1ccc(F)cc1Cl]

To the crude mixture of N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide (0.160 mmol, Intermediate 005), were added 0.022 mL (0.32 mmol) azetidine and 0.278 mL (1.6 mmol) N-ethyl-N-isopropylpropan-2-amine and the mixture was stirred for 20 h at room temperature.

The reaction mixture was concentrated in vacuo and the residue was purified by preparative HPLC chromatography to give 9 mg of the title compound as a solid material.

$^1$H-NMR (400 MHz, DMSO-d$_6$): δ [ppm]=13.75-13.39 (m, 1H), 10.52 (s, 1H), 7.92 (s, 1H), 7.75-7.65 (m, 5H), 7.59 (dd, 1H), 7.36 (td, 1H), 4.68 (t, 2H), 4.16 (t, 2H), 2.37-2.24 (m, 2H).

LC-MS (Method 1): R$_t$=1.04 min; MS (ESIpos) m/z=442 [M+H]$^+$.

Example 143

5-(azetidin-1-ylcarbonyl)-N-{4-[(4-fluorobenzoyl)amino]phenyl}-1H-imidazole-4-carboxamide

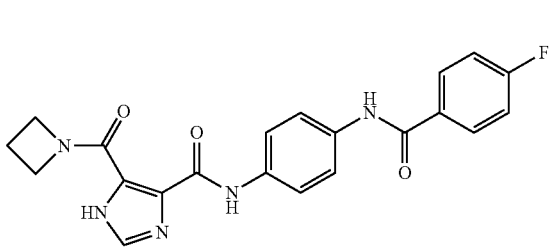 [SMILES: O=C(Nc1ccc(NC(=O)c2nc[nH]c2C(=O)N2CCC2)cc1)c1ccc(F)cc1]

To the crude mixture of N,N'-bis{4-[(4-fluorobenzoyl)amino]phenyl}-5,10-dioxo-5H,10H-diimidazo[1,5-a:1',5'-d]pyrazine-1,6-dicarboxamide (0.160 mmol, Intermediate 018), were added 0.022 mL (0.32 mmol) azetidine and 0.278 mL (1.6 mmol) N-ethyl-N-isopropylpropan-2-amine and the mixture was stirred for 19 h at room temperature.

The reaction mixture was concentrated in vacuo. To the residue were added 2 mL of DMSO. The precipitate was filtered off to give 65 mg of the title compound as a solid material.

$^1$H-NMR (400 MHz, DMSO-$d_6$): δ [ppm]=13.77-13.32 (m, 1H), 10.25 (s, 1H), 8.03 (dd, 2H), 7.89 (s, 1H), 7.82-7.72 (m, 2H), 7.70-7.61 (m, 2H), 7.35 (t, 2H), 4.67 (s, 2H), 4.15 (s, 2H), 2.29 (s, 2H).

LC-MS (Method 1): $R_t$=1.01 min; MS (ESIpos) m/z=408 [M+H]$^+$.

Example 144

$N^4$-{4-[(4-fluorobenzoyl)amino]phenyl}-$N^5$,$N^5$-dimethyl-1H-imidazole-4,5-dicarboxamide

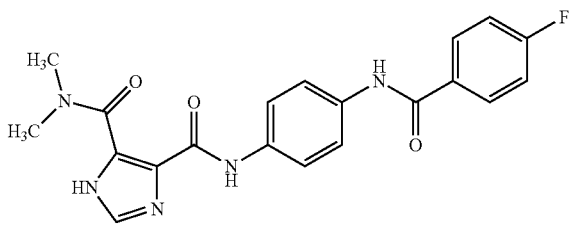 [SMILES: CN(C)C(=O)c1[nH]cnc1C(=O)Nc1ccc(NC(=O)c2ccc(F)cc2)cc1]

To the crude mixture of N,N'-bis{4-[(4-fluorobenzoyl)amino]phenyl}-5,10-dioxo-5H,10H-diimidazo[1,5-a:1',5'-d]pyrazine-1,6-dicarboxamide (0.160 mmol, Intermediate 018), were added 27 mg (0.32 mmol) N-methylmethanamine hydrochloride and 0.278 mL (1.6 mmol) N-ethyl-N-isopropylpropan-2-amine and the mixture was stirred for 19 h at room temperature.

The reaction mixture was concentrated in vacuo. To the residue were added 2 mL of DMSO. The precipitate was filtered off to give 21 mg of the title compound as a solid material.

$^1$H-NMR (400 MHz, DMSO-$d_6$): δ [ppm]=13.41 (br. s., 1H), 12.57 (br. s., 1H), 10.28 (br. s., 1H), 8.09-8.01 (m, 2H), 7.95-7.59 (m, 5H), 7.43-7.32 (m, 2H), 3.39 (br. s., 3H), 3.11 (br. s., 3H).

LC-MS (Method 1): $R_t$=0.92 min; MS (ESIpos) m/z=396 [M+H]$^+$.

Example 145

N-{4-[(2-chloro-4-fluorobenzoyl)amino]phenyl}-5-(2-oxa-6-azaspiro[3.3]hept-6-ylcarbonyl)-1H-imidazole-4-carboxamide

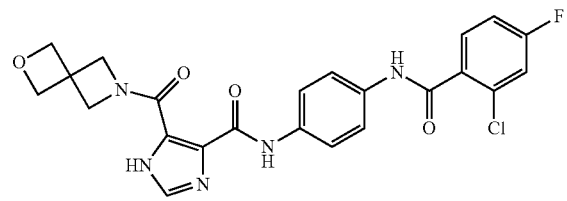 [SMILES: O=C(Nc1ccc(NC(=O)c2nc[nH]c2C(=O)N2CC3(COC3)C2)cc1)c1ccc(F)cc1Cl]

To the crude mixture of N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide (0.160 mmol, Intermediate 005), were added 61 mg (0.32 mmol) 2-oxa-6-azaspiro[3.3]heptane oxalate and 0.278 mL (1.6 mmol) N-ethyl-N-isopropylpropan-2-amine and the mixture was stirred for 5 d at room temperature.

The reaction mixture was concentrated in vacuo and the residue was purified by preparative HPLC chromatography to give 7 mg of the title compound as a solid material.

$^1$H-NMR (400 MHz, DMSO-$d_6$): δ [ppm]=13.60 (br. s., 1H), 10.51 (s, 1H), 7.91 (s, 1H), 7.75-7.64 (m, 5H), 7.59 (dd, 1H), 7.36 (td, 1H), 4.83 (s, 2H), 4.77-4.68 (m, 4H), 4.33 (s, 2H).

LC-MS (Method 1): $R_t$=0.97 min; MS (ESIpos) m/z=484 [M+H]$^+$.

Example 146

$N^4$-{4-[(4-fluorobenzoyl)amino]phenyl}-$N^5$-isobutyl-1H-imidazole-4,5-dicarboxamide

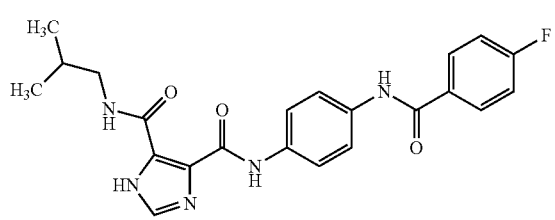 [SMILES: CC(C)CNC(=O)c1[nH]cnc1C(=O)Nc1ccc(NC(=O)c2ccc(F)cc2)cc1]

To the crude mixture of N,N'-bis{4-[(4-fluorobenzoyl)amino]phenyl}-5,10-dioxo-5H,10H-diimidazo[1,5-a:1',5'-d]pyrazine-1,6-dicarboxamide (0.160 mmol, Intermediate 018), were added 0.032 mL (0.32 mmol) 2-methylpropan-1-amine and 0.278 mL (1.6 mmol) N-ethyl-N-isopropylpropan-2-amine and the mixture was stirred for 19 h at room temperature.

The reaction mixture was concentrated in vacuo and the residue was purified by preparative HPLC chromatography to give 34 mg of the title compound as a solid material.

$^1$H-NMR (400 MHz, DMSO-$d_6$): δ [ppm]=13.41 (br. s., 1H), 10.29 (s, 1H), 8.11-8.01 (m, 2H), 7.92 (s, 1H), 7.84-7.65 (m, 4H), 7.44-7.31 (m, 2H), 3.19 (t, 2H), 2.01-1.84 (m, 1H), 0.93 (d, 6H).

LC-MS (Method 1): $R_t$=1.18 min; MS (ESIpos) m/z=424 [M+H]$^+$.

Example 147

$N^4$-{4-[(2-chloro-4-fluorobenzoyl)amino]phenyl}-$N^5$-isobutyl-1H-imidazole-4, 5-dicarboxamide

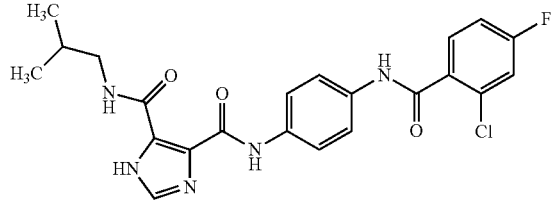 [SMILES: CC(C)CNC(=O)c1[nH]cnc1C(=O)Nc1ccc(NC(=O)c2ccc(F)cc2Cl)cc1]

To the crude mixture of N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide (0.160 mmol, Intermediate 005), were added 0.04 mL (0.32 mmol) 2-methylpropan-1-amine and 0.278 mL (1.6 mmol) N-ethyl-N-isopropylpropan-2-amine and the mixture stirred for 19 h at room temperature.

The reaction mixture was concentrated in vacuo and the residue was purified by preparative HPLC chromatography to give 38 mg of the title compound as a solid material.

$^1$H-NMR (400 MHz, DMSO-$d_6$): δ [ppm]=13.67-13.37 (m, 2H), 10.58-10.30 (m, 1H), 8.81 (t, 1H), 7.93 (s, 1H), 7.82-7.65 (m, 5H), 7.59 (dd, 1H), 7.42-7.31 (m, 1H), 3.19 (q, 2H), 2.01-1.88 (m, 1H), 0.91 (d, 6H).

LC-MS (Method 1): $R_t$=1.21 min; MS (ESIpos) m/z=458 [M+H]$^+$.

Example 148

N$^4$-{4-[(2-chlorobenzoyl)amino]phenyl}-N$^5$-(2,2-dimethylpropyl)-1H-imidazole-4,5-dicarboxamide

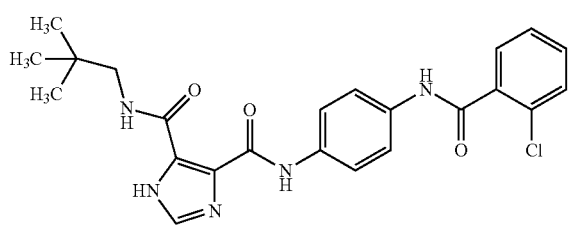 [SMILES: CC(C)(C)CNC(=O)c1[nH]cnc1C(=O)Nc1ccc(NC(=O)c2ccccc2Cl)cc1]

To the crude mixture of N,N'-bis{4-[(2-chlorobenzoyl)amino]phenyl}-5,10-dioxo-5H,10H-diimidazo[1,5-a:1',5'-d]pyrazine-1,6-dicarboxamide (0.2 mmol, Intermediate 052), were added 0.05 mL (0.4 mmol) 2,2-dimethylpropan-1-amine and 0.348 mL (2 mmol) N-ethyl-N-isopropylpropan-2-amine and the mixture was stirred for 72 h at room temperature.

The reaction mixture was concentrated in vacuo and the residue was purified by preparative HPLC chromatography to give 71 mg of the title compound as a solid material.

$^1$H-NMR (400 MHz, DMSO-$d_6$): δ [ppm]=10.52 (s, 1H), 7.93 (s, 1H), 7.72 (s, 5H), 7.62-7.55 (m, 2H), 7.55-7.43 (m, 2H), 3.20 (d, 2H), 0.95 (s, 9H).

LC-MS (Method 1): $R_t$=1.24 min; MS (ESIpos) m/z=454 [M+H]$^+$.

Example 149

N$^5$-(2,2-dimethylpropyl)-N$^4$-{4-[(4-fluorobenzoyl)amino]phenyl}-1H-imidazole-4,5-dicarboxamide

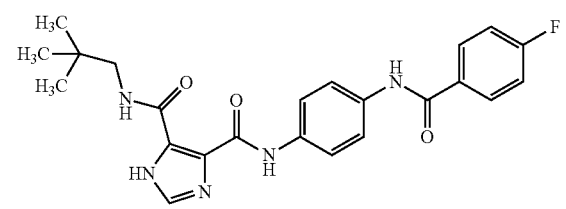 [SMILES: CC(C)(C)CNC(=O)c1[nH]cnc1C(=O)Nc1ccc(NC(=O)c2ccc(F)cc2)cc1]

To the crude mixture of N,N'-bis{4-[(4-fluorobenzoyl)amino]phenyl}-5,10-dioxo-5H,10H-diimidazo[1,5-a:1',5'-d]pyrazine-1,6-dicarboxamide (0.2 mmol, Intermediate 018), were added 0.05 mL (0.4 mmol) 2,2-dimethylpropan-1-amine and 0.348 mL (2 mmol) N-ethyl-N-isopropylpropan-2-amine and the mixture was stirred for 72 h at room temperature.

The reaction mixture was concentrated in vacuo and the residue was purified by preparative HPLC chromatography to give 87 mg of the title compound as a solid material.

$^1$H-NMR (400 MHz, DMSO-$d_6$): δ [ppm]=13.64-13.36 (m, 1H), 10.29 (s, 1H), 8.12-8.00 (m, 2H), 7.94 (s, 1H), 7.88-7.63 (m, 5H), 7.46-7.29 (m, 2H), 3.21 (d, 2H), 1.06-0.86 (m, 9H).

LC-MS (Method 1): $R_t$=1.25 min; MS (ESIpos) m/z=438 [M+H]$^+$.

Example 150

N$^5$-(1,3-dihydroxypropan-2-yl)-N$^4$-{4-[(4-fluorobenzoyl)amino]phenyl}-1H-imidazole-4,5-dicarboxamide

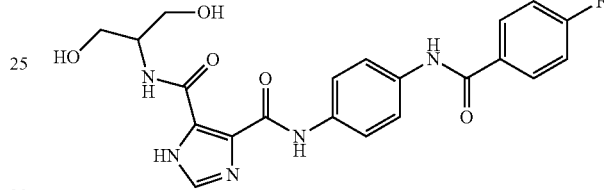

To the crude mixture of N,N'-bis{4-[(4-fluorobenzoyl)amino]phenyl}-5,10-dioxo-5H,10H-diimidazo[1,5-a:1',5'-d]pyrazine-1,6-dicarboxamide (0.2 mmol, Intermediate 018), were added 37 mg (0.4 mmol) 2-aminopropane-1,3-diol and 0.348 mL (2 mmol) N-ethyl-N-isopropylpropan-2-amine and the mixture was stirred for 16 h at room temperature.

The reaction mixture was concentrated in vacuo and the residue was purified by preparative HPLC chromatography to give 32 mg of the title compound as a solid material.

$^1$H-NMR (400 MHz, DMSO-$d_6$): δ [ppm]=13.58-13.45 (m, 1H), 10.29 (s, 1H), 8.28 (d, 1H), 8.09-8.01 (m, 2H), 7.97-7.90 (m, 1H), 7.83-7.66 (m, 4H), 7.44-7.33 (m, 2H), 4.89 (t, 1H), 4.08-4.00 (m, 1H), 3.66-3.51 (m, 4H).

LC-MS (Method 1): $R_t$=0.38 min; MS (ESIpos) m/z=442 [M+H]$^+$.

Example 151

N$^4$-{4-[(4-fluorobenzoyl)amino]phenyl}-N$^5$-[2-(morpholin-4-yl)ethyl]-1H-imidazole-4,5-dicarboxamide

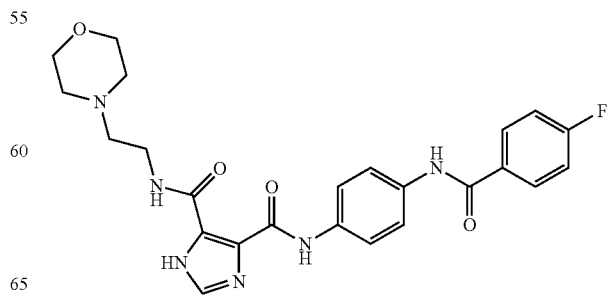

To the crude mixture of N,N'-bis{4-[(4-fluorobenzoyl)amino]phenyl}-5,10-dioxo-5H,10H-diimidazo[1,5-a:1',5'-d]pyrazine-1,6-dicarboxamide (0.2 mmol, Intermediate 018), were added 0.053 mL (0.4 mmol) 2-(morpholin-4-yl)ethanamine and 0.348 mL (2 mmol) N-ethyl-N-isopropylpropan-2-amine and the mixture was stirred for 19 h at room temperature.

The reaction mixture was concentrated in vacuo and the residue was purified by preparative HPLC chromatography to give 34 mg of the title compound as a solid material.

$^1$H-NMR (400 MHz, DMSO-$d_6$): δ [ppm]=13.59 (s, 1H), 13.46 (br. s., 1H), 10.37-10.26 (m, 1H), 8.70 (t, 1H), 8.08-8.02 (m, 2H), 7.97-7.91 (m, 1H), 7.86-7.73 (m, 2H), 7.72-7.65 (m, 1H), 7.42-7.33 (m, 1H), 3.65-3.55 (m, 2H), 3.49 (q, 1H), 2.45 (br. s., 2H).

LC-MS (Method 1): $R_t$=0.71 min; MS (ESIpos) m/z=481 [M+H]$^+$.

Example 152

N$^4$-{4-[(2-chlorobenzoyl)amino]phenyl}-N$^5$-{2-[3-hydroxypiperidin-1-yl]ethyl}-1H-imidazole-4,5-dicarboxamide

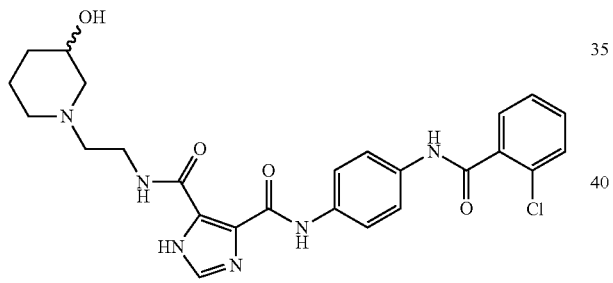

To the crude mixture of N,N'-bis{4-[(2-chlorobenzoyl)amino]phenyl}-5,10-dioxo-5H,10H-diimidazo[1,5-a:1',5'-d]pyrazine-1,6-dicarboxamide (0.2 mmol, Intermediate 052), were added 58 mg (0.4 mmol) 1-(2-aminoethyl)piperidin-3-ol and 0.348 mL (2 mmol) N-ethyl-N-isopropylpropan-2-amine and the mixture was stirred for 72 h at room temperature.

The reaction mixture was concentrated in vacuo and the residue was purified by preparative HPLC chromatography to give 17 mg of the title compound as a solid material.

$^1$H-NMR (500 MHz, DMSO-$d_6$): δ [ppm]=1.08 (d, 1H), 1.43 (br. s., 1H), 1.58-1.68 (m, 1H), 1.79 (d, 2H), 1.86-1.97 (m, 1H), 2.72 (d, 1H), 2.89 (d, 1H), 3.45 (q, 3H), 4.60 (br. s., 1H), 7.44-7.48 (m, 1H), 7.51 (td, 1H), 7.55-7.61 (m, 2H), 7.66-7.77 (m, 4H), 7.92 (s, 1H), 8.66 (br. s., 1H), 10.51 (s, 1H), 13.08-13.85 (m, 2H).

LC-MS (Method 1): $R_t$=0.71 min; MS (ESIpos) m/z=511 [M+H]$^+$.

Example 153

N$^4$-{4-[(2-chlorobenzoyl)amino]phenyl}-N$^5$-[2-(2-methylpiperidin-1-yl)ethyl]-1H-imidazole-4,5-dicarboxamide

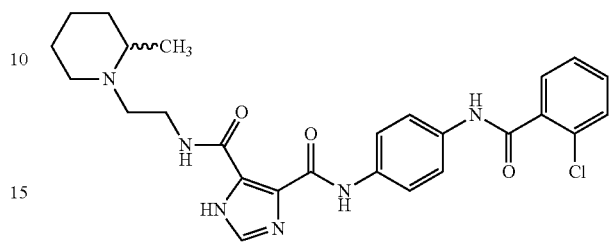

To the crude mixture of N,N'-bis{4-[(2-chlorobenzoyl)amino]phenyl}-5,10-dioxo-5H,10H-diimidazo[1,5-a:1',5'-d]pyrazine-1,6-dicarboxamide (0.2 mmol, Intermediate 052), were added 0.066 mL (0.4 mmol) 1-(2-aminoethyl)piperidin-2-ol and 0.348 mL (2 mmol) N-ethyl-N-isopropylpropan-2-amine and the mixture was stirred for 18 h at room temperature.

The reaction mixture was concentrated in vacuo and the residue was purified by preparative HPLC chromatography to give 30 mg of the title compound as a solid material.

$^1$H-NMR (400 MHz, DMSO-$d_6$): δ [ppm]=13.71-13.28 (m, 2H), 10.57-10.47 (m, 1H), 8.68 (br. s., 1H), 7.93 (s, 1H), 7.84-7.64 (m, 5H), 7.63-7.43 (m, 5H), 3.54-3.36 (m, 2H), 2.94-2.77 (m, 2H), 2.48-2.32 (m, 3H), 2.22 (td, 1H), 1.66-1.37 (m, 4H), 1.33-1.13 (m, 2H), 1.09-0.99 (m, 3H).

LC-MS (Method 1): $R_t$=0.79 min; MS (ESIpos) m/z=510 [M+H]$^+$.

Example 154

N$^4$-{4-[(2-chlorobenzoyl)amino]phenyl}-N$^5$-[2-methyl-1-(morpholin-4-yl)propan-2-yl]-1H-imidazole-4,5-dicarboxamide

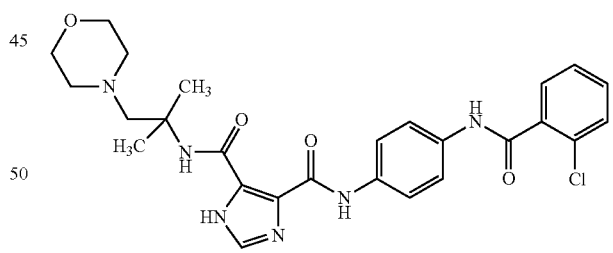

To the crude mixture of N,N'-bis{4-[(2-chlorobenzoyl)amino]phenyl}-5,10-dioxo-5H,10H-diimidazo[1,5-a:1',5'-d]pyrazine-1,6-dicarboxamide (0.2 mmol, Intermediate 052), were added 0.065 mL (0.4 mmol) 2-methyl-1-(morpholin-4-yl)propan-2-amine and 0.348 mL (2 mmol) N-ethyl-N-isopropylpropan-2-amine and the mixture was stirred for 18 h at room temperature.

The reaction mixture was concentrated in vacuo and the residue was purified by preparative HPLC chromatography to give 30 mg of the title compound as a solid material.

$^1$H-NMR (400 MHz, DMSO-$d_6$): δ [ppm]=10.58-10.44 (m, 1H), 7.90 (s, 1H), 7.82-7.66 (m, 5H), 7.63-7.42 (m, 5H), 3.58 (br. s., 4H), 2.63-2.53 (m, 6H), 1.43 (br. s., 6H).

LC-MS (Method 1): R$_t$=0.79 min; MS (ESIpos) m/z=525 [M+H]$^+$.

Example 155

N$^4$-{4-[(2-chloro-4-fluorobenzoyl)amino]phenyl}-N$^5$-[2-methyl-1-(4-methylpiperidin-1-yl)propan-2-yl]-1H-imidazole-4,5-dicarboxamide

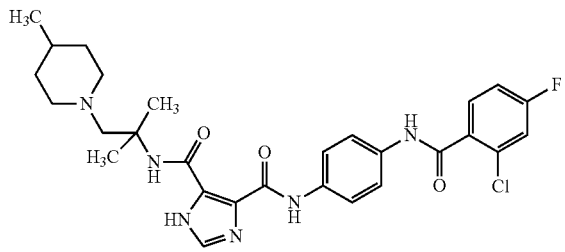 [SMILES: CC1CCN(CC(C)(C)NC(=O)c2[nH]cnc2C(=O)Nc2ccc(NC(=O)c3ccc(F)cc3Cl)cc2)CC1]

To the crude mixture of N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide (0.20 mmol, Intermediate 005), were added 0.077 mL (0.4 mmol) 2-methyl-1-(4-methylpiperidin-1-yl)propan-2-amine and 0.348 mL (2 mmol) N-ethyl-N-isopropylpropan-2-amine and the mixture was stirred for 72 h at room temperature.

The reaction mixture was concentrated in vacuo and the residue was purified by preparative HPLC chromatography to give 35 mg of the title compound as a solid material.

$^1$H-NMR (400 MHz, DMSO-d$_6$): δ [ppm]=13.47 (br. s., 1H), 10.59-10.47 (m, 1H), 7.90 (s, 1H), 7.83-7.65 (m, 6H), 7.60 (dd, 1H), 7.36 (td, 1H), 2.84 (d, 2H), 2.24 (br. s., 2H), 1.62-1.10 (m, 12H), 0.87 (d, 3H)$^1$H-NMR (400 MHz, DMSO-d$_6$): δ [ppm]=13.67-13.37 (m, 2H), 10.58-10.30 (m, 1H), 8.81 (t, 1H), 7.93 (s, 1H), 7.82-7.65 (m, 5H), 7.59 (dd, 1H), 7.42-7.31 (m, 1H), 3.19 (q, 2H), 2.01-1.88 (m, 1H), 0.91 (d, 6H).

LC-MS (Method 1): R$_t$=0.83 min; MS (ESIpos) m/z=556 [M+H]$^+$.

Example 156

N$^4$-{4-[(4-fluorobenzoyl)amino]phenyl}-N$^5$-[2-methyl-1-(piperidin-1-yl)propan-2-yl]-1H-imidazole-4,5-dicarboxamide

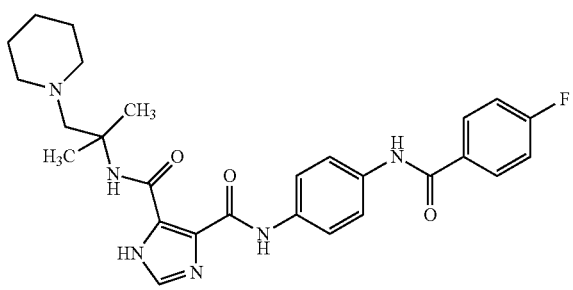 [SMILES: CC(C)(CN1CCCCC1)NC(=O)c1[nH]cnc1C(=O)Nc1ccc(NC(=O)c2ccc(F)cc2)cc1]

To the crude mixture of N,N'-bis{4-[(4-fluorobenzoyl)amino]phenyl}-5,10-dioxo-5H,10H-diimidazo[1,5-a:1',5'-d]pyrazine-1,6-dicarboxamide (0.2 mmol, Intermediate 018), were added 0.072 mL (0.4 mmol) 2-methyl-1-(piperidin-1-yl)propan-2-amine and 0.348 mL (2 mmol) N-ethyl-N-isopropylpropan-2-amine and the mixture was stirred for 19 h at room temperature.

The reaction mixture was concentrated in vacuo and the residue was purified by preparative HPLC chromatography to give 41 mg of the title compound as a solid material.

$^1$H-NMR (500 MHz, DMSO-d$_6$): δ [ppm]=10.34-10.17 (m, 1H), 8.07-7.99 (m, 2H), 7.87 (s, 1H), 7.81-7.62 (m, 5H), 7.39-7.33 (m, 2H), 1.57-1.28 (m, 12H).

LC-MS (Method 1): R$_t$=1.45 min; MS (ESIpos) m/z=507 [M+H]$^+$.

Example 157

N$^4$-{4-[(2-chlorobenzoyl)amino]phenyl}-N$^5$-(1,3-dihydroxypropan-2-yl)-1H-imidazole-4,5-dicarboxamide

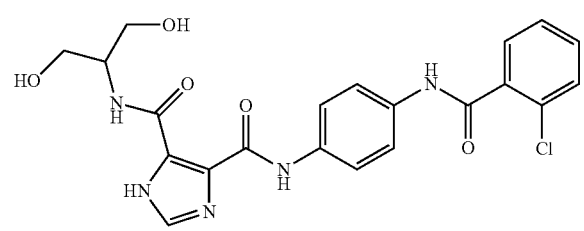 [SMILES: O=C(Nc1ccc(NC(=O)c2nc[nH]c2C(=O)NC(CO)CO)cc1)c1ccccc1Cl]

To the crude mixture of N,N'-bis{4-[(2-chlorobenzoyl)amino]phenyl}-5,10-dioxo-5H,10H-diimidazo[1,5-a:1',5'-d]pyrazine-1,6-dicarboxamide (0.2 mmol, Intermediate 052), were added 37 mg (0.4 mmol) 2-methyl-1-(morpholin-4-yl)propan-2-amine and 0.348 mL (2 mmol) 2-aminopropane-1,3-diol and the mixture was stirred for 18 h at room temperature.

The reaction mixture was concentrated in vacuo and the residue was purified by preparative HPLC chromatography to give 43 mg of the title compound as a solid material.

$^1$H-NMR (400 MHz, DMSO-d$_6$): δ [ppm]=13.61-13.39 (m, 1H), 10.52 (s, 1H), 8.28 (d, 1H), 8.03-7.85 (m, 1H), 7.81-7.37 (m, 9H), 4.90 (t, 1H), 4.11-3.99 (m, 1H), 3.70-3.51 (m, 5H).

LC-MS (Method 1): R$_t$=0.81 min; MS (ESIpos) m/z=458 [M+H]$^+$.

Example 158

N$^4$-{4-[(2-chlorobenzoyl)amino]phenyl}-N$^5$-[2-methyl-1-(4-methylpiperidin-1-yl)propan-2-yl]-1H-imidazole-4,5-dicarboxamide

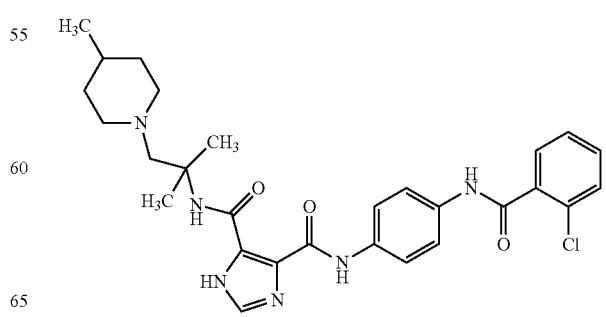

To the crude mixture of N,N'-bis{4-[(2-chlorobenzoyl)amino]phenyl}-5,10-dioxo-5H,10H-diimidazo[1,5-a:1',5'-d]pyrazine-1,6-dicarboxamide (0.2 mmol, Intermediate 052), were added 0.077 mL (0.4 mmol) 2-methyl-1-(piperidin-1-yl)propan-2-amine and 0.348 mL (2 mmol) N-ethyl-N-isopropylpropan-2-amine and the mixture was stirred for 72 h at room temperature.

The reaction mixture was concentrated in vacuo and the residue was purified by preparative HPLC chromatography to give 27 mg of the title compound as a solid material.

$^1$H-NMR (400 MHz, DMSO-$d_6$): δ [ppm]=10.56-10.49 (m, 1H), 7.89 (s, 1H), 7.81-7.67 (m, 5H), 7.63-7.56 (m, 3H), 7.55-7.42 (m, 3H), 2.84 (d, 2H), 2.24 (t, 2H), 1.53 (d, 2H), 1.41 (s, 6H), 1.36-1.13 (m, 4H), 0.87 (d, 3H).

LC-MS (Method 1): $R_t$=0.89 min; MS (ESIpos) m/z=537 [M+H]$^+$.

Example 159

N$^4$-{4-[(2-chloro-4-fluorobenzoyl)amino]phenyl}-N$^5$-[2-methyl-2-(piperidin-1-yl)propyl]-1H-imidazole-4,5-dicarboxamide

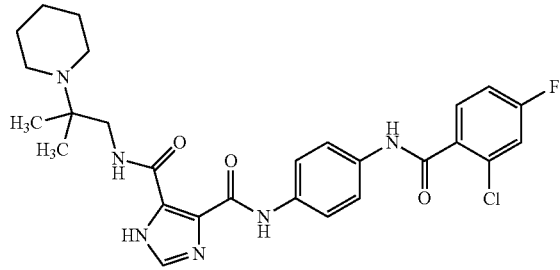 [SMILES: CC(C)(CNC(=O)c1[nH]cnc1C(=O)Nc1ccc(NC(=O)c2ccc(F)cc2Cl)cc1)N1CCCCC1]

To the crude mixture of N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide (0.20 mmol, Intermediate 005), were added 0.077 mL (0.4 mmol) 2-methyl-2-(piperidin-1-yl)propan-1-amine and 0.348 mL (2 mmol) N-ethyl-N-isopropylpropan-2-amine and the mixture was stirred for 19 h at room temperature.

The reaction mixture was concentrated in vacuo and the residue was purified by preparative HPLC chromatography to give 19 mg of the title compound as a solid material.

$^1$H-NMR (500 MHz, DMSO-$d_6$): δ [ppm]=10.58-10.37 (m, 1H), 7.92 (s, 1H), 7.81-7.64 (m, 6H), 7.60-7.55 (m, 1H), 7.38-7.31 (m, 1H), 3.34 (d, 2H), 1.53 (br. s., 4H), 1.39 (br. s., 2H), 1.02 (s, 6H).

LC-MS (Method 1): $R_t$=1.38 min; MS (ESIpos) m/z=541 [M+H]$^+$.

Example 160

N$^4$-{4-[(2-chlorobenzoyl)amino]phenyl}-N$^5$-[2-(4-methylpiperazin-1-yl)ethyl]-1H-imidazole-4,5-dicarboxamide

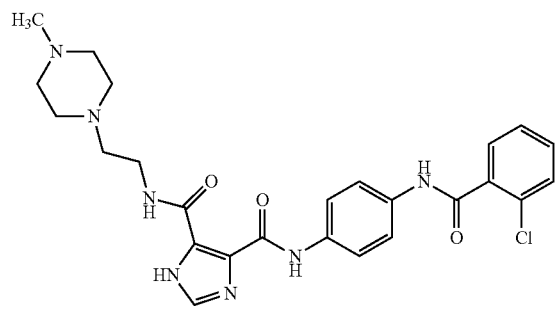 [SMILES: CN1CCN(CCNC(=O)c2[nH]cnc2C(=O)Nc2ccc(NC(=O)c3ccccc3Cl)cc2)CC1]

To the crude mixture of N,N'-bis{4-[(2-chlorobenzoyl)amino]phenyl}-5,10-dioxo-5H,10H-diimidazo[1,5-a:1',5'-d]pyrazine-1,6-dicarboxamide (0.2 mmol, Intermediate 052), were added 0.06 mL (0.4 mmol) 2-(4-methylpiperazin-1-yl)ethanamine and 0.348 mL (2 mmol) N-ethyl-N-isopropylpropan-2-amine and the mixture was stirred for 15 h at room temperature.

The reaction mixture was concentrated in vacuo and the residue was purified by preparative HPLC chromatography to give 35 mg of the title compound as a solid material.

$^1$H-NMR (400 MHz, DMSO-$d_6$): δ [ppm]=10.51 (s, 1H), 7.93 (s, 1H), 7.72 (s, 4H), 7.62-7.55 (m, 2H), 7.55-7.44 (m, 2H), 3.47 (q, 2H), 2.48-2.23 (m, 7H), 2.16 (s, 3H).

LC-MS (Method 1): $R_t$=0.89 min; MS (ESIpos) m/z=537 [M+H]$^+$.

Example 161

N$^4$-{4-[(4-fluorobenzoyl)amino]phenyl}-N$^5$-[2-(4-methylpiperazin-1-yl)ethyl]-1H-imidazole-4,5-dicarboxamide

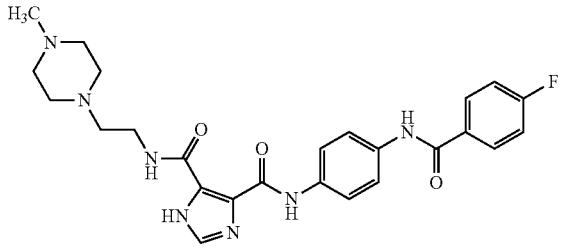 [SMILES: CN1CCN(CCNC(=O)c2[nH]cnc2C(=O)Nc2ccc(NC(=O)c3ccc(F)cc3)cc2)CC1]

To the crude mixture of N,N'-bis{4-[(4-fluorobenzoyl)amino]phenyl}-5,10-dioxo-5H,10H-diimidazo[1,5-a:1',5'-d]pyrazine-1,6-dicarboxamide (0.2 mmol, Intermediate 018), were added 0.072 mL (0.4 mmol) 2-methyl-1-(piperidin-1-yl)propan-2-amine and 0.348 mL (2 mmol) N-ethyl-N-isopropylpropan-2-amine and the mixture was stirred for 19 h at room temperature.

The reaction mixture was concentrated in vacuo and the residue was purified by preparative HPLC chromatography to give 41 mg of the title compound as a solid material.

¹H-NMR (400 MHz, DMSO-d₆): δ [ppm]=13.59 (s, 1H), 10.29 (s, 2H), 8.66 (br. s., 1H), 8.09-8.00 (m, 3H), 7.94 (s, 1H), 7.85 (br. s., 1H), 7.81-7.64 (m, 3H), 7.43-7.32 (m, 2H), 3.47 (q, 2H), 2.48-2.31 (m, 5H), 2.17 (s, 3H).

LC-MS (Method 1): $R_t$=0.71 min; MS (ESIpos) m/z=494 [M+H]⁺.

Example 162

N⁴-{4-[(2-chlorobenzoyl)amino]phenyl}-N⁵-[1-(morpholin-4-yl)propan-2-yl]-1H-imidazole-4,5-dicarboxamide

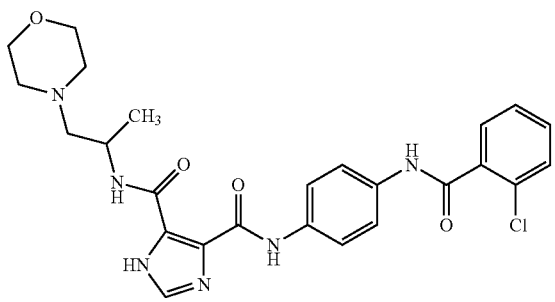 [SMILES: CC(CN1CCOCC1)NC(=O)c1[nH]cnc1C(=O)Nc1ccc(NC(=O)c2ccccc2Cl)cc1]

To the crude mixture of N,N'-bis{4-[(2-chlorobenzoyl)amino]phenyl}-5,10-dioxo-5H,10H-diimidazo[1,5-a:1',5'-d]pyrazine-1,6-dicarboxamide (0.2 mmol, Intermediate 052), were added 0.061 mL (0.4 mmol) 1-(morpholin-4-yl)propan-2-amine and 0.348 mL (2 mmol) N-ethyl-N-isopropylpropan-2-amine and the mixture was stirred for 19 h at room temperature.

The reaction mixture was concentrated in vacuo and the residue was purified by preparative HPLC chromatography to give 23 mg of the title compound as a solid material.

¹H-NMR (400 MHz, DMSO-d₆): δ [ppm]=10.49 (s, 1H), 7.90 (s, 1H), 7.76-7.64 (m, 4H), 7.61-7.53 (m, 2H), 7.52-7.41 (m, 2H), 4.22 (br. s., 1H), 3.53 (t, 4H), 2.46-2.29 (m, 6H), 1.20 (d, 3H).

LC-MS (Method 1): $R_t$=0.75 min; MS (ESIpos) m/z=511 [M+H]⁺.

Example 163

N⁴-{4-[(2-chlorobenzoyl)amino]phenyl}-N⁵-[2-(4-methylpiperidin-1-yl)ethyl]-1H-imidazole-4,5-dicarboxamide

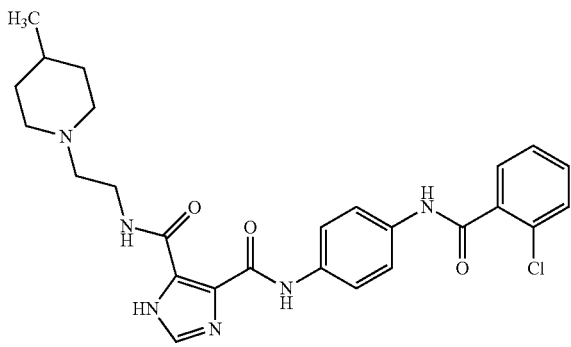 [SMILES: CC1CCN(CCNC(=O)c2[nH]cnc2C(=O)Nc2ccc(NC(=O)c3ccccc3Cl)cc2)CC1]

To the crude mixture of N,N'-bis{4-[(2-chlorobenzoyl)amino]phenyl}-5,10-dioxo-5H,10H-diimidazo[1,5-a:1',5'-d]pyrazine-1,6-dicarboxamide (0.2 mmol, Intermediate 052), were added 0.067 mL (0.4 mmol) 2-(4-methylpiperidin-1-yl)ethanamine and 0.348 mL (2 mmol) N-ethyl-N-isopropylpropan-2-amine and the mixture was stirred for 18 h at room temperature.

The reaction mixture was concentrated in vacuo and the residue was purified by preparative HPLC chromatography to give 52 mg of the title compound as a solid material.

¹H-NMR (400 MHz, DMSO-d₆): δ [ppm]=10.56-10.48 (m, 1H), 7.93 (s, 1H), 7.82-7.67 (m, 5H), 7.63-7.55 (m, 2H), 7.54-7.43 (m, 2H), 3.46 (q, 2H), 2.88 (d, 2H), 2.00-1.89 (m, 2H), 1.59 (d, 2H), 1.41-1.26 (m, 1H), 1.23-1.08 (m, 2H), 0.94-0.85 (m, 3H).

LC-MS (Method 1): $R_t$=0.79 min; MS (ESIpos) m/z=510 [M+H]⁺.

Example 164

N⁴-{4-[(4-fluorobenzoyl)amino]phenyl}-N⁵-[2-(4-methylpiperidin-1-yl)ethyl]-1H-imidazole-4,5-dicarboxamide

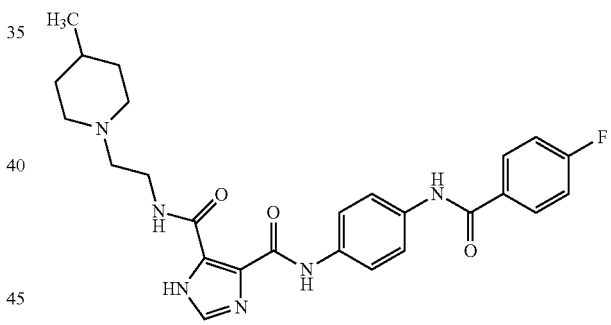

To the crude mixture of N,N'-bis{4-[(4-fluorobenzoyl)amino]phenyl}-5,10-dioxo-5H,10H-diimidazo[1,5-a:1',5'-d]pyrazine-1,6-dicarboxamide (0.2 mmol, Intermediate 018), were added 0.067 mL (0.4 mmol) 2-(4-methylpiperidin-1-yl)ethanamine and 0.348 mL (2 mmol) N-ethyl-N-isopropylpropan-2-amine and the mixture was stirred for 18 h at room temperature.

The reaction mixture was concentrated in vacuo and the residue was digested in DMSO. The solid precipitate was filtered off to give 50 mg of the title compound as a solid material.

¹H-NMR (400 MHz, DMSO-d₆): δ [ppm]=13.64-13.42 (m, 1H), 10.29 (s, 1H), 8.65 (br. s., 1H), 8.10-8.01 (m, 3H), 7.94 (s, 1H), 7.89-7.65 (m, 4H), 7.38 (t, 2H), 3.47 (d, 2H), 2.89 (d, 2H), 1.93 (d, 2H), 1.59 (d, 2H), 1.43-1.03 (m, 3H), 0.89 (d, 3H).

LC-MS (Method 1): $R_t$=0.84 min; MS (ESIpos) m/z=493 [M+H]⁺.

Example 165

N⁴-{4-[(2-chlorobenzoyl)amino]phenyl}-N⁵-[2-methyl-2-(piperidin-1-yl)propyl]-1H-imidazole-4,5-dicarboxamide

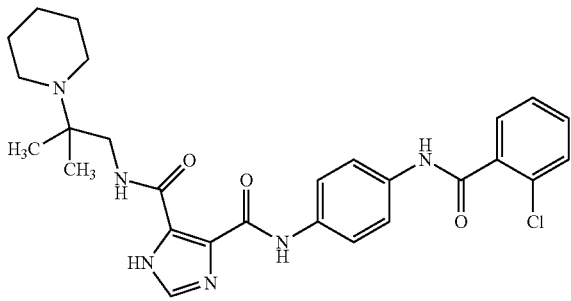 [SMILES: CC(C)(CNC(=O)c1[nH]cnc1C(=O)Nc1ccc(NC(=O)c2ccccc2Cl)cc1)N1CCCCC1]

To the crude mixture of N,N'-bis{4-[(2-chlorobenzoyl)amino]phenyl}-5,10-dioxo-5H,10H-diimidazo[1,5-a:1',5'-d]pyrazine-1,6-dicarboxamide (0.2 mmol, Intermediate 052), were added 0.077 mL (0.4 mmol) 2-methyl-2-(piperidin-1-yl)propan-1-amine and 0.348 mL (2 mmol) N-ethyl-N-isopropylpropan-2-amine and the mixture was stirred for 19 h at room temperature.

The reaction mixture was concentrated in vacuo and the residue was purified by preparative HPLC chromatography to give 34 mg of the title compound as a solid material.

¹H-NMR (500 MHz, DMSO-d₆): δ [ppm]=10.52-10.45 (m, 1H), 7.91 (s, 1H), 7.78-7.65 (m, 4H), 7.57 (ddd, 2H), 7.53-7.42 (m, 2H), 3.34 (d, 2H), 1.53 (br. s., 4H), 1.39 (br. s., 2H), 1.06-0.99 (m, 6H).

LC-MS (Method 1): $R_t$=1.34 min; MS (ESIpos) m/z=523 [M+H]⁺.

Example 166

N⁴-{4-[(2-chlorobenzoyl)amino]phenyl}-N⁵-(2-fluoroethyl)-1H-imidazole-4,5-dicarboxamide

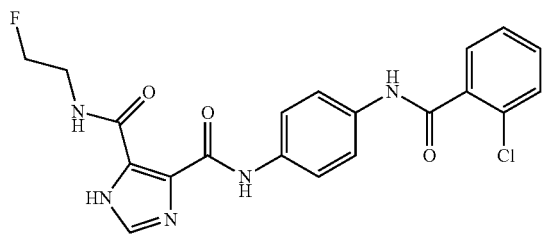 [SMILES: O=C(Nc1ccc(NC(=O)c2nc[nH]c2C(=O)NCCF)cc1)c1ccccc1Cl]

To the crude mixture of N,N'-bis{4-[(2-chlorobenzoyl)amino]phenyl}-5,10-dioxo-5H,10H-diimidazo[1,5-a:1',5'-d]pyrazine-1,6-dicarboxamide (0.2 mmol, Intermediate 052), were added 44 mg (0.4 mmol) 2-fluoroethanamine hydrochloride and 0.348 mL (2 mmol) N-ethyl-N-isopropylpropan-2-amine and the mixture was stirred for 16 h at room temperature.

The reaction mixture was concentrated in vacuo and the residue was purified by preparative HPLC chromatography to give 20 mg of the title compound as a solid material.

¹H-NMR (400 MHz, DMSO-d₆): δ [ppm]=13.54-13.43 (m, 1H), 10.52 (s, 1H), 8.97 (t, 1H), 7.96 (s, 1H), 7.82-7.66 (m, 4H), 7.63-7.55 (m, 2H), 7.55-7.43 (m, 2H), 4.70-4.62 (m, 1H), 4.58-4.50 (m, 1H), 3.71 (q, 1H), 3.64 (q, 1H).

LC-MS (Method 1): $R_t$=1.00 min; MS (ESIpos) m/z=430 [M+H]⁺.

Example 167

N⁴-{4-[(4-fluorobenzoyl)amino]phenyl}-N⁵-[2-(3-hydroxypiperidin-1-yl)ethyl]-1H-imidazole-4,5-dicarboxamide

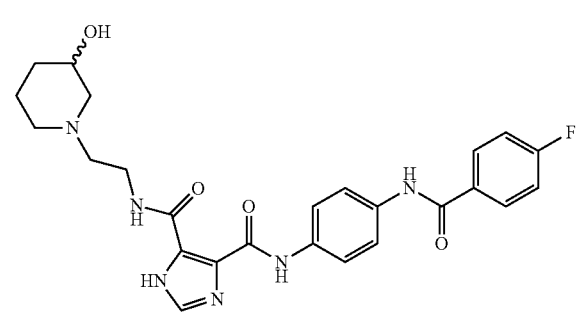 [SMILES: O=C(Nc1ccc(NC(=O)c2nc[nH]c2C(=O)NCCN2CCCC(O)C2)cc1)c1ccc(F)cc1]

To the crude mixture of N,N'-bis{4-[(4-fluorobenzoyl)amino]phenyl}-5,10-dioxo-5H,10H-diimidazo[1,5-a:1',5'-d]pyrazine-1,6-dicarboxamide (0.2 mmol, Intermediate 018), were added 58 mg (0.4 mmol) 1-(2-aminoethyl)piperidin-3-ol and 0.348 mL (2 mmol) N-ethyl-N-isopropylpropan-2-amine and the mixture was stirred for 72 h at room temperature.

The reaction mixture was concentrated in vacuo and the residue The reaction mixture was concentrated in vacuo and the residue was purified by preparative HPLC chromatography to give 33 mg of the title compound as a solid material.

¹H-NMR (400 MHz, DMSO-d₆): δ [ppm]=13.65-13.31 (m, 1H), 10.29 (s, 1H), 8.11-8.02 (m, 2H), 7.93 (s, 1H), 7.83-7.63 (m, 4H), 7.44-7.29 (m, 2H), 3.46 (q, 3H), 2.89 (d, 1H), 2.73 (d, 1H), 1.91 (br. s., 1H), 1.85-1.73 (m, 2H), 1.68-1.58 (m, 1H), 1.52-1.33 (m, 1H), 1.14-1.01 (m, 1H).

LC-MS (Method 1): $R_t$=0.72 min; MS (ESIpos) m/z=495 [M+H]⁺.

Example 168

N⁴-{4-[(2-chlorobenzoyl)amino]phenyl}-N⁵-[2-(pyrrolidin-1-yl)ethyl]-1H-imidazole-4,5-dicarboxamide

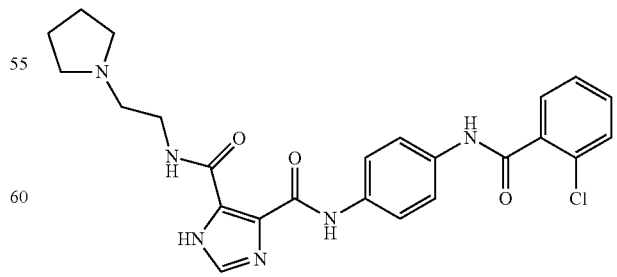

To the crude mixture of N,N'-bis{4-[(2-chlorobenzoyl)amino]phenyl}-5,10-dioxo-5H,10H-diimidazo[1,5-a:1',5'-d]pyrazine-1,6-dicarboxamide (0.2 mmol, Intermediate 052), were added 0.051 mL (0.4 mmol) 2-(pyrrolidin-1-yl)ethanamine and 0.348 mL (2 mmol) N-ethyl-N-isopropylpropan-2-amine and the mixture was stirred for 16 h at room temperature.

The reaction mixture was concentrated in vacuo and the residue was purified by preparative HPLC chromatography to give 18 mg of the title compound as a solid material.

$^1$H-NMR (400 MHz, DMSO-$d_6$): δ [ppm]=10.51 (s, 1H), 7.91 (s, 1H), 7.77-7.66 (m, 4H), 7.63-7.55 (m, 2H), 7.54-7.42 (m, 2H), 3.47 (q, 2H), 2.63 (t, 2H), 1.70 (t, 4H).

LC-MS (Method 1): $R_t$=0.74 min; MS (ESIpos) m/z=481 [M+H]$^+$.

Example 169

$N^4$-{4-[(4-fluorobenzoyl)amino]phenyl}-$N^5$-[2-(2-methylpiperidin-1-yl)ethyl]-1H-imidazole-4,5-dicarboxamide

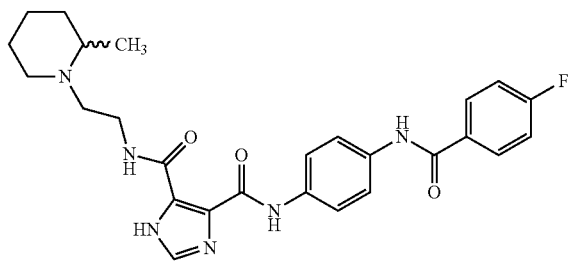 [SMILES: CC1CCCCN1CCNC(=O)c1[nH]cnc1C(=O)Nc1ccc(NC(=O)c2ccc(F)cc2)cc1]

To the crude mixture of N,N'-bis{4-[(4-fluorobenzoyl)amino]phenyl}-5,10-dioxo-5H,10H-diimidazo[1,5-a:1',5'-d]pyrazine-1,6-dicarboxamide (0.2 mmol, Intermediate 018), were added 0.067 mL (0.4 mmol) 2-(2-methylpiperidin-1-yl)ethanamine and 0.348 mL (2 mmol) N-ethyl-N-isopropylpropan-2-amine and the mixture was stirred for 18 h at room temperature.

The reaction mixture was concentrated in vacuo and the residue was purified by preparative HPLC chromatography to give 77 mg of the title compound as a solid material.

$^1$H-NMR (400 MHz, DMSO-$d_6$): δ [ppm]=10.29 (s, 1H), 8.09-8.02 (m, 2H), 7.93 (s, 1H), 7.81-7.65 (m, 4H), 7.45-7.32 (m, 2H), 3.52-3.36 (m, 2H), 2.91-2.79 (m, 2H), 2.48-2.35 (m, 2H), 2.27-2.16 (m, 1H), 1.66-1.49 (m, 3H), 1.49-1.37 (m, 1H), 1.34-1.13 (m, 2H), 1.04 (d, 3H).

LC-MS (Method 1): $R_t$=0.79 min; MS (ESIpos) m/z=493 [M+H]$^+$.

Example 170

$N^4$-{4-[(2-chloro-4-fluorobenzoyl)amino]phenyl}-$N^5$-[2-(piperidin-1-yl)propyl]-1H-imidazole-4,5-dicarboxamide

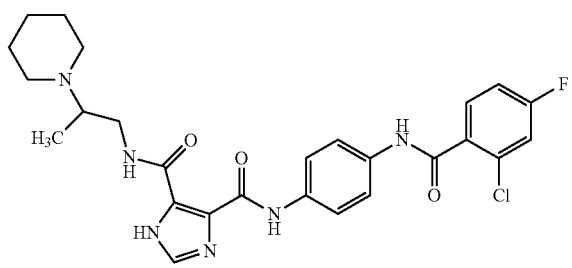 [SMILES: CC(CNC(=O)c1[nH]cnc1C(=O)Nc1ccc(NC(=O)c2ccc(F)cc2Cl)cc1)N1CCCCC1]

To the crude mixture of N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide (0.20 mmol, Intermediate 005), were added 0.065 mL (0.4 mmol) 2-(piperidin-1-yl)propan-1-amine and 0.348 mL (2 mmol) N-ethyl-N-isopropylpropan-2-amine and the mixture was stirred for 18 h at room temperature.

The reaction mixture was concentrated in vacuo and the residue was purified by preparative HPLC chromatography to give 15 mg of the title compound as a solid material.

$^1$H-NMR (400 MHz, DMSO-$d_6$): δ [ppm]=10.57-10.47 (m, 1H), 7.93 (s, 1H), 7.76-7.66 (m, 5H), 7.60 (dd, 1H), 7.36 (td, 1H), 3.43 (dt, 1H), 3.25 (ddd, 1H), 2.83 (br. s., 1H), 2.63-2.53 (m, 2H), 2.38 (d, 2H), 1.52 (br. s., 4H), 1.45-1.34 (m, 2H), 1.00-0.89 (m, 3H).

LC-MS (Method 1): $R_t$=0.82 min; MS (ESIpos) m/z=528 [M+H]$^+$.

Example 171

$N^4$-{4-[(2-chlorobenzoyl)amino]phenyl}-$N^5$-[2-methyl-1-(piperidin-1-yl)propan-2-yl]-1H-imidazole-4,5-dicarboxamide

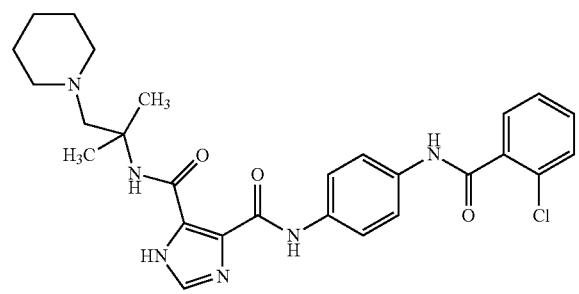 [SMILES: CC(C)(CN1CCCCC1)NC(=O)c1[nH]cnc1C(=O)Nc1ccc(NC(=O)c2ccccc2Cl)cc1]

To the crude mixture of N,N'-bis{4-[(2-chlorobenzoyl)amino]phenyl}-5,10-dioxo-5H,10H-diimidazo[1,5-a:1',5'-d]pyrazine-1,6-dicarboxamide (0.2 mmol, Intermediate 052), were added 0.072 mL (0.4 mmol) 2-methyl-1-(piperidin-1-yl)propan-2-amine and 0.348 mL (2 mmol) N-ethyl-N-isopropylpropan-2-amine and the mixture was stirred for 19 h at room temperature.

The reaction mixture was concentrated in vacuo and the residue was purified by preparative HPLC chromatography to give 29 mg of the title compound as a solid material.

$^1$H-NMR (500 MHz, DMSO-$d_6$): δ [ppm]=10.52-10.46 (m, 1H), 7.87 (s, 1H), 7.80-7.64 (m, 5H), 7.60-7.54 (m, 3H), 7.53-7.42 (m, 3H), 1.50 (br. s., 5H), 1.40 (s, 7H), 1.40-1.29 (m, 6H).

Example 172

N⁴-{4-[(2-chloro-4-fluorobenzoyl)amino]phenyl}-N⁵-(1,3-dihydroxypropan-2-yl)-1H-imidazole-4,5-dicarboxamide

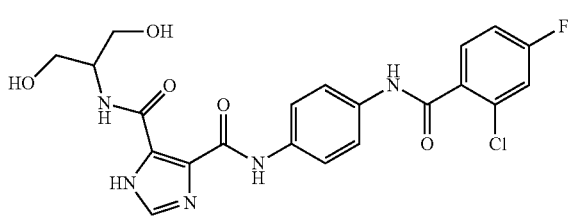 [SMILES: O=C(Nc1ccc(NC(=O)c2nc[nH]c2C(=O)NC(CO)CO)cc1)c1ccc(F)cc1Cl]

To the crude mixture of N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide (0.20 mmol, Intermediate 005), were added 37 mg (0.4 mmol) 2-aminopropane-1,3-diol and 0.348 mL (2 mmol) N-ethyl-N-isopropylpropan-2-amine and the mixture was stirred for 16 h at room temperature.

The reaction mixture was concentrated in vacuo and the residue was purified by preparative HPLC chromatography to give 61 mg of the title compound as a solid material.

¹H-NMR (400 MHz, DMSO-$d_6$): δ [ppm]=3.48-3.70 (m, 4H), 3.91-4.11 (m, 1H), 4.68-4.95 (m, 2H), 7.34 (td, 1H), 7.56 (dd, 1H), 7.62-7.83 (m, 5H), 7.91 (s, 1H), 8.26 (d, 1H), 10.50 (s, 1H), 13.34 (br. s., 1H), 13.46 (s, 1H), 13.52 (s, 1H).

LC-MS (Method 1): $R_t$=0.86 min; MS (ESIpos) m/z=475 [M+H]⁺.

Example 173

N⁴-{4-[(2-chloro-4-fluorobenzoyl)amino]phenyl}-N⁵-(2-fluoroethyl)-1H-imidazole-4,5-dicarboxamide

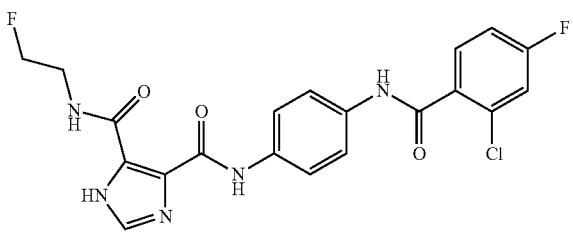 [SMILES: O=C(Nc1ccc(NC(=O)c2nc[nH]c2C(=O)NCCF)cc1)c1ccc(F)cc1Cl]

To the crude mixture of N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide (0.20 mmol, Intermediate 005), were added 44 mg (0.4 mmol) 2-fluoroethanamine hydrochloride and 0.348 mL (2 mmol) N-ethyl-N-isopropylpropan-2-amine and the mixture was stirred for 16 h at room temperature.

The reaction mixture was concentrated in vacuo and the residue was purified by preparative HPLC chromatography to give 53 mg of the title compound as a solid material.

¹H-NMR (400 MHz, DMSO-$d_6$): δ [ppm]=13.49 (s, 1H), 10.53 (s, 1H), 8.98 (t, 1H), 7.96 (s, 1H), 7.83-7.66 (m, 5H), 7.59 (dd, 1H), 7.36 (td, 1H), 4.71-4.62 (m, 1H), 4.58-4.50 (m, 1H), 3.71 (q, 1H), 3.64 (q, 1H).

LC-MS (Method 1): $R_t$=1.04 min; MS (ESIpos) m/z=447 [M+H]⁺.

Example 174

N⁴-{4-[(4-fluorobenzoyl)amino]phenyl}-N⁵-(2-fluoroethyl)-1H-imidazole-4,5-dicarboxamide

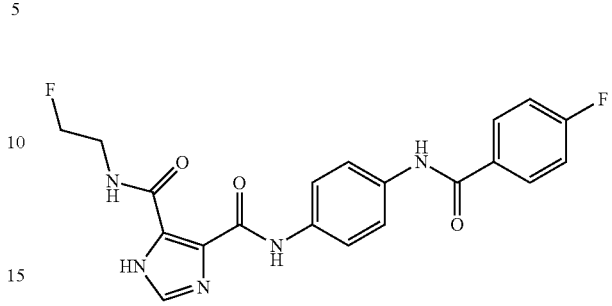

To the crude mixture of N,N'-bis{4-[(4-fluorobenzoyl)amino]phenyl}-5,10-dioxo-5H,10H-diimidazo[1,5-a:1',5'-d]pyrazine-1,6-dicarboxamide (0.2 mmol, Intermediate 018), were added 44 mg (0.4 mmol) 2-fluoroethanamine hydrochloride and 0.348 mL (2 mmol) N-ethyl-N-isopropylpropan-2-amine and the mixture was stirred for 18 h at room temperature.

The reaction mixture was concentrated in vacuo and the residue was purified by preparative HPLC chromatography to give 77 mg of the title compound as a solid material.

¹H-NMR (400 MHz, DMSO-$d_6$): δ [ppm]=13.49 (s, 1H), 10.29 (s, 1H), 8.98 (t, 1H), 8.10-8.02 (m, 3H), 7.96 (s, 1H), 7.83-7.65 (m, 5H), 7.42-7.33 (m, 2H), 4.72-4.61 (m, 1H), 4.60-4.49 (m, 1H), 3.71 (q, 1H), 3.64 (q, 1H).

LC-MS (Method 1): $R_t$=1.01 min; MS (ESIpos) m/z=414 [M+H]⁺.

Example 175

N⁴-{4-[(4-fluorobenzoyl)amino]phenyl}-N⁵-[2-methyl-1-(4-methylpiperidin-1-yl)propan-2-yl]-1H-imidazole-4,5-dicarboxamide

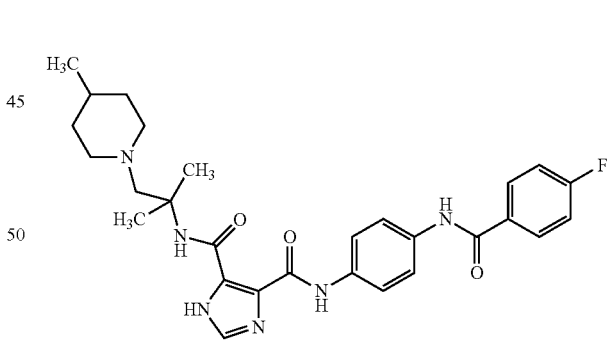

To the crude mixture of N,N'-bis{4-[(4-fluorobenzoyl)amino]phenyl}-5,10-dioxo-5H,10H-diimidazo[1,5-a:1',5'-d]pyrazine-1,6-dicarboxamide (0.2 mmol, Intermediate 018), were added 0.077 mL (0.4 mmol) 2-methyl-1-(piperidin-1-yl)propan-2-amine and 0.348 mL (2 mmol) N-ethyl-N-isopropylpropan-2-amine and the mixture was stirred for 72 h at room temperature.

The reaction mixture was concentrated in vacuo and the residue was purified by preparative HPLC chromatography to give 33 mg of the title compound as a solid material.

¹H-NMR (400 MHz, DMSO-$d_6$): δ [ppm]=10.29 (s, 1H), 8.09-8.01 (m, 2H), 7.89 (s, 1H), 7.83-7.67 (m, 5H), 7.41-

7.33 (m, 2H), 2.84 (d, 2H), 2.54 (d, 2H), 2.25 (t, 2H), 1.53 (d, 2H), 1.41 (s, 6H), 1.37-1.11 (m, 3H), 0.88 (d, 3H).
LC-MS (Method 1): $R_t$=0.90 min; MS (ESIpos) m/z=521 [M+H]$^+$.

Example 176

N$^4$-{4-[(4-fluorobenzoyl)amino]phenyl}-N$^5$-[2-(pyrrolidin-1-yl)ethyl]-1H-imidazole-4,5-dicarboxamide

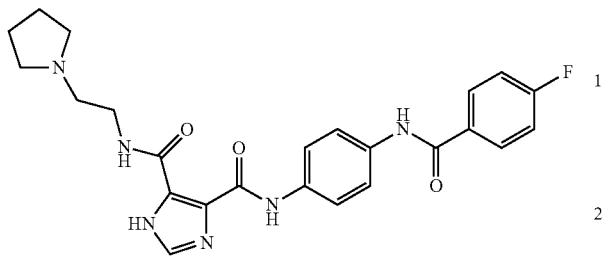

To the crude mixture of N,N'-bis{4-[(4-fluorobenzoyl)amino]phenyl}-5,10-dioxo-5H,10H-diimidazo[1,5-a:1',5'-d]pyrazine-1,6-dicarboxamide (0.2 mmol, Intermediate 018), were added 0.051 mL (0.4 mmol) 2-(pyrrolidin-1-yl)ethanamine and 0.348 mL (2 mmol) N-ethyl-N-isopropylpropan-2-amine and the mixture was stirred for 18 h at room temperature.

The reaction mixture was concentrated in vacuo and the residue was purified by preparative HPLC chromatography to give 26 mg of the title compound as a solid material.

$^1$H-NMR (400 MHz, DMSO-d$_6$): δ [ppm]=10.29 (s, 1H), 8.10-8.01 (m, 2H), 7.93 (s, 1H), 7.81-7.75 (m, 2H), 7.74-7.67 (m, 2H), 7.42-7.33 (m, 2H), 3.47 (q, 2H), 2.63 (t, 2H), 1.75-1.64 (m, 4H).
LC-MS (Method 1): $R_t$=0.74 min; MS (ESIpos) m/z=465 [M+H]$^+$.

Example 177

N$^4$-{4-[(2-chloro-4-fluorobenzoyl)amino]phenyl}-N$^5$-(4-methylpiperazin-1-yl)-1H-imidazole-4,5-dicarboxamide

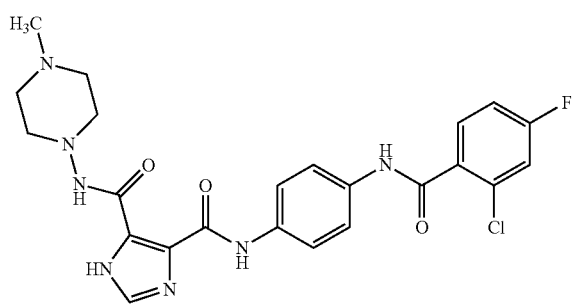 [SMILES: CN1CCN(NC(=O)c2[nH]cnc2C(=O)Nc2ccc(NC(=O)c3ccc(F)cc3Cl)cc2)CC1]

To the crude mixture of N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide (0.20 mmol, Intermediate 005), were added 0.048 mL (0.4 mmol) 1-amino-4-methylpiperazine and 0.348 mL (2 mmol) N-ethyl-N-isopropylpropan-2-amine and the mixture was stirred for 18 h at room temperature.

The reaction mixture was concentrated in vacuo and the residue was purified by preparative HPLC chromatography to give 10 mg of the title compound as a solid material.

$^1$H-NMR (400 MHz, DMSO-d$_6$): δ [ppm]=13.46 (br. s., 1H), 10.52 (s, 1H), 7.93 (s, 1H), 7.77-7.66 (m, 5H), 7.64-7.53 (m, 2H), 7.42-7.28 (m, 2H), 2.98-2.86 (m, 4H), 2.45 (br. s., 4H), 2.20 (s, 3H).

Example 178

N$^4$-{4-[(4-fluorobenzoyl)amino]phenyl}-N$^5$-[2-(4-hydroxypiperidin-1-yl)ethyl]-1H-imidazole-4,5-dicarboxamide

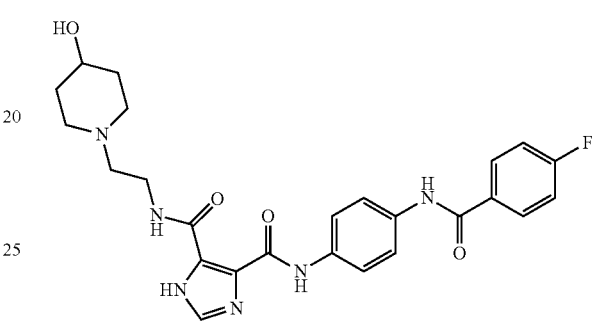

To the crude mixture of N,N'-bis{4-[(4-fluorobenzoyl)amino]phenyl}-5,10-dioxo-5H,10H-diimidazo[1,5-a:1',5'-d]pyrazine-1,6-dicarboxamide (0.2 mmol, Intermediate 018), were added 61 mg (0.4 mmol) 1-(2-aminoethyl)piperidin-4-ol and 0.348 mL (2 mmol) N-ethyl-N-isopropylpropan-2-amine and the mixture was stirred for 19 h at room temperature.

The reaction mixture was concentrated in vacuo and the residue was purified by preparative HPLC chromatography to give 57 mg of the title compound as a solid material.

$^1$H-NMR (400 MHz, DMSO-d$_6$): δ [ppm]=10.26 (s, 1H), 8.09-7.98 (m, 2H), 7.90 (s, 1H), 7.80-7.64 (m, 4H), 7.40-7.30 (m, 2H), 4.51 (d, 1H), 3.44 (q, 3H), 2.81-2.71 (m, 2H), 2.13-2.03 (m, 2H), 1.71 (dd, 2H), 1.45-1.32 (m, 2H).
LC-MS (Method 1): $R_t$=0.71 min; MS (ESIpos) m/z=495 [M+H]$^+$.

Example 180

N$^4$-{4-[(4-fluorobenzoyl)amino]phenyl}-N$^5$-[2-methyl-1-(morpholin-4-yl)propan-2-yl]-1H-imidazole-4,5-dicarboxamide

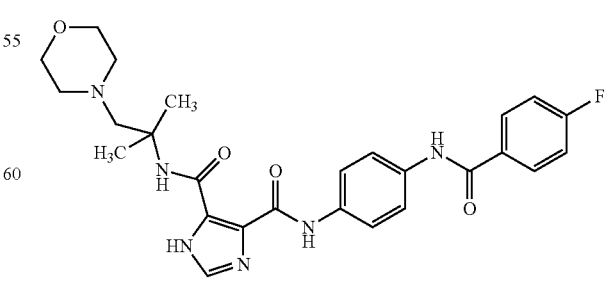

To the crude mixture of N,N'-bis{4-[(4-fluorobenzoyl)amino]phenyl}-5,10-dioxo-5H,10H-diimidazo[1,5-a:1',5'-d]

pyrazine-1,6-dicarboxamide (0.2 mmol, Intermediate 018), were added 0.062 mL (0.4 mmol) 2-methyl-1-(morpholin-4-yl)propan-2-amine and 0.348 mL (2 mmol) N-ethyl-N-isopropylpropan-2-amine and the mixture was stirred for 72 h at room temperature.

The reaction mixture was concentrated in vacuo and the residue was purified by preparative HPLC chromatography to give 69 mg of the title compound as a solid material.

$^1$H-NMR (400 MHz, DMSO-$d_6$): δ [ppm]=10.29 (s, 1H), 8.09-8.02 (m, 2H), 7.88 (s, 1H), 7.81-7.68 (m, 5H), 7.42-7.33 (m, 2H), 3.58 (br. s., 4H), 2.60 (s, 2H), 2.58-2.53 (m, 2H), 1.43 (s, 6H).

LC-MS (Method 1): $R_t$=1.18 min; MS (ESIpos) m/z=509 [M+H]$^+$.

Example 181

N$^4$-{4-[(4-fluorobenzoyl)amino]phenyl}-N$^5$-[3-(4-methylpiperazin-1-yl)propyl]-1H-imidazole-4,5-dicarboxamide

Example 182

N$^4$-{4-[(2-chlorobenzoyl)amino]phenyl}-N$^5$-[2-(piperidin-1-yl)propyl]-1H-imidazole-4,5-dicarboxamide

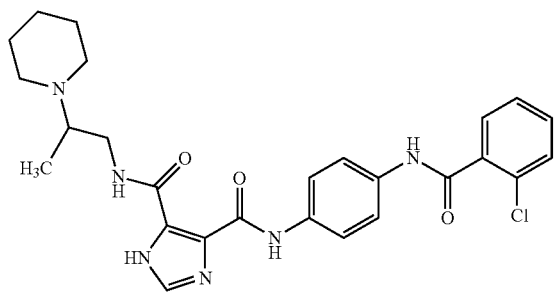

To the crude mixture of N,N'-bis{4-[(2-chlorobenzoyl)amino]phenyl}-5,10-dioxo-5H,10H-diimidazo[1,5-a:1',5'-d]

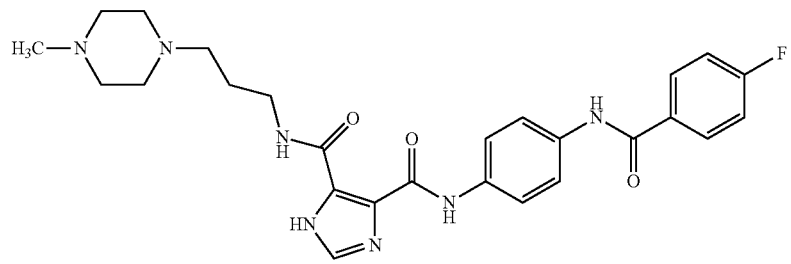 [SMILES: CN1CCN(CCCNC(=O)c2[nH]cnc2C(=O)Nc2ccc(NC(=O)c3ccc(F)cc3)cc2)CC1]

To the crude mixture of N,N'-bis{4-[(4-fluorobenzoyl)amino]phenyl}-5,10-dioxo-5H,10H-diimidazo[1,5-a:1',5'-d] pyrazine-1,6-dicarboxamide (0.2 mmol, Intermediate 018), were added 0.062 mL (0.4 mmol) 3-(4-methylpiperazin-1-yl)propan-1-amine and 0.348 mL (2 mmol) N-ethyl-N-isopropylpropan-2-amine and the mixture was stirred for 18 h at room temperature.

The reaction mixture was concentrated in vacuo and the residue was purified by preparative HPLC chromatography to give 33 mg of the title compound as a solid material.

$^1$H-NMR (400 MHz, DMSO-$d_6$): δ [ppm]=10.29 (s, 1H), 8.10-8.01 (m, 2H), 7.92 (s, 1H), 7.82-7.65 (m, 4H), 7.42-7.32 (m, 2H), 3.39 (q, 2H), 2.46-2.22 (m, 10H), 2.16 (s, 3H), 1.72 (quin, 2H).

LC-MS (Method 1): $R_t$=0.70 min; MS (ESIpos) m/z=508 [M+H]$^+$.

pyrazine-1,6-dicarboxamide (0.2 mmol, Intermediate 052), were added 0.065 mL (0.4 mmol) 2-(piperidin-1-yl)propan-1-amine and 0.348 mL (2 mmol) N-ethyl-N-isopropylpropan-2-amine and the mixture was stirred for 18 h at room temperature.

The reaction mixture was concentrated in vacuo and the residue was purified by preparative HPLC chromatography to give 35 mg of the title compound as a solid material.

$^1$H-NMR (400 MHz, DMSO-$d_6$): δ [ppm]=10.56-10.47 (m, 1H), 7.93 (s, 1H), 7.82-7.65 (m, 5H), 7.63-7.55 (m, 3H), 7.55-7.43 (m, 3H), 3.43 (dt, 1H), 3.25 (ddd, 1H), 2.83 (br. s., 1H), 2.63-2.54 (m, 2H), 2.44-2.28 (m, 2H), 1.52 (br. s., 4H), 1.45-1.34 (m, 2H), 0.95 (d, 3H).

LC-MS (Method 1): $R_t$=0.77 min; MS (ESIpos) m/z=509 [M+H]$^+$.

Example 183

N⁴-{4-[(4-fluorobenzoyl)amino]phenyl}-N⁵-[2-(piperidin-1-yl)propyl]-1H-imidazole-4,5-dicarboxamide

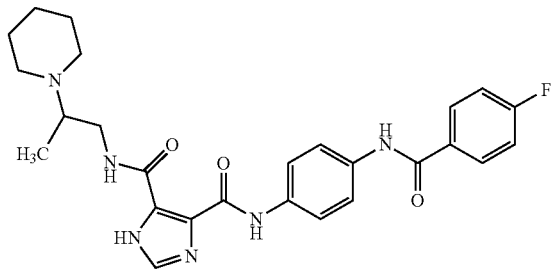 [SMILES: CC(CNC(=O)c1[nH]cnc1C(=O)Nc1ccc(NC(=O)c2ccc(F)cc2)cc1)N1CCCCC1]

To the crude mixture of N,N'-bis{4-[(4-fluorobenzoyl)amino]phenyl}-5,10-dioxo-5H,10H-diimidazo[1,5-a:1',5'-d]pyrazine-1,6-dicarboxamide (0.2 mmol, Intermediate 018), were added 0.065 mL (0.4 mmol) 2-(piperidin-1-yl)propan-1-amine and 0.348 mL (2 mmol) N-ethyl-N-isopropylpropan-2-amine and the mixture was stirred for 18 h at room temperature.

The reaction mixture was concentrated in vacuo and the residue was purified by preparative HPLC chromatography to give 33 mg of the title compound as a solid material.

¹H-NMR (400 MHz, DMSO-d₆): δ [ppm]=10.29-10.23 (m, 1H), 8.07-8.00 (m, 2H), 7.90 (s, 1H), 7.80-7.65 (m, 5H), 7.40-7.31 (m, 3H), 3.42 (dt, 1H), 3.27-3.18 (m, 1H), 2.82 (d, 1H), 2.61-2.52 (m, 2H), 2.37 (d, 2H), 1.51 (d, 4H), 1.44-1.35 (m, 2H), 0.94 (d, 3H).

LC-MS (Method 1): $R_t$=0.80 min; MS (ESIpos) m/z=493 [M+H]⁺.

Example 184

N⁴-{4-[(2-chloro-4-fluorobenzoyl)amino]phenyl}-N⁵-[2-methyl-1-(piperidin-1-yl)propan-2-yl]-1H-imidazole-4,5-dicarboxamide

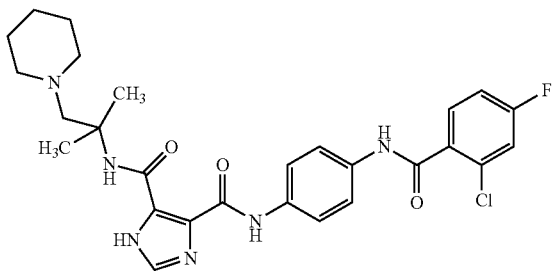 [SMILES: CC(C)(CN1CCCCC1)NC(=O)c1[nH]cnc1C(=O)Nc1ccc(NC(=O)c2ccc(F)cc2Cl)cc1]

To the crude mixture of N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide (0.20 mmol, Intermediate 005), were added 0.072 mL (0.4 mmol) 2-methyl-1-(piperidin-1-yl)propan-2-amine and 0.348 mL (2 mmol) N-ethyl-N-isopropylpropan-2-amine and the mixture was stirred for 19 h at room temperature.

The reaction mixture was concentrated in vacuo and the residue was purified by preparative HPLC chromatography to give 42 mg of the title compound as a solid material.

¹H-NMR (500 MHz, DMSO-d₆): δ [ppm]=10.54-10.47 (m, 1H), 7.87 (s, 1H), 7.75-7.64 (m, 5H), 7.60-7.55 (m, 1H), 7.37-7.30 (m, 1H), 2.54-2.51 (m, 4H), 1.50 (br. s., 4H), 1.44-1.30 (m, 8H).

LC-MS (Method 1): $R_t$=1.47 min; MS (ESIpos) m/z=513 [M+H]⁺.

Example 185

N⁴-{4-[(2-chloro-4-fluorobenzoyl)amino]phenyl}-N⁵-[2-(4-methylpiperazin-1-yl)propyl]-1H-imidazole-4,5-dicarboxamide

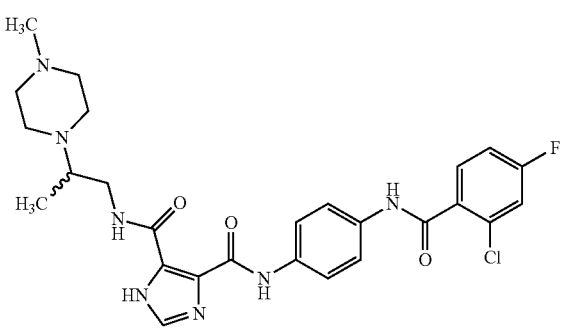 [SMILES: CC(CNC(=O)c1[nH]cnc1C(=O)Nc1ccc(NC(=O)c2ccc(F)cc2Cl)cc1)N1CCN(C)CC1]

To the crude mixture of N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide (0.20 mmol, Intermediate 005), were added 0.078 mL (0.4 mmol) 2-(4-methylpiperazin-1-yl)propan-1-amine and 0.348 mL (2 mmol) N-ethyl-N-isopropylpropan-2-amine and the mixture was stirred for 19 h at room temperature.

The reaction mixture was concentrated in vacuo and the residue was purified by preparative HPLC chromatography to give 16 mg of the title compound as a solid material.

¹H-NMR (500 MHz, DMSO-d₆): δ [ppm]=10.49 (s, 1H), 7.90 (s, 1H), 7.76-7.65 (m, 4H), 7.60-7.55 (m, 1H), 7.37-7.29 (m, 1H), 3.42 (dt, 1H), 3.28-3.23 (m, 1H), 2.84 (br. s., 1H), 2.65-2.55 (m, 3H), 2.47-2.23 (m, 6H), 2.14 (s, 3H), 0.98-0.93 (m, 2H).

LC-MS (Method 1): $R_t$=0.96 min; MS (ESIpos) m/z=543 [M+H]⁺.

Example 186

N⁴-{4-[(2-chlorobenzoyl)amino]phenyl}-N⁵-[2-(4-methylpiperazin-1-yl)propyl]-1H-imidazole-4,5-dicarboxamide

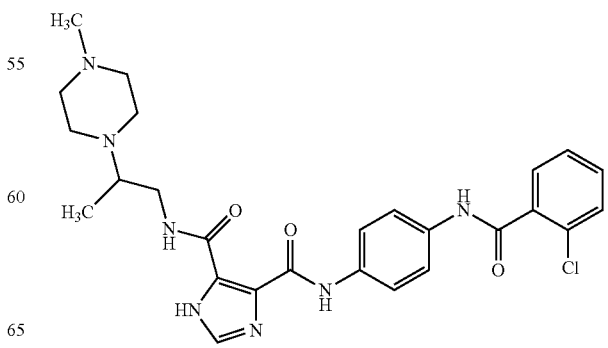

To the crude mixture of N,N'-bis{4-[(2-chlorobenzoyl)amino]phenyl}-5,10-dioxo-5H,10H-diimidazo[1,5-a:1',5'-d]pyrazine-1,6-dicarboxamide (0.2 mmol, Intermediate 052), were added 0.078 mL (0.4 mmol) 2-(4-methylpiperazin-1-yl)propan-1-amine and 0.348 mL (2 mmol) N-ethyl-N-isopropylpropan-2-amine and the mixture was stirred for 19 h at room temperature.

The reaction mixture was concentrated in vacuo and the residue was purified by preparative HPLC chromatography to give 24 mg of the title compound as a solid material.

$^1$H-NMR (500 MHz, DMSO-$d_6$): δ [ppm]=10.49 (s, 1H), 7.92 (s, 1H), 7.75-7.63 (m, 4H), 7.60-7.54 (m, 2H), 7.50 (td, 1H), 7.47-7.42 (m, 1H), 3.47-3.37 (m, 1H), 3.27-3.22 (m, 1H), 2.61-2.55 (m, 2H), 2.46-2.39 (m, 2H), 2.38-2.25 (m, 3H), 2.14 (s, 3H).

LC-MS (Method 1): $R_t$=0.93 min; MS (ESIpos) m/z=525 [M+H]$^+$.

Example 187

N$^4$-{4-[(2-chloro-4-fluorobenzoyl)amino]phenyl}-N$^5$-[2-methyl-2-(4-methylpiperazin-1-yl)propyl]-1H-imidazole-4,5-dicarboxamide

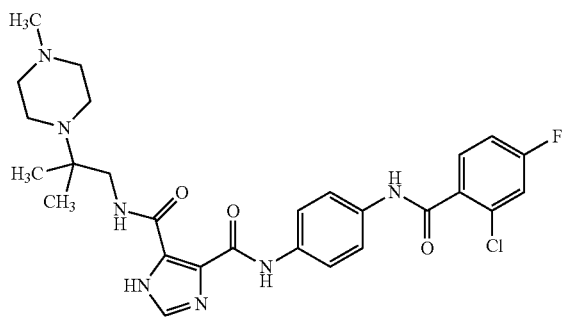 [SMILES: CN1CCN(C(C)(C)CNC(=O)c2[nH]cnc2C(=O)Nc2ccc(NC(=O)c3ccc(F)cc3Cl)cc2)CC1]

To the crude mixture of N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide (0.20 mmol, Intermediate 005), were added 0.085 mL (0.4 mmol) 2-(4-methylpiperazin-1-yl)propan-1-amine and 0.348 mL (2 mmol) N-ethyl-N-isopropylpropan-2-amine and the mixture was stirred for 19 h at room temperature.

The reaction mixture was concentrated in vacuo and the residue was purified by preparative HPLC chromatography to give 53 mg of the title compound as a solid material.

$^1$H-NMR (400 MHz, DMSO-$d_6$): δ [ppm]=10.52 (s, 1H), 7.95 (s, 1H), 7.76-7.65 (m, 4H), 7.60 (dd, 1H), 7.36 (td, 1H), 3.37 (d, 2H), 2.70-2.65 (m, 1H), 2.44-2.28 (m, 4H), 2.20-2.12 (m, 3H), 1.04 (s, 6H).

LC-MS (Method 1): $R_t$=0.81 min; MS (ESIpos) m/z=557 [M+H]$^+$.

Example 188

N$^4$-{4-[(4-fluorobenzoyl)amino]phenyl}-N$^5$-[2-methyl-2-(4-methylpiperazin-1-yl)propyl]-1H-imidazole-4,5-dicarboxamide

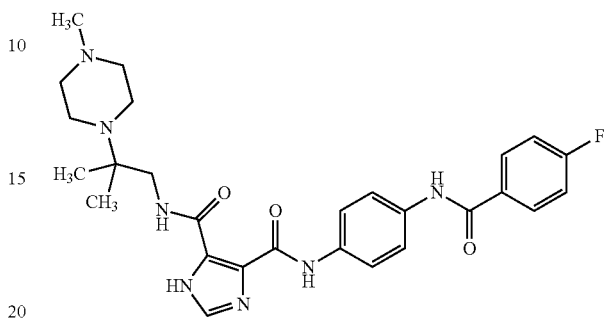

To the crude mixture of N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide (0.20 mmol, Intermediate 018), were added 0.085 mL (0.4 mmol) 2-methyl-2-(4-methylpiperazin-1-yl)propan-1-amine and 0.348 mL (2 mmol) N-ethyl-N-isopropylpropan-2-amine and the mixture was stirred for 19 h at room temperature.

The reaction mixture was concentrated in vacuo and the residue was purified by preparative HPLC chromatography to give 57 mg of the title compound as a solid material.

$^1$H-NMR (400 MHz, DMSO-$d_6$): δ [ppm]=13.56 (s, 1H), 10.29 (br. s., 1H), 8.32 (br. s., 1H), 8.10-8.01 (m, 2H), 7.99-7.88 (m, 2H), 7.82-7.63 (m, 4H), 7.43-7.31 (m, 2H), 3.37 (d, 2H), 2.46-2.28 (m, 4H), 2.23-2.12 (m, 3H), 1.04 (s, 6H).

LC-MS (Method 1): $R_t$=0.78 min; MS (ESIpos) m/z=522 [M+H]$^+$.

Example 189

N$^4$-{4-[(2-chlorobenzoyl)amino]phenyl}-N$^5$-[4-(piperidin-1-yl)butyl]-1H-imidazole-4,5-dicarboxamide

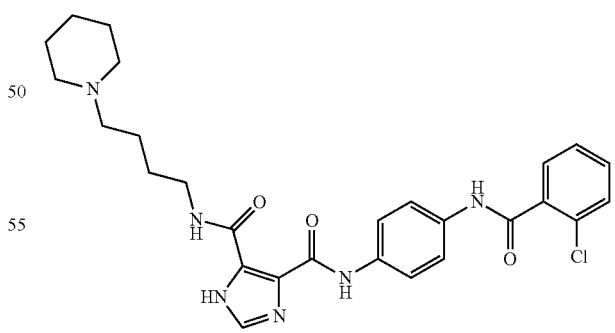

To the crude mixture of N,N'-bis{4-[(2-chlorobenzoyl)amino]phenyl}-5,10-dioxo-5H,10H-diimidazo[1,5-a:1',5'-d]pyrazine-1,6-dicarboxamide (0.2 mmol, Intermediate 052), were added 0.072 mL (0.4 mmol) 4-(piperidin-1-yl)butan-1-amine and 0.348 mL (2 mmol) N-ethyl-N-isopropylpropan-2-amine and the mixture was stirred for 72 h at room temperature.

The reaction mixture was concentrated in vacuo and the residue was purified by preparative HPLC chromatography to give 42 mg of the title compound as a solid material.

$^1$H-NMR (400 MHz, DMSO-d$_6$): δ [ppm]=10.52 (s, 1H), 7.92 (s, 1H), 7.74-7.66 (m, 5H), 7.60 (dd, 1H), 7.36 (td, 1H), 2.32-2.21 (m, 5H), 1.62-1.52 (m, 2H), 1.47 (dt, 6H), 1.36 (d, 2H).

LC-MS (Method 1): R$_t$=0.77 min; MS (ESIpos) m/z=524 [M+H]$^+$.

Example 190

N$^5$-[2-(azetidin-1-yl)ethyl]-N4-{4-[(2-chlorobenzoyl)amino]phenyl}-1H-imidazole-4,5-dicarboxamide

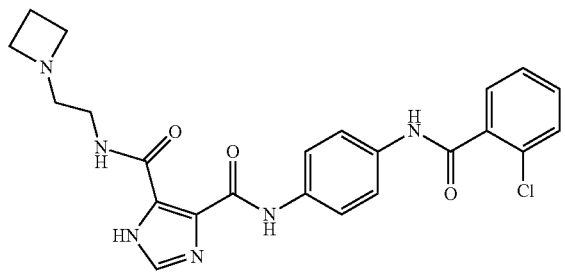 [SMILES: O=C(Nc1ccc(NC(=O)c2nc[nH]c2C(=O)NCCN2CCC2)cc1)c1ccccc1Cl]

To the crude mixture of N,N'-bis{4-[(2-chlorobenzoyl)amino]phenyl}-5,10-dioxo-5H,10H-diimidazo[1,5-a:1',5'-d]pyrazine-1,6-dicarboxamide (0.2 mmol, Intermediate 052), were added 0.05 mL (0.4 mmol) 2-(azetidin-1-yl)ethanamine and 0.348 mL (2 mmol) N-ethyl-N-isopropylpropan-2-amine and the mixture was stirred for 72 h at room temperature.

The reaction mixture was concentrated in vacuo and the residue was purified by preparative HPLC chromatography to give 16 mg of the title compound as a solid material.

$^1$H-NMR (400 MHz, DMSO-d$_6$): δ [ppm]=10.51 (s, 1H), 7.92 (s, 1H), 7.76-7.67 (m, 4H), 7.62-7.55 (m, 2H), 7.54-7.43 (m, 2H), 3.30-3.26 (m, 2H), 3.15 (t, 4H), 2.57-2.53 (m, 2H), 1.97 (quin, 2H).

LC-MS (Method 1): R$_t$=0.72 min; MS (ESIpos) m/z=467 [M+H]$^+$.

Example 191

N$^4$-{4-[(2-chloro-4-fluorobenzoyl)amino]phenyl}-N$^5$-[2-(2-methylpiperidin-1-yl)ethyl]-1H-imidazole-4,5-dicarboxamide

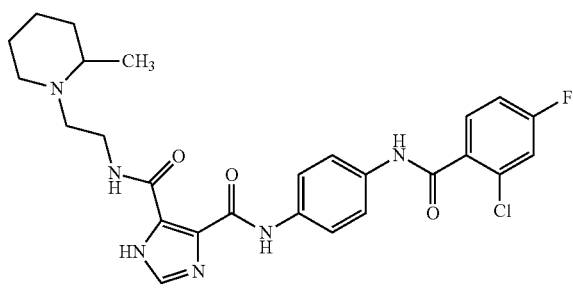 [SMILES: CC1CCCCN1CCNC(=O)c1[nH]cnc1C(=O)Nc1ccc(NC(=O)c2ccc(F)cc2Cl)cc1]

To the crude mixture of N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide (0.20 mmol, Intermediate 005), were added 0.067 mL (0.4 mmol) 2-(2-methylpiperidin-1-yl)ethanamine and 0.348 mL (2 mmol) N-ethyl-N-isopropylpropan-2-amine and the mixture was stirred for 18 h at room temperature.

The reaction mixture was concentrated in vacuo and the residue was purified by preparative HPLC chromatography to give 25 mg of the title compound as a solid material.

$^1$H-NMR (400 MHz, DMSO-d$_6$): δ [ppm]=13.63-13.30 (m, 1H), 10.57-9.97 (m, 1H), 8.68 (br. s., 1H), 8.14 (s, 1H), 7.92 (s, 1H), 7.76-7.49 (m, 5H), 7.38-7.24 (m, 2H), 6.52 (d, 1H), 3.52-3.39 (m, 3H), 2.88 (d, 2H), 2.26 (t, 1H), 1.65-1.36 (m, 4H), 1.33-1.14 (m, 2H), 1.04 (d, 3H).

LC-MS (Method 1): R$_t$=0.81 min; MS (ESIpos) m/z=528 [M+H]$^+$.

Example 192

N$^4$-{4-[(2-chlorobenzoyl)amino]phenyl}-N$^5$-[3-(4-methylpiperazin-1-yl)propyl]-1H-imidazole-4,5-dicarboxamide

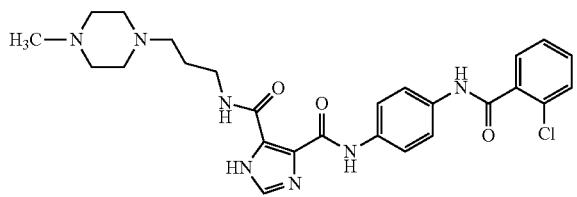 [SMILES: CN1CCN(CCCNC(=O)c2[nH]cnc2C(=O)Nc2ccc(NC(=O)c3ccccc3Cl)cc2)CC1]

To the crude mixture of N,N'-bis{4-[(2-chlorobenzoyl)amino]phenyl}-5,10-dioxo-5H,10H-diimidazo[1,5-a:1',5'-d]pyrazine-1,6-dicarboxamide (0.2 mmol, Intermediate 052), were added 0.068 mL (0.4 mmol) 3-(4-methylpiperazin-1-yl)propan-1-amine and 0.348 mL (2 mmol) N-ethyl-N-isopropylpropan-2-amine and the mixture was stirred for 19 h at room temperature.

The reaction mixture was concentrated in vacuo and the residue was purified by preparative HPLC chromatography to give 19 mg of the title compound as a solid material.

$^1$H-NMR (400 MHz, DMSO-d$_6$): δ [ppm]=10.49 (s, 1H), 8.16 (s, 1H), 7.90 (s, 1H), 7.78-7.62 (m, 4H), 7.60-7.53 (m, 2H), 7.53-7.41 (m, 2H), 2.36 (t, 7H), 2.16 (s, 3H), 1.71 (t, 2H).

LC-MS (Method 1): R$_t$=0.68 min; MS (ESIpos) m/z=525 [M+H]$^+$.

Example 193

N[4]-{4-[(4-fluorobenzoyl)amino]phenyl}-N[5]-(4-methylpiperazin-1-yl)-1H-imidazole-4,5-dicarboxamide

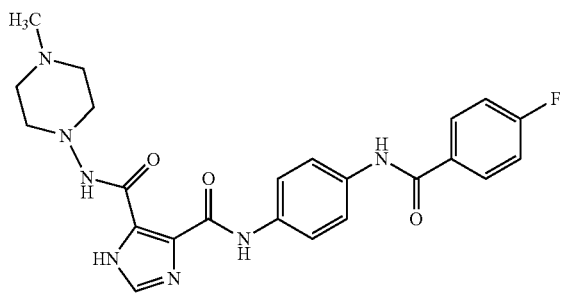 [SMILES: CN1CCN(NC(=O)c2[nH]cnc2C(=O)Nc2ccc(NC(=O)c3ccc(F)cc3)cc2)CC1]

To the crude mixture of N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide (0.20 mmol, Intermediate 018), were added 0.048 mL (0.4 mmol) 4-methylpiperazin-1-amine and 0.348 mL (2 mmol) N-ethyl-N-isopropylpropan-2-amine and the mixture was stirred for 18 h at room temperature.

The reaction mixture was concentrated in vacuo and the residue was purified by preparative HPLC chromatography to give 14 mg of the title compound as a solid material.

$^1$H-NMR (400 MHz, DMSO-$d_6$): δ [ppm]=10.29 (s, 1H), 8.10-8.01 (m, 2H), 7.93 (s, 1H), 7.82-7.63 (m, 4H), 7.43-7.32 (m, 2H), 2.97-2.86 (m, 4H), 2.45 (br. s., 3H), 2.20 (s, 3H).

LC-MS (Method 1): $R_t$=0.71 min; MS (ESIpos) m/z=466 [M+H]$^+$.

Example 194

N[4]-{4-[(2-chloro-4-fluorobenzoyl)amino]phenyl}-N[5]-[2-methyl-1-(4-methylpiperazin-1-yl)propan-2-yl]-1H-imidazole-4,5-dicarboxamide

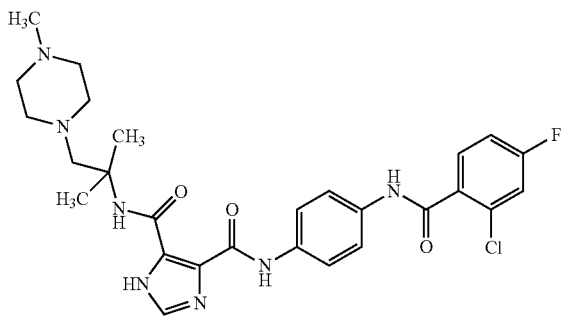 [SMILES: CN1CCN(CC(C)(C)NC(=O)c2[nH]cnc2C(=O)Nc2ccc(NC(=O)c3ccc(F)cc3Cl)cc2)CC1]

To the crude mixture of N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide (0.20 mmol, Intermediate 005), were added 0.077 mL (0.4 mmol) 2-methyl-1-(4-methylpiperazin-1-yl)propan-2-amine and 0.348 mL (2 mmol) N-ethyl-N-isopropylpropan-2-amine and the mixture was stirred for 18 h at room temperature.

The reaction mixture was concentrated in vacuo and the residue was purified by preparative HPLC chromatography to give 25 mg of the title compound as a solid material.

$^1$H-NMR (400 MHz, DMSO-$d_6$): δ [ppm]=10.49 (s, 1H), 7.87 (s, 1H), 7.74-7.64 (m, 5H), 7.57 (dd, 1H), 7.34 (td, 1H), 2.60-2.52 (m, 6H), 2.31 (dd, 4H), 2.15-2.06 (m, 3H), 1.40 (s, 6H).

LC-MS (Method 1): $R_t$=0.85 min; MS (ESIpos) m/z=557 [M+H]$^+$.

Example 195

N[4]-{4-[(4-fluorobenzoyl)amino]phenyl}-N[5]-[2-methyl-1-(4-methylpiperazin-1-yl)propan-2-yl]-1H-imidazole-4,5-dicarboxamide

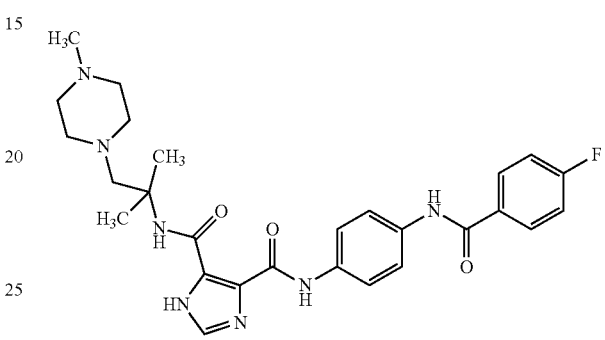

To the crude mixture of N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide (0.20 mmol, Intermediate 018), were added 0.067 mL (0.4 mmol) 0.077 mL (0.4 mmol) 2-methyl-1-(4-methylpiperazin-1-yl)propan-2-amine and 0.348 mL (2 mmol) N-ethyl-N-isopropylpropan-2-amine and the mixture was stirred for 72 h at room temperature.

The reaction mixture was concentrated in vacuo and the residue was purified by preparative HPLC chromatography to give 39 mg of the title compound as a solid material.

$^1$H-NMR (400 MHz, DMSO-$d_6$): δ [ppm]=10.29 (s, 1H), 8.09-8.01 (m, 2H), 7.93-7.88 (m, 1H), 7.81-7.65 (m, 4H), 7.43-7.33 (m, 2H), 2.59 (br. s., 6H), 2.38-2.23 (m, 4H), 2.13 (s, 3H), 1.49-1.34 (m, 6H).

LC-MS (Method 1): $R_t$=1.13 min; MS (ESIpos) m/z=522 [M+H]$^+$.

Example 196

N[4]-{4-[(2-chloro-4-fluorobenzoyl)amino]phenyl}-N[5]-[4-(piperidin-1-yl)butyl]-1H-imidazole-4,5-dicarboxamide

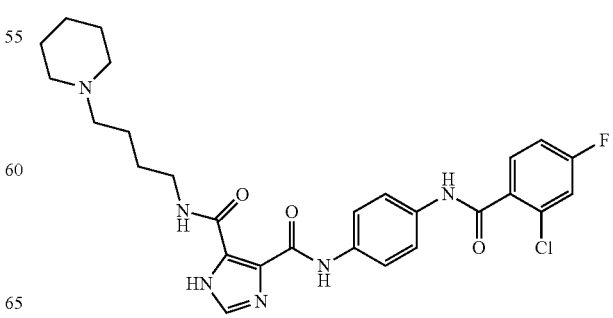

To the crude mixture of N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide (0.20 mmol, Intermediate 005), were added 0.072 mL (0.4 mmol) 4-(piperidin-1-yl)butan-1-amine and 0.348 mL (2 mmol) N-ethyl-N-isopropylpropan-2-amine and the mixture was stirred for 72 h at room temperature.

The reaction mixture was concentrated in vacuo and the residue was purified by preparative HPLC chromatography to give 81 mg of the title compound as a solid material.

$^1$H-NMR (400 MHz, DMSO-d$_6$): δ [ppm]=10.29 (s, 1H), 8.10-8.02 (m, 2H), 7.92 (s, 1H), 7.80-7.75 (m, 2H), 7.74-7.67 (m, 2H), 7.41-7.34 (m, 2H), 3.40-3.34 (m, 2H), 2.32-2.22 (m, 6H), 1.63-1.52 (m, 2H), 1.48 (dt, 6H), 1.36 (d, 2H).

LC-MS (Method 1): R$_t$=0.81 min; MS (ESIpos) m/z=541 [M+H]$^+$.

Example 197

N$^4$-{4-[(2-chlorobenzoyl)amino]phenyl}-N$^5$-[2-(4-hydroxypiperidin-1-yl)ethyl]-1H-imidazole-4,5-dicarboxamide

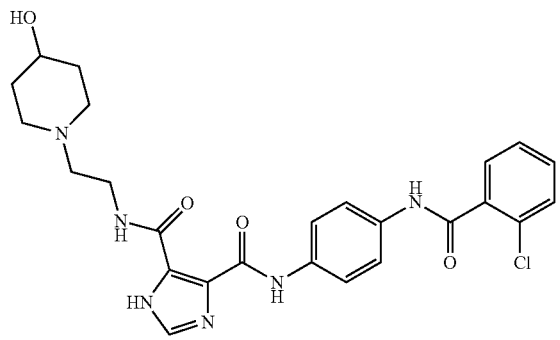 [SMILES: O=C(Nc1ccc(NC(=O)c2nc[nH]c2C(=O)NCCN2CCC(O)CC2)cc1)c1ccccc1Cl]

To the crude mixture of N,N'-bis{4-[(2-chlorobenzoyl)amino]phenyl}-5,10-dioxo-5H,10H-diimidazo[1,5-a:1',5'-d]pyrazine-1,6-dicarboxamide (0.2 mmol, Intermediate 052), were added 61 mg (0.4 mmol) 1-(2-aminoethyl)piperidin-4-ol and 0.348 mL (2 mmol) N-ethyl-N-isopropylpropan-2-amine and the mixture was stirred for 19 h at room temperature.

The reaction mixture was concentrated in vacuo and the residue was purified by preparative HPLC chromatography to give 20 mg of the title compound as a solid material.

$^1$H-NMR (400 MHz, DMSO-d$_6$): δ [ppm]=10.49 (s, 1H), 8.63 (br. s., 1H), 8.16 (s, 1H), 7.91 (s, 1H), 7.76-7.63 (m, 4H), 7.60-7.54 (m, 2H), 7.53-7.41 (m, 2H), 7.36-7.28 (m, 1H), 4.52 (br. s., 1H), 3.50-3.40 (m, 4H), 2.83-2.72 (m, 2H), 2.09 (t, 2H), 1.71 (d, 2H), 1.38 (d, 2H).

LC-MS (Method 1): R$_t$=0.70 min; MS (ESIpos) m/z=512 [M+H]$^+$.

Example 198

N$^5$-[2-(azetidin-1-yl)ethyl]-N$^4$-{4-[(2-chloro-4-fluorobenzoyl)amino]phenyl}-1H-imidazole-4,5-dicarboxamide

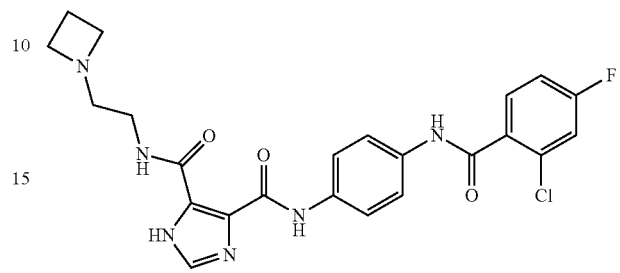

To the crude mixture of N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide (0.20 mmol, Intermediate 005), were added 0.05 mL (0.4 mmol) 2-(azetidin-1-yl)ethanamine and 0.348 mL (2 mmol) N-ethyl-N-isopropylpropan-2-amine and the mixture was stirred for 72 h at room temperature.

The reaction mixture was concentrated in vacuo and the residue was purified by preparative HPLC chromatography to give 41 mg of the title compound as a solid material.

$^1$H-NMR (400 MHz, DMSO-d$_6$): δ [ppm]=10.52 (s, 1H), 7.93 (s, 1H), 7.75-7.65 (m, 5H), 7.60 (dd, 1H), 7.36 (td, 1H), 3.30-3.24 (m, 2H), 3.15 (t, 4H), 2.57-2.53 (m, 2H), 1.97 (quin, 2H).

LC-MS (Method 1): R$_t$=0.74 min; MS (ESIpos) m/z=485 [M+H]$^+$.

Example 199

N$^5$-[2-(azetidin-1-yl)ethyl]-N$^4$-{4-[(4-fluorobenzoyl)amino]phenyl}-1H-imidazole-4,5-dicarboxamide

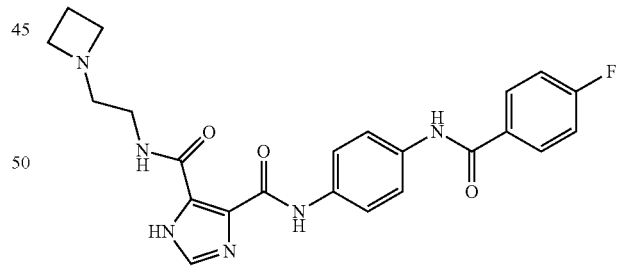

To the crude mixture of N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide (0.20 mmol, Intermediate 018), were added 0.05 mL (0.4 mmol) 2-(azetidin-1-yl)ethanamine and 0.348 mL (2 mmol) N-ethyl-N-isopropylpropan-2-amine and the mixture was stirred for 72 h at room temperature.

The reaction mixture was concentrated in vacuo and the residue was purified by preparative HPLC chromatography to give 19 mg of the title compound as a solid material.

$^1$H-NMR (400 MHz, DMSO-d$_6$): δ [ppm]=10.29 (s, 1H), 8.10-8.01 (m, 2H), 7.93 (s, 1H), 7.82-7.75 (m, 2H), 7.74-

7.65 (m, 2H), 7.42-7.34 (m, 2H), 3.31-3.23 (m, 2H), 3.15 (t, 4H), 2.58-2.53 (m, 2H), 1.97 (quin, 2H).

LC-MS (Method 1): $R_t$=0.72 min; MS (ESIpos) m/z=451 [M+H]$^+$.

Example 200

$N^4$-{4-[(2-chlorobenzoyl)amino]phenyl}-$N^5$-[3-(morpholin-4-yl)propyl]-1H-imidazole-4,5-dicarboxamide

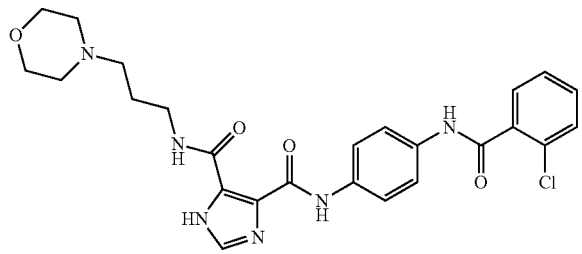 [SMILES: O=C(Nc1ccc(NC(=O)c2nc[nH]c2C(=O)NCCCN2CCOCC2)cc1)c1ccccc1Cl]

To the crude mixture of N,N'-bis{4-[(2-chlorobenzoyl)amino]phenyl}-5,10-dioxo-5H,10H-diimidazo[1,5-a:1',5'-d]pyrazine-1,6-dicarboxamide (0.2 mmol, Intermediate 052), were added 0.062 mL (0.4 mmol) 3-(morpholin-4-yl)propan-1-amine and 0.348 mL (2 mmol) N-ethyl-N-isopropylpropan-2-amine and the mixture was stirred for 72 h at room temperature.

The reaction mixture was concentrated in vacuo and the residue was purified by preparative HPLC chromatography to give 52 mg of the title compound as a solid material.

$^1$H-NMR (400 MHz, DMSO-$d_6$): δ [ppm]=10.51 (s, 1H), 7.93 (s, 1H), 7.78-7.66 (m, 4H), 7.62-7.42 (m, 5H), 3.62 (br. s., 4H), 3.46-3.37 (m, 2H), 2.44-2.31 (m, 6H), 1.74 (quin, 2H).

LC-MS (Method 1): $R_t$=0.72 min; MS (ESIpos) m/z=512 [M+H]$^+$.

Example 201

$N^4$-{4-[(4-fluorobenzoyl)amino]phenyl}-$N^5$-[4-(piperidin-1-yl)butyl]-1H-imidazole-4,5-dicarboxamide

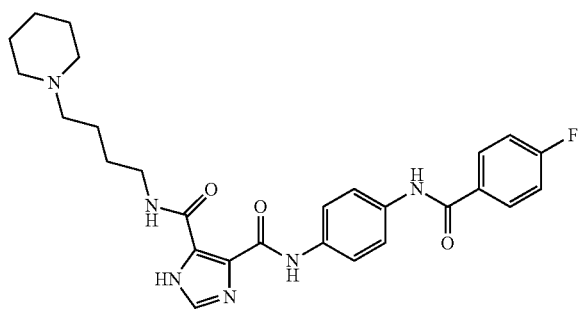 [SMILES: O=C(Nc1ccc(NC(=O)c2nc[nH]c2C(=O)NCCCCN2CCCCC2)cc1)c1ccc(F)cc1]

To the crude mixture of N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide (0.20 mmol, Intermediate 018), were added 0.072 mL (0.4 mmol) 4-(piperidin-1-yl)butan-1-amine and 0.348 mL (2 mmol) N-ethyl-N-isopropylpropan-2-amine and the mixture was stirred for 72 h at room temperature.

The reaction mixture was concentrated in vacuo and the residue was purified by preparative HPLC chromatography to give 43 mg of the title compound as a solid material.

$^1$H-NMR (400 MHz, DMSO-$d_6$): δ [ppm]=10.51 (s, 1H), 7.92 (s, 1H), 7.72 (br. s., 4H), 7.62-7.55 (m, 2H), 7.54-7.43 (m, 2H), 3.39-3.27 (m, 2H), 2.36-2.21 (m, 6H), 1.63-1.52 (m, 2H), 1.48 (dt, 6H), 1.36 (d, 2H).

LC-MS (Method 1): $R_t$=0.79 min; MS (ESIpos) m/z=507 [M+H]$^+$.

Example 202

$N^4$-{4-[(2-chlorobenzoyl)amino]phenyl}-$N^5$-[2-methyl-2-(4-methylpiperazin-1-yl)propyl]-1H-imidazole-4,5-dicarboxamide

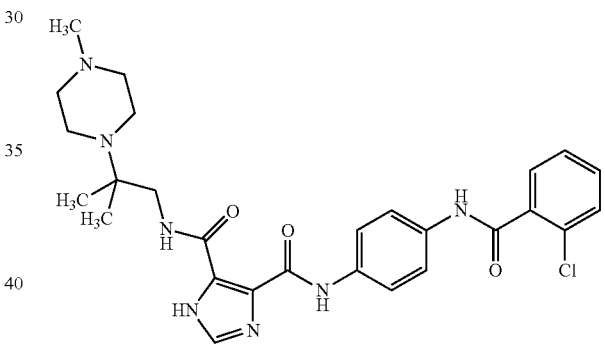

To the crude mixture of N,N'-bis{4-[(2-chlorobenzoyl)amino]phenyl}-5,10-dioxo-5H,10H-diimidazo[1,5-a:1',5'-d]pyrazine-1,6-dicarboxamide (0.2 mmol, Intermediate 052), were added 0.085 mL (0.4 mmol) 2-methyl-2-(4-methylpiperazin-1-yl)propan-1-amine and 0.348 mL (2 mmol) N-ethyl-N-isopropylpropan-2-amine and the mixture was stirred for 19 h at room temperature.

The reaction mixture was concentrated in vacuo and the residue was purified by preparative HPLC chromatography to give 69 mg of the title compound as a solid material.

$^1$H-NMR (400 MHz, DMSO-$d_6$): δ [ppm]=10.51 (s, 2H), 8.33 (br. s., 1H), 7.95 (br. s., 2H), 7.78-7.63 (m, 5H), 7.62-7.55 (m, 3H), 7.54-7.42 (m, 3H), 3.37 (d, 3H), 2.43-2.29 (m, 5H), 2.16 (s, 5H), 1.04 (s, 9H).

LC-MS (Method 1): $R_t$=0.77 min; MS (ESIpos) m/z=539 [M+H]$^+$.

Example 203

N⁴-{4-[(2-chlorobenzoyl)amino]phenyl}-N⁵-[2-methyl-1-(4-methylpiperazin-1-yl)propan-2-yl]-1H-imidazole-4,5-dicarboxamide

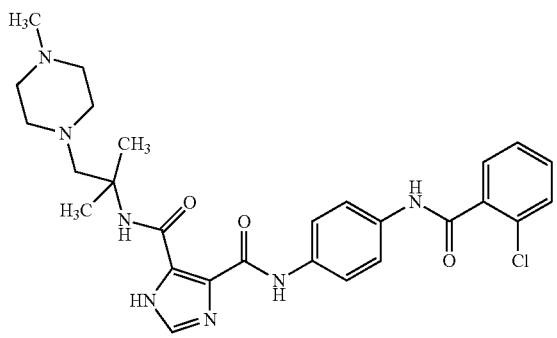 [SMILES: CN1CCN(CC(C)(C)NC(=O)c2[nH]cnc2C(=O)Nc2ccc(NC(=O)c3ccccc3Cl)cc2)CC1]

To the crude mixture of N,N'-bis{4-[(2-chlorobenzoyl)amino]phenyl}-5,10-dioxo-5H,10H-diimidazo[1,5-a:1',5'-d]pyrazine-1,6-dicarboxamide (0.2 mmol, Intermediate 052), were added 0.077 mL (0.4 mmol) 2-methyl-1-(4-methylpiperazin-1-yl)propan-2-amine and 0.348 mL (2 mmol) N-ethyl-N-isopropylpropan-2-amine and the mixture was stirred for 3 d at room temperature.

The reaction mixture was concentrated in vacuo and the residue was purified by preparative HPLC chromatography to give 29 mg of the title compound as a solid material.

¹H-NMR (400 MHz, DMSO-d₆): δ [ppm]=10.53-10.45 (m, 1H), 7.88 (s, 1H), 7.79-7.63 (m, 4H), 7.61-7.41 (m, 5H), 2.61-2.52 (m, 6H), 2.31 (dd, 4H), 2.11 (s, 3H), 1.40 (br. s., 6H).

LC-MS (Method 1): R$_t$=0.81 min; MS (ESIpos) m/z=539 [M+H]⁺.

Example 204

N⁴-{4-[(2-chloro-4-fluorobenzoyl)amino]phenyl}-N⁵-[3-(morpholin-4-yl)propyl]-1H-imidazole-4,5-dicarboxamide

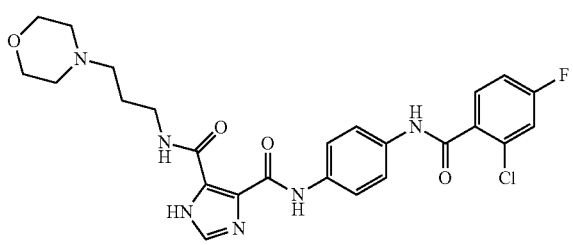 [SMILES: O=C(Nc1ccc(NC(=O)c2nc[nH]c2C(=O)NCCCN2CCOCC2)cc1)c1ccc(F)cc1Cl]

To the crude mixture of N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide (0.20 mmol, Intermediate 005), were added 0.061 mL (0.4 mmol) 3-(morpholin-4-yl)propan-1-amine and 0.348 mL (2 mmol) N-ethyl-N-isopropylpropan-2-amine and the mixture was stirred for 72 h at room temperature.

The reaction mixture was concentrated in vacuo and the residue was purified by preparative HPLC chromatography to give 98 mg of the title compound as a solid material.

¹H-NMR (400 MHz, DMSO-d₆): δ [ppm]=10.52 (s, 1H), 7.93 (s, 1H), 7.76-7.65 (m, 5H), 7.60 (dd, 1H), 7.36 (td, 1H), 3.62 (t, 4H), 3.41 (q, 2H), 2.42-2.35 (m, 6H), 1.73 (quin, 2H).

LC-MS (Method 1): R$_t$=0.75 min; MS (ESIpos) m/z=529 [M+H]⁺.

Example 205

N⁴-{4-[(4-fluorobenzoyl)amino]phenyl}-N⁵-[2-(4-methylpiperazin-1-yl)propyl]-1H-imidazole-4,5-dicarboxamide

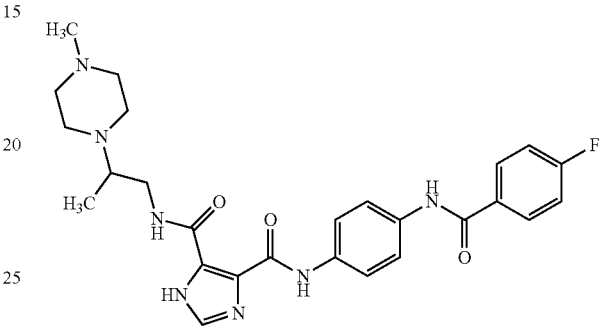

To the crude mixture of N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide (0.20 mmol, Intermediate 018), were added 0.078 mL (0.4 mmol) 2-(4-methylpiperazin-1-yl)propan-1-amine and 0.348 mL (2 mmol) N-ethyl-N-isopropylpropan-2-amine and the mixture was stirred for 19 h at room temperature.

The reaction mixture was concentrated in vacuo and the residue was purified by preparative HPLC chromatography to give 61 mg of the title compound as a solid material.

¹H-NMR (500 MHz, DMSO-d₆): δ [ppm]=10.26 (s, 1H), 8.06-8.01 (m, 2H), 7.90 (s, 1H), 7.78-7.67 (m, 4H), 7.39-7.32 (m, 2H), 3.42 (dt, 1H), 3.28-3.22 (m, 1H), 2.83 (d, 1H), 2.58 (d, 2H), 2.46-2.25 (m, 7H), 2.17-2.12 (m, 3H), 0.98-0.94 (m, 3H).

LC-MS (Method 1): R$_t$=0.75 min; MS (ESIpos) m/z=508 [M+H]⁺.

Example 206

N⁴-{4-[(4-fluorobenzoyl)amino]phenyl}-N⁵-[3-(morpholin-4-yl)propyl]-1H-imidazole-4,5-dicarboxamide

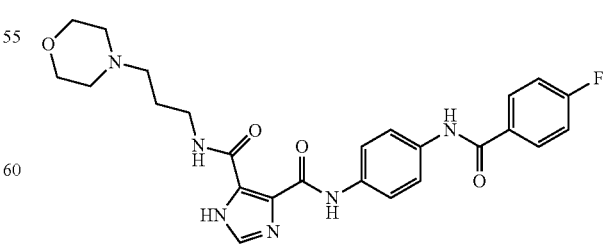

To the crude mixture of N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide (0.20 mmol, Intermediate 018), were added 0.078 mL (0.4 mmol) 3-(morpholin-4-yl)propan-1-amine and 0.348 mL (2 mmol) N-ethyl-N-isopropylpropan-2-amine and the mixture was stirred for 3 d at room temperature.

The reaction mixture was concentrated in vacuo and the residue was purified by preparative HPLC chromatography to give 112 mg of the title compound as a solid material.

$^1$H-NMR (400 MHz, DMSO-$d_6$): δ [ppm]=10.29 (s, 1H), 8.10-8.01 (m, 2H), 7.93 (s, 1H), 7.82-7.67 (m, 4H), 7.38 (t, 2H), 3.62 (t, 4H), 3.42 (q, 2H), 2.43-2.33 (m, 6H), 1.74 (quin, 2H).

LC-MS (Method 1): $R_t$=0.72 min; MS (ESIpos) m/z=495 [M+H]$^+$.

Example 207

N$^4$-{4-[(2-chloro-4-fluorobenzoyl)amino]phenyl}-N$^5$-[2-methyl-1-(morpholin-4-yl)propan-2-yl]-1H-imidazole-4,5-dicarboxamide

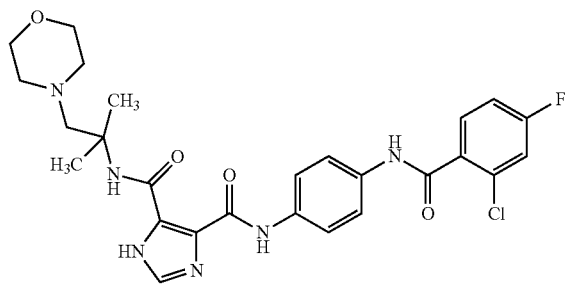 [SMILES: CC(C)(CN1CCOCC1)NC(=O)c1[nH]cnc1C(=O)Nc1ccc(NC(=O)c2ccc(F)cc2Cl)cc1]

To the crude mixture of N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide (0.20 mmol, Intermediate 005), were added 0.065 mL (0.4 mmol) 2-methyl-1-(morpholin-4-yl)propan-2-amine and 0.348 mL (2 mmol) N-ethyl-N-isopropylpropan-2-amine and the mixture was stirred for 72 h at room temperature.

The reaction mixture was concentrated in vacuo and the residue was purified by preparative HPLC chromatography to give 27 mg of the title compound as a solid material.

$^1$H-NMR (400 MHz, DMSO-$d_6$): δ [ppm]=10.52 (s, 1H), 7.89 (s, 1H), 7.83-7.55 (m, 7H), 7.36 (td, 1H), 3.58 (br. s., 4H), 2.60 (s, 2H), 1.52-1.35 (m, 6H).

LC-MS (Method 1): $R_t$=0.86 min; MS (ESIpos) m/z=544 [M+H]$^+$.

Example 208

N$^4$-{4-[(2-chloro-4-fluorobenzoyl)amino]phenyl}-N$^5$-[2-(3-methylpiperidin-1-yl)ethyl]-1H-imidazole-4,5-dicarboxamide

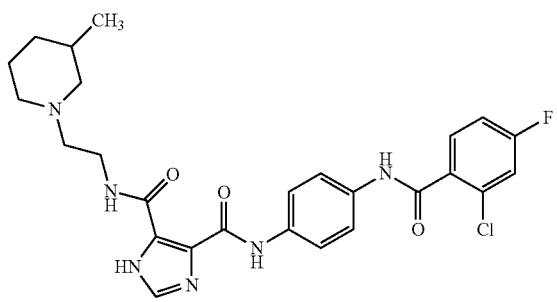

To the crude mixture of N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide (0.20 mmol, Intermediate 005), were added 0.067 mL (0.4 mmol) 2-(3-methylpiperidin-1-yl)ethanamine and 0.348 mL (2 mmol) N-ethyl-N-isopropylpropan-2-amine and the mixture was stirred for 18 h at room temperature.

The reaction mixture was concentrated in vacuo and the residue was purified by preparative HPLC chromatography to give 46 mg of the title compound as a solid material.

$^1$H-NMR (400 MHz, DMSO-$d_6$): δ [ppm]=0.85 (d, 4H), 1.37-1.72 (m, 5H), 1.91 (s, 1H), 2.83 (br. s., 2H), 3.48 (br. s., 2H), 7.35 (td, 1H), 7.58 (dd, 1H), 7.64-7.87 (m, 5H), 7.93 (s, 1H), 8.56-8.75 (m, 1H), 10.52 (s, 1H), 13.46 (br. s., 1H), 13.60 (br. s., 1H).

Example 209

N$^4$-{4-[(4-fluorobenzoyl)amino]phenyl}-N$^5$-[2-methyl-2-(piperidin-1-yl)propyl]-1H-imidazole-4,5-dicarboxamide

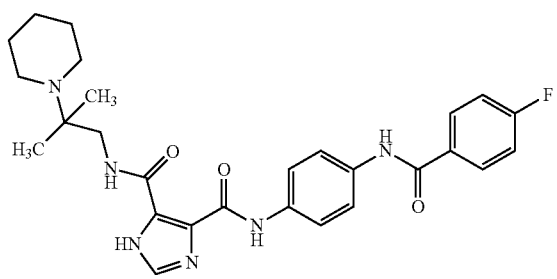 [SMILES: CC(C)(CNC(=O)c1[nH]cnc1C(=O)Nc1ccc(NC(=O)c2ccc(F)cc2)cc1)N1CCCCC1]

To the crude mixture of N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide (0.20 mmol, Intermediate 018), were added 0.077 mL (0.4 mmol) 2-methyl-2-(piperidin-1-yl)propan-1-amine and 0.348 mL (2 mmol) N-ethyl-N-isopropylpropan-2-amine and the mixture was stirred for 19 h at room temperature.

The reaction mixture was concentrated in vacuo and the residue was purified by preparative HPLC chromatography to give 69 mg of the title compound as a solid material.

¹H-NMR (400 MHz, DMSO-d₆): δ [ppm]=10.29 (br. s., 1H), 8.10-8.01 (m, 2H), 8.00-7.63 (m, 5H), 7.43-7.31 (m, 2H), 3.36 (d, 4H), 1.54 (br. s., 4H), 1.42 (d, 2H), 1.04 (s, 6H).

LC-MS (Method 1): R_t=0.82 min; MS (ESIpos) m/z=507 [M+H]⁺.

Example 210

N⁴-{4-[(2-chlorobenzoyl)amino]phenyl}-N⁵-[2-(3-methylpiperidin-1-yl)ethyl]-1H-imidazole-4,5-dicarboxamide

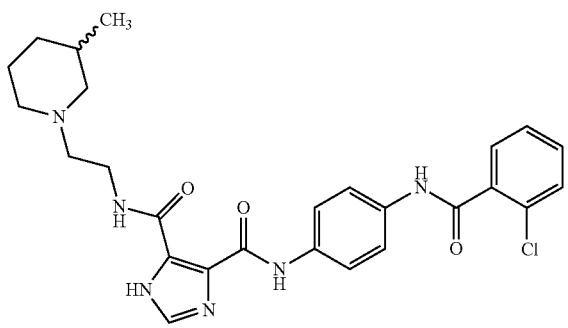 [SMILES: CC1CCCN(CCNC(=O)c2[nH]cnc2C(=O)Nc2ccc(NC(=O)c3ccccc3Cl)cc2)C1]

To the crude mixture of N,N'-bis{4-[(2-chlorobenzoyl)amino]phenyl}-5,10-dioxo-5H,10H-diimidazo[1,5-a:1',5'-d]pyrazine-1,6-dicarboxamide (0.2 mmol, Intermediate 052), were added 0.067 mL (0.4 mmol) 2-(3-methylpiperidin-1-yl)ethanamine and 0.348 mL (2 mmol) N-ethyl-N-isopropylpropan-2-amine and the mixture was stirred for 18 h at room temperature.

The reaction mixture was concentrated in vacuo and the residue was purified by preparative HPLC chromatography to give 51 mg of the title compound as a solid material.

¹H-NMR (500 MHz, DMSO-d₆): δ [ppm]=0.84 (d, 4H), 1.41-1.73 (m, 5H), 1.91 (s, 1H), 2.82 (d, 2H), 3.41-3.50 (m, 2H), 7.43-7.53 (m, 2H), 7.55-7.61 (m, 2H), 7.64-7.76 (m, 4H), 7.92 (s, 1H), 8.65 (br. s., 1H), 10.51 (s, 1H), 13.33-3.73 (m, 2H).

LC-MS (Method 1): R_t=0.81 min; MS (ESIpos) m/z=509 [M+H]⁺.

Example 211

N⁴-{4-[(4-fluorobenzoyl)amino]phenyl}-N⁵-[2-(3-methylpiperidin-1-yl)ethyl]-1H-imidazole-4,5-dicarboxamide

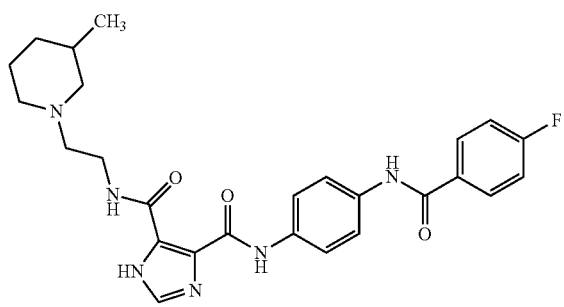 [SMILES: CC1CCCN(CCNC(=O)c2[nH]cnc2C(=O)Nc2ccc(NC(=O)c3ccc(F)cc3)cc2)C1]

To the crude mixture of N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide (0.20 mmol, Intermediate 018), were added 0.067 mL (0.4 mmol) 2-(3-methylpiperidin-1-yl)ethanamine and 0.348 mL (2 mmol) N-ethyl-N-isopropylpropan-2-amine and the mixture was stirred for 18 h at room temperature.

The reaction mixture was concentrated in vacuo and the residue was purified by preparative HPLC chromatography to give 72 mg of the title compound as a solid material.

¹H-NMR (500 MHz, DMSO-d₆): δ [ppm]=0.85 (d, 4H), 1.39-1.70 (m, 5H), 1.85-1.95 (m, 1H), 2.78-2.88 (m, 2H), 3.46 (q, 2H), 7.34-7.40 (m, 2H), 7.64-7.86 (m, 4H), 7.93 (s, 1H), 8.00-8.10 (m, 2H), 8.61-8.69 (m, 1H), 10.29 (s, 1H), 13.46 (br. s., 1H), 13.61 (br. s., 1H).

LC-MS (Method 1): R_t=0.82 min; MS (ESIpos) m/z=483 [M+H]⁺.

Example 212

N⁴-{4-[(2-chloro-4-fluorobenzoyl)amino]phenyl}-N⁵-[2-(4-hydroxypiperidin-1-yl)ethyl]-1H-imidazole-4,5-dicarboxamide

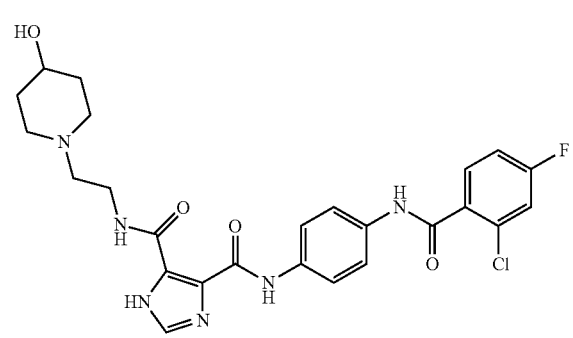

To the crude mixture of N,N'-bis{4-[(2-chloro-4-fluorobenzoyl)amino]phenyl}-5,10-dioxo-5H,10H-diimidazo[1,5-a:1',5'-d]pyrazine-1,6-dicarboxamide (0.20 mmol, Intermediate 005), were added 61 mg (0.4 mmol) 1-(2-aminoethyl)piperidin-4-ol and 0.348 mL (2 mmol) N-ethyl-N-isopropylpropan-2-amine and the mixture was stirred for 19 h at room temperature.

The reaction mixture was concentrated in vacuo and the residue was purified by preparative HPLC chromatography to give 13 mg of the title compound as a solid material.

¹H-NMR (400 MHz, DMSO-d₆): δ [ppm]=10.52 (s, 1H), 7.94 (s, 1H), 7.76-7.65 (m, 5H), 7.60 (dd, 1H), 7.36 (td, 1H), 4.54 (br. s., 1H), 3.50-3.41 (m, 4H), 2.82-2.73 (m, 2H), 2.09 (t, 2H), 1.72 (d, 2H), 1.39 (d, 2H).

LC-MS (Method 1): R_t=0.89 min; MS (ESIpos) m/z=530 [M+H]⁺.

Example 213

N⁴-(4-{[(2,5-dichloro-3-thienyl)carbonyl]amino}phenyl)-N⁵-methyl-1H-imidazole-4,5-dicarboxamide

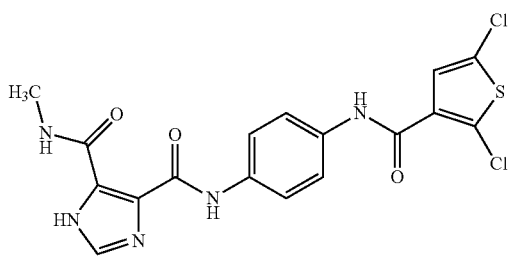 [SMILES: CNC(=O)c1[nH]cnc1C(=O)Nc1ccc(NC(=O)c2cc(Cl)sc2Cl)cc1]

To 152 mg (0.77 mmol) 2,5-dichlorothiophene-3-carboxylic acid in 5 mL DMF were added 293 g (0.77 mmol) HATU and 403 µL N,N-diisopropylethylamine. 200 mg (0.77 mmol) N⁵-(4-aminophenyl)-N⁴-methyl-1H-imidazole-4,5-dicarboxamide (Intermediate 003) were added and the mixture was stirred for 3 days at room temperature. The precipitate was filtered off. And the crude product was purified by preparative HPLC chromatography to give 177 mg of the title compound as a solid material.

¹H-NMR (400 MHz, DMSO-$d_6$): δ [ppm]=13.67 (br. s., 1H), 13.40 (br. s., 1H), 10.29 (s, 1H), 8.81 (br. s., 1H), 7.91 (s, 1H), 7.69 (s, 4H), 7.50 (s, 1H), 2.86 (d, 3H).

LCMS (Method 7): $R_t$=1.19 min; MS (ESIpos) m/z=437.9 [M+H]⁺.

Example 214

N⁴-{4-[(2-chlorobenzoyl)amino]phenyl}-N⁵-[2-(4,4-difluoropiperidin-1-yl)ethyl]-1H-imidazole-4,5-dicarboxamide

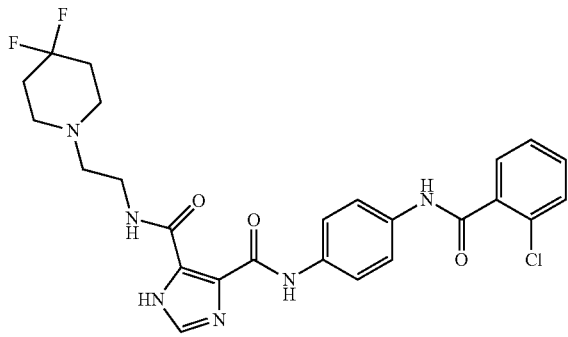 [SMILES: O=C(Nc1ccc(NC(=O)c2nc[nH]c2C(=O)NCCN2CCC(F)(F)CC2)cc1)c1ccccc1Cl]

To 75.0 mg (0.240 mmol) 5,10-Dioxo-5H,10H-diimidazo[1,5-a;1',5'-d]pyrazin-1,6-dicarbonyl-dichloride (Intermediate 001) in 3.6 mL THF were added 118 mg (0.479 mmol) N-(4-aminophenyl)-2-chlorobenzamide (Intermediate 051) and 100 µL (0.719 mmol) triethylamine. The resulting mixture was stirred for 90 min at room temperature and then used directly in the next step.

78.8 mg (0.480 mmol) 2-(4,4-difluoropiperidin-1-yl)ethanamine (Intermediate 057) and 100 µL (0.720 mmol) triethylamine were added and the mixture was stirred overnight at room temperature. Insoluble material was filtrated off. The filtrate was concentrated and purified by preparative HPLC to provide the title compound (21.0 mg).

¹H-NMR (400 MHz, DMSO-$d_6$): δ [ppm]=13.59 (br. s., 1H), 13.25 (br. s, 1H), 10.51 (s, 1H), 8.73 (br. s., 1H), 7.94 (s, 1H), 7.83-7.64 (m, 4H), 7.64-7.55 (m, 2H), 7.55-7.39 (m, 2H), 3.56-3.42 (m, 2H), 2.63-2.56 (m, 6H), 2.13-1.88 (m, 4H).

LC-MS (Method 7): $R_t$=1.06 min; MS (ESIpos) m/z=531.3 [M+H]⁺.

Example 215

N⁴-{4-[(2-bromo-4-fluorobenzoyl)amino]phenyl}-N⁵-[2-(4,4-difluoropiperidin-1-yl)ethyl]-1H-imidazole-4,5-dicarboxamide

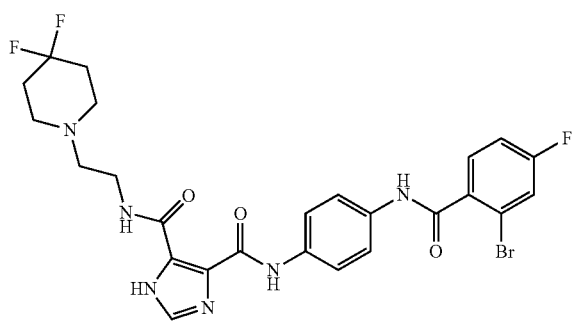 [SMILES: O=C(Nc1ccc(NC(=O)c2nc[nH]c2C(=O)NCCN2CCC(F)(F)CC2)cc1)c1ccc(F)cc1Br]

Step 1: A mixture of 2.93 g (8.48 mmol) N-(4-aminophenyl)-2-bromo-4-fluorobenzamide hydrochloride salt (Intermediate 054) and 2.58 mL (14.8 mmol) N,N-diisopropylethylamine were added in 103 mL THF and stirred for 5 min. 1.33 g (4.24 mmol) 5,10-dioxo-5H,10H-diimidazo[1,5-a;1',5'-d]pyrazin-1,6-dicarbonyl-dichloride (Intermediate 001) was added and the mixture was stirred overnight to give N,N'-bis{4-[(2-bromo-4-fluorobenzoyl)amino]phenyl}-5,10-dioxo-5H,10H-diimidazo[1,5-a:1',5'-d]pyrazine-1,6-dicarboxamide. The reaction mixture was split in 3 parts and used directly in the next step.

Step 2: 463 mg (2.82 mmol) 2-(4,4-difluoropiperidin-1-yl)ethanamine (Intermediate 057) and 0.59 mL (4.2 mmol) triethylamine were added to 30 mL (1.41 mmol) of N,N'-bis{4-[(2-bromo-4-fluorobenzoyl)amino]phenyl}-5,10-dioxo-5H,10H-diimidazo[1,5-a:1',5'-d]pyrazine-1,6-dicarboxamide reaction mixture in THF (Example 215 step 1). The mixture was stirred overnight at room temperature and then concentrated under reduced pressure. The residue was stirred with ethanol, solids were filtered off. The filtrate was concentrated and purified by flash chromatography (50 g Snap Cartridge, hexanes/ethyl acetate gradient, 50 to 100% ethyl acetate followed by dichloromethane/methanol, 0 to 10% methanol) to yield the title compound (35.0 mg).

¹H-NMR (400 MHz, DMSO-$d_6$): δ [ppm]=13.83-13.09 (m, 2H), 10.55-10.39 (m, 1H), 9.14-8.42 (m, 0.5H), 7.97-7.87 (m, 1H), 7.82-7.59 (m, 6.5H), 7.48-7.30 (m, 1H), 3.58-3.42 (m, 2H), 2.65-2.54 (m, 6H), 2.07-1.82 (m, 4H).

LC-MS (Method 8): $R_t$=1.11 min; MS (ESIpos) m/z=593.2 [M+H]⁺.

Example 216

N⁴-{4-[(2-bromo-4-fluorobenzoyl)amino]phenyl}-N⁵-[2-(piperidin-1-yl)ethyl]-1H-imidazole-4,5-dicarboxamide

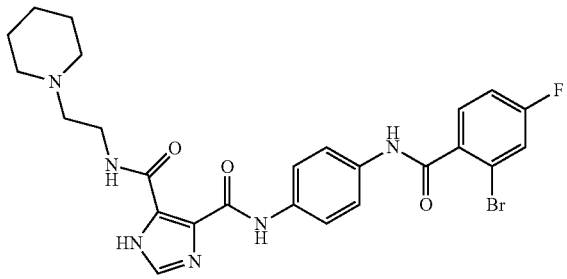 [SMILES: O=C(Nc1ccc(NC(=O)c2nc[nH]c2C(=O)NCCN2CCCCC2)cc1)c1ccc(F)cc1Br]

361 mg, (2.82 mmol) 2-(piperidin-1-yl)ethanamine (CAS No. 27578-60-5) and 0.59 mL (4.2 mmol) triethylamine were added to 30 mL (1.41 mmol) of N,N'-bis{4-[(2-bromo-4-fluorobenzoyl)amino]phenyl}-5,10-dioxo-5H,10H-diimidazo[1,5-a:1',5'-d]pyrazine-1,6-dicarboxamide reaction mixture in THF (Example 215, step 1). The mixture was stirred overnight at room temperature and then concentrated under reduced pressure. The residue was stirred with ethanol. The solid was collected by filtration and purified by preparative HPLC to provide the title compound (12.1 mg).

¹H-NMR (300 MHz, DMSO-d₆): δ [ppm]=13.85-13.0 (m, 2H), 10.55-10.42 (m, 1H), 8.64 (br. s., 1H), 7.92 (s, 1H), 7.80-7.58 (m, 6H), 7.48-7.27 (m, 1H), 3.54-3.37 (m, 2H), 3.44-2.33 (m, 3H), 1.58-1.44 (m, 4H), 1.44-1.31 (m, 2H).

LC-MS (Method 8): R$_t$=1.13 min; MS (ESIpos) m/z=557.2 [M+H]⁺.

Example 217

N⁴-{4-[(2-bromo-4-fluorobenzoyl)amino]phenyl}-N⁵-[2-(dimethylamino)ethyl]-1H-imidazole-4,5-dicarboxamide

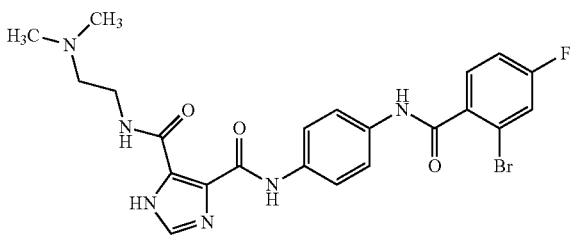 [SMILES: CN(C)CCNC(=O)c1[nH]cnc1C(=O)Nc1ccc(NC(=O)c2ccc(F)cc2Br)cc1]

248 mg (2.82 mmol) N,N-dimethylethane-1,2-diamine (CAS No. 108-00-9) and 0.59 mL (4.2 mmol) triethylamine were added to 30 mL (1.41 mmol) of N,N'-bis{4-[(2-bromo-4-fluorobenzoyl)amino]phenyl}-5,10-dioxo-5H,10H-diimidazo[1,5-a: 1,5'-d]pyrazine-1,6-dicarboxamide reaction mixture in THF (Example 215, step 1). The mixture was stirred for 5 h at room temperature and then concentrated under reduced pressure. The residue was purified by preparative HPLC and the isolated product was recrystallized from ethanol to provide the title compound (25.0 mg).

¹H-NMR (400 MHz, DMSO-d₆): δ [ppm]=13.58 (s, 1H), 13.46 (br. s, 1H), 10.50 (s, 1H), 8.71-8.53 (m, 1H), 7.93 (s, 1H), 7.82-7.56 (m, 6H), 7.47-7.29 (m, 1H), 3.56-3.38 (m, 2H), 2.49-2.42 (m, 2H), 2.21 (s, 6H).

LC-MS (Method 8): R$_t$=0.99 min; MS (ESIpos) m/z=517.0 [M+H]⁺.

Example 218

N⁵-{4-[(2-chloro-4-fluorobenzoyl)amino]phenyl}-N⁴-[2-(4,4-difluoropiperidin-1-yl)ethyl]-1,3-oxazole-4,5-dicarboxamide

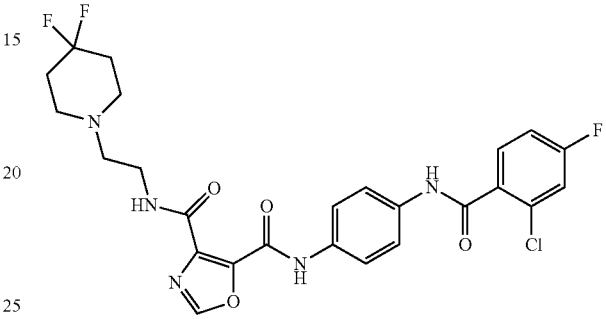

245 mg, (1.49 mmol) 2-(4,4-difluoropiperidin-1-yl)ethanamine (Intermediate 057) were added to 150 mg (83% purity, 0.298 mmol) methyl 5-({4-[(2-chloro-4-fluorobenzoyl)amino]phenyl}carbamoyl)-1,3-oxazole-4-carboxylate (Example 14) in 1.0 mL methanol. The mixture was stirred at room temperature for 18 h. Solids were filtered off and the filtrate was concentrated. The residue was purified by flash chromatography (25 g Snap Cartridge, hexanes/ethyl acetate gradient followed by ethyl acetate/methanol 9:1) to yield the title compound (64.0 mg).

¹H-NMR (400 MHz, DMSO-d₆): δ [ppm]=13.25 (s, 1H), 10.56 (s, 1H), 9.09 (t, 1H), 8.80 (s, 1H), 7.77-7.72 (m, 2H), 7.72-7.64 (m, 3H), 7.60 (dd, 1H), 7.40-7.29 (m, 1H), 3.55-3.42 (m, 2H), 2.65-2.55 (m, 6H), 2.05-1.84 (m, 4H).

LC-MS (Method 8): R$_t$=1.22 min; MS (ESIpos) m/z=550.3 [M+H]⁺.

Example 219

N⁴-(2-amino-2-methylpropyl)-N⁵-{4-[(2-chloro-4-fluorobenzoyl)amino]phenyl}-1,3-oxazole-4,5-dicarboxamide

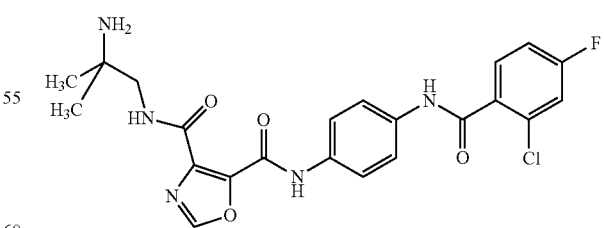

106 mg (1.19 mmol) 2-methylpropane-1,2-diamine (CAS No. 811-93-8) were added to 150 mg (83% purity, 0.298 mmol) methyl 5-({4-[(2-chloro-4-fluorobenzoyl)amino]phenyl}carbamoyl)-1,3-oxazole-4-carboxylate (Example 14) in 0.8 mL methanol and the mixture was stirred at room temperature for 18 h. The reaction mixture was concentrated and the residue was purified by preparative HPLC to yield the title compound (79.1 mg).

¹H-NMR (300 MHz, DMSO-d₆): δ [ppm]=13.57-12.69 (m, 1H), 10.55 (s, 1H), 8.79 (s, 2H), 7.84-7.53 (m, 6H), 7.43-7.23 (m, 1H), 3.25 (s, 2H), 1.06 (s, 6H).

LC-MS (Method 8): $R_t$=1.03 min; MS (ESIpos) m/z=474.2 [M+H]⁺.

Example 220

N⁵-{4-[(2-chloro-4-fluorobenzoyl)amino]phenyl}-N⁴-[2-(3-fluoropiperidin-1-yl)ethyl]-1,3-oxazole-4,5-dicarboxamide

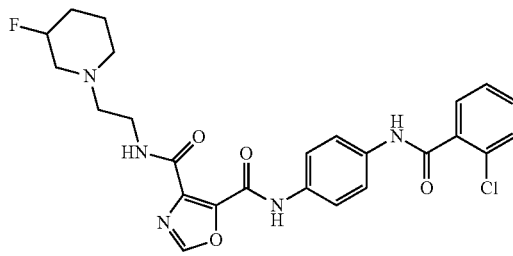

Was prepared in analogy to the synthesis of N⁴-(2-amino-2-methylpropyl)-N⁵-{4-[(2-chloro-4-fluorobenzoyl)amino]phenyl}-1,3-oxazole-4,5-dicarboxamide (Example 219) from 180 mg (83% purity, 0.358 mmol) methyl 5-({4-[(2-chloro-4-fluorobenzoyl)amino]phenyl}carbamoyl)-1,3-oxazole-4-carboxylate (Example 14) and 157 mg (1.07 mmol) 2-(3-fluoropiperidin-1-yl)ethanamine (Intermediate 058) to give the title compound (87.0 mg).

¹H-NMR (400 MHz, DMSO-d₆): δ [ppm]=13.24 (s, 1H), 10.54 (s, 1H), 9.01 (t, 1H), 8.78 (s, 1H), 7.84-7.62 (m, 5H), 7.60-7.53 (m, 1H), 7.39-7.26 (m, 1H), 4.80-4.56 (m, 1H), 3.51-3.44 (m, 2H), 1.94-1.58 (m, 4H).

LC-MS (Method 7): $R_t$=0.89 min; MS (ESIpos) m/z=532.3 [M+H]⁺.

Example 221

N⁵-{4-[(2-chloro-4-fluorobenzoyl)amino]phenyl}-N⁴-{2-[(3S)-3-fluoropyrrolidin-1-yl]ethyl}-1,3-oxazole-4,5-dicarboxamide

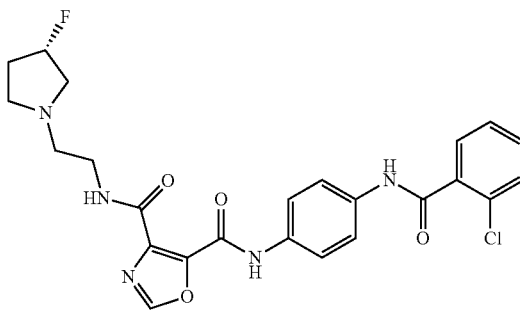

Was prepared in analogy to the synthesis of N⁴-(2-amino-2-methylpropyl)-N⁵-{4-[(2-chloro-4-fluorobenzoyl)amino]phenyl}-1,3-oxazole-4,5-dicarboxamide (Example 219) from 140 mg (83% purity, 0.278 mmol) methyl 5-({4-[(2-chloro-4-fluorobenzoyl)amino]phenyl}carbamoyl)-1,3-oxazole-4-carboxylate (Example 14) and 110 mg (0.834 mmol) 2-[(3S)-3-fluoropyrrolidin-1-yl]ethanamine (Intermediate 061) to give the title compound (51.0 mg).

¹H-NMR (400 MHz, DMSO-d₆): δ [ppm]=13.26 (s, 1H), 10.56 (s, 1H), 9.16-9.02 (m, 1H), 8.80 (s, 1H), 7.84-7.64 (m, 5H), 7.64-7.52 (m, 1H), 7.49-7.21 (m, 1H), 5.35-5.20 (m, 1H), 3.56-3.43 (m, 2H), 3.00-2.78 (m, 2H), 2.74-2.64 (m, 3H), 2.42-2.36 (m, 1H), 2.25-2.01 (m, 1H), 1.99-1.74 (m, 1H).

LC-MS (Method 8): $R_t$=1.15 min; MS (ESIpos) m/z=518.2 [M+H]⁺.

Example 222

N⁵-{4-[(2-chloro-4-fluorobenzoyl)amino]phenyl}-N⁴-{2-[(3R)-3-fluoropyrrolidin-1-yl]ethyl}-1,3-oxazole-4,5-dicarboxamide

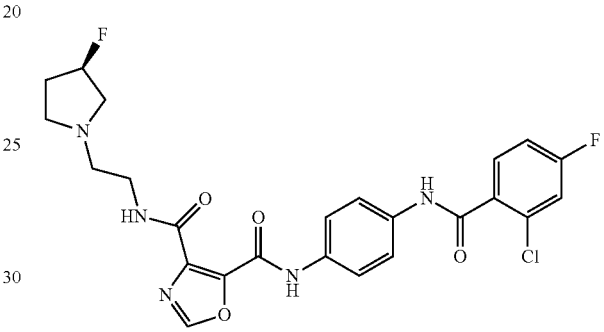

Was prepared in analogy to the synthesis of N⁴-(2-amino-2-methylpropyl)-N⁵-{4-[(2-chloro-4-fluorobenzoyl)amino]phenyl}-1,3-oxazole-4,5-dicarboxamide (Example 219) from 140 mg (83% purity, 0.278 mmol) methyl 5-({4-[(2-chloro-4-fluorobenzoyl)amino]phenyl}carbamoyl)-1,3-oxazole-4-carboxylate (Example 14) and 110 mg (0.834 mmol) 2-[(3R)-3-fluoropyrrolidin-1-yl]ethanamine (Intermediate 062) to give the title compound (51.0 mg).

¹H-NMR (400 MHz, DMSO-d₆): δ [ppm]=13.26 (s, 1H), 10.56 (s, 1H), 9.15-9.02 (m, 1H), 8.80 (s, 1H), 7.84-7.64 (m, 5H), 7.64-7.52 (m, 1H), 7.49-7.21 (m, 1H), 5.35-5.07 (m, 1H), 3.56-3.43 (m, 2H), 3.00-2.78 (m, 2H), 2.74-2.64 (m, 3H), 2.42-2.36 (m, 1H), 2.25-2.01 (m, 1H), 1.99-1.74 (m, 1H).

LC-MS (Method 8): $R_t$=1.15 min; MS (ESIpos) m/z=518.2 [M+H]⁺.

Example 223

N⁴-{4-[(2-chloro-4-fluorobenzoyl)amino]phenyl}-N⁵-(2-hydroxy-2-methylpropyl)-1H-imidazole-4,5-dicarboxamide

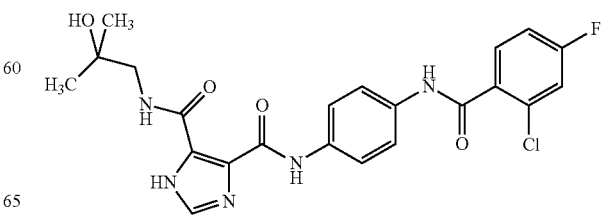

Step 1: 221 mg (0.800 mmol, 2.0 equiv.) 2-chloro-4-fluoro-N-[4-(methylamino)phenyl]benzamide (Intermediate 004) and 167 µL (1.2 mmol, 3.0 equiv.) triethylamine were added to a suspension of 125 mg (0.400 mmol, 1 equiv.) 5,10-dioxo-5H,10H-diimidazo[1, 5-a; 1',5'-d]pyrazin-1,6-dicarbonyl-dichloride (Intermediate 001) in 6.0 mL THF and the mixture was stirred overnight to give N,N'-bis{4-[(2-chloro-4-fluorobenzoyl)amino]phenyl}-5, 10-dioxo-5H, 10H-diimidazo[1,5-a:1',5'-d]pyrazine-1,6-dicarboxamide. The reaction mixture was used directly in the next step.

Step 2: 71.3 mg (0.800 mmol, 1.0 equiv) 1-amino-2-methylpropan-2-ol (CAS No. 2854-16-2) and 167 µl (1.2 mmol, 3.0 equiv.) triethylamine were added to the reaction mixture of step 1 and the mixture was stirred over night at room temperature. The mixture was concentrated and the residue was purified by preparative HPLC followed by recrystallization from methanol to give the title compound (8.0 mg).

$^{1}$H-NMR (400 MHz, DMSO-$d_6$): δ [ppm]=13.84-12.84 (m, 2H), 10.51 (s, 1H), 8.56-8.08 (m, 1H), 7.91 (s, 1H), 7.77-7.63 (m, 5H), 7.59 (dd, 1H), 7.35 (td, 1H), 4.85-4.54 (m, 1H), 1.15 (s, 6H).

LC-MS (Method 8): $R_t$=0.90 min; MS (ESIpos) m/z=474.2 [M+H]$^+$.

Example 224

$N^4$-{4-[(2-chloro-4-fluorobenzoyl)amino]phenyl}-$N^5$-[2-(4,4-difluoropiperidin-1-yl)ethyl]-1H-imidazole-4,5-dicarboxamide

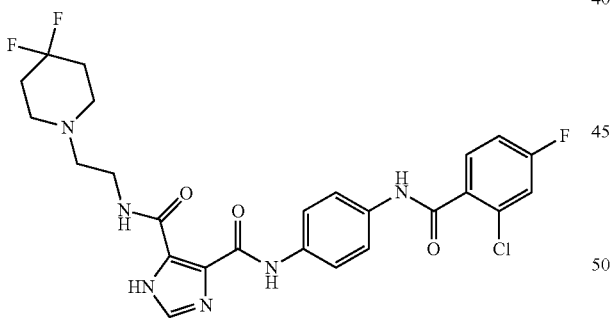

Was prepared in analogy to the synthesis of $N^4$-{4-[(2-chloro-4-fluorobenzoyl)amino]phenyl}-$N^5$-(2-hydroxy-2-methylpropyl)-1H-imidazole-4,5-dicarboxamide (Example 223) using 132 mg (0.800 mmol) 2-(4,4-difluoropiperidin-1-yl)ethanamine (Intermediate 057) and preparative HPLC to give the title compound (185 mg).

$^{1}$H-NMR (300 MHz, DMSO-$d_6$): δ [ppm]=13.55 (br. s., 1H), 13.36 (br. s., 1H), 10.51 (s, 1H), 8.73 (br. s., 1H), 7.92 (s, 1H), 7.80-7.62 (m, 5H), 7.62-7.53 (m, 1H), 7.45-7.24 (m, 1H), 3.55-3.38 (m, 2H), 2.63-2.53 (m, 6H), 2.06-1.82 (m, 4H).

LC-MS (Method 8): $R_t$=1.09 min; MS (ESIpos) m/z=549.3 [M+H]$^+$.

Example 225

$N^4$-{4-[(2-chloro-4-fluorobenzoyl)amino]phenyl}-$N^5$-[2-(3,3-difluoropiperidin-1-yl)ethyl]-1H-imidazole-4,5-dicarboxamide

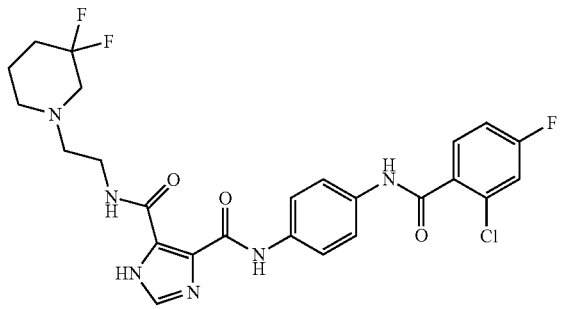 [SMILES: O=C(Nc1ccc(NC(=O)c2nc[nH]c2C(=O)NCCN2CCCC(F)(F)C2)cc1)c1ccc(F)cc1Cl]

Was prepared in analogy to the synthesis of $N^4$-{4-[(2-chloro-4-fluorobenzoyl)amino]phenyl}-$N^5$-(2-hydroxy-2-methylpropyl)-1H-imidazole-4,5-dicarboxamide (Example 223) using 78.8 mg (0.480 mmol) 2-(3,3-difluoropiperidin-1-yl)ethanamine (Intermediate 063) and preparative HPLC followed by recrystallization from ethyl acetate to give the title compound (52 mg).

$^{1}$H-NMR (400 MHz, DMSO-$d_6$): δ [ppm]=13.57 (br. s., 1H), 13.43 (br. s., 1H), 10.52 (s, 1H), 8.71 (br. s., 1H), 7.93 (s, 1H), 7.80-7.64 (m, 5H), 7.63-7.47 (m, 1H), 7.42-7.28 (m, 1H), 3.56-3.40 (m, 2H), 2.82-2.55 (m, 4H), 1.94-1.78 (m, 2H), 1.75-1.57 (m, 2H).

LC-MS (Method 8): $R_t$=1.10 min; MS (ESIpos) m/z=549.3 [M+H]$^+$.

Example 226

$N^4$-{4-[(2-chloro-4-fluorobenzoyl)amino]phenyl}-$N^5$-[2-(3-fluoropiperidin-1-yl)ethyl]-1H-imidazole-4,5-dicarboxamide

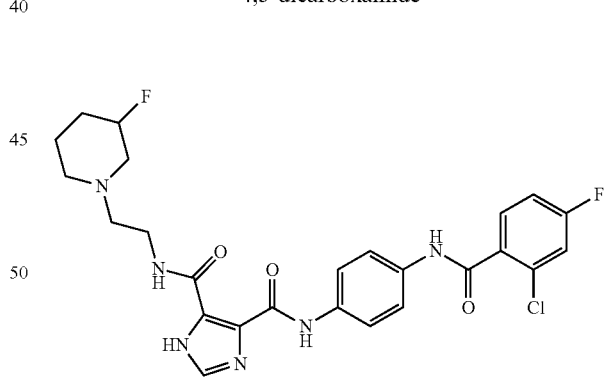

Was prepared in analogy to the synthesis of $N^4$-{4-[(2-chloro-4-fluorobenzoyl)amino]phenyl}-$N^5$-(2-hydroxy-2-methylpropyl)-1H-imidazole-4,5-dicarboxamide (Example 223) using 70.2 mg (0.480 mmol) 2-(3-fluoropiperidin-1-yl)ethanamine (Intermediate 060) and preparative HPLC to give the title compound (43.0 mg).

$^{1}$H-NMR (400 MHz, DMSO-$d_6$): δ [ppm]=13.60-13.00 (m, 2H), 10.49 (s, 1H), 8.89-9.00-8.40 (m, 1H), 7.91 (s, 1H), 7.76-7.63 (m, 5H), 7.61-7.51 (m, 1H), 7.40-7.27 (m, 1H), 4.80-4.53 (m, 1H), 3.52-3.38 (m, 2H), 2.65-2.55 (m, 2H), 2.54-2.52 (m, 2H), 2.41-2.29 (m, 2H), 1.93-1.77 (m, 2H), 1.77-1.63 (m, 2H).

Example 227

N⁴-{4-[(2-chloro-4-fluorobenzoyl)amino]phenyl}-N⁵-[2-(morpholin-4-yl)ethyl]-1H-imidazole-4,5-dicarboxamide

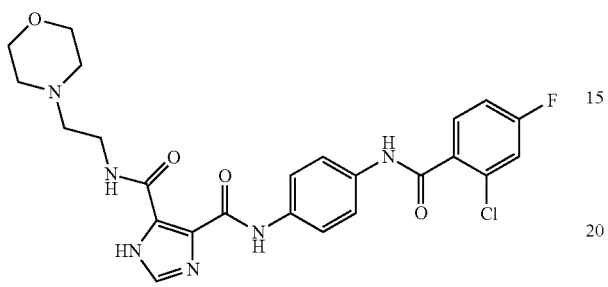

Was prepared in analogy to the synthesis of N⁴-{4-[(2-chloro-4-fluorobenzoyl)amino]phenyl}-N⁵-(2-hydroxy-2-methylpropyl)-1H-imidazole-4,5-dicarboxamide (Example 223) using 62.5 mg (0.480 mmol) 2-(morpholin-4-yl)ethanamine (CAS No. 2038-03-1) and preparative HPLC to give the title compound (31.0 mg).

¹H-NMR (400 MHz, DMSO-$d_6$): δ [ppm]=13.56 (br. s., 1H), 13.36 (br. s., 1H), 10.49 (s, 1H), 8.68 (br. s., 1H), 7.92 (s, 1H), 7.79-7.61 (m, 5H), 7.61-7.51 (m, 1H), 7.40-7.26 (m, 1H), 3.64-3.53 (m, 4H), 3.53-3.40 (m, 2H), 2.46-2.39 (m, 4H).

LC-MS (Method 8): $R_t$=0.90 min; MS (ESIpos) m/z=515.2 [M+H]⁺.

Example 228

N⁴-{4-[(2-chloro-4-fluorobenzoyl)amino]phenyl}-N⁵-[2-(pyrrolidin-1-yl)ethyl]-1H-imidazole-4,5-dicarboxamide

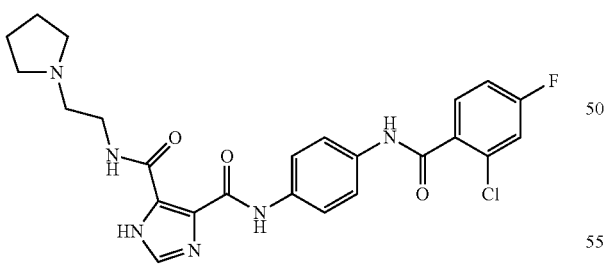

Was prepared in analogy to the synthesis of N⁴-{4-[(2-chloro-4-fluorobenzoyl)amino]phenyl}-N⁵-(2-hydroxy-2-methylpropyl)-1H-imidazole-4, 5-dicarboxamide (Example 223) using 171 mg (1.50 mmol) 2-(pyrrolidin-1-yl)ethanamine (CAS No. 7154-73-6). For work-up solids were filtrated of and washed with THF. The filtrate was concentrated and the residue was purified by flash chromatography (silica gel, dichloromethane/2-propanol 9:1+1% ammonia 7 N in methanol) followed by recrystallization from methanol to give the title compound (72.0 mg).

¹H-NMR (400 MHz, DMSO-$d_6$): δ [ppm]=13.80-13.25 (m, 2H), 10.52 (s, 1H), 9.16-8.38 (m, 1H), 7.91 (s, 1H), 7.76-7.65 (m, 5H), 7.59 (dd, 1H), 7.35 (td, 1H), 3.46 (q, 2H), 2.62 (t, 2H), 1.76-1.61 (m, 4H).

LC-MS (Method 7): $R_t$=0.85 min; MS (ESIpos) m/z=499.2 [M+H]⁺.

Example 229

N⁴-{4-[(2-chloro-4-fluorobenzoyl)amino]phenyl}-N⁵-[2-(3-hydroxypiperidin-1-yl)ethyl]-1H-imidazole-4,5-dicarboxamide

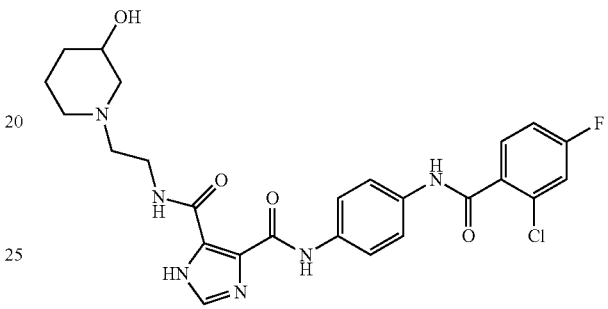

Was prepared in analogy to the synthesis of N⁴-{4-[(2-chloro-4-fluorobenzoyl)amino]phenyl}-N⁵-(2-hydroxy-2-methylpropyl)-1H-imidazole-4, 5-dicarboxamide (Example 223) using 260 mg (1.80 mmol) 1-(2-aminoethyl)piperidin-3-ol (CAS No. 847499-95-0) and preparative HPLC to give the title compound (172 mg).

¹H-NMR (400 MHz, DMSO-$d_6$): δ [ppm]=13.80-12.90 (m, 2H), 10.52 (s, 1H), 9.27-8.26 (m, 1H), 7.93 (s, 1H), 7.80-7.65 (m, 5H), 7.60 (dd, 1H), 7.36 (td, 1H), 4.60 (d, 1H), 3.55-3.39 (m, 3H), 2.94-2.80 (m, 1H), 2.79-2.70 (m, 1H), 2.57-2.54 (m, 1H), 1.99-1.86 (m, 1H), 1.86-1.73 (m, 2H), 1.69-1.54 (m, 1H), 1.50-1.33 (m, 1H), 1.16-0.99 (m, 1H).

LC-MS (Method 8): $R_t$=0.93 min; MS (ESIpos) m/z=529.3 [M+H]⁺.

Example 230

N⁴-{4-[(2-chloro-4-fluorobenzoyl)amino]phenyl}-N⁵-[2-(4-fluoropiperidin-1-yl)ethyl]-1H-imidazole-4,5-dicarboxamide

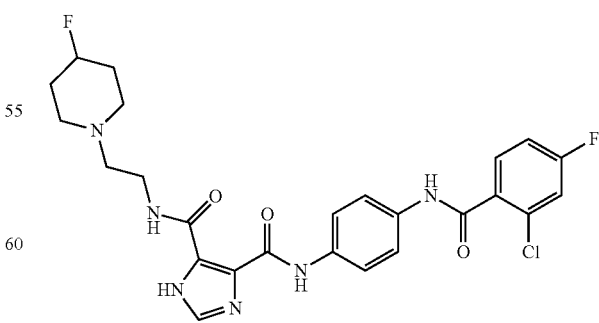

Was prepared in analogy to the synthesis of N⁴-{4-[(2-chloro-4-fluorobenzoyl)amino]phenyl}-N⁵-(2-hydroxy-2-methylpropyl)-1H-imidazole-4,5-dicarboxamide (Example 223) using 70.2 mg (0.480 mmol) 2-(4-fluoropiperidin-1-yl)ethanamine (Intermediate 070) and preparative HPLC followed by recrystallization from ethyl acetate to give the title compound (8.0 mg).

$^1$H-NMR (400 MHz, DMSO-$d_6$): δ [ppm]=13.60 (s, 1H), 13.45 (br. s., 1H), 10.52 (s, 1H), 8.76-8.61 (m, 1H), 7.94 (s, 1H), 7.77-7.64 (m, 5H), 7.64-7.56 (m, 1H), 7.41-7.30 (m, 1H), 4.74-4.62 (m, 1H), 3.54-3.40 (m, 2H), 2.94-2.75 (m, 1H), 2.63-2.54 (m, 3H), 2.46-2.21 (m, 2H), 1.95-1.77 (m, 1H), 1.77-1.66 (m, 1H), 1.60-1.38 (m, 2H).

LC-MS (Method 8): $R_t$=1.09 min; MS (ESIpos) m/z=531.3 [M+H]$^+$.

Example 231

$N^4$-{4-[(2-chloro-4-fluorobenzoyl)amino]phenyl}-$N^5$-{2-[(3R)-3-fluoropyrrolidin-1-yl]ethyl}-1H-imidazole-4,5-dicarboxamide

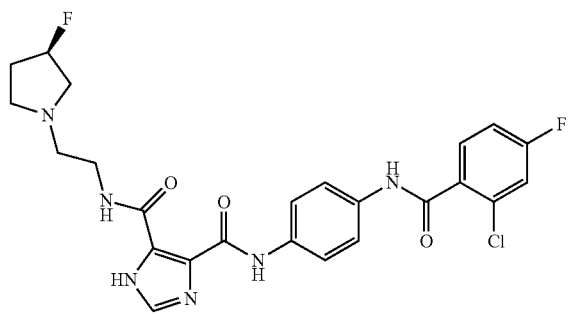 [SMILES: O=C(Nc1ccc(NC(=O)c2nc[nH]c2C(=O)NCCN2CC[C@@H](F)C2)cc1)c1ccc(F)cc1Cl]

Was prepared in analogy to the synthesis of $N^4$-{4-[(2-chloro-4-fluorobenzoyl)amino]phenyl}-$N^5$-(2-hydroxy-2-methylpropyl)-1H-imidazole-4,5-dicarboxamide (Example 223) using 80.9 mg (0.60 mmol) 2-[(3R)-3-fluoropyrrolidin-1-yl]ethanamine (Intermediate 062) and preparative HPLC to give the title compound (10.0 mg).

$^1$H-NMR (400 MHz, DMSO-$d_6$): δ [ppm]=13.56 (br. s., 1H), 13.33 (br. s., 1H), 10.49 (s, 1H), 8.71 (br. s., 1H), 7.90 (s, 1H), 7.78-7.62 (m, 5H), 7.57 (dd, 1H), 7.34 (td, 1H), 5.30-5.07 (m, 1H), 3.56-3.37 (m, 2H), 2.95-2.77 (m, 2H), 2.73-2.61 (m, 3H), 2.43-2.33 (m, 1H), 2.23-1.99 (m, 1H), 1.96-1.72 (m, 1H).

LC-MS (Method 8): $R_t$=1.02 min; MS (ESIpos) m/z=517.3 [M+H]$^+$.

Example 232

$N^4$-{4-[(2-chloro-4-fluorobenzoyl)amino]phenyl}-$N^5$-{2-[(3S)-3-fluoropyrrolidin-1-yl]ethyl}-1H-imidazole-4,5-dicarboxamide

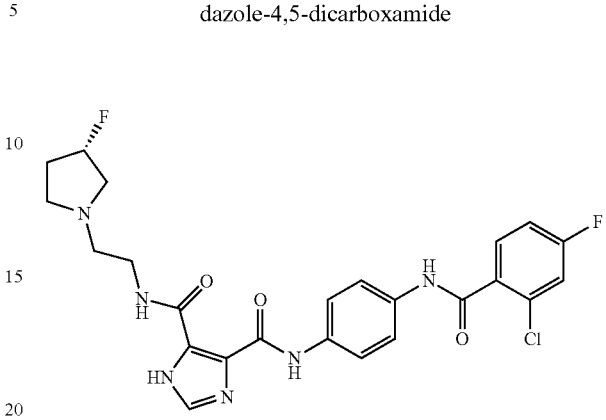

Was prepared in analogy to the synthesis of $N^4$-{4-[(2-chloro-4-fluorobenzoyl)amino]phenyl}-$N^5$-(2-hydroxy-2-methylpropyl)-1H-imidazole-4,5-dicarboxamide (Example 223) using 80.9 mg (0.60 mmol) 2-[(3S)-3-fluoropyrrolidin-1-yl]ethanamine (Intermediate 061) and preparative HPLC to give the title compound (10.0 mg).

$^1$H-NMR (400 MHz, DMSO-$d_6$): δ [ppm]=13.74-13.10 (m, 2H), 10.52 (s, 1H), 8.73 (br. s., 1H), 7.93 (s, 1H), 7.78-7.64 (m, 5H), 7.64-7.55 (m, 1H), 7.42-7.30 (m, 1H), 5.35-5.02 (m, 1H), 3.50-3.45 (m, 2H), 2.95-2.80 (m, 2H), 2.73-2.66 (m, 3H), 2.42-2.34 (m, 1H), 2.22-2.03 (m, 1H), 1.97-1.78 (m, 1H).

LC-MS (Method 8): $R_t$=1.02 min; MS (ESIpos) m/z=517.3 [M+H]$^+$.

Example 233

$N^4$-{4-[(2-chloro-4-fluorobenzoyl)amino]phenyl}-$N^5$-(tetrahydro-2H-pyran-4-ylmethyl)-1H-imidazole-4,5-dicarboxamide

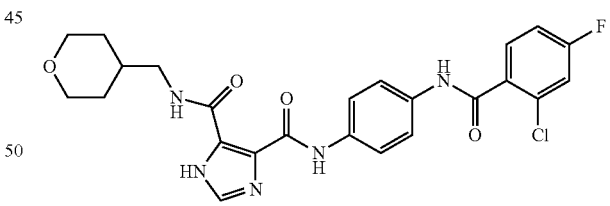

Was prepared in analogy to the synthesis of $N^4$-{4-[(2-chloro-4-fluorobenzoyl)amino]phenyl}-$N^5$-(2-hydroxy-2-methylpropyl)-1H-imidazole-4, 5-dicarboxamide (Example 223) using 70.5 mg (0.60 mmol) 1-(tetrahydro-2H-pyran-4-yl)methanamine (CAS No. 130290-79-8) with N,N-diisopropylethylamine as base and preparative HPLC to give the title compound (4.0 mg).

$^1$H-NMR (400 MHz, DMSO-$d_6$): δ [ppm]=13.57 (br. s., 1H), 13.38 (br. s., 1H), 10.50 (s, 1H), 8.84 (br. s., 1H), 7.91 (s, 1H), 7.78-7.62 (m, 5H), 7.57 (dd, 1H), 7.34 (td, 1H), 3.88-3.77 (m, 2H), 3.27-3.21 (m, 3H), 2.56-2.53 (m, 1H), 1.96-1.71 (m, 1H), 1.65-1.52 (m, 2H), 1.31-1.15 (m, 2H).

LC-MS (Method 8): $R_t$=1.01 min; MS (ESIpos) m/z=500.2 [M+H]$^+$.

Example 234

N⁴-{4-[(2-chloro-4-fluorobenzoyl)amino]phenyl}-N⁵-(tetrahydro-2H-pyran-4-yl)-1H-imidazole-4,5-dicarboxamide

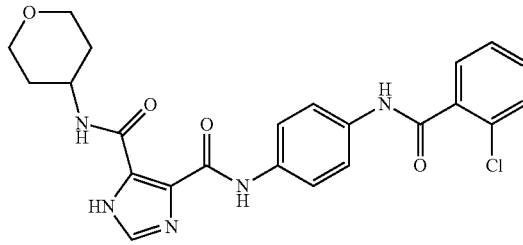

Was prepared in analogy to the synthesis of N⁴-{4-[(2-chloro-4-fluorobenzoyl)amino]phenyl}-N⁵-(2-hydroxy-2-methylpropyl)-1H-imidazole-4, 5-dicarboxamide (Example 223) using 62.6 mg (0.60 mmol) tetrahydro-2H-pyran-4-amine (CAS No. 38041-19-9) with N,N-diisopropylethylamine as base and preparative HPLC to give the title compound (12.0 mg).

¹H-NMR (400 MHz, DMSO-d₆): δ [ppm]=13.58 (br. s., 1H), 13.44 (br. s., 1H), 10.52 (s, 1H), 8.72 (d, 1H), 7.94 (s, 1H), 7.77 (br. s., 1H), 7.74-7.64 (m, 4H), 7.60 (dd, 1H), 7.36 (td, 1H), 4.20-3.96 (m, 1H), 3.94-3.80 (m, 2H), 3.50-3.37 (m, 2H), 1.83-1.66 (m, 3H), 0.97 (br. s., 1H).

LC-MS (Method 8): R$_t$=0.97 min; MS (ESIpos) m/z=486.2 [M+H]⁺.

Example 235

N⁴-{4-[(2-chloro-4-fluorobenzoyl)amino]phenyl}-N⁵-(tetrahydrofuran-3-ylmethyl)-1H-imidazole-4,5-dicarboxamide

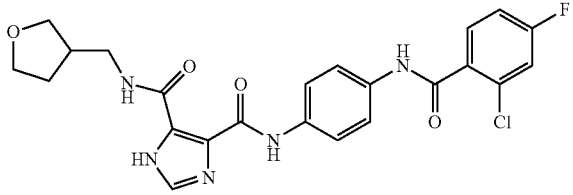 [SMILES: O=C(Nc1ccc(NC(=O)c2nc[nH]c2C(=O)NCC2CCOC2)cc1)c1ccc(F)cc1Cl]

Was prepared in analogy to the synthesis of N⁴-{4-[(2-chloro-4-fluorobenzoyl)amino]phenyl}-N⁵-(2-hydroxy-2-methylpropyl)-1H-imidazole-4, 5-dicarboxamide (Example 223) using 62.6 mg (0.60 mmol) 1-(tetrahydrofuran-3-yl)methanamine (CAS No. 165253-31-6) with N,N-diisopropylethylamine as base and preparative HPLC followed by recrystallization from methanol to give the title compound (12.0 mg).

¹H-NMR (400 MHz, DMSO-d₆): δ [ppm]=13.88-13.21 (m, 2H), 10.52 (s, 1H), 9.29-8.73 (m, 1H), 7.93 (s, 1H), 7.78-7.65 (m, 5H), 7.60 (dd, 1H), 7.36 (td, 1H), 3.82-3.67 (m, 2H), 3.67-3.59 (m, 1H), 3.54-3.44 (m, 1H), 3.38-3.35 (m, 2H), 2.61-2.54 (m, 1H), 2.05-1.89 (m, 1H), 1.70-1.58 (m, 1H).

LC-MS (Method 8): R$_t$=0.97 min; MS (ESIpos) m/z=486.2 [M+H]⁺.

Example 236

N⁴-{4-[(2-chloro-4-fluorobenzoyl)amino]phenyl}-N⁵-(tetrahydrofuran-3-yl)-1H-imidazole-4,5-dicarboxamide

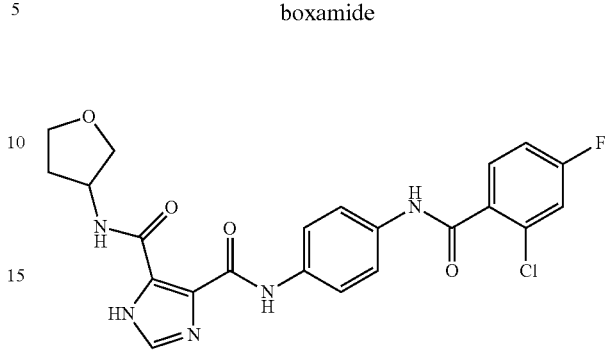

Was prepared in analogy to the synthesis of N⁴-{4-[(2-chloro-4-fluorobenzoyl)amino]phenyl}-N⁵-(2-hydroxy-2-methylpropyl)-1H-imidazole-4,5-dicarboxamide (Example 223) using 53.9 mg (0.60 mmol) tetrahydrofuran-3-amine (CAS No. 88675-24-5) with N,N-diisopropylethylamine as base and preparative HPLC followed by recrystallization from methanol to give the title compound (8.0 mg).

¹H-NMR (400 MHz, DMSO-d₆): δ [ppm]=13.43 (br. s., 2H), 10.50 (s, 1H), 8.75 (br. s., 1H), 8.00-7.87 (m, 1H), 7.83-7.62 (m, 5H), 7.57 (dd, 1H), 7.34 (td, 1H), 4.65-4.37 (m, 1H), 3.95-3.80 (m, 2H), 3.80-3.68 (m, 1H), 3.68-3.53 (m, 1H), 2.26-2.10 (m, 1H), 2.10-1.96 (m, 1H).

LC-MS (Method 8): R$_t$=0.93 min; MS (ESIpos) m/z=472.2 [M+H]⁺.

Example 237

N⁴-{4-[(2-chloro-4-fluorobenzoyl)amino]phenyl}-N⁵-(tetrahydrofuran-2-ylmethyl)-1H-imidazole-4,5-dicarboxamide

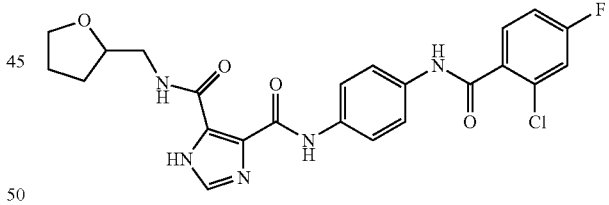

Was prepared in analogy to the synthesis of N⁴-{4-[(2-chloro-4-fluorobenzoyl)amino]phenyl}-N⁵-(2-hydroxy-2-methylpropyl)-1H-imidazole-4, 5-dicarboxamide (Example 223) using 61.9 mg (0.600 mmol) 1-(tetrahydrofuran-2-yl)methanamine (CAS No. 4795-29-3) with N,N-diisopropylethylamine as base and preparative HPLC followed by recrystallization from methanol to give the title compound (26.0 mg).

¹H-NMR (400 MHz, DMSO-d₆): δ [ppm]=13.80-13.12 (m, 2H), 10.52 (s, 1H), 8.97-8.43 (m, 1H), 7.92 (s, 1H), 7.77-7.64 (m, 5H), 7.59 (dd, 1H), 7.36 (td, 1H), 4.14-3.97 (m, 1H), 3.85-3.73 (m, 1H), 3.71-3.58 (m, 1H), 3.45-3.40 (m, 2H), 1.98-1.89 (m, 1H), 1.89-1.72 (m, 2H), 1.68-1.53 (m, 1H).

LC-MS (Method 8): R$_t$=1.03 min; MS (ESIpos) m/z=486.2 [M+H]⁺.

Example 238

N⁴-{4-[(2-chloro-4-fluorobenzoyl)amino]phenyl}-N⁵-[2-(4-methylpiperazin-1-yl)ethyl]-1H-imidazole-4,5-dicarboxamide

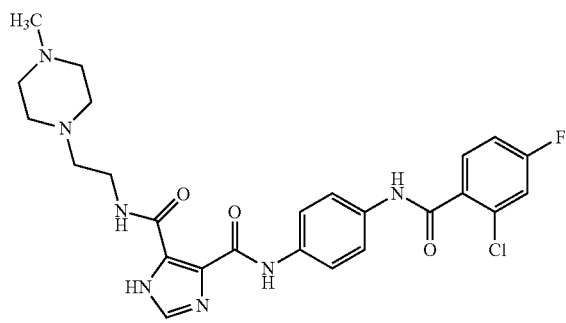 [SMILES: CN1CCN(CCNC(=O)c2[nH]cnc2C(=O)Nc2ccc(NC(=O)c3ccc(F)cc3Cl)cc2)CC1]

Was prepared in analogy to the synthesis of N⁴-{4-[(2-chloro-4-fluorobenzoyl)amino]phenyl}-N⁵-(2-hydroxy-2-methylpropyl)-1H-imidazole-4, 5-dicarboxamide (Example 223) using 206 mg (1.44 mmol) 2-(4-methylpiperazin-1-yl)ethanamine (CAS No. 934-98-5) with N,N-diisopropylethylamine as base. For work-up the reaction mixture was concentrated and the residue was recrystallized from methanol followed by preparative HPLC to give the title compound (112 mg).

¹H-NMR (400 MHz, DMSO-d₆): δ [ppm]=13.76-13.27 (m, 2H), 10.51 (s, 1H), 8.78-8.45 (m, 1H), 7.92 (s, 1H), 7.81-7.64 (m, 5H), 7.59 (dd, 1H), 7.35 (td, 1H), 3.46 (q, 2H), 2.46-2.22 (m, 6H), 2.15 (s, 3H).

LC-MS (Method 8): $R_t$=0.89 min; MS (ESIpos) m/z=528.3 [M+H]⁺.

Example 239

N⁵-{4-[(2-hydroxybenzoyl)amino]phenyl}-N⁴-methyl-1H-imidazole-4,5-dicarboxamide

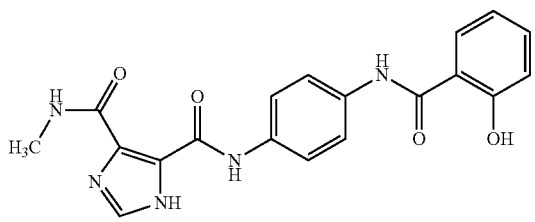 [SMILES: CNC(=O)c1nc[nH]c1C(=O)Nc1ccc(NC(=O)c2ccccc2O)cc1]

214 mg (0.562 mmol, 1.4 equiv.) HATU was added to a mixture of 104 mg (0.401 mmol, 1.0 equiv.) N⁵-(4-aminophenyl)-N⁴-methyl-1H-imidazole-4,5-dicarboxamide (Intermediate 003), 72.0 mg (0.521 mmol, 1.3 equiv.) 2-hydroxybenzoic acid and 279 μL (1.61 mmol, 4.0 equiv.) N,N-diisopropylethylamine in 2.3 mL DMF and the mixture was stirred at room temperature overnight. Water was added, the precipitate collected by filtration and purified by preparative HPLC to give the title compound (21.8 mg).

¹H-NMR (400 MHz, DMSO-d6) delta [ppm]: 1.907 (0.49), 2.073 (2.73), 2.085 (1.14), 2.318 (0.61), 2.323 (1.38), 2.327 (1.90), 2.331 (1.38), 2.337 (0.64), 2.523 (5.22), 2.540 (0.74), 2.659 (0.64), 2.665 (1.41), 2.669 (1.90), 2.674 (1.35), 2.678 (0.64), 2.867 (8.08), 2.879 (8.75), 6.932 (1.44), 6.951 (2.95), 6.958 (3.65), 6.970 (1.93), 6.978 (3.75), 7.410 (1.60), 7.414 (1.66), 7.428 (1.97), 7.431 (2.67), 7.435 (1.90), 7.448 (1.38), 7.453 (1.44), 7.693 (0.92), 7.716 (16.00), 7.741 (0.74), 7.927 (11.45), 7.966 (2.27), 7.970 (2.40), 7.985 (2.24), 7.990 (2.03), 8.832 (1.29), 8.844 (1.29), 10.509 (0.55), 11.908 (0.49), 13.433 (1.63), 13.711 (3.59).

LC-MS (Method 8): $R_t$=0.50 min; MS (ESIpos) m/z=380.2 [M+H]⁺.

Example 240

N⁵-{4-[(2-chloro-4,5-dimethoxybenzoyl)amino]phenyl}-N⁴-methyl-1H-imidazole-4,5-dicarboxamide

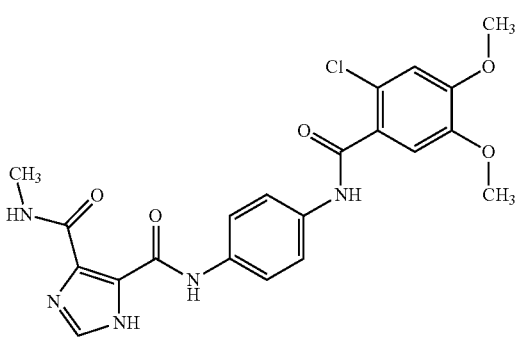

0.34 mL (0.58 mmol, 1.5 equiv., 50% solution in DMF) 1-propanephosphonic anhydride (T₃P) was added to a mixture of 100 mg (0.386 mmol, 1.0 equiv.) N⁵-(4-aminophenyl)-N⁴-methyl-1H-imidazole-4,5-dicarboxamide (Intermediate 003), 109 mg (0.501 mmol, 1.3 equiv.) 2-chloro-4,5-dimethoxybenzoic acid (CAS No. 60032-95-3) and 0.35 mL (1.9 mmol, 5.0 equiv.) N,N-diisopropylethylamine in 2.5 mL DMF and the mixture was stirred at room temperature overnight. The reaction mixture was concentrated and the residue was purified by preparative HPLC to give the title compound (45.5 mg).

¹H-NMR (400 MHz, DMSO-d₆): δ [ppm]=13.67 (br. s., 1H), 13.31-12.08 (m, 1H), 10.36 (s, 1H), 8.84 (br. s., 1H), 7.93 (s, 1H), 7.83-7.60 (m, 4H), 7.18 (s, 1H), 7.12 (s, 1H), 3.84 (s, 3H), 3.82 (s, 3H), 2.88 (d, 3H).

LC-MS (Method 8): $R_t$=0.87 min; MS (ESIpos) m/z=458.2 [M+H]⁺.

Example 241

N⁵-(4-{[2-(difluoromethyl)benzoyl]amino}phenyl)-N⁴-methyl-1H-imidazole-4,5-dicarboxamide

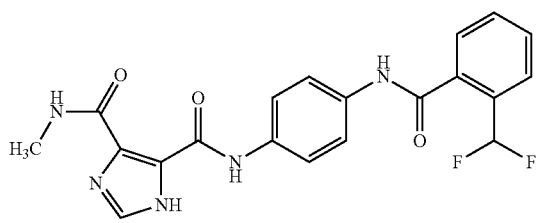 [SMILES: CNC(=O)c1nc[nH]c1C(=O)Nc1ccc(NC(=O)c2ccccc2C(F)F)cc1]

0.33 mL (0.56 mmol, 1.4 equiv., 50% solution in DMF) 1-propanephosphonic anhydride (T3P) was added to a mixture of 104 mg (0.401 mmol, 1.0 equiv.) $N^5$-(4-aminophenyl)-$N^4$-methyl-1H-imidazole-4,5-dicarboxamide (Intermediate 003), 89.8 mg (0.521 mmol, 1.3 equiv.) 2-(difluoromethyl)benzoic acid (CAS No. 799814-32-7) and 0.28 mL (1.6 mmol, 4.0 equiv) N,N-diisopropylethylamine in 3.0 mL DMF and the mixture was stirred at room temperature overnight. Water and a mixture of dichloromethane/2-propanol 4:1 were added. The precipitate was collected by filtration and recrystallized from water/methanol to yield the title compound (58.0 mg).

$^1$H-NMR (400 MHz, DMSO-$d_6$): δ [ppm]=13.00-13.00 (m, 2H), 10.58 (s, 1H), 9.21-8.56 (m, 1H), 7.93 (s, 1H), 7.83-7.62 (m, 8H), 7.34 (t, 1H), 2.88 (d, 3H).

LC-MS (Method 8): $R_t$=0.91 min; MS (ESIpos) m/z=414.2 [M+H]$^+$.

Example 242

$N^5$-{4-[(2-chloro-4,5-difluorobenzoyl)amino]phenyl}-$N^4$-methyl-1H-imidazole-4,5-dicarboxamide

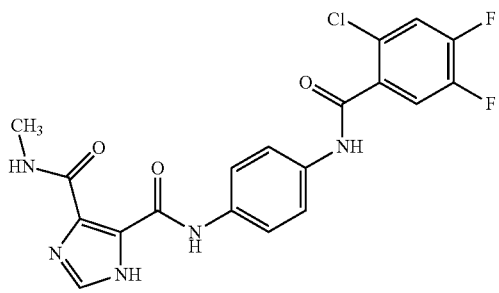 [SMILES: CNC(=O)c1nc[nH]c1C(=O)Nc1ccc(NC(=O)c2cc(F)c(F)cc2Cl)cc1]

537 mg (2.55 mmol) 2-chloro-4,5-difluorobenzoyl chloride (CAS No. 121872-95-5) was added to a solution of 600 mg (2.31 mmol) $N^5$-(4-aminophenyl)-$N^4$-methyl-1H-imidazole-4,5-dicarboxamide (Intermediate 003) in 15 mL of pyridine and the mixture was stirred at room temperature for 12 h. Water was added, the precipitate was collected by filtration and washed with water and methanol. The crude product was recrystallized several times from water/methanol to give the title compound (676 mg).

$^1$H-NMR (400 MHz, DMSO-$d_6$): δ [ppm]=13.96-12.88 (m, 2H), 10.57 (s, 1H), 9.52-8.42 (m, 1H), 7.94-7.83 (m, 3H), 7.75-7.66 (m, 4H), 2.86 (d, 3H).

LC-MS (Method 8): $R_t$=0.96 min; MS (ESIpos) m/z=434.2 [M+H]$^+$.

Example 243

$N^4$-methyl-$N^5$-(4-{[2-(trifluoromethoxy)benzoyl]amino}phenyl)-1H-imidazole-4,5-dicarboxamide

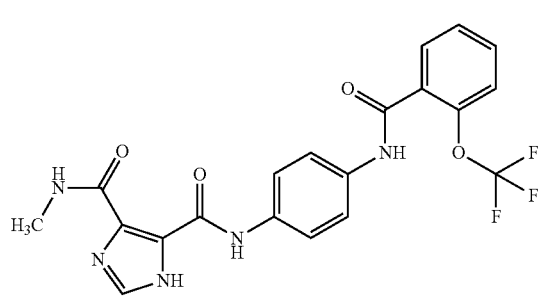 [SMILES: CNC(=O)c1nc[nH]c1C(=O)Nc1ccc(NC(=O)c2ccccc2OC(F)(F)F)cc1]

89.8 mg (0.550 mmol) 2-(trifluoromethoxy)benzoyl chloride (CAS No. 162046-61-9) was added to a solution of 104 mg (0.400 mmol) $N^5$-(4-aminophenyl)-$N^4$-methyl-1H-imidazole-4,5-dicarboxamide (Intermediate 003) in 2.6 mL pyridine and the mixture was stirred at room temperature overnight. Water was added, the precipitate was collected by filtration, washed with water and methanol and dried under high vacuum to give the title compound (111 mg).

$^1$H-NMR (400 MHz, DMSO-$d_6$): δ [ppm]=13.86-13.51 (m, 1H), 13.51-13.19 (m, 1H), 10.47 (s, 1H), 9.20-8.44 (m, 1H), 7.90 (s, 1H), 7.73-7.67 (m, 5H), 7.64 (td, 1H), 7.56-7.45 (m, 2H), 2.86 (d, 3H).

LC-MS (Method 8): $R_t$=0.97 min; MS (ESIpos) m/z=448.2 [M+H]$^+$.

Example 244

$N^5$-{4-[(2-chloro-4-methylbenzoyl)amino]phenyl}-$N^4$-methyl-1H-imidazole-4, 5-dicarboxamide

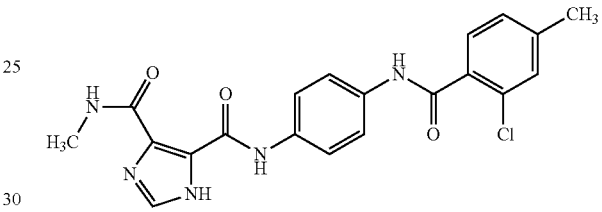

Was prepared in analogy to the synthesis of $N^5$-(4-{[2-(difluoromethyl)benzoyl]amino}phenyl)-$N^4$-methyl-1H-imidazole-4,5-dicarboxamide (Example 241) using 88.9 mg (0.521 mmol) 2-chloro-4-methylbenzoic acid (CAS No. 7697-25-8). For work-up, water was added and the precipitate was collected by filtration, washed with methanol and dried to give the title compound (61.0 mg).

$^1$H-NMR (500 MHz, DMSO-$d_6$): δ [ppm]=13.80-13.53 (m, 1H), 13.40 (br. s., 1H), 10.40 (s, 1H), 8.99-8.64 (m, 1H), 7.93-7.89 (m, 1H), 7.73-7.65 (m, 4H), 7.46 (d, 1H), 7.39 (s, 1H), 7.25 (d, 1H), 2.86 (d, 3H), 2.36 (s, 3H).

LC-MS (Method 8): $R_t$=0.96 min; MS (ESIpos) m/z=412.2 [M+H]$^+$.

Example 245

$N^5$-{4-[(4-fluoro-2-hydroxybenzoyl)amino]phenyl}-$N^4$-methyl-1H-imidazole-4, 5-dicarboxamide

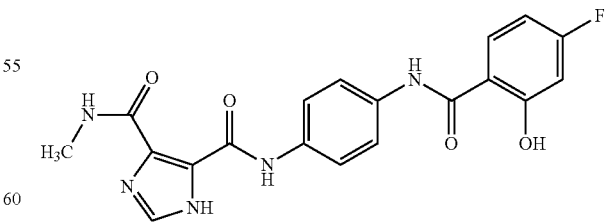

292 mg (0.562 mmol, 1.4 equiv.) PyBOP was added to a mixture of 104 mg (0.401 mmol, 1.0 equiv.) $N^5$-(4-aminophenyl)-$N^4$-methyl-1H-imidazole-4,5-dicarboxamide (Intermediate 003), 81.4 mg (0.521 mmol, 1.3 equiv.) 4-fluoro-2-hydroxybenzoic acid and 279 μL (1.61 mmol, 4.0 equiv.)

N,N-diisopropylethylamine in 3.0 mL DMF and the mixture was stirred at room temperature overnight. Water was added and the mixture was extracted with a mixture of dichloromethane and 2-propanol 4:1 and the organic phase was dried and concentrated. The residue was combined with a second batch from similar reaction conditions and purified by preparative HPLC to give the title compound (53.0 mg)

$^1$H-NMR (400 MHz, DMSO-d$_6$): δ [ppm]=13.71 (s, 1H), 13.43 (s, 1H), 12.69-12.23 (m, 1H), 10.39 (s, 1H), 8.88-8.79 (m, 1H), 8.05 (dd, 1H), 7.93 (s, 1H), 7.86-7.61 (m, 4H), 6.87-6.72 (m, 2H), 2.91-2.83 (m, 3H).

LC-MS (Method 11): R$_t$=1.12 min; MS (ESIneg) m/z=396.1 [M−H].

Example 246

N$^5$-{4-[(2-chloro-4-methoxybenzoyl)amino]phenyl}-N$^4$-methyl-1H-imidazole-4,5-dicarboxamide

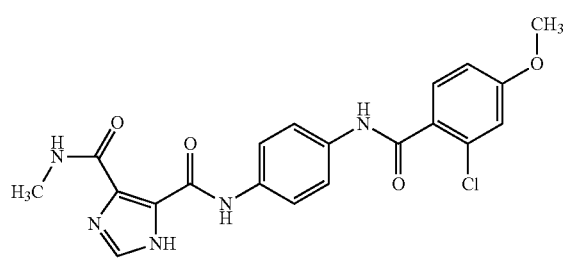

Was prepared in analogy to the synthesis of N$^5$-(4-{[2-(difluoromethyl)benzoyl]amino}phenyl)-N$^4$-methyl-1H-imidazole-4,5-dicarboxamide (Example 241) using 97.3 mg (0.521 mmol) 2-chloro-4-methoxybenzoic acid (CAS No. 21971-21-1). For work-up, water was added and the precipitate was collected by filtration, washed with methanol and purified by preparative HPLC to give the title compound (11.0 mg).

$^1$H-NMR (400 MHz, DMSO-d$_6$): δ [ppm]=13.85-13.50 (m, 1H), 13.50-13.20 (m, 1H), 10.38 (s, 1H), 9.06-8.65 (m, 1H), 7.92 (s, 1H), 7.78-7.62 (m, 4H), 7.54 (d, 1H), 7.14 (d, 1H), 7.02 (dd, 1H), 3.84 (s, 3H), 2.88 (d, 3H).

LC-MS (Method 8): R$_t$=0.93 min; MS (ESIpos) m/z=428.0 [M+H]$^+$.

Example 247

N$^5$-(4-{[(3-chloropyridin-2-yl)carbonyl]amino}phenyl)-N$^4$-methyl-1H-imidazole-4,5-dicarboxamide

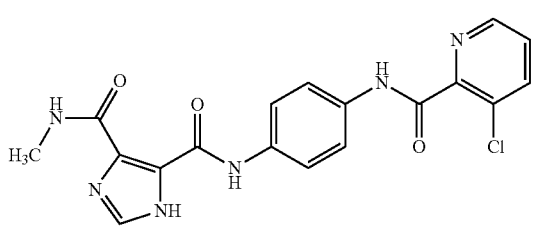 [SMILES: CNC(=O)c1nc[nH]c1C(=O)Nc1ccc(NC(=O)c2ncccc2Cl)cc1]

Was prepared in analogy to the synthesis of N$^5$-(4-{[2-(difluoromethyl)benzoyl]amino}phenyl)-N$^4$-methyl-1H-imidazole-4,5-dicarboxamide (Example 241) using 79.0 mg (0.501 mmol) 3-chloropyridine-2-carboxylic acid (CAS No. 57266-69-0). The reaction mixture was concentrated and the residue was purified by preparative HPLC to give the title compound (30.0 mg).

$^1$H-NMR (400 MHz, DMSO-d6) delta [ppm]: 1.100 (7.28), 1.131 (1.16), 1.751 (0.61), 2.076 (1.39), 2.110 (0.50), 2.472 (0.53), 2.535 (1.54), 2.862 (11.59), 2.874 (12.68), 7.585 (4.53), 7.597 (4.41), 7.606 (4.70), 7.617 (5.06), 7.693 (3.98), 7.715 (7.71), 7.756 (8.53), 7.778 (4.31), 7.798 (0.74), 7.800 (0.69), 7.821 (0.41), 7.927 (16.00), 7.939 (0.52), 8.092 (4.92), 8.096 (5.67), 8.113 (5.09), 8.117 (4.73), 8.614 (4.91), 8.618 (5.49), 8.626 (5.37), 8.630 (5.26), 8.827 (0.84), 8.840 (2.04), 8.853 (2.05), 8.865 (0.86), 10.675 (9.30), 13.444 (2.55), 13.707 (5.26).

LC-MS (Method 14) R$_t$=0.82 min; MS (ESIpos) m/z=399.15 [M+H]$^+$.

Example 248

N$^5$-{4-[(2-chloro-5-methoxybenzoyl)amino]phenyl}-N$^4$-methyl-1H-imidazole-4, 5-dicarboxamide

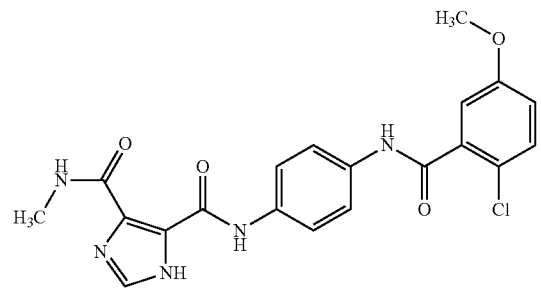 [SMILES: CNC(=O)c1nc[nH]c1C(=O)Nc1ccc(NC(=O)c2cc(OC)ccc2Cl)cc1]

Was prepared in analogy to the synthesis of N$^5$-(4-{[2-(difluoromethyl)benzoyl]amino}phenyl)-N$^4$-methyl-1H-imidazole-4,5-dicarboxamide (Example 241) using 70.2 mg (0.376 mmol) 2-chloro-5-methoxybenzoic acid (CAS No. 6280-89-3). The reaction mixture was concentrated and the residue was purified by preparative HPLC to give the title compound (30.0 mg).

$^1$H-NMR (400 MHz, DMSO-d$_6$): δ [ppm]=13.96-12.98 (m, 2H), 10.49 (s, 1H), 9.03-8.57 (m, 1H), 7.93 (s, 1H), 7.82-7.62 (m, 4H), 7.45 (d, 1H), 7.17-7.14 (m, 1H), 7.10-7.04 (m, 1H), 3.81 (s, 3H), 2.87 (d, 3H).

LC-MS (Method 14): R$_t$=0.91 min; MS (ESIpos) m/z=428.2 [M+H]$^+$.

Example 249

N$^4$-methyl-N$^5$-(4-{[2-(methylsulfonyl)benzoyl]amino}phenyl)-1H-imidazole-4,5-dicarboxamide

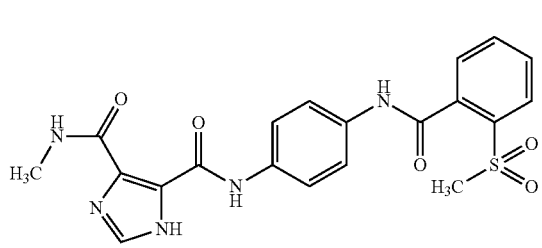 [SMILES: CNC(=O)c1nc[nH]c1C(=O)Nc1ccc(NC(=O)c2ccccc2S(C)(=O)=O)cc1]

Was prepared in analogy to the synthesis of N⁵-(4-{[2-(difluoromethyl)benzoyl]amino}phenyl)-N⁴-methyl-1H-imidazole-4,5-dicarboxamide (Example 241) using 75.3 mg (0.376 mmol) 2-(methylsulfonyl)benzoic acid (CAS No. 33963-55-2). The reaction mixture was concentrated and the residue was purified by preparative HPLC to give the title compound (30.0 mg).

¹H-NMR (400 MHz, DMSO-d₆): δ [ppm]=13.68 (s, 1H), 13.44 (br. s., 1H), 10.66 (br. s., 1H), 8.85 (d, 1H), 8.12-7.42 (m, 9H), 3.39 (s, 3H), 2.94-2.80 (m, 3H).

LC-MS (Method 13): $R_t$=0.99 min; MS (ESIpos) m/z=442.2 [M+H]⁺.

Example 250

N⁵-{4-[(2-chloro-4-ethoxybenzoyl)amino]phenyl}-N⁴-methyl-1H-imidazole-4,5-dicarboxamide

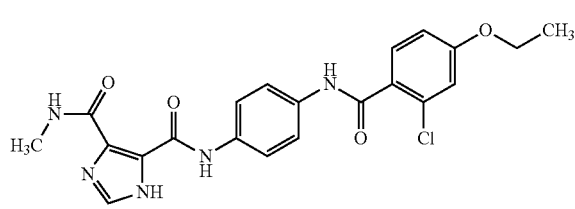 [SMILES: CCOc1ccc(C(=O)Nc2ccc(NC(=O)c3[nH]cnc3C(=O)NC)cc2)c(Cl)c1]

Was prepared in analogy to the synthesis of N⁵-(4-{[2-(difluoromethyl)benzoyl]amino}phenyl)-N⁴-methyl-1H-imidazole-4,5-dicarboxamide (Example 241) using 75.4 mg (0.376 mmol) 2-chloro-4-ethoxybenzoic acid (CAS No. 334018-28-9). The reaction mixture was concentrated and the residue was purified by preparative HPLC to give the title compound (29.0 mg).

¹H-NMR (400 MHz, DMSO-d6) delta [ppm]: 1.106 (8.32), 1.137 (0.72), 1.323 (7.47), 1.340 (16.00), 1.358 (7.94), 2.083 (4.04), 2.322 (0.50), 2.326 (0.69), 2.332 (0.53), 2.477 (0.77), 2.523 (3.88), 2.539 (0.69), 2.543 (0.60), 2.547 (0.47), 2.664 (0.52), 2.669 (0.72), 2.673 (0.56), 2.860 (8.37), 2.872 (9.46), 3.309 (0.60), 3.384 (0.84), 4.085 (2.21), 4.102 (7.24), 4.120 (7.11), 4.137 (2.27), 6.984 (2.59), 6.989 (2.85), 7.005 (2.66), 7.011 (3.17), 7.106 (5.88), 7.112 (5.52), 7.508 (5.59), 7.530 (5.01), 7.660 (2.24), 7.683 (5.51), 7.712 (5.78), 7.735 (2.61), 7.770 (0.52), 7.775 (0.47), 7.925 (14.00), 8.837 (1.42), 8.850 (1.48), 10.381 (6.26), 13.428 (1.50), 13.669 (3.64).

LC-MS (Method 13): $R_t$=1.30 min; MS (ESIpos) m/z=442.2 [M+H]⁺.

Example 251

N⁵-(4-{[4-(difluoromethoxy)-2-fluorobenzoyl]amino}phenyl)-N⁴-methyl-1H-imidazole-4,5-dicarboxamide

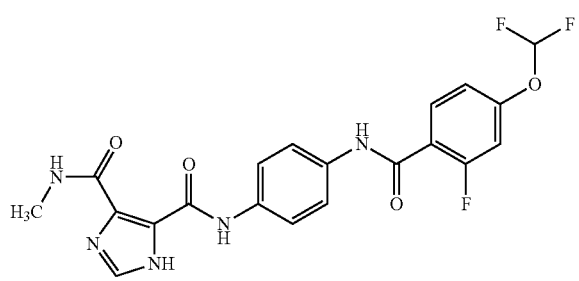 [SMILES: CNC(=O)c1nc[nH]c1C(=O)Nc1ccc(NC(=O)c2ccc(OC(F)F)cc2F)cc1]

Was prepared in analogy to the synthesis of N⁵-(4-{[2-(difluoromethyl)benzoyl]amino}phenyl)-N⁴-methyl-1H-imidazole-4,5-dicarboxamide (Example 241) using 77.5 mg (0.376 mmol) 4-(difluoromethoxy)-2-fluorobenzoic acid (CAS No. 1214347-60-0). The reaction mixture was concentrated and the residue was purified by preparative HPLC to give the title compound (13.0 mg).

¹H-NMR (400 MHz, DMSO-d6) delta [ppm]: 1.107 (1.03), 1.221 (0.65), 1.230 (0.65), 2.074 (8.43), 2.084 (2.86), 2.318 (0.49), 2.323 (1.14), 2.327 (1.57), 2.332 (1.14), 2.337 (0.54), 2.523 (4.81), 2.540 (0.65), 2.660 (0.49), 2.665 (1.14), 2.669 (1.57), 2.674 (1.14), 2.679 (0.54), 2.859 (15.57), 2.871 (16.00), 2.879 (3.24), 2.891 (2.11), 3.301 (0.59), 3.377 (1.30), 3.383 (0.81), 3.390 (0.54), 7.144 (2.76), 7.150 (2.97), 7.166 (2.86), 7.172 (3.14), 7.232 (4.65), 7.281 (3.19), 7.287 (3.03), 7.308 (3.03), 7.314 (2.92), 7.415 (9.51), 7.598 (4.43), 7.676 (3.62), 7.682 (1.95), 7.693 (3.08), 7.699 (13.24), 7.714 (11.89), 7.721 (2.81), 7.731 (1.84), 7.738 (6.32), 7.758 (6.05), 7.779 (3.35), 7.787 (1.35), 7.810 (0.81), 7.927 (14.76), 8.829 (0.65), 8.831 (0.76), 8.843 (2.27), 8.855 (2.27), 8.867 (0.81), 10.381 (0.97), 10.423 (7.46), 13.438 (3.57), 13.698 (7.78).

LC-MS (Method 14): $R_t$=0.96 min; MS (ESIpos) m/z=448.2 [M+H]⁺.

Example 252

N⁵-{4-[(2-chloro-3-methoxybenzoyl)amino]phenyl}-N⁴-methyl-1H-imidazole-4,5-dicarboxamide Was prepared in analogy to the synthesis of N⁵-(4-{[2-(difluoromethyl)benzoyl]amino}phenyl)-N⁴-methyl-1H-imidazole-4,5-dicarboxamide (Example 241) using 70.2 mg (0.376 mmol) 2-chloro-3-methoxybenzoic acid (CAS No. 33234-36-5). The reaction mixture was concentrated and the residue was purified by preparative HPLC to give the title compound (37.0 mg).

¹H-NMR (400 MHz, DMSO-d6) delta [ppm]: 1.106 (12.48), 1.137 (0.44), 2.523 (1.02), 2.539 (1.04), 2.861 (5.41), 2.873 (6.05), 2.891 (0.85), 3.904 (16.00), 7.116 (1.91), 7.120 (2.08), 7.135 (2.31), 7.138 (2.34), 7.244 (1.55), 7.248 (1.77), 7.265 (2.10), 7.269 (2.23), 7.393 (2.07), 7.413 (2.62), 7.433 (1.42), 7.668 (1.55), 7.674 (0.99), 7.691 (4.83), 7.713 (4.85), 7.729 (1.07), 7.736 (1.71), 7.927 (6.82), 8.839 (0.97), 8.851 (1.02), 8.864 (0.43), 10.487 (3.80), 13.435 (1.44), 13.679 (2.76).

LC-MS (Method 14): $R_t$=0.87 min; MS (ESIpos) m/z=428.2 [M+H]⁺.

Example 253

N$^5$-(4-{[2-fluoro-4-(trifluoromethoxy)benzoyl]amino}phenyl)-N$^4$-methyl-1H-imidazole-4,5-dicarboxamide

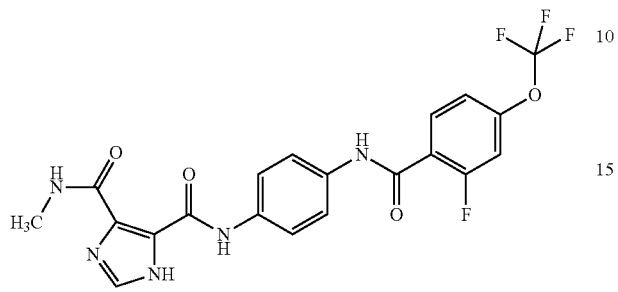

Was prepared in analogy to the synthesis of N$^5$-(4-{[2-(difluoromethyl)benzoyl]amino}phenyl)-N$^4$-methyl-1H-imidazole-4,5-dicarboxamide (Example 241) using 84.3 mg (0.376 mmol) 2-fluoro-4-(trifluoromethoxy)benzoic acid (CAS No. 1073477-22-1). The reaction mixture was concentrated and the residue was purified by preparative HPLC to give the title compound (6.0 mg).

$^1$H-NMR (500 MHz, DMSO-d$_6$): δ [ppm]=13.89-12.81 (m, 2H), 10.51 (s, 1H), 9.40-8.53 (m, 1H), 7.90 (s, 1H), 7.83 (t, 1H), 7.71 (s, 4H), 7.60-7.55 (m, 1H), 7.40-7.36 (m, 1H), 2.87 (d, 3H).

LC-MS (Method 10): R$_t$=1.07 min; MS (ESIpos) m/z=466.2 [M+H]$^+$.

Example 254

N$^5$-(4-{[(4-chloropyridin-3-yl)carbonyl]amino}phenyl)-N$^4$-methyl-1H-imidazole-4,5-dicarboxamide

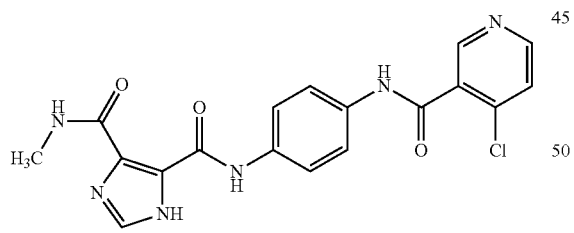

Was prepared in analogy to the synthesis of N$^5$-(4-{[2-(difluoromethyl)benzoyl]amino}phenyl)-N$^4$-methyl-1H-imidazole-4,5-dicarboxamide (Example 241) using 79.0 mg (0.501 mmol) 4-chloropyridine-3-carboxylic acid (CAS No. 10177-29-4). The reaction mixture was concentrated and the residue was purified by preparative HPLC to give the title compound (6.0 mg).

$^1$H-NMR (400 MHz, DMSO-d$_6$): δ [ppm]=13.96-12.72 (m, 2H), 10.70 (s, 1H), 9.19-8.81 (m, 1H), 8.78 (s, 1H), 8.65 (d, 1H), 7.88 (s, 1H), 7.78-7.61 (m, 5H), 2.87 (d, 3H).

LC-MS (Method 8): R$_t$=0.73 min; MS (ESIpos) m/z=399.2 [M+H]$^+$.

Example 255

N$^5$-(4-{[2-chloro-4-(S-ethylsulfonimidoyl)benzoyl]amino}phenyl)-N$^4$-methyl-1H-imidazole-4,5-dicarboxamide

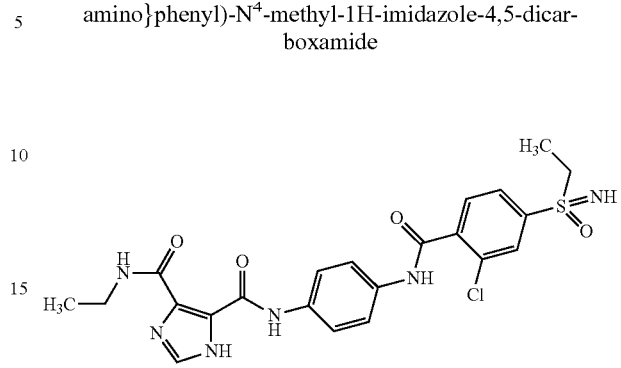

152 mg (0.400 mmol) HATU was added to a mixture of 103 mg (0.400 mmol) N$^5$-(4-aminophenyl)-N$^4$-methyl-1H-imidazole-4,5-dicarboxamide (Intermediate 003), 99.1 mg (0.400 mmol) 2-chloro-4-(S-ethylsulfonimidoyl)benzoic acid (Intermediate 080) and 0.21 mL (1.2 mmol) N,N-diisopropylethylamine in 5.2 mL DMF and the mixture was stirred for 3 h at room temperature. Water was added and the mixture was extracted 3× with a mixture of dichloromethane/2-propanol (4:1). The combined organic phases were filtrated through a silicone filter and concentrated. The residue was purified by flash chromatography (25 g Snap Cartridge, ethyl acetate/methanol 9:1) to give the title compound (97.0 mg).

$^1$H-NMR (400 MHz, DMSO-d$_6$): δ [ppm]=13.70 (s, 1H), 13.43 (s, 1H), 10.68 (s, 1H), 8.88-8.80 (m, 1H), 8.00 (d, 1H), 7.88-7.97 (m, 2H), 7.78-7.88 (m, 1H), 7.63-7.77 (m, 4H), 4.53 (s, 1H), 3.25 (q, 2H), 2.83-2.92 (m, 3H), 1.11 (t, 3H).

LC-MS (Method 8): R$_t$=0.73 min; MS (ESIpos) m/z=489.2 [M+H]$^+$.

Example 256

N$^5$-(4-{[2-chloro-4-(S-ethylsulfonimidoyl)benzoyl]amino}phenyl)-N$^4$-[2-(piperidin-1-yl)ethyl]-1H-imidazole-4,5-dicarboxamide

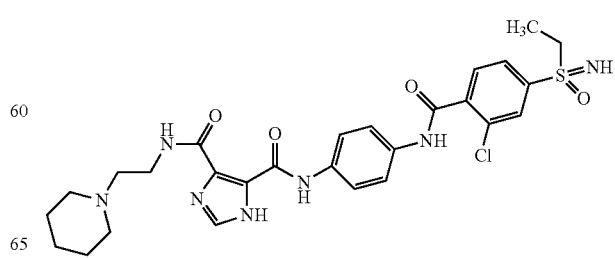

Step 1: methyl 5-[(4-{[2-chloro-4-(S-ethylsulfonimidoyl)benzoyl]amino}phenyl)carbamoyl]-1H-imidazole-4-carboxylate

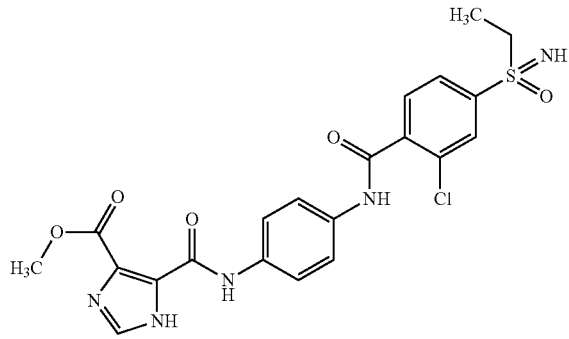 [SMILES: CCS(=N)(=O)c1ccc(C(=O)Nc2ccc(NC(=O)c3[nH]cnc3C(=O)OC)cc2)c(Cl)c1]

304 mg (0.800 mmol) HATU was added to a mixture of 208 mg (0.800 mmol) methyl 5-[(4-aminophenyl)carbamoyl]-1H-imidazole-4-carboxylate (Intermediate 015), 198 mg (0.800 mmol) 2-chloro-4-(S-ethylsulfonimidoyl)benzoic acid (Intermediate 080) and 0.41 mL (2.4 mmol) N,N-diisopropylethylamine in 10 mL DMF and the mixture was stirred for 3 h at room temperature. Water was added and the mixture was extracted 3× with a mixture of dichloromethane/2-propanol (4:1). The combined organic phases were filtrated through a silicone filter and concentrated. The residue was purified by flash chromatography (25 g Snap Cartridge, ethyl acetate/methanol 9:1) to give 135 mg of methyl 5-[(4-{[2-chloro-4-(S-ethylsulfonimidoyl)benzoyl]amino}phenyl)carbamoyl]-1H-imidazole-4-carboxylate which used directly in the next step.

$^1$H-NMR (400 MHz, DMSO-$d_6$): δ [ppm]=13.91-13.07 (m, 1H), 11.89 (br. s., 1H), 10.68 (br. s., 1H), 8.00 (d, 1H), 7.97-7.90 (m, 3H), 7.83 (d, 1H), 7.78-7.67 (m, 4H), 4.51 (s, 1H), 3.92 (br. s., 3H), 3.24 (q, 2H), 1.11 (t, 3H).

LC-MS (Method 8): $R_t$=0.63 min; MS (ESIpos) m/z=490.2 [M+H]$^+$.

Step 2

A mixture of 130 mg (0.265 mmol) methyl 5-[(4-{[2-chloro-4-(S-ethylsulfonimidoyl)benzoyl]amino}phenyl)carbamoyl]-1H-imidazole-4-carboxylate and 170 mg (1.33 mmol) 2-(piperidin-1-yl)ethanamine (CAS No. 27578-60-5) in 4.0 mL ethanol was heated for 3 h at 150° C. in a microwave reactor. Upon cooling the mixture was concentrated and the residue was purified by flash chromatography (25 g Snap cartridge, dichloromethane/methanol gradient) followed by preparative HPLC to give N$^5$-(4-{[2-chloro-4-(S-ethylsulfonimidoyl)benzoyl]amino}phenyl)-N$^4$-[2-(piperidin-1-yl)ethyl]-1H-imidazole-4,5-dicarboxamide (54.0 mg).

$^1$H-NMR (400 MHz, DMSO-$d_6$): δ [ppm]=13.62 (br. s., 1H), 13.52-13.16 (m, 1H), 10.68 (s, 1H), 8.65 (br. s., 1H), 8.00 (d, 1H), 7.97-7.89 (m, 2H), 7.88-7.81 (m, 1H), 7.72 (br. s., 4H), 4.53 (s, 1H), 3.55-3.41 (m, 2H), 3.25 (q, 2H), 2.46-2.35 (m, 4H), 1.58-1.44 (m, 4H), 1.44-1.34 (m, 2H), 1.11 (t, 3H).

LC-MS (Method 8): $R_t$=0.92 min; MS (ESIpos) m/z=586.3 [M+H]$^+$.

Example 257

N$^4$-ethyl-N$^5$-(4-{[2-(methylsulfonyl)benzoyl]amino}phenyl)-1H-imidazole-4,5-dicarboxamide

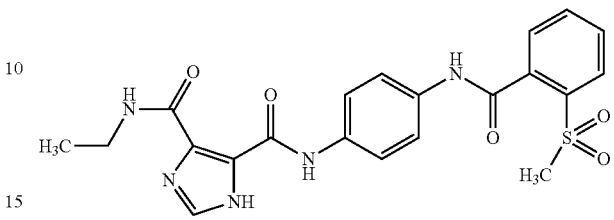

0.22 mL (0.38 mmol, 50% solution in DMF) 1-propanephosphonic anhydride (T3P) was added to a mixture of 75.0 mg (0.274 mmol) N$^5$-(4-aminophenyl)-N$^4$-ethyl-1H-imidazole-4,5-dicarboxamide (Intermediate 056), 71.4 mg (0.357 mmol) 2-(methylsulfonyl)benzoic acid (CAS No. 33963-55-2) and 0.19 mL (1.1 mmol) N,N-diisopropylethylamine in 2.1 mL DMF and the mixture was stirred at room temperature overnight. The reaction mixture was concentrated and the residue was purified by preparative HPLC to give the title compound (30.0 mg).

$^1$H-NMR (400 MHz, DMSO-$d_6$): δ [ppm]=13.93-12.23 (m, 2H), 10.66 (s, 1H), 9.00-8.41 (m, 1H), 8.02 (dd, 1H), 7.93 (s, 1H), 7.88-7.81 (m, 1H), 7.79-7.64 (m, 6H), 3.39 (s, 3H), 1.16 (t, 3H).

LC-MS (Method 13): $R_t$=1.09 min; MS (ESIpos) m/z=456.2 [M+H]$^+$.

Example 258

N$^5$-(4-{[4-(difluoromethoxy)-2-fluorobenzoyl]amino}phenyl)-N$^4$-ethyl-1H-imidazole-4,5-dicarboxamide

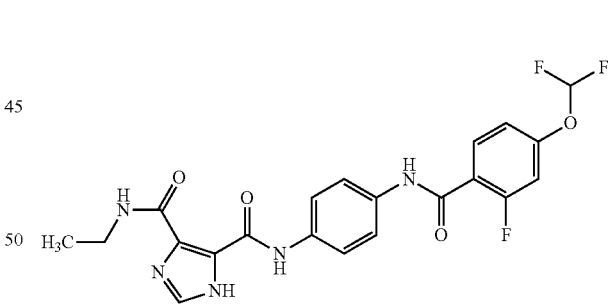

Was prepared in analogy to the synthesis of N$^4$-ethyl-N$^5$-(4-{[2-(methylsulfonyl)benzoyl]amino}phenyl)-1H-imidazole-4,5-dicarboxamide (Example 257) using 73.5 mg (0.357 mmol) 4-(difluoromethoxy)-2-fluorobenzoic acid (CAS No. 1214347-60-0) to give the title compound (27.5 mg).

$^1$H-NMR (400 MHz, DMSO-$d_6$) δ [ppm]: 1.141 (4.78), 1.159 (9.84), 1.177 (4.79), 1.230 (0.79), 1.864 (0.53), 2.318 (0.47), 2.322 (0.88), 2.327 (1.18), 2.331 (0.91), 2.337 (0.47), 2.523 (3.97), 2.659 (0.46), 2.664 (0.84), 2.669 (1.16), 2.673 (0.88), 2.678 (0.44), 3.367 (3.48), 3.383 (2.39), 3.400 (0.77), 5.760 (1.72), 7.144 (1.48), 7.150 (1.55), 7.165 (1.46), 7.171 (1.65), 7.233 (1.69), 7.280 (1.60), 7.286 (1.55), 7.308 (1.55), 7.314 (1.46), 7.416 (3.34), 7.599 (1.63), 7.685 (0.72), 7.709 (16.00), 7.738 (1.77), 7.759 (2.65), 7.780 (1.37), 7.896 (5.08), 10.417 (3.93).

LC-MS (Method 8): $R_t$=1.05 min; MS (ESIpos) m/z=462.2 [M+H]$^+$.

Example 259

N$^5$-{4-[(2-chloro-4-ethoxybenzoyl)amino]phenyl}-N$^4$-ethyl-1H-imidazole-4,5-dicarboxamide

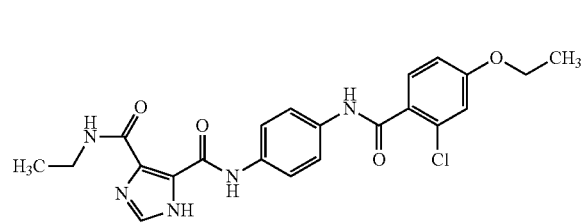 [SMILES: CCNC(=O)c1nc[nH]c1C(=O)Nc1ccc(NC(=O)c2ccc(OCC)cc2Cl)cc1]

Was prepared in analogy to the synthesis of N$^4$-ethyl-N$^5$-(4-{[2-(methylsulfonyl)benzoyl]amino}phenyl)-1H-imidazole-4,5-dicarboxamide (Example 257) using 71.6 mg (0.357 mmol) 2-chloro-4-ethoxybenzoic acid (CAS No. 334018-28-9) to give the title compound (11.5 mg).

$^1$H-NMR (400 MHz, DMSO-d$_6$) δ [ppm]: 1.142 (7.30), 1.160 (16.00), 1.178 (7.55), 1.232 (0.43), 1.324 (6.44), 1.342 (14.14), 1.359 (6.80), 1.881 (0.82), 2.085 (0.86), 2.318 (0.72), 2.323 (1.57), 2.327 (2.08), 2.332 (1.57), 2.337 (0.68), 2.523 (10.77), 2.540 (4.12), 2.660 (0.68), 2.665 (1.43), 2.669 (1.97), 2.673 (1.40), 2.679 (0.64), 3.351 (5.73), 3.366 (4.87), 3.368 (4.94), 3.384 (3.51), 3.402 (1.22), 4.087 (1.93), 4.105 (6.16), 4.123 (6.05), 4.140 (1.97), 6.984 (2.00), 6.990 (2.26), 7.005 (2.18), 7.012 (2.54), 7.105 (4.87), 7.111 (4.65), 7.508 (3.62), 7.530 (3.36), 7.670 (1.65), 7.693 (6.16), 7.706 (8.77), 7.729 (2.26), 7.905 (6.48), 10.369 (4.94).

LC-MS (Method 8): $R_t$=1.08 min; MS (ESIpos) m/z=2456.2 [M+H]$^+$.

Example 260

N$^5$-{4-[(2-chloro-3-methoxybenzoyl)amino]phenyl}-N$^4$-ethyl-1H-imidazole-4,5-dicarboxamide

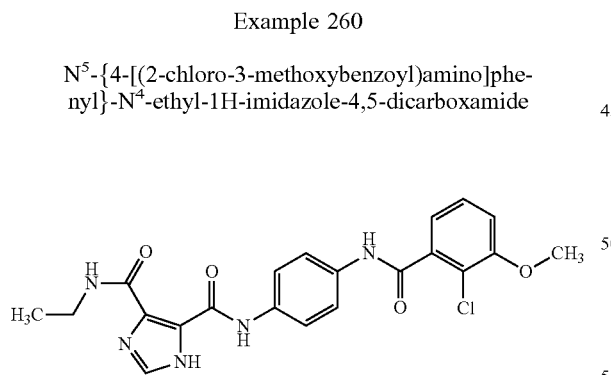

Was prepared in analogy to the synthesis of N$^4$-ethyl-N$^5$-(4-{[2-(methylsulfonyl)benzoyl]amino}phenyl)-1H-imidazole-4,5-dicarboxamide (Example 257) using 66.6 mg (0.357 mmol) 2-chloro-3-methoxybenzoic acid (CAS No. 33234-36-5) to give the title compound (26.5 mg).

$^1$H-NMR (400 MHz, DMSO-d$_6$) δ [ppm]: 1.108 (6.88), 1.142 (4.66), 1.160 (10.30), 1.178 (4.69), 1.879 (0.64), 2.323 (0.72), 2.327 (1.01), 2.332 (0.74), 2.523 (5.00), 2.539 (2.57), 2.665 (0.74), 2.669 (1.01), 2.673 (0.74), 3.351 (2.52), 3.366 (2.48), 3.370 (2.48), 3.385 (1.98), 3.403 (0.60), 3.905 (16.00), 7.115 (1.99), 7.119 (2.06), 7.134 (2.37), 7.138 (2.04), 7.246 (1.57), 7.250 (1.68), 7.268 (2.30), 7.271 (1.94), 7.394 (2.39), 7.414 (2.52), 7.434 (1.59), 7.674 (0.78), 7.698 (5.87), 7.704 (8.47), 7.720 (0.69), 7.728 (0.95), 7.904 (6.41), 10.472 (3.86).

LC-MS (Method 8): $R_t$=0.95 min; MS (ESIpos) m/z=442.2 [M+H]$^+$.

Example 261

N$^5$-(4-{[(3-chloropyridin-2-yl)carbonyl]amino}phenyl)-N$^4$-ethyl-1H-imidazole-4,5-dicarboxamide

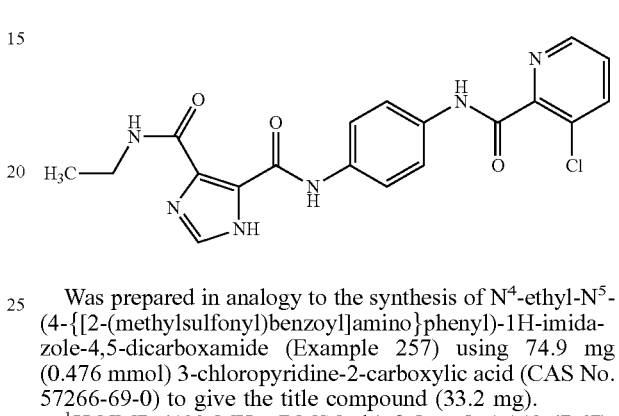

Was prepared in analogy to the synthesis of N$^4$-ethyl-N$^5$-(4-{[2-(methylsulfonyl)benzoyl]amino}phenyl)-1H-imidazole-4,5-dicarboxamide (Example 257) using 74.9 mg (0.476 mmol) 3-chloropyridine-2-carboxylic acid (CAS No. 57266-69-0) to give the title compound (33.2 mg).

$^1$H-NMR (400 MHz, DMSO-d$_6$) δ [ppm]: 1.142 (7.67), 1.160 (16.00), 1.178 (7.60), 1.230 (1.22), 1.852 (1.06), 2.318 (0.89), 2.322 (1.69), 2.327 (2.25), 2.331 (1.75), 2.337 (0.89), 2.659 (0.83), 2.664 (1.59), 2.669 (2.18), 2.673 (1.69), 2.678 (0.79), 3.369 (5.65), 3.385 (3.93), 3.402 (1.29), 7.592 (3.37), 7.604 (3.34), 7.613 (3.50), 7.624 (3.74), 7.702 (3.27), 7.724 (8.99), 7.745 (11.40), 7.762 (2.05), 7.769 (3.74), 7.890 (7.11), 8.099 (3.57), 8.103 (4.20), 8.120 (3.64), 8.124 (3.54), 8.620 (3.93), 8.623 (4.23), 8.631 (3.97), 8.635 (3.70), 10.669 (6.71).

LC-MS (Method 10): $R_t$=0.90 min; MS (ESIpos) m/z=413.1 [M+H]$^+$.

Example 262

N$^4$-ethyl-N$^5$-(4-{[2-fluoro-4-(trifluoromethoxy)benzoyl]amino}phenyl)-1H-imidazole-4,5-dicarboxamide

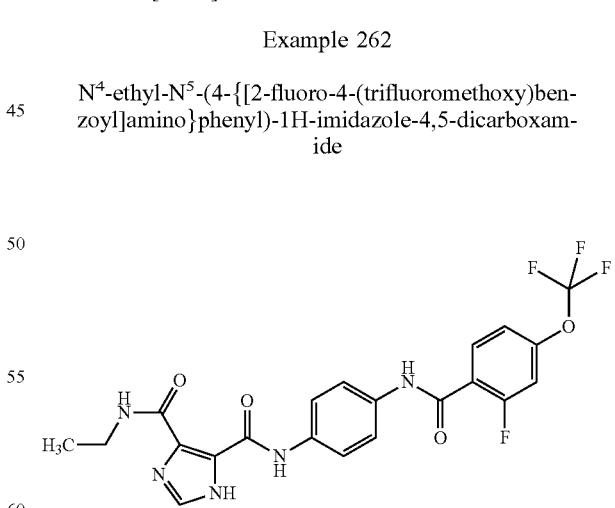

Was prepared in analogy to the synthesis of N$^4$-ethyl-N$^5$-(4-{[2-(methylsulfonyl)benzoyl]amino}phenyl)-1H-imidazole-4,5-dicarboxamide (Example 257) using 80.0 mg (0.357 mmol) 2-fluoro-4-(trifluoromethoxy)benzoic acid (CAS No. 1073477-22-1) to give the title compound (31.2 mg).

¹H-NMR (400 MHz, DMSO-d₆) δ [ppm]: 1.141 (3.10), 1.159 (6.63), 1.177 (3.12), 1.229 (0.45), 2.322 (0.54), 2.327 (0.73), 2.331 (0.57), 2.523 (2.10), 2.664 (0.53), 2.669 (0.72), 2.673 (0.55), 3.332 (16.00), 3.350 (2.20), 3.367 (1.94), 3.383 (1.40), 3.401 (0.42), 7.372 (0.73), 7.376 (0.86), 7.397 (0.93), 7.400 (0.86), 7.573 (0.86), 7.575 (0.88), 7.579 (0.83), 7.598 (0.82), 7.602 (0.86), 7.605 (0.79), 7.713 (11.16), 7.807 (1.05), 7.828 (1.71), 7.849 (0.91), 7.904 (3.55), 10.530 (2.58).

LC-MS (Method 8): $R_t$=1.16 min; MS (ESIpos) m/z=480.2 [M+H]⁺.

Example 263

N⁵-(4-{[(4-chloropyridin-3-yl)carbonyl]amino}phenyl)-N⁴-ethyl-1H-imidazole-4,5-dicarboxamide

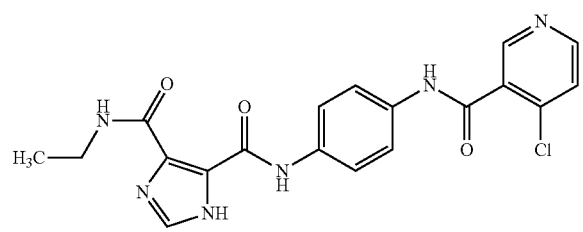 [SMILES: CCNC(=O)c1nc[nH]c1C(=O)Nc1ccc(NC(=O)c2cnccc2Cl)cc1]

Was prepared in analogy to the synthesis of N⁴-ethyl-N⁵-(4-{[2-(methylsulfonyl)benzoyl]amino}phenyl)-1H-imidazole-4,5-dicarboxamide (Example 257) using 74.9 mg (0.474 mmol) 4-chloropyridine-3-carboxylic acid (CAS No. 10177-29-4). For work-up, the reaction mixture was concentrated and the residue was purified by preparative HPLC followed by recrystallization from methanol to give the title compound (27.5 mg).

¹H-NMR (400 MHz, DMSO-d₆) δ [ppm]: 1.134 (0.70), 1.143 (4.83), 1.152 (1.15), 1.160 (10.78), 1.179 (4.83), 1.876 (0.86), 2.317 (0.58), 2.322 (1.31), 2.326 (1.79), 2.331 (1.38), 2.336 (0.64), 2.523 (5.25), 2.660 (0.61), 2.664 (1.38), 2.669 (1.86), 2.674 (1.31), 2.678 (0.58), 3.352 (2.69), 3.369 (2.62), 3.385 (1.98), 3.403 (0.58), 7.696 (3.87), 7.710 (4.45), 7.721 (16.00), 7.906 (4.74), 8.641 (4.80), 8.655 (4.90), 8.782 (6.59), 10.703 (3.65).

LC-MS (Method 8): $R_t$=0.80 min; MS (ESIpos) m/z=413.2 [M+H]⁺.

Example 264

N⁵-{4-[(2-chloro-5-methoxybenzoyl)amino]phenyl}-N⁴-ethyl-1H-imidazole-4,5-dicarboxamide

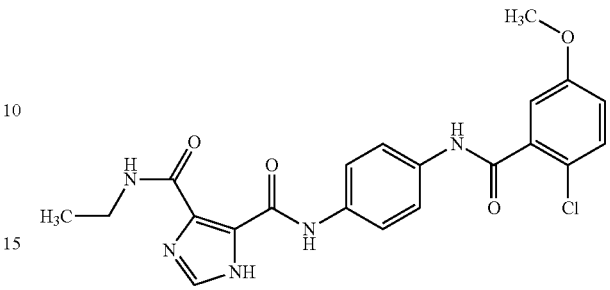

Was prepared in analogy to the synthesis of N⁴-ethyl-N⁵-(4-{[2-(methylsulfonyl)benzoyl]amino}phenyl)-1H-imidazole-4,5-dicarboxamide (Example 257) using 66.6 mg (0.357 mmol) 2-chloro-5-methoxybenzoic acid (CAS No. 6280-89-3) to give the title compound (33.2 mg).

¹H-NMR (400 MHz, DMSO-d₆): δ [ppm]=13.97-12.99 (m, 2H), 10.49 (s, 1H), 9.51-8.31 (m, 1H), 7.91 (s, 1H), 7.76-7.63 (m, 4H), 7.45 (d, 1H), 7.16 (d, 1H), 7.07 (dd, 1H), 3.81 (s, 3H), 3.41-3.36 (m, 2H), 1.16 (t, 3H).

LC-MS (Method 8): $R_t$=0.99 min; MS (ESIpos) m/z=442.2 [M+H]⁺.

Example 265

N⁴-{4-[(2-chloro-4-fluorobenzoyl)amino]phenyl}-N⁵-[2-(3-methoxypyrrolidin-1-yl)ethyl]-1H-imidazole-4,5-dicarboxamide

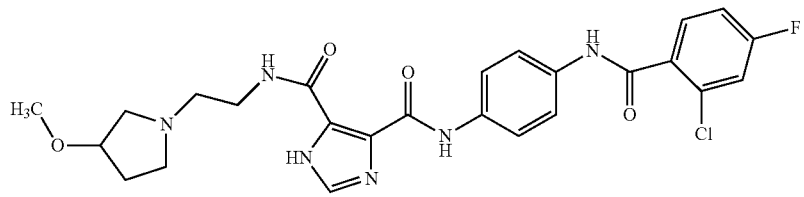 [SMILES: COC1CCN(CCNC(=O)c2[nH]cnc2C(=O)Nc2ccc(NC(=O)c3ccc(F)cc3Cl)cc2)C1]

To a suspension of 93.9 mg (0.300 mmol) 5,10-Dioxo-5H,10H-diimidazo[1,5-a; 1',5'-d]pyrazin-1,6-dicarbonyl-dichloride (Intermediate 001) in 4.5 mL THF were added 159 mg (0.600 mmol) N-(4-aminophenyl)-2-chloro-4-fluorobenzamide (Intermediate 004) and 157 μL (0.900 mmol) N,N-diisopropylethylamine and the mixture was stirred for 6 h at room temperature. A solution of 86.5 mg (0.600 mmol) 2-(3-methoxypyrrolidin-1-yl)ethanamine and 157 μL (0.900 mmol) N,N-diisopropylethylamine in 3.5 mL THF were added. The mixture was stirred overnight at room temperature. The mixture was filtered. The filtrate was purified by preparative HPLC to provide the title compound (45.0 mg).

¹H-NMR (400 MHz, DMSO-d₆): δ [ppm]=13.79-13.46 (m, 1H), 13.50-13.14 (m, 1H), 10.49 (s, 1H), 8.82-8.45 (m, 1H), 7.91 (s, 1H), 7.80-7.64 (m, 5H), 7.64-7.52 (m, 1H), 7.43-7.16 (m, 1H), 3.93-3.80 (m, 1H), 3.54-3.38 (m, 2H), 3.16 (s, 3H), 2.77-2.67 (m, 1H), 2.63-2.56 (m, 3H), 2.02-1.91 (m, 1H), 1.70-1.57 (m, 1H).

LC-MS (Method 8): $R_t$=1.00 min; MS (ESIpos) m/z=529.3 [M+H]⁺.

Example 266

N⁴-{4-[(2-chloro-4-fluorobenzoyl)amino]phenyl}-N⁵-{2-[(2S)-2-methylpiperidin-1-yl]ethyl}-1H-imidazole-4,5-dicarboxamide formic acid salt

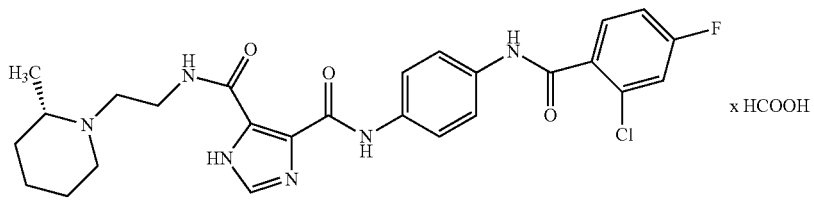 [SMILES: C[C@H]1CCCCN1CCNC(=O)c1[nH]cnc1C(=O)Nc1ccc(NC(=O)c2ccc(F)cc2Cl)cc1]
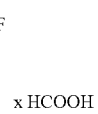

x HCOOH

To a suspension of 93.9 mg (0.300 mmol) 5,10-Dioxo-5H,10H-diimidazo[1,5-a; 1',5'-d]pyrazin-1,6-dicarbonyl-dichloride (Intermediate 001) in 4.5 mL THF were added 159 mg (0.600 mmol) N-(4-aminophenyl)-2-chloro-4-fluorobenzamide (Intermediate 004) and 157 µL (0.900 mmol) N,N-diisopropylethylamine and the mixture was stirred for 6 h at room temperature. A solution of 85.3 mg (0.600 mmol) 2-[(2S)-2-methylpiperidin-1-yl]ethanamine (intermediate 058) and 157 µL (0.900 mmol) N,N-diisopropylethylamine in 3.5 mL THF were added and the mixture was stirred overnight at room temperature. The mixture was concentrated and the residue was purified by preparative HPLC. The combined product fractions were stirred with methanol. The precipitate was collected by filtration and re-purified by preparative HPLC to provide the title compound (43.0 mg).

¹H-NMR (400 MHz, DMSO-d₆): δ [ppm]=13.90-12.88 (m, 2H), 10.52 (s, 1H), 8.75-8.64 (m, 1H), 8.16 (s, 1H), 7.93 (s, 1H), 7.88-7.61 (m, 5H), 7.59 (dd, 1H), 7.39-7.31 (m, 1H), 2.91-2.80 (m, 2H), 2.30-2.21 (m, 1H), 1.68-1.14 (m, 7H), 1.05 (d, 3H).

LC-MS (Method 8): R$_t$=1.20 min; MS (ESIpos) m/z=527.3 [M+H]⁺.

Example 267

N⁴-{4-[(2-chloro-4-fluorobenzoyl)amino]phenyl}-N⁵-{2-[(2R)-2-methylpiperidin-1-yl]ethyl}-1H-imidazole-4,5-dicarboxamide

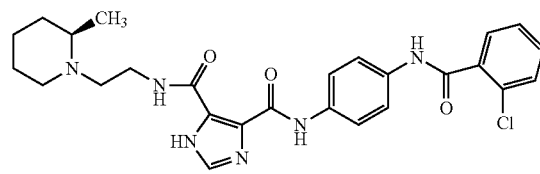

Was prepared in analogy to the synthesis N⁴-{4-[(2-chloro-4-fluorobenzoyl)amino]phenyl}-N⁵-{2-[(2S)-2-methylpiperidin-1-yl]ethyl}-1H-imidazole-4,5-dicarboxamide formic acid salt (Example 266) using 85.3 mg (0.600 mmol) 2-[(2R)-2-methylpiperidin-1-yl]ethanamine (Intermediate 059). For work-up the reaction mixture was concentrated and the residue was purified by preparative HPLC to give the title compound (127 mg).

¹H-NMR (400 MHz, DMSO-d₆): δ [ppm]=13.00-13.00 (m, 2H), 10.51 (s, 1H), 9.14-8.20 (m, 1H), 7.91 (s, 1H), 7.81-7.65 (m, 5H), 7.59 (dd, 1H), 7.35 (td, 1H), 3.52-3.36 (m, 2H), 2.90-2.78 (m, 2H), 2.47-2.34 (m, 2H), 2.25-2.16 (m, 1H), 1.66-1.11 (m, 6H), 1.04 (d, 3H).

LC-MS (Method 8): R$_t$=1.21 min; MS (ESIpos) m/z=527.3 [M+H]⁺.

Example 268

N⁴-{4-[(2-chloro-4-fluorobenzoyl)amino]phenyl}-N⁵-[1-(morpholin-4-yl)propan-2-yl]-1H-imidazole-4,5-dicarboxamide

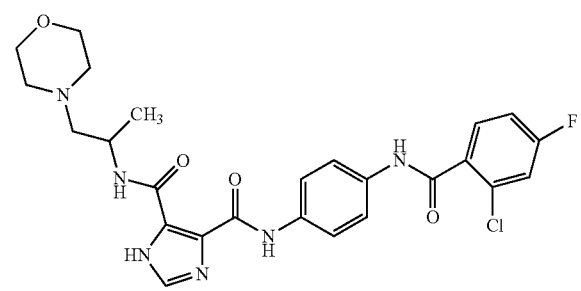 [SMILES: CC(CN1CCOCC1)NC(=O)c1[nH]cnc1C(=O)Nc1ccc(NC(=O)c2ccc(F)cc2Cl)cc1]

Was prepared in analogy to the synthesis N⁴-{4-[(2-chloro-4-fluorobenzoyl)amino]phenyl}-N⁵-{2-[(2S)-2-methylpiperidin-1-yl]ethyl}-1H-imidazole-4,5-dicarboxamide formic acid salt (Example 266) using 346 mg (2.40 mmol) 1-(morpholin-4-yl)propan-2-amine (CAS No. 50998-05-5). For work-up the reaction mixture was concentrated and the residue was purified by flash chromatography (50 g Snap Cartridge, hexane/ethylacetate gradient 50%→100% ethyl acetate followed by ethyl acetate/methanol 9:1) to give the title compound (559 mg).

¹H-NMR (300 MHz, DMSO-d₆): δ [ppm]=14-00-13.20 (m, 2H), 10.52 (s, 1H), 8.96-8.16 (m, 1H), 7.92 (s, 1H), 7.82-7.63 (m, 5H), 7.59 (dd, 1H), 7.35 (td, 1H), 4.36-4.08 (m, 1H), 3.60-3.46 (m, 4H), 2.46-2.30 (m, 4H), 1.20 (d, 3H).

LC-MS (Method 8): R$_t$=1.03 min; MS (ESIpos) m/z=529.3 [M+H]⁺.

532 mg (1.01 mmol) of N⁴-{4-[(2-chloro-4-fluorobenzoyl)amino]phenyl}-N⁵-[1-(morpholin-4-yl)propan-2-yl]-1H-imidazole-4,5-dicarboxamide (Example 268) was separated into enantiomers by chiral HPLC to give 134 mg enantiomer 1 (Example 269,) and 120 mg enantiomer 2 (Example 270)

Preparative chiral HPLC method: Instrument: Sepiatec: Prep SFC100; column: Chiralpak IC 5 µm 250×30 mm; eluent: carbon dioxide/2-propanol 72:28; flow 100 mL/min; pressure (outlet): 150 bar; temperature: 40° C.; Sample preparation: 532 mg dissolved in 4.2 mL of mixture of DMSO/acetone 2:1; injection: 42×0.1 mL; detection: UV 254 nm;

analytical chiral HPLC method: Instrument: Agilent: 1260 AS, MWD, Aurora SFC-Modul; column: Chiralpak IC 5 μm 100×4.6 mm; eluent: carbon dioxide/ethanol 72:28; flow 4.0 mL/min; pressure (outlet): 100 bar; temperature: 37.5° C.; injection: 10 μL; detection: DAD 254 nm;

Example 269

$N^4$-{4-[(2-chloro-4-fluorobenzoyl)amino]phenyl}-$N^5$-[1-(morpholin-4-yl)propan-2-yl]-1H-imidazole-4,5-dicarboxamide (enantiomer 1)

Analytical chiral HPLC: $R_t$=1.03 min; ee=91.9

Specific optical rotation: (DMSO, 589 nM, 20° C.): −12.8°

Example 270

$N^4$-{4-[(2-chloro-4-fluorobenzoyl)amino]phenyl}-$N^5$-[1-(morpholin-4-yl)propan-2-yl]-1H-imidazole-4,5-dicarboxamide (enantiomer 2)

Analytical chiral HPLC: $R_t$=3.38 min; ee=97.0

Specific optical rotation: (DMSO, 589 nM, 20° C.): +12.3°

Example 271

$N^4$-{4-[(2-chloro-4-fluorobenzoyl)amino]phenyl}-$N^5$-{2-[(3S)-3-hydroxypiperidin-1-yl]ethyl}-1H-imidazole-4,5-dicarboxamide

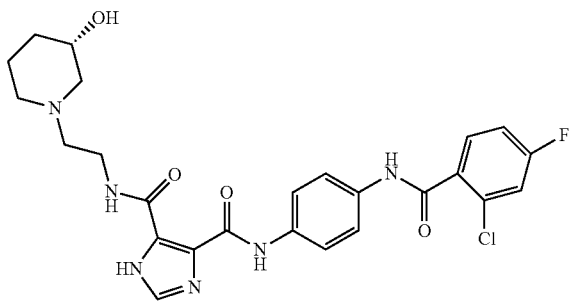 [SMILES: O=C(Nc1ccc(NC(=O)c2nc[nH]c2C(=O)NCCN2CCC[C@H](O)C2)cc1)c1ccc(F)cc1Cl]

Was prepared in analogy to the synthesis $N^4$-{4-[(2-chloro-4-fluorobenzoyl)amino]phenyl}-$N^5$-{2-[(2S)-2-methylpiperidin-1-yl]ethyl}-1H-imidazole-4,5-dicarboxamide formic acid salt (Example 266) using 116 mg (0.800 mmol) (3S)-1-(2-aminoethyl)piperidin-3-ol (Intermediate 066) and purification by preparative HPLC to give the title compound (133 mg).

$^1$H-NMR (400 MHz, DMSO-$d_6$): δ [ppm]=13.74-13.18 (m, 2H), 10.94-10.20 (m, 1H), 8.78-8.42 (m, 1H), 7.93 (s, 1H), 7.87-7.63 (m, 5H), 7.59 (dd, 1H), 7.35 (td, 1H), 4.70-4.46 (m, 1H), 3.59-3.39 (m, 3H), 2.98-2.80 (m, 1H), 2.78-2.67 (m, 1H), 2.01-1.30 (m, 5H), 1.18-0.96 (m, 1H).

LC-MS (Method 8): $R_t$=0.92 min; MS (ESIpos) m/z=529.3 [M+H]$^+$.

analytical chiral HPLC method: Instrument: Agilent: 1260 AS, MWD, Aurora SFC-Modul; column: Chiralpak ID 5 μm 100×4.6 mm; eluent: carbon dioxide/2-propanol+0.2% diethyl amine 60:40; flow 4.0 mL/min; pressure (outlet): 100 bar; temperature: 37.5° C.; injection: 10 μL; detection: DAD 254 nm;

Analytical chiral HPLC: $R_t$=3.30 min; ee=100% (compare retention time with Example 272)

Example 272

$N^4$-{4-[(2-chloro-4-fluorobenzoyl)amino]phenyl}-$N^5$-{2-[(3R)-3-hydroxypiperidin-1-yl]ethyl}-1H-imidazole-4,5-dicarboxamide

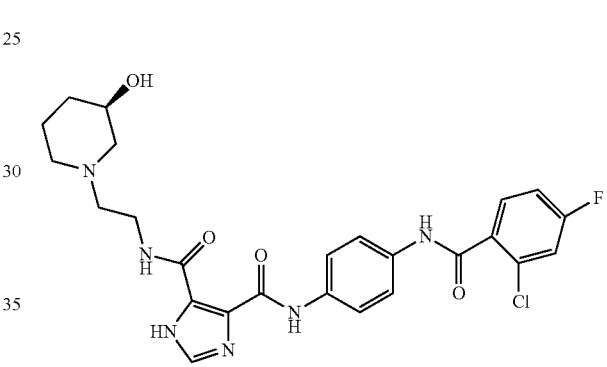

Was prepared in analogy to the synthesis $N^4$-{4-[(2-chloro-4-fluorobenzoyl)amino]phenyl}-$N^5$-{2-[(2S)-2-methylpiperidin-1-yl]ethyl}-1H-imidazole-4,5-dicarboxamide formic acid salt (Example 266) using 88.3 mg (0.600 mmol) (3R)-1-(2-aminoethyl)piperidin-3-ol (Intermediate 067) and purification by preparative HPLC to give the title compound (140 mg).

$^1$H-NMR (400 MHz, DMSO-$d_6$): δ [ppm]=13.99-12.78 (m, 2H), 10.52 (s, 1H), 9.19-8.21 (m, 1H), 7.92 (s, 1H), 7.77-7.65 (m, 5H), 7.60 (dd, 1H), 7.36 (td, 1H), 4.60 (d, 1H), 3.54-3.41 (m, 3H), 2.93-2.82 (m, 1H), 2.77-2.68 (m, 1H), 1.97-1.71 (m, 3H), 1.68-1.56 (m, 1H), 1.50-1.31 (m, 1H), 1.19-0.97 (m, 1H).

LC-MS (Method 8): $R_t$=0.91 min; MS (ESIpos) m/z=529.3 [M+H]$^+$.

Analytical chiral HPLC (method described in Example 271): $R_t$=major isomer: 2.71 min, minor isomer: 3.30; ee=92.9% (compare retention time with Example 271)

Example 273

N⁴-{4-[(2-chloro-4-fluorobenzoyl)amino]phenyl}-N⁵-[3-(3-hydroxypiperidin-1-yl)propyl]-1H-imidazole-4,5-dicarboxamide

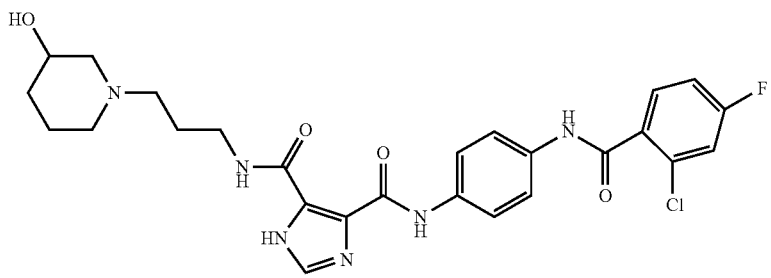 [SMILES: O=C(Nc1ccc(NC(=O)c2nc[nH]c2C(=O)NCCCN2CCCC(O)C2)cc1)c1ccc(F)cc1Cl]

Was prepared in analogy to the synthesis N⁴-{4-[(2-chloro-4-fluorobenzoyl)amino]phenyl}-N⁵-{2-[(2S)-2-methylpiperidin-1-yl]ethyl}-1H-imidazole-4,5-dicarboxamide formic acid salt (Example 266) using 101 mg (0.639 mmol) 1-(3-aminopropyl)piperidin-3-ol and purification by preparative HPLC to give the title compound (18.0 mg).

¹H-NMR (400 MHz, DMSO-d₆): δ [ppm]=13.84-13.07 (m, 2H), 10.50 (s, 1H), 9.11 (br. s., 1H), 7.92 (s, 1H), 7.77-7.63 (m, 5H), 7.58 (dd, 1H), 7.35 (td, 1H), 4.58 (d, 1H), 3.62-3.47 (m, 1H), 3.44-3.36 (m, 2H), 2.89-2.79 (m, 1H), 2.72-2.58 (m, 1H), 2.44-2.28 (m, 2H), 1.93-1.36 (m, 7H), 1.17-1.01 (m, 1H).

LC-MS (Method 8): R$_t$=0.95 min; MS (ESIpos) m/z=543.2 [M+H]⁺.

Example 274

N⁴-{4-[(2-chloro-4-fluorobenzoyl)amino]phenyl}-N⁵-[3-(pyrrolidin-1-yl)propyl]-1H-imidazole-4,5-dicarboxamide

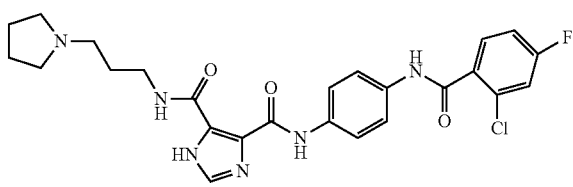 [SMILES: O=C(Nc1ccc(NC(=O)c2nc[nH]c2C(=O)NCCCN2CCCC2)cc1)c1ccc(F)cc1Cl]

Was prepared in analogy to the synthesis N⁴-{4-[(2-chloro-4-fluorobenzoyl)amino]phenyl}-N⁵-{2-[(2S)-2-methylpiperidin-1-yl]ethyl}-1H-imidazole-4,5-dicarboxamide formic acid salt (Example 266) using 91.9 mg (0.639 mmol) 3-(pyrrolidin-1-yl)propan-1-amine (CAS No. 23159-07-1) and purification by preparative HPLC to give the title compound (55.0 mg).

¹H-NMR (400 MHz, DMSO-d₆): δ [ppm]=13.82-13.09 (m, 2H), 10.50 (s, 1H), 9.10 (br. s., 1H), 7.91 (s, 1H), 7.79-7.63 (m, 5H), 7.58 (dd, 1H), 7.35 (td, 1H), 3.41 (q, 2H), 2.47-2.39 (m, 4H), 1.79-1.61 (m, 6H).

LC-MS (Method 8): R$_t$=1.12 min; MS (ESIpos) m/z=513.3 [M+H]⁺.

Example 275

N⁴-{4-[(2-chloro-4-fluorobenzoyl)amino]phenyl}-N⁵-[3-(4-hydroxypiperidin-1-yl)propyl]-1H-imidazole-4,5-dicarboxamide

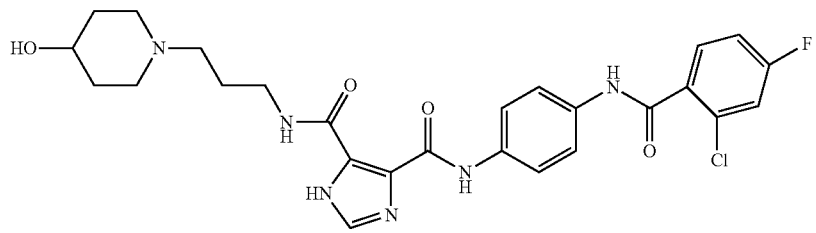 [SMILES: O=C(Nc1ccc(NC(=O)c2nc[nH]c2C(=O)NCCCN2CCC(O)CC2)cc1)c1ccc(F)cc1Cl]

Was prepared in analogy to the synthesis of N⁴-{4-[(2-chloro-4-fluorobenzoyl)amino]phenyl}-N⁵-{2-[(2S)-2-methylpiperidin-1-yl]ethyl}-1H-imidazole-4,5-dicarboxamide formic acid salt (Example 266) using 101 mg (0.639 mmol) 1-(3-aminopropyl)piperidin-4-ol (CAS No. 4608-78-0) and purification by preparative HPLC followed by recrystallization from methanol and preparative HPLC to give the title compound (12.0 mg).

¹H-NMR (400 MHz, DMSO-d₆): δ [ppm]=13.82-13.17 (m, 2H), 10.51 (s, 1H), 9.11 (br. s., 1H), 7.90 (s, 1H), 7.83-7.63 (m, 5H), 7.59 (dd, 1H), 7.35 (td, 1H), 4.49 (d, 1H), 3.54-3.37 (m, 3H), 2.75-2.65 (m, 2H), 2.35-2.29 (m, 2H), 1.99 (t, 2H), 1.76-1.62 (m, 4H), 1.53-1.35 (m, 2H).

LC-MS (Method 14): R$_t$=0.87 min; MS (ESIpos) m/z=543.2 [M+H]⁺.

Example 276

N⁴-{4-[(2-chloro-4-fluorobenzoyl)amino]phenyl}-N⁵-{2-[(3S)-3-fluoropiperidin-1-yl]ethyl}-1H-imidazole-4,5-dicarboxamide

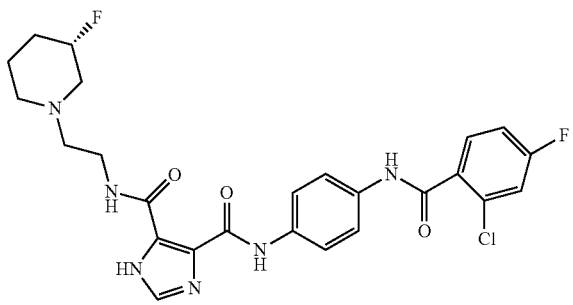 [SMILES: O=C(Nc1ccc(NC(=O)c2nc[nH]c2C(=O)NCCN2CCC[C@H](F)C2)cc1)c1ccc(F)cc1Cl]

Was prepared in analogy to the synthesis N⁴-{4-[(2-chloro-4-fluorobenzoyl)amino]phenyl}-N⁵-{2-[(2S)-2-methylpiperidin-1-yl]ethyl}-1H-imidazole-4,5-dicarboxamide formic acid salt (Example 266) using 117 mg (0.800 mmol) 2-[(3S)-3-fluoropiperidin-1-yl]ethanamine (Intermediate 064). For work-up the reaction mixture was concentrated and residue was stirred with methanol. The precipitate was collected by filtration and the filtrate was concentrated and repurified by preparative HPC to give the title compound (23.0 mg).

¹H-NMR (400 MHz, DMSO-d₆): δ [ppm]=13.88-12.88 (m, 2H), 10.51 (s, 1H), 9.22-8.36 (m, 1H), 7.90 (s, 1H), 7.80-7.53 (m, 6H), 7.35 (td, 1H), 4.73-4.47 (m, 1H), 3.53-3.41 (m, 2H), 2.90-2.78 (m, 1H), 2.59-2.53 (m, 2H), 2.43-2.19 (m, 2H), 1.91-1.62 (m, 2H), 1.56-1.39 (m, 2H).

LC-MS (Method 8): R$_t$=1.08 min; MS (ESIpos) m/z=531.3 [M+H]⁺.

analytical chiral HPLC method: Instrument: Agilent: 1260; column: Chiralpak IC 3 µm 100×4.6 mm; eluent/gradient: hexane/ethanol/diethylamine 95:5:0.1 gradient to 50:50:0.1 over 10 min; flow 1.0 mL/min; temperature: 25° C.; injection: 1.0 µL; detection: DAD 254 nm;

Analytical chiral HPLC: R$_t$=major isomer 9.36, minor isomer (corresponds to Example 277) 9.85 min; ee=70.7% (compare retention time with Example 277

Example 277

N⁴-{4-[(2-chloro-4-fluorobenzoyl)amino]phenyl}-N⁵-{2-[(3R)-3-fluoropiperidin-1-yl]ethyl}-1H-imidazole-4,5-dicarboxamide

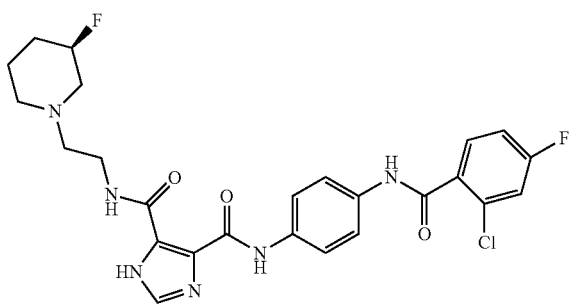 [SMILES: O=C(Nc1ccc(NC(=O)c2nc[nH]c2C(=O)NCCN2CCC[C@@H](F)C2)cc1)c1ccc(F)cc1Cl]

Was prepared in analogy to the synthesis N⁴-{4-[(2-chloro-4-fluorobenzoyl)amino]phenyl}-N⁵-{2-[(2S)-2-methylpiperidin-1-yl]ethyl}-1H-imidazole-4,5-dicarboxamide formic acid salt (Example 266) using 117 mg (0.800 mmol) 2-[(3R)-3-fluoropiperidin-1-yl]ethanamine (Intermediate 065). For work-up the reaction mixture was concentrated and residue was stirred with methanol. The precipitate was collected by filtration and the filtrate was concentrated and repurified by preparative HPLC to give the title compound (80.0 mg).

¹H-NMR (400 MHz, DMSO-d₆): δ [ppm]=13.76-12.97 (m, 2H), 10.50 (s, 1H), 9.19-8.24 (m, 1H), 7.92 (s, 1H), 7.80-7.63 (m, 5H), 7.58 (dd, 1H), 7.35 (td, 1H), 4.73-4.50 (m, 1H), 3.55-3.38 (m, 2H), 2.92-2.76 (m, 1H), 2.62-2.52 (m, 2H), 2.44-2.21 (m, 2H), 1.92-1.61 (m, 2H), 1.56-1.35 (m, 2H).

LC-MS (Method 8): R$_t$=1.06 min; MS (ESIpos) m/z=531.3 [M+H]⁺.

Analytical chiral HPLC (method see Example 276): R$_t$=minor isomer 9.39 (corresponds to Example 276), major isomer 9.82 min; ee=73.5% (compare retention time with Example 276)

Example 278

N⁴-{4-[(2-chloro-4-fluorobenzoyl)amino]phenyl}-N⁵-{2-[(3R)-3-methylpiperidin-1-yl]ethyl}-1H-imidazole-4,5-dicarboxamide

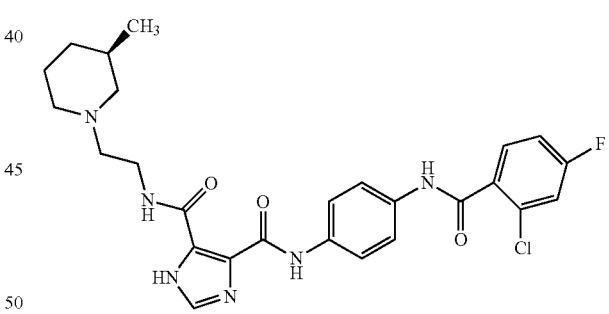

Was prepared in analogy to the synthesis N⁴-{4-[(2-chloro-4-fluorobenzoyl)amino]phenyl}-N⁵-{2-[(2S)-2-methylpiperidin-1-yl]ethyl}-1H-imidazole-4,5-dicarboxamide formic acid salt (Example 266) using 114 mg (0.800 mmol) 2-[(3R)-3-methylpiperidin-1-yl]ethanamine (Intermediate 069). For work-up the reaction mixture was concentrated and residue was stirred with methanol. The precipitate was collected by filtration and the filtrate was concentrated and repurified by preparative HPLC to give the title compound (47.0 mg).

¹H-NMR (400 MHz, DMSO-d₆): δ [ppm]=13.96-12.79 (m, 2H), 10.52 (s, 1H), 8.92-8.30 (m, 1H), 7.91 (s, 1H), 7.83-7.63 (m, 5H), 7.59 (dd, 1H), 7.35 (td, 1H), 3.46 (q, 2H), 2.88-2.74 (m, 2H), 1.96-1.82 (m, 1H), 1.68-1.37 (m, 5H), 0.94-0.77 (m, 4H).

LC-MS (Method 8): $R_t$=1.25 min; MS (ESIpos) m/z=527.3 [M+H]$^+$.

Specific optical rotation: (DMSO, 589 nM, 20° C.): −2.9°

Example 279

N$^4$-{4-[(2-chloro-4-fluorobenzoyl)amino]phenyl}-N$^5$-[2-(3,3-difluoropyrrolidin-1-yl)ethyl]-1H-imidazole-4,5-dicarboxamide

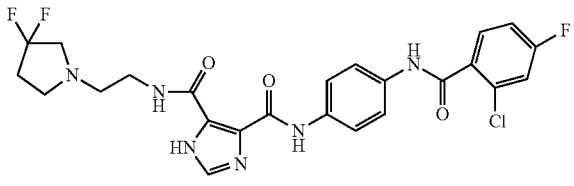 [SMILES: O=C(Nc1ccc(NC(=O)c2nc[nH]c2C(=O)NCCN2CCC(F)(F)C2)cc1)c1ccc(F)cc1Cl]

Was prepared in analogy to the synthesis N$^4$-{4-[(2-chloro-4-fluorobenzoyl)amino]phenyl}-N$^5$-{2-[(2S)-2-methylpiperidin-1-yl]ethyl}-1H-imidazole-4,5-dicarboxamide formic acid salt (Example 266) using 90.1 mg (0.600 mmol) 2-(3,3-difluoropyrrolidin-1-yl)ethanamine (Intermediate 068). For work-up the reaction mixture was concentrated and the residue was purified by preparative HPLC to give the title compound (46.0 mg).

$^1$H-NMR (400 MHz, DMSO-d$_6$): δ [ppm]=13.55 (s, 1H), 13.43 (s, 1H), 10.49 (s, 1H), 8.74 (t, 1H), 7.92 (s, 1H), 7.82-7.64 (m, 5H), 7.60-7.52 (m, 1H), 7.37-7.31 (m, 1H), 3.54-3.39 (m, 2H), 3.04-2.91 (m, 2H), 2.81-2.72 (m, 2H), 2.70-2.58 (m, 2H), 2.29-2.15 (m, 2H).

Example 280

N$^5$-(2-amino-2-methylpropyl)-N$^4$-{4-[(2-chloro-4-fluorobenzoyl)amino]phenyl}-1H-imidazole-4,5-dicarboxamide

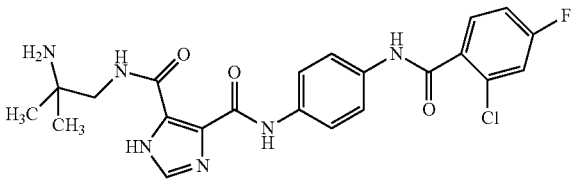 [SMILES: CC(C)(N)CNC(=O)c1[nH]cnc1C(=O)Nc1ccc(NC(=O)c2ccc(F)cc2Cl)cc1]

To a suspension of 188 mg (0.600 mmol) 5,10-Dioxo-5H,10H-diimidazo[1,5-a; 1',5'-d]pyrazin-1,6-dicarbonyl-dichloride (Intermediate 001) in 9.0 mL THF were added 318 mg (1.20 mmol) N-(4-aminophenyl)-2-chloro-4-fluorobenzamide (Intermediate 004) and 251 μL (1.80 mmol) triethylamine. The resulting mixture was stirred for 90 min at room temperature. A solution of 106 mg (1.20 mmol) 2-methylpropane-1,2-diamine and 251 μL (1.80 mmol) triethylamine in 2.0 mL THF was then added and the mixture was stirred overnight at room temperature. The precipitate was collected by filtration and purified by preparative HPLC to provide the title compound (27.0 mg).

$^1$H-NMR (400 MHz, DMSO-d$_6$): δ [ppm]=10.50 (s, 1H), 7.92 (s, 1H), 7.73-7.63 (m, 5H), 7.56 (dd, 1H), 7.34 (dt, 1H), 1.10 (s, 6H).

LC-MS (Method 7): $R_t$=0.85 min; MS (ESIpos) m/z=473.2 [M+H]$^+$.

Example 281

N$^4$-{4-[(2-chloro-4-fluorobenzoyl)amino]phenyl}-N$^5$-[(3S)-pyrrolidin-3-yl]-1H-imidazole-4,5-dicarboxamide

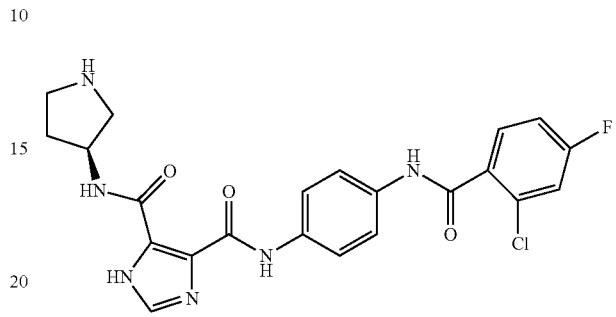

0.54 mL (2.2 mmol) 4 M hydrochloric acid in dioxane was added to a suspension of 84.0 mg (0.144 mmol) tert-butyl (3S)-3-({[4-({4-[(2-chloro-4-fluorobenzoyl)amino]phenyl}carbamoyl)-1H-imidazol-5-yl]carbonyl}amino)pyrrolidine-1-carboxylate (Intermediate 071) in 2.0 mL dichloromethane and the mixture was stirred at room temperature overnight. The resulting precipitate was collected by filtration and purified by preparative HPLC to provide the title compound (15.0 mg).

$^1$H-NMR (400 MHz, DMSO-d$_6$): δ [ppm]=14.02-12.70 (m, 1H), 10.52 (s, 1H), 9.22-8.40 (m, 1H), 7.92 (s, 1H), 7.77-7.63 (m, 5H), 7.60 (dd, 1H), 7.36 (td, 1H), 4.45-4.34 (m, 1H), 3.08-2.88 (m, 2H), 2.83-2.69 (m, 2H), 2.55-2.53 (m, 1H), 2.14-1.94 (m, 1H), 1.79-1.58 (m, 1H).

LC-MS (Method 8): $R_t$=0.83 min; MS (ESIpos) m/z=471.2 [M+H]$^+$.

Example 282

N$^4$-{4-[(2-chloro-4-fluorobenzoyl)amino]phenyl}-N$^5$-[(3R)-pyrrolidin-3-yl]-1H-imidazole-4,5-dicarboxamide hydrochloride salt

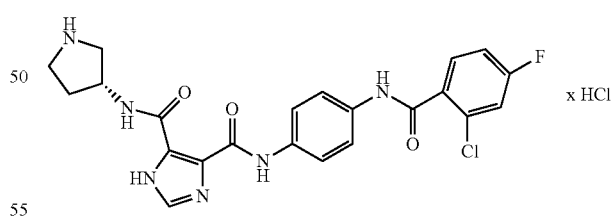

Was prepared in analogy to the synthesis of N$^4$-{4-[(2-chloro-4-fluorobenzoyl)amino]phenyl}-N$^5$[(3S)-pyrrolidin-3-yl]-1H-imidazole-4, 5-dicarboxamide (Example 281) using 110 mg (0.192 mmol) tert-butyl (3R)-3-({[4-({4-[(2-chloro-4-fluorobenzoyl)amino]phenyl}carbamoyl)-1H-imidazol-5-yl]carbonyl}amino)pyrrolidine-1-carboxylate (Intermediate 072) as starting material. For work-up the precipitated solid was collected by filtration and dried to provide the title compound (84.0 mg).

$^1$H-NMR (400 MHz, DMSO-d$_6$): δ [ppm]=13.86-11.92 (m, 1H), 10.53 (s, 1H), 9.82-9.23 (m, 1H), 9.20-9.06 (m, 1H), 9.01-8.83 (m, 1H), 7.98 (s, 1H), 7.75-7.63 (m, 5H), 7.59 (dd, 1H), 7.35 (td, 1H), 4.75-4.63 (m, 1H), 3.51-3.31 (m, 2H), 3.31-3.18 (m, 2H), 2.30-2.22 (m, 1H), 2.10-1.98 (m, 1H).

LC-MS (Method 8): $R_t$=0.89 min; MS (ESIpos) m/z=471.2 [M+H]$^+$.

Example 283

N$^5$-(3-amino-3-methylbutyl)-N$^4$-{4-[(2-chlorobenzoyl)amino]phenyl}-1H-imidazole-4,5-dicarboxamide hydrochloride salt

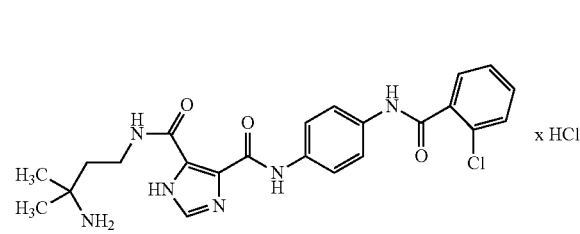 [SMILES: CC(C)(N)CCNC(=O)c1[nH]cnc1C(=O)Nc1ccc(NC(=O)c2ccccc2Cl)cc1]

Was prepared in analogy to the synthesis of N$^4$-{4-[(2-chloro-4-fluorobenzoyl)amino]phenyl}-N$^5$-[(3S)-pyrrolidin-3-yl]-1H-imidazole-4,5-dicarboxamide (Example 281) using 59.0 (0.104 mmol) tert-butyl [4-({[4-({4-[(2-chlorobenzoyl)amino]phenyl}carbamoyl)-1H-imidazol-5-yl]carbonyl}amino)-2-methylbutan-2-yl]carbamate (Intermediate 073) as starting material. For work-up the precipitated solid was collected by filtration and dried to provide the title compound (58.0 mg).

$^1$H-NMR (400 MHz, DMSO-d$_6$): δ [ppm]=13.31-12.24 (m, 1H), 10.53 (s, 1H), 9.68-9.05 (m, 1H), 8.0-7.87 (m, 4H), 7.80-7.63 (m, 4H), 7.63-7.40 (m, 4H), 3.53-3.34 (m, 2H), 2.02-1.78 (m, 2H), 1.31 (s, 6H).

LC-MS (Method 8): $R_t$=0.94 min; MS (ESIpos) m/z=471.2 [M+H]$^+$.

Example 284

N$^4$-{4-[(2-chloro-4-fluorobenzoyl)amino]phenyl}-N$^5$-(pyrrolidin-2-ylmethyl)-1H-imidazole-4,5-dicarboxamide hydrochloride salt

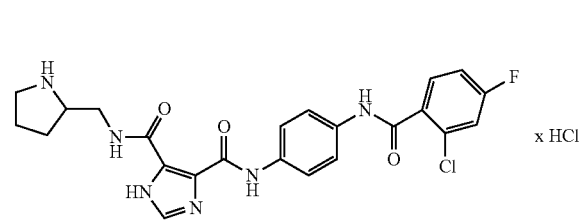 [SMILES: O=C(Nc1ccc(NC(=O)c2nc[nH]c2C(=O)NCC2CCCN2)cc1)c1ccc(F)cc1Cl]

Was prepared in analogy to the synthesis of N$^4$-{4-[(2-chloro-4-fluorobenzoyl)amino]phenyl}-N$^5$[(3S)-pyrrolidin-3-yl]-1H-imidazole-4, 5-dicarboxamide (Example 281) using 102 (0.174 mmol) tert-butyl 2-[({[4-({4-[(2-chloro-4-fluorobenzoyl)amino]phenyl}carbamoyl)-1H-imidazol-5-yl]carbonyl}amino)methyl]pyrrolidine-1-carboxylate (Intermediate 074) as starting material. For work-up the precipitated solid was collected by filtration and dried to provide the title compound (78.0 mg).

$^1$H-NMR (400 MHz, DMSO-d$_6$): δ [ppm]=14.00-12.50 (m, 1H), 10.53 (s, 1H), 9.55-8.98 (m, 2H), 8.80-8.61 (m, 1H), 7.99 (s, 1H), 7.82-7.63 (m, 5H), 7.59 (dd, 1H), 7.35 (td, 1H), 3.79-3.69 (m, 1H), 3.68-3.63 (m, 2H), 3.30-3.08 (m, 2H), 2.14-1.80 (m, 3H), 1.77-1.64 (m, 1H).

LC-MS (Method 8): $R_t$=0.99 min; MS (ESIneg) m/z=483.2 [M–H]$^-$.

Example 285

5-[(3-aminopyrrolidin-1-yl)carbonyl]-N-{4-[(2-chloro-4-fluorobenzoyl)amino]phenyl}-1H-imidazole-4-carboxamide hydrochloride salt

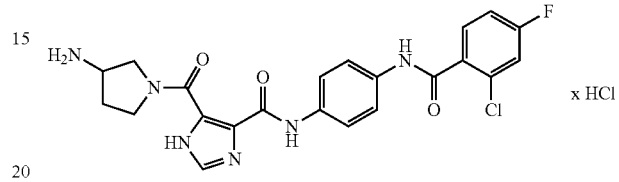

Was prepared in analogy to the synthesis of N$^4$-{4-[(2-chloro-4-fluorobenzoyl)amino]phenyl}-N$^5$[(3S)-pyrrolidin-3-yl]-1H-imidazole-4, 5-dicarboxamide (Example 281) using 80.0 mg (0.140 mmol) tert-butyl (1-{[4-({4-[(2-chloro-4-fluorobenzoyl)amino]phenyl}carbamoyl)-1H-imidazol-5-yl]carbonyl}pyrrolidin-3-yl)carbamate (Intermediate 075) as starting material. For work-up the precipitated solid was collected by filtration and dried to provide the title compound (65.5 mg).

$^1$H-NMR (400 MHz, DMSO-d$_6$): δ [ppm]=14.00-12.77 (m, 2H), 10.53 (s, 1H), 8.29-8.08 (m, 3H), 7.98-7.95 (m, 1H), 7.83-7.63 (m, 5H), 7.59 (dd, 1H), 7.35 (td, 1H), 4.29-4.11 (m, 2H), 2.31-2.17 (m, 1H), 2.12-1.96 (m, 1H).

LC-MS (Method 8): $R_t$=0.77 min; MS (ESIpos) m/z=471.2 [M+H]$^+$.

Example 286

N$^5$-(3-amino-3-methylbutyl)-N$^4$-{4-[(2-chloro-4-fluorobenzoyl)amino]phenyl}-1H-imidazole-4,5-dicarboxamide

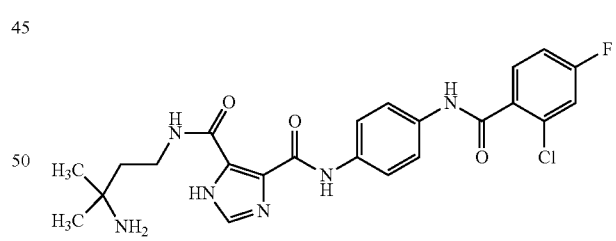

Was prepared in analogy to the synthesis of N$^4$-{4-[(2-chloro-4-fluorobenzoyl)amino]phenyl}-N$^5$-[(3S)-pyrrolidin-3-yl]-1H-imidazole-4,5-dicarboxamide (Example 281) using 75.0 mg (0.128 mmol) tert-butyl [4-({[4-({4-[(2-chloro-4-fluorobenzoyl)amino]phenyl}carbamoyl)-1H-imidazol-5-yl]carbonyl}amino)-2-methylbutan-2-yl]carbamate (Intermediate 076) as starting material. For work-up the precipitated solid was collected by filtration and the purified by preparative HPLC to give the title compound (16.5 mg).

$^1$H-NMR (400 MHz, DMSO-d$_6$): δ [ppm]=13.97-12.67 (m, 1H), 10.50 (s, 1H), 10.10-9.05 (m, 1H), 7.89 (s, 1H), 7.73-7.65 (m, 5H), 7.58 (dd, 1H), 7.35 (td, 1H), 3.44 (t, 2H), 1.62 (t, 2H), 1.10 (s, 6H).

LC-MS (Method 10): $R_t$=0.96 min; MS (ESIpos) m/z=487.3 [M+H]$^+$.

Example 287

N$^4$-{4-[(2-chloro-4-fluorobenzoyl)amino]phenyl}-N$^5$-[2-(methylamino)ethyl]-1H-imidazole-4,5-dicarboxamide

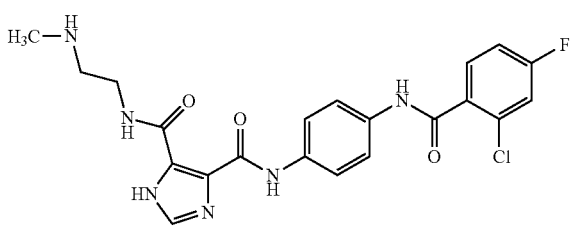 [SMILES: CNCCNC(=O)c1[nH]cnc1C(=O)Nc1ccc(NC(=O)c2ccc(F)cc2Cl)cc1]

Was prepared in analogy to the synthesis of N$^4$-{4-[(2-chloro-4-fluorobenzoyl)amino]phenyl}-N$^5$-[(3S)-pyrrolidin-3-yl]-1H-imidazole-4,5-dicarboxamide (Example 281) using 60.0 mg (0.107 mmol) tert-butyl [2-({[4-({4-[(2-chloro-4-fluorobenzoyl)amino]phenyl}carbamoyl)-1H-imidazol-5-yl]carbonyl}amino)ethyl]methylcarbamate (Intermediate 077) as starting material. For work-up the precipitated solid was collected by filtration and the purified by preparative HPLC to give the title compound (9.1 mg).

$^1$H-NMR (400 MHz, DMSO-d$_6$): δ [ppm]=14.03-12.85 (m, 1H), 10.49 (s, 1H), 9.33-8.51 (m, 1H), 7.89 (s, 1H), 7.75-7.63 (m, 5H), 7.57 (dd, 1H), 7.34 (td, 1H), 3.44-3.38 (m, 2H), 2.67 (t, 2H), 2.33-2.28 (m, 3H).

LC-MS (Method 10): $R_t$=0.86 min; MS (ESIpos) m/z=459.2 [M+H]$^+$.

Example 288

N$^4$-{4-[(2-chloro-4-fluorobenzoyl)amino]phenyl}-N$^5$-[2-(isopropylamino)ethyl]-1H-imidazole-4,5-dicarboxamide

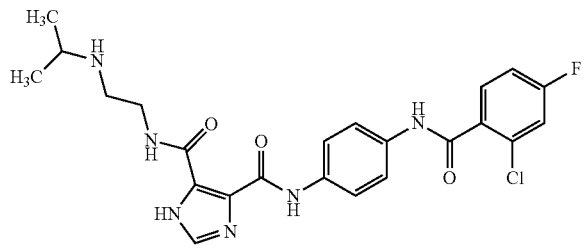 [SMILES: CC(C)NCCNC(=O)c1[nH]cnc1C(=O)Nc1ccc(NC(=O)c2ccc(F)cc2Cl)cc1]

Was prepared in analogy to the synthesis of N$^4$-{4-[(2-chloro-4-fluorobenzoyl)-amino]phenyl}-N$^5$-(2-hydroxy-2-methylpropyl)-1H-imidazole-4,5-dicarboxamide (Example 223) using 61.3 mg (0.600 mmol) N-(propan-2-yl)ethane-1,2-diamine (CAS No. 19522-67-9) and preparative HPLC to give the title compound (9.0 mg).

$^1$H-NMR (400 MHz, DMSO-d$_6$): δ [ppm]=13.60 (br. s., 1H), 10.51 (s, 1H), 8.91-8.58 (m, 1H), 7.93 (s, 1H), 7.83-7.64 (m, 5H), 7.59 (dd, 1H), 7.39-7.28 (m, 1H), 3.44-3.39 (m, 2H), 2.83-2.69 (m, 3H), 1.05-0.96 (m, 6H).

LC-MS (Method 8): $R_t$=1.02 min; MS (ESIpos) m/z=487.2 [M+H]$^+$.

Example 289

N-{4-[(2-chloro-4-fluorobenzoyl)amino]phenyl}-5-(piperazin-1-ylcarbonyl)-1H-imidazole-4-carboxamide hydrochloric acid salt

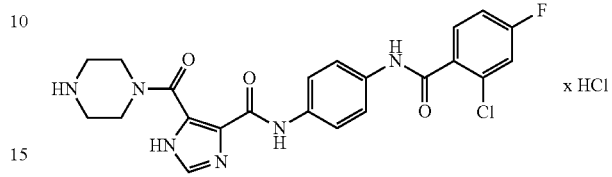

Was prepared in analogy to the synthesis of N$^4$-{4-[(2-chloro-4-fluorobenzoyl)-amino]phenyl}-N$^5$-[(3S)-pyrrolidin-3-yl]-1H-imidazole-4,5-dicarboxamide (Example 281) using 37.0 mg (0.056 mmol) tert-butyl 4-{[4-({4-[(2-chloro-4-fluorobenzoyl)amino]phenyl}carbamoyl)-1H-imidazol-5-yl]carbonyl}piperazine-1-carboxylate (Intermediate 078) as starting material. For work-up the precipitated solid was collected by filtration and dried to give the title compound (16.0 mg).

$^1$H-NMR (400 MHz, DMSO-d$_6$): δ [ppm]=10.52 (s, 1H), 9.50-9.00 (m, 2H), 7.96 (s, 1H), 7.72-7.52 (m, 6H), 7.35 (td, 1H), 4.37-4.02 (m, 2H), 3.92 (br. s., 2H).

LC-MS (Method 8): $R_t$=0.70 min; MS (ESIpos) m/z=471.2 [M+H]$^+$.

Example 290

N$^5$-(2-aminoethyl)-N$^4$-{4-[(2-chloro-4-fluorobenzoyl)amino]phenyl}-1H-imidazole-4,5-dicarboxamide

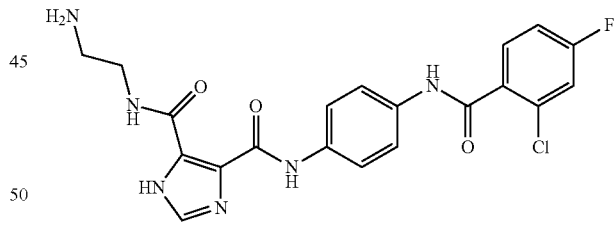

Was prepared in analogy to the synthesis of N$^4$-{4-[(2-chloro-4-fluorobenzoyl)-amino]phenyl}-N$^5$-[(3S)-pyrrolidin-3-yl]-1H-imidazole-4,5-dicarboxamide (Example 281) using 37.0 mg (0.059 mmol) tert-butyl [2-({[4-({4-[(2-chloro-4-fluorobenzoyl)amino]phenyl}carbamoyl)-1H-imidazol-5-yl]carbonyl}amino)ethyl]carbamate (Intermediate 079) as starting material. For work-up the precipitated solid was collected by filtration purified by preparative HPLC to give the title compound (7.0 mg).

$^1$H-NMR (400 MHz, DMSO-d$_6$): δ [ppm]=13.99-12.58 (m, 1H), 10.51 (s, 1H), 9.63-8.43 (m, 1H), 7.90 (s, 1H), 7.81-7.63 (m, 5H), 7.59 (dd, 1H), 7.35 (td, 1H), 2.74 (t, 2H).)

LC-MS (Method 8): $R_t$=0.81 min; MS (ESIpos) m/z=445.2 [M+H]$^+$.

Example 291

N⁴-{4-[(2-chloro-4-fluorobenzoyl)amino]-3-(trifluoromethoxy)phenyl}-N⁵-methyl-1H-imidazole-4,5-dicarboxamide

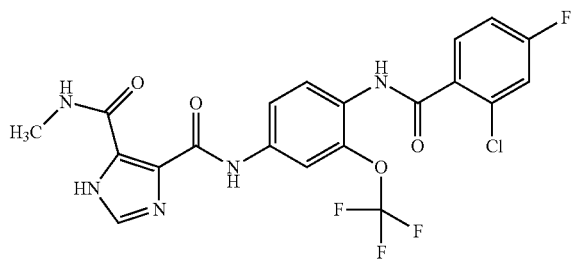 [SMILES: CNC(=O)c1[nH]cnc1C(=O)Nc1ccc(NC(=O)c2ccc(F)cc2Cl)c(OC(F)(F)F)c1]

To a suspension of 62.6 mg (0.200 mmol) 5,10-Dioxo-5H,10H-diimidazo[1,5-a; 1',5'-d]pyrazin-1,6-dicarbonyl-dichloride (Intermediate 001) in 10 mL THF were added 139 mg (0.400 mmol) N-[4-amino-2-(trifluoromethoxy)phenyl]-2-chloro-4-fluorobenzamide (Intermediate 055) and 105 µL (0.600 mmol) N,N-diisopropylethylamine and the mixture was stirred for 6 h at room temperature. 0.20 mL (2 M solution in THF, 0.40 mmol) methylamine and 105 µL (0.600 mmol) N,N-diisopropylethylamine in 10 mL THF were added and the mixture was stirred at room temperature overnight. The resulting precipitate was collected by filtration, washed with methanol and water and tried to provide the title compound (124 mg).

¹H-NMR (400 MHz, DMSO-d₆): δ [ppm]=13.98 (br. s, 1H), 13.51 (br. s., 1H), 10.35 (s, 1H), 8.88 (br. s, 1H), 8.15 (br. s., 1H), 7.95 (s, 1H), 7.90-7.74 (m, 1H), 7.66-7.57 (m, 2H), 7.52 (br. s., 1H), 7.43-7.30 (m, 1H), 2.89 (d, 3H).

LC-MS (Method 8): $R_t$=1.09 min; MS (ESIpos) m/z=500.2 [M+H]⁺.

Example 292

N⁴-{4-[(2-chloro-4-fluorobenzoyl)amino]-3-(trifluoromethoxy)phenyl}-N⁵-(2,2,2-trifluoroethyl)-1H-imidazole-4,5-dicarboxamide

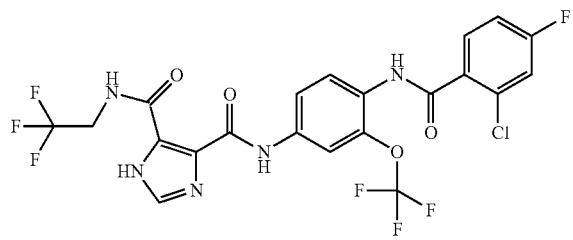 [SMILES: O=C(Nc1ccc(NC(=O)c2nc[nH]c2C(=O)NCC(F)(F)F)cc1OC(F)(F)F)c1ccc(F)cc1Cl]

Was prepared in analogy to the synthesis of N⁴-{4-[(2-chloro-4-fluorobenzoyl)-amino]-3-(trifluoromethoxy)phenyl}-N⁵-methyl-1H-imidazole-4,5-dicarboxamide (Example 291) using 31 µL, (0.400 mmol) 2,2,2-trifluoroethanamine as second amine. For workup, the precipitate was collected by filtration, washed with water and methanol and purified by preparative HPLC followed by recrystallization from methanol to give the title compound (82.0 mg).

¹H-NMR (400 MHz, DMSO-d₆): δ [ppm]=14.00-12.85 (m, 1H), 10.36 (s, 1H), 8.13 (br. s., 1H), 8.04 (s, 1H), 7.81 (d, 1H), 7.72-7.40 (m, 3H), 7.37 (td, 1H), 4.28-4.06 (m, 2H).

LC-MS (Method 8): $R_t$=1.17 min; MS (ESIpos) m/z=568.2 [M+H]⁺.

Example 293

N⁴-{4-[(2-chloro-4-fluorobenzoyl)amino]-3-(trifluoromethoxy)phenyl}-N⁵-[2-(piperidin-1-yl)ethyl]-1H-imidazole-4,5-dicarboxamide

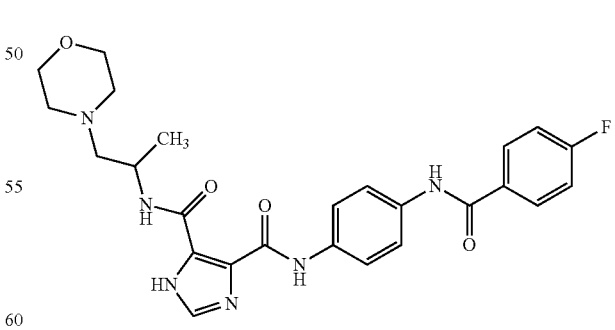

Was prepared in analogy to the synthesis of N⁴-{4-[(2-chloro-4-fluorobenzoyl)-amino]-3-(trifluoromethoxy)phenyl}-N⁵-methyl-1H-imidazole-4,5-dicarboxamide (Example 291) using 51.3 mg, (0.400 mmol) 2-(piperidin-1-yl)ethanamine (CAS No. 27578-60-5) as second amine. For workup, the precipitate was collected by filtration, washed with water and methanol and purified by preparative HPLC followed by recrystallization from methanol to give the title compound (51.0 mg).

¹H-NMR (400 MHz, DMSO-d₆): δ [ppm]=13.94 (br. s., 1H), 13.54 (br. s., 1H), 10.35 (s, 1H), 8.70 (br. s., 1H), 8.16 (br. s., 1H), 7.97 (s, 1H), 7.88-7.73 (m, 1H), 7.68-7.55 (m, 2H), 7.46 (br. s., 1H), 7.37 (td, 1H), 3.46 (q, 2H), 2.44-2.35 (m, 4H), 1.56-1.44 (m, 4H), 1.43-1.33 (m, 2H).

LC-MS (Method 8): $R_t$=1.33 min; MS (ESIpos) m/z=597.1 [M+H]⁺.

Example 294

N⁴-{4-[(4-fluorobenzoyl)amino]phenyl}-N⁵-[1-(morpholin-4-yl)propan-2-yl]-1H-imidazole-4,5-dicarboxamide To a suspension of 62.6 mg (0.200 mmol) 5,10-Dioxo-5H,10H-diimidazo[1,5-a; 1',5'-d]pyrazin-1,6-dicarbonyl-dichloride (Intermediate 001) in 3 mL THF were added 95.9 mg (0.400 mmol) N-(4-aminophenyl)-4-fluorobenzamide (Intermediate 017) and 83.6 µl (0.600 mmol) triethylamine. The mixture was stirred for 30 min at room temperature.

61.8 μl (0.400 mmol) 1-(morpholin-4-yl)propan-2-amine (CAS No. 50998-05-5) and 348 μl (2.00 mmol, 10 equiv.) N,N-diisopropylethylamine were added and the mixture was stirred overnight at room temperature. The mixture was concentrated and the residue was purified by preparative HPLC to provide the title compound (68.9 mg).

$^1$H-NMR (500 MHz, DMSO-d$_6$): δ [ppm]=13.60 (br. s, 1H), 13.38 (br. s, 1H), 10.27 (s, 1H), 8.07-8.02 (m, 2H), 7.92 (s, 1H), 7.80-7.63 (m, 4H), 7.37 (t, 2H), 4.31-4.20 (m, 1H), 3.54 (br. s., 4H), 2.48-2.33 (m, 5H), 1.21 (d, 3H).

LC-MS (Method 8): R$_t$=1.01 min; MS (ESIpos) m/z=495.0 [M+H]$^+$.

63.0 mg (0.127 mmol) of N$^4$-{4-[(4-fluorobenzoyl)amino]phenyl}-N$^5$-[1-(morpholin-4-yl)propan-2-yl]-1H-imidazole-4,5-dicarboxamide (Example 294) was separated into enantiomers by chiral HPLC to give 14.6 mg enantiomer 1 (Example 295) and 13.3 mg enantiomer 2 (Example 296)

Preparative chiral HPLC method: Instrument: Sepiatec: Prep SFC100; column: Chiralpak IC 5 μm 250×20 mm; eluent: carbon dioxide/ethanol+0.2% diethylamine 72:28; flow 80 mL/min; pressure (outlet): 150 bar; temperature: 40° C.; Sample preparation: 63 mg dissolved in 1 mL of mixture of dichloromethane/methanol 1:1; injection: 10×0.1 mL; detection: UV 254 nm;

analytical chiral HPLC method: Instrument: Agilent: 1260 AS, MWD, Aurora SFC-Modul; column: Chiralpak IC 5 μm 100×4.6 mm; eluent: carbon dioxide/ethanol+0.2% diethylamine 72:28; flow 4.0 mL/min; pressure (outlet): 100 bar; temperature: 37.5° C.; injection: 10 μL; detection: DAD 254 nm;

Example 295

N$^4$-{4-[(4-fluorobenzoyl)amino]phenyl}-N$^5$-[1-(morpholin-4-yl)propan-2-yl]-1H-imidazole-4,5-dicarboxamide (enantiomer 1)

Analytical chiral HPLC: R$_t$=2.43 min; ee=100
Specific optical rotation: (DMSO, 589 nM, 20° C.): +9.7°

Example 296

N$^4$-{4-[(4-fluorobenzoyl)amino]phenyl}-N$^5$-[1-(morpholin-4-yl)propan-2-yl]-1H-imidazole-4,5-dicarboxamide (enantiomer 2)

Analytical chiral HPLC: R$_t$=3.59 min; ee=90.4
Specific optical rotation: (DMSO, 589 nM, 20° C.): −6.8°

Example 297

N$^4$-{4-[(2-chloro-4-fluorobenzoyl)amino]phenyl}-N$^5$-[3-(piperidin-1-yl)propyl]-1H-imidazole-4,5-dicarboxamide

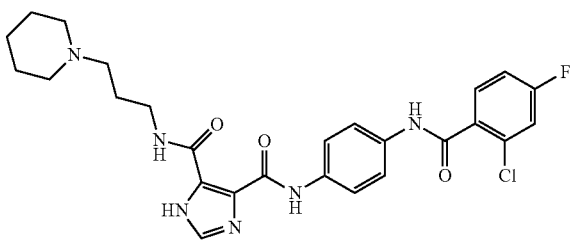 [SMILES: O=C(Nc1ccc(NC(=O)c2nc[nH]c2C(=O)NCCCN2CCCCC2)cc1)c1ccc(F)cc1Cl]

Step 1: To 4.0 g (13.1 mmol) 5,10-Dioxo-5H,10H-diimidazo[1,5-a; 1',5'-d]pyrazin-1,6-dicarbonyl-dichloride (Intermediate 001) in 120 mL dichloromethane were added 6.96 g (26.3 mmol) N-(4-aminophenyl)-2-chloro-4-fluorobenzamide (Intermediate 004) and 3.7 mL (26.3 mmol) triethylamine and the mixture was stirred overnight at 40° C. The reaction mixture was poured into saturated sodium chloride solution and extracted with ethyl acetate. The organic phase was dried and concentrated under reduced pressure. The residue was purified by flash chromatography on silica gel (dichloromethane dichloromethane/methanol 7:3) to give 430 mg of methyl 5-({4-[(2-chloro-4-fluorobenzoyl)amino]phenyl}carbamoyl)-1H-imidazole-4-carboxylate.

The aqueous phase was filtered over sea sand and the filtrate was concentrated under reduced pressure. The residue was recrystallized with once methanol. The collected solid was recrystallized with ethyl acetate/hexane (4:1) to give further 5.73 g of methyl 5-({4-[(2-chloro-4-fluorobenzoyl)amino]phenyl}carbamoyl)-1H-imidazole-4-carboxylate.

Step 2: To 50.0 mg (0.120 mmol) methyl 5-({4-[(2-chloro-4-fluorobenzoyl)amino]phenyl}carbamoyl)-1H-imidazole-4-carboxylate (step 1) in 3 ml DMF was added 176 mg (1.20 mmol, 10 equiv.) 3-(piperidin-1-yl)propan-1-amine (CAS No. 3529-08-6). The reaction mixture was stirred overnight at 80° C. and was then concentrated under reduced pressure. The residue was purified by preparative HPLC to give 19.3 mg of the title compound.

$^1$H-NMR (500 MHz, DMSO-d$_6$): δ [ppm]=13.65 (br. s., 1H), 13.39 (br. s., 1H), 10.49 (s, 1H), 9.07 (br. s., 1H), 7.89 (s, 1H), 7.63-7.80 (m, 5H), 7.56 (dd, 1H), 7.34 (td, 1H), 3.40 (d, 3H), 2.33-2.45 (m, 6H), 1.74 (t, 2H), 1.48-1.62 (m, 4H), 1.40 (br. s., 2H).

LC-MS (Method 7): R$_t$=0.81 min; MS (ESIpos) m/z=526.9 [M+H]$^+$.

Example 298

N$^4$-{4-[(2-chloro-4-fluorobenzoyl)amino]phenyl}-N$^5$-[(1-methylpiperidin-3-yl)methyl]-1H-imidazole-4,5-dicarboxamide

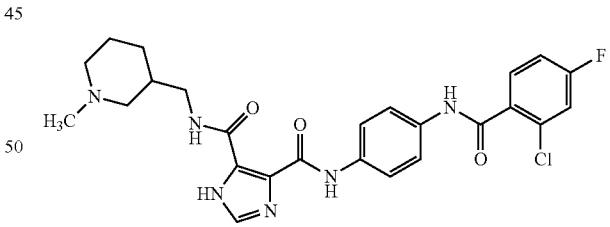

Was prepared in analogy to the synthesis of N$^4$-{4-[(2-chloro-4-fluorobenzoyl)-amino]phenyl}-N$^5$-[3-(piperidin-1-yl)propyl]-1H-imidazole-4,5-dicarboxamide (Example 297) using 171 mg (90% purity; 1.20 mmol) 1-(1-methylpiperidin-3-yl)methanamine (CAS No. 14613-37-7) as starting material to give the title compound (14.5 mg).

$^1$H-NMR (500 MHz, DMSO-d$_6$): δ [ppm]=13.59 (br. s., 1H), 13.42 (br. s., 1H), 10.49 (s, 1H), 8.83 (br. s., 1H), 7.91 (s, 1H), 7.64-7.75 (m, 4H), 7.56 (dd, 1H), 7.34 (td, 1H), 2.73 (br. s., 1H), 2.17 (s, 3H), 1.91 (d, 2H), 1.59-1.82 (m, 4H), 1.46 (d, 1H), 0.97 (br. s., 1H).

LC-MS (Method 7): R$_t$=0.78 min; MS (ESIpos) m/z=512.9 [M+H]$^+$.

Example 299

N⁴-{4-[(2-chloro-4-fluorobenzoyl)amino]phenyl}-N⁵-[3-(2-oxopyrrolidin-1-yl)-propyl]-1H-imidazole-4,5-dicarboxamide

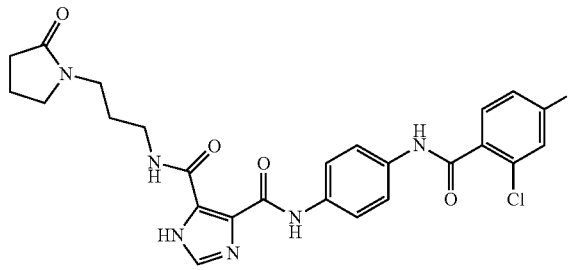

Was prepared in analogy to the synthesis of N⁴-{4-[(2-chloro-4-fluorobenzoyl)-amino]phenyl}-N⁵-[3-(piperidin-1-yl)propyl]-1H-imidazole-4,5-dicarboxamide (Example 297) using 171 mg (1.20 mmol) 1-(3-aminopropyl)pyrrolidin-2-one (CAS No. 7663-77-6) as starting material to give the title compound (13.7 mg).

¹H-NMR (500 MHz, DMSO-d₆): δ [ppm]=13.59 (s, 1H), 13.37-13.48 (m, 1H), 10.50 (s, 1H), 8.87 (t, 1H), 7.92 (s, 1H), 7.65-7.74 (m, 5H), 7.57 (dd, 1H), 7.34 (td, 1H), 3.37 (t, 2H), 3.25 (t, 2H), 2.17-2.26 (m, 2H), 1.89-1.98 (m, 2H), 1.76 (quin, 2H).

LC-MS (Method 7): $R_t$=1.00 min; MS (ESIpos) m/z=526.9 [M+H]⁺.

Example 300

N⁴-{4-[(2-chlorobenzoyl)amino]phenyl}-N⁵-[2-(2,6-dimethylmorpholin-4-yl)-ethyl]-1H-imidazole-4,5-dicarboxamide

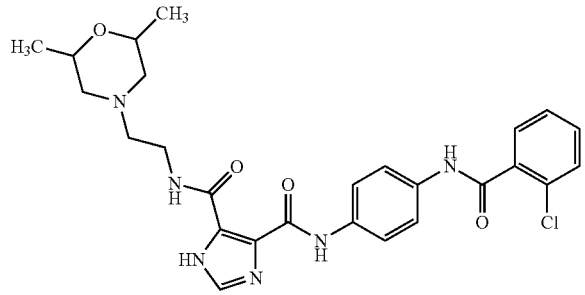 [SMILES: CC1CN(CCNC(=O)c2[nH]cnc2C(=O)Nc2ccc(NC(=O)c3ccccc3Cl)cc2)CC(C)O1]

Was prepared in analogy to the synthesis of N⁴-{4-[(2-chlorobenzoyl)amino]phenyl}-N⁵-[2-(4,4-difluoropiperidin-1-yl)ethyl]-1H-imidazole-4,5-dicarboxamide (Example 214) from 62.6 mg (0.200 mmol) 5,10-dioxo-5H,10H-diimidazo[1,5-a:1',5'-d]pyrazine-1,6-dicarbonyl dichloride (Intermediate 001), 103 mg (0.400 mmol) N-(4-aminophenyl)-2-chlorobenzamide (Intermediate 051) and 83.6 µl triethylamine in 3 ml THF in the first step and using 143 µl (0.800 mmol) 2-(2,6-dimethylmorpholin-4-yl)ethanamine (CAS No. 244789-18-2) as starting material and 697 µl (4.00 mmol, 10 equiv.) N,N-diisopropylethylamine as base in the second step to give the title compound (117 mg).

LC-MS (Method 7): $R_t$=0.77 min; MS (ESIpos) m/z=524.9 [M+H]⁺.

Example 301

N⁴-{4-[(2-4-fluorochlorobenzoyl)amino]phenyl}-N⁵-[2-(2,6-dimethylmorpholin-4-yl)ethyl]-1H-imidazole-4,5-dicarboxamide

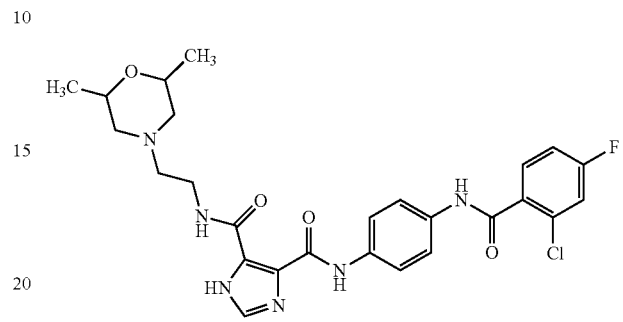

Was prepared in analogy to the synthesis of N⁴-{4-[(2-chloro-4-fluorobenzoyl)-amino]phenyl}-N⁵-(2-hydroxy-2-methylpropyl)-1H-imidazole-4,5-dicarboxamide (Example 223) using 143 µl (0.800 mmol) 2-(2,6-dimethylmorpholin-4-yl)ethanamine (CAS No. 244789-18-2) as starting material and 697 µl (4.00 mmol, 10 equiv.) N,N-diisopropylethylamine as base in the second step to give the title compound (73.1 mg).

LC-MS (Method 7): $R_t$=0.82 min; MS (ESIpos) m/z=542.9 [M+H]⁺.

Example 302

N⁴-{4-[(2-chlorobenzoyl)amino]phenyl}-N⁵-(4-methylpiperazin-1-yl)-1H-imidazole-4,5-dicarboxamide

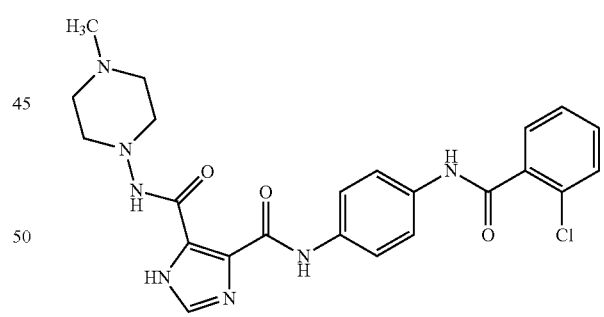

Was prepared in analogy to the synthesis of N⁴-{4-[(2-chlorobenzoyl)amino]phenyl}-N⁵-[2-(4,4-difluoropiperidin-1-yl)ethyl]-1H-imidazole-4,5-dicarboxamide (Example 214) from 62.6 mg (0.200 mmol) 5,10-dioxo-5H,10H-diimidazo[1,5-a:1',5'-d]pyrazine-1,6-dicarbonyl dichloride (Intermediate 001), 103 mg N-(4-aminophenyl)-2-chlorobenzamide (Intermediate 051) and 83.6 µl triethylamine in 3 ml THF in the first step and using 46.1 mg (0.400 mmol) 4-methylpiperazin-1-amine (CAS No. 6928-85-4) as starting material and 348 µl (2.00 mmol, 10 equiv.) N,N-diisopropylethylamine as base in the second step to give the title compound (10.5 mg).

¹H-NMR (400 MHz, DMSO-d₆): δ [ppm]=13.44 (br. s, 1H), 10.53-10.50 (m, 1H), 7.92 (s, 1H), 7.72 (s, 4H), 7.61-7.55 (m, 2H), 7.54-7.41 (m, 3H), 2.94-2.87 (m, 4H), 2.47-2.37 (m, 4H), 2.19 (s, 3H).

LC-MS (Method 7): $R_t$=0.78 min; MS (ESIneg) m/z=480.2 [M–H]⁻.

Example 303

$N^5$-{4-[(2-chloro-4-fluorobenzoyl)amino]phenyl}-$N^4$-[2-(piperidin-1-yl)ethyl]-1,3-oxazole-4,5-dicarboxamide

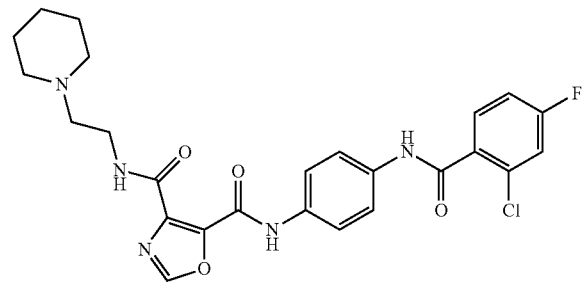 [SMILES: O=C(Nc1ccc(NC(=O)c2ocnc2C(=O)NCCN2CCCCC2)cc1)c1ccc(F)cc1Cl]

Was prepared in analogy to the synthesis of $N^4$-(2-amino-2-methylpropyl)-$N^5$-{4-[(2-chloro-4-fluorobenzoyl)amino]phenyl}-1,3-oxazole-4,5-dicarboxamide (Example 219) from 300 mg (83% purity, 0.596 mmol) methyl 5-({4-[(2-chloro-4-fluoro-benzoyl)amino]phenyl}carbamoyl)-1,3-oxazole-4-carboxylate (Example 14) and 425 µl (2.98 mmol) 2-(piperidin-1-yl)ethanamine (CAS No. 27578-60-5) and 2 ml methanol to give the title compound (95.8 mg).

¹H-NMR (400 MHz, DMSO-d₆): δ [ppm]=13.24 (1H), 10.54 (1H), 8.94-9.02 (1H), 8.78 (1H), 7.64-7.81 (5H), 7.58 (1H), 7.35 (1H), 3.48 (3H), 2.54 (1H), 2.43 (4H), 1.46-1.55 (4H), 1.39 (2H).

LC-MS (Method 7): $R_t$=0.77 min; MS (ESIpos) m/z=514.1 [M+H]⁺.

Example 304

$N^5$-{4-[(4-methoxybenzoyl)amino]phenyl}-$N^4$-methyl-1H-imidazole-4,5-dicarboxamide

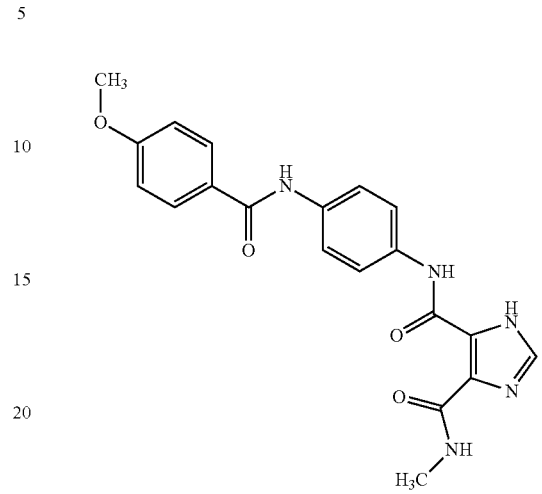

To 39 mg (150 µmol) $N^5$-(4-aminophenyl)-$N^4$-methyl-1H-imidazole-4,5-dicarboxamide and 50 mg (390 µmol)N-ethyl-N-isopropylpropan-2-amine in 1 mL DMF were added 27 mg (195 µmol) N,N,N'-trimethylethane-1,2-diamine in 0.35 mL DMF and 84 mg (195 µmol) COMU ({[(Z)-(1-cyano-2-ethoxy-2-oxoethylidene)amino]oxy}-N,N-dimethylmorpholin-4-ylmethaniminium hexafluorophosphate) in 0.4 mL DMF. The obtained mixture was shaken for 12 h at room temperature.

Any precipitate was filtered off and the crude mixture was subjected to preparative HPLC purification. 9 mg of the title compound were obtained.

LC-MS (Method 15): $R_t$=0.97 min; MS (ESIpos) m/z=394 [M+H]⁺.

The examples 304-415 were prepared in analogy to example 304:

| Example No | Structure | MS (ESIpos) m/z [M + H]+ | Name | Retention time [min] |
|---|---|---|---|---|
| 305 | 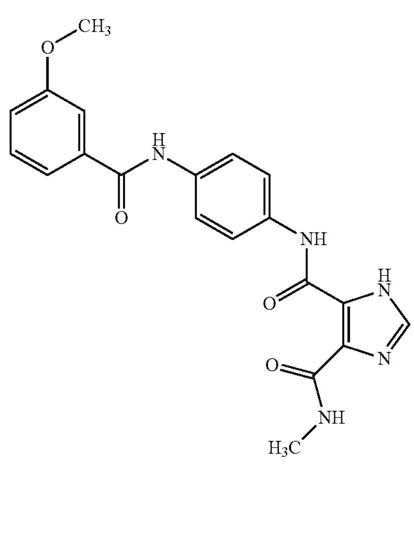 [SMILES: CNC(=O)c1nc[nH]c1C(=O)Nc1ccc(NC(=O)c2cccc(OC)c2)cc1] | 394 | $N^5$-{4-[(3-methoxybenzoyl)amino]phenyl}-$N^4$-methyl-1H-imidazole-4,5-dicarboxamide | 0.99 |

-continued

| Example No | Structure | MS (ESIpos) m/z [M + H]+ | Name | Retention time [min] |
|---|---|---|---|---|
| 306 | 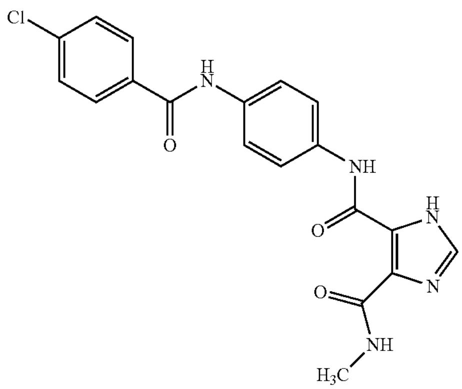 [SMILES: CNC(=O)c1nc[nH]c1C(=O)Nc1ccc(NC(=O)c2ccc(Cl)cc2)cc1] | 398 | N⁵-{4-[(4-chlorobenzoyl)amino]phenyl}-N⁴-methyl-1H-imidazole-4,5-dicarboxamide | 1.08 |
| 307 | 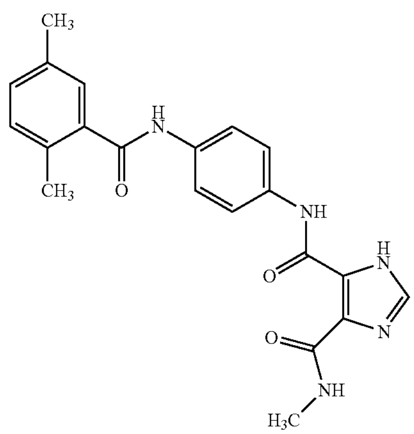 [SMILES: CNC(=O)c1nc[nH]c1C(=O)Nc1ccc(NC(=O)c2cc(C)ccc2C)cc1] | 392 | N⁵-{4-[(2,5-dimethylbenzoyl)amino]phenyl}-N⁴-methyl-1H-imidazole-4,5-dicarboxamide | 1.08 |
| 308 | 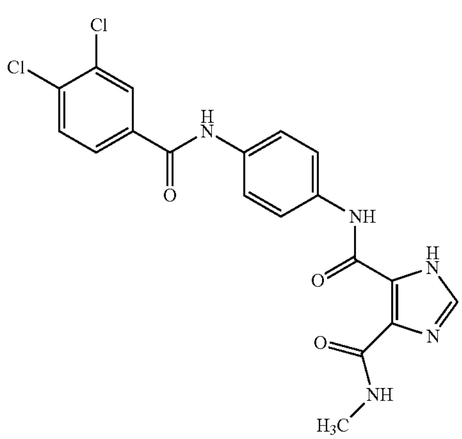 [SMILES: CNC(=O)c1nc[nH]c1C(=O)Nc1ccc(NC(=O)c2ccc(Cl)c(Cl)c2)cc1] | 432 | N⁵-{4-[(3,4-dichlorobenzoyl)amino]phenyl}-N⁴-methyl-1H-imidazole-4,5-dicarboxamide | 1.20 |

-continued

| Example No | Structure | MS (ESIpos) m/z [M + H]+ | Name | Retention time [min] |
|---|---|---|---|---|
| 309 | 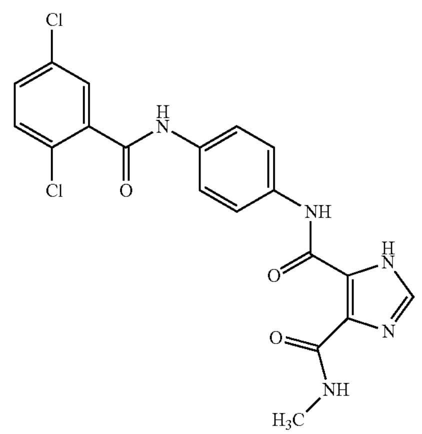 [SMILES: CNC(=O)c1nc[nH]c1C(=O)Nc1ccc(NC(=O)c2cc(Cl)ccc2Cl)cc1] | 432 | N⁵-{4-[(2,5-dichlorobenzoyl)amino]phenyl}-N⁴-methyl-1H-imidazole-4,5-dicarboxamide | 1.10 |
| 310 | 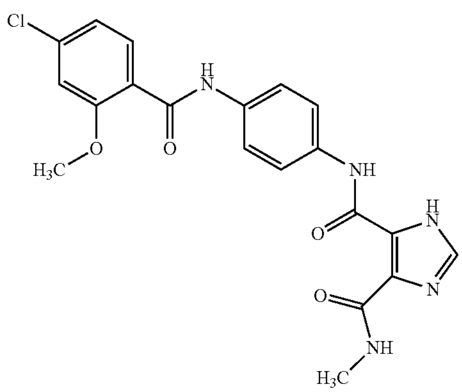 [SMILES: CNC(=O)c1nc[nH]c1C(=O)Nc1ccc(NC(=O)c2ccc(Cl)cc2OC)cc1] | 428 | N⁵-{4-[(4-chloro-2-methoxybenzoyl)amino]phenyl}-N⁴-methyl-1H-imidazole-4,5-dicarboxamide | 1.16 |
| 311 | 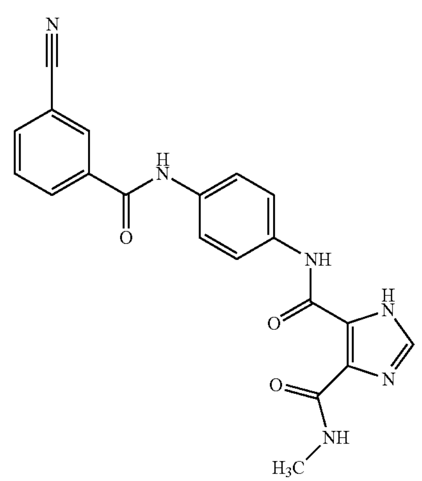 [SMILES: CNC(=O)c1nc[nH]c1C(=O)Nc1ccc(NC(=O)c2cccc(C#N)c2)cc1] | 389 | N⁵-{4-[(3-cyanobenzoyl)amino]phenyl}-N⁴-methyl-1H-imidazole-4,5-dicarboxamide | 0.94 |

-continued

| Example No | Structure | MS (ESIpos) m/z [M + H]+ | Name | Retention time [min] |
|---|---|---|---|---|
| 312 | 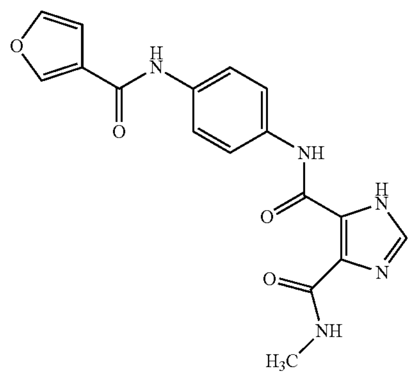 [SMILES: CNC(=O)c1nc[nH]c1C(=O)Nc1ccc(NC(=O)c2ccoc2)cc1] | 354 | N⁵-{4-[(furan-3-ylcarbonyl)amino]phenyl}-N⁴-methyl-1H-imidazole-4,5-dicarboxamide | 0.86 |
| 313 | 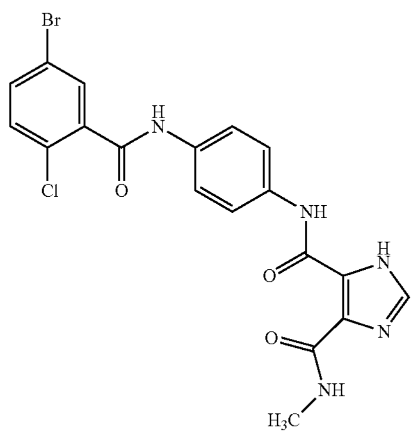 | 476 | N⁵-{4-[(5-bromo-2-chlorobenzoyl)amino]phenyl}-N⁴-methyl-1H-imidazole-4,5-dicarboxamide | 1.12 |
| 314 | 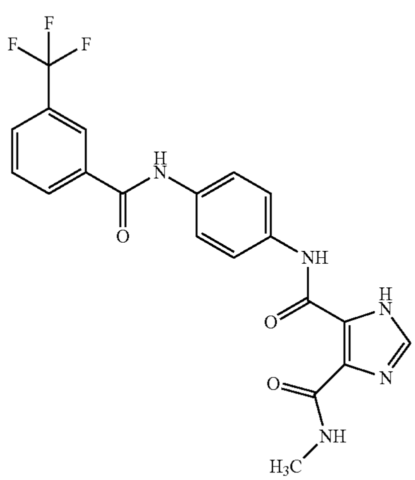 [SMILES: CNC(=O)c1nc[nH]c1C(=O)Nc1ccc(NC(=O)c2cccc(C(F)(F)F)c2)cc1] | 432 | N⁴-methyl-N⁵-(4-{[3-(trifluoromethyl)benzoyl]amino}phenyl)-1H-imidazole-4,5-dicarboxamide | 1.14 |

-continued

| Example No | Structure | MS (ESIpos) m/z [M + H]+ | Name | Retention time [min] |
|---|---|---|---|---|
| 315 | 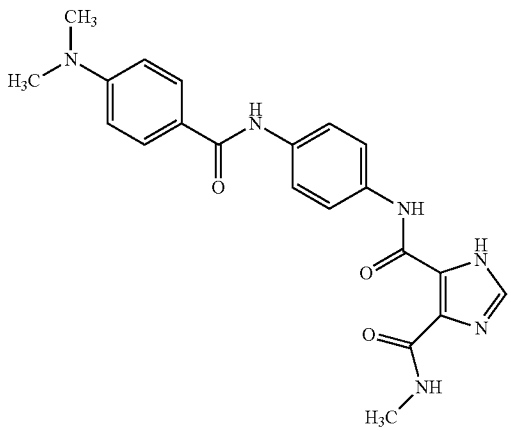 [SMILES: CNC(=O)c1nc[nH]c1C(=O)Nc1ccc(NC(=O)c2ccc(N(C)C)cc2)cc1] | 407 | N⁵-(4-{[4-(dimethylamino)benzoyl]amino}phenyl)-N⁴-methyl-1H-imidazole-4,5-dicarboxamide | 1.01 |
| 316 | 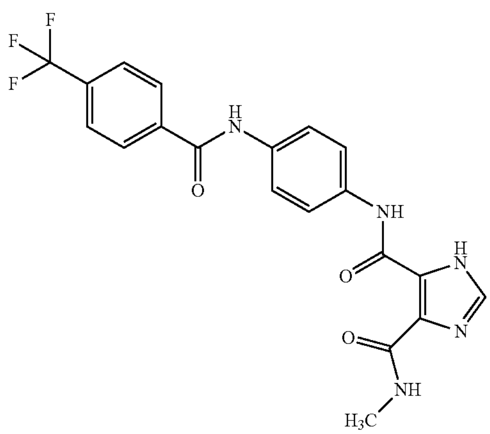 [SMILES: CNC(=O)c1nc[nH]c1C(=O)Nc1ccc(NC(=O)c2ccc(C(F)(F)F)cc2)cc1] | 432 | N⁴-methyl-N⁵-(4-{[4-(trifluoromethyl)benzoyl]amino}phenyl)-1H-imidazole-4,5-dicarboxamide | 1.14 |
| 317 | 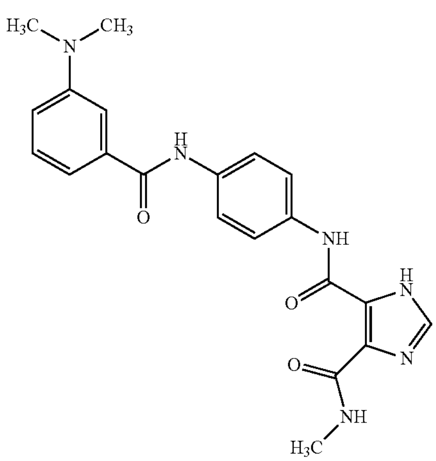 [SMILES: CNC(=O)c1nc[nH]c1C(=O)Nc1ccc(NC(=O)c2cccc(N(C)C)c2)cc1] | 407 | N⁵-(4-{[3-(dimethylamino)benzoyl]amino}phenyl)-N⁴-methyl-1H-imidazole-4,5-dicarboxamide | 0.97 |

| Example No | Structure | MS (ESIpos) m/z [M + H]+ | Name | Retention time [min] |
|---|---|---|---|---|
| 318 | 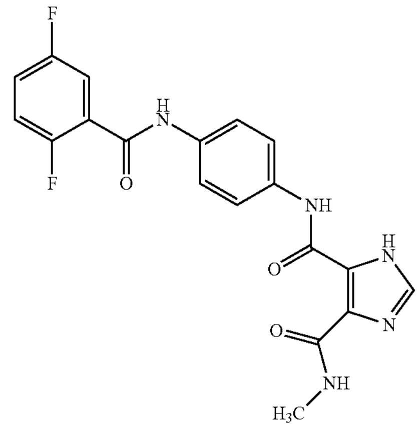 [SMILES: CNC(=O)c1nc[nH]c1C(=O)Nc1ccc(NC(=O)c2cc(F)ccc2F)cc1] | 400 | N⁵-{4-[(2,5-difluorobenzoyl)amino]phenyl}-N⁴-methyl-1H-imidazole-4,5-dicarboxamide | 1.01 |
| 319 | 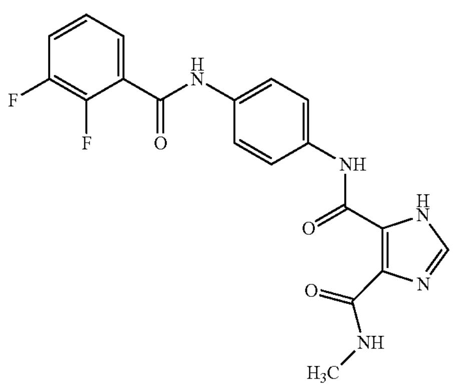 [SMILES: CNC(=O)c1nc[nH]c1C(=O)Nc1ccc(NC(=O)c2cccc(F)c2F)cc1] | 400 | N⁵-{4-[(2,3-difluorobenzoyl)amino]phenyl}-N⁴-methyl-1H-imidazole-4,5-dicarboxamide | 1.01 |
| 320 | 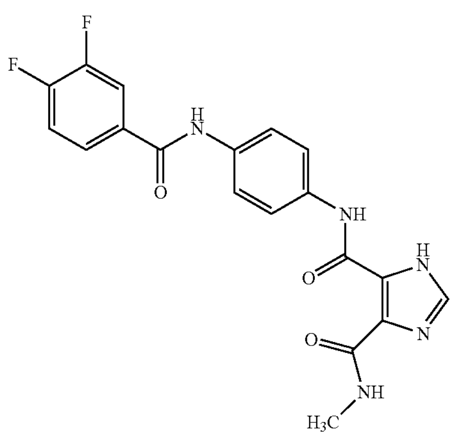 | 400 | N⁵-{4-[(3,4-difluorobenzoyl)amino]phenyl}-N⁴-methyl-1H-imidazole-4,5-dicarboxamide | 1.05 |

| Example No | Structure | MS (ESIpos) m/z [M + H]+ | Name | Retention time [min] |
|---|---|---|---|---|
| 321 | 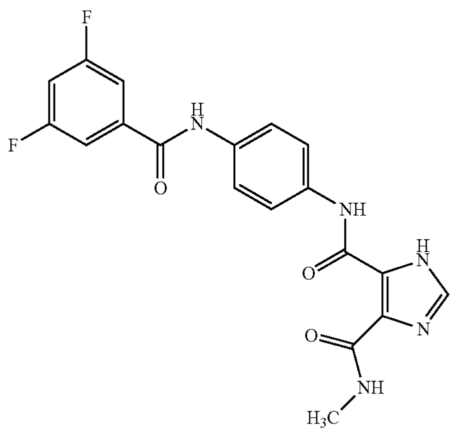 | 400 | N⁵-{4-[(3,5-difluorobenzoyl)amino]phenyl}-N⁴-methyl-1H-imidazole-4,5-dicarboxamide | 1.06 |
| 322 | 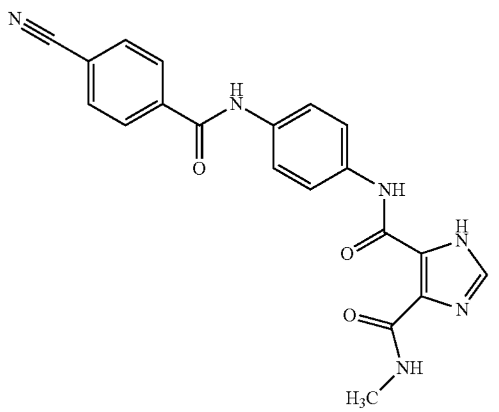 [SMILES: CNC(=O)c1nc[nH]c1C(=O)Nc1ccc(NC(=O)c2ccc(C#N)cc2)cc1] | 389 | N⁵-{4-[(4-cyanobenzoyl)amino]phenyl}-N⁴-methyl-1H-imidazole-4,5-dicarboxamide | 0.94 |
| 323 | 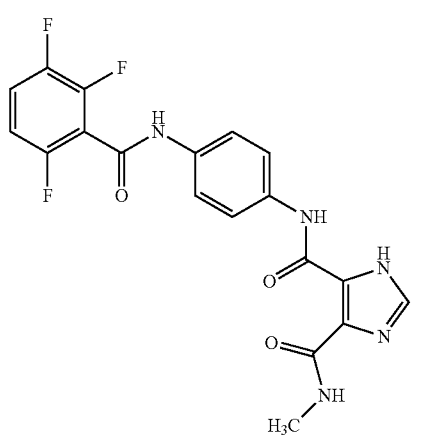 | 418 | N⁴-methyl-N⁵-{4-[(2,3,6-trifluorobenzoyl)amino]phenyl}-1H-imidazole-4,5-dicarboxamide | 1.00 |

-continued

| Example No | Structure | MS (ESIpos) m/z [M + H]+ | Name | Retention time [min] |
|---|---|---|---|---|
| 324 | 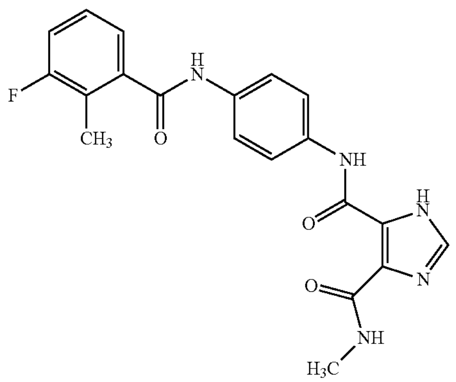 [SMILES: CNC(=O)c1nc[nH]c1C(=O)Nc1ccc(NC(=O)c2cccc(F)c2C)cc1] | 396 | N⁵-{4-[(3-fluoro-2-methylbenzoyl)amino]phenyl}-N⁴-methyl-1H-imidazole-4,5-dicarboxamide | 1.03 |
| 325 | 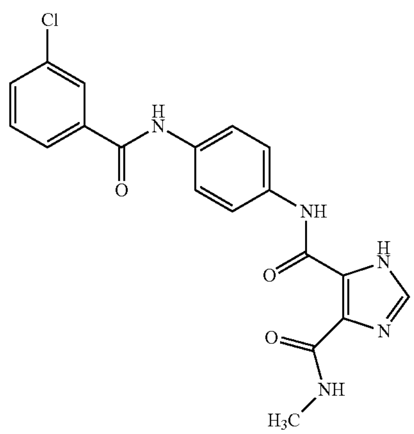 [SMILES: CNC(=O)c1nc[nH]c1C(=O)Nc1ccc(NC(=O)c2cccc(Cl)c2)cc1] | 398 | N⁵-{4-[(3-chlorobenzoyl)amino]phenyl}-N⁴-methyl-1H-imidazole-4,5-dicarboxamide | 1.09 |
| 326 | 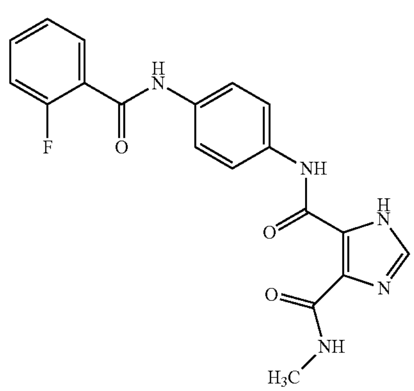 [SMILES: CNC(=O)c1nc[nH]c1C(=O)Nc1ccc(NC(=O)c2ccccc2F)cc1] | 382 | N⁵-{4-[(2-fluorobenzoyl)amino]phenyl}-N⁴-methyl-1H-imidazole-4,5-dicarboxamide | 0.98 |

-continued

| Example No | Structure | MS (ESIpos) m/z [M + H]+ | Name | Retention time [min] |
|---|---|---|---|---|
| 327 | 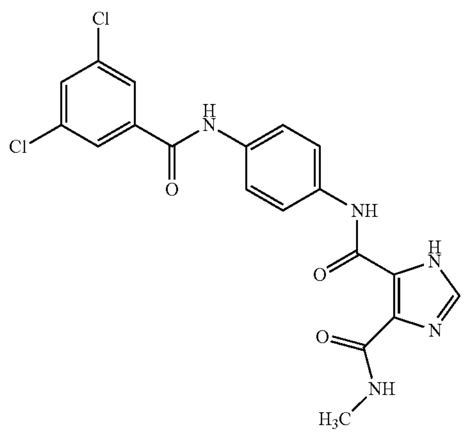 [SMILES: CNC(=O)c1nc[nH]c1C(=O)Nc1ccc(NC(=O)c2cc(Cl)cc(Cl)c2)cc1] | 432 | N[5]-{4-[(3,5-dichlorobenzoyl)amino]phenyl}-N[4]-methyl-1H-imidazole-4,5-dicarboxamide | 1.23 |
| 328 | 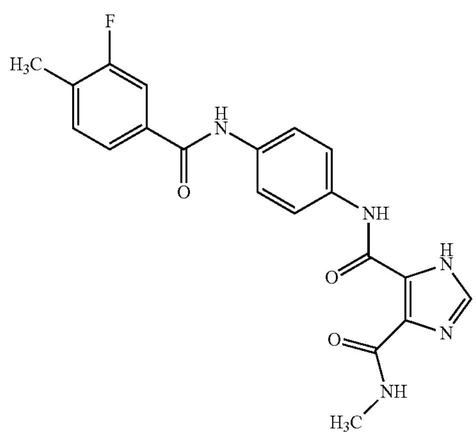 | 396 | N[5]-{4-[(3-fluoro-4-methylbenzoyl)amino]phenyl}-N[4]-methyl-1H-imidazole-4,5-dicarboxamide | 1.09 |
| 329 | 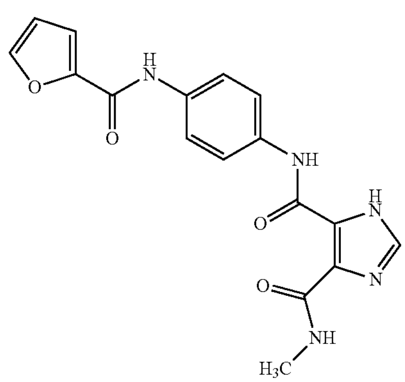 [SMILES: CNC(=O)c1nc[nH]c1C(=O)Nc1ccc(NC(=O)c2ccco2)cc1] | 354 | N[5]-{4-[(furan-2-ylcarbonyl)amino]phenyl}-N[4]-methyl-1H-imidazole-4,5-dicarboxamide | 0.85 |

-continued

| Example No | Structure | MS (ESIpos) m/z [M + H]+ | Name | Retention time [min] |
|---|---|---|---|---|
| 331 | 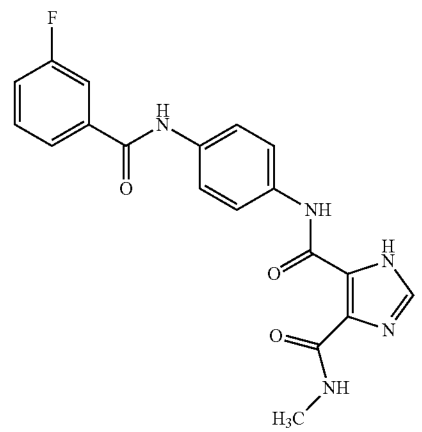 | 382 | N5-{4-[(3-fluorobenzoyl)amino]phenyl}-N4-methyl-1H-imidazole-4,5-dicarboxamide | 1.00 |
| 332 | 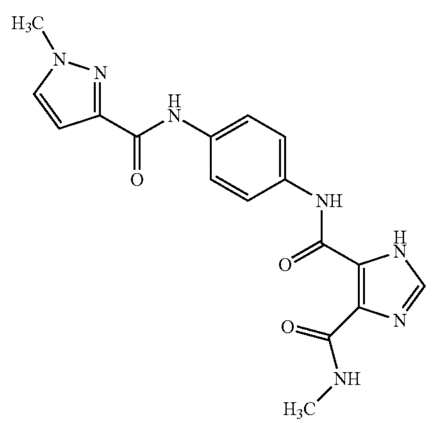 [SMILES: CNC(=O)c1nc[nH]c1C(=O)Nc1ccc(NC(=O)c2ccn(C)n2)cc1] | 368 | N4-methyl-N5-(4-{[(1-methyl-1H-pyrazol-3-yl)carbonyl]amino}phenyl)-1H-imidazole-4,5-dicarboxamide | 0.82 |
| 333 | 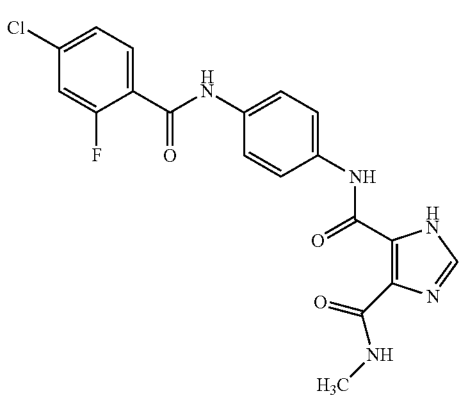 [SMILES: CNC(=O)c1nc[nH]c1C(=O)Nc1ccc(NC(=O)c2ccc(Cl)cc2F)cc1] | 416 | N5-{4-[(4-chloro-2-fluorobenzoyl)amino]phenyl}-N4-methyl-1H-imidazole-4,5-dicarboxamide | 1.11 |

-continued

| Example No | Structure | MS (ESIpos) m/z [M + H]+ | Name | Retention time [min] |
|---|---|---|---|---|
| 334 | 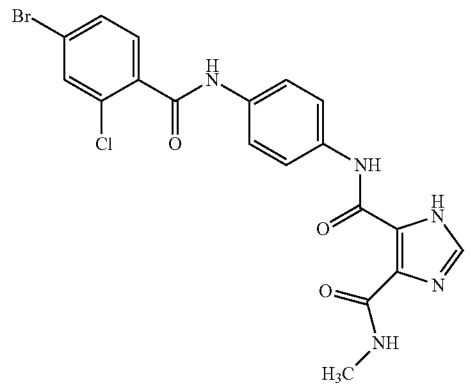 [SMILES: CNC(=O)c1nc[nH]c1C(=O)Nc1ccc(NC(=O)c2ccc(Br)cc2Cl)cc1] | 476 | N⁵-{4-[(4-bromo-2-chlorobenzoyl)amino]phenyl}-N⁴-methyl-1H-imidazole-4,5-dicarboxamide | 1.13 |
| 335 | 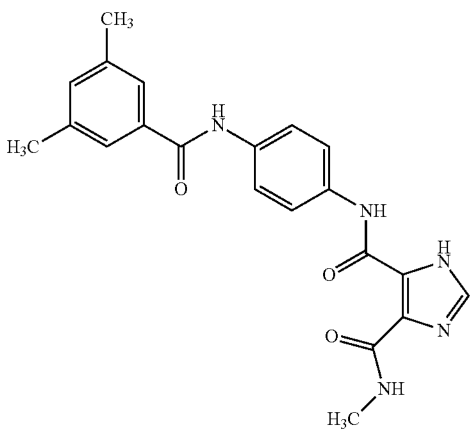 [SMILES: CNC(=O)c1nc[nH]c1C(=O)Nc1ccc(NC(=O)c2cc(C)cc(C)c2)cc1] | 392 | N⁵-{4-[(3,5-dimethylbenzoyl)amino]phenyl}-N⁴-methyl-1H-imidazole-4,5-dicarboxamide | 1.13 |
| 336 | 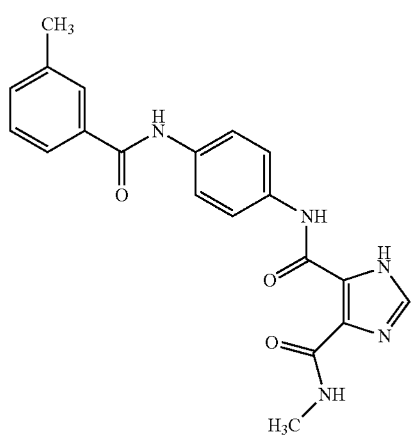 [SMILES: CNC(=O)c1nc[nH]c1C(=O)Nc1ccc(NC(=O)c2cccc(C)c2)cc1] | 378 | N⁴-methyl-N⁵-{4-[(3-methylbenzoyl)amino]phenyl}-1H-imidazole-4,5-dicarboxamide | 1.04 |

-continued

| Example No | Structure | MS (ESIpos) m/z [M + H]+ | Name | Retention time [min] |
|---|---|---|---|---|
| 337 | 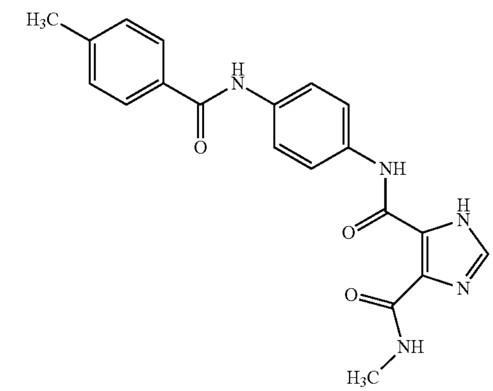 [SMILES: CNC(=O)c1nc[nH]c1C(=O)Nc1ccc(NC(=O)c2ccc(C)cc2)cc1] | 378 | N⁴-methyl-N⁵-{4-[(4-methylbenzoyl)amino]phenyl}-1H-imidazole-4,5-dicarboxamide | 1.04 |
| 338 | 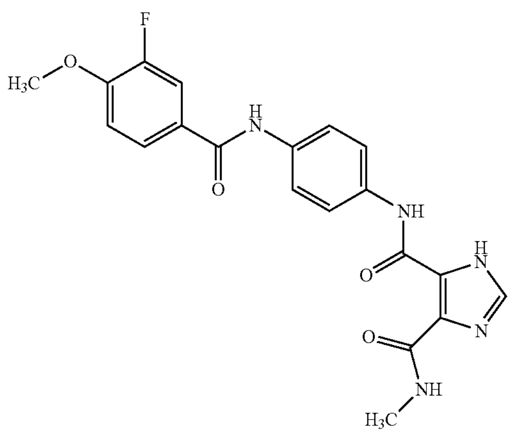 [SMILES: CNC(=O)c1nc[nH]c1C(=O)Nc1ccc(NC(=O)c2ccc(OC)c(F)c2)cc1] | 412 | N⁵-{4-[(3-fluoro-4-methoxybenzoyl)amino]phenyl}-N⁴-methyl-1H-imidazole-4,5-dicarboxamide | 1.00 |
| 339 | 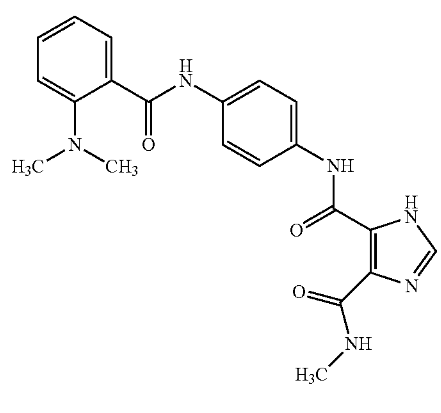 [SMILES: CNC(=O)c1nc[nH]c1C(=O)Nc1ccc(NC(=O)c2ccccc2N(C)C)cc1] | 407 | N⁵-(4-{[2-(dimethylamino)benzoyl]amino}phenyl)-N⁴-methyl-1H-imidazole-4,5-dicarboxamide | 0.94 |

-continued

| Example No | Structure | MS (ESIpos) m/z [M + H]+ | Name | Retention time [min] |
|---|---|---|---|---|
| 340 | 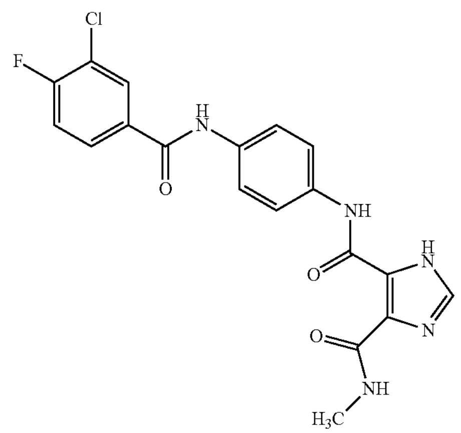 [SMILES: CNC(=O)c1nc[nH]c1C(=O)Nc1ccc(NC(=O)c2ccc(F)c(Cl)c2)cc1] | 416 | N⁵-{4-[(3-chloro-4-fluorobenzoyl)amino]phenyl}-N⁴-methyl-1H-imidazole-4,5-dicarboxamide | 1.12 |
| 341 | 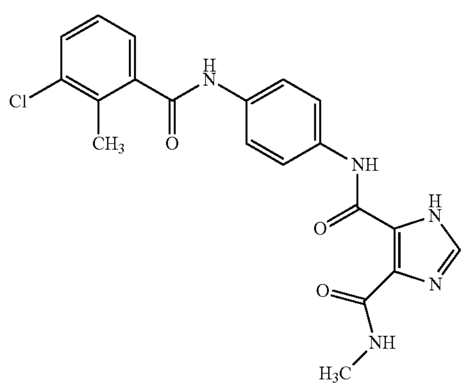 [SMILES: CNC(=O)c1nc[nH]c1C(=O)Nc1ccc(NC(=O)c2cccc(Cl)c2C)cc1] | 412 | N⁵-{4-[(3-chloro-2-methylbenzoyl)amino]phenyl}-N⁴-methyl-1H-imidazole-4,5-dicarboxamide | 1.11 |
| 342 | 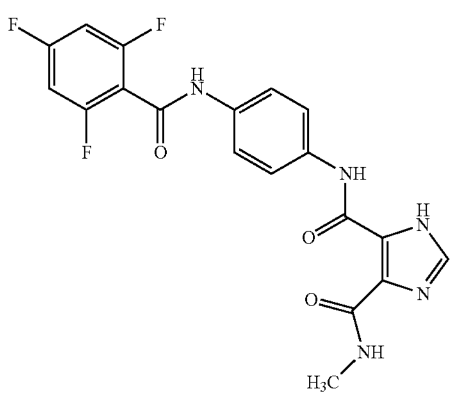 [SMILES: CNC(=O)c1nc[nH]c1C(=O)Nc1ccc(NC(=O)c2c(F)cc(F)cc2F)cc1] | 418 | N⁴-methyl-N⁵-{4-[(2,4,6-trifluorobenzoyl)amino]phenyl}-1H-imidazole-4,5-dicarboxamide | 1.00 |

-continued
| Example No | Structure | MS (ESIpos) m/z [M + H]+ | Name | Retention time [min] |
|---|---|---|---|---|
| 343 | 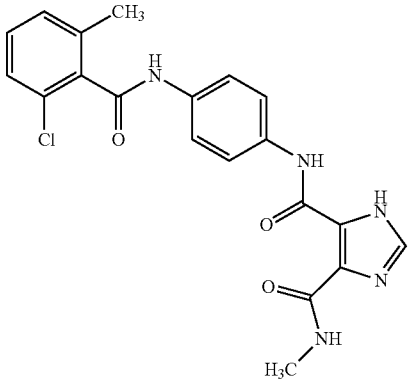 | 412 | $N^5$-{4-[(2-chloro-6-methylbenzoyl)amino]phenyl}-$N^4$-methyl-1H-imidazole-4,5-dicarboxamide | 1.02 |
| 344 | 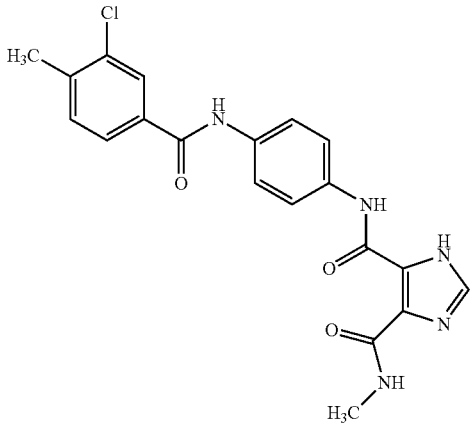 [SMILES: CNC(=O)c1nc[nH]c1C(=O)Nc1ccc(NC(=O)c2ccc(C)c(Cl)c2)cc1] | 412 | $N^5$-{4-[(3-chloro-4-methylbenzoyl)amino]phenyl}-$N^4$-methyl-1H-imidazole-4,5-dicarboxamide | 1.16 |
| 345 | 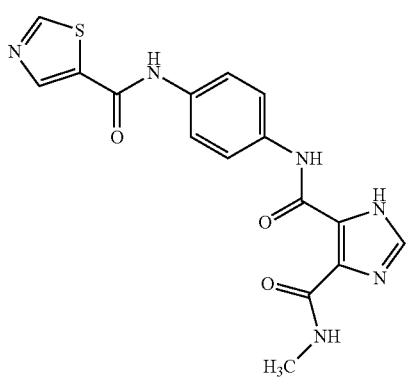 [SMILES: CNC(=O)c1nc[nH]c1C(=O)Nc1ccc(NC(=O)c2cncs2)cc1] | 371 | $N^4$-methyl-$N^5$-{4-[(1,3-thiazol-5-ylcarbonyl)amino]phenyl}-1H-imidazole-4,5-dicarboxamide | 0.79 |

-continued

| Example No | Structure | MS (ESIpos) m/z [M + H]+ | Name | Retention time [min] |
|---|---|---|---|---|
| 346 | 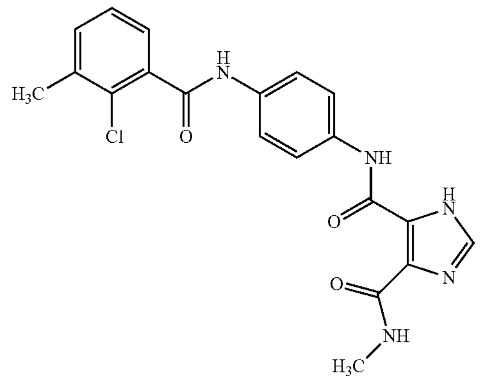 [SMILES: CNC(=O)c1nc[nH]c1C(=O)Nc1ccc(NC(=O)c2cccc(C)c2Cl)cc1] | 412 | $N^5$-{4-[(2-chloro-3-methylbenzoyl)amino]phenyl}-$N^4$-methyl-1H-imidazole-4,5-dicarboxamide | 1.05 |
| 347 | 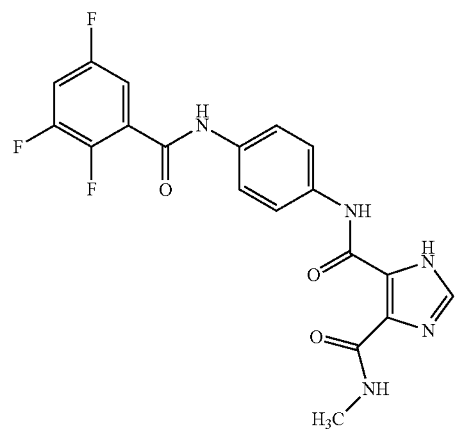 [SMILES: CNC(=O)c1nc[nH]c1C(=O)Nc1ccc(NC(=O)c2cc(F)cc(F)c2F)cc1] | 418 | $N^4$-methyl-$N^5$-{4-[(2,3,5-trifluorobenzoyl)amino]phenyl}-1H-imidazole-4,5-dicarboxamide | 1.06 |
| 348 | 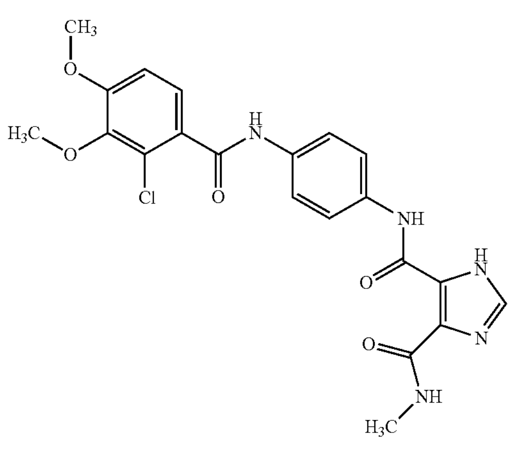 [SMILES: CNC(=O)c1nc[nH]c1C(=O)Nc1ccc(NC(=O)c2ccc(OC)c(OC)c2Cl)cc1] | 458 | $N^5$-{4-[(2-chloro-3,4-dimethoxybenzoyl)amino]phenyl}-$N^4$-methyl-1H-imidazole-4,5-dicarboxamide | 0.99 |

| Example No | Structure | MS (ESIpos) m/z [M + H]+ | Name | Retention time [min] |
|---|---|---|---|---|
| 349 | 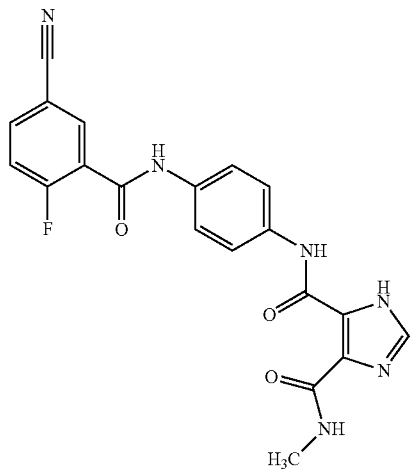 [SMILES: CNC(=O)c1nc[nH]c1C(=O)Nc1ccc(NC(=O)c2cc(C#N)ccc2F)cc1] | 407 | N⁵-{4-[(5-cyano-2-fluorobenzoyl)amino]phenyl}-N⁴-methyl-1H-imidazole-4,5-dicarboxamide | 0.94 |
| 350 | 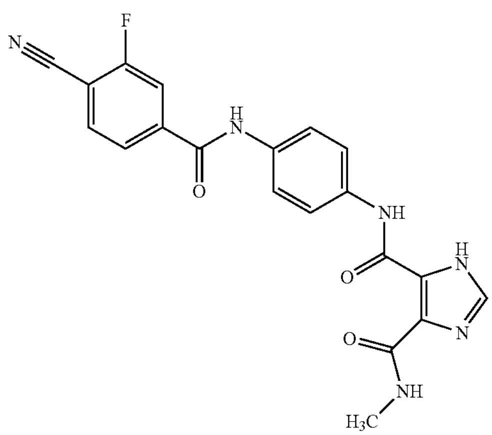 [SMILES: CNC(=O)c1nc[nH]c1C(=O)Nc1ccc(NC(=O)c2ccc(C#N)c(F)c2)cc1] | 407 | N⁵-{4-[(4-cyano-3-fluorobenzoyl)amino]phenyl}-N⁴-methyl-1H-imidazole-4,5-dicarboxamide | 1.00 |
| 351 | 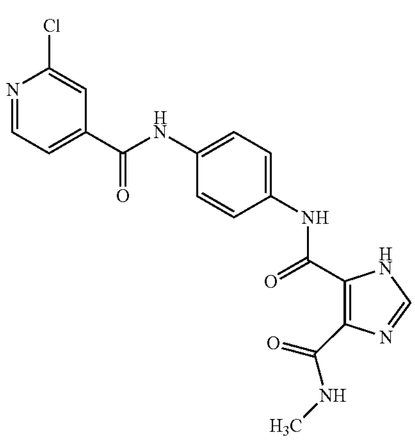 [SMILES: CNC(=O)c1nc[nH]c1C(=O)Nc1ccc(NC(=O)c2ccnc(Cl)c2)cc1] | 399 | N⁵-(4-{[(2-chloropyridin-4-yl)carbonyl]amino}phenyl)-N⁴-methyl-1H-imidazole-4,5-dicarboxamide | 0.94 |

-continued

| Example No | Structure | MS (ESIpos) m/z [M + H]+ | Name | Retention time [min] |
|---|---|---|---|---|
| 352 | 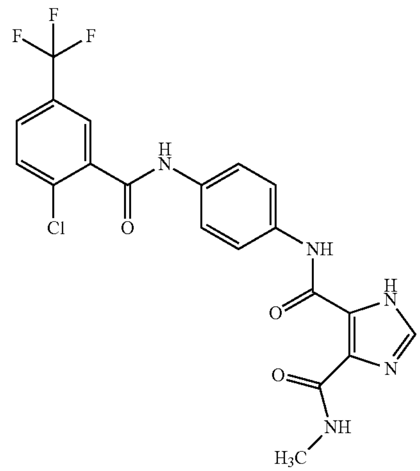 [SMILES: CNC(=O)c1nc[nH]c1C(=O)Nc1ccc(NC(=O)c2cc(C(F)(F)F)ccc2Cl)cc1] | 466 | N⁵-(4-{[2-chloro-5-(trifluoromethyl)benzoyl]amino}phenyl)-N⁴-methyl-1H-imidazole-4,5-dicarboxamide | 1.15 |
| 353 | 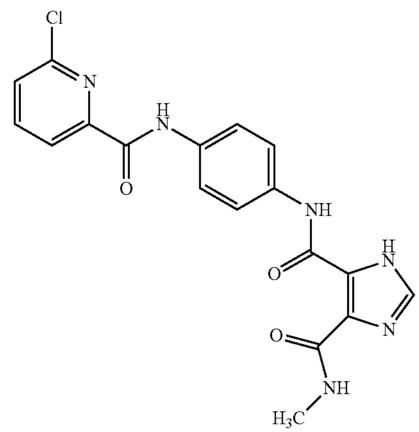 [SMILES: CNC(=O)c1nc[nH]c1C(=O)Nc1ccc(NC(=O)c2cccc(Cl)n2)cc1] | 399 | N⁵-(4-{[(6-chloropyridin-2-yl)carbonyl]amino}phenyl)-N⁴-methyl-1H-imidazole-4,5-dicarboxamide | 1.06 |
| 354 | 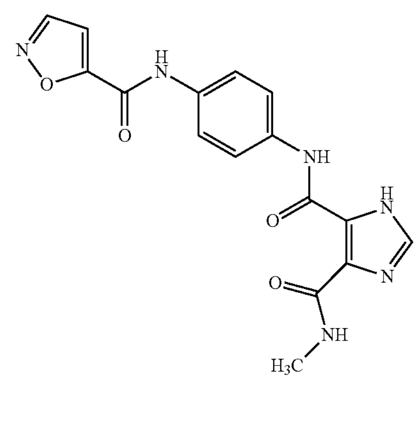 [SMILES: CNC(=O)c1nc[nH]c1C(=O)Nc1ccc(NC(=O)c2ccno2)cc1] | 355 | N⁴-methyl-N⁵-{4-[(1,2-oxazol-5-ylcarbonyl)amino]phenyl}-1H-imidazole-4,5-dicarboxamide | 0.81 |

-continued

| Example No | Structure | MS (ESIpos) m/z [M + H]+ | Name | Retention time [min] |
|---|---|---|---|---|
| 355 | 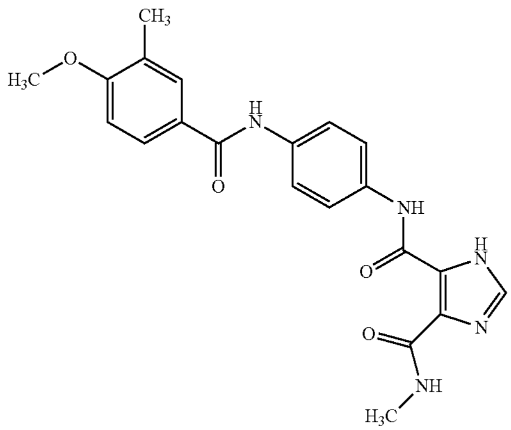 [SMILES: CNC(=O)c1nc[nH]c1C(=O)Nc1ccc(NC(=O)c2ccc(OC)c(C)c2)cc1] | 408 | N$^5$-{4-[(4-methoxy-3-methylbenzoyl)amino]phenyl}-N$^4$-methyl-1H-imidazole-4,5-dicarboxamide | 1.06 |
| 356 | 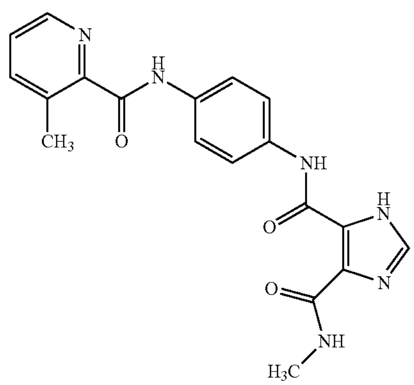 [SMILES: CNC(=O)c1nc[nH]c1C(=O)Nc1ccc(NC(=O)c2ncccc2C)cc1] | 379 | N$^4$-methyl-N$^5$-(4-{[(3-methylpyridin-2-yl)carbonyl]amino}phenyl)-1H-imidazole-4,5-dicarboxamide | 1.01 |
| 357 | 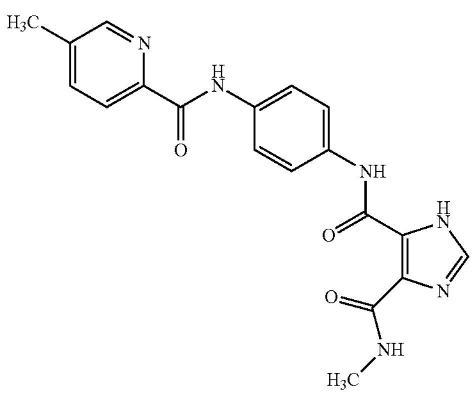 [SMILES: CNC(=O)c1nc[nH]c1C(=O)Nc1ccc(NC(=O)c2ccc(C)cn2)cc1] | 379 | N$^4$-methyl-N$^5$-(4-{[(5-methylpyridin-2-yl)carbonyl]amino}phenyl)-1H-imidazole-4,5-dicarboxamide | 1.04 |

-continued

| Example No | Structure | MS (ESIpos) m/z [M + H]+ | Name | Retention time [min] |
|---|---|---|---|---|
| 358 | 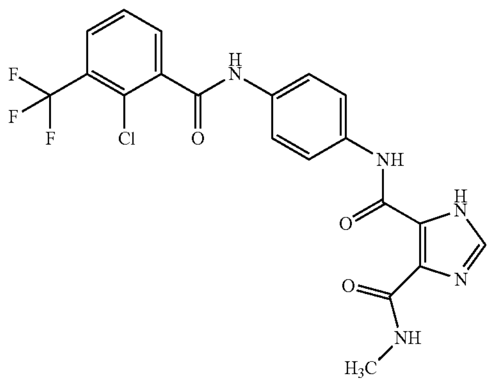 [SMILES: CNC(=O)c1nc[nH]c1C(=O)Nc1ccc(NC(=O)c2cccc(C(F)(F)F)c2Cl)cc1] | 466 | $N^5$-(4-{[2-chloro-3-(trifluoromethyl)benzoyl]amino}phenyl)-$N^4$-methyl-1H-imidazole-4,5-dicarboxamide | 1.13 |
| 359 | 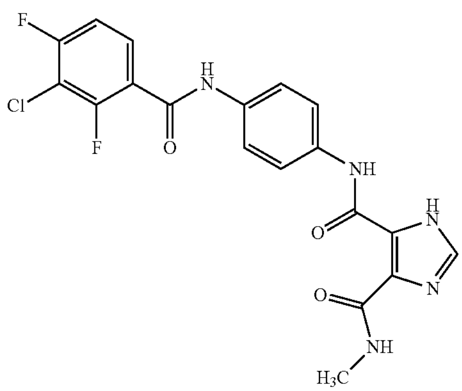 [SMILES: CNC(=O)c1nc[nH]c1C(=O)Nc1ccc(NC(=O)c2ccc(F)c(Cl)c2F)cc1] | 434 | $N^5$-{4-[(3-chloro-2,4-difluorobenzoyl)amino]phenyl}-$N^4$-methyl-1H-imidazole-4,5-dicarboxamide | 1.12 |
| 360 | 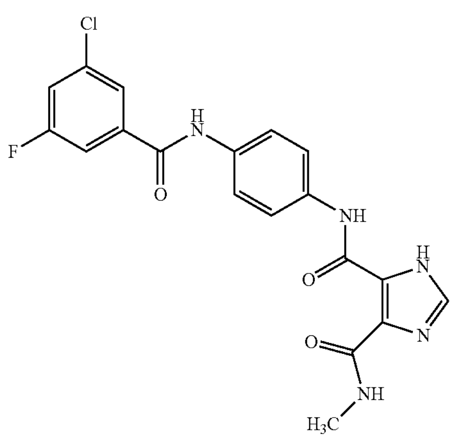 [SMILES: CNC(=O)c1nc[nH]c1C(=O)Nc1ccc(NC(=O)c2cc(F)cc(Cl)c2)cc1] | 416 | $N^5$-{4-[(3-chloro-5-fluorobenzoyl)amino]phenyl}-$N^4$-methyl-1H-imidazole-4,5-dicarboxamide | 1.15 |

-continued

| Example No | Structure | MS (ESIpos) m/z [M + H]+ | Name | Retention time [min] |
|---|---|---|---|---|
| 361 | 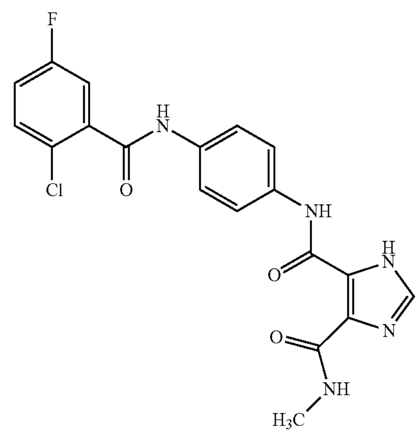 | 416 | N$^5$-{4-[(2-chloro-5-fluorobenzoyl)amino]phenyl}-N$^4$-methyl-1H-imidazole-4,5-dicarboxamide | 1.02 |
| 362 | 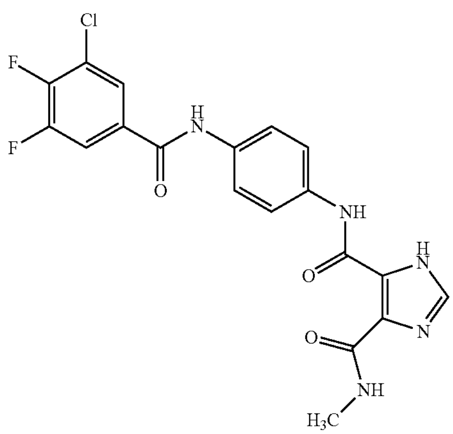 [SMILES: CNC(=O)c1nc[nH]c1C(=O)Nc1ccc(NC(=O)c2cc(F)c(F)c(Cl)c2)cc1] | 434 | N$^5$-{4-[(3-chloro-4,5-difluorobenzoyl)amino]phenyl}-N$^4$-methyl-1H-imidazole-4,5-dicarboxamide | 1.18 |
| 363 | 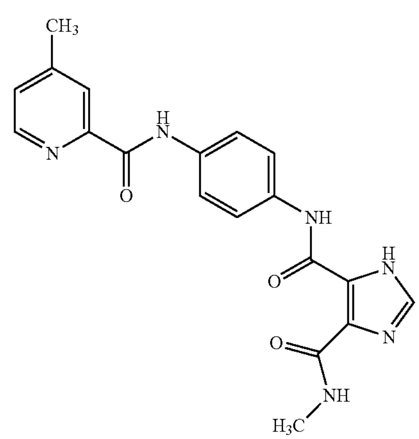 [SMILES: CNC(=O)c1nc[nH]c1C(=O)Nc1ccc(NC(=O)c2cc(C)ccn2)cc1] | 379 | N$^4$-methyl-N$^5$-(4-{[(4-methylpyridin-2-yl)carbonyl]amino}phenyl)-1H-imidazole-4,5-dicarboxamide | 1.04 |

-continued

| Example No | Structure | MS (ESIpos) m/z [M + H]+ | Name | Retention time [min] |
|---|---|---|---|---|
| 364 | 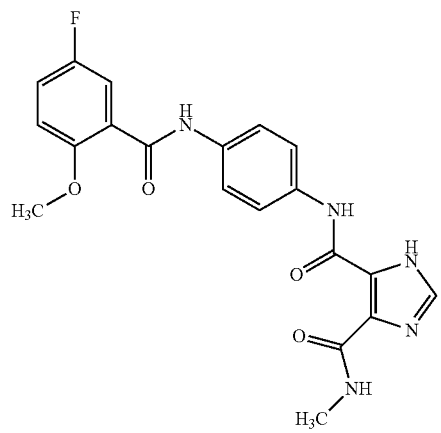 [SMILES: CNC(=O)c1nc[nH]c1C(=O)Nc1ccc(NC(=O)c2cc(F)ccc2OC)cc1] | 412 | $N^5$-{4-[(5-fluoro-2-methoxybenzoyl)amino]phenyl}-$N^4$-methyl-1H-imidazole-4,5-dicarboxamide | 1.08 |
| 365 | 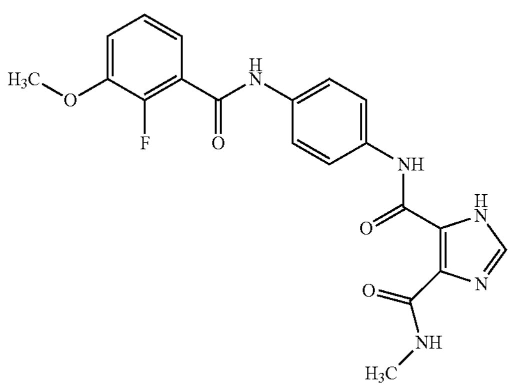 [SMILES: CNC(=O)c1nc[nH]c1C(=O)Nc1ccc(NC(=O)c2cccc(OC)c2F)cc1] | 412 | $N^5$-{4-[(2-fluoro-3-methoxybenzoyl)amino]phenyl}-$N^4$-methyl-1H-imidazole-4,5-dicarboxamide | 0.98 |
| 366 | 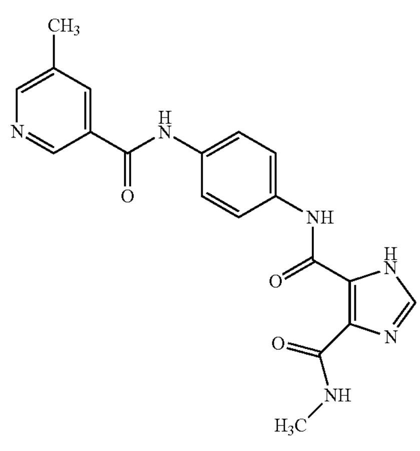 [SMILES: CNC(=O)c1nc[nH]c1C(=O)Nc1ccc(NC(=O)c2cncc(C)c2)cc1] | 379 | $N^4$-methyl-$N^5$-(4-{[(5-methylpyridin-3-yl)carbonyl]amino}phenyl)-1H-imidazole-4,5-dicarboxamide | 0.77 |

-continued

| Example No | Structure | MS (ESIpos) m/z [M + H]+ | Name | Retention time [min] |
|---|---|---|---|---|
| 367 | 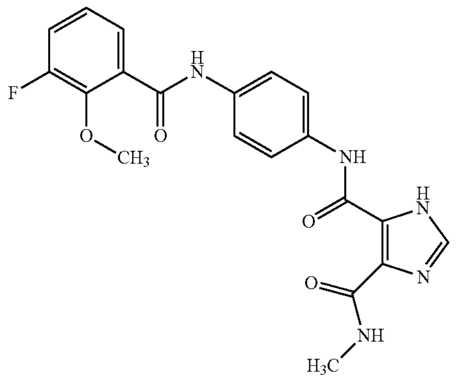 [SMILES: CNC(=O)c1nc[nH]c1C(=O)Nc1ccc(NC(=O)c2cccc(F)c2OC)cc1] | 412 | N⁵-{4-[(3-fluoro-2-methoxybenzoyl)amino]phenyl}-N⁴-methyl-1H-imidazole-4,5-dicarboxamide | 1.07 |
| 369 | 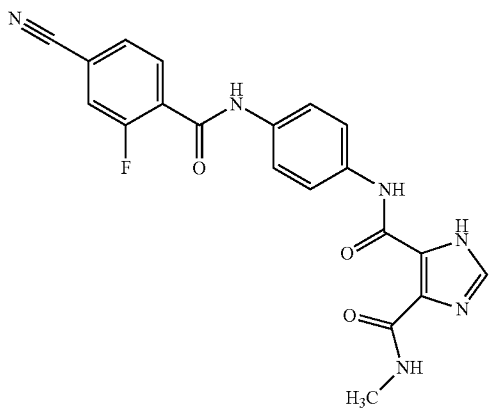 [SMILES: CNC(=O)c1nc[nH]c1C(=O)Nc1ccc(NC(=O)c2ccc(C#N)cc2F)cc1] | 407 | N⁵-{4-[(4-cyano-2-fluorobenzoyl)amino]phenyl}-N⁴-methyl-1H-imidazole-4,5-dicarboxamide | 0.95 |
| 370 | 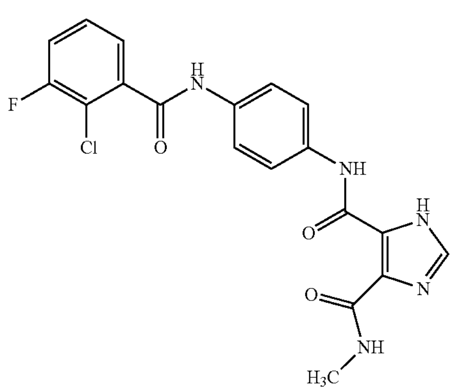 | 416 | N⁵-{4-[(2-chloro-3-fluorobenzoyl)amino]phenyl}-N⁴-methyl-1H-imidazole-4,5-dicarboxamide | 1.02 |

-continued

| Example No | Structure | MS (ESIpos) m/z [M + H]+ | Name | Retention time [min] |
|---|---|---|---|---|
| 371 | 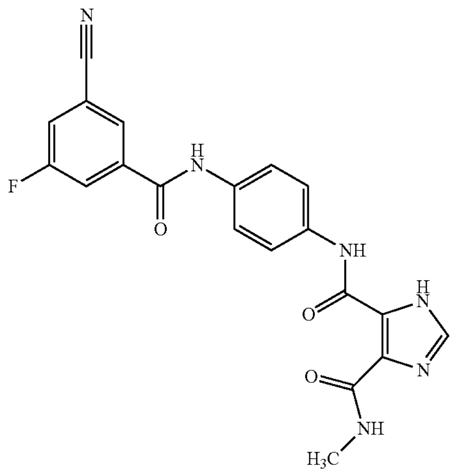 [SMILES: CNC(=O)c1nc[nH]c1C(=O)Nc1ccc(NC(=O)c2cc(F)cc(C#N)c2)cc1] | 407 | N⁵-{4-[(3-cyano-5-fluorobenzoyl)amino]phenyl}-N⁴-methyl-1H-imidazole-4,5-dicarboxamide | 1.01 |
| 372 | 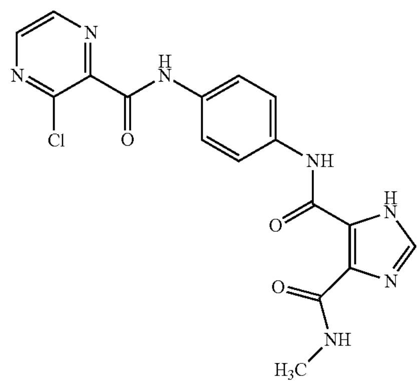 [SMILES: CNC(=O)c1nc[nH]c1C(=O)Nc1ccc(NC(=O)c2nccnc2Cl)cc1] | 400 | N⁵-(4-{[(3-chloropyrazin-2-yl)carbonyl]amino}phenyl)-N⁴-methyl-1H-imidazole-4,5-dicarboxamide | 0.87 |
| 373 | 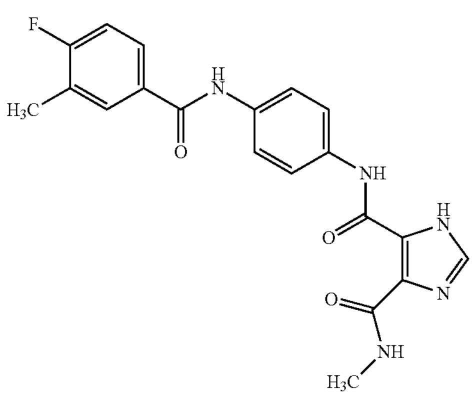 [SMILES: CNC(=O)c1nc[nH]c1C(=O)Nc1ccc(NC(=O)c2ccc(F)c(C)c2)cc1] | 396 | N⁵-{4-[(4-fluoro-3-methylbenzoyl)amino]phenyl}-N⁴-methyl-1H-imidazole-4,5-dicarboxamide | 1.08 |

-continued

| Example No | Structure | MS (ESIpos) m/z [M + H]+ | Name | Retention time [min] |
|---|---|---|---|---|
| 374 | 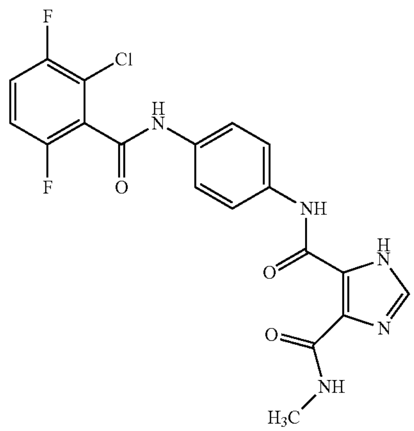 [SMILES: CNC(=O)c1nc[nH]c1C(=O)Nc1ccc(NC(=O)c2c(F)ccc(F)c2Cl)cc1] | 434 | N⁵-{4-[(2-chloro-3,6-difluorobenzoyl)amino]phenyl}-N⁴-methyl-1H-imidazole-4,5-dicarboxamide | 1.03 |
| 375 | 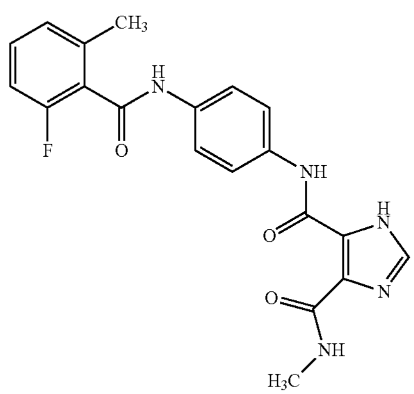 [SMILES: CNC(=O)c1nc[nH]c1C(=O)Nc1ccc(NC(=O)c2c(C)cccc2F)cc1] | 396 | N⁵-{4-[(2-fluoro-6-methylbenzoyl)amino]phenyl}-N⁴-methyl-1H-imidazole-4,5-dicarboxamide | 0.99 |
| 376 | 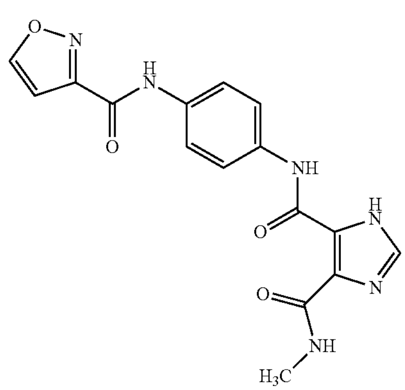 [SMILES: CNC(=O)c1nc[nH]c1C(=O)Nc1ccc(NC(=O)c2ccon2)cc1] | 355 | N⁴-methyl-N⁵-{4-[(1,2-oxazol-3-ylcarbonyl)amino]phenyl}-1H-imidazole-4,5-dicarboxamide | 0.84 |

-continued

| Example No | Structure | MS (ESIpos) m/z [M + H]+ | Name | Retention time [min] |
|---|---|---|---|---|
| 377 | 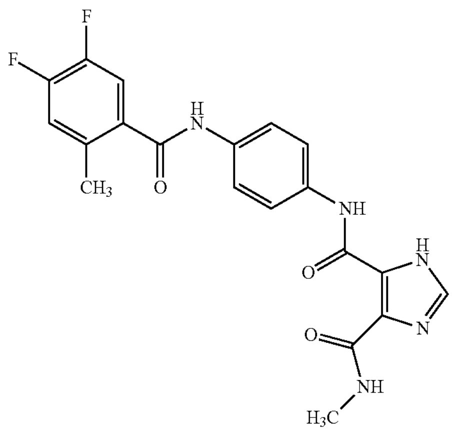 [SMILES: CNC(=O)c1nc[nH]c1C(=O)Nc1ccc(NC(=O)c2cc(F)c(F)cc2C)cc1] | 414 | N⁵-{4-[(4,5-difluoro-2-methylbenzoyl)amino]phenyl}-N⁴-methyl-1H-imidazole-4,5-dicarboxamide | 1.07 |
| 378 | 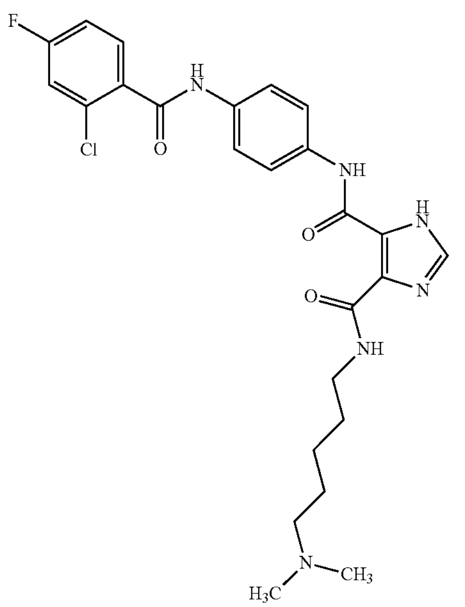 [SMILES: CN(C)CCCCCNC(=O)c1nc[nH]c1C(=O)Nc1ccc(NC(=O)c2ccc(F)cc2Cl)cc1] | 515 | N⁵-{4-[(2-chloro-4-fluorobenzoyl)amino]phenyl}-N⁴-[5-(dimethylamino)pentyl]-1H-imidazole-4,5-dicarboxamide | 0.75 |
| 379 | Chiral | 488 | N⁵-{4-[(2-chloro-4-fluorobenzoyl)amino]phenyl}-N⁴-[(2S)-1-hydroxy-3-methylbutan-2-yl]-1H-imidazole-4,5-dicarboxamide | 1.08 |

-continued

| Example No | Structure | MS (ESIpos) m/z [M + H]+ | Name | Retention time [min] |
|---|---|---|---|---|
| 380 | 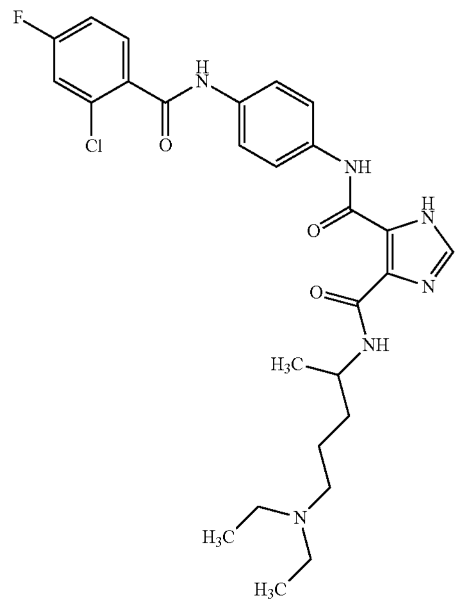 [SMILES: CCN(CC)CCCC(C)NC(=O)c1nc[nH]c1C(=O)Nc1ccc(NC(=O)c2ccc(F)cc2Cl)cc1] | 543 | $N^5$-{4-[(2-chloro-4-fluorobenzoyl)amino]phenyl}-$N^4$-[5-(diethylamino)pentan-2-yl]-1H-imidazole-4,5-dicarboxamide | 0.79 |
| 381 | 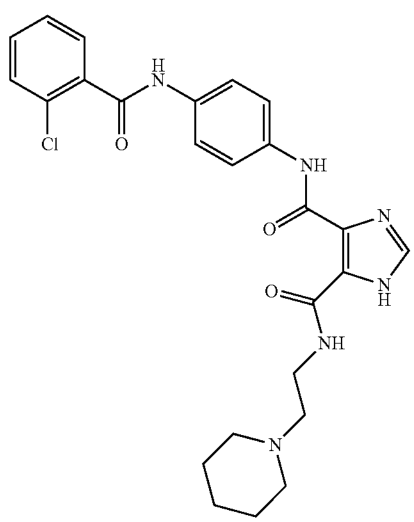 [SMILES: O=C(Nc1ccc(NC(=O)c2nc[nH]c2C(=O)NCCN2CCCCC2)cc1)c1ccccc1Cl] | 495 | $N^4$-{4-[(2-chlorobenzoyl)amino]phenyl}-$N^5$-[2-(piperidin-1-yl)ethyl]-1H-imidazole-4,5-dicarboxamide | 0.74 |

| Example No | Structure | MS (ESIpos) m/z [M + H]+ | Name | Retention time [min] |
|---|---|---|---|---|
| 382 | 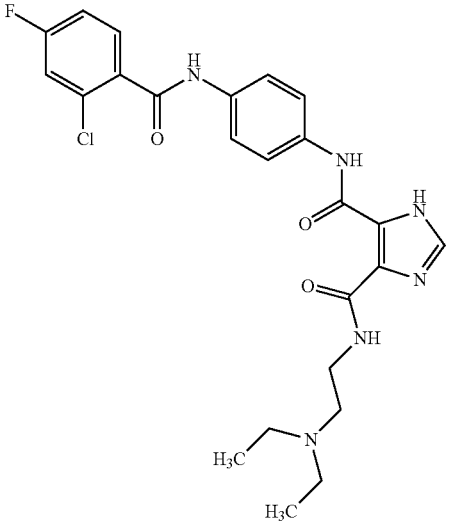 [SMILES: CCN(CC)CCNC(=O)c1nc[nH]c1C(=O)Nc1ccc(NC(=O)c2ccc(F)cc2Cl)cc1] | 501 | $N^5$-{4-[(2-chloro-4-fluorobenzoyl)amino]phenyl}-$N^4$-[2-(diethylamino)ethyl]-1H-imidazole-4,5-dicarboxamide | 0.74 |
| 383 | 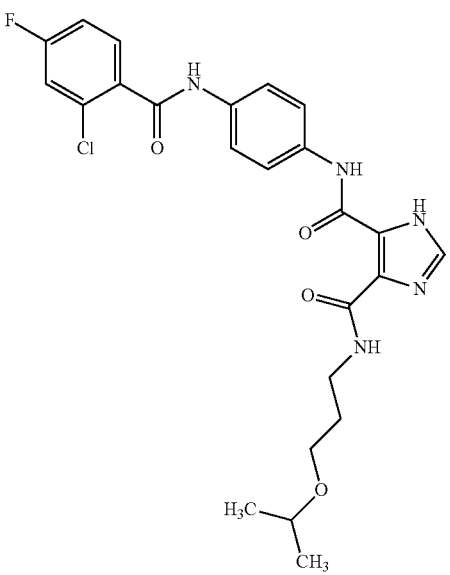 [SMILES: CC(C)OCCCNC(=O)c1nc[nH]c1C(=O)Nc1ccc(NC(=O)c2ccc(F)cc2Cl)cc1] | 502 | $N^5$-{4-[(2-chloro-4-fluorobenzoyl)amino]phenyl}-$N^4$-[3-(propan-2-yloxy)propyl]-1H-imidazole-4,5-dicarboxamide | 1.20 |

-continued

| Example No | Structure | MS (ESIpos) m/z [M + H]+ | Name | Retention time [min] |
|---|---|---|---|---|
| 384 | 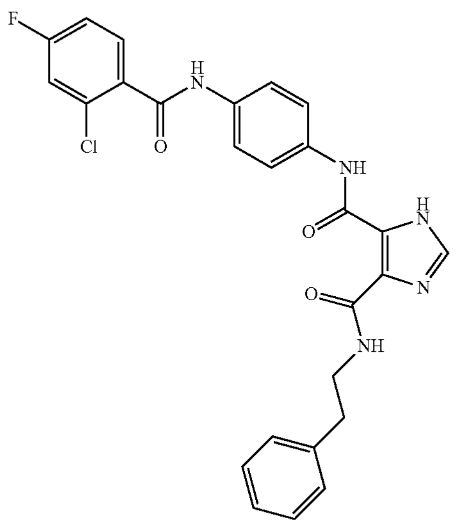 [SMILES: O=C(Nc1ccc(NC(=O)c2[nH]cnc2C(=O)NCCc2ccccc2)cc1)c1ccc(F)cc1Cl] | 506 | N⁵-{4-[(2-chloro-4-fluorobenzoyl)amino]phenyl}-N⁴-(2-phenylethyl)-1H-imidazole-4,5-dicarboxamide | 1.25 |
| 385 | 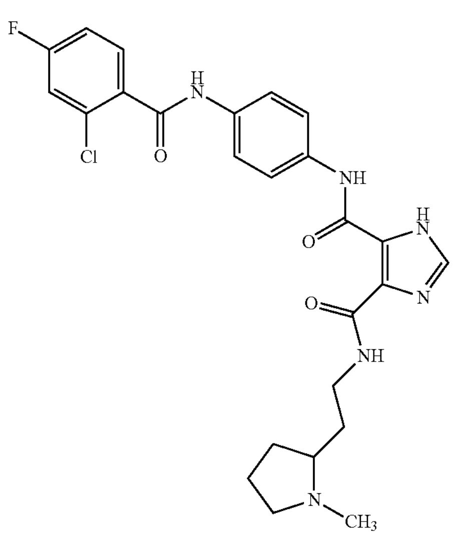 [SMILES: CN1CCCC1CCNC(=O)c1nc[nH]c1C(=O)Nc1ccc(NC(=O)c2ccc(F)cc2Cl)cc1] | 513 | N⁵-{4-[(2-chloro-4-fluorobenzoyl)amino]phenyl}-N⁴-[2-(1-methylpyrrolidin-2-yl)ethyl]-1H-imidazole-4,5-dicarboxamide | 0.73 |

-continued

| Example No | Structure | MS (ESIpos) m/z [M + H]+ | Name | Retention time [min] |
|---|---|---|---|---|
| 386 | 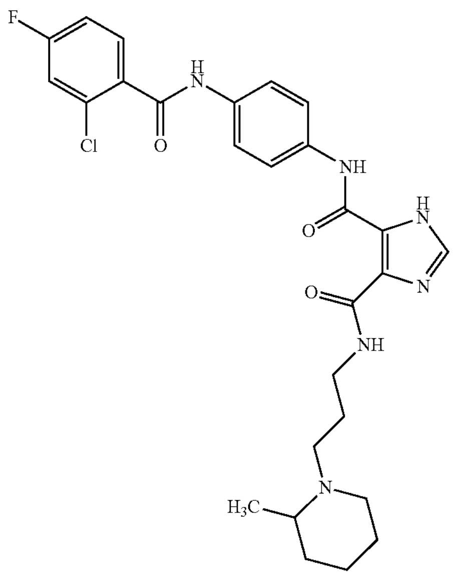 [SMILES: CC1CCCCN1CCCNC(=O)c1nc[nH]c1C(=O)Nc1ccc(NC(=O)c2ccc(F)cc2Cl)cc1] | 541 | N⁵-{4-[(2-chloro-4-fluorobenzoyl)amino]phenyl}-N⁴-[3-(2-methylpiperidin-1-yl)propyl]-1H-imidazole-4,5-dicarboxamide | 0.77 |
| 387 | 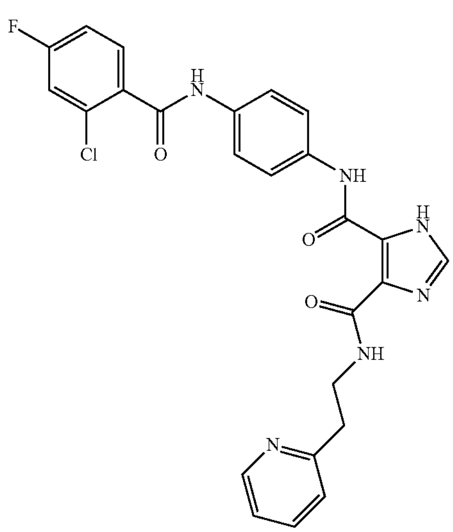 [SMILES: O=C(Nc1ccc(NC(=O)c2[nH]cnc2C(=O)NCCc2ccccn2)cc1)c1ccc(F)cc1Cl] | 507 | N⁵-{4-[(2-chloro-4-fluorobenzoyl)amino]phenyl}-N⁴-[2-(pyridin-2-yl)ethyl]-1H-imidazole-4,5-dicarboxamide | 0.81 |

-continued
| Example No | Structure | MS (ESIpos) m/z [M + H]+ | Name | Retention time [min] |
|---|---|---|---|---|
| 388 | 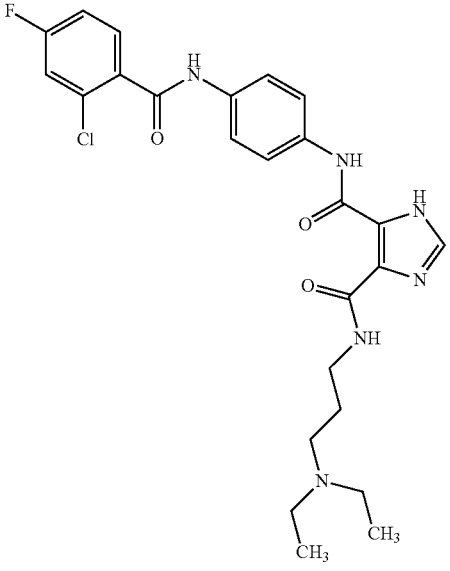 [SMILES: CCN(CC)CCCNC(=O)c1nc[nH]c1C(=O)Nc1ccc(NC(=O)c2ccc(F)cc2Cl)cc1] | 515 | N⁵-{4-[(2-chloro-4-fluorobenzoyl)amino]phenyl}-N⁴-[3-(diethylamino)propyl]-1H-imidazole-4,5-dicarboxamide | 0.74 |
| 389 | 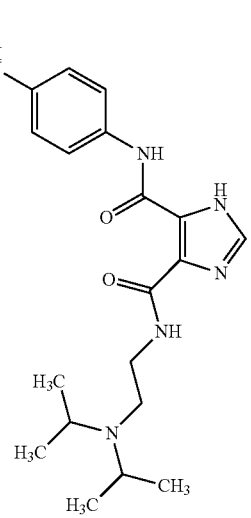 | 529 | N⁵-{4-[(2-chloro-4-fluorobenzoyl)amino]phenyl}-N⁴-{2-[di(propan-2-yl)amino]ethyl}-1H-imidazole-4,5-dicarboxamide | 0.77 |

| Example No | Structure | MS (ESIpos) m/z [M + H]+ | Name | Retention time [min] |
|---|---|---|---|---|
| 390 | 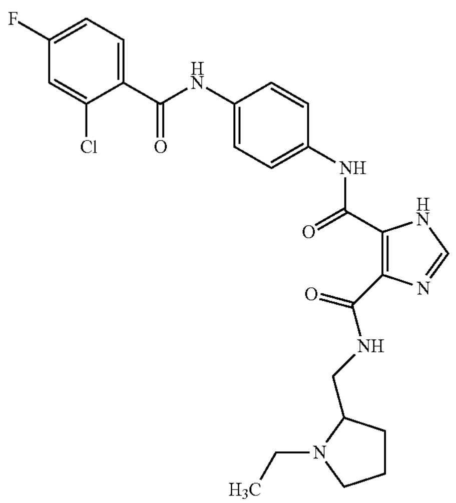 [SMILES: CCN1CCCC1CNC(=O)c1nc[nH]c1C(=O)Nc1ccc(NC(=O)c2ccc(F)cc2Cl)cc1] | 513 | $N^5$-{4-[(2-chloro-4-fluorobenzoyl)amino]phenyl}-$N^4$-[(1-ethylpyrrolidin-2-yl)methyl]-1H-imidazole-4,5-dicarboxamide | 0.74 |
| 391 | 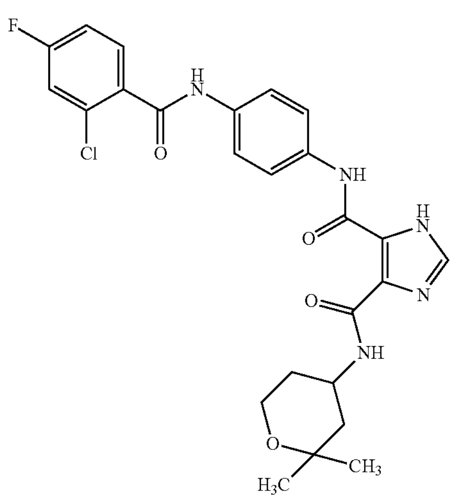 [SMILES: CC1(C)CC(NC(=O)c2nc[nH]c2C(=O)Nc2ccc(NC(=O)c3ccc(F)cc3Cl)cc2)CCO1] | 514 | $N^5$-{4-[(2-chloro-4-fluorobenzoyl)amino]phenyl}-$N^4$-(2,2-dimethyltetrahydro-2H-pyran-4-yl)-1H-imidazole-4,5-dicarboxamide | 1.14 |

-continued
| Example No | Structure | MS (ESIpos) m/z [M + H]+ | Name | Retention time [min] |
|---|---|---|---|---|
| 392 | 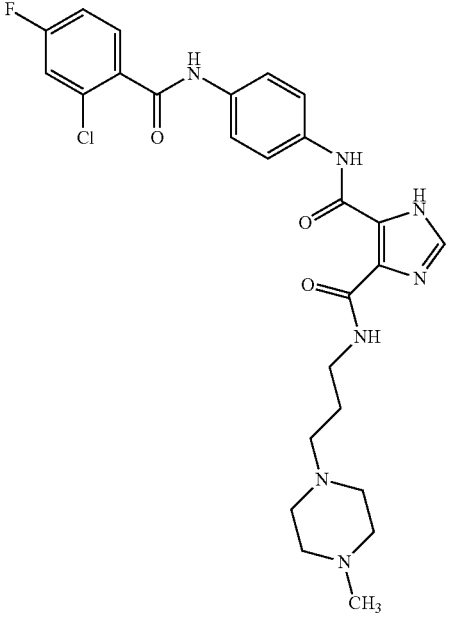 [SMILES: CN1CCN(CCCNC(=O)c2nc[nH]c2C(=O)Nc2ccc(NC(=O)c3ccc(F)cc3Cl)cc2)CC1] | 542 | N⁵-{4-[(2-chloro-4-fluorobenzoyl)amino]phenyl}-N⁴-[3-(4-methylpiperazin-1-yl)propyl]-1H-imidazole-4,5-dicarboxamide | 0.69 |
| 393 | 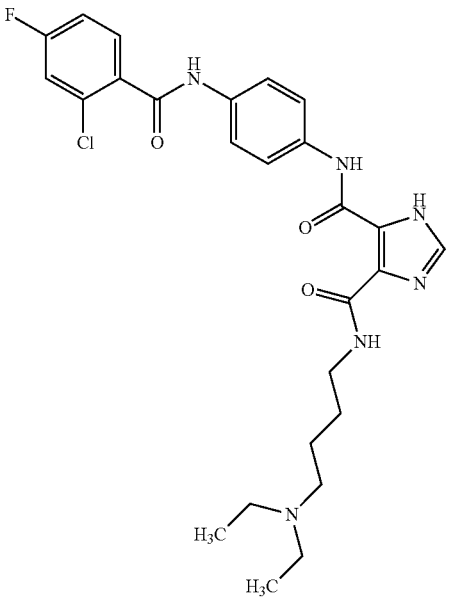 [SMILES: CCN(CC)CCCCNC(=O)c1nc[nH]c1C(=O)Nc1ccc(NC(=O)c2ccc(F)cc2Cl)cc1] | 529 | N⁵-{4-[(2-chloro-4-fluorobenzoyl)amino]phenyl}-N⁴-[4-(diethylamino)butyl]-1H-imidazole-4,5-dicarboxamide | 0.77 |

-continued

| Example No | Structure | MS (ESIpos) m/z [M + H]+ | Name | Retention time [min] |
|---|---|---|---|---|
| 394 | 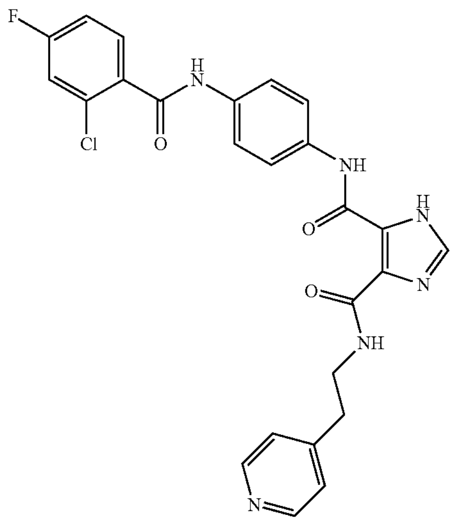 [SMILES: O=C(Nc1ccc(NC(=O)c2[nH]cnc2C(=O)NCCc2ccncc2)cc1)c1ccc(F)cc1Cl] | 507 | N⁵-{4-[(2-chloro-4-fluorobenzoyl)amino]phenyl}-N⁴-[2-(pyridin-4-yl)ethyl]-1H-imidazole-4,5-dicarboxamide | 0.76 |
| 396 | 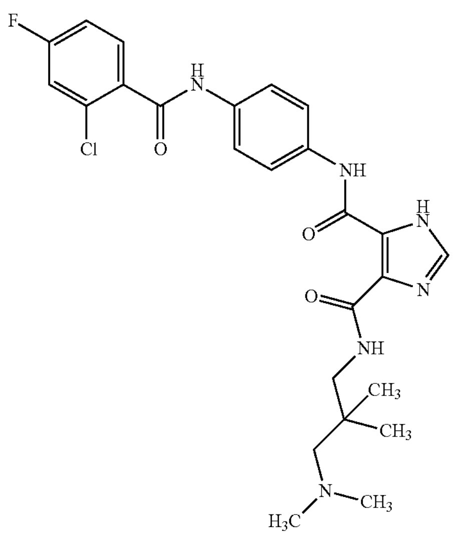 [SMILES: CN(C)CC(C)(C)CNC(=O)c1nc[nH]c1C(=O)Nc1ccc(NC(=O)c2ccc(F)cc2Cl)cc1] | 515 | N⁵-{4-[(2-chloro-4-fluorobenzoyl)amino]phenyl}-N⁴-[3-(dimethylamino)-2,2-dimethylpropyl]-1H-imidazole-4,5-dicarboxamide | 0.75 |
| 397 | 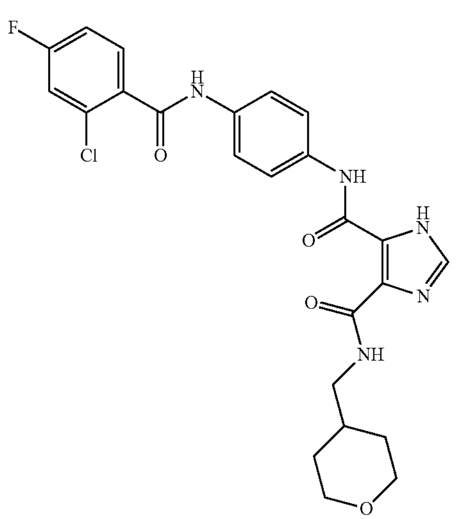 [SMILES: O=C(Nc1ccc(NC(=O)c2[nH]cnc2C(=O)NCC2CCOCC2)cc1)c1ccc(F)cc1Cl] | 500 | N⁵-{4-[(2-chloro-4-fluorobenzoyl)amino]phenyl}-N⁴-(tetrahydro-2H-pyran-4-ylmethyl)-1H-imidazole-4,5-dicarboxamide | 1.07 |

-continued

| Example No | Structure | MS (ESIpos) m/z [M + H]+ | Name | Retention time [min] |
|---|---|---|---|---|
| 398 | 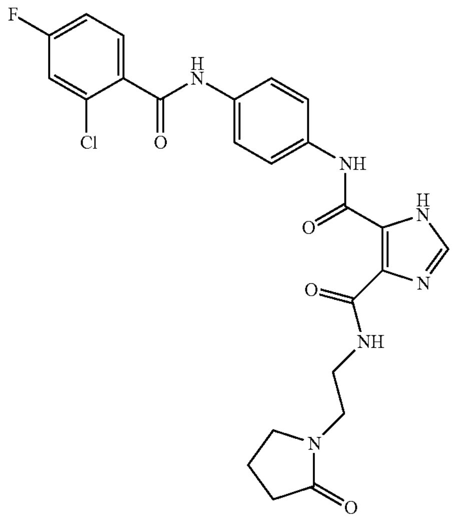 [SMILES: O=C(Nc1ccc(NC(=O)c2[nH]cnc2C(=O)NCCN2CCCC2=O)cc1)c1ccc(F)cc1Cl] | 513 | $N^5$-{4-[(2-chloro-4-fluorobenzoyl)amino]phenyl}-$N^4$-[2-(2-oxopyrrolidin-1-yl)ethyl]-1H-imidazole-4,5-dicarboxamide | 0.97 |
| 399 | 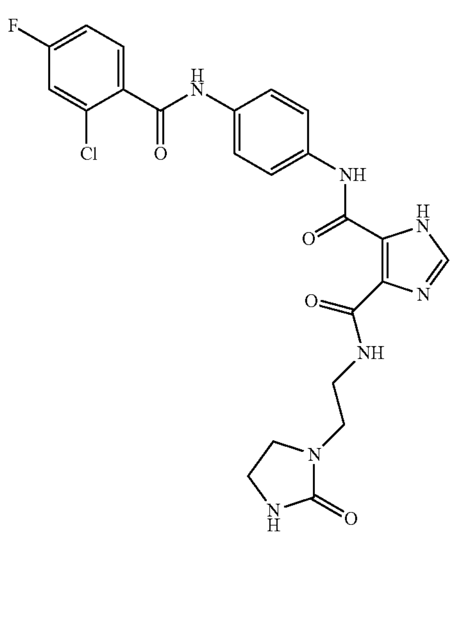 [SMILES: O=C(Nc1ccc(NC(=O)c2[nH]cnc2C(=O)NCCN2CCNC2=O)cc1)c1ccc(F)cc1Cl] | 514 | $N^5$-{4-[(2-chloro-4-fluorobenzoyl)amino]phenyl}-$N^4$-[2-(2-oxoimidazolidin-1-yl)ethyl]-1H-imidazole-4,5-dicarboxamide | 0.93 |

| Example No | Structure | MS (ESIpos) m/z [M + H]+ | Name | Retention time [min] |
|---|---|---|---|---|
| 400 | 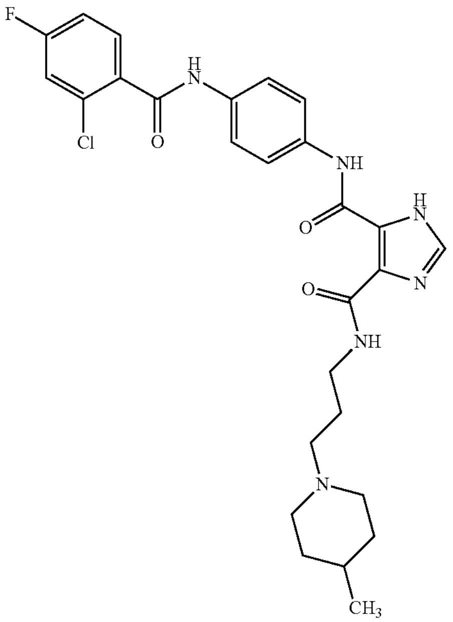 [SMILES: CC1CCN(CCCNC(=O)c2nc[nH]c2C(=O)Nc2ccc(NC(=O)c3ccc(F)cc3Cl)cc2)CC1] | 541 | $N^5$-{4-[(2-chloro-4-fluorobenzoyl)amino]phenyl}-$N^4$-[3-(4-methylpiperidin-1-yl)propyl]-1H-imidazole-4,5-dicarboxamide | 0.79 |
| 401 | 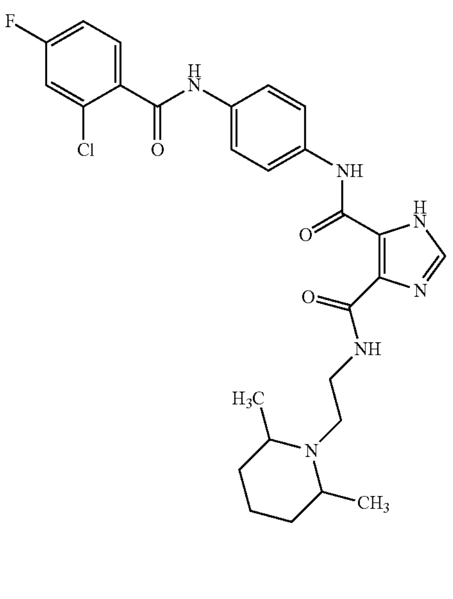 [SMILES: CC1CCCC(C)N1CCNC(=O)c1nc[nH]c1C(=O)Nc1ccc(NC(=O)c2ccc(F)cc2Cl)cc1] | 541 | $N^5$-{4-[(2-chloro-4-fluorobenzoyl)amino]phenyl}-$N^4$-[2-(2,6-dimethylpiperidin-1-yl)ethyl]-1H-imidazole-4,5-dicarboxamide | 0.78 |

-continued

| Example No | Structure | MS (ESIpos) m/z [M + H]+ | Name | Retention time [min] |
|---|---|---|---|---|
| 402 | 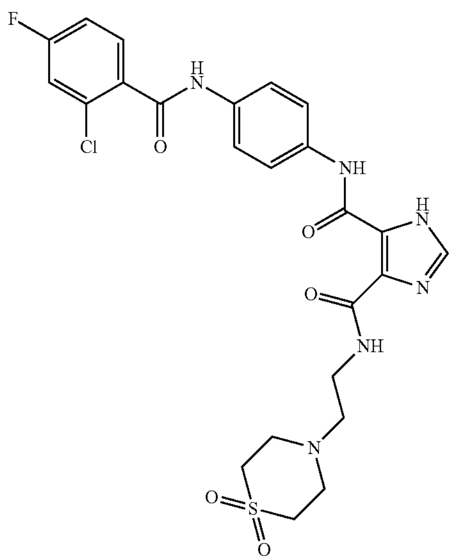 [SMILES: O=C(Nc1ccc(NC(=O)c2[nH]cnc2C(=O)NCCN2CCS(=O)(=O)CC2)cc1)c1ccc(F)cc1Cl] | 563 | N⁵-{4-[(2-chloro-4-fluorobenzoyl)amino]phenyl}-N⁴-[2-(1,1-dioxidothiomorpholin-4-yl)ethyl]-1H-imidazole-4,5-dicarboxamide | 0.95 |
| 404 | Chiral | 513 | N⁵-{4-[(2-chloro-4-fluorobenzoyl)amino]phenyl}-N⁴-{[(2S)-1-ethylpyrrolidin-2-yl]methyl}-1H-imidazole-4,5-dicarboxamide | 0.74 |

-continued

| Example No | Structure | MS (ESIpos) m/z [M + H]+ | Name | Retention time [min] |
|---|---|---|---|---|
| 405 | 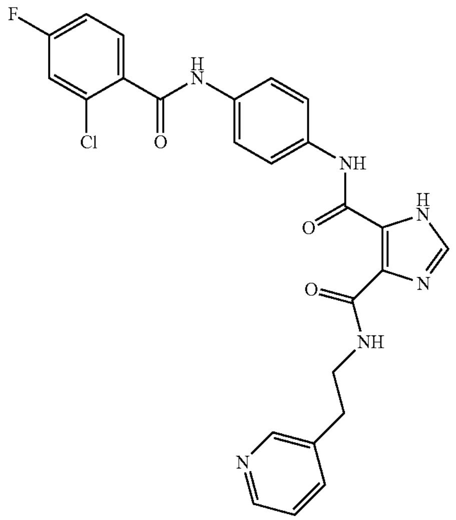 [SMILES: O=C(Nc1ccc(NC(=O)c2[nH]cnc2C(=O)NCCc2cccnc2)cc1)c1ccc(F)cc1Cl] | 507 | N⁵-{4-[(2-chloro-4-fluorobenzoyl)amino]phenyl}-N⁴-[2-(pyridin-3-yl)ethyl]-1H-imidazole-4,5-dicarboxamide | 0.79 |
| 406 | 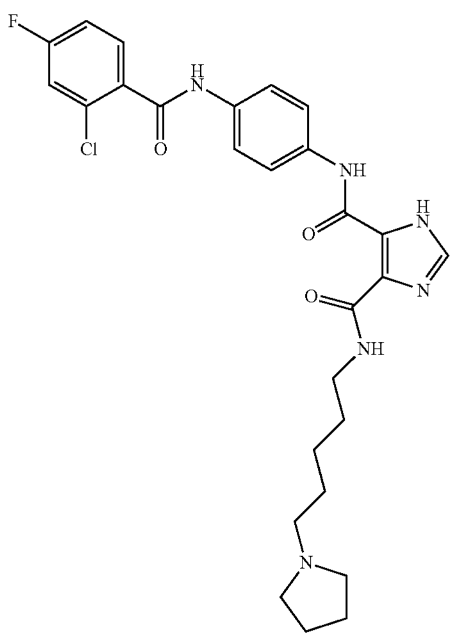 [SMILES: O=C(Nc1ccc(NC(=O)c2[nH]cnc2C(=O)NCCCCCN2CCCC2)cc1)c1ccc(F)cc1Cl] | 541 | N⁵-{4-[(2-chloro-4-fluorobenzoyl)amino]phenyl}-N⁴-[5-(pyrrolidin-1-yl)pentyl]-1H-imidazole-4,5-dicarboxamide | 0.77 |

| Example No | Structure | MS (ESIpos) m/z [M + H]+ | Name | Retention time [min] |
|---|---|---|---|---|
| 407 | 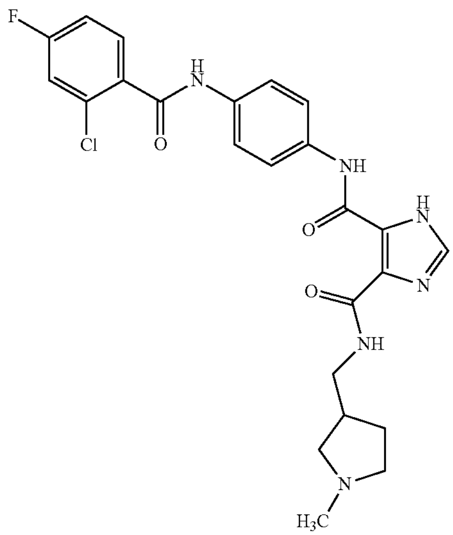 [SMILES: CN1CCC(CNC(=O)c2nc[nH]c2C(=O)Nc2ccc(NC(=O)c3ccc(F)cc3Cl)cc2)C1] | 499 | N5-{4-[(2-chloro-4-fluorobenzoyl)amino]phenyl}-N4-[(1-methylpyrrolidin-3-yl)methyl]-1H-imidazole-4,5-dicarboxamide | 0.72 |
| 408 | 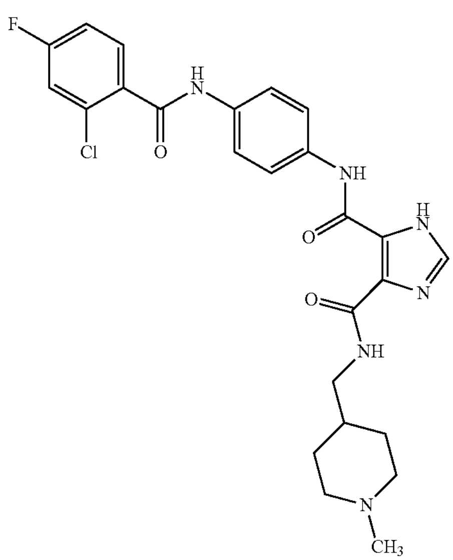 [SMILES: CN1CCC(CNC(=O)c2nc[nH]c2C(=O)Nc2ccc(NC(=O)c3ccc(F)cc3Cl)cc2)CC1] | 513 | N5-{4-[(2-chloro-4-fluorobenzoyl)amino]phenyl}-N4-[(1-methylpiperidin-4-yl)methyl]-1H-imidazole-4,5-dicarboxamide | 0.72 |

-continued
| Example No | Structure | MS (ESIpos) m/z [M + H]+ | Name | Retention time [min] |
|---|---|---|---|---|
| 409 | 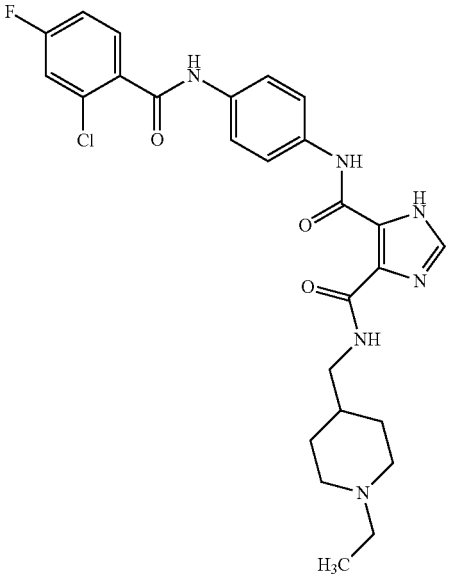 [SMILES: CCN1CCC(CNC(=O)c2nc[nH]c2C(=O)Nc2ccc(NC(=O)c3ccc(F)cc3Cl)cc2)CC1] | 527 | $N^5$-{4-[(2-chloro-4-fluorobenzoyl)amino]phenyl}-$N^4$-[(1-ethylpiperidin-4-yl)methyl]-1H-imidazole-4,5-dicarboxamide | 0.74 |
| 410 | 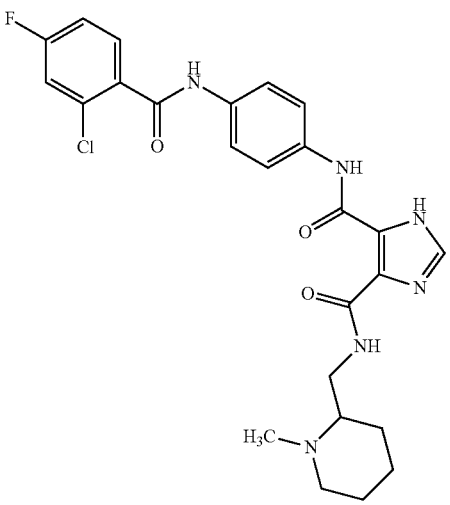 [SMILES: CN1CCCCC1CNC(=O)c1nc[nH]c1C(=O)Nc1ccc(NC(=O)c2ccc(F)cc2Cl)cc1] | 513 | $N^5$-{4-[(2-chloro-4-fluorobenzoyl)amino]phenyl}-$N^4$-[(1-methylpiperidin-2-yl)methyl]-1H-imidazole-4,5-dicarboxamide | 0.74 |

| Example No | Structure | MS (ESIpos) m/z [M + H]+ | Name | Retention time [min] |
|---|---|---|---|---|
| 411 | 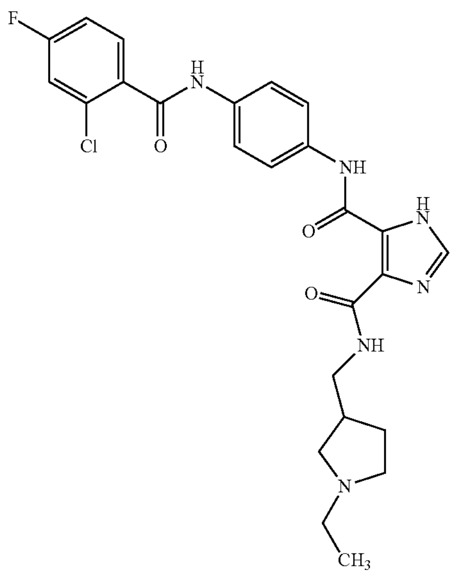 [SMILES: CCN1CCC(CNC(=O)c2nc[nH]c2C(=O)Nc2ccc(NC(=O)c3ccc(F)cc3Cl)cc2)C1] | 513 | N⁵-{4-[(2-chloro-4-fluorobenzoyl)amino]phenyl}-N⁴-[(1-ethylpyrrolidin-3-yl)methyl]-1H-imidazole-4,5-dicarboxamide | 0.73 |
| 412 | 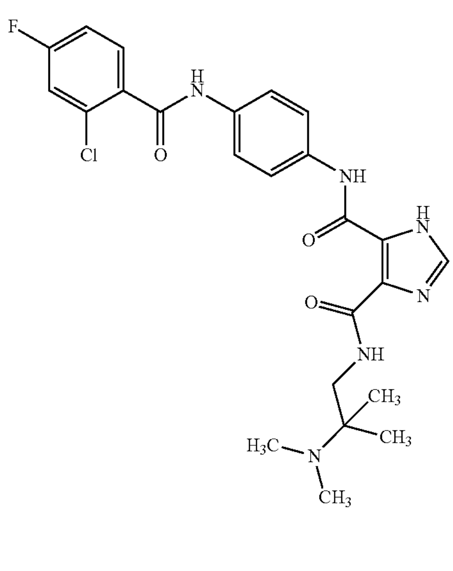 [SMILES: CN(C)C(C)(C)CNC(=O)c1nc[nH]c1C(=O)Nc1ccc(NC(=O)c2ccc(F)cc2Cl)cc1] | 501 | N⁵-{4-[(2-chloro-4-fluorobenzoyl)amino]phenyl}-N⁴-[2-(dimethylamino)-2-methylpropyl]-1H-imidazole-4,5-dicarboxamide | 0.74 |

-continued

| Example No | Structure | MS (ESIpos) m/z [M + H]+ | Name | Retention time [min] |
|---|---|---|---|---|
| 413 | Chiral | 513 | $N^5$-{4-[(2-chloro-4-fluorobenzoyl)amino]phenyl}-$N^4$-{[(2R)-1-ethylpyrrolidin-2-yl]methyl}-1H-imidazole-4,5-dicarboxamide | 0.74 |
| 414 | 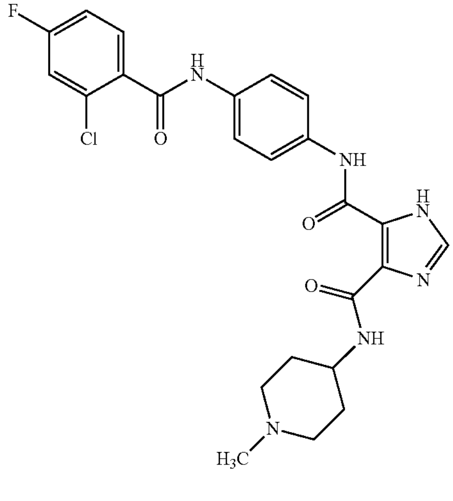 [SMILES: CN1CCC(NC(=O)c2nc[nH]c2C(=O)Nc2ccc(NC(=O)c3ccc(F)cc3Cl)cc2)CC1] | 499 | $N^5$-{4-[(2-chloro-4-fluorobenzoyl)amino]phenyl}-$N^4$-(1-methylpiperidin-4-yl)-1H-imidazole-4,5-dicarboxamide | 0.71 |

| Example No | Structure | MS (ESIpos) m/z [M + H]+ | Name | Retention time [min] |
|---|---|---|---|---|
| 415 | 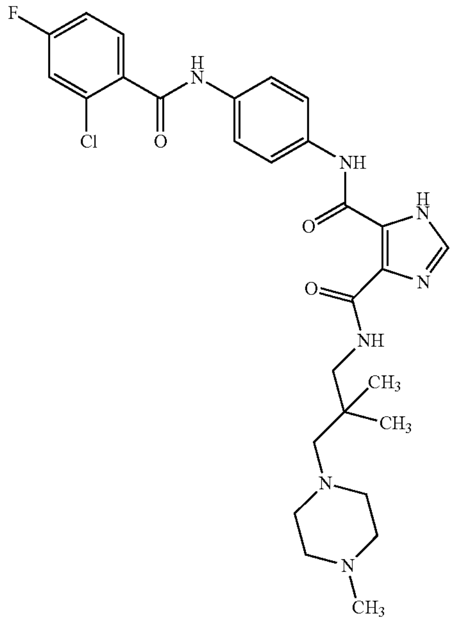 [SMILES: CN1CCN(CC(C)(C)CNC(=O)c2nc[nH]c2C(=O)Nc2ccc(NC(=O)c3ccc(F)cc3Cl)cc2)CC1] | 570 | $N^5$-{4-[(2-chloro-4-fluorobenzoyl)amino]phenyl}-$N^4$-[2,2-dimethyl-3-(4-methylpiperazin-1-yl)propyl]-1H-imidazole-4,5-dicarboxamide | 0.83 |

Further, the compounds of formula (I) of the present invention can be converted to any salt as described herein, by any method which is known to the person skilled in the art. Similarly, any salt of a compound of formula (I) of the present invention can be converted into the free compound, by any method which is known to the person skilled in the art.

Pharmaceutical Compositions of the Compounds of the Invention

This invention also relates to pharmaceutical compositions containing one or more compounds of the present invention. These compositions can be utilised to achieve the desired pharmacological effect by administration to a patient in need thereof. A patient, for the purpose of this invention, is a mammal, including a human, in need of treatment for the particular condition or disease. Therefore, the present invention includes pharmaceutical compositions that are comprised of a pharmaceutically acceptable carrier and a pharmaceutically effective amount of a compound, or salt thereof, of the present invention. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is preferably that amount which produces a result or exerts an influence on the particular condition being treated. The compounds of the present invention can be administered with pharmaceutically-acceptable carriers well known in the art using any effective conventional dosage unit forms, including immediate, slow and timed release preparations, orally, parenterally, topically, nasally, ophthalmically, optically, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatine type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatine, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, colouring agents, and flavouring agents such as peppermint, oil of wintergreen, or cherry flavouring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavouring and colouring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavouring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more colouring agents; one or more flavouring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavouring and colouring agents.

The compounds of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutical adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimise or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethylcellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: Powell, M. F. et al., "Compendium of Excipients for Parenteral Formulations" PDA Journal of Pharmaceutical Science & Technology 1998, 52(5), 238-311; Strickley, R. G "Parenteral Formulations of Small Molecule Therapeutics Marketed in the United States (1999)-Part-1" PDA Journal of Pharmaceutical Science & Technology 1999, 53(6), 324-349; and Nema, S. et al., "Excipients and Their Use in Injectable Products" PDA Journal of Pharmaceutical Science & Technology 1997, 51(4), 166-171.

Commonly used pharmaceutical ingredients that can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC$—$CClF_2$ and $CClF_3$)

air displacement agents (examples include but are not limited to nitrogen and argon);

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate)

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection)

chelating agents (examples include but are not limited to edetate disodium and edetic acid)

colourants (examples include but are not limited to FD&C Red No. 3, FD&C Red No. 20, FD&C Yellow No. 6, FD&C Blue No. 2, D&C Green No. 5, D&C Orange No. 5, DC Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate)

flavourants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);
tablet anti-adherents (examples include but are not limited to magnesium stearate and talc);
tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);
tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);
tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);
tablet direct compression excipients (examples include but are not limited to dibasic calcium phosphate);
tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);
tablet glidants (examples include but are not limited to colloidal silica, corn starch and talc);
tablet lubricants (examples include but are not limited to calcium stearate, magnesium stearate, mineral oil, stearic acid and zinc stearate);
tablet/capsule opaquants (examples include but are not limited to titanium dioxide);
tablet polishing agents (examples include but are not limited to carnuba wax and white wax);
thickening agents (examples include but are not limited to beeswax, cetyl alcohol and paraffin);
tonicity agents (examples include but are not limited to dextrose and sodium chloride);
viscosity increasing agents (examples include but are not limited to alginic acid, bentonite, carbomers, carboxymethylcellulose sodium, methylcellulose, polyvinyl pyrrolidone, sodium alginate and tragacanth); and
wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:
Sterile IV Solution:
A 5 mg/mL solution of the desired compound of this invention can be made using sterile, injectable water, and the pH is adjusted if necessary. The solution is diluted for administration to 1-2 mg/mL with sterile 5% dextrose and is administered as an IV infusion over about 60 min.
Lyophilised Powder for IV Administration:
A sterile preparation can be prepared with (i) 100-1000 mg of the desired compound of this invention as a lyophilised powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 min.
Intramuscular Suspension:
The following solution or suspension can be prepared, for intramuscular injection:

50 mg/mL of the desired, water-insoluble compound of this invention
5 mg/mL sodium carboxymethylcellulose
4 mg/mL TWEEN 80
9 mg/mL sodium chloride
9 mg/mL benzyl alcohol
Hard Shell Capsules:
A large number of unit capsules are prepared by filling standard two-piece hard galantine capsules each with 100 mg of powdered active ingredient, 150 mg of lactose, 50 mg of cellulose and 6 mg of magnesium stearate.
Soft Gelatin Capsules:
A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.
Tablets:
A large number of tablets are prepared by conventional procedures so that the dosage unit is 100 mg of active ingredient, 0.2 mg. of colloidal silicon dioxide, 5 mg of magnesium stearate, 275 mg of microcrystalline cellulose, 11 mg of starch, and 98.8 mg of lactose. Appropriate aqueous and non-aqueous coatings may be applied to increase palatability, improve elegance and stability or delay absorption.
Immediate Release Tablets/Capsules:
These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.
Combination Therapies
The term "combination" in the present invention is used as known to persons skilled in the art and may be present as a fixed combination, a non-fixed combination or kit-of-parts.
A "fixed combination" in the present invention is used as known to persons skilled in the art and is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.
A non-fixed combination or "kit-of-parts" in the present invention is used as known to persons skilled in the art and is defined as a combination wherein the said first active ingredient and the said second active ingredient are present in more than one unit. One example of a non-fixed combination or kit-of-parts is a combination wherein the said first active ingredient and the said second active ingredient are present separately. The components of the non-fixed combination or kit-of-parts may be administered separately, sequentially, simultaneously, concurrently or chronologically staggered.

The compounds of this invention can be administered as the sole pharmaceutical agent or in combination with one or more other pharmaceutical agents where the combination causes no unacceptable adverse effects. The present invention relates also to such combinations. For example, the compounds of this invention can be combined with known chemotherapeutic agents or anti-cancer agents, e.g. anti-hyper-proliferative or other indication agents, and the like, as well as with admixtures and combinations thereof. Other indication agents include, but are not limited to, anti-angiogenic agents, mitotic inhibitors, alkylating agents, antimetabolites, DNA-intercalating antibiotics, growth factor inhibitors, cell cycle inhibitors, enzyme inhibitors, toposisomerase inhibitors, biological response modifiers, or anti-hormones.

The term "chemotherapeutic anti-cancer agents", includes but is not limited to 131I-chTNT, abarelix, abiraterone, aclarubicin, ado-trastuzumab emtansine, afatinib, aflibercept, aldesleukin, alemtuzumab, Alendronic acid, alitretinoin, altretamine, amifostine, aminoglutethimide, Hexyl aminolevulinate, amrubicin, amsacrine, anastrozole, ancestim, anethole dithiolethione, angiotensin II, antithrombin III, aprepitant, arcitumomab, arglabin, arsenic trioxide, asparaginase, axitinib, azacitidine, basiliximab, belotecan, bendamustine, belinostat, bevacizumab, bexarotene, bicalutamide, bisantrene, bleomycin, bortezomib, buserelin, bosutinib, brentuximab vedotin, busulfan, cabazitaxel, cabozantinib, calcium folinate, calcium levofolinate, capecitabine, capromab, carboplatin, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, copanlisib, crisantaspase, cyclophosphamide, cyproterone, cytarabine, dacarbazine, dactinomycin, darbepoetin alfa, dabrafenib, dasatinib, daunorubicin, decitabine, degarelix, denileukin diftitox, denosumab, depreotide, deslorelin, dexrazoxane, dibrospidium chloride, dianhydrogalactitol, diclofenac, docetaxel, dolasetron, doxifluridine, doxorubicin, doxorubicin+estrone, dronabinol, eculizumab, edrecolomab, elliptinium acetate, eltrombopag, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, interferon alfa, interferon beta, interferon gamma, iobitridol, iobenguane (123I), iomeprol, ipilimumab, irinotecan, Itraconazole, ixabepilone, lanreotide, lapatinib, lasocholine, lenalidomide, lenograstim, lentinan, letrozole, leuprorelin, levamisole, levonorgestrel, levothyroxine sodium, lisuride, lobaplatin, lomustine, lonidamine, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, nabilone, nabiximols, nafarelin, naloxone+pentazocine, naltrexone, nartograstim, nedaplatin, nelarabine, neridronic acid, nivolumabpentetreotide, nilotinib, nilutamide, nimorazole, nimotuzumab, nimustine, nitracrine, nivolumab, obinutuzumab, octreotide, ofatumumab, omacetaxine mepesuccinate, omeprazole, ondansetron, oprelvekin, orgotein, orilotimod, oxaliplatin, oxycodone, oxymetholone, ozogamicine, p53 gene therapy, paclitaxel, palifermin, palladium-103 seed, palonosetron, pamidronic acid, panitumumab, pantoprazole, pazopanib, pegaspargase, PEG-epoetin beta (methoxy PEG-epoetin beta), pembrolizumab, pegfilgrastim, peginterferon alfa-2b, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, risedronic acid, rhenium-186 etidronate, rituximab, romidepsin, romiplostim, romurtide, roniciclib, samarium (153Sm) lexidronam, sargramostim, satumomab, secretin, sipuleucel-T, sizofiran, sobuzoxane, sodium glycididazole, sorafenib, stanozolol, streptozocin, sunitinib, talaporfin, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

The compounds of the invention may also be administered in combination with protein therapeutics. Such protein therapeutics suitable for the treatment of cancer or other angiogenic disorders and for use with the compositions of the invention include, but are not limited to, an interferon (e.g., interferon .alpha., .beta., or .gamma.) supraagonistic monoclonal antibodies, Tuebingen, TRP-1 protein vaccine, Colostrinin, anti-FAP antibody, YH-16, gemtuzumab, infliximab, cetuximab, trastuzumab, denileukin diftitox, rituximab, thymosin alpha 1, bevacizumab, mecasermin, mecasermin rinfabate, oprelvekin, natalizumab, rhMBL, MFE-CP1+ZD-2767-P, ABT-828, ErbB2-specific immunotoxin, SGN-35, MT-103, rinfabate, AS-1402, B43-genistein, L-19 based radioimmunotherapeutics, AC-9301, NY-ESO-1 vaccine, IMC-1C11, CT-322, rhCC10, r(m)CRP, MORAb-009, aviscumine, MDX-1307, Her-2 vaccine, APC-8024, NGR-hTNF, rhH1.3, IGN-311, Endostatin, volociximab, PRO-1762, lexatumumab, SGN-40, pertuzumab, EMD-273063, L19-IL-2 fusion protein, PRX-321, CNTO-328, MDX-214, tigapotide, CAT-3888, labetuzumab, alpha-particle-emitting radioisotope-linked lintuzumab, EM-1421, HyperAcute vaccine, tucotuzumab celmoleukin, galiximab, HPV-16-E7, Javelin—prostate cancer, Javelin—melanoma, NY-ESO-1 vaccine, EGF vaccine, CYT-004-MelQbG10, WT1 peptide, oregovomab, ofatumumab, zalutumumab, cintredekin besudotox, VVX-G250, Albuferon, aflibercept, denosumab, vaccine, CTP-37, efungumab, or 131I-chTNT-1/B. Monoclonal antibodies useful as the protein therapeutic include, but are not limited to, muromonab-CD3, abciximab, edrecolomab, daclizumab, gentuzumab, alemtuzumab, ibritumomab, cetuximab, bevicizumab, efalizumab, adalimumab, omalizumab, muromomab-CD3, rituximab, daclizumab, trastuzumab, palivizumab, basiliximab, and infliximab.

A compound of general formula (I) as defined herein can optionally be administered in combination with one or more of the following: ARRY-162, ARRY-300, ARRY-704, AS-703026, AZD-5363, AZD-8055, BEZ-235, BGT-226, BKM-120, BYL-719, CAL-101, CC-223, CH-5132799, deforolimus, E-6201, enzastaurin, GDC-0032, GDC-0068, GDC-0623, GDC-0941, GDC-0973, GDC-0980, GSK-2110183, GSK-2126458, GSK-2141795, MK-2206, novolimus, OSI-027, perifosine, PF-04691502, PF-05212384, PX-866, rapamycin, RG-7167, RO-4987655, RO-5126766, selumetinib, TAK-733, trametinib, triciribine, UCN-01, WX-554, XL-147, XL-765, zotarolimus, ZSTK-474.

Generally, the use of cytotoxic and/or cytostatic agents in combination with a compound or composition of the present invention will serve to:

(1) yield better efficacy in reducing the growth of a tumor or even eliminate the tumor as compared to administration of either agent alone,
(2) provide for the administration of lesser amounts of the administered chemotherapeutic agents,
(3) provide for a chemotherapeutic treatment that is well tolerated in the patient with fewer deleterious pharmacological complications than observed with single agent chemotherapies and certain other combined therapies,
(4) provide for treating a broader spectrum of different cancer types in mammals, especially humans,
(5) provide for a higher response rate among treated patients,
(6) provide for a longer survival time among treated patients compared to standard chemotherapy treatments,
(7) provide a longer time for tumor progression, and/or
(8) yield efficacy and tolerability results at least as good as those of the agents used alone, compared to known instances where other cancer agent combinations produce antagonistic effects.

Methods of Sensitizing Cells to Radiation

In a distinct embodiment of the present invention, a compound of the present invention may be used to sensitize a cell to radiation. That is, treatment of a cell with a compound of the present invention prior to radiation treatment of the cell renders the cell more susceptible to DNA damage and cell death than the cell would be in the absence of any treatment with a compound of the invention. In one aspect, the cell is treated with at least one compound of the invention.

Thus, the present invention also provides a method of killing a cell, wherein a cell is administered one or more compounds of the invention in combination with conventional radiation therapy.

The present invention also provides a method of rendering a cell more susceptible to cell death, wherein the cell is treated with one or more compounds of the invention prior to the treatment of the cell to cause or induce cell death. In one aspect, after the cell is treated with one or more compounds of the invention, the cell is treated with at least one compound, or at least one method, or a combination thereof, in order to cause DNA damage for the purpose of inhibiting the function of the normal cell or killing the cell.

In one embodiment, a cell is killed by treating the cell with at least one DNA damaging agent. That is, after treating a cell with one or more compounds of the invention to sensitize the cell to cell death, the cell is treated with at least one DNA damaging agent to kill the cell. DNA damaging agents useful in the present invention include, but are not limited to, chemotherapeutic agents (e.g., cisplatinum), ionizing radiation (X-rays, ultraviolet radiation), carcinogenic agents, and mutagenic agents.

In another embodiment, a cell is killed by treating the cell with at least one method to cause or induce DNA damage. Such methods include, but are not limited to, activation of a cell signalling pathway that results in DNA damage when the pathway is activated, inhibiting of a cell signalling pathway that results in DNA damage when the pathway is inhibited, and inducing a biochemical change in a cell, wherein the change results in DNA damage. By way of a non-limiting example, a DNA repair pathway in a cell can be inhibited, thereby preventing the repair of DNA damage and resulting in an abnormal accumulation of DNA damage in a cell.

In one aspect of the invention, a compound of the invention is administered to a cell prior to the radiation or other induction of DNA damage in the cell. In another aspect of the invention, a compound of the invention is administered to a cell concomitantly with the radiation or other induction of DNA damage in the cell. In yet another aspect of the invention, a compound of the invention is administered to a cell immediately after radiation or other induction of DNA damage in the cell has begun.

In another aspect, the cell is in vitro. In another embodiment, the cell is in vivo.

As mentioned supra, the compounds of the present invention have surprisingly been found to effectively inhibit tankyrases and may therefore be used for the treatment or prophylaxis of diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses are affected by inhibition of tankyrases, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

In accordance with another aspect therefore, the present invention covers a compound of general formula (I), or a stereoisomer, a tautomer, an N-oxide, a hydrate, a solvate, or a salt thereof, particularly a pharmaceutically acceptable salt thereof, or a mixture of same, as described and defined herein, for use in the treatment or prophylaxis of a disease, as mentioned supra.

Another particular aspect of the present invention is therefore the use of a compound of general formula (I), described supra, or a stereoisomer, a tautomer, an N-oxide, a hydrate, a solvate, or a salt thereof, particularly a pharmaceutically acceptable salt thereof, or a mixture of same, for the prophylaxis or treatment of a disease.

Another particular aspect of the present invention is therefore the use of a compound of general formula (I) described supra or a stereoisomer, a tautomer, an N-oxide, a hydrate, a solvate, or a salt thereof, particularly a pharmaceutically acceptable salt thereof, or a mixture of same. for manufacturing a pharmaceutical composition for the treatment or prophylaxis of a disease.

Another aspect of the present invention is the use of a compound of formula (I) or a stereoisomer, a tautomer, an N-oxide, a hydrate, a solvate, or a salt thereof, particularly a pharmaceutically acceptable salt thereof, or a mixture of same, as described herein, in the manufacture of a medicament for the treatment or prophylaxis of a disease.

The diseases referred to in the three preceding paragraphs are diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The term "inappropriate" within the context of the present invention, in particular in the context of "inappropriate cellular immune responses, or inappropriate cellular inflammatory responses", as used herein, is to be understood as meaning a response which is less than, or greater than normal, and which is associated with, responsible for, or results in, the pathology of said diseases.

Preferably, the use is in the treatment or prophylaxis of diseases, wherein the diseases are haemotological tumours, solid tumours and/or metastases thereof.

Diseases further included in the context of the present invention are metabolic diseases (e.g. diabetes and obesity), fibrosis (e.g. lung fibrogenesis) and viral infection.

Method of Treating Hyper-Proliferative Disorders

The present invention relates to a method for using the compounds of the present invention and compositions thereof, to treat mammalian hyper-proliferative disorders. Compounds can be utilized to inhibit, block, reduce, decrease, etc., cell proliferation and/or cell division, and/or produce apoptosis. This method comprises administering to a mammal in need thereof, including a human, an amount of a compound of this invention, or a pharmaceutically acceptable salt, isomer, polymorph, metabolite, hydrate, solvate or ester thereof; etc. which is effective to treat the disorder. Hyperproliferative disorders include but are not limited, e.g., psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukaemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumour.

Tumours of the male reproductive organs include, but are not limited to prostate and testicular cancer. Tumours of the female reproductive organs include, but are not limited to endometrial, cervical, ovarian, vaginal, and vulvar cancer, as well as sarcoma of the uterus.

Tumours of the digestive tract include, but are not limited to anal, colon, colorectal, oesophageal, gallbladder, gastric, pancreatic, rectal, small-intestine, and salivary gland cancers.

Tumours of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma. Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

Methods of Treating Angiogenic Disorders

The present invention also provides methods of treating disorders and diseases associated with excessive and/or abnormal angiogenesis.

Inappropriate and ectopic expression of angiogenesis can be deleterious to an organism. A number of pathological conditions are associated with the growth of extraneous blood vessels. These include, e.g., diabetic retinopathy, ischemic retinal-vein occlusion, and retinopathy of prematurity [Aiello et al. New Engl. J. Med. 1994, 331, 1480; Peer et al. Lab. Invest. 1995, 72, 638], age-related macular degeneration [AMD; see, Lopez et al. Invest. Opththalmol. Vis. Sci. 1996, 37, 855], neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumour enlargement and metastasis. Moreover, the growth of new blood and lymph vessels in a tumour provides an escape route for renegade cells, encouraging metastasis and the consequence spread of the cancer. Thus, compounds of the present invention can be utilized to treat and/or prevent any of the aforementioned angiogenesis disorders, e.g., by inhibiting and/or reducing blood vessel formation; by inhibiting, blocking, reducing, decreasing, etc. endothelial cell proliferation or other types involved in angiogenesis, as well as causing cell death or apoptosis of such cell types.

Dose and Administration

Based upon standard laboratory techniques known to evaluate compounds useful for the treatment of hyperproliferative disorders and angiogenic disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Preferably, the diseases of said method are haematological tumours, solid tumour and/or metastases thereof.

The compounds of the present invention can be used in particular in therapy and prevention, i.e. prophylaxis, of tumour growth and metastases, especially in solid tumours of all indications and stages with or without pre-treatment of the tumour growth.

Methods of testing for a particular pharmacological or pharmaceutical property are well known to persons skilled in the art.

The example testing experiments described herein serve to illustrate the present invention and the invention is not limited to the examples given.

Biological Assays:

Examples were tested in selected biological assays one or more times. When tested more than once, data are reported as either average values or as median values, wherein the average value, also referred to as the arithmetic mean value, represents the sum of the values obtained divided by the number of times tested, and the median value represents the middle number of the group of values when ranked in ascending or descending order. If the number of values in the data set is odd, the median is the middle value. If the number of values in the data set is even, the median is the arithmetic mean of the two middle values.

When no meaningful calculation of average values or median values is possible due to the existence of measurement values falling outside of the detection range of the assay (indicated by < or > in the tables below) all individual measurement values are indicated.

Examples were synthesized one or more times. When synthesized more than once, data from biological assays represent average values or median values calculated utilizing data sets obtained from testing of one or more synthetic batch.

6 BIOCHEMICAL ASSAYS

In general the potency assessment of the compounds of the present invention reveal consistent data applying orthogonal biochemical test formats (compare identical example Nos. in the tables below showing results for the TNKS1 Assay 1, Modified TNKS1 Assay 2 and Modified TNKS1 Assay 3, or for the TNKS2 Assay 1, Modified TNKS2 Assay 2 and Modified TNKS2 Assay 3). For those particular cases where the correlation of test results between different assays is less good, it could not be excluded that any differences may be due to different potencies of the compound dependent on the assay setup itself. Another factor to explain any potency differences between assays may be the use of different batches of the particular test compound applied in those orthogonal tests. Here, in some cases the test compound has been supplied as stock solution in DMSO, and in other cases the compound has been taken from solid material and dissolved freshly in DMSO solvent prior to the experiment. A different solubilization would have resulted in different apparent concentrations used for testing and would have translated into different apparent potencies.

6.1 TNKS1 Assays

TNKS1 Assay 1

The potency of the compounds according to the invention was assessed by applying an in vitro inhibition assay. The TNKS1 catalyzed $NAD^+$-dependent ribosylation of a suitable protein substrate was detected using a commercially available biotin/streptavidin binding based assay format [TNKS1 Histone Ribosylation Assay Kit (Biotin-labeled NAD+), Catalog #80579; BPS Bioscience, San Diego, USA]. Here, the incorporation of a biotin-labeled NAD+ during the TNKS1 catalyzed ribosylation reaction was detected with a streptavidin-HRP coupled chemi-luminescent readout. The intensity of the readout signal is proportional to the incorporated $NAD^+$. Inhibition of TNKS1 leads to a decreased incorporation of $NAD^+$ and consequently to a lower readout signal intensity. The concentration of a test compound which inhibits the enzyme activity by 50% (corresponds to half of the normed readout signal intensity) is reported as $IC_{50}$.

Protocol

The assay was conducted in a 384 well MTP format according to the manufacturer's protocol [bpsbioscience.com/poly-adp-ribose-polymerase/assay-kit/tnks1-histone-ribosylation-assay-kit-biotin-labeled-nad-80579 referencing: Brown, J. A., Marala, R. B. *J. Pharmacol. Toxicol. Methods* 2002 47:137-41] and using a BMG Pherastar MTP reader [BMG-Labtech, Offenburg, Germany].

TABLE $IC_{50}$ values of selected examples in TNKS1 assay 1

| Example | TNKS1 Assay 1 $IC_{50}$ [µM] |
|---|---|
| 1 | 1.01 |
| 4 | 0.12 |
| 5 | 0.32 |
| 6 | 0.05 |
| 7 | 1.3 |
| 8 | 2.27 |
| 9 | 0.11 |
| 10 | 0.31 |
| 11 | 0.16 |
| 12 | 0.02 |
| 14 | 0.42 |
| 15 | 0.9 |
| 16 | 0.07 |
| 17 | 100 |
| 18 | 0.42 |
| 19 | 1.7 |
| 20 | 1.7 |
| 23 | 0.77 |
| 24 | 0.28 |
| 25 | 0.07 |
| 26 | 0.4 |
| 27 | 0.1 |
| 28 | 0.07 |
| 30 | 0.14 |

Modified TNKS1 Assay 2

The potency of selected compounds according to the invention was assessed applying an modified in vitro inhibition assay. Here, the TNKS1 catalyzed $NAD^+$-dependent ribosylation of the enzyme itself (auto-parsylation) was detected using $[^3H]$-$NAD^+$ as substrate and applying the scintillation proximity assay (SPA) method to detect tritium-labeled, parsylated TNKS1. The intensity of the readout signal is proportional to the incorporated $[^3H]$-$NAD^+$. Inhibition of TNKS1 leads to a decreased incorporation of $[^3H]$-$NAD^+$ and consequently to a lower readout signal intensity. The concentration of a test compound which inhibits the enzyme activity by 50% (corresponds to half of the normed readout signal intensity) is reported as $IC_{50}$.

Protocol Auto-Parsylation Assay

The assay was conducted in a 96 well MTP format with the identical TNKS1 enzyme sample and $NAD^+$ sample as in the histone ribosylation assay with the following modifications: TNKS1 enzyme sample was diluted with a modified assay buffer (50 mM MES pH 7.0, 1 mM DTT, 0.01% Triton X-100) to a final concentration of 6 nM TNKS1 and 10×$NAD^+$ solution was diluted with the modified assay buffer (s. above) to a final 0.445×$NAD^+$ solution doped with 100 Bq/ul $[^3H]$-$NAD^+$[Catalog #NET443H050UC, Perkin Elmer, Waltham, Mass., USA]. Substrate solution (10 ul) was incubated with different test compound concentrations (2.5 ul in 10% DMSO in modified assay buffer) or control (2.5 ul 10% DMSO in modified assay buffer only) and enzyme (10 ul) over night at room temperature. Incorporated tritium was measured after addition of 50 ul SPA beads (1 mg/ml) [Catalog #RPNQ0095 20 mg/ml, Perkin Elmer, Waltham, Mass., USA; diluted 1:10 with Dulbecco's phosphate buffered saline, PBS Catalog #D8537, Sigma-Aldrich, Steinheim, Germany] and detection of the photon emission with a beta count plate reader [Wallac MicroBeta®, Perkin Elmer, Waltham, Mass., USA].

Modified TNKS1 Assay 3

The potency of the compounds against human TNKS1 according to the invention was assessed using a commercially available biotin/streptavidin binding assay kits from BPS Bioscience, San Diego, USA (Catalog #80573 for TNKS1). The incorporation of a biotin-labeled NAD+ during the PAPR1 catalyzed ribosylation of a suitable protein substrate was detected using with a streptavidin-HRP coupled chemi-luminescent readout. The intensity of the readout signal is proportional to the incorporated $NAD^+$. Inhibition of TNKS1 leads to a decreased incorporation of $NAD^+$ and consequently to a lower readout signal intensity in the corresponding TNKS1 assays. The concentration of a test compound that inhibits the enzyme activity by 50% (corresponds to half of the normed readout signal intensity) is reported as $IC_{50}$. The assay was conducted in a 96 well MTP format according to the manufacturer's protocol and using a BMG Pherastar MTP reader [BMG-Labtech, Offenburg, Germany].

TABLE 1

$IC_{50}$ values of selected examples in TNKS1 assays

| Example | TNKS1 Assay 1 $IC_{50}$ [µM] | Modified TNKS1 Assay 2 $IC_{50}$ [µM] | Modified TNKS1 Assay 3 $IC_{50}$ [µM] |
|---|---|---|---|
| 1 | 1.01 | 10 | |
| 2 | | 10 | |
| 3 | >100 | | |
| 4 | 0.12 | 0.08 | |
| 5 | 0.32 | 0.32 | |
| 6 | 0.05 | 0.15 | |
| 7 | 1.30 | | |
| 8 | 2.27 | | |
| 9 | 0.11 | 0.15 | |
| 10 | 0.31 | 0.29 | |
| 11 | 0.22 | 0.15 | |
| 12 | 0.02 | 0.02 | 0.26 |
| 13 | | | 0.06 |
| 14 | 0.42 | | |
| 15 | 0.90 | | |
| 16 | 0.07 | 0.03 | 0.13 |
| 17 | >100 | | |
| 18 | 0.42 | | |
| 19 | 1.70 | 1.80 | |
| 20 | 1.70 | >10 | |
| 21 | | >10 | |
| 22 | | 0.01 | 0.03 |
| 23 | 0.77 | | |
| 24 | 0.28 | 2.60 | |
| 25 | 0.07 | 0.08 | |

TABLE 1-continued

IC$_{50}$ values of selected examples in TNKS1 assays

| Example | TNKS1 Assay 1 IC$_{50}$ [μM] | Modified TNKS1 Assay 2 IC$_{50}$ [μM] | Modified TNKS1 Assay 3 IC$_{50}$ [μM] |
|---|---|---|---|
| 26 | 0.41 | 1.70 | |
| 27 | 0.10 | 0.63 | |
| 28 | 0.07 | 0.06 | |
| 29 | | 2.10 | |
| 30 | 0.14 | 0.05 | 0.40 |
| 31 | | | 0.13 |
| 32 | | 0.009 | 0.008 |
| 33 | | | >0.50 |
| 35 | | | >0.50 |
| 36 | | >10 | |
| 37 | | | 0.33 |
| 39 | | 2.70 | |
| 41 | | | >0.50 |
| 42 | | >10 | |
| 43 | | 9.2 | |
| 45 | | | 0.07 |
| 46 | | 0.68 | |
| 47 | | | >0.50 |
| 48 | | >10 | |
| 49 | | | >0.50 |
| 50 | | | 0.13 |
| 51 | | 0.02 | 0.23 |
| 52 | | 0.03 | >0.50 |
| 53 | | 0.02 | 0.002 |
| 54 | | | 0.02 |
| 55 | | 0.12 | 0.03 |
| 56 | | 0.53 | 0.09 |
| 60 | | >10 | |
| 61 | | 0.03 | 0.14 |
| 62 | | 0.84 | |
| 63 | | | 0.07 |
| 64 | | >10 | |
| 65 | | | 0.16 |
| 66 | | 0.02 | |
| 67 | | 0.004 | 0.005 |
| 68 | | >10 | |
| 69 | | | 0.05 |
| 70 | | | 0.02 |
| 71 | | 0.10 | |
| 73 | | 0.01 | |
| 74 | | | 0.002 |
| 77 | | 0.99 | |
| 78 | | >10 | |
| 80 | | 0.69 | |
| 81 | | 0.06 | |
| 82 | | | 0.01 |
| 84 | | 0.17 | |
| 85 | | 0.009 | |
| 86 | | 2.6 | |
| 87 | | 10 | |
| 89 | | 0.03 | |
| 94 | | 0.44 | |
| 95 | | 0.08 | |
| 96 | | 0.03 | |
| 97 | | 0.06 | 0.09 |
| 98 | | 0.34 | |
| 99 | | | 0.50 |
| | | | >0.50 |
| 100 | | 0.05 | |
| 101 | | | 0.04 |
| 102 | | >10 | |
| 106 | | >10 | |
| 108 | | | 0.46 |
| 109 | | | 0.001 |
| 110 | | | 0.04 |
| 112 | | 0.25 | |
| 113 | | 0.02 | |
| 114 | | | <0.0005 |
| 118 | | 0.08 | >0.50 |
| 119 | | 0.002 | 0.01 |
| | | | <0.0005 |
| 120 | | | >0.50 |
| 121 | | 0.04 | >0.50 |
| 122 | | 0.95 | |
| 123 | | 0.09 | |
| 124 | | >10 | |
| 125 | | >10 | |
| 126 | | 0.01 | 0.002 |
| 127 | | | 0.002 |
| 128 | | | >0.50 |
| 130 | | 0.03 | 0.15 |
| 131 | | >10 | |
| 132 | | | >0.50 |
| 133 | | | 0.20 |
| 134 | | | 0.36 |
| 138 | | | 0.26 |
| 139 | | | 0.29 |
| 142 | | | 0.19 |
| 145 | | | >0.50 |
| 147 | | 0.11 | |
| 148 | | 1.3 | |
| 155 | | 0.06 | |
| 157 | | 1.2 | |
| 160 | | 0.08 | |
| 164 | | 0.04 | |
| 165 | | 0.03 | |
| 166 | | 0.24 | |
| 169 | | 0.09 | |
| 171 | | 0.20 | |
| 173 | | 0.03 | |
| 176 | | 0.05 | |
| 180 | | 4.0 | |
| 182 | | 0.01 | |
| 184 | | 0.03 | |
| 187 | | 0.05 | |
| 189 | | 0.22 | |
| 199 | | 0.06 | |
| 200 | | 0.35 | |
| 206 | | 4.1 | |
| 207 | | 0.11 | |
| 208 | | 0.003 | 0.04 |
| 209 | | 0.40 | |
| 210 | | | 0.02 |
| 212 | | | 0.005 |
| 213 | >100 | | |
| 214 | | | 0.20 |
| 215 | | | 0.21 |
| 216 | | 0.007 | 0.003 |
| 217 | | 0.01 | |
| 218 | | 0.07 | |
| 219 | | | >0.50 |
| 220 | | | 0.26 |
| 221 | | | >0.50 |
| 222 | | | 0.22 |
| 223 | | | >0.50 |
| 224 | | | 0.26 |
| 225 | | | 0.18 |
| 226 | | 0.004 | 0.04 |
| 227 | | | 0.20 |
| 228 | | | 0.02 |
| 230 | | | 0.09 |
| 231 | | | 0.17 |
| 232 | | | 0.29 |
| 233 | | | 0.48 |
| 234 | | | 0.22 |
| 235 | | | 0.27 |
| 236 | | 0.03 | 0.43 |
| 237 | | | >0.50 |
| 238 | | | 0.03 |
| | | | <0.0005 |
| 239 | | >10 | |
| 240 | | 0.008 | 0.02 |
| 241 | | 2.50 | |
| 242 | | 0.02 | 0.38 |
| 243 | | >10 | |
| 244 | | 0.04 | 0.15 |
| 246 | | | >0.50 |
| 247 | | 0.91 | |

TABLE 1-continued

IC$_{50}$ values of selected examples in TNKS1 assays

| Example | TNKS1 Assay 1 IC$_{50}$ [μM] | Modified TNKS1 Assay 2 IC$_{50}$ [μM] | Modified TNKS1 Assay 3 IC$_{50}$ [μM] |
|---|---|---|---|
| 248 | | 0.24 | |
| 249 | | 10 | |
| 250 | | 0.23 | |
| 251 | | >10 | |
| 252 | | 9.3 | |
| 253 | | >10 | |
| 254 | | 0.57 | |
| 255 | | 0.68 | |
| 256 | | 0.009 | |
| 257 | | 7.8 | |
| 258 | | 10 | |
| 259 | | 0.30 | |
| 260 | | 3.0 | |
| 261 | | 0.23 | |
| 262 | | 10 | |
| 263 | | 0.30 | |
| 264 | | 0.09 | |
| 265 | | | 0.007 |
| 266 | | | 0.02 |
| 267 | | 0.007 | 0.02 |
| 268 | | | 0.11 |
| 269 | | | 0.08 |
| 270 | | 0.004 | 0.007 |
| 271 | | | 0.006 |
| 272 | | | 0.07 |
| 273 | | | 0.03 |
| 274 | | | 0.01 |
| 276 | | | 0.05 |
| 277 | | | 0.07 |
| 278 | | 0.005 | <0.0005 |
| 279 | | 0.02 | |
| 280 | | | 0.06 |
| 281 | | 0.06 | |
| 282 | | | 0.06 |
| 283 | | | 0.11 |
| 284 | | | 0.06 |
| 286 | | | 0.07 |
| 287 | | | 0.08 |
| 288 | | | 0.03 |
| 290 | | 0.04 | |
| 293 | | 0.08 | |
| 294 | | 0.21 | |
| 295 | | >0.50 | |
| 296 | | >0.50 | |
| 297 | | >0.50 | |
| 298 | | 0.04 | |
| 303 | | 0.008 | |
| 309 | | 0.41 | |
| 313 | | 0.42 | |
| 322 | | 1.00 | |
| 326 | | 10 | |
| 333 | | 0.96 | |
| 334 | | 0.06 | |
| 340 | | >10 | |
| 342 | | 0.64 | |
| 343 | | 2.00 | |
| 344 | | >10 | |
| 346 | | >0.50 | |
| 349 | | 2.7 | |
| 352 | | 0.58 | |
| 353 | | >10 | |
| 356 | | 2.0 | |
| 359 | | >10 | |
| 361 | | 0.14 | |
| 363 | | >10 | |
| 364 | | 6.1 | |
| 366 | | >10 | |
| 367 | | >10 | |
| 369 | | | 0.26 |
| 370 | | >10 | |
| 372 | | 5.7 | |
| 374 | | 1.6 | |
| 375 | | 1.2 | |
| 376 | | >10 | |
| 377 | | 0.47 | |
| 378 | | | 0.06 |
| 379 | | | 0.19 |
| 381 | | 0.02 | |
| 382 | | | 0.02 |
| 384 | | 1.5 | |
| 385 | | | 0.05 |
| 386 | | | 0.06 |
| 387 | | 0.10 | |
| 388 | | | 0.03 |
| 389 | | 0.15 | |
| 390 | | | 0.0009 |
| 391 | | 0.40 | |
| 392 | | | 0.02 |
| 393 | | 0.30 | |
| 394 | | 0.05 | |
| 396 | | | 0.18 |
| 397 | | 0.24 | |
| 400 | | | 0.02 |
| 401 | | | 0.18 |
| 402 | | | 0.26 |
| 404 | | | 0.001 |
| 405 | | 0.10 | |
| 406 | | | 0.07 |
| 407 | | | 0.01 |
| 408 | | | 0.08 |
| 409 | | | 0.08 |
| 410 | | | 0.09 |
| 411 | | | 0.07 |
| 412 | | | 0.03 |
| 413 | | 0.08 | |
| 414 | | | 0.05 |
| 415 | | 0.07 | |

6.2 TNKS2 Assays

TNKS2 Assay 1

The potency of the compounds according to the invention was assessed applying an in vitro inhibition assay. The TNKS2 catalyzed NAD$^+$-dependent ribosylation of a suitable protein substrate was detected using a commercially available biotin/streptavidin binding based assay format [TNKS2 Histone Ribosylation Assay Kit (Biotin-labeled NAD+), Catalog #80572; BPS Bioscience, San Diego, USA]. Here, the incorporation of a biotin-labeled NAD+ during the TNKS2 catalyzed ribosylation reaction was detected with a streptavidin-HRP coupled chemi-luminescent readout. The intensity of the readout signal is proportional to the incorporated NAD$^+$. Inhibition of TNKS2 leads to a decreased incorporation of NAD$^+$ and consequently to a lower readout signal intensity. The concentration of a test compound which inhibits the enzyme activity by 50% (corresponds to half of the normed readout signal intensity) is reported as IC$_{50}$.

Protocol

The assay was conducted in a 384 well MTP format according to the manufacturer's protocol [bpsbioscience.com/poly-adp-ribose-polymerase/assay-kit/tnks2-histone-ribosylation-assay-kit-biotin-labeled-nad-80572 referencing: Brown, J. A., Marala, R. B. J. Pharmacol. Toxicol. Methods 2002 47:137-41]. and using a BMG Pherastar MTP reader [BMG-Labtech, Offenburg, Germany].

TABLE

IC$_{50}$ values of selected examples in TNKS2 assay 1

| Example | TNKS2 Assay 1 IC$_{50}$ [µM] |
|---|---|
| 1 | 0.02 |
| 4 | 0.09 |
| 5 | 0.47 |
| 6 | 0.05 |
| 7 | 19.1 |
| 8 | 7.0 |
| 9 | 0.02 |
| 10 | 0.23 |
| 11 | 0.12 |
| 12 | 0.02 |
| 14 | 0.3 |
| 15 | 1.14 |
| 16 | 0.04 |
| 17 | 2.2 |
| 18 | 0.85 |
| 19 | 0.29 |
| 20 | 1.7 |
| 23 | 0.34 |
| 24 | 0.5 |
| 25 | 0.06 |
| 26 | 0.16 |
| 27 | 0.04 |
| 28 | 0.06 |
| 30 | 0.07 |

Modified TNKS2 Assay 2

The potency of selected compounds according to the invention was assessed applying an modified in vitro inhibition assay. Here, the TNKS2 catalyzed NAD$^+$-dependent ribosylation of the enzyme itself (auto-parsylation) was detected using [$^3$H]-NAD$^+$ as substrate and applying the scintillation proximity assay (SPA) method to detect tritium-labeled, parsylated TNKS2. The intensity of the readout signal is proportional to the incorporated [$^3$H]-NAD$^+$. Inhibition of TNKS2 leads to a decreased incorporation of [$^3$H]-NAD$^+$ and consequently to a lower readout signal intensity. The concentration of a test compound which inhibits the enzyme activity by 50% (corresponds to half of the normed readout signal intensity) is reported as IC$_{50}$.

Protocol Auto-Parsylation Assay

The assay was conducted in a 96 well MTP format with the identical TNKS2 enzyme sample and NAD$^+$ sample as in the histone ribosylation assay with the following modifications: TNKS2 enzyme sample was diluted with a modified assay buffer (50 mM MES pH 7.0, 1 mM DTT, 0.01% Triton X-100) to a final concentration of 6 nM TNKS2 and 10×NAD$^+$ solution was diluted with the modified assay buffer (s. above) to a final 0.445×NAD$^+$ solution doped with 100 Bq/ul [$^3$H]-NAD$^+$ [Catalog #NET443H050UC, Perkin Elmer, Waltham, Mass., USA]. Substrate solution (10 ul) was incubated with different test compound concentrations (2.5 ul in 10% DMSO in modified assay buffer) or control (2.5 ul 10% DMSO in modified assay buffer only) and enzyme (10 ul) over night at room temperature. Incorporated tritium was measured after addition of 50 ul SPA beads (1 mg/ml) [Catalog #RPNQ0095 20 mg/ml, Perkin Elmer, Waltham, Mass., USA; diluted 1:10 with Dulbecco's phosphate buffered saline, PBS Catalog #D8537, Sigma-Aldrich, Steinheim, Germany] and detection of the photon emission with a beta count plate reader [Wallac MicroBeta®, Perkin Elmer, Waltham, Mass., USA].

Modified TNKS2 Assay 3

The potency of the compounds against human TNKS2 according to the invention was assessed using a commercially available biotin/streptavidin binding assay kits from BPS Bioscience, San Diego, USA (Catalog #80578 for TNKS2). The incorporation of a biotin-labeled NAD+ during the PAPR1 catalyzed ribosylation of a suitable protein substrate was detected using with a streptavidin-HRP coupled chemi-luminescent readout. The intensity of the readout signal is proportional to the incorporated NAD$^+$. Inhibition of TNKS2 leads to a decreased incorporation of NAD$^+$ and consequently to a lower readout signal intensity in the corresponding TNKS2 assays. The concentration of a test compound that inhibits the enzyme activity by 50% (corresponds to half of the normed readout signal intensity) is reported as IC$_{50}$. The assay conducted in a 96 well MTP format according to the manufacturer's protocol and using a BMG Pherastar MTP reader [BMG-Labtech, Offenburg, Germany].

TABLE 2

IC$_{50}$ values of selected examples in TNKS2 assays

| Example | TNKS2 Assay 1 IC$_{50}$ [µM] | Modified TNKS2 Assay 2 IC$_{50}$ [µM] | Modified TNKS2 Assay 3 IC$_{50}$ [µM] |
|---|---|---|---|
| 1 | 0.02 | 3.3 | |
| 2 | | >10 | |
| 3 | 30 | | |
| 4 | 0.09 | >10 | |
| 5 | 0.47 | 0.77 | |
| 6 | 0.05 | 0.18 | |
| 7 | 19 | | |
| 8 | 7.0 | | |
| 9 | 0.03 | 0.08 | |
| 10 | 0.23 | 0.35 | |
| 11 | 0.09 | 0.91 | |
| 12 | 0.02 | 0.06 | 0.06 |
| 13 | | | 0.02 |
| 14 | 0.30 | | |
| 15 | 1.1 | | |
| 16 | 0.04 | 0.10 | 0.04 |
| 17 | 2.20 | | |
| 18 | 0.85 | | |
| 19 | 0.29 | 1.80 | |
| 20 | 1.70 | >10 | |
| 21 | | >10 | |
| 22 | | 0.02 | 0.01 |
| 23 | 0.34 | | |
| 24 | 0.50 | 3.4 | |
| 25 | 0.06 | 0.22 | |
| 26 | 0.16 | 1.60 | |
| 27 | 0.04 | 0.53 | |
| 28 | 0.06 | 0.18 | |
| 29 | | 1.90 | |
| 30 | 0.07 | 0.04 | 0.13 |
| 31 | | | 0.13 |
| 32 | | 0.0003 | 0.001 |
| 33 | | | >0.50 |
| 35 | | | >0.50 |
| 36 | | >10 | |
| 37 | | | 0.26 |
| 39 | | 2.2 | |
| 41 | | | 0.07 |
| 42 | | >10 | |
| 43 | | >10 | |
| 45 | | | 0.04 |
| 46 | | 1.1 | |
| 47 | | | >0.50 |
| 48 | | >10 | |
| 49 | | | >0.50 |
| 51 | | 0.05 | 0.01 |
| 52 | | 0.22 | 0.25 |
| 53 | | 0.01 | |
| 54 | | | 0.006 |
| 55 | | 0.07 | 0.01 |
| 56 | | 0.57 | 0.06 |
| 60 | | >10 | |
| 61 | | 0.06 | 0.003 |
| 62 | | 0.31 | |

TABLE 2-continued

IC$_{50}$ values of selected examples in TNKS2 assays

| Example | TNKS2 Assay 1 IC$_{50}$ [μM] | Modified TNKS2 Assay 2 IC$_{50}$ [μM] | Modified TNKS2 Assay 3 IC$_{50}$ [μM] |
|---|---|---|---|
| 63 | | | 0.004 |
| 64 | >10 | | |
| 65 | | | 0.36 |
| 66 | | 0.04 | |
| 67 | | 0.03 | 0.005 |
| 68 | >10 | | |
| 69 | | | 0.19 |
| 70 | | | 0.02 |
| 71 | | 0.11 | |
| 72 | | | 0.06 |
| 73 | | 0.03 | |
| 74 | | | <0.0005 |
| 77 | | 1.8 | |
| 78 | >10 | | |
| 80 | | 0.70 | |
| 81 | | 0.16 | |
| 82 | | | <0.0005 |
| 84 | | 0.26 | |
| 85 | | 0.01 | |
| 86 | | 3.4 | |
| 87 | | 10 | |
| 89 | | 0.05 | |
| 94 | | 0.50 | |
| 95 | | 0.47 | 0.06 |
| 96 | | 0.04 | |
| 97 | | 0.005 | 0.02 |
| 98 | | 0.37 | |
| 99 | | | 0.09 |
| 100 | | 0.16 | |
| 101 | | | 0.01 |
| 102 | >10 | | |
| 106 | >10 | | |
| 108 | | >0.50 | |
| 110 | | | 0.004 |
| 112 | | 0.37 | |
| 113 | | 0.04 | |
| 118 | | 0.14 | 0.23 |
| 119 | | 0.005 | <0.0005 |
| 120 | | | 0.14 |
| 121 | | 0.07 | 0.11 |
| 122 | | 0.53 | |
| 123 | | 0.10 | |
| 124 | >10 | | |
| 125 | >10 | | |
| 126 | | 0.007 | 0.001 |
| 128 | | >0.50 | |
| 130 | | 0.07 | 0.17 |
| 131 | >10 | | |
| 132 | | | 0.43 |
| 133 | | | 0.50 |
| 134 | | | 0.51 |
| 138 | | | 0.15 |
| 139 | | | 0.35 |
| 142 | | | 0.06 |
| 145 | | | >0.50 |
| 147 | | 0.11 | |
| 148 | | 1.1 | |
| 153 | | | 0.005 |
| 155 | | 0.08 | |
| 157 | | 1.40 | |
| 159 | | | 0.002 |
| 160 | | 0.11 | |
| 162 | | | 0.02 |
| 163 | | | 0.01 |
| 164 | | 0.06 | |
| 165 | | 0.07 | |
| 166 | | 0.33 | |
| 168 | | | <0.0005 |
| 169 | | 0.18 | |
| 170 | | | 0.002 |
| 171 | | 0.34 | |
| 173 | | 0.05 | |
| 176 | | 0.06 | |
| 180 | | 6.9 | |
| 182 | | 0.01 | |
| 184 | | 0.05 | |
| 185 | | | 0.02 |
| 187 | | 0.10 | |
| 189 | | 0.26 | |
| 190 | | | 0.002 |
| 191 | | | 0.002 |
| 196 | | | 0.02 |
| 197 | | | 0.001 |
| 198 | | | <0.0005 |
| 199 | | 0.13 | |
| 200 | | 0.58 | |
| 204 | | | 0.02 |
| 206 | | 5.3 | |
| 207 | | 0.21 | |
| 208 | | 0.002 | 0.003 |
| 209 | | 0.46 | |
| 210 | | | 0.003 |
| 213 | >100 | | |
| 214 | | | 0.07 |
| 215 | | | 0.12 |
| 216 | | 0.002 | |
| 217 | | 0.008 | |
| 218 | | 0.11 | |
| 219 | | | 0.42 |
| 220 | | | 0.10 |
| 221 | | | 0.49 |
| 222 | | | 0.19 |
| 223 | | | 0.34 |
| 224 | | | 0.14 |
| 225 | | | 0.05 |
| 226 | | 0.002 | 0.0009 |
| 227 | | | 0.02 |
| 228 | | | 0.004 |
| 229 | | | <0.0005 |
| 230 | | | 0.004 |
| 231 | | | 0.02 |
| 232 | | | 0.02 |
| 233 | | | 0.04 |
| 234 | | | 0.16 |
| 235 | | | 0.02 |
| 236 | | 0.06 | 0.15 |
| 237 | | | 0.08 |
| 238 | | | 0.23 |
| 239 | >10 | | 0.002 |
| 240 | | 0.03 | 0.03 |
| 241 | | 1.80 | |
| 242 | | 0.03 | 0.12 |
| 243 | >10 | | |
| 244 | | 0.09 | 0.03 |
| 246 | | | 0.06 |
| 247 | | 0.57 | |
| 248 | | 0.48 | |
| 249 | | 5.70 | |
| 250 | | 0.22 | |
| 251 | >10 | | |
| 252 | | 3.80 | |
| 253 | >10 | | |
| 254 | | 0.43 | |
| 255 | | 0.64 | |
| 256 | | 0.01 | |
| 257 | | 5.0 | |
| 258 | >10 | | |
| 259 | | 7.6 | |
| 260 | | 6.2 | |
| 261 | | 0.21 | |
| 262 | >10 | | |
| 263 | | 0.50 | |
| 264 | | 0.48 | |
| 266 | | | 0.0009 |
| 267 | | 0.003 | <0.0005 |
| 268 | | | 0.003 |
| 269 | | | 0.13 |

TABLE 2-continued

IC$_{50}$ values of selected examples in TNKS2 assays

| Example | TNKS2 Assay 1 IC$_{50}$ [μM] | Modified TNKS2 Assay 2 IC$_{50}$ [μM] | Modified TNKS2 Assay 3 IC$_{50}$ [μM] |
|---|---|---|---|
| 270 | | 0.003 | 0.01 |
| 271 | | | 0.002 |
| 274 | | | 0.009 |
| 277 | | | 0.03 |
| 278 | | 0.005 | 0.001 |
| 279 | | 0.02 | |
| 280 | | | 0.03 |
| 281 | | 0.07 | |
| 282 | | | 0.01 |
| 284 | | | 0.01 |
| 286 | | | 0.01 |
| 287 | | | 0.02 |
| 288 | | | 0.003 |
| 290 | | 0.11 | |
| 293 | | 0.11 | |
| 294 | | 0.15 | |
| 295 | | | 0.19 |
| 296 | | | >0.50 |
| 298 | | 0.06 | |
| 303 | | 0.01 | |
| 309 | | 0.34 | |
| 313 | | 1.0 | |
| 322 | | 0.95 | |
| 326 | | >10 | |
| 333 | | 0.58 | |
| 334 | | 0.03 | |
| 340 | | >10 | |
| 342 | | 0.54 | |
| 343 | | 1.70 | |
| 344 | | >10 | |
| 346 | | | >0.50 |
| 349 | | 2.2 | |
| 352 | | 1.3 | |
| 353 | | >10 | |
| 356 | | 0.94 | |
| 359 | | >10 | |
| 361 | | 0.10 | |
| 363 | | >10 | |
| 364 | | 7.9 | |
| 366 | | >10 | |
| 367 | | >10 | |
| 369 | | | 0.04 |
| 370 | | 2.2 | |
| 372 | | 4.8 | |
| 374 | | 1.3 | |
| 375 | | 1.2 | |
| 376 | | >10 | |
| 377 | | 0.33 | |
| 381 | | 0.02 | |
| 384 | | 1.7 | |
| 387 | | 0.15 | |
| 389 | | 0.28 | |
| 390 | | | 0.003 |
| 391 | | 0.45 | |
| 392 | | | 0.007 |
| 393 | | 0.75 | |
| 394 | | 0.06 | |
| 397 | | 0.20 | |
| 400 | | | 0.02 |
| 404 | | | 0.0007 |
| 405 | | 0.10 | |
| 407 | | | 0.008 |
| 413 | | 0.09 | |
| 415 | | 0.08 | |

6.3 PARP1 Assay

The potency of the compounds according to the invention was assessed using a commercially available biotin/streptavidin binding assay kits from BPS Bioscience, San Diego, USA (Catalog #80551). The incorporation of a biotin-labeled NAD+ during the PARP1 catalyzed ribosylation of a suitable protein substrate was detected using with a streptavidin-HRP coupled chemi-luminescent readout. The intensity of the readout signal is proportional to the incorporated NAD+. Inhibition of PARP1 leads to a decreased incorporation of NAD+ and consequently to a lower readout signal intensity. The concentration of a test compound that inhibits the enzyme activity by 50% (corresponds to half of the normed readout signal intensity) is reported as IC50.

Protocol

The assay was conducted in a 96 well MTP format according to the manufacturer's protocol (Catalog No. 80551) and using a BMG Pherastar MTP reader [BMG-Labtech, Offenburg, Germany].

6.4 PARP2 Assay

The potency of the compounds according to the invention was assessed using a commercially available biotin/streptavidin binding assay kits from BPS Bioscience, San Diego, USA (Catalog #80551). The incorporation of a biotin-labeled NAD+ during the PARP2 catalyzed ribosylation of a suitable protein substrate was detected using with a streptavidin-HRP coupled chemi-luminescent readout. The intensity of the readout signal is proportional to the incorporated $NAD^+$. Inhibition of PARP2 leads to a decreased incorporation of $NAD^+$ and consequently to a lower readout signal intensity. The concentration of a test compound that inhibits the enzyme activity by 50% (corresponds to half of the normed readout signal intensity) is reported as $IC_{50}$.

Protocol

The assay was conducted in a 96 well MTP format according to the manufacturer's protocol (Catalog No. 80552) and using a BMG Pherastar MTP reader [BMG-Labtech, Offenburg, Germany].

7 CELLULAR ASSAYS

7.1 Measurement of the Inhibitory Activity of Selected Compounds on the Wildtype Wnt Signaling Cascade: HEK293 TOP/FOP Assay In order to discover and characterize small molecules which inhibit the wildtype Wnt pathway, a cellular reporter assay was employed. The corresponding assay cell was generated by transfection of the mammalian cell line HEK293 (ATCC, #CRL-1573) with the Super TopFlash vector (Morin, Science 275, 1997, 1787-1790; Molenaar et al., Cell 86 (3), 1996, 391-399). The HEK293 cell line is cultivated at 37° C. and 5% $CO_2$ in DMEM (Life Technologies, #41965-039), supplemented with 2 mM glutamine, 20 mM HEPES, 1.4 mM pyruvate, 0.15% Na-bicarbonate and 10% foetal bovine serum (GIBCO, #10270). Stable transfectants were generated by selection with 300 μg/ml Hygromycin.

In a parallel approach, HEK293 cells were cotransfected with the FOP control vector and pcDNA3. The FOP vector is identical to the TOP construct, but it contains instead of functional TCF elements a randomized, non-functional sequence. For this transfection a stable transfected cell line was generated as well, based on selection with Geneticin (1 mg/ml).

In preparation of the assay, the two cell lines were plated 24 hrs before beginning the test at 10000 cells per well in a 384 micro titre plate (MTP) in 30 μl growth medium. Before compound testing a dose response curve for the Wnt dependent luciferase expression was recorded by stimulating the assay cell line with human recombinant Wnt-3a (R&D, #5036-WN-010) at different concentrations for 16 hrs at 37° C. and 5% $CO_2$ followed by subsequent luciferase measurement, to determine the Wnt-3a EC50 for the HEK293 TOP cell line on the day of testing. The recombinant human Wnt-3a was thereby applied between 2500 and 5 ng/ml in two-fold dilution steps.

Selective inhibitory activity for small molecules on the wildtype Wnt pathway was determined after parallel incubation of both (TOP and FOP) HEK293 reporter cell lines with a compound dilution series from 50 μM to 15 nM in steps of 3.16-fold dilutions in CAFTY buffer (130 mM sodium chloride, 5 mM potassium chloride, 20 mM HEPES, 1 mM magnesium chloride, 5 mM sodium bicarbonate, pH 7.4) containing 2 mM $Ca^{2+}$ and 0.01% BSA.

The compounds were thereby serially prediluted in 100% DMSO and thereafter 50 fold into the CAFTY compound dilution buffer (described above). From this dilution 10 μl were added in combination with the EC50 concentration of recombinant Wnt3a to the cells in 30 μl growth medium and incubated for 16 hours at 37° C. and 5% $CO_2$. Thereafter luciferase assay buffer (1:1 mixture of luciferase substrate buffer (20 mM Tricine, 2.67 mM magnesium sulfate, 0.1 mM EDTA, 4 mM DTT, 270 μM Coenzyme A, 470 μM Luciferin, 530 μM ATP, ph adjusted to pH 7.8 with a sufficient volume of 5M sodium hydroxide) and Triton buffer (30 ml Triton X-100, 115 ml glycerol, 308 mg Dithiothreitol, 4.45 g disodium hydrogen phosphate $2H_2O$, 3.03 g Tris.HCL, ad 1 l $H_2O$, pH 7.8) was added in an equal volume to determine luciferase expression as a measure of Wnt signaling activity in a luminometer. The Wnt inhibitory activity was determined as IC50 of resulting dose response curves.

TABLE $IC_{50}$ values of selected examples in HEK293 TOP Assay

| Example | HEK293 TOP $IC_{50}$ [μM] |
|---|---|
| 1 | 1.1 |
| 2 | 6.1 |
| 3 | 9.7 |
| 4 | 0.91 |
| 5 | 0.24 |
| 6 | 0.23 |
| 7 | 5.65 |
| 8 | 4.6 |
| 9 | 0.15 |
| 10 | 0.18 |
| 11 | 0.73 |
| 12 | 0.15 |
| 13 | 0.13 |
| 14 | 11.5 |
| 15 | 1.25 |
| 16 | 0.18 |
| 17 | 3.55 |
| 18 | 0.34 |
| 19 | 1.25 |
| 20 | 3.35 |
| 21 | 12.0 |
| 22 | 0.13 |
| 23 | 0.66 |
| 24 | 2.05 |
| 25 | 0.72 |
| 26 | 0.8 |
| 27 | 0.34 |
| 28 | 0.68 |
| 29 | 3.92 |
| 30 | 0.16 |
| 31 | 1.6 |
| 32 | 0.02 |
| 33 | 0.63 |
| 34 | 12.0 |
| 35 | 0.76 |
| 36 | 6.15 |
| 37 | 0.33 |
| 38 | 2.3 |
| 39 | 1.7 |
| 40 | 12.0 |

TABLE $IC_{50}$ values of selected examples in HEK293 FOP Assay

| Example | HEK293 FOP $IC_{50}$ [μM] |
|---|---|
| 1 | 25.0 |
| 2 | 50.0 |
| 3 | 50.0 |
| 4 | 42.0 |
| 5 | 11.0 |
| 6 | 50.0 |
| 7 | 45.0 |
| 8 | 50.0 |
| 9 | 40.0 |
| 10 | 50.0 |
| 11 | 50.0 |
| 12 | 50.0 |
| 13 | 25.0 |
| 14 | 50.0 |
| 15 | 50.0 |
| 16 | 50.0 |
| 17 | 26.0 |
| 18 | 50.0 |
| 19 | 11.0 |
| 20 | 31.0 |
| 21 | 35.0 |
| 22 | 50.0 |
| 23 | 50.0 |
| 24 | 50.0 |
| 25 | 34.0 |
| 26 | 50.0 |
| 27 | 50.0 |
| 28 | 42.0 |
| 29 | 50.0 |
| 30 | 37.5 |
| 31 | 50.0 |
| 32 | 42.0 |
| 33 | 50.0 |
| 34 | 50.0 |
| 35 | 50.0 |
| 36 | 50.0 |
| 37 | 20.0 |
| 38 | 14.0 |
| 39 | 5.5 |
| 40 | 50.0 |

TABLE $IC_{50}$ values of selected examples in HEK293 TOP/FOP Assay

| Example | HEK293-TOP $IC_{50}$ [μM] | HEK293-FOP $IC_{50}$ [μM] |
|---|---|---|
| 1 | 1.20 | 24.0 |
| 2 | 7.05 | 50.0 |
| 3 | 9.70 | 50.0 |
| 4 | 0.91 | 42.0 |
| 5 | 0.24 | 11.0 |
| 6 | 0.23 | 50.0 |
| 7 | 5.65 | 45.0 |
| 8 | 4.60 | 50.0 |
| 9 | 0.14 | 31.5 |
| 10 | 0.17 | 46.0 |
| 11 | 0.73 | 50.0 |

TABLE-continued

IC$_{50}$ values of selected examples in HEK293 TOP/FOP Assay

| Example | HEK293-TOP IC$_{50}$ [μM] | HEK293-FOP IC$_{50}$ [μM] |
|---|---|---|
| 12 | 0.14 | 50.0 |
| 13 | 0.13 | 25.0 |
| 14 | 9.35 | 50.0 |
| 15 | 1.25 | 50.0 |
| 16 | 0.18 | 50.0 |
| 17 | 3.55 | 26.0 |
| 18 | 0.41 | 50.0 |
| 19 | 1.15 | 26.5 |
| 20 | 11.2 | 40.5 |
| 21 | 12.0 | 35.0 |
| 22 | 0.14 | 50.0 |
| 23 | 0.66 | 50.0 |
| 24 | 2.13 | 50.0 |
| 25 | 0.72 | 34.0 |
| 26 | 1.35 | 50.0 |
| 27 | 0.39 | 50.0 |
| 28 | 0.53 | 36.0 |
| 29 | 3.93 | 50.0 |
| 30 | 0.19 | 50.0 |
| 31 | 1.60 | 50.0 |
| 32 | 0.02 | 30.0 |
| 33 | 0.45 | 50.0 |
| 34 | 12.0 | 50.0 |
| 35 | 0.76 | 50.0 |
| 36 | 6.15 | 50.0 |
| 37 | 0.33 | 20.0 |
| 38 | 2.30 | 14.0 |
| 39 | 1.70 | 5.5 |
| 40 | 12.0 | 50.0 |
| 41 | 0.09 | 50.0 |
| 42 | 2.30 | 50.0 |
| 43 | 0.53 | 50.0 |
| 45 | 0.19 | 40.0 |
| 46 | 0.29 | 12.0 |
| 47 | 0.34 | 50.0 |
| 48 | 2.65 | 17.0 |
| 49 | 0.35 | 17.0 |
| 50 | 0.12 | 13.0 |
| 51 | 0.14 | 50.0 |
| 52 | 0.61 | 50.0 |
| 53 | 0.04 | 50.0 |
| 54 | 1.45 | 50.0 |
| 55 | 0.27 | 50.0 |
| 56 | 0.12 | 10.0 |
| 57 | 33.0 | 50.0 |
| 58 | 3.35 | 29.0 |
| 59 | 6.58 | 50.0 |
| 60 | 15.5 | 9.75 |
| 61 | 0.10 | 50.0 |
| 62 | 0.01 | 24.0 |
| 63 | 0.11 | 11.0 |
| 64 | 1.45 | 50.0 |
| 65 | 0.80 | 9.50 |
| 66 | 0.31 | 6.20 |
| 67 | 0.07 | 13.0 |
| 68 | 2.15 | 50.0 |
| 69 | 0.19 | 50.0 |
| 70 | 0.13 | 50.0 |
| 71 | 0.34 | 50.0 |
| 72 | 0.49 | 50.0 |
| 73 | 0.36 | 33.0 |
| 74 | 0.07 | 14.0 |
| 75 | 13.0 | 50.0 |
| 76 | 12.0 | 7.40 |
| 77 | 4.40 | 50.0 |
| 78 | 0.28 | 50.0 |
| 79 | 0.51 | 8.20 |
| 80 | 0.82 | 50.0 |
| 81 | 0.66 | 50.0 |
| 82 | 0.09 | 44.0 |
| 83 | 0.39 | 29.0 |
| 84 | 0.62 | 50.0 |
| 85 | 0.16 | 50.0 |
| 86 | 0.42 | 23.0 |
| 87 | 1.25 | 28.0 |
| 88 | 2.40 | 50.0 |
| 89 | 0.60 | 50.0 |
| 90 | 4.90 | 13.0 |
| 91 | 44.5 | 50.0 |
| 92 | 6.95 | 13.0 |
| 93 | 2.65 | 50.0 |
| 94 | 0.83 | 50.0 |
| 95 | 0.27 | 50.0 |
| 96 | 0.31 | 50.0 |
| 97 | 0.08 | 29.0 |
| 98 | 1.15 | 50.0 |
| 99 | 0.54 | 50.0 |
| 100 | 0.79 | 50.0 |
| 101 | 0.22 | 29.0 |
| 102 | 50.0 | 50.0 |
| 103 | 38.0 | 50.0 |
| 104 | 7.20 | 50.0 |
| 105 | 1.65 | 29.0 |
| 106 | 27.0 | 13.0 |
| 107 | 7.25 | 39.0 |
| 108 | 5.00 | 50.0 |
| 109 | 0.14 | 43.0 |
| 110 | 0.06 | 50.0 |
| 111 | 0.77 | 50.0 |
| 112 | 2.55 | 50.0 |
| 113 | 0.46 | 50.0 |
| 114 | 0.07 | 50.0 |
| 115 | 3.55 | 50.0 |
| 116 | 44.0 | 50.0 |
| 117 | 40.0 | 50.0 |
| 118 | 0.62 | 50.0 |
| 119 | 0.07 | 20.0 |
| 120 | 1.20 | 50.0 |
| 121 | 0.27 | 50.0 |
| 122 | 0.28 | 50.0 |
| 123 | 0.74 | 50.0 |
| 124 | 50.0 | 50.0 |
| 125 | 4.10 | 15.0 |
| 126 | 0.04 | 27.0 |
| 127 | 0.01 | 50.0 |
| 128 | 0.26 | 50.0 |
| 129 | 6.75 | 15.0 |
| 130 | 0.25 | 50.0 |
| 131 | 9.20 | 50.0 |
| 132 | 0.14 | 50.0 |
| 133 | 0.43 | 8.70 |
| 134 | 0.64 | 6.30 |
| 135 | 7.25 | 22.0 |
| 136 | 2.40 | 50.0 |
| 137 | 2.35 | 8.00 |
| 138 | 0.26 | 50.0 |
| 139 | 0.36 | 50.0 |
| 140 | 5.70 | 50.0 |
| 141 | 3.00 | 50.0 |
| 142 | 0.12 | 50.0 |
| 143 | 29.5 | 50.0 |
| 144 | 50.0 | 50.0 |
| 145 | 0.29 | 50.0 |
| 146 | 5.15 | 50.0 |
| 147 | 0.32 | 6.00 |
| 148 | 1.75 | 16.0 |
| 149 | 5.20 | 22.0 |
| 150 | 50.0 | 50.0 |
| 151 | 0.95 | 50.0 |
| 152 | 0.46 | 30.0 |
| 153 | 0.19 | 35.0 |
| 154 | 1.25 | 50.0 |
| 155 | 0.66 | 50.0 |
| 156 | 2.50 | 15.0 |
| 157 | 8.40 | 50.0 |
| 158 | 1.20 | 29.0 |
| 159 | 0.09 | 50.0 |
| 160 | 0.58 | 50.0 |
| 161 | 36.5 | 50.0 |
| 162 | 0.27 | 50.0 |

TABLE-continued

IC$_{50}$ values of selected examples in HEK293 TOP/FOP Assay

| Example | HEK293-TOP IC$_{50}$ [μM] | HEK293-FOP IC$_{50}$ [μM] |
|---|---|---|
| 163 | 0.10 | 37.0 |
| 164 | 0.91 | 50.0 |
| 165 | 0.29 | 31.0 |
| 166 | 0.53 | 50.0 |
| 167 | 1.45 | 44.0 |
| 168 | 0.08 | 27.0 |
| 169 | 0.80 | 50.0 |
| 170 | 0.18 | 50.0 |
| 171 | 0.67 | 6.5 |
| 172 | 2.25 | 50.0 |
| 173 | 0.27 | 50.0 |
| 174 | 1.05 | 50.0 |
| 175 | 3.50 | 27.0 |
| 176 | 0.34 | 50.0 |
| 177 | 0.63 | 17.0 |
| 178 | 1.17 | 50.0 |
| 180 | 5.35 | 37.0 |
| 181 | 6.70 | 50.0 |
| 182 | 0.64 | 50.0 |
| 183 | 0.68 | 28.0 |
| 184 | 0.82 | 50.0 |
| 185 | 0.20 | 50.0 |
| 186 | 0.42 | 28.0 |
| 187 | 0.35 | 28.0 |
| 188 | 5.90 | 15.0 |
| 189 | 0.89 | 28.0 |
| 190 | 0.19 | 18.0 |
| 191 | 0.04 | 31.0 |
| 192 | 0.46 | 50.0 |
| 193 | 5.70 | 50.0 |
| 194 | 0.41 | 2.30 |
| 195 | 1.01 | 12.0 |
| 196 | 0.65 | 30.0 |
| 197 | 0.14 | 50.0 |
| 198 | 0.11 | 50.0 |
| 199 | 1.03 | 50.0 |
| 200 | 0.87 | 20.0 |
| 201 | 4.50 | 0.03 |
| 202 | 1.60 | 9.80 |
| 203 | 3.05 | 28.0 |
| 204 | 0.31 | 34.5 |
| 205 | 2.65 | 50.0 |
| 206 | 2.10 | 50.0 |
| 207 | 0.71 | 50.0 |
| 208 | 0.03 | 23.0 |
| 209 | 0.85 | 22.0 |
| 210 | 0.13 | 24.0 |
| 211 | 0.77 | 24.0 |
| 212 | 0.07 | 50.0 |
| 213 | 0.46 | 8.40 |
| 214 | 1.25 | 22.0 |
| 215 | 0.40 | 29.5 |
| 216 | 0.02 | 11.0 |
| 217 | 0.12 | 50.0 |
| 218 | 1.61 | 31.5 |
| 219 | 7.50 | 50.0 |
| 220 | 0.69 | 36.0 |
| 221 | 0.82 | 12.0 |
| 222 | 0.67 | 23.0 |
| 223 | 0.33 | 50.0 |
| 224 | 1.25 | 27.0 |
| 225 | 0.80 | 44.0 |
| 226 | 0.05 | 50.0 |
| 227 | 0.12 | 23.0 |
| 228 | 0.03 | 50.0 |
| 229 | 0.11 | 44.5 |
| 230 | 0.20 | 27.0 |
| 231 | 0.07 | 50.0 |
| 232 | 0.22 | 35.0 |
| 233 | 0.45 | 50.0 |
| 234 | 0.46 | 16.0 |
| 235 | 0.24 | 50.0 |
| 236 | 0.42 | 34.0 |
| 237 | 0.43 | 50.0 |
| 238 | 0.18 | 29.0 |
| 239 | 46.5 | 50.0 |
| 240 | 0.08 | 50.0 |
| 241 | 1.90 | 50.0 |
| 242 | 0.08 | 50.0 |
| 243 | 11.5 | 50.0 |
| 244 | 0.17 | 50.0 |
| 245 | 50.0 | 50.0 |
| 246 | 0.20 | 50.0 |
| 247 | 0.40 | 35.0 |
| 248 | 0.85 | 50.0 |
| 249 | 2.40 | 50.0 |
| 250 | 0.92 | 50.0 |
| 251 | 7.90 | 50.0 |
| 252 | 4.05 | 50.0 |
| 253 | 12.0 | 50.0 |
| 254 | 0.75 | 50.0 |
| 255 | 1.24 | 50.0 |
| 256 | 0.90 | 50.0 |
| 257 | 2.60 | 50.0 |
| 258 | 4.50 | 50.0 |
| 259 | 0.88 | 33.0 |
| 260 | 2.10 | 50.0 |
| 261 | 22.2 | 50.0 |
| 262 | 8.70 | 50.0 |
| 263 | 0.36 | 27.5 |
| 264 | 1.60 | 16.0 |
| 265 | 0.12 | 50.0 |
| 266 | 0.03 | 20.0 |
| 267 | 0.02 | 20.0 |
| 268 | 0.06 | 41.0 |
| 269 | 0.44 | 50.0 |
| 270 | 0.04 | 50.0 |
| 271 | 0.03 | 50.0 |
| 272 | 0.12 | 50.0 |
| 273 | 1.55 | 21.0 |
| 274 | 0.29 | 45.0 |
| 275 | 0.47 | 9.60 |
| 276 | 0.11 | 31.0 |
| 277 | 0.12 | 36.0 |
| 278 | 0.09 | 25.0 |
| 279 | 0.91 | 12.0 |
| 280 | 1.05 | 50.0 |
| 281 | 1.20 | 50.0 |
| 282 | 0.97 | 50.0 |
| 283 | 0.84 | 50.0 |
| 284 | 0.68 | 50.0 |
| 285 | 1.15 | 50.0 |
| 286 | 0.46 | 50.0 |
| 287 | 0.75 | 50.0 |
| 288 | 0.99 | 50.0 |
| 289 | 2.70 | 50.0 |
| 290 | 0.71 | 50.0 |
| 291 | 14.3 | 50.0 |
| 292 | 11.0 | 50.0 |
| 293 | 0.57 | 50.0 |
| 294 | 1.55 | 50.0 |
| 295 | 0.69 | 50.0 |
| 296 | 6.45 | 50.0 |
| 297 | 1.05 | 22.5 |
| 298 | 0.30 | 17.0 |
| 299 | 0.74 | 43.0 |
| 300 | 0.56 | 31.0 |
| 301 | 1.20 | 50.0 |
| 302 | 1.06 | 26.0 |
| 303 | 0.14 | 8.10 |
| 304 | 11.4 | 50.0 |
| 305 | 31.5 | 50.0 |
| 306 | 3.15 | 50.0 |
| 307 | 1.08 | 18.0 |
| 308 | 3.35 | 50.0 |
| 309 | 0.24 | 38.0 |
| 310 | 10.5 | 50.0 |
| 311 | 50.0 | 50.0 |
| 312 | 50.0 | 50.0 |
| 313 | 0.41 | 25.0 |

TABLE-continued

IC$_{50}$ values of selected examples in HEK293 TOP/FOP Assay

| Example | HEK293-TOP IC$_{50}$ [μM] | HEK293-FOP IC$_{50}$ [μM] |
|---|---|---|
| 314 | 6.90 | 24.0 |
| 315 | 14.0 | 41.0 |
| 316 | 13.5 | 50.0 |
| 317 | 50.0 | 50.0 |
| 318 | 1.30 | 50.0 |
| 319 | 8.90 | 37.0 |
| 320 | 4.80 | 50.0 |
| 321 | 50.0 | 50.0 |
| 322 | 2.30 | 50.0 |
| 323 | 1.45 | 50.0 |
| 324 | 3.20 | 50.0 |
| 325 | 4.90 | 10.0 |
| 326 | 3.00 | 50.0 |
| 327 | 39.5 | 37.0 |
| 328 | 5.25 | 50.0 |
| 329 | 50.0 | 50.0 |
| 331 | 8.60 | 50.0 |
| 332 | 9.65 | 50.0 |
| 333 | 0.95 | 40.0 |
| 334 | 0.86 | 50.0 |
| 335 | 21.5 | 50.0 |
| 336 | 11.0 | 50.0 |
| 337 | 23.5 | 50.0 |
| 338 | 2.80 | 50.0 |
| 339 | 45.5 | 50.0 |
| 340 | 3.85 | 50.0 |
| 341 | 2.65 | 45.0 |
| 342 | 0.80 | 50.0 |
| 343 | 1.45 | 50.0 |
| 344 | 27.0 | 50.0 |
| 345 | 50.0 | 50.0 |
| 346 | 0.90 | 26.0 |
| 347 | 34.5 | 50.0 |
| 348 | 7.05 | 50.0 |
| 349 | 0.72 | 50.0 |
| 350 | 6.50 | 50.0 |
| 351 | 12.5 | 50.0 |
| 352 | 0.71 | 50.0 |
| 353 | 50.0 | 50.0 |
| 354 | 50.0 | 50.0 |
| 355 | 25.0 | 50.0 |
| 356 | 0.72 | 50.0 |
| 357 | 11.2 | 50.0 |
| 358 | 4.10 | 50.0 |
| 359 | 8.60 | 50.0 |
| 360 | 15.2 | 50.0 |
| 361 | 0.26 | 50.0 |
| 362 | 50.0 | 50.0 |
| 363 | 50.0 | 50.0 |
| 364 | 50.0 | 50.0 |
| 365 | 50.0 | 50.0 |
| 366 | 50.0 | 50.0 |
| 367 | 12.4 | 50.0 |
| 369 | 0.75 | 50.0 |
| 370 | 4.95 | 50.0 |
| 371 | 50.0 | 50.0 |
| 372 | 9.70 | 50.0 |
| 373 | 4.20 | 50.0 |
| 374 | 1.80 | 50.0 |
| 375 | 1.12 | 50.0 |
| 376 | 50.0 | 50.0 |
| 377 | 0.95 | 50.0 |
| 378 | 0.23 | 27.0 |
| 379 | 3.20 | 50.0 |
| 380 | 0.47 | 24.0 |
| 381 | 0.08 | 50.0 |
| 382 | 0.12 | 50.0 |
| 383 | 50.0 | 50.0 |
| 384 | 1.90 | 50.0 |
| 385 | 0.31 | 50.0 |
| 386 | 0.46 | 15.0 |
| 387 | 0.80 | 50.0 |
| 388 | 0.44 | 17.0 |
| 389 | 0.75 | 11.0 |
| 390 | 0.25 | 18.0 |
| 391 | 0.67 | 27.0 |
| 392 | 0.16 | 18.0 |
| 393 | 0.88 | 50.0 |
| 394 | 0.70 | 50.0 |
| 396 | 0.34 | 25.0 |
| 397 | 0.46 | 50.0 |
| 398 | 0.71 | 50.0 |
| 399 | 1.20 | 50.0 |
| 400 | 0.36 | 13.0 |
| 401 | 0.33 | 21.0 |
| 402 | 0.17 | 50.0 |
| 404 | 0.09 | 29.0 |
| 405 | 0.71 | 50.0 |
| 406 | 0.35 | 26.0 |
| 407 | 0.23 | 50.0 |
| 408 | 0.30 | 50.0 |
| 409 | 0.19 | 32.0 |
| 410 | 0.11 | 18.0 |
| 411 | 0.29 | 50.0 |
| 412 | 0.14 | 50.0 |
| 413 | 0.70 | 26.0 |
| 414 | 0.27 | 33.0 |
| 415 | 0.56 | 7.80 |

7.2 Axin Stabilization Assay

The in vitro and in vivo effect of Tankyrase inhibition on the stabilization of cellular Axin was assessed using Peggy Simple Western assay with size-based separation and immunodetection of Axin2. 5W403 cells (but not limited to) were seeded at 50000 cells per well in 96-well plates. After overnight incubation, cells were treated with testing compounds and vehicle at 37° C. for 24 hours. Thereafter, cells were washed with PBS and then lysed in 15 μL of lysis buffer (M-PER buffer, Thermo Scientific #78505) with complete proteinase and phosphatase inhibitors (Roche, #11836153001 and #04906837001). The lysates were centrifuged and the supernatants were harvested for analysis. Tumor xenografts from in vivo studies were homogenized in a 2 mL tubes of Precellys®24 (Bertin Technologies, Villeurbanne, France) following with centrifugation to obtain tumor lysates. Capillary electrophoresis-based Simple Western assays were carried out with Peggy Sue™ NanoPro 1000 (ProteinSimple, California, USA). The protein amounts of Axin2 (but not limited to) were detected using anti-Axin2 antibody (Cell Signaling, Catalog #2151), quantified using the area under the curve, and normalized against GAPDH (anti-GAPDH, Zytomed Systems GmbH, Catalog #RGM2-6C5, Berlin, Germany).

7.3 Real-Time RT-PCR for Quantitative Analysis of Gene Transcription

Real-time RT-PCR using a TaqMan fluorogenic detection system is a simple and sensitive assay for quantitative analysis of gene transcription. The TaqMan fluorogenic detection system can monitor PCR in real time using a dual-labeled fluorogenic hybridization probe (TaqMan probe) and a polymerase with 5'-3' exonuclease activity.

Cells from different cancer cell lines (as HCT116, but not limited to) were grown at 500-1000 cells/well in 384 well cell culture plates. For cell lysis the cell medium was carefully removed. The cells were washed carefully once with 50 μl/well PBS. Then 9.75 μl/well cell lysis buffer (50 mM Tris HCl pH 8.0, 40 mM sodium chloride, 1.5 mM magnesium chloride, 0.5% IGEPAL CA 630, 50 mM Guanidium thiocyanate) and 0.25 μl RNASeOUT (40 U/μl, Invitrogen, 10777-019)) per well were added. The plate was incubated for 5 min at room temperature. Then 30 µl DNAse/RNAse-free water per well was added and the lysates mixed. Isolation of total RNA from tumor tissues was conducted using InviTrape Spin Tissue RNA Mini Kit (#1062100300, STRATEC MOLECULAR).

For the One-Step RT-PCR 2 µl lysate (each) was transferred to a 384 well PCR plate. The PCR reaction was composed by 5 µl 2× One Step RT qPCR MasterMix Plus, 0.05 µl Euroscript RT/RNAse Inhibitor (50 U/µl, 20 U/µl) and 200 nM of the appropriate Primer/Hydrolysis Probe mix (primer sequences of forward, reverse and probe are given below for each analysed gene of interest or house keeping gene). 10 µl water were added per well. The plate was sealed with an adhesive optical film. The RT-PCR protocol was setup with 30 min 48° C., then 10 min 95° C. followed by 50 cycles of 15 sec 95° C./1 min 60° C. and a cooling step of 40° C. for 30 sec using a Lightcycler LS440 from Roche. Relative expression was calculated using CP values from the gene of interest (e.g. AXIN2, but not limited to) and a house keeping gene (L32).
Used Primers

```
L32 (forward primer: AAGTTCATCCGGCACCAGTC
(SEQ ID NO. 1); reverse primer: TGGCCCTTGAATCTTCTA
CGA (SEQ ID NO. 2); probe: CCCAGAGGCATTGACAACAGGG
(SEQ ID NO. 3))
AXIN2 (forward primer: AGGCCAGTGAGTTGGTTGTC
(SEQ ID NO. 4); reverse primer: AGCTCTGAGCCTTCAGCA
TC (SEQ ID NO. 5); probe: TCTGTGGGGAAGAAATTCCATACC
G (SEQ ID NO. 6))
```

8 IN VIVO EFFICACY IN XENOGRAFT MODELS

Subcutaneous xenograft models in immunocompromised mice were used to evaluate in vivo anti-tumor efficacy of the compounds.

8.1 Maximum Tolerable Dose (MTD) Studies

Prior to efficacy studies, the maximal tolerable dose (MTD) was determined by the following protocol: Female nude mice (NMRI (nu/nu), Taconic M&B A/S) received a defined oral dose of the test compound daily or bi-daily for 7 consecutive days followed by a 7 day observation period without dosing. Individual body weight and lethality were monitored daily.

The MTD is defined as the maximal applicable dose with a) no animal losing more than 10% body weight compared to initial body weight and b) no lethality during treatment phase.

8.2 In Vivo Efficacy Studies

To measure anti-tumor efficacy, the test compounds were analysed in xenograft models on mice. Test compounds were dosed orally at their respective MTD as well as at sub-MTD dosages. In case the MTD could not be determined in previous MTD studies, the compounds were dosed at a maximum daily dose of 200 mg/kg (applied either in one single dose or split in 2 doses at 100 mg/kg).

Compounds were primarily analyzed in an ovarian teratocarcinoma model (PA-1) and in various colorectal cancer models on female immunocompromised mice.

For this purpose, $1-5\times10^6$ tumor cells (suspended in 0.1 ml of 50% cell culture medium/50% Matrigel) were subcutaneously injected into the flank of each animal. Animals were randomized into treatment groups when tumors had reached an average area of 20-30 mm$^2$ and treatment was started. Body weight and tumor area of each animal were measured 2-3 times weekly, depending on tumor growth. Studies were terminated, when animals in the control groups (receiving only compound vehicle solutions) or treatment groups reached tumor areas ~150 mm$^2$. At that time point, all groups in the study were terminated, tumors were isolated and weighed.

As primary parameter for anti-tumor efficacy the Treatment/Control (T/C) ratio of the final tumor weights were calculated (mean tumor weight of treatment group divided by mean tumor weight of vehicle group).

8.3 In Vivo Mode of Action Studies

To determine in vivo Mode of Action (MoA) of the test compounds, the same in vivo models as described under 8.2 were utilized. Tumor-bearing animals were treated for at least 3 days at MTD and also sub-MTD dosages. At study end, tumors were isolated and snap frozen in liquid N2. Total RNA and protein were isolated from tumor samples following standard protocols.

Wnt/β-catenin target gene expression and Axin2 protein abundance were measured by standard qRT-PCR and Western blotting methods (see 7.2 and 7.3).

The invention claimed is:

1. A compound of formula (I)

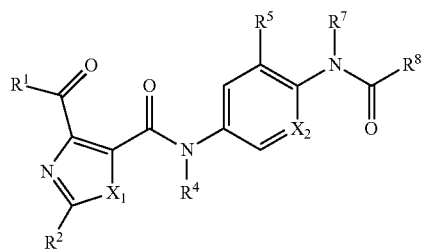

wherein:
$X_1$ is $NR^3$ or O;
$X_2$ is $CR^6$ or N;
$R^1$ is a group selected from:
—$OR^9$ and —$N(R^{10})R^{11}$;
$R^2$ is a group selected from:
hydrogen, $C_1$-$C_3$-alkyl, and $C_3$-$C_4$-cycloalkyl;
$R^3$ is a hydrogen atom;
$R^4$ is a hydrogen atom;
$R^5$ is a group selected from:
hydrogen, $C_1$-$C_3$-alkyl, $C_1$-$C_3$-alkoxy, $C_1$-$C_3$-haloalkyl, $C_1$-$C_3$-haloalkoxy, and halogen;
$R^6$ is a group selected from:
hydrogen and halogen;
$R^7$ is a hydrogen atom;
$R^8$ is a group selected from:
aryl and heteroaryl,
wherein said aryl and heteroaryl groups are optionally substituted with one, two, or three substituents, which are independently selected from:
$C_1$-$C_6$-alkyl, $C_1$-$C_3$-alkoxy, $C_3$-$C_6$-cycloalkyl, $C_3$-$C_6$-cycloalkoxy, $C_1$-$C_3$-haloalkyl, $C_1$-$C_3$-haloalkoxy, halogen, cyano, nitro, hydroxy, ($C_1$-$C_6$-alkyl)-S—, ($C_1$-$C_6$-alkyl)-S(=O)—, ($C_1$-$C_6$-alkyl)-S(=O)$_2$—, —S(=O)(=$NR^{15}$)$R^{16}$, —N($R^{10}$)$R^{11}$, $R^{10}$($R^{11}$)N—($C_1$-$C_6$-alkyl)-, $R^{10}$($R^{11}$)N—($C_2$-$C_6$-alkoxy)-, phenyl, phenoxy, —N($R^{12}$)C(=O)$R^{13}$, —C(=O)OH, —C(=O)$OR^9$, and —C(=O)N($R^{12}$)$_2$,
wherein two substituents of said aryl group, when positioned ortho to each other, are optionally linked to one another to form methanediylbisoxy, ethane-1,2-diylbisoxy, propane-1,3-diyl, or butane-1,4-diyl;
$R^9$ is a group selected from:
$C_1$-$C_6$-alkyl, $C_3$-$C_6$-cycloalkyl, $C_2$-$C_6$-hydroxyalkyl-, and ($C_1$-$C_3$-alkoxy)-($C_1$-$C_6$-alkyl)-;
$R^{10}$ and $R^{11}$ are independently selected from:
hydrogen, $C_1$-$C_6$-alkyl, $C_3$-$C_6$-cycloalkyl, ($C_3$-$C_6$-cycloalkyl)-($C_1$-$C_6$-alkyl)-, $C_2$-$C_6$-hydroxyalkyl, ($C_1$-$C_3$-alkoxy)-($C_2$-$C_6$-alkyl)-, $C_1$-$C_6$-haloalkyl, $H_2N$—($C_2$-$C_6$-alkyl)-, ($C_1$-$C_3$-alkyl)N(H)($C_2$-$C_6$-alkyl)-, ($C_1$-$C_3$-alkyl)$_2$N($C_2$-$C_6$-alkyl)-, HOC(=O)—($C_1$-

$C_6$-alkyl)-, $R^9OC(=O)$—$(C_1$-$C_6$-alkyl)-, 4-6 membered heterocycloalkyl, (4-6 membered heterocycloalkyl)-$(C_2$-$C_6$-alkyl)-, aryl, heteroaryl, aryl-$(C_1$-$C_6$-alkyl)-, and heteroaryl-$(C_1$-$C_6$-alkyl)-, wherein said 4-6-membered heterocycloalkyl groups are optionally substituted with one or two substituents, which are independently selected from:

$C_1$-$C_3$-alkyl, $C_1$-$C_3$-haloalkyl, $C_1$-$C_3$-alkoxy, $C_1$-$C_3$-haloalkoxy, $C_3$-$C_4$-cycloalkyl, $C_3$-$C_4$-cycloalkoxy, amino, hydroxy, halogen, and cyano, and wherein said aryl and heteroaryl groups are optionally substituted with one or two substituents, which are independently selected from:

$C_1$-$C_3$-alkyl, $C_3$-$C_6$-cycloalkyl, $C_1$-$C_3$-alkoxy, $C_3$-$C_6$-cycloalkoxy, $C_1$-$C_3$-haloalkyl, $C_1$-$C_3$-haloalkoxy, halogen, cyano, —C(=O)OH, —C(=O)OR$^9$, and —C(=O)N(R$^{12}$)$_2$;

or $R^{10}$ and $R^{11}$ are taken together with the nitrogen atom to which they are attached to form a 4-6-membered heterocycloalkyl group, wherein one carbon atom of said 4-6 membered heterocycloalkyl group is optionally replaced by an additional heteroatom-containing group selected from NR$^{14}$, O, S, S(=O), and S(=O)$_2$, and wherein one additional ring atom is optionally replaced by C(=O), wherein said 4-6-membered heterocycloalkyl group is optionally substituted with one or two substituents, which are independently selected from:

$C_1$-$C_3$-alkyl, $C_1$-$C_3$-haloalkyl, $C_1$-$C_3$-alkoxy, $C_1$-$C_3$-haloalkoxy, $C_3$-$C_4$-cycloalkyl, $C_3$-$C_4$-cycloalkoxy, amino, hydroxy, halogen, and cyano;

or $R^{10}$ and $R^{11}$ are taken together with the nitrogen atom to which they are attached to form a group selected from:

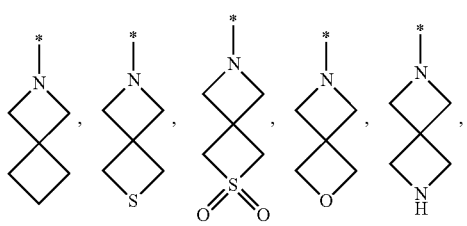

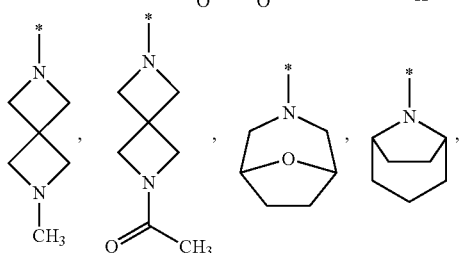

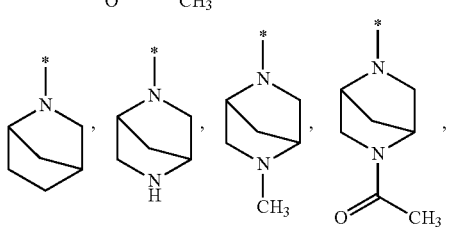

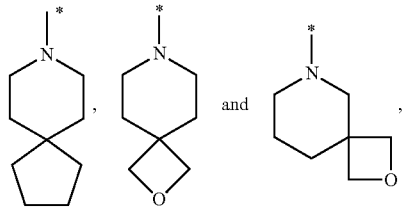

wherein * indicates the point of attachment of said group to the rest of the molecule;

$R^{12}$ is a group selected from:
hydrogen and $C_1$-$C_3$-alkyl;

$R^{13}$ is a group selected from:
hydrogen, $C_1$-$C_6$-alkyl, $C_1$-$C_6$-hydroxyalkyl, $C_3$-$C_6$-cycloalkyl, $C_1$-$C_6$-haloalkyl, $(C_1$-$C_3$-alkoxy)-$(C_1$-$C_6$-alkyl)-, aryl, and heteroaryl, wherein said aryl and heteroaryl groups are optionally substituted with one or two substituents, which are independently selected from:

$C_1$-$C_3$-alkyl, $C_3$-$C_6$-cycloalkyl, $C_1$-$C_3$-alkoxy, $C_3$-$C_6$-cycloalkoxy, $C_1$-$C_3$-haloalkyl, $C_1$-$C_3$-haloalkoxy, halogen, cyano, and hydroxyl;

$R^{14}$ is a group selected from:
hydrogen, $C_1$-$C_3$-alkyl, $C_1$-$C_3$-haloalkyl, and $C_3$-$C_4$-cycloalkyl;

$R^{15}$ is a group selected from:
hydrogen, cyano, $(C_1$-$C_3$-alkyl)-C(=O)—, and $(C_1$-$C_3$-haloalkyl)-C(=O)—; and $R^{16}$ is a group selected from:
$C_1$-$C_4$-alkyl and $C_3$-$C_4$-cycloalkyl, or a stereoisomer, a tautomer, an N-oxide, a hydrate, a solvate, or a salt thereof, or a mixture of any of the foregoing.

2. The compound according to claim 1, wherein:
$X_1$ is NR$^3$ or O;
$X_2$ is CR$^6$ or N;
$R^1$ is a group selected from:
—OR$^9$ and —N(R$^{10}$)R$^{11}$;
$R^2$ is a group selected from:
hydrogen and $C_1$-$C_3$-alkyl;
$R^3$ is a hydrogen atom;
$R^4$ is a hydrogen atom;
$R^5$ is a group selected from:
hydrogen, $C_1$-$C_3$-alkyl, $C_1$-$C_3$-alkoxy, and $C_1$-$C_3$-haloalkoxy;
$R^6$ is a group selected from:
hydrogen and halogen;
$R^7$ is a hydrogen atom;
$R^8$ is a group selected from:
aryl and heteroaryl,
wherein said aryl and heteroaryl groups are optionally substituted with one, two, or three substituents, which are independently selected from:
$C_1$-$C_6$-alkyl, $C_1$-$C_3$-alkoxy, $C_3$-$C_6$-cycloalkyl, $C_3$-$C_6$-cycloalkoxy, $C_1$-$C_3$-haloalkyl, $C_1$-$C_3$-haloalkoxy, halogen, cyano, nitro, hydroxy, $(C_1$-$C_6$-alkyl)-S—, $(C_1$-$C_6$-alkyl)-S(=O)—, $(C_1$-$C_6$-alkyl)-S(=O)$_2$—, —S(=O)(=NR$^{15}$)R$^{16}$, —N(R$^{10}$)R$^{11}$, R$^{10}$(R$^{11}$)N—$(C_1$-$C_6$-alkyl)-, R$^{10}$(R$^{11}$)N—$(C_2$-$C_6$-alkoxy)-, phenyl, phenoxy, —N(R$^{12}$)C(=O)R$^{13}$, —C(=O)OH, —C(=O)OR$^9$, and —C(=O)N(R$^{12}$)$_2$, wherein two substituents of said aryl group, when positioned ortho to each other, are optionally linked to one another to form methanediylbisoxy, ethane-1,2-diylbisoxy, propane-1,3-diyl, or butane-1,4-diyl;

$R^9$ is a group selected from:
  $C_1$-$C_6$-alkyl, $C_3$-$C_6$-cycloalkyl, $C_2$-$C_6$-hydroxyalkyl-, and ($C_1$-$C_3$-alkoxy)-($C_1$-$C_6$-alkyl)-;

$R^{10}$ and $R^{11}$ are independently selected from:
  hydrogen, $C_1$-$C_6$-alkyl, $C_3$-$C_6$-cycloalkyl, ($C_3$-$C_6$-cycloalkyl)-($C_1$-$C_6$-alkyl)-, $C_2$-$C_6$-hydroxyalkyl, ($C_1$-$C_3$-alkoxy)-($C_2$-$C_6$-alkyl)-, $C_1$-$C_6$-haloalkyl, $H_2N$—($C_2$-$C_6$-alkyl)-, ($C_1$-$C_3$-alkyl)N(H)($C_2$-$C_6$-alkyl)-, ($C_1$-$C_3$-alkyl)$_2$N($C_2$-$C_6$-alkyl)-, HOC(=O)—($C_1$-$C_6$-alkyl)-, $R^9$OC(=O)—($C_1$-$C_6$-alkyl)-, 4-6 membered heterocycloalkyl, (4-6 membered heterocycloalkyl)-($C_2$-$C_6$-alkyl)-, aryl, heteroaryl, aryl-($C_1$-$C_6$-alkyl)-, and heteroaryl-($C_1$-$C_6$-alkyl)-,
    wherein said 4-6-membered heterocycloalkyl groups are optionally substituted with one or two substituents, which are independently selected from:
      $C_1$-$C_3$-alkyl, $C_1$-$C_3$-haloalkyl, $C_1$-$C_3$-alkoxy, $C_1$-$C_3$-haloalkoxy, $C_3$-$C_4$-cycloalkyl, $C_3$-$C_4$-cycloalkoxy, amino, hydroxy, halogen, and cyano, and
    wherein said aryl and heteroaryl groups are optionally substituted with one or two substituents, which are independently selected from:
      $C_1$-$C_3$-alkyl, $C_3$-$C_6$-cycloalkyl, $C_1$-$C_3$-alkoxy, $C_3$-$C_6$-cycloalkoxy, $C_1$-$C_3$-haloalkyl, $C_1$-$C_3$-haloalkoxy, halogen, cyano, —C(=O)OH, —C(=O)OR$^9$, and —C(=O)N(R$^{12}$)$_2$;
or
$R^{10}$ and $R^{11}$ are taken together with the nitrogen atom to which they are attached to form a 4-6-membered heterocycloalkyl group, wherein one carbon atom of said 4-6 membered heterocycloalkyl group is optionally replaced by an additional heteroatom-containing group selected from NR$^{14}$, O, S, S(=O), and S(=O)$_2$, and wherein one additional ring atom is optionally replaced by C(=O),
  wherein said 4-6-membered heterocycloalkyl group is optionally substituted with one or two substituents, which are independently selected from:
    $C_1$-$C_3$-alkyl, $C_1$-$C_3$-haloalkyl, $C_1$-$C_3$-alkoxy, $C_1$-$C_3$-haloalkoxy, $C_3$-$C_4$-cycloalkyl, $C_3$-$C_4$-cycloalkoxy, amino, hydroxy, halogen, and cyano;
or
$R^{10}$ and $R^{11}$ are taken together with the nitrogen atom to which they are attached to form a group selected from:

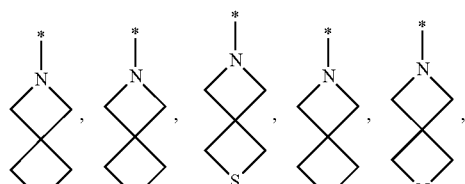

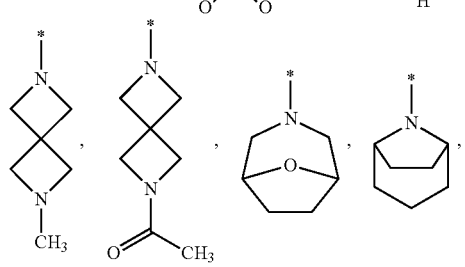

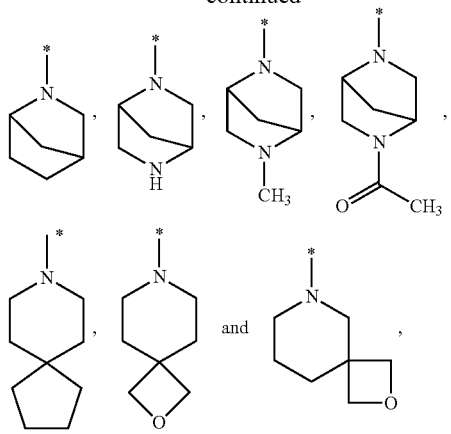

wherein * indicates the point of attachment of said group to the rest of the molecule;

$R^{12}$ is a group selected from:
  hydrogen and $C_1$-$C_3$-alkyl;

$R^{13}$ is a group selected from:
  hydrogen, $C_1$-$C_6$-alkyl, $C_1$-$C_6$-hydroxyalkyl, $C_3$-$C_6$-cycloalkyl, $C_1$-$C_6$-haloalkyl, ($C_1$-$C_3$-alkoxy)-($C_1$-$C_6$-alkyl)-, aryl, and heteroaryl,
    wherein said aryl and heteroaryl groups are optionally substituted with one or two substituents, which are independently selected from:
      $C_1$-$C_3$-alkyl, $C_3$-$C_6$-cycloalkyl, $C_1$-$C_3$-alkoxy, $C_3$-$C_6$-cycloalkoxy, $C_1$-$C_3$-haloalkyl, $C_1$-$C_3$-haloalkoxy, halogen, cyano, and hydroxyl;

$R^{14}$ is a group selected from:
  hydrogen, $C_1$-$C_3$-alkyl, $C_1$-$C_3$-haloalkyl, and $C_3$-$C_4$-cycloalkyl;

$R^{15}$ is a group selected from:
  hydrogen, cyano, ($C_1$-$C_3$-alkyl)-C(=O)—, and ($C_1$-$C_3$-haloalkyl)-C(=O)—; and $R^{16}$ is a group selected from:
  $C_1$-$C_4$-alkyl and $C_3$-$C_4$-cycloalkyl, or a stereoisomer, a tautomer, an N-oxide, a hydrate, a solvate, or a salt thereof, or a mixture of any of the foregoing.

3. The compound according to claim 1, wherein:
$X_1$ is NR$^3$ or O;
$X_2$ is CR$^6$ or N;
$R^1$ is a group selected from:
  —OR$^9$ and —N(R$^{10}$)R$^{11}$;
$R^2$ is a group selected from:
  hydrogen and $C_1$-$C_3$-alkyl;
$R^3$ is a hydrogen atom;
$R^4$ is a hydrogen atom;
$R^5$ is a group selected from:
  hydrogen, $C_1$-$C_3$-alkyl, $C_1$-$C_3$-alkoxy, and $C_1$-$C_3$-haloalkoxy;
$R^6$ is a group selected from:
  hydrogen and halogen;
$R^7$ is a hydrogen atom;
$R^8$ is a group selected from:
  aryl and heteroaryl,
    wherein said aryl and heteroaryl groups are optionally substituted with one, two, or three substituents, which are independently selected from:
      $C_1$-$C_6$-alkyl, $C_1$-$C_3$-alkoxy, $C_3$-$C_6$-cycloalkyl, $C_3$-$C_6$-cycloalkoxy, $C_1$-$C_3$-haloalkyl, $C_1$-$C_3$-haloalkoxy, halogen, cyano, nitro, hydroxy, ($C_1$-$C_6$- alkyl)-S—, ($C_1$-$C_6$-alkyl)-S(=O)—, ($C_1$-$C_6$-alkyl)-S(=O)$_2$—, —S(=O)(=NR$^{15}$)R$^{16}$, —N(R$^{10}$)R$^{11}$, R$^{10}$(R$^{11}$)N—($C_1$-$C_6$-alkyl)-, R$^{10}$(R$^{11}$)N—($C_2$-$C_6$-alkoxy)-, phenyl, phenoxy, —N(R$^{12}$)C(=O)R$^{13}$, —C(=O)OH, —C(=O)OR$^9$, and —C(=O)N(R$^{12}$)$_2$, wherein two substituents of said aryl group, when positioned ortho to each other, are optionally linked to one another to form methanediylbisoxy, ethane-1,2-diylbisoxy, propane-1,3-diyl, or butane-1,4-diyl;

$R^9$ is a $C_1$-$C_6$-alkyl group;

$R^{10}$ and $R^{11}$ are independently selected from:

hydrogen, $C_1$-$C_6$-alkyl, $C_3$-$C_6$-cycloalkyl, ($C_3$-$C_6$-cycloalkyl)-($C_1$-$C_6$-alkyl)-, $C_2$-$C_6$-hydroxyalkyl, ($C_1$-$C_3$-alkoxy)-($C_2$-$C_6$-alkyl)-, $C_1$-$C_6$-haloalkyl, H$_2$N—($C_2$-$C_6$-alkyl)-, ($C_1$-$C_3$-alkyl)N(H)($C_2$-$C_6$-alkyl)-, ($C_1$-$C_3$-alkyl)$_2$N($C_2$-$C_6$-alkyl)-, 4-6 membered heterocycloalkyl, (4-6 membered heterocycloalkyl)-($C_2$-$C_6$-alkyl)-, aryl-($C_1$-$C_6$-alkyl)-, and heteroaryl-($C_1$-$C_6$-alkyl)-, wherein said 4-6-membered heterocycloalkyl groups are optionally substituted with one or two substituents, which are independently selected from:

$C_1$-$C_3$-alkyl, $C_1$-$C_3$-haloalkyl, $C_1$-$C_3$-alkoxy, $C_1$-$C_3$-haloalkoxy, $C_3$-$C_4$-cycloalkyl, $C_3$-$C_4$-cycloalkoxy, amino, hydroxy, halogen, and cyano, and wherein said aryl groups are optionally substituted with one or two substituents, which are independently selected from:

$C_1$-$C_3$-alkyl, $C_3$-$C_6$-cycloalkyl, $C_1$-$C_3$-alkoxy, $C_3$-$C_6$-cycloalkoxy, $C_1$-$C_3$-haloalkyl, $C_1$-$C_3$-haloalkoxy, halogen, cyano, —C(=O)OH, —C(=O)OR$^9$, and —C(=O)N(R$^{12}$)$_2$;

or $R^{10}$ and $R^{11}$ are taken together with the nitrogen atom to which they are attached to form a 4-6-membered heterocycloalkyl group, wherein one carbon atom of said heterocycloalkyl group is optionally replaced by an additional heteroatom-containing group selected from NR$^{14}$, O, S, S(=O), and S(=O)$_2$, and wherein one additional ring atom is optionally replaced by C(=O), wherein said 4-6-membered heterocycloalkyl group is optionally substituted with one or two substituents, which are independently selected from:

$C_1$-$C_3$-alkyl, $C_1$-$C_3$-haloalkyl, $C_1$-$C_3$-alkoxy, $C_1$-$C_3$-haloalkoxy, $C_3$-$C_4$-cycloalkyl, $C_3$-$C_4$-cycloalkoxy, amino, hydroxy, halogen, and cyano;

or $R^{10}$ and $R^{11}$ are taken together with the nitrogen atom to which they are attached to form a group selected from:

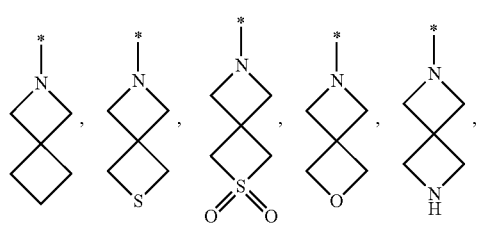

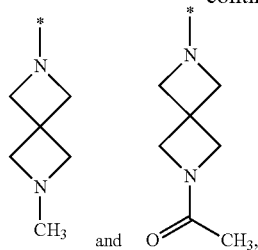

wherein * indicates the point of attachment of said group to the rest of the molecule;

$R^{12}$ is a group selected from:
hydrogen and $C_1$-$C_3$-alkyl;

$R^{13}$ is a group selected from:
hydrogen, $C_1$-$C_6$-alkyl, $C_1$-$C_6$-hydroxyalkyl, $C_3$-$C_6$-cycloalkyl, $C_1$-$C_6$-haloalkyl, ($C_1$-$C_3$-alkoxy)-($C_1$-$C_6$-alkyl)-, aryl, and heteroaryl, wherein said aryl and heteroaryl groups are optionally substituted with one or two substituents, which are independently selected from:
$C_1$-$C_3$-alkyl, $C_3$-$C_6$-cycloalkyl, $C_1$-$C_3$-alkoxy, $C_3$-$C_6$-cycloalkoxy, $C_1$-$C_3$-haloalkyl, $C_1$-$C_3$-haloalkoxy, halogen, cyano, and hydroxyl;

$R^{14}$ is a group selected from:
hydrogen, $C_1$-$C_3$-alkyl, $C_1$-$C_3$-haloalkyl, and $C_3$-$C_4$-cycloalkyl;

$R^{15}$ is a group selected from:
hydrogen, cyano, ($C_1$-$C_3$-alkyl)-C(=O)—, and ($C_1$-$C_3$-haloalkyl)-C(=O)—; and $R^{16}$ is a group selected from:
$C_1$-$C_4$-alkyl and $C_3$-$C_4$-cycloalkyl, or a stereoisomer, a tautomer, an N-oxide, a hydrate, a solvate, or a salt thereof, or a mixture of any of the foregoing.

4. The compound according to claim 1, wherein:

$X_1$ is NR$^3$ or O;
$X_2$ is CR$^6$ or N;
$R^1$ is a group selected from:
—OR$^9$ and —N(R$^{10}$)R$^{11}$;
$R^2$ is a group selected from:
hydrogen and $C_1$-$C_3$-alkyl;
$R^3$ is a hydrogen atom;
$R^4$ is a hydrogen atom;
$R^5$ is a group selected from:
hydrogen, $C_1$-$C_3$-alkyl, $C_1$-$C_3$-alkoxy, and $C_1$-$C_3$-haloalkoxy;
$R^6$ is a group selected from:
hydrogen and halogen;
$R^7$ is a hydrogen atom;
$R^8$ is a group selected from:
aryl and heteroaryl, wherein said aryl and heteroaryl groups are optionally substituted with one, two, or three substituents, which are independently selected from:
$C_1$-$C_6$-alkyl, $C_1$-$C_3$-alkoxy, $C_1$-$C_3$-haloalkyl, $C_1$-$C_3$-haloalkoxy, halogen, cyano, nitro, hydroxy, ($C_1$-$C_6$-alkyl)-S(=O)$_2$—, —S(=O)(=NR$^{15}$)R$^{16}$, —N(R$^{10}$)R$^{11}$, R$^{10}$(R$^{11}$)N—($C_2$-$C_6$-alkoxy)-, phenyl, phenoxy, and —N(R$^{12}$)C(=O)R$^{13}$, wherein two substituents of said aryl group, when positioned ortho to each other, are optionally linked to one another to form methanediylbisoxy, ethane-1,2-diylbisoxy, propane-1,3-diyl, or butane-1,4-diyl;

$R^9$ is a $C_1$-$C_6$-alkyl group;
$R^{10}$ and $R^{11}$ are independently selected from:
hydrogen, $C_1$-$C_6$-alkyl, $C_3$-$C_6$-cycloalkyl, ($C_3$-$C_6$-cycloalkyl)-($C_1$-$C_6$-alkyl)-, $C_2$-$C_6$-hydroxyalkyl, ($C_1$-$C_3$-alkoxy)-($C_2$-$C_6$-alkyl)-, $C_1$-$C_6$-haloalkyl, $H_2N$—($C_2$-$C_6$-alkyl)-, ($C_1$-$C_3$-alkyl)N(H)($C_2$-$C_6$-alkyl)-, ($C_1$-$C_3$-alkyl)$_2$N($C_2$-$C_6$-alkyl)-, 4-6 membered heterocycloalkyl, (4-6 membered heterocycloalkyl)-($C_2$-$C_6$-alkyl)-, aryl-($C_1$-$C_6$-alkyl)-, and heteroaryl-($C_1$-$C_6$-alkyl)-,
wherein said 4-6-membered heterocycloalkyl groups are optionally substituted with one or two substituents, which are independently selected from:
$C_1$-$C_3$-alkyl, $C_1$-$C_3$-haloalkyl, $C_1$-$C_3$-alkoxy, $C_1$-$C_3$-haloalkoxy, $C_3$-$C_4$-cycloalkyl, $C_3$-$C_4$-cycloalkoxy, amino, hydroxy, halogen, and cyano, and
wherein said aryl groups are optionally substituted with one or two substituents, which are independently selected from:
$C_1$-$C_3$-alkyl, $C_3$-$C_6$-cycloalkyl, $C_1$-$C_3$-alkoxy, $C_3$-$C_6$-cycloalkoxy, $C_1$-$C_3$-haloalkyl, $C_1$-$C_3$-haloalkoxy, halogen, cyano, —C(=O)OH, —C(=O)OR$^9$, and —C(=O)N(R$^{12}$)$_2$;
or
$R^{10}$ and $R^{11}$ are taken together with the nitrogen atom to which they are attached to form a 4-6-membered heterocycloalkyl group, wherein one carbon atom of said 4-6 membered heterocycloalkyl group is optionally replaced by an additional heteroatom-containing group selected from NR$^{14}$, O, S, S(=O), and S(=O)$_2$, and wherein one additional ring atom is optionally replaced by C(=O),
wherein said 4-6-membered heterocycloalkyl group is optionally substituted with one or two substituents, which are independently selected from:
$C_1$-$C_3$-alkyl, $C_1$-$C_3$-haloalkyl, $C_1$-$C_3$-alkoxy, $C_1$-$C_3$-haloalkoxy, $C_3$-$C_4$-cycloalkyl, $C_3$-$C_4$-cycloalkoxy, amino, hydroxy, halogen, and cyano;
or
$R^{10}$ and $R^{11}$ are taken together with the nitrogen atom to which they are attached to form a group selected from:

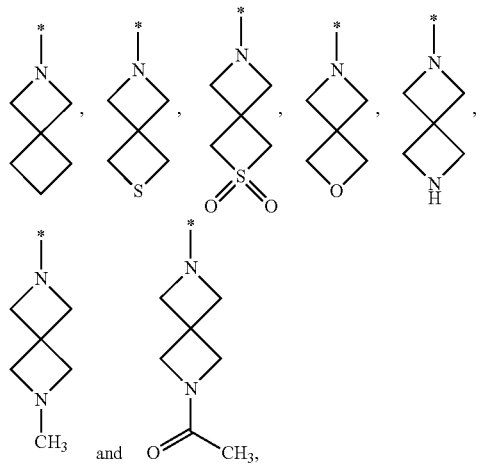

wherein * indicates the point of attachment of said group to the rest of the molecule;
$R^{12}$ is a hydrogen atom;

$R^{13}$ is a group selected from:
hydrogen and $C_1$-$C_6$-alkyl;
$R^{14}$ is a group selected from:
hydrogen, $C_1$-$C_3$-alkyl, $C_1$-$C_3$-haloalkyl, and $C_3$-$C_4$-cycloalkyl;
$R^{15}$ is a group selected from:
hydrogen, cyano, methyl-C(=O)—, and trifluoromethyl-C(=O)—; and
$R^{16}$ is a $C_1$-$C_4$-alkyl group,
or a stereoisomer, a tautomer, an N-oxide, a hydrate, a solvate, or a salt thereof, or a mixture of any of the foregoing.

5. The compound according to claim 1, wherein:
$X_1$ is NR$^3$ or O;
$X_2$ is CR$^6$ or N;
$R^1$ is a group selected from:
—OR$^9$ and —N(R$^{10}$)R$^{11}$;
$R^2$ is a group selected from:
hydrogen and $C_1$-$C_3$-alkyl;
$R^3$ is a hydrogen atom;
$R^4$ is a hydrogen atom;
$R^5$ is a group selected from:
hydrogen, methoxy, trifluoromethoxy, and methyl;
$R^6$ is a hydrogen or a fluorine atom;
$R^7$ is a hydrogen atom;
$R^8$ is a group selected from:
phenyl, pyrazolyl, thienyl, pyridyl, furanyl, thiazolyl, oxazolyl, and pyrazinyl,
each of which is optionally substituted with one, two, or three substituents, which are independently selected from:
$C_1$-$C_5$-alkyl, $C_1$-$C_3$-alkoxy, $C_1$-haloalkyl, $C_1$-haloalkoxy, fluorine, chlorine, bromine, iodine, hydroxy, cyano, nitro, methyl-S(=O)$_2$—, —S(=O)(=NR$^{15}$)R$^{16}$, —N(R$^{10}$)R$^{11}$, R$^{10}$(R$^{11}$)N—(C$_2$-alkoxy)-, phenyl, phenoxy, and —N(R$^{12}$)C(=O)R$^{13}$,
wherein two substituents of said phenyl group, when positioned ortho to each other, are optionally linked to one another to form methanediylbisoxy;
$R^9$ is a $C_1$-$C_2$-alkyl group;
$R^{10}$ and $R^{11}$ are independently:
hydrogen, $C_1$-$C_5$-alkyl, cyclopropyl, ($C_3$-$C_5$-cycloalkyl)-($C_1$-$C_2$-alkyl)-, $C_2$-$C_5$-hydroxyalkyl, ($C_1$-$C_3$-alkoxy)-($C_2$-$C_3$-alkyl)-, $C_1$-$C_2$-haloalkyl, $H_2N$—($C_2$-$C_5$-alkyl)-, ($C_1$-$C_3$-alkyl)N(H)($C_2$-alkyl)-, or ($C_1$-$C_3$-alkyl)$_2$N($C_2$-$C_5$-alkyl)-,
or $R^{10}$ and $R^{11}$ are independently a 4-6-membered heterocycloalkyl group selected from the group consisting of piperazin-1-yl, tetrahydro-2H-pyran-4-yl, tetrahydrofuran-3-yl, pyrrolidin-3-yl, piperidin-4-yl, (piperidin-1-yl)-($C_2$-alkyl)-, (piperidin-1-yl)-($C_3$-$C_4$-alkyl)-, (piperidin-2-yl)-($C_1$-alkyl)-, (piperidin-3-yl)-($C_1$-alkyl)-, (piperidin-4-yl)-($C_1$-alkyl)-, (morpholin-4-yl)-($C_2$-$C_4$-alkyl)-, (piperazin-1-yl)-($C_2$-$C_5$-alkyl)-, (pyrrolidin-1-yl)-($C_2$-$C_5$-alkyl)-, (pyrrolidin-2-yl)-($C_1$-$C_2$-alkyl), (pyrrolidin-3-yl)-($C_1$-alkyl), (azetidin-1-yl)-($C_2$-alkyl), (tetrahydro-2H-pyran-4-yl)-($C_1$-alkyl)-, (tetrahydrofuran-3-yl)-($C_1$-alkyl)-, (tetrahydrofuran-2-yl)-($C_1$-alkyl)-, (2-oxoimidazolidin-1-yl)-($C_2$-alkyl)-, (2-oxopyrrolidin-1-yl)-($C_2$-$C_3$-alkyl)-, (1,1-dioxidothiomorpholin-4-yl)-($C_2$-alkyl)-, phenyl-($C_1$-$C_2$-alkyl)-, and pyridinyl-($C_2$-alkyl),
wherein said 4-6-membered heterocycloalkyl groups are optionally substituted with one or two substituents, which are independently selected from:
$C_1$-$C_2$-alkyl, methoxy, hydroxy, and fluorine;

or

R[10] and R[11] are taken together with the nitrogen atom to which they are attached to form a:

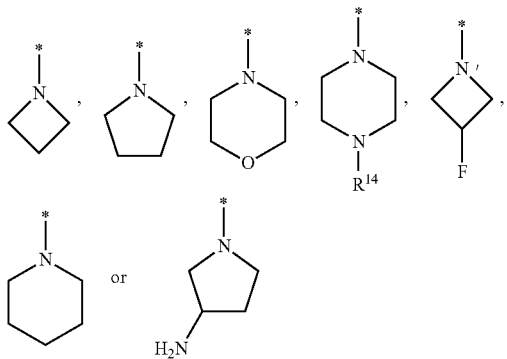

group, wherein * indicates the point of attachment of said group to the rest of the molecule;

or

R[10] and R[11] are taken together with the nitrogen atom to which they are attached to form a:

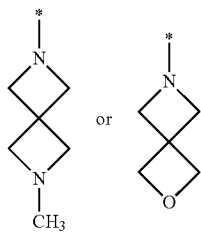

group,
wherein * indicates the point of attachment of said group to the rest of the molecule;

R[12] is a hydrogen atom;
R[13] is a methyl group;
R[14] is hydrogen or a methyl group;
R[15] is a hydrogen atom; and
R[16] is an ethyl group, or a stereoisomer, a tautomer, an N-oxide, a hydrate, a solvate, or a salt thereof, or a mixture of any of the foregoing.

6. The compound according to claim 1, which is selected from the group consisting of:

$N^5$-{4-[(2,3-dichlorobenzoyl)amino]phenyl}-$N^4$-methyl-1H-imidazole-4,5-dicarboxamide;

$N^5$-(4-{[(2-chloropyridin-3-yl)carbonyl]amino}phenyl)-$N^4$-methyl-1H-imidazole-4,5-dicarboxamide;

$N^5$-(4-{[2-fluoro-4-(pyrrolidin-1-yl)benzoyl]amino}phenyl)-$N^4$-methyl-1H-imidazole-4,5-dicarboxamide;

$N^5$-(4-{[2-chloro-4-(dimethylamino)benzoyl]amino}phenyl)-$N^4$-methyl-1H-imidazole-4,5-dicarboxamide;

$N^5$-{4-[(2-chloro-4-fluorobenzoyl)amino]-3-methylphenyl}-$N^4$-methyl-1H-imidazole-4,5-dicarboxamide;

$N^5$-{4-[(3-chloroisonicotinoyl)amino]phenyl}-$N^4$-methyl-1H-imidazole-4,5-dicarboxamide;

$N^4$-sec-butyl-$N^5$-{4-[(2-chloro-4-fluorobenzoyl)amino]phenyl}-1,3-oxazole-4,5-dicarboxamide;

$N^5$-{4-[(2-chloro-4-fluorobenzoyl)amino]phenyl}-$N^4$-(1-phenylethyl)-1,3-oxazole-4,5-dicarboxamide;

$N^5$-{4-[(2,4-dichlorobenzoyl)amino]phenyl}-$N^4$-methyl-1H-imidazole-4,5-dicarboxamide;

$N^4$-{4-[(2-chloro-4-fluorobenzoyl)amino]phenyl}-$N^5$-isopropyl-1H-imidazole-4,5-dicarboxamide;

$N^5$-{4-[(2-chloro-4-fluorobenzoyl)amino]phenyl}-$N^4$-methyl-1,3-oxazole-4,5-dicarboxamide;

$N^4$-{4-[(2-chloro-4-fluorobenzoyl)amino]phenyl}-$N^5$-methyl-1H-imidazole-4,5-dicarboxamide;

methyl 5-({4-[(2-chloro-4-fluorobenzoyl)amino]phenyl}carbamoyl)-1H-imidazole-4-carboxylate;

methyl 5-({4-[(2-chloro-4-fluorobenzoyl)amino]phenyl}carbamoyl)-1,3-oxazole-4-carboxylate;

$N^5$-{4-[(2-chloro-4-fluorobenzoyl)amino]phenyl}-$N^4$-isopropyl-1,3-oxazole-4,5-dicarboxamide;

$N^5$-{6-[(2-chloro-4-fluorobenzoyl)amino]pyridin-3-yl}-$N^4$-methyl-1H-imidazole-4,5-dicarboxamide;

$N^5$-(4-{[(5-chloro-1-methyl-3-phenyl-1H-pyrazol-4-yl)carbonyl]amino}phenyl)-$N^4$-methyl-1H-imidazole-4,5-dicarboxamide;

$N^5$-benzyl-$N^4$-{4-[(2-chloro-4-fluorobenzoyl)amino]phenyl}-1H-imidazole-4,5-dicarboxamide;

$N^4$-methyl-$N^5$-{4-[(2-methylbenzoyl)amino]phenyl}-1H-imidazole-4,5-dicarboxamide;

$N^5$-{4-[(4-fluorobenzoyl)amino]phenyl}-$N^4$-methyl-1H-imidazole-4,5-dicarboxamide;

$N^5$-[4-(benzoylamino)phenyl]-$N^4$-methyl-1H-imidazole-4,5-dicarboxamide;

$N^4$-{4-[(2-chloro-4-fluorobenzoyl)amino]phenyl}-$N^5$-[2-(dimethylamino)ethyl]-1H-imidazole-4,5-dicarboxamide;

$N^5$-{4-[(4-fluoro-2,6-dimethylbenzoyl)amino]phenyl}-$N^4$-methyl-1H-imidazole-4,5-dicarboxamide;

$N^4$-{4-[(2-chloro-4-fluorobenzoyl)amino]phenyl}-$N^5$,$N^5$-dimethyl-1H-imidazole-4,5-dicarboxamide;

$N^5$-[4-({2-chloro-4-[2-(dimethylamino)ethoxy]benzoyl}amino)phenyl]-$N^4$-methyl-1H-imidazole-4,5-dicarboxamide;

$N^5$-{4-[(2,6-dichlorobenzoyl)amino]phenyl}-$N^4$-methyl-1H-imidazole-4,5-dicarboxamide;

$N^5$-{4-[(2-chlorobenzoyl)amino]phenyl}-$N^4$-methyl-1H-imidazole-4,5-dicarboxamide;

$N^5$-[4-({2-chloro-4-[2-(4-methylpiperazin-1-yl)ethoxy]benzoyl}amino)phenyl]-$N^4$-methyl-1H-imidazole-4,5-dicarboxamide;

N-{4-[(2-chloro-4-fluorobenzoyl)amino]phenyl}-5-(morpholin-4-ylcarbonyl)-1H-imidazole-4-carboxamide;

$N^4$-{4-[(2-chloro-4-fluorobenzoyl)amino]phenyl}-$N^5$-(2,2,2-trifluoroethyl)-1H-imidazole-4,5-dicarboxamide;

$N^5$-{4-[(2-chloro-4-fluorobenzoyl)amino]phenyl}-$N^4$-[2-(dimethylamino)ethyl]-1,3-oxazole-4,5-dicarboxamide;

$N^4$-{4-[(2-chloro-4-fluorobenzoyl)amino]phenyl}-$N^5$-[2-(piperidin-1-yl)ethyl]-1H-imidazole-4,5-dicarboxamide;

$N^4$-{4-[(4-fluorobenzoyl)amino]phenyl}-$N^5$-[2-(piperidin-1-yl)ethyl]-1H-imidazole-4,5-dicarboxamide;

N-{4-[(4-fluorobenzoyl)amino]phenyl}-5-(2-oxa-6-azaspiro[3.3]hept-6-ylcarbonyl)-1H-imidazole-4-carboxamide;

$N^5$-{4-[(mesitylcarbonyl)amino]phenyl}-$N^4$-methyl-1H-imidazole-4,5-dicarboxamide;

$N^5$-(4-{[2-chloro-6-(trifluoromethyl)benzoyl]amino}phenyl)-$N^4$-methyl-1H-imidazole-4,5-dicarboxamide;

$N^5$-{4-[(2-bromobenzoyl)amino]phenyl}-$N^4$-methyl-1H-imidazole-4,5-dicarboxamide;
$N^5$-{4-[(2,6-difluorobenzoyl)amino]phenyl}-$N^4$-methyl-1H-imidazole-4,5-dicarboxamide;
$N^5$-{4-[(2-ethylbenzoyl)amino]phenyl}-$N^4$-methyl-1H-imidazole-4,5-dicarboxamide;
$N^4$-methyl-$N^5$-{4-[(2,3,4-trimethoxybenzoyl)amino]phenyl}-1H-imidazole-4,5-dicarboxamide;
N-{4-[(2-chloro-4-fluorobenzoyl)amino]phenyl}-4-[(3-fluoroazetidin-1-yl)carbonyl]-1H-imidazole-5-carboxamide;
$N^5$-{4-[(2-chloro-4-fluorobenzoyl)amino]phenyl}-$N^4$-(2-cyclopentylethyl)-1H-imidazole-4,5-dicarboxamide;
$N^5$-{4-[(2-chloro-4-fluorobenzoyl)amino]phenyl}-$N^4$-(2-cyclopropylethyl)-1H-imidazole-4,5-dicarboxamide;
$N^5$-{4-[(2-chloro-4-fluorobenzoyl)amino]phenyl}-$N^4$-cyclopropyl-1H-imidazole-4,5-dicarboxamide;
N-{4-[(2-chloro-4-fluorobenzoyl)amino]phenyl}-4-[(6-methyl-2,6-diazaspiro[3.3]hept-2-yl)carbonyl]-1H-imidazole-5-carboxamide;
N-{4-[(2-chloro-4,5-difluorobenzoyl)amino]phenyl}-4-[(3-fluoroazetidin-1-yl)carbonyl]-1H-imidazole-5-carboxamide;
$N^5$-{4-[(2-chloro-4,5-difluorobenzoyl)amino]phenyl}-$N^4$-(2-cyclopentylethyl)-1H-imidazole-4,5-dicarboxamide;
$N^5$-{4-[(2-chloro-4,5-difluorobenzoyl)amino]phenyl}-$N^4$-(2-cyclopropylethyl)-1H-imidazole-4,5-dicarboxamide;
N-{4-[(2-chloro-4,5-difluorobenzoyl)amino]phenyl}-4-[(6-methyl-2,6-diazaspiro[3.3]hept-2-yl)carbonyl]-1H-imidazole-5-carboxamide;
$N^5$-{4-[(2-chloro-4,5-difluorobenzoyl)amino]phenyl}-$N^4$-cyclopropyl-1H-imidazole-4,5-dicarboxamide;
N-{4-[(2-chloro-4,5-difluorobenzoyl)amino]phenyl}-4-(2-oxa-6-azaspiro[3.3]hept-6-ylcarbonyl)-1H-imidazole-5-carboxamide;
$N^5$-(4-{[2-chloro-4-(methylsulfonyl)benzoyl]amino}phenyl)-$N^4$-[2-(piperidin-1-yl)ethyl]-1H-imidazole-4,5-dicarboxamide;
$N^5$-(4-{[2-chloro-4-(methylsulfonyl)benzoyl]amino}phenyl)-$N^4$-[2-(dimethylamino)ethyl]-1H-imidazole-4,5-dicarboxamide;
$N^5$-(4-{[2-chloro-4-(methylsulfonyl)benzoyl]amino}phenyl)-$N^4$-methyl-1H-imidazole-4,5-dicarboxamide;
$N^5$-{4-[(2-bromo-4-fluorobenzoyl)amino]phenyl}-$N^4$-methyl-1H-imidazole-4,5-dicarboxamide;
$N^5$-{4-[(2,6-dimethoxybenzoyl)amino]phenyl}-$N^4$-methyl-1H-imidazole-4,5-dicarboxamide;
$N^4$-methyl-$N^5$-(4-{[2-(trifluoromethyl)benzoyl]amino}phenyl)-1H-imidazole-4,5-dicarboxamide;
$N^4$-methyl-$N^5$-{4-[(2,4,6-trichlorobenzoyl)amino]phenyl}-1H-imidazole-4,5-dicarboxamide;
$N^5$-{4-[(2-methoxybenzoyl)amino]phenyl}-$N^4$-methyl-1H-imidazole-4,5-dicarboxamide;
$N^5$-{4-[(4-fluoro-2-iodobenzoyl)amino]phenyl}-$N^4$-methyl-1H-imidazole-4,5-dicarboxamide;
$N^5$-{4-[(4-fluoro-2-iodobenzoyl)amino]phenyl}-$N^4$-[2-(piperidin-1-yl)ethyl]-1H-imidazole-4,5-dicarboxamide;
$N^5$-(4-{[2-bromo-5-(trifluoromethoxy)benzoyl]amino}phenyl)-$N^4$-[2-(piperidin-1-yl)ethyl]-1H-imidazole-4,5-dicarboxamide;
$N^5$-(4-{[2-bromo-5-(trifluoromethoxy)benzoyl]amino}phenyl)-$N^4$-methyl-1H-imidazole-4,5-dicarboxamide;
$N^5$-{4-[(2-chloro-4-fluorobenzoyl)amino]phenyl}-$N^4$,2-dimethyl-1H-imidazole-4,5-dicarboxamide;
$N^4$-{4-[(2-chloro-4-fluorobenzoyl)amino]phenyl}-$N^5$-[2-(dimethylamino)ethyl]-2-methyl-1H-imidazole-4,5-dicarboxamide;
$N^5$-{4-[(2-chloro-4-fluorobenzoyl)amino]phenyl}-2-methyl-$N^4$-[2-(piperidin-1-yl)ethyl]-1H-imidazole-4,5-dicarboxamide;
$N^5$-{4-[(2-chloro-4-fluorobenzoyl)amino]phenyl}-2-ethyl-$N^4$-methyl-1H-imidazole-4,5-dicarboxamide;
$N^4$-{4-[(2-chloro-4-fluorobenzoyl)amino]phenyl}-$N^5$-[2-(dimethylamino)ethyl]-2-ethyl-1H-imidazole-4,5-dicarboxamide;
$N^4$-{4-[(2-chloro-4-fluorobenzoyl)amino]phenyl}-2-ethyl-$N^5$-[2-(piperidin-1-yl)ethyl]-1H-imidazole-4,5-dicarboxamide;
methyl 5-({4-[(2-chloro-4-fluorobenzoyl)amino]-3-fluorophenyl}carbamoyl)-1H-imidazole-4-carboxylate;
$N^5$-{4-[(2-chloro-4-fluorobenzoyl)amino]-3-fluorophenyl}-$N^4$-methyl-1H-imidazole-4,5-dicarboxamide;
$N^5$-{4-[(2-chloro-4-fluorobenzoyl)amino]-3-fluorophenyl}-$N^4$-[2-(dimethylamino)ethyl]-1H-imidazole-4,5-dicarboxamide;
$N^5$-{4-[(2-chloro-4-fluorobenzoyl)amino]-3-fluorophenyl}-$N^4$-[2-(piperidin-1-yl)ethyl]-1H-imidazole-4,5-dicarboxamide;
methyl 5-({3-fluoro-4-[(4-fluorobenzoyl)amino]phenyl}carbamoyl)-1H-imidazole-4-carboxylate;
$N^5$-{3-fluoro-4-[(4-fluorobenzoyl)amino]phenyl}-$N^4$-methyl-1H-imidazole-4,5-dicarboxamide;
$N^4$-[2-(dimethylamino)ethyl]-$N^5$-{3-fluoro-4-[(4-fluorobenzoyl)amino]phenyl}-1H-imidazole-4,5-dicarboxamide;
$N^5$-{3-fluoro-4-[(4-fluorobenzoyl)amino]phenyl}-$N^4$-[2-(piperidin-1-yl)ethyl]-1H-imidazole-4,5-dicarboxamide;
methyl 5-({4-[(2-chlorobenzoyl)amino]-3-fluorophenyl}carbamoyl)-1H-imidazole-4-carboxylate;
$N^5$-{4-[(2-chlorobenzoyl)amino]-3-fluorophenyl}-$N^4$-methyl-1H-imidazole-4,5-dicarboxamide;
$N^5$-{4-[(2-chlorobenzoyl)amino]-3-fluorophenyl}-$N^4$-[2-(dimethylamino)ethyl]-1H-imidazole-4,5-dicarboxamide;
$N^5$-{4-[(2-chlorobenzoyl)amino]-3-fluorophenyl}-$N^4$-[2-(piperidin-1-yl)ethyl]-1H-imidazole-4,5-dicarboxamide;
methyl 5-({4-[(2-chloro-4-fluorobenzoyl)amino]-3-methylphenyl}carbamoyl)-1H-imidazole-4-carboxylate;
$N^5$-{4-[(2-chloro-4-fluorobenzoyl)amino]-3-methylphenyl}-$N^4$-[2-(dimethylamino)ethyl]-1H-imidazole-4,5-dicarboxamide;
$N^5$-{4-[(2-chloro-4-fluorobenzoyl)amino]-3-methylphenyl}-$N^4$-[2-(piperidin-1-yl)ethyl]-1H-imidazole-4,5-dicarboxamide;
methyl 5-({4-[(2-chlorobenzoyl)amino]-3-methylphenyl}carbamoyl)-1H-imidazole-4-carboxylate;
$N^5$-{4-[(2-chlorobenzoyl)amino]-3-methylphenyl}-$N^4$-methyl-1H-imidazole-4,5-dicarboxamide;
$N^5$-{4-[(2-chlorobenzoyl)amino]-3-methylphenyl}-$N^4$-[2-(dimethylamino)ethyl]-1H-imidazole-4,5-dicarboxamide;

N$^5$-{4-[(2-chlorobenzoyl)amino]-3-methylphenyl}-N$^4$-[2-(piperidin-1-yl)ethyl]-1H-imidazole-4,5-dicarboxamide;

methyl 5-({4-[(4-fluorobenzoyl)amino]-3-methylphenyl}carbamoyl)-1H-imidazole-4-carboxylate;

N$^5$-{4-[(4-fluorobenzoyl)amino]-3-methylphenyl}-N$^4$-methyl-1H-imidazole-4,5-dicarboxamide;

N$^4$-[2-(dimethylamino)ethyl]-N$^4$-{4-[(4-fluorobenzoyl)amino]-3-methylphenyl}-1H-imidazole-4,5-dicarboxamide;

N$^5$-{4-[(4-fluorobenzoyl)amino]-3-methylphenyl}-N$^4$-[2-(piperidin-1-yl)ethyl]-1H-imidazole-4,5-dicarboxamide;

methyl 5-({4-[(2-chloro-4-fluorobenzoyl)amino]-3-methoxyphenyl}carbamoyl)-1H-imidazole-4-carboxylate;

N$^5$-{4-[(2-chloro-4-fluorobenzoyl)amino]-3-methoxyphenyl}-N$^4$-methyl-1H-imidazole-4,5-dicarboxamide;

N$^5$-{4-[(2-chloro-4-fluorobenzoyl)amino]-3-methoxyphenyl}-N$^4$-[2-(dimethylamino)ethyl]-1H-imidazole-4,5-dicarboxamide;

N$^5$-{4-[(2-chloro-4-fluorobenzoyl)amino]-3-methoxyphenyl}-N$^4$-[2-(piperidin-1-yl)ethyl]-1H-imidazole-4,5-dicarboxamide;

methyl 5-({4-[(2-chlorobenzoyl)amino]-3-methoxyphenyl}carbamoyl)-1H-imidazole-4-carboxylate;

N$^5$-{4-[(2-chlorobenzoyl)amino]-3-methoxyphenyl}-N$^4$-methyl-1H-imidazole-4,5-dicarboxamide;

N$^5$-{4-[(2-chlorobenzoyl)amino]-3-methoxyphenyl}-N$^4$-[2-(dimethylamino)ethyl]-1H-imidazole-4,5-dicarboxamide;

N$^5$-{4-[(2-chlorobenzoyl)amino]-3-methoxyphenyl}-N$^4$-[2-(piperidin-1-yl)ethyl]-1H-imidazole-4,5-dicarboxamide;

methyl 5-({4-[(4-fluorobenzoyl)amino]-3-methoxyphenyl}carbamoyl)-1H-imidazole-4-carboxylate;

N$^5$-{4-[(4-fluorobenzoyl)amino]-3-methoxyphenyl}-N$^4$-methyl-1H-imidazole-4,5-dicarboxamide;

N$^4$-[2-(dimethylamino)ethyl]-N$^5$-{4-[(4-fluorobenzoyl)amino]-3-methoxyphenyl}-1H-imidazole-4,5-dicarboxamide;

N$^5$-{4-[(4-fluorobenzoyl)amino]-3-methoxyphenyl}-N$^4$-[2-(piperidin-1-yl)ethyl]-1H-imidazole-4,5-dicarboxamide;

N$^5$-{4-[(2-chloro-4-fluorobenzoyl)amino]phenyl}-2-isopropyl-N$^4$-methyl-1H-imidazole-4,5-dicarboxamide;

N$^4$-{4-[(2-chloro-4-fluorobenzoyl)amino]phenyl}-N$^5$-[2-(dimethylamino)ethyl]-2-isopropyl-1H-imidazole-4,5-dicarboxamide;

N$^4$-{4-[(2-chloro-4-fluorobenzoyl)amino]phenyl}-2-isopropyl-N$^5$-[2-(piperidin-1-yl)ethyl]-1H-imidazole-4,5-dicarboxamide;

N$^5$-{6-[(2-chloro-4-fluorobenzoyl)amino]pyridin-3-yl}-N$^4$-[2-(dimethylamino)ethyl]-1H-imidazole-4,5-dicarboxamide;

N$^5$-{6-[(2-chloro-4-fluorobenzoyl)amino]pyridin-3-yl}-N$^4$-[2-(piperidin-1-yl)ethyl]-1H-imidazole-4,5-dicarboxamide;

methyl 5-({6-[(2-chlorobenzoyl)amino]pyridin-3-yl}carbamoyl)-1H-imidazole-4-carboxylate;

N$^5$-{6-[(2-chlorobenzoyl)amino]pyridin-3-yl}-N$^4$-methyl-1H-imidazole-4,5-dicarboxamide;

N$^5$-{6-[(2-chlorobenzoyl)amino]pyridin-3-yl}-N$^4$-[2-(dimethylamino)ethyl]-1H-imidazole-4,5-dicarboxamide;

N$^5$-{6-[(2-chlorobenzoyl)amino]pyridin-3-yl}-N$^4$-[2-(piperidin-1-yl)ethyl]-1H-imidazole-4,5-dicarboxamide;

N$^5$-{6-[(4-fluorobenzoyl)amino]pyridin-3-yl}-N$^4$-methyl-1H-imidazole-4,5-dicarboxamide;

N$^4$-[2-(dimethylamino)ethyl]-N$^5$-{6-[(4-fluorobenzoyl)amino]pyridin-3-yl}-1H-imidazole-4,5-dicarboxamide;

N$^5$-{6-[(4-fluorobenzoyl)amino]pyridin-3-yl}-N$^4$-[2-(piperidin-1-yl)ethyl]-1H-imidazole-4,5-dicarboxamide;

N$^5$-{4-[(2-chloro-4,6-difluorobenzoyl)amino]phenyl}-N$^4$-methyl-1H-imidazole-4,5-dicarboxamide;

N$^5$-{4-[(2-chloro-4,6-difluorobenzoyl)amino]phenyl}-N$^4$-[2-(piperidin-1-yl)ethyl]-1H-imidazole-4,5-dicarboxamide;

N$^5$-{4-[(2-chlorobenzoyl)amino]phenyl}-1H-imidazole-4,5-dicarboxamide;

N$^5$-{4-[(2-chloro-4-fluorobenzoyl)amino]phenyl}-1H-imidazole-4,5-dicarboxamide;

N$^5$-{4-[(2-chloro-4-hydroxybenzoyl)amino]phenyl}-N$^4$-methyl-1H-imidazole-4,5-dicarboxamide;

N$^5$-{4-[(2-chloro-5-hydroxybenzoyl)amino]phenyl}-N$^4$-methyl-1H-imidazole-4,5-dicarboxamide;

N$^5$-[4-({2-chloro-5-[2-(4-methylpiperazin-1-yl)ethoxy]benzoyl}amino)phenyl]-N$^4$-methyl-1H-imidazole-4,5-dicarboxamide;

N$^5$-[4-({2-chloro-5-[2-(piperidin-1-yl)ethoxy]benzoyl}amino)phenyl]-N$^4$-methyl-1H-imidazole-4,5-dicarboxamide;

N$^4$-{4-[(2-chloro-4-fluorobenzoyl)amino]phenyl}-N$^5$-[2-(4-methylpiperidin-1-yl)ethyl]-1H-imidazole-4,5-dicarboxamide;

N$^4$-{4-[(2-chloro-4-fluorobenzoyl)amino]phenyl}-N$^5$-[2-(piperidin-1-yl)ethyl]-1H-imidazole-4,5-dicarboxamide hydrochloric acid salt;

N$^4$-{4-[(2-chloro-4-fluorobenzoyl)amino]phenyl}-N$^5$-(cyclopropylmethyl)-1H-imidazole-4,5-dicarboxamide;

N$^5$-tert-butyl-N$^4$-{4-[(4-fluorobenzoyl)amino]phenyl}-1H-imidazole-4,5-dicarboxamide;

N$^4$-{4-[(2-chloro-4-fluorobenzoyl)amino]phenyl}-N$^5$-(2-methoxyethyl)-1H-imidazole-4,5-dicarboxamide;

N$^5$-cyclopropyl-N$^4$-{4-[(4-fluorobenzoyl)amino]phenyl}-1H-imidazole-4,5-dicarboxamide;

N$^4$-{4-[(2-chloro-4-fluorobenzoyl)amino]phenyl}-N$^5$-(2-hydroxyethyl)-1H-imidazole-4,5-dicarboxamide;

N$^5$-tert-butyl-N$^4$-{4-[(2-chloro-4-fluorobenzoyl)amino]phenyl}-1H-imidazole-4,5-dicarboxamide;

N$^4$-{4-[(2-chloro-4-fluorobenzoyl)amino]phenyl}-N$^5$-[(2R)-3-methylbutan-2-yl]-1H-imidazole-4,5-dicarboxamide;

N$^4$-{4-[(4-fluorobenzoyl)amino]phenyl}-N$^5$-[(2R)-3-methylbutan-2-yl]-1H-imidazole-4,5-dicarboxamide;

N$^4$-{4-[(4-fluorobenzoyl)amino]phenyl}-N$^5$-(2-hydroxyethyl)-1H-imidazole-4,5-dicarboxamide;

N$^5$-ethyl-N$^4$-{4-[(4-fluorobenzoyl)amino]phenyl}-1H-imidazole-4,5-dicarboxamide;

N$^4$-{4-[(2-chloro-4-fluorobenzoyl)amino]phenyl}-N$^5$-ethyl-1H-imidazole-4,5-dicarboxamide;

N$^4$-{4-[(2-chloro-4-fluorobenzoyl)amino]phenyl}-N$^5$-(2,2-difluoroethyl)-1H-imidazole-4,5-dicarboxamide;

N$^4$-{4-[(4-fluorobenzoyl)amino]phenyl}-N$^5$-(2-methoxyethyl)-1H-imidazole-4,5-dicarboxamide;

N$^5$-(2,2-difluoroethyl)-N$^4$-{4-[(4-fluorobenzoyl)amino]phenyl}-1H-imidazole-4,5-dicarboxamide;

5-(azetidin-1-ylcarbonyl)-N-{4-[(2-chloro-4-fluorobenzoyl)amino]phenyl}-1H-imidazole-4-carboxamide;

5-(azetidin-1-ylcarbonyl)-N-{4-[(4-fluorobenzoyl)amino]phenyl}-1H-imidazole-4-carboxamide;

$N^4$-{4-[(4-fluorobenzoyl)amino]phenyl}-$N^5$,$N^5$-dimethyl-1H-imidazole-4,5-dicarboxamide;

N-{4-[(2-chloro-4-fluorobenzoyl)amino]phenyl}-5-(2-oxa-6-azaspiro[3.3]hept-6-ylcarbonyl)-1H-imidazole-4-carboxamide;

$N^4$-{4-[(4-fluorobenzoyl)amino]phenyl}-$N^5$-isobutyl-1H-imidazole-4,5-dicarboxamide;

$N^4$-{4-[(2-chloro-4-fluorobenzoyl)amino]phenyl}-$N^5$-isobutyl-1H-imidazole-4,5-dicarboxamide;

$N^4$-{4-[(2-chlorobenzoyl)amino]phenyl}-$N^5$-(2,2-dimethylpropyl)-1H-imidazole-4,5-dicarboxamide;

$N^5$-(2,2-dimethylpropyl)-$N^4$-{4-[(4-fluorobenzoyl)amino]phenyl}-1H-imidazole-4,5-dicarboxamide;

$N^5$-(1,3-dihydroxypropan-2-yl)-$N^4$-{4-[(4-fluorobenzoyl)amino]phenyl}-1H-imidazole-4,5-dicarboxamide;

$N^4$-{4-[(4-fluorobenzoyl)amino]phenyl}-$N^5$-[2-(morpholin-4-yl)ethyl]-1H-imidazole-4,5-dicarboxamide;

$N^4$-{4-[(2-chlorobenzoyl)amino]phenyl}-$N^5$-[2-(3-hydroxypiperidin-1-yl)ethyl]-1H-imidazole-4,5-dicarboxamide;

$N^4$-{4-[(2-chlorobenzoyl)amino]phenyl}-$N^5$-[2-(2-methylpiperidin-1-yl)ethyl]-1H-imidazole-4,5-dicarboxamide;

$N^4$-{4-[(2-chlorobenzoyl)amino]phenyl}-$N^5$-[2-methyl-1-(morpholin-4-yl)propan-2-yl]-1H-imidazole-4,5-dicarboxamide;

$N^4$-{4-[(2-chloro-4-fluorobenzoyl)amino]phenyl}-$N^5$-[2-methyl-1-(4-methylpiperidin-1-yl)propan-2-yl]-1H-imidazole-4,5-dicarboxamide;

$N^4$-{4-[(4-fluorobenzoyl)amino]phenyl}-$N^5$-[2-methyl-1-(piperidin-1-yl)propan-2-yl]-1H-imidazole-4,5-dicarboxamide;

$N^4$-{4-[(2-chlorobenzoyl)amino]phenyl}-$N^5$-(1,3-dihydroxypropan-2-yl)-1H-imidazole-4,5-dicarboxamide;

$N^4$-{4-[(2-chlorobenzoyl)amino]phenyl}-$N^5$-[2-methyl-1-(4-methylpiperidin-1-yl)propan-2-yl]-1H-imidazole-4,5-dicarboxamide;

$N^4$-{4-[(2-chloro-4-fluorobenzoyl)amino]phenyl}-$N^5$-[2-methyl-2-(piperidin-1-yl)propyl]-1H-imidazole-4,5-dicarboxamide;

$N^4$-{4-[(2-chlorobenzoyl)amino]phenyl}-$N^5$-[2-(4-methylpiperazin-1-yl)ethyl]-1H-imidazole-4,5-dicarboxamide;

$N^4$-{4-[(4-fluorobenzoyl)amino]phenyl}-$N^5$-[2-(4-methylpiperazin-1-yl)ethyl]-1H-imidazole-4,5-dicarboxamide;

$N^4$-{4-[(2-chlorobenzoyl)amino]phenyl}-$N^5$-[1-(morpholin-4-yl)propan-2-yl]-1H-imidazole-4,5-dicarboxamide;

$N^4$-{4-[(2-chlorobenzoyl)amino]phenyl}-$N^5$-[2-(4-methylpiperidin-1-yl)ethyl]-1H-imidazole-4,5-dicarboxamide;

$N^4$-{4-[(4-fluorobenzoyl)amino]phenyl}-$N^5$-[2-(4-methylpiperidin-1-yl)ethyl]-1H-imidazole-4,5-dicarboxamide;

$N^4$-{4-[(2-chlorobenzoyl)amino]phenyl}-$N^5$-[2-methyl-2-(piperidin-1-yl)propyl]-1H-imidazole-4,5-dicarboxamide;

$N^4$-{4-[(2-chlorobenzoyl)amino]phenyl}-$N^5$-(2-fluoroethyl)-1H-imidazole-4,5-dicarboxamide;

$N^4$-{4-[(4-fluorobenzoyl)amino]phenyl}-$N^5$-[2-(3-hydroxypiperidin-1-yl)ethyl]-1H-imidazole-4,5-dicarboxamide;

$N^4$-{4-[(2-chlorobenzoyl)amino]phenyl}-$N^5$-[2-(pyrrolidin-1-yl)ethyl]-1H-imidazole-4,5-dicarboxamide;

$N^4$-{4-[(4-fluorobenzoyl)amino]phenyl}-$N^5$-[2-(2-methylpiperidin-1-yl)ethyl]-1H-imidazole-4,5-dicarboxamide;

$N^4$-{4-[(2-chloro-4-fluorobenzoyl)amino]phenyl}-$N^5$-[2-(piperidin-1-yl)propyl]-1H-imidazole-4,5-dicarboxamide;

$N^4$-{4-[(2-chloro-4-fluorobenzoyl)amino]phenyl}-$N^5$-[2-methyl-1-(piperidin-1-yl)propan-2-yl]-1H-imidazole-4,5-dicarboxamide;

$N^4$-{4-[(2-chloro-4-fluorobenzoyl)amino]phenyl}-$N^5$-(1,3-dihydroxypropan-2-yl)-1H-imidazole-4,5-dicarboxamide;

$N^4$-{4-[(2-chloro-4-fluorobenzoyl)amino]phenyl}-$N^5$-(2-fluoroethyl)-1H-imidazole-4,5-dicarboxamide;

$N^4$-{4-[(4-fluorobenzoyl)amino]phenyl}-$N^5$-(2-fluoroethyl)-1H-imidazole-4,5-dicarboxamide;

$N^4$-{4-[(4-fluorobenzoyl)amino]phenyl}-$N^5$-[2-methyl-1-(4-methylpiperidin-1-yl)propan-2-yl]-1H-imidazole-4,5-dicarboxamide;

$N^4$-{4-[(4-fluorobenzoyl)amino]phenyl}-$N^5$-[2-(pyrrolidin-1-yl)ethyl]-1H-imidazole-4,5-dicarboxamide;

$N^4$-{4-[(2-chloro-4-fluorobenzoyl)amino]phenyl}-$N^5$-(4-methylpiperazin-1-yl)-1H-imidazole-4,5-dicarboxamide;

$N^4$-{4-[(4-fluorobenzoyl)amino]phenyl}-$N^5$-[2-(4-hydroxypiperidin-1-yl)ethyl]-1H-imidazole-4,5-dicarboxamide;

$N^4$-{4-[(4-fluorobenzoyl)amino]phenyl}-$N^5$-[2-methyl-1-(morpholin-4-yl)propan-2-yl]-1H-imidazole-4,5-dicarboxamide;

$N^4$-{4-[(4-fluorobenzoyl)amino]phenyl}-$N^5$-[3-(4-methylpiperazin-1-yl)propyl]-1H-imidazole-4,5-dicarboxamide;

$N^4$-{4-[(2-chlorobenzoyl)amino]phenyl}-$N^5$-[2-(piperidin-1-yl)propyl]-1H-imidazole-4,5-dicarboxamide;

$N^4$-{4-[(4-fluorobenzoyl)amino]phenyl}-$N^5$-[2-(piperidin-1-yl)propyl]-1H-imidazole-4,5-dicarboxamide;

$N^4$-{4-[(2-chloro-4-fluorobenzoyl)amino]phenyl}-$N^5$-[2-methyl-1-(piperidin-1-yl)propan-2-yl]-1H-imidazole-4,5-dicarboxamide;

$N^4$-{4-[(2-chloro-4-fluorobenzoyl)amino]phenyl}-$N^5$-[2-(4-methylpiperazin-1-yl)propyl]-1H-imidazole-4,5-dicarboxamide;

$N^4$-{4-[(2-chlorobenzoyl)amino]phenyl}-$N^5$-[2-(4-methylpiperazin-1-yl)propyl]-1H-imidazole-4,5-dicarboxamide;

$N^4$-{4-[(2-chloro-4-fluorobenzoyl)amino]phenyl}-$N^5$-[2-methyl-2-(4-methylpiperazin-1-yl)propyl]-1H-imidazole-4,5-dicarboxamide;

$N^4$-{4-[(4-fluorobenzoyl)amino]phenyl}-$N^5$-[2-methyl-2-(4-methylpiperazin-1-yl)propyl]-1H-imidazole-4,5-dicarboxamide;

$N^4$-{4-[(2-chlorobenzoyl)amino]phenyl}-$N^5$-[4-(piperidin-1-yl)butyl]-1H-imidazole-4,5-dicarboxamide;

$N^5$-[2-(azetidin-1-yl)ethyl]-$N^4$-{4-[(2-chlorobenzoyl)amino]phenyl}-1H-imidazole-4,5-dicarboxamide;

$N^4$-{4-[(2-chloro-4-fluorobenzoyl)amino]phenyl}-$N^5$-[2-(2-methylpiperidin-1-yl)ethyl]-1H-imidazole-4,5-dicarboxamide;

$N^4$-{4-[(2-chlorobenzoyl)amino]phenyl}-$N^5$-[3-(4-methylpiperazin-1-yl)propyl]-1H-imidazole-4,5-dicarboxamide;

$N^4$-{4-[(4-fluorobenzoyl)amino]phenyl}-$N^5$-(4-methylpiperazin-1-yl)-1H-imidazole-4,5-dicarboxamide;

N⁴-{4-[(2-chloro-4-fluorobenzoyl)amino]phenyl}-N⁵-[2-methyl-1-(4-methylpiperazin-1-yl)propan-2-yl]-1H-imidazole-4,5-dicarboxamide;
N⁴-{4-[(4-fluorobenzoyl)amino]phenyl}-N⁵-[2-methyl-1-(4-methylpiperazin-1-yl)propan-2-yl]-1H-imidazole-4,5-dicarboxamide;
N⁴-{4-[(2-chloro-4-fluorobenzoyl)amino]phenyl}-N⁵-[4-(piperidin-1-yl)butyl]-1H-imidazole-4,5-dicarboxamide;
N⁴-{4-[(2-chlorobenzoyl)amino]phenyl}-N⁵-[2-(4-hydroxypiperidin-1-yl)ethyl]-1H-imidazole-4,5-dicarboxamide;
N⁵-[2-(azetidin-1-yl)ethyl]-N⁴-{4-[(2-chloro-4-fluorobenzoyl)amino]phenyl}-1H-imidazole-4,5-dicarboxamide;
N⁵-[2-(azetidin-1-yl)ethyl]-N⁴-{4-[(4-fluorobenzoyl)amino]phenyl}-1H-imidazole-4,5-dicarboxamide;
N⁴-{4-[(2-chlorobenzoyl)amino]phenyl}-N⁵-[3-(morpholin-4-yl)propyl]-1H-imidazole-4,5-dicarboxamide;
N⁴-{4-[(4-fluorobenzoyl)amino]phenyl}-N⁵-[4-(piperidin-1-yl)butyl]-1H-imidazole-4,5-dicarboxamide;
N⁴-{4-[(2-chlorobenzoyl)amino]phenyl}-N⁵-[2-methyl-2-(4-methylpiperazin-1-yl)propyl]-1H-imidazole-4,5-dicarboxamide;
N⁴-{4-[(2-chlorobenzoyl)amino]phenyl}-N⁵-[2-methyl-1-(4-methylpiperazin-1-yl)propan-2-yl]-1H-imidazole-4,5-dicarboxamide;
N⁴-{4-[(2-chloro-4-fluorobenzoyl)amino]phenyl}-N⁵-[3-(morpholin-4-yl)propyl]-1H-imidazole-4,5-dicarboxamide;
N⁴-{4-[(4-fluorobenzoyl)amino]phenyl}-N⁵-[2-(4-methylpiperazin-1-yl)propyl]-1H-imidazole-4,5-dicarboxamide;
N⁴-{4-[(4-fluorobenzoyl)amino]phenyl}-N⁵-[3-(morpholin-4-yl)propyl]-1H-imidazole-4,5-dicarboxamide;
N⁴-{4-[(2-chloro-4-fluorobenzoyl)amino]phenyl}-N⁵-[2-methyl-1-(morpholin-4-yl)propan-2-yl]-1H-imidazole-4,5-dicarboxamide;
N⁴-{4-[(2-chloro-4-fluorobenzoyl)amino]phenyl}-N⁵-[2-(3-methylpiperidin-1-yl)ethyl]-1H-imidazole-4,5-dicarboxamide;
N⁴-{4-[(4-fluorobenzoyl)amino]phenyl}-N⁵-[2-methyl-2-(piperidin-1-yl)propyl]-1H-imidazole-4,5-dicarboxamide;
N⁴-{4-[(2-chlorobenzoyl)amino]phenyl}-N⁵-[2-(3-methylpiperidin-1-yl)ethyl]-1H-imidazole-4,5-dicarboxamide;
N⁴-{4-[(4-fluorobenzoyl)amino]phenyl}-N⁵-[2-(3-methylpiperidin-1-yl)ethyl]-1H-imidazole-4,5-dicarboxamide;
N⁴-{4-[(2-chloro-4-fluorobenzoyl)amino]phenyl}-N⁵-[2-(4-hydroxypiperidin-1-yl)ethyl]-1H-imidazole-4,5-dicarboxamide;
N⁵-(4-{[(2,5-dichloro-3-thienyl)carbonyl]amino}phenyl)-N⁴-methyl-1H-imidazole-4,5-dicarboxamide;
N⁴-{4-[(2-chlorobenzoyl)amino]phenyl}-N⁵-[2-(4,4-difluoropiperidin-1-yl)ethyl]-1H-imidazole-4,5-dicarboxamide;
N⁴-{4-[(2-bromo-4-fluorobenzoyl)amino]phenyl}-N⁵-[2-(4,4-difluoropiperidin-1-yl)ethyl]-1H-imidazole-4,5-dicarboxamide;
N⁴-{4-[(2-bromo-4-fluorobenzoyl)amino]phenyl}-N⁵-[2-(piperidin-1-yl)ethyl]-1H-imidazole-4,5-dicarboxamide;
N⁴-{4-[(2-bromo-4-fluorobenzoyl)amino]phenyl}-N⁵-[2-(dimethylamino)ethyl]-1H-imidazole-4,5-dicarboxamide;
N⁵-{4-[(2-chloro-4-fluorobenzoyl)amino]phenyl}-N⁴-[2-(4,4-difluoropiperidin-1-yl)ethyl]-1,3-oxazole-4,5-dicarboxamide;
N⁴-(2-amino-2-methylpropyl)-N⁵-{4-[(2-chloro-4-fluorobenzoyl)amino]phenyl}-1,3-oxazole-4,5-dicarboxamide;
N⁵-{4-[(2-chloro-4-fluorobenzoyl)amino]phenyl}-N⁴-[2-(3-fluoropiperidin-1-yl)ethyl]-1,3-oxazole-4,5-dicarboxamide;
N⁵-{4-[(2-chloro-4-fluorobenzoyl)amino]phenyl}-N⁴-{2-[(3S)-3-fluoropyrrolidin-1-yl]ethyl}-1,3-oxazole-4,5-dicarboxamide;
N⁵-{4-[(2-chloro-4-fluorobenzoyl)amino]phenyl}-N⁴-{2-[(3R)-3-fluoropyrrolidin-1-yl]ethyl}-1,3-oxazole-4,5-dicarboxamide;
N⁴-{4-[(2-chloro-4-fluorobenzoyl)amino]phenyl}-N⁵-(2-hydroxy-2-methylpropyl)-1H-imidazole-4,5-dicarboxamide;
N⁴-{4-[(2-chloro-4-fluorobenzoyl)amino]phenyl}-N⁵-[2-(4,4-difluoropiperidin-1-yl)ethyl]-1H-imidazole-4,5-dicarboxamide;
N⁴-{4-[(2-chloro-4-fluorobenzoyl)amino]phenyl}-N⁵-[2-(3,3-difluoropiperidin-1-yl)ethyl]-1H-imidazole-4,5-dicarboxamide;
N⁴-{4-[(2-chloro-4-fluorobenzoyl)amino]phenyl}-N⁵-[2-(3-fluoropiperidin-1-yl)ethyl]-1H-imidazole-4,5-dicarboxamide;
N⁴-{4-[(2-chloro-4-fluorobenzoyl)amino]phenyl}-N⁵-[2-(morpholin-4-yl)ethyl]-1H-imidazole-4,5-dicarboxamide;
N⁴-{4-[(2-chloro-4-fluorobenzoyl)amino]phenyl}-N⁵-[2-(pyrrolidin-1-yl)ethyl]-1H-imidazole-4,5-dicarboxamide;
N⁴-{4-[(2-chloro-4-fluorobenzoyl)amino]phenyl}-N⁵-[2-(3-hydroxypiperidin-1-yl)ethyl]-1H-imidazole-4,5-dicarboxamide;
N⁴-{4-[(2-chloro-4-fluorobenzoyl)amino]phenyl}-N⁵-[2-(4-fluoropiperidin-1-yl)ethyl]-1H-imidazole-4,5-dicarboxamide;
N⁴-{4-[(2-chloro-4-fluorobenzoyl)amino]phenyl}-N⁵-{2-[(3R)-3-fluoropyrrolidin-1-yl]ethyl}-1H-imidazole-4,5-dicarboxamide;
N⁴-{4-[(2-chloro-4-fluorobenzoyl)amino]phenyl}-N⁵-{2-[(3S)-3-fluoropyrrolidin-1-yl]ethyl}-1H-imidazole-4,5-dicarboxamide;
N⁴-{4-[(2-chloro-4-fluorobenzoyl)amino]phenyl}-N⁵-(tetrahydro-2H-pyran-4-ylmethyl)-1H-imidazole-4,5-dicarboxamide;
N⁴-{4-[(2-chloro-4-fluorobenzoyl)amino]phenyl}-N⁵-(tetrahydro-2H-pyran-4-yl)-1H-imidazole-4,5-dicarboxamide;
N⁴-{4-[(2-chloro-4-fluorobenzoyl)amino]phenyl}-N⁵-(tetrahydrofuran-3-ylmethyl)-1H-imidazole-4,5-dicarboxamide;
N⁴-{4-[(2-chloro-4-fluorobenzoyl)amino]phenyl}-N⁵-(tetrahydrofuran-3-yl)-1H-imidazole-4,5-dicarboxamide;
N⁴-{4-[(2-chloro-4-fluorobenzoyl)amino]phenyl}-N⁵-(tetrahydrofuran-2-ylmethyl)-1H-imidazole-4,5-dicarboxamide;
N⁴-{4-[(2-chloro-4-fluorobenzoyl)amino]phenyl}-N⁵-[2-(4-methylpiperazin-1-yl)ethyl]-1H-imidazole-4,5-dicarboxamide;

$N^5$-{4-[(2-hydroxybenzoyl)amino]phenyl}-$N^4$-methyl-1H-imidazole-4,5-dicarboxamide;

$N^5$-{4-[(2-chloro-4,5-dimethoxybenzoyl)amino]phenyl}-$N^4$-methyl-1H-imidazole-4,5-dicarboxamide;

$N^5$-(4-{[2-(difluoromethyl)benzoyl]amino}phenyl)-$N^4$-methyl-1H-imidazole-4,5-dicarboxamide;

$N^5$-{4-[(2-chloro-4,5-difluorobenzoyl)amino]phenyl}-$N^4$-methyl-1H-imidazole-4,5-dicarboxamide;

$N^4$-methyl-$N^5$-(4-{[2-(trifluoromethoxy)benzoyl]amino}phenyl)-1H-imidazole-4,5-dicarboxamide;

$N^5$-{4-[(2-chloro-4-methylbenzoyl)benzoyl)amino]phenyl}-$N^4$-methyl-1H-imidazole-4,5-dicarboxamide;

$N^5$-{4-[(4-fluoro-2-hydroxybenzoyl)amino]phenyl}-$N^4$-methyl-1H-imidazole-4,5-dicarboxamide;

$N^5$-{4-[(2-chloro-4-methoxybenzoyl)amino]phenyl}-$N^4$-methyl-1H-imidazole-4,5-dicarboxamide;

$N^5$-(4-{[(3-chloropyridin-2-yl)carbonyl]amino}phenyl)-$N^4$-methyl-1H-imidazole-4,5-dicarboxamide;

$N^5$-{4-[(2-chloro-5-methoxybenzoyl)amino]phenyl}-$N^4$-methyl-1H-imidazole-4,5-dicarboxamide;

$N^4$-methyl-$N^5$-(4-{[2-(methylsulfonyl)benzoyl]amino}phenyl)-1H-imidazole-4,5-dicarboxamide;

$N^5$-{4-[(2-chloro-4-ethoxybenzoyl)amino]phenyl}-$N^4$-methyl-1H-imidazole-4,5-dicarboxamide;

$N^5$-(4-{[4-(difluoromethoxy)-2-fluorobenzoyl]amino}phenyl)-$N^4$-methyl-1H-imidazole-4,5-dicarboxamide;

$N^5$-{4-[(2-chloro-3-methoxybenzoyl)amino]phenyl}-$N^4$-methyl-1H-imidazole-4,5-dicarboxamide;

$N^5$-(4-{[2-fluoro-4-(trifluoromethoxy)benzoyl]amino}phenyl)-$N^4$-methyl-1H-imidazole-4,5-dicarboxamide;

$N^5$-(4-{[(4-chloropyridin-3-yl)carbonyl]amino}phenyl)-$N^4$-methyl-1H-imidazole-4,5-dicarboxamide;

$N^5$-(4-{[2-chloro-4-(S-ethylsulfonimidoyl)benzoyl]amino}phenyl)-$N^4$-methyl-1H-imidazole-4,5-dicarboxamide;

$N^5$-(4-{[2-chloro-4-(S-ethylsulfonimidoyl)benzoyl]amino}phenyl)-$N^4$-[2-(piperidin-1-yl)ethyl]-1H-imidazole-4,5-dicarboxamide;

$N^4$-ethyl-$N^5$-(4-{[2-(methylsulfonyl)benzoyl]amino}phenyl)-1H-imidazole-4,5-dicarboxamide;

$N^5$-(4-{[4-(difluoromethoxy)-2-fluorobenzoyl]amino}phenyl)-$N^4$-ethyl-1H-imidazole-4,5-dicarboxamide;

$N^5$-{4-[(2-chloro-4-ethoxybenzoyl)amino]phenyl}-$N^4$-ethyl-1H-imidazole-4,5-dicarboxamide;

$N^5$-{4-[(2-chloro-3-methoxybenzoyl)amino]phenyl}-$N^4$-ethyl-1H-imidazole-4,5-dicarboxamide;

$N^5$-(4-{[(3-chloropyridin-2-yl)carbonyl]amino}phenyl)-$N^4$-ethyl-1H-imidazole-4,5-dicarboxamide;

$N^4$-ethyl-$N^5$-(4-{[2-fluoro-4-(trifluoromethoxy)benzoyl]amino}phenyl)-1H-imidazole-4,5-dicarboxamide;

$N^5$-(4-{[(4-chloropyridin-3-yl)carbonyl]amino}phenyl)-$N^4$-ethyl-1H-imidazole-4,5-dicarboxamide;

$N^5$-{4-[(2-chloro-5-methoxybenzoyl)amino]phenyl}-$N^4$-ethyl-1H-imidazole-4,5-dicarboxamide;

$N^4$-{4-[(2-chloro-4-fluorobenzoyl)amino]phenyl}-$N^5$-[2-(3-methoxypyrrolidin-1-yl)ethyl]-1H-imidazole-4,5-dicarboxamide;

$N^4$-{4-[(2-chloro-4-fluorobenzoyl)amino]phenyl}-$N^5$-{2-[(2S)-2-methylpiperidin-1-yl]ethyl}-1H-imidazole-4,5-dicarboxamide;

$N^4$-{4-[(2-chloro-4-fluorobenzoyl)amino]phenyl}-$N^5$-{2-[(2S)-2-methylpiperidin-1-yl]ethyl}-1H-imidazole-4,5-dicarboxamide formic acid salt;

$N^4$-{4-[(2-chloro-4-fluorobenzoyl)amino]phenyl}-$N^5$-{2-[(2R)-2-methylpiperidin-1-yl]ethyl}-1H-imidazole-4,5-dicarboxamide;

$N^4$-{4-[(2-chloro-4-fluorobenzoyl)amino]phenyl}-$N^5$-[1-(morpholin-4-yl)propan-2-yl]-1H-imidazole-4,5-dicarboxamide;

$N^4$-{4-[(2-chloro-4-fluorobenzoyl)amino]phenyl}-$N^5$-[1-(morpholin-4-yl)propan-2-yl]-1H-imidazole-4,5-dicarboxamide;

$N^4$-{4-[(2-chloro-4-fluorobenzoyl)amino]phenyl}-$N^5$-[1-(morpholin-4-yl)propan-2-yl]-1H-imidazole-4,5-dicarboxamide;

$N^4$-{4-[(2-chloro-4-fluorobenzoyl)amino]phenyl}-$N^5$-{2-[(3S)-3-hydroxypiperidin-1-yl]ethyl}-1H-imidazole-4,5-dicarboxamide;

$N^4$-{4-[(2-chloro-4-fluorobenzoyl)amino]phenyl}-$N^5$-{2-[(3R)-3-hydroxypiperidin-1-yl]ethyl}-1H-imidazole-4,5-dicarboxamide;

$N^4$-{4-[(2-chloro-4-fluorobenzoyl)amino]phenyl}-$N^5$-[3-(3-hydroxypiperidin-1-yl)propyl]-1H-imidazole-4,5-dicarboxamide;

$N^4$-{4-[(2-chloro-4-fluorobenzoyl)amino]phenyl}-$N^5$-[3-(pyrrolidin-1-yl)propyl]-1H-imidazole-4,5-dicarboxamide;

$N^4$-{4-[(2-chloro-4-fluorobenzoyl)amino]phenyl}-$N^5$-[3-(4-hydroxypiperidin-1-yl)propyl]-1H-imidazole-4,5-dicarboxamide;

$N^4$-{4-[(2-chloro-4-fluorobenzoyl)amino]phenyl}-$N^5$-{2-[(3S)-3-fluoropiperidin-1-yl]ethyl}-1H-imidazole-4,5-dicarboxamide;

$N^4$-{4-[(2-chloro-4-fluorobenzoyl)amino]phenyl}-$N^5$-{2-[(3R)-3-fluoropiperidin-1-yl]ethyl}-1H-imidazole-4,5-dicarboxamide;

$N^4$-{4-[(2-chloro-4-fluorobenzoyl)amino]phenyl}-$N^5$-{2-[(3R)-3-methylpiperidin-1-yl]ethyl}-1H-imidazole-4,5-dicarboxamide;

$N^4$-{4-[(2-chloro-4-fluorobenzoyl)amino]phenyl}-$N^5$-[2-(3,3-difluoropyrrolidin-1-yl)ethyl]-1H-imidazole-4,5-dicarboxamide;

$N^5$-(2-amino-2-methylpropyl)-$N^4$-{4-[(2-chloro-4-fluorobenzoyl)amino]phenyl}-1H-imidazole-4,5-dicarboxamide;

$N^4$-{4-[(2-chloro-4-fluorobenzoyl)amino]phenyl}-$N^5$-[(3S)-pyrrolidin-3-yl]-1H-imidazole-4,5-dicarboxamide;

$N^4$-{4-[(2-chloro-4-fluorobenzoyl)amino]phenyl}-$N^5$-[(3R)-pyrrolidin-3-yl]-1H-imidazole-4,5-dicarboxamide;

$N^4$-{4-[(2-chloro-4-fluorobenzoyl)amino]phenyl}-$N^5$-[(3R)-pyrrolidin-3-yl]-1H-imidazole-4,5-dicarboxamide hydrochloric acid salt;

$N^5$-(3-amino-3-methylbutyl)-$N^4$-{4-[(2-chlorobenzoyl)amino]phenyl}-1H-imidazole-4,5-dicarboxamide;

$N^5$-(3-amino-3-methylbutyl)-$N^4$-{4-[(2-chlorobenzoyl)amino]phenyl}-1H-imidazole-4,5-dicarboxamide hydrochloric acid salt;

$N^4$-{4-[(2-chloro-4-fluorobenzoyl)amino]phenyl}-$N^5$-(pyrrolidin-2-ylmethyl)-1H-imidazole-4,5-dicarboxamide;

$N^4$-{4-[(2-chloro-4-fluorobenzoyl)amino]phenyl}-$N^5$-(pyrrolidin-2-ylmethyl)-1H-imidazole-4,5-dicarboxamide hydrochloric acid salt;

5-[(3-aminopyrrolidin-1-yl)carbonyl]-N-{4-[(2-chloro-4-fluorobenzoyl)amino]phenyl}-1H-imidazole-4-carboxamide;

5-[(3-aminopyrrolidin-1-yl)carbonyl]-N-{4-[(2-chloro-4-fluorobenzoyl)amino]phenyl}-1H-imidazole-4-carboxamide hydrochloric acid salt;

$N^5$-(3-amino-3-methylbutyl)-$N^4$-{4-[(2-chloro-4-fluorobenzoyl)amino]phenyl}-1H-imidazole-4,5-dicarboxamide;

$N^4$-{4-[(2-chloro-4-fluorobenzoyl)amino]phenyl}-$N^5$-[2-(methylamino)ethyl]-1H-imidazole-4,5-dicarboxamide;

$N^4$-{4-[(2-chloro-4-fluorobenzoyl)amino]phenyl}-$N^5$-[2-(isopropylamino)ethyl]-1H-imidazole-4,5-dicarboxamide;

N-{4-[(2-chloro-4-fluorobenzoyl)amino]phenyl}-5-(piperazin-1-ylcarbonyl)-1H-imidazole-4-carboxamide;

N-{4-[(2-chloro-4-fluorobenzoyl)amino]phenyl}-5-(piperazin-1-ylcarbonyl)-1H-imidazole-4-carboxamide hydrochloric acid salt;

$N^5$-(2-aminoethyl)-$N^4$-{4-[(2-chloro-4-fluorobenzoyl)amino]phenyl}-1H-imidazole-4,5-dicarboxamide;

$N^4$-{4-[(2-chloro-4-fluorobenzoyl)amino]-3-(trifluoromethoxy)phenyl}-$N^5$-methyl-1H-imidazole-4,5-dicarboxamide;

$N^4$-{4-[(2-chloro-4-fluorobenzoyl)amino]-3-(trifluoromethoxy)phenyl}-$N^5$-(2,2,2-trifluoroethyl)-1H-imidazole-4,5-dicarboxamide;

$N^4$-{4-[(2-chloro-4-fluorobenzoyl)amino]-3-(trifluoromethoxy)phenyl}-$N^5$-[2-(piperidin-1-yl)ethyl]-1H-imidazole-4,5-dicarboxamide;

$N^4$-{4-[(4-fluorobenzoyl)amino]phenyl}-$N^5$-[1-(morpholin-4-yl)propan-2-yl]-1H-imidazole-4,5-dicarboxamide;

$N^4$-{4-[(4-fluorobenzoyl)amino]phenyl}-$N^5$-[1-(morpholin-4-yl)propan-2-yl]-1H-imidazole-4,5-dicarboxamide;

$N^4$-{4-[(4-fluorobenzoyl)amino]phenyl}-$N^5$-[1-(morpholin-4-yl)propan-2-yl]-1H-imidazole-4,5-dicarboxamide;

$N^4$-{4-[(2-chloro-4-fluorobenzoyl)amino]phenyl}-$N^5$-[3-(piperidin-1-yl)propyl]-1H-imidazole-4,5-dicarboxamide;

$N^4$-{4-[(2-chloro-4-fluorobenzoyl)amino]phenyl}-$N^5$-[(1-methylpiperidin-3-yl)methyl]-1H-imidazole-4,5-dicarboxamide;

$N^4$-{4-[(2-chloro-4-fluorobenzoyl)amino]phenyl}-$N^5$-[3-(2-oxopyrrolidin-1-yl)propyl]-1H-imidazole-4,5-dicarboxamide;

$N^4$-{4-[(2-chlorobenzoyl)amino]phenyl}-$N^5$-[2-(2,6-dimethylmorpholin-4-yl)ethyl]-1H-imidazole-4,5-dicarboxamide;

$N^4$-{4-[(2-4-fluorochlorobenzoyl)amino]phenyl}-$N^5$-[2-(2,6-dimethylmorpholin-4-yl)ethyl]-1H-imidazole-4,5-dicarboxamide;

$N^4$-{4-[(2-chlorobenzoyl)amino]phenyl}-$N^5$-(4-methylpiperazin-1-yl)-1H-imidazole-4,5-dicarboxamide;

$N^5$-{4-[(2-chloro-4-fluorobenzoyl)amino]phenyl}-$N^4$-[2-(piperidin-1-yl)ethyl]-1,3-oxazole-4,5-dicarboxamide;

$N^5$-{4-[(4-methoxybenzoyl)amino]phenyl}-$N^4$-methyl-1H-imidazole-4,5-dicarboxamide;

$N^5$-{4-[(3-methoxybenzoyl)amino]phenyl}-$N^4$-methyl-1H-imidazole-4,5-dicarboxamide;

$N^5$-{4-[(4-chlorobenzoyl)amino]phenyl}-$N^4$-methyl-1H-imidazole-4,5-dicarboxamide;

$N^5$-{4-[(2,5-dimethylbenzoyl)amino]phenyl}-$N^4$-methyl-1H-imidazole-4,5-dicarboxamide;

$N^5$-{4-[(3,4-dichlorobenzoyl)amino]phenyl}-$N^4$-methyl-1H-imidazole-4,5-dicarboxamide;

$N^5$-{4-[(2,5-dichlorobenzoyl)amino]phenyl}-$N^4$-methyl-1H-imidazole-4,5-dicarboxamide;

$N^5$-{4-[(4-chloro-2-methoxybenzoyl)amino]phenyl}-$N^4$-methyl-1H-imidazole-4,5-dicarboxamide;

$N^5$-{4-[(3-cyanobenzoyl)amino]phenyl}-$N^4$-methyl-1H-imidazole-4,5-dicarboxamide;

$N^5$-[4-(3-furoylamino)phenyl]-$N^4$-methyl-1H-imidazole-4,5-dicarboxamide;

$N^5$-{4-[(5-bromo-2-chlorobenzoyl)amino]phenyl}-$N^4$-methyl-1H-imidazole-4,5-dicarboxamide;

$N^4$-methyl-$N^5$-(4-{[3-(trifluoromethyl)benzoyl]amino}phenyl)-1H-imidazole-4,5-dicarboxamide;

$N^5$-(4-{[4-(dimethylamino)benzoyl]amino}phenyl)-$N^4$-methyl-1H-imidazole-4,5-dicarboxamide;

$N^4$-methyl-$N^5$-(4-{[4-(trifluoromethyl)benzoyl]amino}phenyl)-1H-imidazole-4,5-dicarboxamide;

$N^5$-(4-{[3-(dimethylamino)benzoyl]amino}phenyl)-$N^4$-methyl-1H-imidazole-4,5-dicarboxamide;

$N^5$-{4-[(2,5-difluorobenzoyl)amino]phenyl}-$N^4$-methyl-1H-imidazole-4,5-dicarboxamide;

$N^5$-{4-[(2,3-difluorobenzoyl)amino]phenyl}-$N^4$-methyl-1H-imidazole-4,5-dicarboxamide;

$N^5$-{4-[(3,4-difluorobenzoyl)amino]phenyl}-$N^4$-methyl-1H-imidazole-4,5-dicarboxamide;

$N^5$-{4-[(3,5-difluorobenzoyl)amino]phenyl}-$N^4$-methyl-1H-imidazole-4,5-dicarboxamide;

$N^5$-{4-[(4-cyanobenzoyl)amino]phenyl}-$N^4$-methyl-1H-imidazole-4,5-dicarboxamide;

$N^4$-methyl-$N^5$-{4-[(2,3,6-trifluorobenzoyl)amino]phenyl}-1H-imidazole-4,5-dicarboxamide;

$N^5$-{4-[(3-fluoro-2-methylbenzoyl)amino]phenyl}-$N^4$-methyl-1H-imidazole-4,5-dicarboxamide;

$N^5$-{4-[(3-chlorobenzoyl)amino]phenyl}-$N^4$-methyl-1H-imidazole-4,5-dicarboxamide;

$N^5$-{4-[(2-fluorobenzoyl)amino]phenyl}-$N^4$-methyl-1H-imidazole-4,5-dicarboxamide;

$N^5$-{4-[(3,5-dichlorobenzoyl)amino]phenyl}-$N^4$-methyl-1H-imidazole-4,5-dicarboxamide;

$N^5$-{4-[(3-fluoro-4-methylbenzoyl)amino]phenyl}-$N^4$-methyl-1H-imidazole-4,5-dicarboxamide;

$N^5$-[4-(2-furoylamino)phenyl]-$N^4$-methyl-1H-imidazole-4,5-dicarboxamide;

$N^5$-{4-[(3-fluorobenzoyl)amino]phenyl}-$N^4$-methyl-1H-imidazole-4,5-dicarboxamide;

$N^4$-methyl-$N^5$-(4-{[(1-methyl-1H-pyrazol-3-yl)carbonyl]amino}phenyl)-1H-imidazole-4,5-dicarboxamide;

$N^5$-{4-[(4-chloro-2-fluorobenzoyl)amino]phenyl}-$N^4$-methyl-1H-imidazole-4,5-dicarboxamide;

$N^5$-{4-[(4-bromo-2-chlorobenzoyl)amino]phenyl}-$N^4$-methyl-1H-imidazole-4,5-dicarboxamide;

$N^5$-{4-[(3,5-dimethylbenzoyl)amino]phenyl}-$N^4$-methyl-1H-imidazole-4,5-dicarboxamide;

$N^4$-methyl-$N^5$-{4-[(3-methylbenzoyl)amino]phenyl}-1H-imidazole-4,5-dicarboxamide;

$N^4$-methyl-$N^5$-{4-[(4-methylbenzoyl)amino]phenyl}-1H-imidazole-4,5-dicarboxamide;

$N^5$-{4-[(3-fluoro-4-methoxybenzoyl)amino]phenyl}-$N^4$-methyl-1H-imidazole-4,5-dicarboxamide;

$N^5$-(4-{[2-(dimethylamino)benzoyl]amino}phenyl)-$N^4$-methyl-1H-imidazole-4,5-dicarboxamide;

$N^5$-{4-[(3-chloro-4-fluorobenzoyl)amino]phenyl}-$N^4$-methyl-1H-imidazole-4,5-dicarboxamide;

$N^5$-{4-[(3-chloro-2-methylbenzoyl)amino]phenyl}-$N^4$-methyl-1H-imidazole-4,5-dicarboxamide;

$N^4$-methyl-$N^5$-{4-[(2,4,6-trifluorobenzoyl)amino]phenyl}-1H-imidazole-4,5-dicarboxamide;

$N^5$-{4-[(2-chloro-6-methylbenzoyl)amino]phenyl}-$N^4$-methyl-1H-imidazole-4,5-dicarboxamide;
$N^5$-{4-[(3-chloro-4-methylbenzoyl)amino]phenyl}-$N^4$-methyl-1H-imidazole-4,5-dicarboxamide;
$N^4$-methyl-$N^5$-{4-[(1,3-thiazol-5-ylcarbonyl)amino]phenyl}-1H-imidazole-4,5-dicarboxamide;
$N^5$-{4-[(2-chloro-3-methylbenzoyl)amino]phenyl}-$N^4$-methyl-1H-imidazole-4,5-dicarboxamide;
$N^4$-methyl-$N^5$-{4-[(2,3,5-trifluorobenzoyl)amino]phenyl}-1H-imidazole-4,5-dicarboxamide;
$N^5$-{4-[(2-chloro-3,4-dimethoxybenzoyl)amino]phenyl}-$N^4$-methyl-1H-imidazole-4,5-dicarboxamide;
$N^5$-{4-[(5-cyano-2-fluorobenzoyl)amino]phenyl}-$N^4$-methyl-1H-imidazole-4,5-dicarboxamide;
$N^5$-{4-[(4-cyano-3-fluorobenzoyl)amino]phenyl}-$N^4$-methyl-1H-imidazole-4,5-dicarboxamide;
$N^5$-{4-[(2-chloroisonicotinoyl)amino]phenyl}-$N^4$-methyl-1H-imidazole-4,5-dicarboxamide;
$N^5$-(4-{[2-chloro-5-(trifluoromethyl)benzoyl]amino}phenyl)-$N^4$-methyl-1H-imidazole-4,5-dicarboxamide;
$N^5$-(4-{[(6-chloropyridin-2-yl)carbonyl]amino}phenyl)-$N^4$-methyl-1H-imidazole-4,5-dicarboxamide;
$N^4$-methyl-$N^5$-{4-[(1,2-oxazol-5-ylcarbonyl)amino]phenyl}-1H-imidazole-4,5-dicarboxamide;
$N^5$-{4-[(4-methoxy-3-methylbenzoyl)amino]phenyl}-$N^4$-methyl-1H-imidazole-4,5-dicarboxamide;
$N^4$-methyl-$N^5$-(4-{[(3-methylpyridin-2-yl)carbonyl]amino}phenyl)-1H-imidazole-4,5-dicarboxamide;
$N^4$-methyl-$N^5$-(4-{[(5-methylpyridin-2-yl)carbonyl]amino}phenyl)-1H-imidazole-4,5-dicarboxamide;
$N^5$-(4-{[2-chloro-3-(trifluoromethyl)benzoyl]amino}phenyl)-$N^4$-methyl-1H-imidazole-4,5-dicarboxamide;
$N^5$-{4-[(3-chloro-2,4-difluorobenzoyl)amino]phenyl}-$N^4$-methyl-1H-imidazole-4,5-dicarboxamide;
$N^5$-{4-[(3-chloro-5-fluorobenzoyl)amino]phenyl}-$N^4$-methyl-1H-imidazole-4,5-dicarboxamide;
$N^5$-{4-[(2-chloro-5-fluorobenzoyl)amino]phenyl}-$N^4$-methyl-1H-imidazole-4,5-dicarboxamide;
$N^5$-{4-[(3-chloro-4,5-difluorobenzoyl)amino]phenyl}-$N^4$-methyl-1H-imidazole-4,5-dicarboxamide;
$N^4$-methyl-$N^5$-(4-{[(4-methylpyridin-2-yl)carbonyl]amino}phenyl)-1H-imidazole-4,5-dicarboxamide;
$N^5$-{4-[(5-fluoro-2-methoxybenzoyl)amino]phenyl}-$N^4$-methyl-1H-imidazole-4,5-dicarboxamide;
$N^5$-{4-[(2-fluoro-3-methoxybenzoyl)amino]phenyl}-$N^4$-methyl-1H-imidazole-4,5-dicarboxamide;
$N^4$-methyl-$N^5$-(4-{[(5-methylpyridin-3-yl)carbonyl]amino}phenyl)-1H-imidazole-4,5-dicarboxamide;
$N^5$-{4-[(3-fluoro-2-methoxybenzoyl)amino]phenyl}-$N^4$-methyl-1H-imidazole-4,5-dicarboxamide;
$N^5$-{4-[(4-cyano-2-fluorobenzoyl)amino]phenyl}-$N^4$-methyl-1H-imidazole-4,5-dicarboxamide;
$N^5$-{4-[(2-chloro-3-fluorobenzoyl)amino]phenyl}-$N^4$-methyl-1H-imidazole-4,5-dicarboxamide;
$N^5$-{4-[(3-cyano-5-fluorobenzoyl)amino]phenyl}-$N^4$-methyl-1H-imidazole-4,5-dicarboxamide;
$N^5$-(4-{[(3-chloropyrazin-2-yl)carbonyl]amino}phenyl)-$N^4$-methyl-1H-imidazole-4,5-dicarboxamide;
$N^5$-{4-[(4-fluoro-3-methylbenzoyl)amino]phenyl}-$N^4$-methyl-1H-imidazole-4,5-dicarboxamide;
$N^5$-{4-[(2-chloro-3,6-difluorobenzoyl)amino]phenyl}$N^4$-methyl-1H-imidazole-4,5-dicarboxamide;
$N^5$-{4-[(2-fluoro-6-methylbenzoyl)amino]phenyl}-$N^4$-methyl-1H-imidazole-4,5-dicarboxamide;
$N^4$-methyl-$N^5$-{4-[(1,2-oxazol-3-ylcarbonyl)amino]phenyl}-1H-imidazole-4,5-dicarboxamide;
$N^5$-{4-[(4,5-difluoro-2-methylbenzoyl)amino]phenyl}-$N^4$-methyl-1H-imidazole-4,5-dicarboxamide;
$N^5$-{4-[(2-chloro-4-fluorobenzoyl)amino]phenyl}-$N^4$-[5-(dimethylamino)pentyl]-1H-imidazole-4,5-dicarboxamide;
$N^5$-{4-[(2-chloro-4-fluorobenzoyl)amino]phenyl}-$N^4$-[(2S)-1-hydroxy-3-methylbutan-2-yl]-1H-imidazole-4,5-dicarboxamide;
$N^5$-{4-[(2-chloro-4-fluorobenzoyl)amino]phenyl}-$N^4$-[5-(diethylamino)pentan-2-yl]-1H-imidazole-4,5-dicarboxamide;
$N^4$-{4-[(2-chlorobenzoyl)amino]phenyl}-$N^5$-[2-(piperidin-1-yl)ethyl]-1H-imidazole-4,5-dicarboxamide;
$N^5$-{4-[(2-chloro-4-fluorobenzoyl)amino]phenyl}-$N^4$-[2-(diethylamino)ethyl]-1H-imidazole-4,5-dicarboxamide;
$N^5$-{4-[(2-chloro-4-fluorobenzoyl)amino]phenyl}-$N^4$-(3-isopropoxypropyl)-1H-imidazole-4,5-dicarboxamide;
$N^5$-{4-[(2-chloro-4-fluorobenzoyl)amino]phenyl}-$N^4$-(2-phenylethyl)-1H-imidazole-4,5-dicarboxamide;
$N^5$-{4-[(2-chloro-4-fluorobenzoyl)amino]phenyl}-$N^4$-[2-(1-methylpyrrolidin-2-yl)ethyl]-1H-imidazole-4,5-dicarboxamide;
$N^5$-{4-[(2-chloro-4-fluorobenzoyl)amino]phenyl}-$N^4$-[3-(2-methylpiperidin-1-yl)propyl]-1H-imidazole-4,5-dicarboxamide;
$N^5$-{4-[(2-chloro-4-fluorobenzoyl)amino]phenyl}-$N^4$-[2-(pyridin-2-yl)ethyl]-1H-imidazole-4,5-dicarboxamide;
$N^5$-{4-[(2-chloro-4-fluorobenzoyl)amino]phenyl}-$N^4$-[3-(diethylamino)propyl]-1H-imidazole-4,5-dicarboxamide;
$N^5$-{4-[(2-chloro-4-fluorobenzoyl)amino]phenyl}-$N^4$-[2-(diisopropylamino)ethyl]-1H-imidazole-4,5-dicarboxamide;
$N^5$-{4-[(2-chloro-4-fluorobenzoyl)amino]phenyl}-$N^4$-[(1-ethylpyrrolidin-2-yl)methyl]-1H-imidazole-4,5-dicarboxamide;
$N^5$-{4-[(2-chloro-4-fluorobenzoyl)amino]phenyl}-$N^4$-(2,2-dimethyltetrahydro-2H-pyran-4-yl)-1H-imidazole-4,5-dicarboxamide;
$N^5$-{4-[(2-chloro-4-fluorobenzoyl)amino]phenyl}-$N^4$-[3-(4-methylpiperazin-1-yl)propyl]-1H-imidazole-4,5-dicarboxamide;
$N^5$-{4-[(2-chloro-4-fluorobenzoyl)amino]phenyl}-$N^4$-[4-(diethylamino)butyl]-1H-imidazole-4,5-dicarboxamide;
$N^5$-{4-[(2-chloro-4-fluorobenzoyl)amino]phenyl}-$N^4$-[2-(pyridin-4-yl)ethyl]-1H-imidazole-4,5-dicarboxamide;
$N^5$-{4-[(2-chloro-4-fluorobenzoyl)amino]phenyl}-$N^4$-[3-(dimethylamino)-2,2-dimethylpropyl]-1H-imidazole-4,5-dicarboxamide;
$N^5$-{4-[(2-chloro-4-fluorobenzoyl)amino]phenyl}-$N^4$-(tetrahydro-2H-pyran-4-ylmethyl)-1H-imidazole-4,5-dicarboxamide;
$N^5$-{4-[(2-chloro-4-fluorobenzoyl)amino]phenyl}-$N^4$-[2-(2-oxopyrrolidin-1-yl)ethyl]-1H-imidazole-4,5-dicarboxamide;
$N^5$-{4-[(2-chloro-4-fluorobenzoyl)amino]phenyl}-$N^4$-[2-(2-oxoimidazolidin-1-yl)ethyl]-1H-imidazole-4,5-dicarboxamide;
$N^5$-{4-[(2-chloro-4-fluorobenzoyl)amino]phenyl}-$N^4$-[3-(4-methylpiperidin-1-yl)propyl]-1H-imidazole-4,5-dicarboxamide;

N⁵-{4-[(2-chloro-4-fluorobenzoyl)amino]phenyl}-N⁴-[2-(2,6-dimethylpiperidin-1-yl)ethyl]-1H-imidazole-4,5-dicarboxamide;

N⁵-{4-[(2-chloro-4-fluorobenzoyl)amino]phenyl}-N⁴-[2-(1,1-dioxidothiomorpholin-4-yl)ethyl]-1H-imidazole-4,5-dicarboxamide;

N⁵-{4-[(2-chloro-4-fluorobenzoyl)amino]phenyl}-N⁴-{[(2S)-1-ethylpyrrolidin-2-yl]methyl}-1H-imidazole-4,5-dicarboxamide;

N⁵-{4-[(2-chloro-4-fluorobenzoyl)amino]phenyl}-N⁴-[2-(pyridin-3-yl)ethyl]-1H-imidazole-4,5-dicarboxamide;

N⁵-{4-[(2-chloro-4-fluorobenzoyl)amino]phenyl}-N⁴-[5-(pyrrolidin-1-yl)pentyl]-1H-imidazole-4,5-dicarboxamide;

N⁵-{4-[(2-chloro-4-fluorobenzoyl)amino]phenyl}-N⁴-[(1-methylpyrrolidin-3-yl)methyl]-1H-imidazole-4,5-dicarboxamide;

N⁵-{4-[(2-chloro-4-fluorobenzoyl)amino]phenyl}-N⁴-[(1-methylpiperidin-4-yl)methyl]-1H-imidazole-4,5-dicarboxamide;

N⁵-{4-[(2-chloro-4-fluorobenzoyl)amino]phenyl}-N⁴-[(1-ethylpiperidin-4-yl)methyl]-1H-imidazole-4,5-dicarboxamide;

N⁵-{4-[(2-chloro-4-fluorobenzoyl)amino]phenyl}-N⁴-[(1-methylpiperidin-2-yl)methyl]-1H-imidazole-4,5-dicarboxamide;

N⁵-{4-[(2-chloro-4-fluorobenzoyl)amino]phenyl}-N⁴-[(1-ethylpyrrolidin-3-yl)methyl]-1H-imidazole-4,5-dicarboxamide;

N⁵-{4-[(2-chloro-4-fluorobenzoyl)amino]phenyl}-N⁴-[2-(dimethylamino)-2-methylpropyl]-1H-imidazole-4,5-dicarboxamide;

N⁵-{4-[(2-chloro-4-fluorobenzoyl)amino]phenyl}-N⁴-{[(2R)-1-ethylpyrrolidin-2-yl]methyl}-1H-imidazole-4,5-dicarboxamide;

N⁵-{4-[(2-chloro-4-fluorobenzoyl)amino]phenyl}-N⁴-(1-methylpiperidin-4-yl)-1H-imidazole-4,5-dicarboxamide; and N⁵-{4-[(2-chloro-4-fluorobenzoyl)amino]phenyl}-N⁴-[2,2-dimethyl-3-(4-methylpiperazin-1-yl)propyl]-1H-imidazole-4,5-dicarboxamide, or a stereoisomer, a tautomer, an N-oxide, a hydrate, a solvate, or a salt thereof, or a mixture of any of the foregoing.

7. A method of preparing the compound of formula (I) according to claim 1, comprising reacting a compound of formula (II):

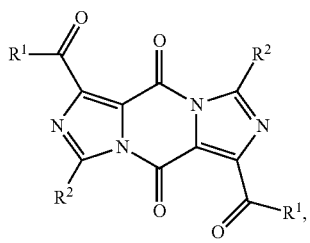

wherein R¹ and R² are as defined for the compound of formula (I) according to claim 1, with a compound of formula (III):

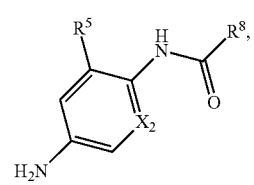

wherein $X_2$, $R^5$, and $R^8$ are as defined for the compound of formula (I) according to claim 1,
to form the compound of formula (I):

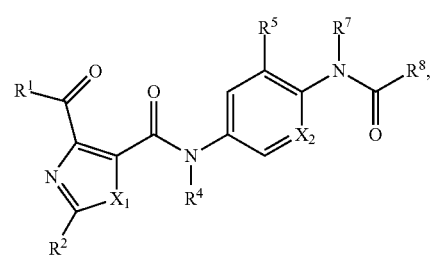

wherein $X_1$ is $NR^3$, and $X_2$, $R^1$, $R^2$, $R^3$, $R^4$, $R^5$, $R^7$, and $R^8$ are as defined for the compound of formula (I) according to claim 1.

8. A method of preparing the compound of formula (I) according to claim 1, comprising reacting a compound of formula (IV):

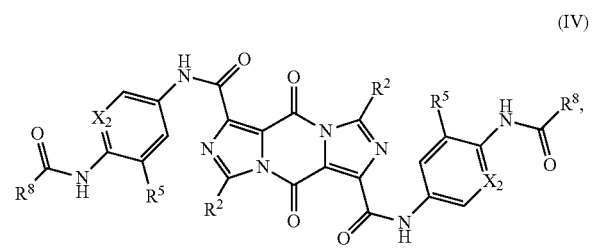

wherein $X_2$, $R^2$, $R^5$, and $R^8$ are as defined for the compound of formula (I) according to claim 1,
with a compound of formula (V):

YH      (V), wherein YH is an alcohol $R^9OH$ or an amine $R^{11}(R^{10})NH_2$, wherein $R^9$, $R^{10}$, and $R^{11}$ are as defined for the compound of formula (I) according to claim 1,
to form the compound of formula (I):

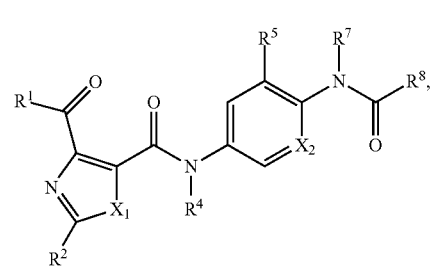

wherein $X_1$ is $NR^3$, and $X_2$, $R^1$, $R^2$, $R^3$, $R^4$, $R^5$, $R^7$, and $R^8$ are as defined for the compound of formula (I) according to claim 1.

9. A method of preparing the compound of formula (I) according to claim 1, comprising reacting a compound of formula (VI):

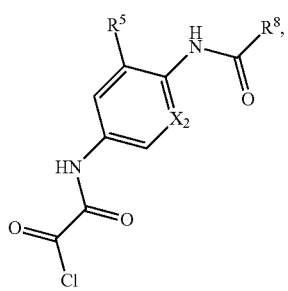

(VI)

wherein $X_2$, $R^5$, and $R^8$ are as defined for the compound of formula (I) according to claim 1, with a compound of formula (VII):

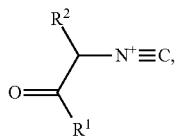

(VII)

wherein $R^1$ and $R^2$ are as defined for the compound of formula (I) according to claim 1, to form the compound of formula (I):

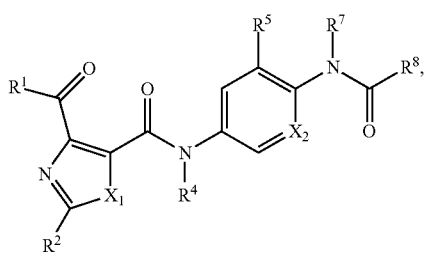

(I)

wherein $X_1$ is O, and $X_2$, $R^1$, $R^2$, $R^4$, $R^5$, $R^7$, and $R^8$ are as defined for the compound of formula (I) according to claim 1.

10. A method of preparing the compound of formula (I) according to claim 1, comprising reacting a compound of formula (IX)

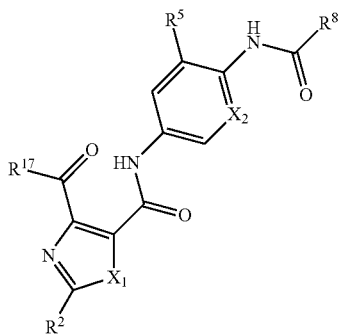

(IX)

wherein:

$X_1$ is $NR^3$;

$R^{17}$ is $OR^{18}$;

$R^{18}$ is hydrogen or phenyl; and $X_2$, $R^2$, $R^3$, $R^5$, and $R^8$ are as defined for the compound of formula (I) according to claim 1, with a compound of formula $HN(R^{10})(R^{11})$, wherein $R^{10}$ and $R^{11}$ are as defined for the compound of formula (I) according to claim 1, to form the compound of formula (I):

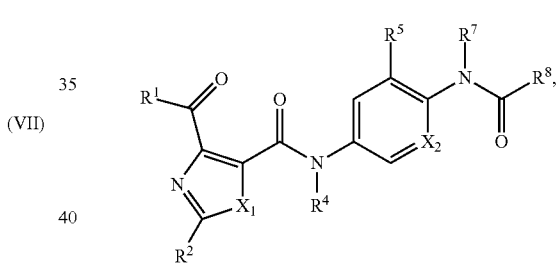

(I)

wherein $X_1$ is $NR^3$, $R^1$ is $-N(R^{10})R^{11}$, and $X_2$, $R^2$, $R^4$, $R^5$, $R^7$, $R^8$, $R^{10}$, and $R^{11}$ are as defined for the compound of formula (I) according to claim 1.

11. A pharmaceutical composition comprising the compound of claim 1, or a stereoisomer, a tautomer, an N-oxide, a hydrate, a solvate, or a salt thereof, or a mixture of any of the foregoing, and a pharmaceutically acceptable diluent or carrier.

12. A pharmaceutical combination comprising:
one or more first active ingredients selected from a compound of formula (I) according to claim 1, or a stereoisomer, a tautomer, an N-oxide, a hydrate, a solvate, or a salt thereof, or a mixture of any of the foregoing;
and
one or more second active ingredients selected from chemotherapeutic anti-cancer agents.

13. A method of preparing the compound of formula (I) according to claim 1, comprising reacting a compound of formula (VIII)

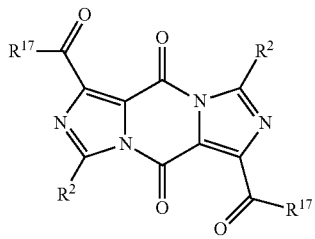

(VIII)

wherein:
R$^{17}$ is OR$^{18}$;
R$^{18}$ is hydrogen or phenyl; and
R$^2$ is as defined for the compound of formula (I) according to claim 1,
with a compound of formula (III):

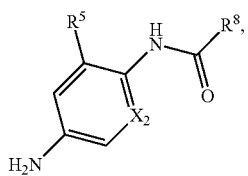

(III)

wherein X$_2$, R$^5$, and R$^8$ are as defined for the compound of formula (I) according to claim 1,
to form a compound of formula (IX)

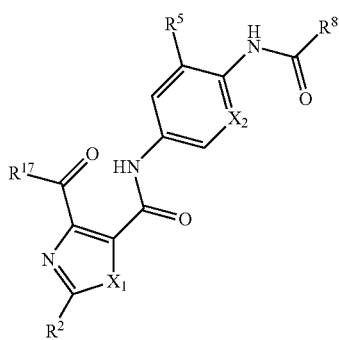

(IX)

wherein:
X$_1$ is NR$^3$;
R$^{17}$ is OR$^{18}$;
R$^{18}$ is hydrogen or phenyl; and
X$_2$, R$^2$, R$^3$, R$^5$, and R$^8$ are as defined for the compound of formula (I) according to claim 1,
and further comprising reacting the compound of formula (IX) with a compound of formula HN(R$^{10}$)(R$^{11}$), wherein R$^{10}$ and R$^{11}$ are as defined for the compound of formula (I) according to claim 1,
to form the compound of formula (I):

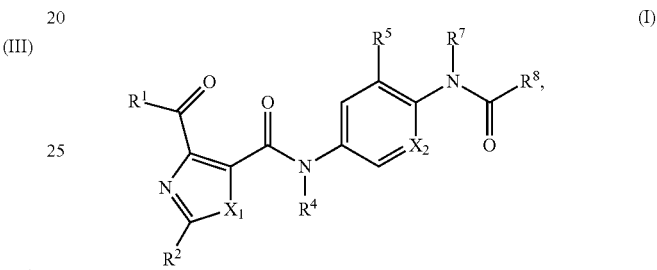

(I)

wherein X$_1$ is NR$^3$, R$^1$ is —N(R$^{10}$)R$^{11}$, and X$_2$, R$^2$, R$^4$, R$^5$, R$^7$, R$^8$, R$^{10}$, and R$^{11}$ are as defined for the compound of formula (I) according to claim 1.

14. The compound of claim 1 or a salt thereof.

15. The compound of claim 6 or a salt thereof.

16. The pharmaceutical composition of claim 11, comprising the compound of formula (I) or a pharmaceutically acceptable salt thereof.

17. The pharmaceutical combination of claim 12, comprising one or more compounds of formula (I) or a salt thereof.

* * * * *

SEQUENCE LISTING

```
<160> NUMBER OF SEQ ID NOS: 6

<210> SEQ ID NO 1
<211> LENGTH: 20
<212> TYPE: DNA
<213> ORGANISM: human

<400> SEQUENCE: 1
aagttcatcc ggcaccagtc                                              20

<210> SEQ ID NO 2
<211> LENGTH: 21
<212> TYPE: DNA
<213> ORGANISM: human

<400> SEQUENCE: 2
```

```
tggcccttga atcttctacg a                                                21

<210> SEQ ID NO 3
<211> LENGTH: 22
<212> TYPE: DNA
<213> ORGANISM: human

<400> SEQUENCE: 3
cccagaggca ttgacaacag gg                                               22

<210> SEQ ID NO 4
<211> LENGTH: 20
<212> TYPE: DNA
<213> ORGANISM: human

<400> SEQUENCE: 4
aggccagtga gttggttgtc                                                  20

<210> SEQ ID NO 5
<211> LENGTH: 20
<212> TYPE: DNA
<213> ORGANISM: human

<400> SEQUENCE: 5
agctctgagc cttcagcatc                                                  20

<210> SEQ ID NO 6
<211> LENGTH: 25
<212> TYPE: DNA
<213> ORGANISM: human

<400> SEQUENCE: 6
tctgtgggga agaaattcca taccg                                            25
```